US011884949B2

(12) United States Patent
Smolke et al.

(10) Patent No.: US 11,884,949 B2
(45) Date of Patent: *Jan. 30, 2024

(54) METHODS OF PRODUCING MORPHINAN ALKALOIDS AND DERIVATIVES

(71) Applicant: Antheia, Inc., Menlo Park, CA (US)

(72) Inventors: Christina D. Smolke, Menlo Park, CA (US); Isis Trenchard, Redwood City, CA (US); Kristy M. Hawkins, Menlo Park, CA (US); Catherine Thodey, Mountain View, CA (US)

(73) Assignee: Antheia, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/984,900

(22) Filed: Aug. 4, 2020

(65) Prior Publication Data

US 2021/0062235 A1 Mar. 4, 2021

Related U.S. Application Data

(63) Continuation of application No. PCT/US2019/017357, filed on Feb. 8, 2019.

(60) Provisional application No. 62/628,264, filed on Feb. 8, 2018.

(51) Int. Cl.
*C12P 17/12* (2006.01)
*C12N 9/88* (2006.01)
*C12N 9/90* (2006.01)
*C12N 15/52* (2006.01)

(52) U.S. Cl.
CPC .............. *C12P 17/12* (2013.01); *C12N 9/88* (2013.01); *C12N 9/90* (2013.01); *C12N 15/52* (2013.01); *C12Y 402/99* (2013.01)

(58) Field of Classification Search
CPC .......... C12P 17/12; C12P 17/188; C12N 9/88; C12N 9/90; C12N 15/52; C12Y 402/99; C07D 217/16; C07D 221/28
See application file for complete search history.

(56) References Cited

U.S. PATENT DOCUMENTS

| 6,573,428 | B1 | 6/2003 | Vodkin et al. | |
|---|---|---|---|---|
| 10,544,420 | B2 * | 1/2020 | Smolke | C12N 9/0014 |
| 11,142,780 | B2 | 10/2021 | Facchini et al. | |
| 11,479,586 | B2 | 10/2022 | Facchini et al. | |
| 2009/0156815 | A1 | 7/2009 | Wang et al. | |
| 2016/0208269 | A1 | 7/2016 | Smolke et al. | |
| 2020/0325509 | A1 * | 10/2020 | Enquist-Newman | C12N 9/88 |
| 2021/0062235 | A1 * | 3/2021 | Smolke | C12P 17/188 |
| 2022/0205004 | A1 | 6/2022 | Facchini et al. | |

FOREIGN PATENT DOCUMENTS

| WO | 2011058446 | A2 | 5/2011 |
|---|---|---|---|
| WO | 2015081437 | A1 | 6/2015 |
| WO | 2015173590 | A1 | 11/2015 |
| WO | 2018000089 | A1 | 1/2018 |
| WO | 2018005553 | A1 | 1/2018 |

OTHER PUBLICATIONS

Facchini, P.J., "GenBank Accession No. FE967184". Mar. 31, 2008, [online] [retrieved on Sep. 19, 2017]. Retrieved from the internet: <https://www.ncbi.nlm.nih.gov/nucest/FE967184>.
Shitan et al., "Alkaloid Transporters in Plants", Plant Biotechnology, 31:453-463 (2014), DOI 10.5511/plantbiotechnology.14.1002a.
Fossati et al., "Synthesis of Morphinan Alkaloids in *Saccharomyces cerevisiae*", PLOS ONE, DOI: 10.1371/journal.pone.0124453 (2015).
Sabarna, "Approaches to isolating a cDNA encoding thebaine synthase or morphine biosynthesis from opium poppy *Papaver somniferum* L.", Internet Citation, [Online], Retrieved from the Internet: URL:http://sundoc.bibliothek.uni-halle.de/ Jun. 22, 2007 (Jun. 22, 2007).
Fisinger et al., "Thebaine synthase: A new enzyme in the morphone pathway in Papaver somniferum", Natural Product Communications, 2: 249-253 (2007).
Beaudoin et al., "Benzylisoquinoline alkaloid biosynthesis in opium poppy", Planta, 240: 19-32 (2014), DOI 10.1007/S00425-014-2056-8.
Database EMBL [Online] Jul. 2, 2015 (Jul. 2, 2015), "*Papaver somniferum* (opium poppy) reticuline epimerase ID-AKO60181 ; SV 1 ; linearl; genomic DNA; STD; PLN; 2703 BP.", retrieved from EBI accession No. EM_CDS: AKO60181.
Database Geneseq [Online] Apr. 9, 2015 (Apr. 9, 2015), "Papaver somniferum OMT protein, SEQ ID 543.", retrieved from EBI accession No. GSP:BBU80692 Database accession No. BBU80692.
Winzer et al., "A Papaver somniferum 10-Gene Cluster for Synthesis of the Anticancer Alkaloid Noscapine", Science, 336:1704-1708 (2012), DOI: 10.1126/science.1220757.
Hagel et al., "Dioxygenases catalyze the O-demethylation steps of morphine biosynthesis in opium poppy", Nature Chemical Biology, 6:273-275 (2010).
Morris et al., "Plug-and-Play Benzylisoquinoline Alkaloid Biosynthetic Gene Discovery in Engineered Yeast" in Methods in Enzymology, 144-178 (Elsevier 2016).
Galanie et al., "Complete biosynthesis of opioids in yeast", Science, 349:1095-1100 (2015).
Glenn, W.S. et al., "Recent progress in the metabolic engineering of alkaloids in plant 1-49 systems", Curr. Opin. Biotechnol., Apr. 2013 (Apr. 2013), vol. 24(2), pp. 354-365.
Chen et al, "A pathogenesis-related 10 protein catalyzes the final step in thebaine biosynthesis", 2018, Nature Chemical Biology, 14:738-743.

(Continued)

*Primary Examiner* — Ganapathirama Raghu
(74) *Attorney, Agent, or Firm* — Mintz, Levin, Cohn, Ferris, Glovsky and Popeo, P.C.

(57) ABSTRACT

A method of producing promorphinan, morphinan, nal-opioid, and nor-opioid alkaloid products through the increased conversion of a promorphinan alkaloid to a morphinan alkaloid. The method comprises contacting the promorphinan alkaloid with at least one enzyme. Contacting the promorphinan alkaloid with the at least one enzyme converts the promorphinan alkaloid to a morphinan alkaloid.

19 Claims, 29 Drawing Sheets

Specification includes a Sequence Listing.

(56) References Cited

OTHER PUBLICATIONS

Zulak et al, "Gene transcript and metabolite profiling of elicitor-induced opium poppy cell cultures reveals the coordinate regulation of primary and secondary metabolism", 2007, Planta, 225:1085-1106, DOI: 10.1007/s00425-006-0419-5.

Dastmalchi et al, "Purine Permease-Type Benzylisoquinoline Alkaloid Transporters in Opium Poppy", 2019, Plant Psychology, 181:916-933.

Grothe et al, "Molecular Characterization of the Salutaridinol 7-O-Acetyltransferase Involved in Morphine Biosynthesis in Opium Poppy *Papaver somniferum*", 2001, The Journal of Biological Chemistry, 276:30717-30723.

Choe et al., "Genetic and chemical components analysis of Papaver setigerum naturalized in Korea", Forensic Science International, 222:387-393 (2012).

Samanani et al., "The role of phloem sieve elements and laticifers in the biosynthesis and accumulation of alkaloids in opium poppy", Plant Journal, 47:547-563 (2006), DOI: 10.111/j.1365-313X.2006.02801.x.

Facchini et al., "Developmental and inducible accumulation of gene transcripts involved in alkaloid biosynthesis in opium poppy", Phytochemistry, 64:177-186 (2003).

Kisselev L., "Polypeptide Release Factors in Prokaryotes and Eukaryotes: Same Function, Different Structure", Structure, 2002, vol. 10: 8-9.

Witkowski et al., "Conversion of a B-Ketoacyl Synthase to a Malonyl Decazrboxylase by Replacement of the Active-Site Cysteine with Glutamine", Biochemistry 38:11643-11650, 1999.

Whisstock et al., Quarterly Reviews of Biophysics 2003, vol. 36 (3): 307-340.

Devos et al., "Practical Limits of Function Prediction", Proteins: Structure, Function and Genetics, 2000, vol. 41: 98-107.

U.S. Non-Final Office Action dated May 20, 2020 in U.S. Appl. No. 16/312,895.

U.S. Final Office Action dated Nov. 25, 2020 in U.S. Appl. No. 16/312,895.

U.S. Non-Final Office Action dated Aug. 28, 2020 in U.S. Appl. No. 16/312,776.

U.S. Notice of Allowance dated Mar. 15, 2021 in U.S. Appl. No. 16/312,776.

Farrow et al. "Stereochemical inversion of (S)-reticuline by a cytochrome P450 fusion in opium poppy" Nature Chemical Biology, vol. 11, Sep. 2015, p. 728-732; abstract.

U.S. Office Action dated Apr. 23, 2021 in U.S. Appl. No. 16/312,895.

\* cited by examiner

SEQ ID No. 16

MELQYISYFQPTSSVVALLLALVSILSSVVVLRKTFLNNYSSSPAS
STKTAVLSHQRQQSCALPISGLLH
IFMNKNGLIHVTLGNMADKYGPIFSFPTGSHRTLVVSSWEMV
KECFTGNNDTAFSNRPIPLAFKTIFYAC
GGIDSYGLSSVPYGKYWRELRKVCVHNLLSNQQLLKFRHLIIS
QVDTSFNKLYELCKNSEDNQGNYPTTT
TAAGMVRIDDWLAELSFNVIGRIVCGFQSGPKTGAPSRVEQF
KEAINEASYFMSTSPVSDNVPMLGWIDQ
LTGLTRNMKHCGKKLDLVVESIINDHRQKRRFSRTKGGDEKD
DEQDDFIDICLSIMEQPQLPGNNNPSQI
PIKSIVLDMIGGGTDTTKLTTIWTLSLLLNNPHVLDKAKQEVD
AHFRTKRRSTNDAAAAVVDFDDIRNLV
YIQAIIKESMRLYPASPVVERLSGEDCVVGGFHVPAGTRLWAN
VWKMQRDPKVWDDPLVFRPDRFLSDEQ
KMVDVRGQNYELLPFGAGRRVCPGVSFSLDLMQLVLTRLILE
FEMKSPSGKVDMTATPGLMSYKVIPLDI
LLTHRRIKPCVQSAASERDMESSGVPVITLGSGKVMPVLGMG
TFEKVGKGSERERLAILKAIEVGYRYFD
TAAAYETEEVLGEAIAEALQLGLVKSRDELFISSMLWCTDAHA
DRVLLALQNSLRNLKLEYVDLYMLPFP
ASLKPGKITMDIPEEDICRMDYRSVWAAMEECQNLGFTKSIG
VSNFSCKKLQELMATANIPPAVNQVEMS
PAFQQKKLREYCNANNILVSAISVLGSNGTPWGSNAVLGSEVL
KKIAMAKGKSVAQVSMRWVYEQGASLV
VKSFSEERLRENLNIFDWELTKEDHEKIGEIPQCRILSAYFLVSP
NGPFKSQEELWDDEA

FIG. 4

Split Enzymes originating from SEQ ID No. 16

DRS enzyme (SEQ ID No. 17):

MELQYFSYFQPTSSVVALLALVSILFSVVVLRKTFSNNYSSPASSTETAVLCHQRQQSC
ALPISGLLHVFMNKNGLIHVTLGNMADKYGPIFSFPTGSHRTLVSSWEMVKECFTGN
NDTAFSNRPIPLAFQTIFYACGGIDSYGLSSVPYGKYWRELRKVCVHNLLSNQQLLKFR
HLIISQVDTSFNKLYELCKNSEDNQGMVRMDDWLAQLSFNVIGRIVCGFQSDPKTGA
PSRVEQFKEVINEASYFMSTSPVSDNVPMLGWIDQLTGLTRNMKHCGKKLDLVVESII
KDHRQKRRFSRTKGGDEKDDEQDDFIDICLSIMEQPQLPGNNSPPQIPIKSIVLDMIG
GGTDTTKLTTIWTLSLLLNNPHVLDKAKQEVDAHFRKKRRSTDDAAAAVVDFDDIRNL
VYIQAIIKESMRLYPASPVVERLSGEDCVVGGFHVPAGTRLWANVWKMQRDPKVWD
DPLVFRPERFLSDEQKMVDVRGQNYELLPFGAGRRICPGVSFSLDLMQLVTRLILEFE
MKSPSGKVDMTATPGLMSYKVVPLDILLTHRRIKSCVQLASSERD*

DRR enzyme (SEQ ID No. 18):

MESSGVPVITLSSGKVMPVLGMGTFEKVGKGSERERLAILKAIEVGYRYFDTAAAYETE
EVLGEAIAEALQLGLIESRDELFISSMLWCTDAHPDRVLLALQNSLRNLKLEYLDYMLP
FPASLKPGKITMDIPEEDICRMDYRSVWSAMEECQNLGFTKSIGVSNFSCKKLQELMA
TANIPPAVNQVEMSPAFQQKKLREYCNANNILVSAVSILGSNGTPWGSNAVLGSEVLK
QIAMAKGKSVAQVSMRWVYEQGASLVVKSFSEERLRENLNIFDWELTKEDNEKIGEIP
QCRILTAYFLVSPNGPFKSQEELWDDKA*

FIG. 5

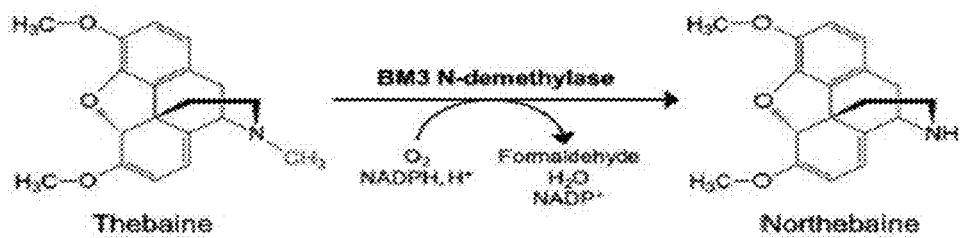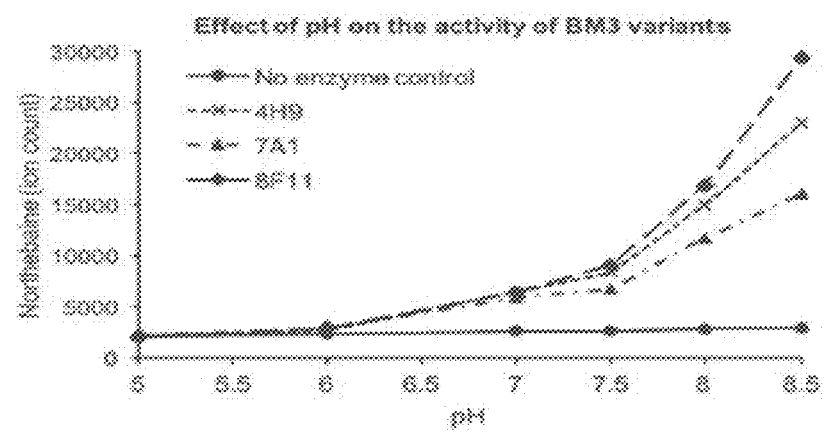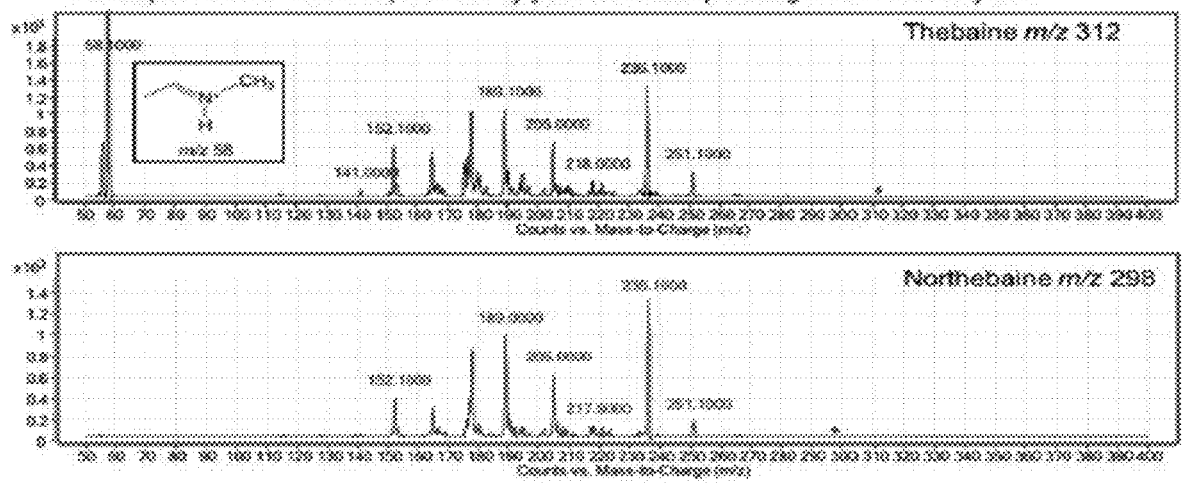
FIG. 9

Example reaction scheme:

PrDRS      TQGLMSYRVVPLDILLTRRML---------------------------------
PbDRS-     TPGLMSYRVVPLDILLTRRR|KSCVQLASSERI|MESSGVPVITLSSGKVMPVLGMGTFEK
DRR
PrDRR                                      MDSSGVPVTPLSSGKMPALALGTFET

Alignment between PbDRS-DRR, PrDRS, and PrDRR

FIG. 17

Four genetic constructs integrated into the yeast genome:

1. YBR197CΔ::P$_{TPI1}$-RnSepR-T$_{STE2}$, P$_{TEF1}$-RnPTPS-T$_{CYC1}$, KanMX marker, P$_{GPD}$-RnQDHPR-T$_{AHD1}$, P$_{PGK1}$-RnPCD-T$_{PHO5}$ 2. HIS3 Δ ::P$_{GPD}$-RnTyrH-T$_{ADH1}$, P$_{TPI1}$-PpDODC-T$_{STE2}$, HIS5 marker, P$_{TEF1}$-RnDHFR-T$_{CYC1}$, P$_{PGK1}$-CjNCS-T$_{PHO5}$ 3. YDR514CΔ::P$_{PYK1}$-PsCNMT-T$_{MFa1}$, P$_{PGK1}$-Ps6OMT-T$_{PHO5}$, P$_{GPD}$-EcCYP80B1-T$_{ADH1}$, LEU2 marker, P$_{TEF1}$-PsCPR-T$_{CYC1}$, P$_{TPI1}$-Ps4OMT-T$_{STE2}$ 4. ARO4Δ::P$_{TEF1}$-ARO4$^{FBR}$-T$_{CYC1}$, P$_{GPD}$-ARO7$^{FBR}$-T$_{ADH1}$, HygR marker, P$_{PGK1}$-TKL1-T$_{PHO5}$, P$_{TPI1}$-ARO10-T$_{STE2}$

FIG. 18

Example genetic constructs:

5. YPL250CΔ::$P_{GPD}$-RnTyrH-$T_{ADH1}$, $P_{TEF1}$-Ps4OMT-$T_{CYC1}$, $P_{PGK1}$-CjNCS-$T_{PHO5}$, bleR marker 6. TRP1::$P_{PGK1}$-PsSalAT-$T_{PHO5}$, $P_{TPI1}$-PbSalR-$T_{STE2}$, URA3 marker, $P_{GPD}$-EcCFS$^{1-83}$-PbSalSyn$^{92-504}$-$T_{ADH1}$, $P_{HXT7}$-PbCYP-COR-$T_{CYC1}$ 7. HOΔ::$P_{GPD}$-PsT6ODM-$T_{ADH1}$, $P_{PGK1}$-PbmorB-$T_{PHO5}$

FIG. 19

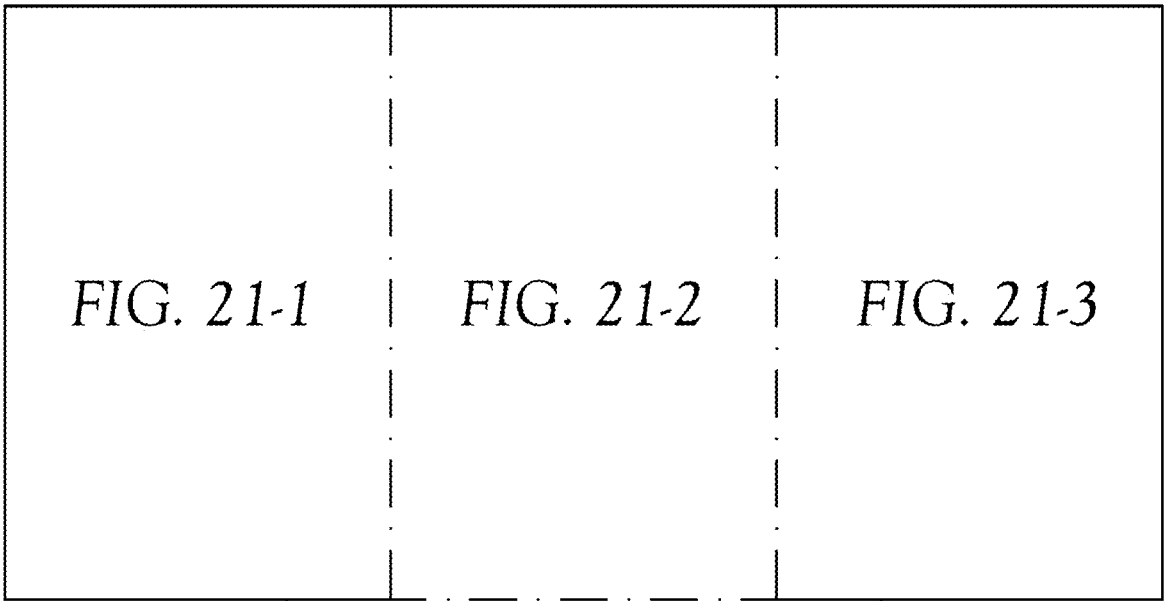
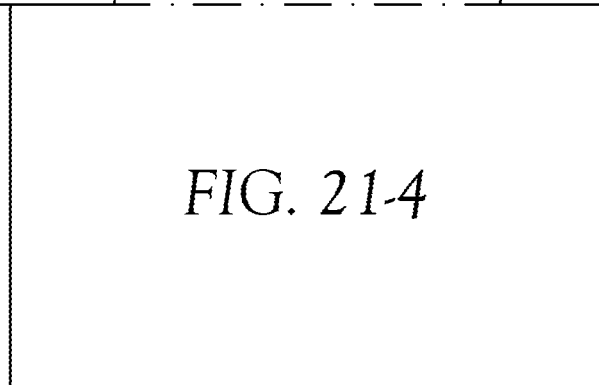
FIG. 21

METHODS OF PRODUCING MORPHINAN ALKALOIDS AND DERIVATIVES

CROSS REFERENCE

This application is continuation application of International Application No. PCT/US19/17357, filed Feb. 8, 2019, which claims the benefit of U.S. Provisional Application No. 62/628,264, which was filed Feb. 8, 2018. This application is related to: U.S. patent application Ser. No. 14/211,611 now published as US 2014-0273109, which application was filed on Mar. 14, 2014; PCT Application Serial No. PCT/US2014/027833 now published as WO 2014/143744, which application was filed on Mar. 14, 2014; U.S. patent application Ser. No. 15/031,618, which application was filed on Apr. 22, 2016; Application Serial No. PCT/US2014/063738 now published as WO 2015/066642, which application was filed on Nov. 3, 2014; U.S. Provisional Patent Application Ser. No. 62/080,610, which was filed Nov. 17, 2014; U.S. Provisional Patent Application Ser. No. 62/107,238, which was filed Jan. 23, 2015; Application Serial No. PCT/US2015/060891 which application was filed on Nov. 16, 2015; U.S. Provisional Patent Application Ser. No. 62/156,701, which was filed May 4, 2015; Application Serial No. PCT/US2016/030808 which application was filed on May 4, 2016; Application Serial No. PCT/US2016/031506 which application was filed on May 9, 2016; Application Serial No. PCT/US2017/057237 which application was filed Oct. 18, 2017; Application Ser. No. 62/541,038 which application was filed on Aug. 3, 2017; and Application Serial No. PCT/US2018/045222 which application was filed on Aug. 3, 2018; and application Ser. No. 16/149,025 which application was filed on Oct. 1, 2018; the disclosures of which applications are herein incorporated by reference.

The instant application contains a Sequence Listing which has been submitted electronically in ASCII format and is hereby incorporated by reference in its entirety. Said ASCII copy, created on Aug. 3, 2020, is named 47840-708_301_SL.txt and is 620,839 bytes in size.

SUMMARY OF THE INVENTION

The present disclosure provides methods for the production of diverse benzylisoquinoline alkaloids (BIAs) in engineered host cells. The present disclosure further provides compositions of diverse alkaloids produced in engineered host cells. Additionally, the present disclosure provides methods for the production of a thebaine synthase in engineered host cells. In particular cases, the disclosure provides methods for producing diverse alkaloid products through the conversion of a promorphinan alkaloid into a morphinan alkaloid in an engineered host cell. In further particular cases, the present disclosure provides methods for producing diverse alkaloid products through the conversion of salutaridinol-7-O-acetate to thebaine.

An aspect of the invention provides an engineered non-plant cell having increased tyrosine hydroxylase activity relative to a non-engineered cell. Another aspect of the invention provides an engineered non-plant cell having increased tyrosine hydroxylase activity relative to a cell that expresses wild-type TyrH. An additional aspect of the invention provides an engineered non-plant cell having increased tyrosine hydroxylase activity relative to a cell that expresses wild-type TyrH without mutations that increase tyrosine hydroxylase activity as provided herein. In particular, the engineered non-plant cell has at least one modification selected from a group consisting of: a substrate inhibition alleviating mutation; a product inhibition alleviating mutation; and a cofactor recovery promoting mechanism.

An aspect of the invention provides an engineered plant cell having increased tyrosine hydroxylase activity relative to a non-engineered cell. Another aspect of the invention provides an engineered plant cell having increased tyrosine hydroxylase (TyrH) activity relative to a cell that expresses wild-type TyrH. An additional aspect of the invention provides an engineered plant cell having increased tyrosine hydroxylase activity relative to a cell that expresses wild-type TyrH without mutations that increase tyrosine hydroxylase activity as provided herein. In particular, the engineered plant cell has at least one modification selected from a group consisting of: a substrate inhibition alleviating mutation; a product inhibition alleviating mutation; and a cofactor recovery promoting mechanism.

In some embodiments, the disclosure provides methods for increasing production of diverse alkaloid products through the epimerization of a (S)-1-benzylisoquinoline alkaloid to a (R)-1-benyzlisoquinoline alkaloid via engineered epimerases in an engineered host cell. In further embodiments, the present disclosure provides methods for increasing production of diverse alkaloid products through the epimerization of (S)-reticuline to (R)-reticuline via an engineered epimerase comprising two separate enzymes encoding an oxidase and a reductase compared to the production of diverse alkaloid products through the epimerization of (S)-reticuline to (R)-reticuline via a wild-type epimerase.

While engineered split epimerases may be composed of a separate oxidase enzyme and reductase enzyme that originate from a parent or wild-type epimerase, engineered epimerases may also comprise a separate oxidase enzyme and reductase enzyme that originate from separate parent or wild-type epimerases. Examples of parent epimerases having an oxidase and reductase component comprise amino acid sequences selected from the group consisting of: SEQ ID NOs: 1, 2, 3, 4, 5, 6, 7, 8, 9, 10, 11, 12, 13, 14, 15, and 16, as listed in Table 1.

In some embodiments, the disclosure provides methods for increasing production of diverse alkaloid products through the conversion of a promorphinan alkaloid to a morphinan alkaloid via thebaine synthases in an engineered host cell. In further embodiments, the present disclosure provides methods for increasing production of diverse alkaloid products through the conversion of salutaridinol-7-O-acetate to thebaine via a thebaine synthase. Examples of parent thebaine synthases comprise amino acid sequences selected from the group consisting of: SEQ ID NOs: 30, 31, 32, 33, 34, 35, 36, and 37 as listed in Table 2.

In some embodiments, the disclosure provides methods for increasing production of diverse alkaloid products through the conversion of a promorphinan alkaloid to a morphinan alkaloid via engineered thebaine synthases in an engineered host cell. In further embodiments, the present disclosure provides methods for increasing production of diverse alkaloid products through the conversion of salutaridinol-7-O-acetate to thebaine via an engineered thebaine synthase.

In some embodiments, the engineered thebaine synthase is a fusion enzyme. In further embodiments, the thebaine synthase is fused to an acetyl transferase enzyme. In further embodiments, the thebaine synthase is encoded within an acetyl transferase enzyme. In other embodiments, the thebaine synthase is fused to a reductase enzyme.

In some examples, an engineered non-plant cell comprises a plurality of coding sequences each encoding an enzyme that is selected from the group of enzymes listed in Table 3. In some examples, the heterologous coding sequences may be operably connected. Heterologous coding sequences that are operably connected may be within the same pathway of producing a particular benzylisoquinoline alkaloid product via a thebaine synthase activity or an engineered thebaine synthase activity.

In some embodiments this disclosure provides a method of converting a tetracyclic promorphinan precursor to a thebaine, comprising contacting the tetracyclic promorphinan precursor with at least one enzyme, wherein contacting the tetracyclic promorphinan precursor with the at least one enzyme converts the tetracyclic promorphinan precursor to a thebaine. In some cases, the at least one enzyme is produced by culturing an engineered non-plant cell having a coding sequence for encoding the at least one enzyme. In some cases, the method further comprises adding a tetracyclic promorphinan precursor to the cell culture. In some cases, the method further comprises recovering the thebaine, or a derivative thereof, from the cell culture. In some cases, the at least one enzyme comprises a thebaine synthase. In some cases, the thebaine synthase comprises an amino acid sequence selected from the group consisting of: SEQ ID NOs: 30, 31, 32, 33, 34, 35, 36, and 37. In some cases, the thebaine synthase enzyme is a Bet v 1 fold protein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the invention will be obtained by reference to the following detailed description that sets forth illustrative embodiments, in which the principles of the invention are utilized, and the accompanying drawings of which:

FIG. 4 illustrates an amino acid sequence of a parent DRS-DRR enzyme, in accordance with embodiments of the invention.

FIG. 5 illustrates amino acid sequences of a DRS enzyme and a DRR enzyme, respectively, that are derived from a parent fusion enzyme illustrated in FIG. 4, in accordance with embodiments of the invention.

FIG. 9 illustrates the functional expression of BM3 variants, in accordance with embodiments of the invention.

FIG. 17 illustrates an alignment between PbDRS-DRR, PrDRS, and PrDRR, in accordance with embodiments of the invention.

DETAILED DESCRIPTION OF THE INVENTION

Figure 1:
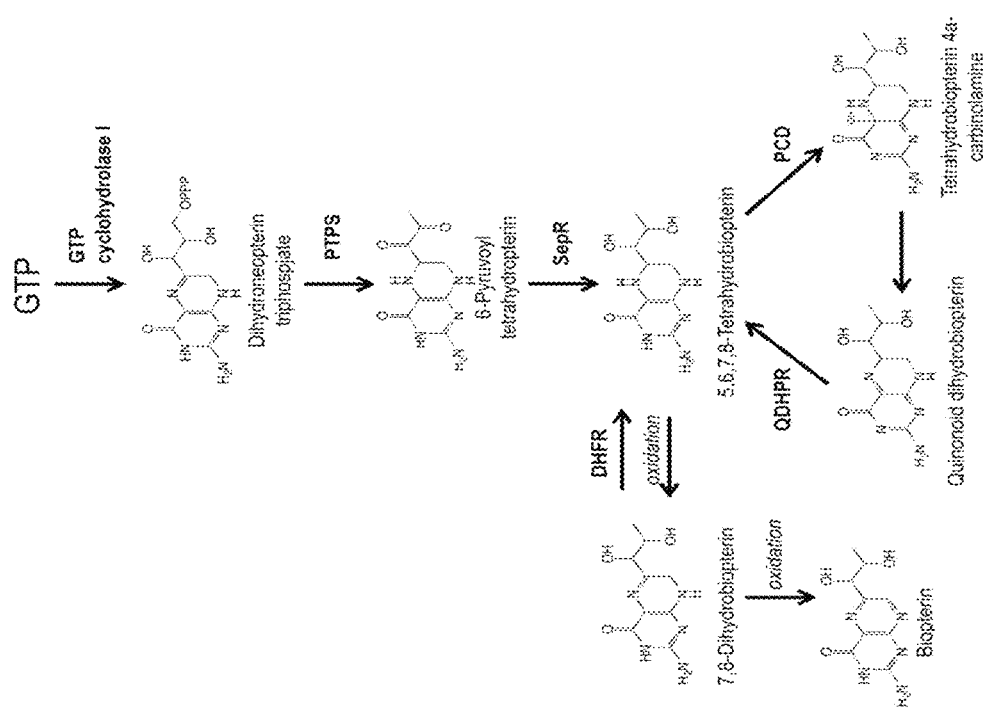
FIG. 1 illustrates examples of synthesis, recycling, and salvage pathways of tetrahydrobiopterin, in accordance with embodiments of the invention.

The present disclosure provides methods for the production of diverse benzylisoquinoline alkaloids (BIAS) in engineered host cells. The present disclosure further provides compositions of diverse alkaloids produced in engineered host cells. Additionally, the present disclosure provides methods for the production of a thebaine synthase in engineered host cells. Additionally, the present disclosure provides methods for the production of an engineered thebaine synthase in engineered host cells. In particular cases, the disclosure provides methods for producing promorphinan, morphinan, nal-opioid and nor-opioid alkaloid products through the increased conversion of a promorphinan alkaloid to a morphinan alkaloid in an engineered host cell. In further particular cases, the disclosure provides methods for producing morphinan, nal-opioid and nor-opioid alkaloid products through the increased conversion of a promorphinan alkaloid to a morphinan alkaloid in an engineered host cell. In further particular cases, the present disclosure provides methods for producing diverse alkaloid products through the increased conversion of a promorphinan alkaloid to a morphinan alkaloid.

Benzylisoquinoline Alkaloids (BIAs) of Interest

Host cells which produce BIAs of interest are provided. In some examples, engineered strains of host cells such as the engineered strains of embodiments discussed herein may provide a platform for producing benzylisoquinoline alkaloids of interest and modifications thereof across several structural classes including, but not limited to, precursor BIAs, benzylisoquinolines, promorphinans, morphinans, nal-opioids, nor-opioids, and others. Each of these classes may include biosynthetic precursors, intermediates, and metabolites thereof, of any convenient member of an engineered host cell biosynthetic pathway that may lead to a member of the class. Non-limiting examples of compounds are given below for each of these structural classes. In some cases, the structure of a given example may or may not be characterized itself as a benzylisoquinoline alkaloid. In some cases, the present chemical entities may include all possible isomers, including single enantiomers, racemic mixtures, optically pure forms, mixtures of diastereomers, and intermediate mixtures.

BIA precursors may include, but are not limited to, norcoclaurine (NC) and norlaudanosoline (NL), as well as NC and NL precursors, such as tyrosine, tyramine, 4-hydroxyphenylacetaldehyde (4-HPA), 4-hydroxyphenylpyruvic acid (4-HPPA), L-3,4-dihydroxyphenylalanine (L-DOPA), 3,4-dihydroxyphenylacetaldehyde (3,4-DHPA), and dopamine. In some embodiments, the one or more BIA precursors are 3,4-dihydroxyphenylacetaldehyde (3,4-DHPA) and dopamine. In certain instances, the one or more BIA precursors are 4-hydroxyphenylacetaldehyde (4-HPA) and dopamine. In particular, NL and NC may be synthesized, respectively, from precursor molecules via a Pictet-Spengler condensation reaction, where the reaction may occur spontaneously or may by catalyzed by any convenient enzymes.

Benzylisoquinolines may include, but are not limited to, norcoclaurine, norlaudanosoline, coclaurine, 3'-hydroxycoclaurine, 4'-O-methylnorlaudanosoline, 4'-O-methyl-laudanosoline, N-methylnorcoclaurine, laudanosoline, N-methylcoclaurine, 3'-hydroxy-N-methylcoclaurine, reticuline, norreticuline, papaverine, laudanine, laudanosine, tetrahydropapaverine, 1,2-dihydropapaverine, and orientaline.

Promorphinans may include, but are not limited to, salutaridine, salutaridinol, and salutaridinol-7-O-acetate.

Morphinans may include, but are not limited to, thebaine, codeinone, codeine, morphine, morphinone, oripavine, neopinone, neopine, neomorphine, hydrocodone, dihydrocodeine, 14-hydroxycodeinone, oxycodone, 14-hydroxycodeine, morphinone, hydromorphone, dihydromorphine, dihydroetorphine, ethylmorphine, etorphine, metopon, buprenorphine, pholcodine, heterocodeine, and oxymorphone. In particular, thebaine may be synthesized from salutaridinol-7-O-acetate, where the reaction may occur spontaneously or may be catalyzed by any convenient enzymes.

Nal-opioids may include, but are not limited to, naltrexone, naloxone, nalmefene, nalorphine, nalorphine, nalodeine, naldemedine, naloxegol, 6β-naltrexol, naltrindole, methylnaltrexone, methylsamidorphan, alvimopan, axelopran, bevenpran, dinicotinate, levallorphan, samidorphan, buprenorphine, dezocine, eptazocine, butorphanol, levorphanol, nalbuphine, pentazocine, phenazocine, norbinaltorphimine, and diprenorphine.

Nor-opioids may include, but are not limited to, norcodeine, noroxycodone, northebaine, norhydrocodone, nordihydro-codeine, nor-14-hydroxy-codeine, norcodeinone, nor-14-hydroxy-codeinone, normorphine, noroxymorphone, nororipavine, norhydro-morphone, nordihydro-morphone, nor-14-hydroxy-morphine, normorphinone, and nor-14-hydroxy-morphinone.

In certain embodiments, the engineered strains of the invention may provide a platform for producing compounds related to tetrahydrobiopterin synthesis including, but not limited to, dihydroneopterin triphosphate, 6-pyruvoyl tetrahydropterin, 5,6,7,8-tetrahydrobiopterin, 7,8-dihydrobiopterin, tetrahydrobiopterin 4a-carbinolamine, quinonoid dihydrobiopterin, and biopterin.

Host Cells

Any convenient cells may be utilized in the subject host cells and methods. In some cases, the host cells are non-plant cells. In some instances, the host cells may be characterized as microbial cells. In certain cases, the host cells are insect cells, mammalian cells, bacterial cells, or yeast cells. Any convenient type of host cell may be utilized in producing the subject BIA-producing cells, see, e.g., US2008/0176754, and US2014/0273109 the disclosures of which are incorporated by reference in their entirety. Host cells of interest include, but are not limited to, bacterial cells, which may be either Gram positive bacterial cells or Gram negative bacterial cells, insect cells such as *Drosophila melanogaster* S2 and *Spodoptera frugiperda* Sf9 cells, and yeast cells such as *Saccharomyces cerevisiae*, *Schizosaccharomyces pombe*, and *Pichia pastoris* cells. Non-limiting examples of bacterial cells include *Bacillus subtilis, Escherichia coli, Streptomyces, Anabaena, Arthrobacter, Acetobacter, Acetobacterium, Bacillus, Bifidobacterium, Brachybacterium, Brevibacterium, Carnobacterium, Clostridium, Corynebacterium, Enterobacter, Escherichia, Gluconacetobacter, Gluconobacter, Hafnia, Halomonas, Klebsiella, Kocuria, Lactobacillus, Leuconostoc, Macrococcus, Methylomonas, Methylobacter, Methylocella, Methylococcus, Microbacterium, Micrococcus, Microcystis, Moorella, Oenococcus, Pediococcus, Prochlorococcus, Propionibacterium, Proteus, Pseudoalteromonas, Pseudomonas, Psychrobacter, Rhodobacter, Rhodococcus, Rhodopseudomonas, Serratia, Staphylococcus, Streptococcus, Streptomyces, Synechococcus, Synechocystis, Tetragenococcus, Weissella, Zymomonas,* and *Salmonella typhimuium* cells. In some examples, the host cells are yeast cells or *E. coli* cells. In some cases, the host cells are yeast cells or *E. coli* cells. In some cases, the host cell is a yeast cell. In some instances, the host cell is from a strain of yeast engineered to produce a BIA of interest, such as a morphinan alkaloid. In some instances, the host cell is from a strain of yeast engineered to produce an enzyme of interest. In some instances, the host cell is from a strain of yeast engineered to produce a thebaine synthase.

The thebaine synthase may be able to more efficiently convert a salutaridinol-7-O-acetate to a thebaine relative to a spontaneous reaction. In some instances, the host cell is from a strain of yeast engineered to produce an engineered thebaine synthase. In some embodiments, an engineered thebaine synthase may be an engineered fusion enzyme. Additionally, the engineered thebaine synthase may be able to more efficiently convert a salutaridinol-7-O-acetate to a thebaine relative to a thebaine synthase. In some embodiments, the thebaine synthase may be a wild-type thebaine synthase. In some embodiments, a thebaine synthase may be substantially similar to a wild-type thebaine synthase. In some cases, a thebaine synthase that is substantially similar to a wild-type thebaine synthase may have an amino acid sequence that is at least 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more similar to an amino acid sequence of a wild-type thebaine synthase. The engineered thebaine synthase may be engineered as a fusion enzyme to another enzyme to more efficiently convert a salutaridinol-7-O-acetate to a thebaine relative to the thebaine synthase.

Any of the host cells described in US2008/0176754 and US2014/0273109 by Smolke et al. may be adapted for use in the subject cells and methods. In certain embodiments, the yeast cells may be of the species *Saccharomyces cerevisiae* (*S. cerevisiae*). In certain embodiments, the yeast cells may be of the species *Schizosaccharomyces pombe*. In certain embodiments, the yeast cells may be of the species *Pichia pastoris*. Yeast is of interest as a host cell because cytochrome P450 proteins are able to fold properly into the endoplasmic reticulum membrane so that their activity is maintained. In examples, cytochrome P450 proteins are involved in some biosynthetic pathways of interest. In additional examples, cytochrome P450 proteins are involved in the production of BIAs of interest. In further examples, cytochrome P450 proteins are involved in the production of an enzyme of interest.

Yeast strains of interest that find use in the invention include, but are not limited to, CEN.PK (Genotype: MATa/α ura3-52/ura3-52 trpl-289/trpl-289 leu2-3_112/1eu2-3_112 his3 Δ1/his3 Δ1 MAL2-8C/MAL2-8C SUC2/SUC2), S288C, W303, D273-10B, X2180, A364A, Σ1278B, AB972, SK1, and FL100. In certain cases, the yeast strain is any of S288C (MATα; SUC2 mal mel gal2 CUP1 flo1 flo8-1 hap1), BY4741 (MATα; his3Δ1; leu2Δ0; met15Δ0; ura3Δ0), BY4742 (MATα; his3Δ1; leu2Δ0; lys2Δ0; ura3Δ0), BY4743 (MATα/MATα; his3Δ1/his3Δ1; leu2Δ0/leu2Δ0; met15Δ0/MET15; LYS2/lys2Δ0; ura3Δ0/ura3A0), and WAT11 or W(R), derivatives of the W303-B strain (MATα; ade2-1; his3-11, -15; leu2-3, -112; ura3-1; canR; cyr+) which express the *Arabidopsis thaliana* NADPH-P450 reductase ATR1 and the yeast NADPH-P450 reductase CPR1, respectively. In another embodiment, the yeast cell is W303alpha (MATα; his3-11,15 trpl-1 leu2-3 ura3-1 ade2-1). The identity and genotype of additional yeast strains of interest may be found at EUROSCARF (web.uni-frankfurt.de/fb15/mikro/euroscarf/col_index.html).

In some instances the host cell is a fungal cell. In certain embodiments, the fungal cells may be of the *Aspergillus* species and strains include *Aspergillus Niger* (ATCC 1015, ATCC 9029, CBS 513.88), *Aspergillus oryzae* (ATCC 56747, RIB40), *Aspergillus terreus* (NIH 2624, ATCC 20542) and *Aspergillus nidulans* (FGSC A4).

In certain embodiments, heterologous coding sequences may be codon optimized for expression in *Aspergillus* sp. and expressed from an appropriate promoter. In certain embodiments, the promoter may be selected from phosphoglycerate kinase promoter (PGK), MbfA promoter, cytochromes oxidase subunit promoter (CoxA), SrpB promoter, TvdA promoter, malate dehydrogenase promoter (MdhA), beta-mannosidase promoter (ManB). In certain embodiments, a terminator may be selected from glucoamylase terminator (GlaA) or TrpC terminator. In certain embodiments, the expression cassette consisting of a promoter, heterologous coding sequence, and terminator may be expressed from a plasmid or integrated into the genome of the host. In certain embodiments, selection of cells maintaining the plasmid or integration cassette may be performed with antibiotic selection such as hygromycin or nitrogen source utilization, such as using acetamide as a sole nitrogen source. In certain embodiments, DNA constructs may be introduced into the host cells using established transformation methods such as protoplast transformation, lithium acetate, or electroporation. In certain embodiments, cells may be cultured in liquid ME or solid MEA (3% malt extract, 0.5% peptone, and ±1.5% agar) or in Vogel's minimal medium with or without selection.

In some instances the host cell is a bacterial cell. The bacterial cell may be selected from any bacterial genus. Examples of genuses from which the bacterial cell may come include *Anabaena, Arthrobacter, Acetobacter, Acetobacterium, Bacillus, Bifidobacterium, Brachybacterium, Brevibacterium, Carnobacterium, Clostridium, Corynebacterium, Enterobacter, Escherichia, Gluconacetobacter, Gluconobacter, Hafnia, Halomonas, Klebsiella, Kocuria, Lactobacillus, Leucononstoc, Macrococcus, Methylomonas, Methylobacter, Methylocella, Methylococcus, Microbacterium, Micrococcus, Microcystis, Moorella, Oenococcus, Pediococcus, Prochlorococcus, Propionibacterium, Proteus, Pseudoalteromonas, Pseudomonas, Psychrobacter, Rhodobacter, Rhodococcus, Rhodopseudomonas, Serratia, Staphylococcus, Streptococcus, Streptomyces, Synechococcus, Synechocystis, Tetragenococcus, Weissella,* and *Zymomonas*. Examples of bacterial species which may be used with the methods of this disclosure include *Arthrobacter nicotianae, Acetobacter aceti, Arthrobacter arilaitensis, Bacillus cereus, Bacillus coagulans, Bacillus licheniformis, Bacillus pumilus, Bacillus sphaericus, Bacillus stearothermophilus, Bacillus subtilis, Bifidobacterium adolescentis, Brachybacterium tyrofermentans, Brevibacterium linens, Carnobacterium divergens, Corynebacterium flavescens, Enterococcus faecium, Gluconacetobacter europaeus, Gluconacetobacter johannae, Gluconobacter oxydans, Hafnia alvei, Halomonas elongata, Kocuria rhizophila, Lactobacillus acidifarinae, Lactobacillus jensenii, Lactococcus lactis, Lactobacillus yamanashiensis, Leuconostoc citreum, Macrococcus caseolyticus, Microbacterium foliorum, Micrococcus lylae, Oenococcus oeni, Pediococcus acidilactici, Propionibacterium acidipropionici, Proteus vulgaris, Pseudomonas fluorescens, Psychrobacter celer, Staphylococcus condiments, Streptococcus thermophilus, Streptomyces griseus, Tetragenococcus halophilus, Weissella cibaria, Weissella koreensis, Zymomonas mobilis, Corynebacterium glutamicum, Bifidobacterium bifidum/breve/longum, Streptomyces lividans, Streptomyces coelicolor, Lactobacillus plantarum, Lactobacillus sakei, Lactobacillus casei, Pseudoalteromonas citrea, Pseudomonas putida, Clostridium ljungdahlii/aceticum/acetobutylicum/beijerinckii/butyricum,* and *Moorella themocellum/thermoacetica*.

In certain embodiments, the bacterial cells may be of a strain of *Escherichia coli*. In certain embodiments, the strain of *E. coli* may be selected from BL21 DH5a, XL1-Blue, HB101, BL21, and K12. In certain embodiments, heterologous coding sequences may be codon optimized for expression in *E. coli* and expressed from an appropriate promoter. In certain embodiments, the promoter may be selected from T7 promoter, tac promoter, trc promoter, tetracycline-inducible promoter (tet), lac operon promoter (lac), lacO1 promoter. In certain embodiments, the expression cassette consisting of a promoter, heterologous coding sequence, and terminator may be expressed from a plasmid or integrated into the genome. In certain embodiments, the plasmid is selected from pUC19 or pBAD. In certain embodiments, selection of cells maintaining the plasmid or integration cassette may be performed with antibiotic selection such as kanamycin, chloramphenicol, streptomycin, spectinomycin, gentamycin, erythromycin or ampicillin. In certain embodiments, DNA constructs may be introduced into the host cells using established transformation methods such as conjugation, heat shock chemical transformation, or electroporation. In certain embodiments, cells may be cultured in liquid Luria-Bertani (LB) media at about 37° C. with or without antibiotics.

In certain embodiments, the bacterial cells may be a strain of *Bacillus subtilis*. In certain embodiments, the strain of *B. subtilis* may be selected from 1779, GP25, RO-NN-1, 168, BSn5, BEST195, 1A382, and 62178. In certain embodiments, heterologous coding sequences may be codon optimized for expression in *Bacillus* sp. and expressed from an appropriate promoter. In certain embodiments, the promoter may be selected from grac promoter, p43 promoter, or trnQ promoter. In certain embodiments, the expression cassette consisting of the promoter, heterologous coding sequence, and terminator may be expressed from a plasmid or integrated into the genome. In certain embodiments, the plasmid is selected from pHP13, pE194, pC194, pHT01, or pHT43. In certain embodiments, integrating vectors such as pDG364 or pDG1730 may be used to integrate the expression cassette into the genome. In certain embodiments, selection of cells maintaining the plasmid or integration cassette may be performed with antibiotic selection such as erythromycin, kanamycin, tetracycline, and spectinomycin. In certain embodiments, DNA constructs may be introduced into the host cells using established transformation methods such as natural competence, heat shock, or chemical transformation. In certain embodiments, cells may be cultured in liquid Luria-Bertani (LB) media at 37° C. or M9 medium plus glucose and tryptophan.

Genetic Modifications to Host Cells

The host cells may be engineered to include one or more modifications (such as two or more, three or more, four or more, five or more, or even more modifications) that provide for the production of BIAs of interest. Additionally or alternatively, the host cells may be engineered to include one or more modifications (such as two or more, three or more, four or more, five or more, or even more modifications) that provide for the production of enzymes of interest. In some cases, a modification is a genetic modification, such as a mutation, addition, or deletion of a gene or fragment thereof, or transcription regulation of a gene or fragment thereof. As used herein, the term "mutation" refers to a deletion, insertion, or substitution of an amino acid(s) residue or nucleotide(s) residue relative to a reference sequence or motif. The mutation may be incorporated as a directed mutation to the native gene at the original locus. In some cases, the mutation may be incorporated as an additional copy of the gene introduced as a genetic integration at a separate locus, or as an additional copy on an episomal vector such as a 2μ or centromeric plasmid. In certain instances, the substrate inhibited copy of the enzyme is under the native cell transcriptional regulation. In some instances, the substrate inhibited copy of the enzyme is introduced with engineered constitutive or dynamic regulation of protein expression by placing it under the control of a synthetic promoter. In some examples, the object of one or more modifications may be a native gene. In some examples, the object of one or more modifications may be a non-native gene. In some examples, a non-native gene may be inserted into a host cell. In further examples, a non-native gene may be altered by one or more modifications prior to being inserted into a host cell.

An engineered host cell may overproduce one or more BIAs of interest. By overproduce is meant that the cell has an improved or increased production of a BIA molecule of interest relative to a control cell (e.g., an unmodified cell). By improved or increased production is meant both the production of some amount of the BIA of interest where the control has no BIA of interest production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some BIA of interest production.

An engineered host cell may overproduce one or more (S)-1-benzylisoquinoline alkaloids. In some cases, the engineered host cell may produce some amount of the (S)-1-benzylisoquinoline alkaloid of interest where the control has no (S)-1-benzylisoquinoline alkaloid production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some (S)-1-benzylisoquinoline alkaloid of interest production.

An engineered host cell may further overproduce one or more (R)-1-benzylisoquinoline alkaloids. In some cases, the engineered host cell may produce some amount of the (R)-1-benzylisoquinoline alkaloid of interest where the control has no (R)-1-benzylisoquinoline alkaloid production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some (R)-1-benzylisoquinoline alkaloid of interest production.

An engineered host cell may further overproduce one or more morphinan alkaloids. In some cases, the engineered host cell may produce some amount of the morphinan alkaloid of interest where the control has no morphinan alkaloid production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some morphinan alkaloid of interest production. An engineered host cell may further overproduce one or more of promorphinan, nor-opioid, or nal-opioid alkaloids.

In some cases, the engineered host cell is capable of producing an increased amount of (R)-reticuline relative to a control host cell that lacks the one or more modifications (e.g., as described herein). In some cases, the engineered host cell having an engineered split epimerase is capable of producing an increased amount of (R)-reticuline relative to a host cell having a fused epimerase. In some cases, the engineered host cell having modifications to an oxidase portion of an engineered epimerase is capable of producing an increased amount of (R)-reticuline relative to a control host cell that lacks the one or more modifications to the oxidase portion of the engineered epimerase. In certain instances, the increased amount of (R)-reticuline is about 10% or more relative to the control host cell, such as about 20% or more, about 30% or more, about 40% or more, about 50% or more, about 60% or more, about 80% or more, about 100% or more, about 2-fold or more, about 5-fold or more, or even about 10-fold or more relative to the control host cell. In some cases, (R)-reticuline is the product of an epimerization reaction within an engineered host cell. In some cases, (R)-reticuline is the product of an epimerization reaction catalyzed by at least one engineered epimerase within an engineered host cell. In these cases, (S)-reticuline may be the substrate of the epimerization reaction.

In some cases, the engineered host cell is capable of producing an increased amount of thebaine relative to a control host cell that lacks the one or more modifications (e.g., as described herein). In some cases, the engineered host cell having a thebaine synthase is capable of producing an increased amount of thebaine relative to a host cell that lacks a thebaine synthase. In some cases, the engineered host cell having an engineered thebaine synthease is capable of producing an increased amount of thebaine relative to a host cell having a non-engineered thebaine synthase (e.g., as described herein). In certain instances, the increased amount of thebaine is about 10% or more relative to the control host cell, such as about 20% or more, about 30% or more, about 40% or more, about 50% or more, about 60% or more, about 80% or more, about 100% or more, about 2-fold or more, about 5-fold or more, or even about 10-fold or more relative to the control host cell. In some cases, thebaine is the product of a thebaine synthase reaction within an engineered host cell. In some cases, thebaine is the product of a thebaine synthase reaction catalyzed by at least one engineered thebaine synthase within an engineered host cell. In these cases, salutaridinol-7-O-acetate may be the substrate of the thebaine synthase reaction.

Additionally, an engineered host cell may overproduce one or more enzymes of interest. By overproduce is meant that the cell has an improved or increased production of an enzyme of interest relative to a control cell (e.g., an unmodified cell). By improved or increased production is meant both the production of some amount of the enzyme of interest where the control has no production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some enzyme of interest production.

An engineered host cell may overproduce one or more DRS-DRR enzymes. In some cases, the engineered host cell may produce some amount of the DRS-DRR enzyme where the control has no DRS-DRR enzyme production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some DRS-DRR enzyme production.

An engineered host cell may overproduce one or more engineered DRS-DRR enzymes. In some cases, the engineered host cell may produce some amount of the engineered DRS-DRR epimerase where the control has no DRS-DRR enzyme production, or where the control has a same level of production of wild-type epimerases in comparison to the engineered host cell, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some DRS-DRR enzyme production. In some cases, an engineered DRS-DRR epimerase may be an engineered split epimerase. In some cases, an engineered DRS-DRR epimerase may be an engineered fused epimerase.

An engineered host cell may further overproduce one or more enzymes that are derived from the DRS-DRR enzyme. In some cases, the engineered host cell may produce some amount of the enzymes that are derived from the DRS-DRR enzyme, where the control has no production of enzymes that are derived from the DRS-DRR enzyme, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some production of enzymes that are derived from the DRS-DRR enzyme.

An engineered host cell may overproduce one or more thebaine synthase enzymes. In some cases, the engineered host cell may produce some amount of the thebaine synthase enzyme where the control has no thebaine synthase enzyme production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some thebaine synthase enzyme production.

An engineered host cell may overproduce one or more engineered thebaine synthase enzymes. In some cases, the engineered host cell may produce some amount of the engineered thebaine synthase where the control has no thebaine synthase enzyme production, or where the control has a same level of production of wild-type thebaine synthase in comparison to the engineered host cell, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some thebaine synthase enzyme production. In some cases, an engineered thebaine synthase may be an engineered fusion enzyme.

An engineered host cell may further overproduce one or more enzymes that are derived from the thebaine synthase enzyme. In some cases, the engineered host cell may produce some amount of the enzymes that are derived from the thebaine synthase enzyme, where the control has no production of enzymes that are derived from the thebaine synthase enzyme, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some production of enzymes that are derived from the thebaine synthase enzyme.

In some cases, the one or more (such as two or more, three or more, or four or more) modifications may be selected from: a substrate inhibition alleviating mutation in a biosynthetic enzyme gene; a product inhibition alleviating mutation in a biosynthetic enzyme gene; a cofactor recovery promoting mechanism; a feedback inhibition alleviating mutation in a biosynthetic enzyme gene; a transcriptional modulation modification of a biosynthetic enzyme gene; an inactivating mutation in an enzyme gene; an epimerization modification; and a heterologous coding sequence that encodes an enzyme. A cell that includes one or more modifications may be referred to as an engineered cell.

In some cases, the one or more (such as two or more, three or more, or four or more) modifications may be selected from: a localization mutation; a cytochrome P450 reductase interaction mutation; an accessibility mutation; an activity enhancing mutation; an engineered fused thebaine synthase modification, and an engineered split epimerase modification. A cell that includes one or more modifications may be referred to as an engineered cell.

Substrate Inhibition Alleviating Mutations

In some instances, the engineered host cells are cells that include one or more substrate inhibition alleviating mutations (such as two or more, three or more, four or more, five or more, or even more) in one or more biosynthetic enzyme genes of the cell. In some examples, the one or more biosynthetic enzyme genes are native to the cell (e.g., is present in an unmodified cell). In some examples, the one or more biosynthetic enzyme genes are non-native to the cell. As used herein, the term "substrate inhibition alleviating mutation" refers to a mutation that alleviates a substrate inhibition control mechanism of the cell.

A mutation that alleviates substrate inhibition reduces the inhibition of a regulated enzyme in the cell of interest relative to a control cell and provides for an increased level of the regulated compound or a downstream biosynthetic product thereof. In some cases, by alleviating inhibition of the regulated enzyme is meant that the $IC_{50}$ of inhibition is increased by 2-fold or more, such as by 3-fold or more, 5-fold or more, 10-fold or more, 30-fold or more, 100-fold or more, 300-fold or more, 1000-fold or more, or even more. By increased level is meant a level that is 110% or more of that of the regulated compound in a control cell or a downstream product thereof, such as 120% or more, 130% or more, 140% or more, 150% or more, 160% or more, 170% or more, 180% or more, 190% or more, or 200% or more, such as at least 3-fold or more, at least 5-fold or more, at least 10-fold or more or even more of the regulated compound in the engineered host cell or a downstream product thereof.

A variety of substrate inhibition control mechanisms and biosynthetic enzymes in the engineered host cell that are directed to regulation of levels of BIAs of interest, or precursors thereof, may be targeted for substrate inhibition alleviation. The engineered host cell may include one or more substrate inhibition alleviating mutations in one or more biosynthetic enzyme genes. The one or more mutations may be located in any convenient biosynthetic enzyme genes where the biosynthetic enzyme is subject to regulatory control. In some embodiments, the one or more biosynthetic enzyme genes encode one or more tyrosine hydroxylase enzymes. In certain instances, the one or more substrate inhibition alleviating mutations are present in a biosynthetic enzyme gene that is TyrH. In some embodiments, the engineered host cell may include one or more substrate inhibition alleviating mutations in one or more biosynthetic enzyme genes such as one of those genes described in Table 3.

In certain embodiments, the one or more substrate inhibition alleviating mutations are present in the TyrH gene. The TyrH gene encodes tyrosine hydroxylase, which is an enzyme that converts tyrosine to L-DOPA. However, TyrH is inhibited by its substrate, tyrosine. Mammalian tyrosine hydroxylase activity, such as that seen in humans or rats, can be improved through mutations to the TyrH gene that relieve substrate inhibition. In particular, substrate inhibition from tyrosine can be relieved by a point mutation W166Y in the TyrH gene. The point mutation W166Y in the TyrH gene may also improve the binding of the cosubstrate of tyrosine hydroxylase, BILI, to catalyze the reaction of tyrosine to L-DOPA. The mutants of TyrH, when expressed in yeast strains to produce BIAs from sugar (such as those described in U.S. Provisional Patent Application Ser. No. 61/899,496) can significantly improve the production of BIAs.

Any convenient numbers and types of mutations may be utilized to alleviate a substrate inhibition control mechanism. In certain embodiments, the engineered host cells of the present invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even or more substrate inhibition alleviating mutations, such as 1, 2, 3, 4, 5, 6, 7, 8, 9, 10, 11, 12, 13, 14 or 15 substrate inhibition alleviating mutations in one or more biosynthetic enzyme genes within the engineered host cell.

Cofactor Recovery Promoting Mechanisms

In some instances, the engineered host cells are cells that include one or more cofactor recovery promoting mechanisms (such as two or more, three or more, four or more, five or more, or even more) in one or more biosynthetic enzyme genes of the cell. In some examples, the one or more biosynthetic enzyme genes are native to the cell (e.g., is present in an unmodified cell). In some examples, the one or more biosynthetic enzyme genes are non-native to the cell. As used herein, the term "cofactor recovery promoting mechanism" refers to a mechanism that promotes a cofactor recovery control mechanism of the cell.

A variety of cofactor recovery control mechanisms and biosynthetic enzymes in the engineered host cell that are directed to regulation of levels of BIAs of interest, or precursors thereof, may be targeted for cofactor recovery promotion. The engineered host cell may include one or more cofactor recovery promoting mechanism in one or more biosynthetic enzyme genes. In examples, the engineered host cell may include a heterologous coding sequence that encodes dihydrofolate reductase (DHFR). When DHFR is expressed, it may convert 7,8-dihydrobiopterin ($BH_2$) to the tetrahydrobiopterin ($BH_4$), thereby recovering $BH_4$ as a TyrH cosubstrate. In some examples, the engineered host cell may include one or more cofactor recovery promoting mechanisms in one or more biosynthetic enzyme genes such as one of those genes described in Table 2.

Any convenient numbers and types of mechanisms may be utilized to promote a cofactor recovery control mechanism. In certain embodiments, the engineered host cells of the present invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more cofactor recovery promoting mechanisms such as 1, 2, 3, 4, 5, 6, 7, 8, 9, 10, 11, 12, 13, 14 or 15 cofactor recovery promoting mechanisms in one or more biosynthetic enzyme genes within the engineered host cell.

Product Inhibition Alleviating Mutations

In some instances, the engineered host cells are cells that include one or more product inhibition alleviating mutations (such as two or more, three or more, four or more, five or more, or even more) in one or more biosynthetic enzyme genes of the cell. In some examples, the one or more biosynthetic enzyme genes are native to the cell (e.g., is present in an unmodified cell). In some examples, the one or more biosynthetic enzyme genes are non-native to the cell. As used herein, the term "product inhibition alleviating mutation" refers to a mutation that alleviates a short term and/or long term product inhibition control mechanism of an engineered host cell. Short term product inhibition is a control mechanism of the cell in which there is competitive binding at a cosubstrate binding site. Long term product inhibition is a control mechanism of the cell in which there is irreversible binding of a compound away from a desired pathway.

A mutation that alleviates product inhibition reduces the inhibition of a regulated enzyme in the cell of interest relative to a control cell and provides for an increased level of the regulated compound or a downstream biosynthetic product thereof. In some cases, by alleviating inhibition of the regulated enzyme is meant that the $IC_{50}$ of inhibition is increased by 2-fold or more, such as by 3-fold or more, 5-fold or more, 10-fold or more, 30-fold or more, 100-fold or more, 300-fold or more, 1000-fold or more, or even more. By increased level is meant a level that is 110% or more of that of the regulated compound in a control cell or a downstream product thereof, such as 120% or more, 130% or more, 140% or more, 150% or more, 160% or more, 170% or more, 180% or more, 190% or more, or 200% or more, such as at least 3-fold or more, at least 5-fold or more, at least 10-fold or more or even more of the regulated compound in the engineered host cell or a downstream product thereof.

A variety of product inhibition control mechanisms and biosynthetic enzymes in the engineered host cell that are directed to regulation of levels of BIAs of interest may be targeted for product inhibition alleviation. The engineered host cell may include one or more product inhibition alleviating mutations in one or more biosynthetic enzyme genes. The mutation may be located in any convenient biosynthetic enzyme genes where the biosynthetic enzyme is subject to regulatory control. In some embodiments, the one or more biosynthetic enzyme genes encode one or more tyrosine hydroxylase enzymes. In certain instances, the one or more product inhibition alleviating mutations are present in a biosynthetic enzyme gene that is TyrH. In some embodiments, the engineered host cell includes one or more product inhibition alleviating mutations in one or more biosynthetic enzyme genes such as one of those genes described in Table 3.

In certain embodiments, the one or more product inhibition alleviating mutations are present in the TyrH gene. The TyrH gene encodes tyrosine hydroxylase, which is an enzyme that converts tyrosine to L-DOPA. TyrH requires tetrahydrobiopterin ($BH_4$) as a cosubstrate to catalyze the hydroxylation reaction. Some microbial strains, such as *Saccharomyces cerevisiae*, do not naturally produce $BH_4$, but can be engineered to produce this substrate through a four-enzyme synthesis and recycling pathway, as illustrated in FIG. 1. FIG. 1 illustrates examples of synthesis, recycling, and salvage pathways of tetrahydrobiopterin, in accordance with embodiments of the invention. FIG. 1 provides the use of the enzymes PTPS, pyruvoyl tetrahydropterin synthase; SepR, sepiapterin reductase; PCD, pterin 4a-carbinolamine dehydratase; QDHPR, dihydropteridine reductase; and DHFR, dihydrofolate reductase. Of the enzymes that are illustrated in FIG. 1, yeast synthesizes an endogenous GTP cyclohydrolase I. GTP and dihydroneopterin triphosphate are naturally synthesized in yeast. Additionally, other metabolites in FIG. 1 are not naturally produced in yeast.

TyrH is inhibited by its product L-DOPA, as well as other catecholamines, particularly dopamine. Mammalian tyrosine hydroxylase activity, such as from humans or rats, can be improved through mutations that relieve product inhibition. For example, short term product inhibition, such as competitive binding at the cosubstrate binding site, can be relieved by a point mutation W166Y on the TyrH gene. In particular, the point mutation W166Y on the TyrH gene may improve binding of the cosubstrate. Additionally, short term product inhibition to relieve competitive binding at the cosubstrate binding site may be improved by a point mutation S40D on the TyrH gene. Short term product inhibition may also be improved by the joint mutations of R37E, R38E on the TyrH gene. In particular, R37E, R38E mutations may together specifically improve tyrosine hydroxylase activity in the presence of dopamine.

Additionally, long term product inhibition may be relieved by point mutations on the TyrH gene. Long term product inhibition relief may include the irreversible binding of catecholamine to iron in the active site such that there is less catecholamine present to act as a product inhibitor of tyrosine hydroxylase activity. Long term product inhibition can be relieved by the mutations E332D and Y371F, respectively, in the TyrH gene.

Combinations of the mutations can be made (such as two or three or more mutations at once) to relieve multiple types of substrate and product inhibition to further improve the activity of TyrH. The mutants of TyrH, when expressed in yeast strains to produce BIAs from sugar (such as those described in U.S. Provisional Patent Application Ser. No. 61/899,496) can significantly improve the production of BIAs.

Any convenient numbers and types of mutations may be utilized to alleviate a product inhibition control mechanism. In certain embodiments, the engineered host cells of the present invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more product inhibition alleviating mutations, such as 1, 2, 3, 4, 5, 6, 7, 8, 9, 10, 11, 12, 13, 14 or 15 product inhibition alleviating mutations in one or more biosynthetic enzyme genes within the engineered host cell.

Feedback Inhibition Alleviating Mutations

In some instances, the engineered host cells are cells that include one or more feedback inhibition alleviating mutations (such as two or more, three or more, four or more, five or more, or even more) in one or more biosynthetic enzyme genes of the cell. In some cases, the one or more biosynthetic enzyme genes are native to the cell (e.g., is present in an unmodified cell). Additionally or alternatively, in some examples the one or more biosynthetic enzyme genes are non-native to the cell. As used herein, the term "feedback inhibition alleviating mutation" refers to a mutation that alleviates a feedback inhibition control mechanism of an engineered host cell. Feedback inhibition is a control mechanism of the cell in which an enzyme in the synthetic pathway of a regulated compound is inhibited when that compound has accumulated to a certain level, thereby balancing the amount of the compound in the cell. A mutation that alleviates feedback inhibition reduces the inhibition of a regulated enzyme in the engineered host cell relative to a control cell. In this way, engineered host cell provides for an increased level of the regulated compound or a downstream biosynthetic product thereof. In some cases, by alleviating inhibition of the regulated enzyme is meant that the IC 50 of inhibition is increased by 2-fold or more, such as by 3-fold or more, 5-fold or more, 10-fold or more, 30-fold or more, 100-fold or more, 300-fold or more, 1000-fold or more, or even more. By increased level is meant a level that is 110% or more of that of the regulated compound in a control cell or a downstream product thereof, such as 120% or more, 130% or more, 140% or more, 150% or more, 160% or more, 170% or more, 180% or more, 190% or more, or 200% or more, such as at least 3-fold or more, at least 5-fold or more, at least 10-fold or more or even more of the regulated compound in the host cell or a downstream product thereof.

A variety of feedback inhibition control mechanisms and biosynthetic enzymes that are directed to regulation of levels of BIAs of interest may be targeted for alleviation in the host cell. The host cell may include one or more feedback inhibition alleviating mutations in one or more biosynthetic enzyme genes native to the cell. The one or more mutations may be located in any convenient biosynthetic enzyme genes where the biosynthetic enzyme is subject to regulatory control. In some embodiments, the one or more biosynthetic enzyme genes may encode one or more enzymes selected from a 3-deoxy-d-arabinose-heptulosonate-7-phosphate (DAHP) synthase and a chorismate mutase. In some embodiments, the one or more biosynthetic enzyme genes encode a 3-deoxy-d-arabinose-heptulosonate-7-phosphate (DAHP) synthase. In some instances, the one or more biosynthetic enzyme genes may encode a chorismate mutase. In certain instances, the one or more feedback inhibition alleviating mutations may be present in a biosynthetic enzyme gene selected from ARO4 and ARO7. In certain instances, the one or more feedback inhibition alleviating mutations may be present in a biosynthetic enzyme gene that is ARO4. In certain instances, the one or more feedback inhibition alleviating mutations are present in a biosynthetic enzyme gene that is ARO7. In some embodiments, the engineered host cell may include one or more feedback inhibition alleviating mutations in one or more biosynthetic enzyme genes such as one of those genes described in Table 3.

Any convenient numbers and types of mutations may be utilized to alleviate a feedback inhibition control mechanism. As used herein, the term "mutation" refers to a deletion, insertion, or substitution of an amino acid(s) residue or nucleotide(s) residue relative to a reference sequence or motif. The mutation may be incorporated as a directed mutation to the native gene at the original locus. In some cases, the mutation may be incorporated as an additional copy of the gene introduced as a genetic integration at a separate locus, or as an additional copy on an episomal vector such as a 2μ or centromeric plasmid. In certain instances, the feedback inhibited copy of the enzyme is under the native cell transcriptional regulation. In some instances, the feedback inhibited copy of the enzyme is introduced with engineered constitutive or dynamic regulation of protein expression by placing it under the control of a synthetic promoter.

In certain embodiments, the one or more feedback inhibition alleviating mutations may be present in the ARO4 gene. ARO4 mutations of interest may include, but are not limited to, substitution of the lysine residue at position 229 with a leucine, a substitution of the glutamine residue at position 166 with a lysine residue, or a mutation as described by Hartmann M, et al. ((2003) Proc Natl Acad Sci USA 100(3):862-867) or Fukuda et al. ((1992) J Ferment Bioeng 74(2):117-119). In some instances, mutations for conferring feedback inhibition may be selected from a mutagenized library of enzyme mutants. Examples of such selections may include rescue of growth of o-fluoro-D,L-phenylalanine or growth of aro3 mutant yeast strains in media with excess tyrosine as described by Fukuda et al. ((1990) Breeding of Brewing Yeast Producing a Large Amount of Beta-Phenylethyl Alcohol and Beta-Phenylethyl Acetate. Agr Biol Chem Tokyo 54(1):269-271).

In certain embodiments, the engineered host cells of the present invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more feedback inhibition alleviating mutations, such as 1, 2, 3, 4, 5, 6, 7, 8, 9, 10, 11, 12, 13, 14 or 15 feedback inhibition alleviating mutations in one or more biosynthetic enzyme genes within the engineered host cell.

Transcriptional Modulation Modifications

The host cells may include one or more transcriptional modulation modifications (such as two or more, three or more, four or more, five or more, or even more modifications) of one or more biosynthetic enzyme genes of the cell. In some examples, the one or more biosynthetic enzyme genes are native to the cell. In some examples, the one or more biosynthetic enzyme genes are non-native to the cell. Any convenient biosynthetic enzyme genes of the cell may be targeted for transcription modulation. By transcription modulation is meant that the expression of a gene of interest in a modified cell is modulated, e.g., increased or decreased, enhanced or repressed, relative to a control cell (e.g., an unmodified cell). In some cases, transcriptional modulation of the gene of interest includes increasing or enhancing expression. By increasing or enhancing expression is meant that the expression level of the gene of interest is increased by 2-fold or more, such as by 5-fold or more and sometimes by 25-, 50-, or 100-fold or more and in certain embodiments 300-fold or more or higher, as compared to a control, i.e., expression in the same cell not modified (e.g., by using any convenient gene expression assay). Alternatively, in cases where expression of the gene of interest in a cell is so low that it is undetectable, the expression level of the gene of interest is considered to be increased if expression is increased to a level that is easily detectable. In certain instances, transcriptional modulation of the gene of interest includes decreasing or repressing expression. By decreasing or repressing expression is meant that the expression level of the gene of interest is decreased by 2-fold or more, such as by 5-fold or more and sometimes by 25-, 50-, or 100-fold or more and in certain embodiments 300-fold or more or higher, as compared to a control. In some cases, expression is decreased to a level that is undetectable. Modifications of host cell processes of interest that may be adapted for use in the subject host cells are described in U.S. Publication No. 20140273109 (Ser. No. 14/211,611) by Smolke et al., the disclosure of which is herein incorporated by reference in its entirety.

Figure 2:
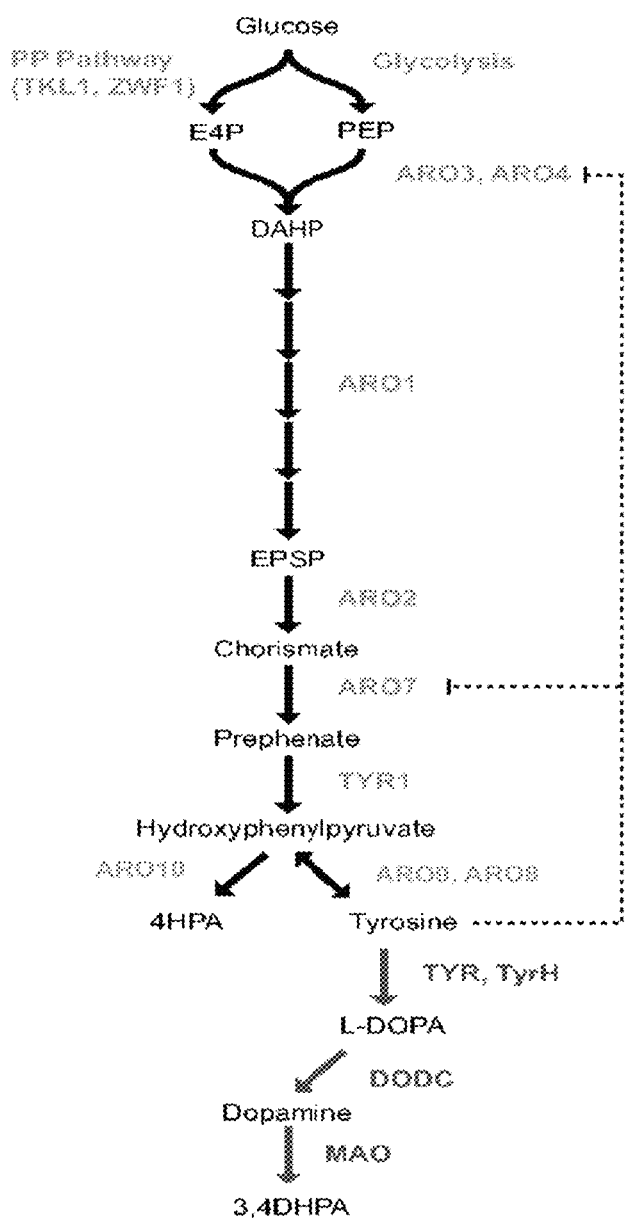
FIG. 2 illustrates a biosynthetic scheme for conversion of glucose to 4-HPA, dopamine, and 3,4-DHPA, in accordance with embodiments of the invention.

Any convenient biosynthetic enzyme genes may be transcriptionally modulated, and include but are not limited to, those biosynthetic enzymes described in FIG. 2. In particular, FIG. 2 illustrates a biosynthetic scheme for conversion of glucose to 4-HPA, dopamine, and 3,4-DHPA, in accordance with embodiments of the invention. Examples of enzymes described in FIG. 2 include ARO3, ARO4, ARO1, ARO7, TYR1, TYR, TyrH, DODC, MAO, ARO10, ARO9, ARO8, and TKL. In some instances, the one or more biosynthetic enzyme genes may be selected from ARO10, ARO9, ARO8, and TKL. In some cases, the one or more biosynthetic enzyme genes may be ARO10. In certain instances, the one or more biosynthetic enzyme genes may be ARO9. In some embodiments, the one or more biosynthetic enzyme genes may be TKL. In some embodiments, the host cell includes one or more transcriptional modulation modifications to one or more genes such as one of those genes described in Table 3.

In some embodiments, the transcriptional modulation modification may include a substitution of a strong promoter for a native promoter of the one or more biosynthetic enzyme genes or the expression of an additional copy(ies) of the gene or genes under the control of a strong promoter. The promoters driving expression of the genes of interest may be constitutive promoters or inducible promoters, provided that the promoters may be active in the host cells. The genes of interest may be expressed from their native promoters. Additionally or alternatively, the genes of interest may be expressed from non-native promoters. Although not a requirement, such promoters may be medium to high strength in the host in which they are used. Promoters may be regulated or constitutive. In some embodiments, promoters that are not glucose repressed, or repressed only mildly by the presence of glucose in the culture medium, may be used. There are numerous suitable promoters, examples of which include promoters of glycolytic genes such as the promoter of the *B. subtilis* tsr gene (encoding fructose biphosphate aldolase) or GAPDH promoter from yeast *S. cerevisiae* (coding for glyceraldehyde-phosphate dehydrogenase) (Bitter G. A., *Meth. Enzymol.* 152:673 684 (1987)). Other strong promoters of interest include, but are not limited to, the ADHI promoter of baker's yeast (Ruohonen L., et al, *J. Biotechnol.* 39:193 203 (1995)), the phosphate-starvation induced promoters such as the PHO5 promoter of yeast (Hinnen, A., et al, in *Yeast Genetic Engineering*, Barr, P. J., et al. eds, Butterworths (1989), the alkaline phosphatase promoter from *B. licheniformis* (Lee. J. W. K., et al., *J. Gen. Microbiol.* 137:1127 1133 (1991)), GPD1, and TEF1. Yeast promoters of interest include, but are not limited to, inducible promoters such as Gall-10, Gall, GalL, GalS, repressible promoter Met25, tetO, and constitutive promoters such as glyceraldehyde 3-phosphate dehydrogenase promoter (GPD), alcohol dehydrogenase promoter (ADH), translation-elongation factor-1-alpha promoter (TEF), cytochrome c-oxidase promoter (CYC1), MRP7 promoter, etc. In some instances, the strong promoter is GPD1. In certain instances, the strong promoter is TEF1. Autonomously replicating yeast expression vectors containing promoters inducible by hormones such as glucocorticoids, steroids, and thyroid hormones are also known and include, but are not limited to, the glucorticoid responsive element (GRE) and thyroid hormone responsive element (TRE), see e.g., those promoters described in U.S. Pat. No. 7,045,290. Vectors containing constitutive or inducible promoters such as alpha factor, alcohol oxidase, and PGH may be used. Additionally any promoter/enhancer combination (as per the Eukaryotic Promoter Data Base EPDB) could also be used to drive expression of genes of interest. It is understood that any convenient promoters specific to the host cell may be selected, e.g., *E. coli*. In some cases, promoter selection may be used to optimize transcription, and hence, enzyme levels to maximize production while minimizing energy resources.

Inactivating Mutations

The engineered host cells may include one or more inactivating mutations to an enzyme of the cell (such as two or more, three or more, four or more, five or more, or even more). The inclusion of one or more inactivating mutations may modify the flux of a synthetic pathway of an engineered host cell to increase the levels of a BIA of interest or a desirable enzyme or precursor leading to the same. In some examples, the one or more inactivating mutations are to an enzyme native to the cell. Additionally or alternatively, the one or more inactivating mutations are to an enzyme non-native to the cell. As used herein, by "inactivating mutation" is meant one or more mutations to a gene or regulatory DNA sequence of the cell, where the mutation(s) inactivates a biological activity of the protein expressed by that gene of interest. In some cases, the gene is native to the cell. In some instances, the gene encodes an enzyme that is inactivated and is part of or connected to the synthetic pathway of a BIA of interest produced by the host cell. In some instances, an inactivating mutation is located in a regulatory DNA sequence that controls a gene of interest. In certain cases, the inactivating mutation is to a promoter of a gene. Any convenient mutations (e.g., as described herein) may be utilized to inactivate a gene or regulatory DNA sequence of interest. By "inactivated" or "inactivates" is meant that a biological activity of the protein expressed by the mutated gene is reduced by 10% or more, such as by 20% or more, 30% or more, 40% or more, 50% or more, 60% or more, 70% or more, 80% or more, 90% or more, 95% or more, 97% or more, or 99% or more, relative to a control protein expressed by a non-mutated control gene. In some cases, the protein is an enzyme and the inactivating mutation reduces the activity of the enzyme.

In some examples, the engineered host cell includes an inactivating mutation in an enzyme native to the cell. Any convenient enzymes may be targeted for inactivation. Enzymes of interest may include, but are not limited to those enzymes, described in Table 3 whose action in the synthetic pathway of the engineered host cell tends to reduce the levels of a BIA of interest. In some cases, the enzyme has glucose-6-phosphate dehydrogenase activity. In certain embodiments, the enzyme that includes an inactivating mutation is ZWF1. In some cases, the enzyme has alcohol dehydrogenase activity. In some embodiments, the enzyme that includes an inactivating mutation is selected from ADH2, ADH3, ADH4, ADH5, ADH6, ADH7, and SFA1. In certain embodiments, the enzyme that includes an inactivating mutation(s) is ADH2. In certain embodiments, the enzyme that includes an inactivating mutation(s) is ADH3. In certain embodiments, the enzyme that includes an inactivating mutation(s) is ADH4. In certain embodiments, the enzyme that includes an inactivating mutation(s) is ADH5. In certain embodiments, the enzyme that includes an inactivating mutation(s) is ADH6. In certain embodiments, the enzyme that includes an inactivating mutation(s) is ADH7. In some cases, the enzyme has aldehyde oxidoreductase activity. In certain embodiments, the enzyme that includes an inactivating mutation is selected from ALD2, ALD3, ALD4, ALD5, and ALD6. In certain embodiments, the enzyme that includes an inactivating mutation(s) is ALD2. In certain embodiments, the enzyme that includes an inactivating mutation(s) is ALD3. In certain embodiments, the enzyme that includes an inactivating mutation(s) is ALD4. In certain embodiments, the enzyme that includes an inactivating mutation(s) is ALD5. In certain embodiments, the enzyme that includes an inactivating mutation(s) is ALD6. In some embodiments, the host cell includes one or more inactivating mutations to one or more genes described in Table 3.

Epimerization Modifications

Figure 3:
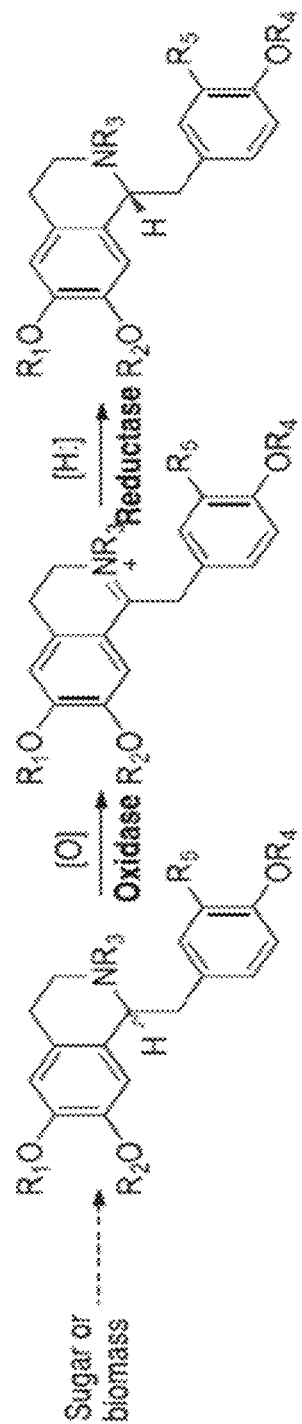
FIG. 3 illustrates a schematic example of (R)-1-benzylisoquinoline alkaloid formation, in accordance with embodiments of the invention.

Some methods, processes, and systems provided herein describe the conversion of (S)-1-benzylisoquinoline alkaloids to (R)-1-benzylisoquinoline alkaloids. Some of these methods, processes, and systems may comprise an engineered host cell. In some examples, the conversion of (S)-1-benzylisoquinoline alkaloids to (R)-1-benzylisoquinoline alkaloids is a key step in the conversion of a substrate to a diverse range of alkaloids. In some examples, the conversion of (S)-1-benzylisoquinoline alkaloids to (R)-1-benzylisoquinoline alkaloids comprises an epimerization reaction. In some examples, the conversion of (S)-1-benzylisoquinoline alkaloids to (R)-1-benzylisoquinoline alkaloids comprises an epimerization reaction via an engineered epimerase. In some cases, epimerization of a substrate alkaloid may be performed by oxidizing an (S)-substrate to the corresponding Schiff base or imine intermediate, then stereospecifically reducing this intermediate to an (R)-product as provided in FIG. 3 and as represented generally in Scheme 1. As provided in Scheme 1, $R_1$, $R_2$, $R_3$, and $R_4$ may be H or $CH_3$. $R_5$ may be H, OH, or $OCH_3$.

Scheme 1

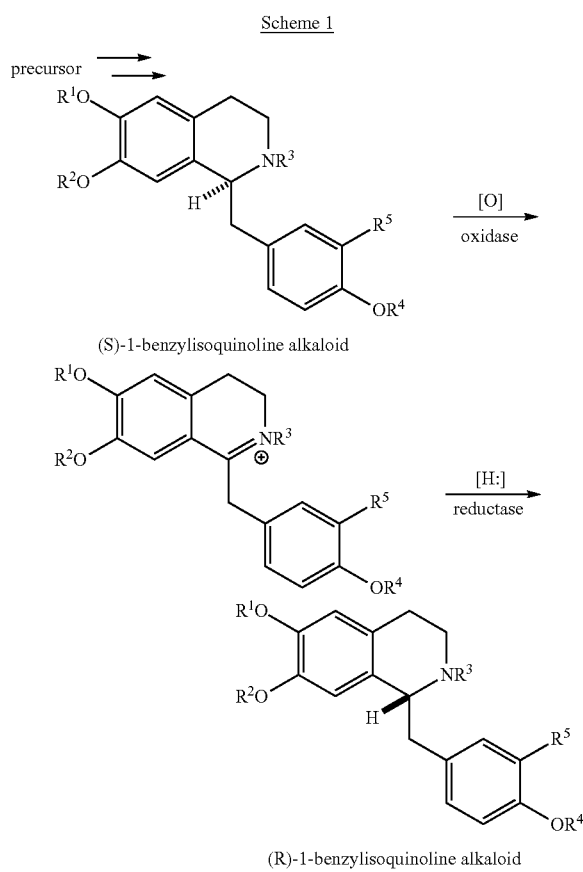

(S)-1-benzylisoquinoline alkaloid (R)-1-benzylisoquinoline alkaloid

In some examples, the conversion of the (S)-substrate to the (R)-product may involve at least one oxidation reaction and at least one reduction reaction. In some cases, an oxidation reaction is optionally followed by a reduction reaction. In some cases, at least one of the oxidation and reduction reactions is carried out in the presence of an enzyme. In some cases, at least one of the oxidation and reduction reactions is catalyzed by an enzyme. In some cases, the oxidation and reduction reactions are both carried out in the presence of at least one enzyme. In some cases, at least one enzyme is useful to catalyze the oxidation and reduction reactions. The oxidation and reduction reactions may be catalyzed by the same enzyme. In some cases, at least one of the oxidation and reduction reactions is catalyzed by an engineered epimerase. In some cases, the oxidation and reduction reactions are both carried out in the presence of an engineered fused epimerase. In some cases, the oxidation and reduction reactions are both carried out in the presence of an engineered split epimerase having a separately expressed oxidase component and reductase component, respectively. In some cases, an engineered epimerase is useful to catalyze the oxidation and reduction reactions. The oxidation and reduction reactions may be catalyzed by the same engineered epimerase.

In some methods, processes and systems described herein, an oxidation reaction may be performed in the presence of an enzyme. In some examples, the enzyme may be an oxidase. In some examples, the enzyme may be part of an engineered epimerase. In some examples, the engineered epimerase may have an oxidase component. In some cases, the oxidase component may be a component of an engineered fused epimerase. In some cases, the oxidase component may be independently expressed as part of an engineered split epimerase. The oxidase may use an (S)-1-benzylisoquinoline as a substrate. The oxidase may convert the (S)-substrate to a corresponding imine or Schiff base derivative. The oxidase may be referred to as 1,2-dehydroreticuline synthase (DRS). Non-limiting examples of enzymes suitable for oxidation of (S)-1-benzylisoquinoline alkaloids in this disclosure include a cytochrome P450 oxidase, a 2-oxoglutarate-dependent oxidase, and a flavoprotein oxidase. For example, (S)-tetrahydroprotoberberine oxidase (STOX, E.C 1.3.3.8) may oxidize (S)-norreticuline and other (S)-1-benzylisoquinoline alkaloids to 1,2-dehydronorreticuline and other corresponding 1,2-dehydro products. In some examples, a protein that comprises an oxidase domain of any one of the preceding examples may perform the oxidation. In some examples, the oxidase may catalyze the oxidation reaction within a host cell, such as an engineered host cell, as described herein.

In some examples, a reduction reaction may follow the oxidation reaction. In some examples, the reduction reaction may be performed by an enzyme. In some examples, the reduction reaction may be performed by an enzyme that is part of an engineered epimerase. In some examples, the reductase may use an imine or Schiff base derived from a 1-benzylisoquinoline as a substrate. The reductase may convert the imine or Schiff base derivative to an (R)-1-benzylisoquinoline. The reductase may be referred to as 1,2-dehydroreticuline reductase (DRR). Non-limiting examples of enzymes suitable for reduction of an imine or Schiff base derived from an (S)-1-benzylisoquinoline alkaloid include an aldo-keto reductase (e.g., a codeinone reductase-like enzyme (EC 1.1.1.247)) and a short chain dehydrogenase (e.g., a salutaridine reductase-like enzyme (EC 1.1.1.248)). In some examples, a protein that comprises a reductase domain of any one of the preceding examples may perform the reduction. In a further embodiment, the reduction is stereospecific. In some examples, the reductase may catalyze the reduction reaction within a host cell, such as an engineered host cell, as described herein.

An example of an enzyme that can perform an epimerization reaction that converts (S)-1-benzylisoquinoline alkaloids to (R)-1-benzylisoquinoline alkaloids includes an epimerase having an oxidase domain and a reductase domain. In particular, the epimerase may have a cytochrome P450 oxidase 82Y2-like domain. Additionally, the epimerase may have a codeinone reductase-like domain. Further, an epimerase having a cytochrome P450 oxidase 82Y2-like domain and also having a codeinone reductase-like domain may be referred to as a DRS-DRR enzyme. In particular, a DRS-DRR enzyme may be a fusion enzyme that is a fusion epimerase. Further, when a DRS-DRR enzyme is modified by at least one activity-increasing modification, the fusion enzyme may be an engineered fusion epimerase.

An example of an amino acid sequence of a DRS-DRR enzyme that may be used to perform the conversion of (S)-1-benzylisoquinoline alkaloids to (R)-1-benzylisoquinoline alkaloids is provided in FIG. 4. In particular, FIG. 4 illustrates an amino acid sequence of a DRS-DRR enzyme, in accordance with embodiments of the invention. As seen in FIG. 4, underlined text denotes the cytochrome P450 CYP82Y2-like domain (59% identity to AFB74617.1). The dotted underlined text denotes the aldo-keto reductase NADPH-dependent codeinone reductase-like domain (75% identity to ACM44066.1). Additional amino acid sequences of a DRS-DRR enzyme are set forth in Table 1. An amino acid sequence for an epimerase that is utilized in converting an (S)-1-benzylisoquinoline alkaloid to an (R)-1-benzylisoquinoline alkaloid may be 75% or more identical to a given amino acid sequence as listed in Table 1. For example, an amino acid sequence for such an epimerase may comprise an amino acid sequence that is at least 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to an amino acid sequence as provided herein. Additionally, in certain embodiments, an "identical" amino acid sequence contains at least 80%-99% identity at the amino acid level to the specific amino acid sequence. In some cases an "identical" amino acid sequence contains at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

An engineered host cell may be provided that produces an epimerase that converts (S)-1-benzylisoquinoline alkaloid to (R)-1-benzylisoquinoline alkaloid, wherein the epimerase comprises an amino acid sequence selected from the group consisting of: SEQ ID NOs: 1, 2, 3, 4, 5, 6, 7, 8, 9, 10, 11, 12, 13, 14, and 15. The epimerase that is produced within the engineered host cell may be recovered and purified so as to form a biocatalyst. In some cases, the epimerase may be split into one or more enzymes. Additionally, one or more enzymes that are produced by splitting the epimerase may be recovered from the engineered host cell. These one or more enzymes that result from splitting the epimerase may also be used to catalyze the conversion of (S)-1-benzylisoquinoline alkaloids to (R)-1-benzylisoquinoline alkaloids. In particular, the one or more enzymes that are recovered from the engineered host cell that produces the epimerase may be used in a process for converting an (S)-1-benzylisoquinoline alkaloid to an (R)-1-benzylisoquinoline alkaloid. The process may include contacting the (S)-1-benzylisoquinoline alkaloid with an epimerase in an amount sufficient to convert said (S)-1-benzylisoquinoline alkaloid to (R)-1-benzylisoquinoline alkaloid. In examples, the (S)-1-benzylisoquinoline alkaloid may be contacted with a sufficient amount of the one or more enzymes such that at least 5% of said (S)-1-benzylisoquinoline alkaloid is converted to (R)-1-benzylisoquinoline alkaloid. In further examples, the (S)-1-benzylisoquinoline alkaloid may be contacted with a sufficient amount of the one or more enzymes such that at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said (S)-1-benzylisoquinoline alkaloid is converted to (R)-1-benzylisoquinoline alkaloid.

An example of an amino acid sequence of a DRS-DRR enzyme that may be used to perform the conversion of (S)-1-benzylisoquinoline alkaloids to (R)-1-benzylisoquinoline alkaloids is provided in FIG. 4. In particular, FIG. 4 illustrates an amino acid sequence of a DRS-DRR enzyme that has been codon-optimized, in accordance with embodiments of the invention. Further, FIG. 5 illustrates a split of an oxidase portion and reductase portion, each of the DRS-DRR enzyme of FIG. 4. Additional amino acid sequences of a DRS-DRR enzyme are set forth in Table 1. An amino acid sequence for an epimerase that is utilized in converting an (S)-1-benzylisoquinoline alkaloid to an (R)-1-benzylisoquinoline alkaloid may be 75% or more identical to a given amino acid sequence as listed in Table 1. For example, an amino acid sequence for such an epimerase may comprise an amino acid sequence that is at least 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to an amino acid sequence as provided herein. Additionally, in certain embodiments, an "identical" amino acid sequence contains at least 80%-99% identity at the amino acid level to the specific amino acid sequence. In some cases an "identical" amino acid sequence contains at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

Amino acid residues of homologous epimerases may be referenced according to the numbering scheme of SEQ ID NO. 16, and this numbering system is used throughout the disclosure to refer to specific amino acid residues of epimerases which are homologous to SEQ ID NO. 16. Epimerases homologous to SEQ ID NO. 16 may have at least about 70%, 75%, 80%, 85%, 90%, 95%, 97%, 98%, or 99% sequence identity to SEQ ID NO. 16. In some cases, an amino acid referred to as position 50 in a homologous epimerase may not be the $50^{th}$ amino acid in the homologous epimerase, but would be the amino acid which corresponds to the amino acid at position 50 in SEQ ID NO. 16 in a protein alignment of the homologous epimerase with SEQ ID NO. 16. In some cases, homologous enzymes may be aligned with SEQ ID NO. 16 either according to primary sequence, secondary structure, or tertiary structure.

An engineered host cell may be provided that produces an engineered epimerase that converts (S)-1-benzylisoquinoline alkaloid to (R)-1-benzylisoquinoline alkaloid, wherein the epimerase comprises an amino acid sequence selected from the group consisting of: SEQ ID NOs: 1, 2, 3, 4, 5, 6, 7, 8, 9, 10, 11, 12, 13, 14, 15, 16, 17, and 18, and having one or more activity-enhancing modifications. The epimerase that is produced within the engineered host cell may be recovered and purified so as to form a biocatalyst. In some cases, the epimerase may be split into one or more enzymes. Additionally, one or more enzymes that are produced by splitting the epimerase may be recovered from the engineered host cell. These one or more enzymes that result from splitting the epimerase may also be used to catalyze the conversion of (S)-1-benzylisoquinoline alkaloids to (R)-1- benzylisoquinoline alkaloids. Additionally, the use of an engineered split epimerase may be used to increase the production of benzylisoquinoline alkaloid products within a cell when compared to the production of benzylisoquinoline alkaloid products within a cell utilizing a fused epimerase.

In additional cases, the one or more enzymes that are recovered from the engineered host cell that produces the epimerase may be used in a process for converting an (S)-1-benzylisoquinoline alkaloid to an (R)-1-benzylisoquinoline alkaloid. The process may include contacting the (S)-1-benzylisoquinoline alkaloid with an epimerase in an amount sufficient to convert said (S)-1-benzylisoquinoline alkaloid to (R)-1-benzylisoquinoline alkaloid. In examples, the (S)-1-benzylisoquinoline alkaloid may be contacted with a sufficient amount of the one or more enzymes such that at least 5% of said (S)-1-benzylisoquinoline alkaloid is converted to (R)-1-benzylisoquinoline alkaloid. In further examples, the (S)-1-benzylisoquinoline alkaloid may be contacted with a sufficient amount of the one or more enzymes such that at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said (S)-1-benzylisoquinoline alkaloid is converted to (R)-1-benzylisoquinoline alkaloid.

The one or more enzymes that may be used to convert an (S)-1-benzylisoquinoline alkaloid to an (R)-1-benzylisoquinoline alkaloid may contact the (S)-1-benzylisoquinoline alkaloid in vitro. Additionally, or alternatively, the one or more enzymes that may be used to convert an (S)-1-benzylisoquinoline alkaloid to an (R)-1-benzylisoquinoline alkaloid may contact the (S)-1-benzylisoquinoline alkaloid in vivo. Additionally, the one or more enzymes that may be used to convert an (S)-1-benzylisoquinoline alkaloid to an (R)-1-benzylisoquinoline alkaloid may be provided to a cell having the (S)-1-benzylisoquinoline alkaloid within, or may be produced within an engineered host cell.

In some examples, the methods provide for engineered host cells that produce an alkaloid product, wherein the epimerization of an (S)-substrate to an (R)-product may comprise a key step in the production of an alkaloid product. In some examples, the alkaloid produced is an (R)-1-benzylisoquinoline alkaloid. In still other embodiments, the alkaloid produced is derived from an (R)-1-benzylisoquinoline alkaloid, including, for example, 4-ring promorphinan and 5-ring morphinan alkaloids. In another embodiment, an (S)-1-benzylisoquinoline alkaloid is an intermediate toward the product of the engineered host cell. In still other embodiments, the alkaloid product is selected from the group consisting of 1-benzylisoquinoline, morphinan, promorphinan, nor-opioid, or nal-opioid alkaloids.

In some examples, the (S)-substrate is an (S)-1-benzylisoquinoline alkaloid selected from the group consisting of (S)-norreticuline, (S)-reticuline, (S)-tetrahydropapaverine, (S)-norcoclaurine, (S)-coclaurine, (S)—N-methylcoclaurine, (S)-3'-hydroxy-N-methylcoclaurine, (S)-norisoorientaline, (S)-orientaline, (S)-isoorientaline, (S)-norprotosinomenine, (S)-protosinomenine, (S)-norlaudanosoline, (S)-laudanosoline, (S)-4'-O-methyllaudanosoline, (S)-6-O-methylnorlaudanosoline, (S)-4'-O-methylnorlaudanosoline.

In some examples, the (S)-substrate is a compound of Formula I:

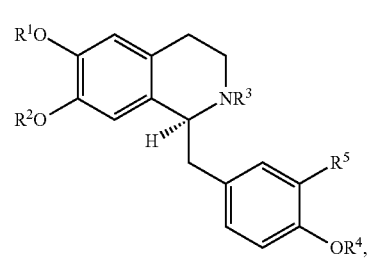

Formula I or a salt thereof, wherein:
$R^1$, $R^2$, $R^3$, and $R^4$ are independently selected from hydrogen and methyl; and
$R^5$ is selected from hydrogen, hydroxy, and methoxy.

In some other examples, at least one of $R^1$, $R^2$, $R^3$, $R^4$, and $R^5$ is hydrogen.

In still other examples, the (S)-substrate is a compound of Formula II:

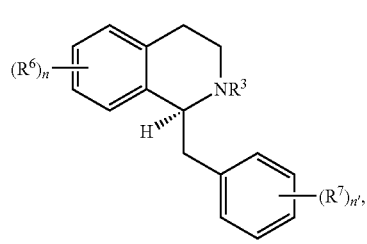

Formula II or a salt thereof, wherein:
$R^3$ is selected from hydrogen and $C_1$-$C_4$ alkyl;
$R^6$ and $R^7$ are independently selected at each occurrence from hydroxy, fluoro, chloro, bromo, carboxaldehyde, $C_1$-$C_4$ acyl, $C_1$-$C_4$ alkyl, and $C_1$-$C_4$ alkoxy;
n is 0, 1, 2, 3, or 4; and
n' is 0, 1, 2, 3, 4 or 5.

When a bond is drawn across a ring, it means substitution may occur at a non-specific ring atom or position. For example, in Formula II shown above, the hydrogen of any —CH— in the 6-membered ring may be replaced with $R^7$ to form —CR'—.

In some examples, $R^6$ and $R^7$ are independently methyl or methoxy. In some other examples, n and n' are independently 1 or 2. In still other embodiments, $R^3$ is hydrogen or methyl.

In some examples, the methods provide for engineered host cells that produce alkaloid products from (S)-reticuline. The epimerization of (S)-reticuline to (R)-reticuline may comprise a key step in the production of diverse alkaloid products from a precursor. In some examples, the precursor is L-tyrosine or a sugar (e.g., glucose). The diverse alkaloid products can include, without limitation, 1-benzylisoquinoline, morphinan, promorphinan, nor-opioid, or nal-opioid.alkaloids.

Any suitable carbon source may be used as a precursor toward an epimerized 1-benzylisoquinoline alkaloid. Suitable precursors can include, without limitation, monosaccharides (e.g., glucose, fructose, galactose, xylose), oligosaccharides (e.g., lactose, sucrose, raffinose), polysaccharides (e.g., starch, cellulose), or a combination thereof. In some examples, unpurified mixtures from renewable feedstocks can be used (e.g., cornsteep liquor, sugar beet molasses, barley malt, biomass hydrolysate). In still other embodiments, the carbon precursor can be a one-carbon compound (e.g., methanol, carbon dioxide) or a two-carbon compound (e.g., ethanol). In yet other embodiments, other carbon-containing compounds can be utilized, for example, methylamine, glucosamine, and amino acids (e.g., L-tyrosine). In some examples, a 1-benzylisoquinoline alkaloid may be added directly to an engineered host cell of the invention, including, for example, norlaudanosoline, laudanosoline, norreticuline, and reticuline. In still further embodiments, a 1-benzylisoquinoline alkaloid may be added to the engineered host cell as a single enantiomer (e.g., an (S)-1-benzylisoquinoline alkaloid), or a mixture of enantiomers, including, for example, a racemic mixture.

In some examples, the methods provide for the epimerization of a stereocenter of a 1-benzylisoquinoline alkaloid, or a derivative thereof. In a further embodiment, the method comprises contacting the 1-benzylisoquinoline alkaloid with at least one enzyme. The at least one enzyme may invert the stereochemistry of a stereocenter of a 1-benzylisoquinoline alkaloid, or derivative thereof, to the opposite stereochemistry. In some examples, the at least one enzyme converts an (S)-1-benzylisoquinoline alkaloid to an (R)-1-benzylisoquinoline alkaloid. In some examples of this conversion of an (S)-1-benzylisoquinoline alkaloid to an (R)-1-benzylisoquinoline alkaloid utilizing the at least one enzyme, the (S)-1-benzylisoquinoline alkaloid is selected from the group consisting of (S)-norreticuline, (S)-reticuline, (S)-tetrahydropapaverine, (S)-norcoclaurine, (S)-coclaurine, (S)—N-methylcoclaurine, (S)-3'-hydroxy-N-methylcoclaurine, (S)-norisoorientaline, (S)-orientaline, (S)-isoorientaline, (S)-norprotosinomenine, (S)-protosinomenine, (S)-norlaudanosoline, (S)-laudanosoline, (S)-4'-O-methyllaudanosoline, (S)-6-O-methylnorlaudanosoline, and (S)-4'-O-methylnorlaudanosoline.

In still other embodiments, the 1-benzylisoquinoline alkaloid that is epimerized may comprise two or more stereocenters, wherein only one of the two or more stereocenters is inverted to produce a diastereomer of the substrate (e.g., (S, R)-1-benzylisoquinoline alkaloid converted to (R, R)-1-benzylisoquinoline alkaloid). In examples where only one stereocenter of a 1-benzylisoquinoline alkaloid is inverted when contacted with the at least one enzyme, the product is referred to as an epimer of the 1-benzylisoquinoline alkaloid.

In some examples, the 1-benzylisoquinoline alkaloid is presented to the enzyme as a single stereoisomer. In some other examples, the 1-benzylisoquinoline alkaloid is presented to the enzyme as a mixture of stereoisomers. In still further embodiments, the mixture of stereoisomers may be a racemic mixture. In some other examples, the mixture of stereoisomers may be enriched in one stereoisomer as compared to another stereoisomer.

In some examples, an 1-benzylisoquinoline alkaloid, or a derivative thereof, is recovered. In some examples, the 1-benzylisoquinoline alkaloid is recovered from a cell culture. In still further embodiments, the recovered 1-benzylisoquinoline alkaloid is enantiomerically enriched in one stereoisomer as compared to the original mixture of 1-benzylisoquinoline alkaloids presented to the enzyme. In still further embodiments, the recovered 1-benzylisoquinoline alkaloid has an enantiomeric excess of at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100%.

In some examples, a promorphinan, or a derivative thereof, is recovered. In some examples, the promorphinan is recovered from a cell culture.

In some examples, a morphinan, or a derivative thereof, is recovered. In some examples, the morphinan is recovered from a cell culture.

In some examples, a nal-opioid, or a derivative thereof, is recovered. In some examples, the nal-opioid is recovered from a cell culture.

In some examples, a nor-opioid, or a derivative thereof, is recovered. In some examples, the nor-opioid is recovered from a cell culture.

"Isomers" are different compounds that have the same molecular formula. "Stereoisomers" are isomers that differ only in the way the atoms are arranged in space. "Enantiomers" are a pair of stereoisomers that are non superimposable mirror images of each other. A 1:1 mixture of a pair of enantiomers is a "racemic" mixture. "Diastereoisomers" or "diastereomers" are stereoisomers that have at least two asymmetric atoms but are not mirror images of each other. The term "epimer" as used herein refers to a compound having the identical chemical formula but a different optical configuration at a particular position. For example, the (R,S) and (S,S) stereoisomers of a compound are epimers of one another. In some examples, a 1-benzylisoquinoline alkaloid is converted to its epimer (e.g., epi-1-benzylisoquinoline alkaloid). The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms that can be defined, in terms of absolute stereochemistry, as (R)- or (S)-.

TABLE 1 example amino acid sequences of DRS-DRR enzymes, split DRS and DRR enzymes, and other nucleotide sequences.

| Sequence | Description | SEQ. ID NO. |
|---|---|---|
| MELQYISYFQPTSSVVALLLALVSILSSVVVLRKTFLNNYSSSPASSTK TAVLSHQRQQSCALPISGLLHIFMNKNGLIHVTLGNMADKYGPIFSFPT GSHRTLVVSSWEMVKECFTGNNDTAFSNRPIPLAFKTIFYACGGIDSY GLSSVPYGKYWRELRKVCVHNLLSNQQLLKFRHLIISQVDTSFNKLYE LCKNSEDNHGNYTTTTTTAAGMVRIDDWLAELSFNVIGRIVCGFQSG PKTGAPSRVEQFKEAINEASYFMSTSPVSDNVPMLGWIDQLTGLTRN MKHCGKKLDLVVESIINDHRQKRRFSRTKGGDEKDDEQDDFIDICLSI MEQPQLPGNNNPSQIPIKSIVLDMIGGGTDTTKLTTIWTLSLLLNNPHV | P. somniferum plant source; full-length amino acid sequence >RQNK-2062398 (also FPYZ- | SEQ. ID NO. 1 |

TABLE 1-continued example amino acid sequences of DRS-DRR enzymes, split DRS and DRR enzymes, and other nucleotide sequences.

| Sequence | Description | SEQ. ID NO. |
|---|---|---|
| LDKAKQEVDAHFRTKRRSTNDAAAAVVDFDDIRNLVYIQAIIKESMR<br>LYPASPVVERLSGEDCVVGGFHVPAGTRLWANVWKMQRDPKVWDD<br>PLVFRPDRFLSDEQKMVDVRGQNYELLPFGAGRRVCPGVSFSLDLMQ<br>LVLTRLILEFEMKSPSGKVDMTATPGLMSYKVIPLDILLTHRRIKPCVQ<br>SAASERDMESSGVPVITLGSGKVMPVLGMGTFEKVGKGSERERLAIL<br>KAIEVGYRYFDTAAAYETEEVLGEAIAEALQLGLVKSRDELFISSMLW<br>CTDAHADRVLLALQNSLRNLKLEYVDLYMLPFPASLKPGKITMDIPEE<br>DICRMDYRSVWAAMEECQNLGFTKSIGVSNFSCKKLQELMATANIPP<br>AVNQVEMSPAFQQKKLREYCNANNILVSAISVLGSNGTPWGSNAVLG<br>SEVLKKIAMAKGKSVAQVSMRWVYEQGASLVVKSFSEERLRENLNIF<br>DWELTKEDHEKIGEIPQCRILSAYFLVSPNGPFKSQEELWDDEA* | 2037562,<br>BMRX-<br>2007040, and<br>MLPX-<br>2016197) | |
| MELQYISYFQPTSSVVALLLALVSILSSVVVLRKTFLNNYSSSPASSTK<br>TAVLSHQRQQSCALPISGLLHIFMNKNGLIHVTLGNMADKYGPIFSFPT<br>GSHRTLVVSSWEMVKECFTGNNDTAFSNRPIPLAFKTIFYACGGIDSY<br>GLSSVPYGKYWRELRKVCVHNLLSNQQLLKFRHLIISQVDTSFNKLYE<br>LCKNSEDNHGNYTTXLLLPQLAWRQPWKLYYXTTTTAAGMVRIDD<br>WLAELSFNVIGRIVCGFQSGPKTGAPSRVEQFKEAINEASYFMSTSPVS<br>DNVPMLGWIDQLTGLTRNMKHCGKKLDLVVESIINDHRQKRRFSRTK<br>GGDEKDDEQDDFIDICLSIMEQPQLPGNNNPSQIPIKSIVLDMIGGGTD<br>TTKLTTIWTLSLLLNNPHVLDKAKQEVDAHFRTKRRSTNDAAAAVVD<br>FDDIRNLVYIQAIIKESMRLYPASPVVERLSGEDCVVGGFHVPAGTRL<br>WANVWKMQRDPKVWDDPLVFRPDRFLSDEQKMVDVRGQNYELLPF<br>GAGRRVCPGVSFSLDLMQLVLTRLILEFEMKSPSGKVDMTATPGLMS<br>YKVIPLDILLTHRRIKPCVQSAASERDMESSGVPVITLGSGKVMPVLG<br>MGTFEKVGKGSERERLAILKAIEVGYRYFDTAAAYETEEVLGEAIAEA<br>LQLGLVKSRDELFISSMLWCTDAHADRVLLALQNSLRNLKLEYVDLY<br>MLPFPASLKPGKITMDIPEEDICRMDYRSVWAAMEECQNLGFTKSIGV<br>SNFSCKKLQELMATANIPPAVNQVEMSPAFQQKKLREYCNANNILVS<br>AISVLGSNGTPWGSNAVLGSEVLKKIAMAKGKSVAQVSMRWVYEQG<br>ASLVVKSFSEERLRENLNIFDWELTKEDHEKIGEIPQCRILSAYFLVSPN<br>GPFKSQEELWDDEA* | P. somniferum<br>plant source;<br>full-length<br>amino acid<br>sequence<br>>KKCW-<br>2026866<br>(also FPYZ-<br>2037562,<br>MLPX-<br>2016197) | SEQ. ID<br>NO. 2 |
| MELQYISYFQPTSSVVALLLALVSILSSVVVLRKTFLNNYSSSPASSTK<br>TAVLSHQRQQSCALPISGLLHIFMNKNGLIHVTLGNMADKYGPIFSFPT<br>GSHRTLVVSSWEMVKECFTGNNDTAFSNRPIPLAFKTIFYACGGIDSY<br>GLSSVPYGKYWRELRKVCVHNLLSNQQLLKFRHLIISQVDTSFNKLYE<br>LCKNSEDNHGNYTTTTTTAAGMVRIDDWLAELSFNVIGRIVCGFQSG<br>PKTGAPSRVEQFKEAINEASYFMSTSPVSDNVPMLGWIDQLTGLTRN<br>MKHCGKKLDLVVESIINDHRQKRRFSRTKGGDEKDDEQDDFIDICLSI<br>MEQPQLPGNNNPSQIPIKSIVLDMIGGGTDTTKLTTIWTLSLLLNNPHV<br>LDKAKQEVDAHFRTKRRSTNDAAAAVVDFDDIRNLVYIQAIIKESMR<br>LYPASPVVERLSGEDCVVGGFHVPAGTRLWANVWKMQRDPKVWDD<br>PLVFRPDRFLSDEQKMVDVRGQNYELLPFGAGRRVCPGVSFSLDLMQ<br>LVLTRLILEFEMKSPSGKVDMTATPGLMSYKVIPLDILLTHRRIKPCVQ<br>SAASERDMESSGVPVITLGSGKVMPVLGMGTFEKVGKGSERERLAIL<br>KAIEVGYRYFDTAAAYETEEVLGEAIAEALQLGLVKSRDELFISSMLW<br>CTDAHADRVLLALQNSLRNLKLEYVDLYMLPFPASLKPGKITMDIPEE<br>DICRMDYRXVSKPWLH* | P. somniferum<br>plant source;<br>partial-length<br>amino acid<br>sequence<br>>SUFP-<br>2025636 | SEQ. ID<br>NO. 3 |
| MRWHRXIDSYGLSSVPYGKYWRELRKVCVHNLLSNQQLLKFRHLIIS<br>QVDTSFNKLYELCKNSEDNQGNYPTTTTAAGMVRIDDWLAELSFNVI<br>GRIVCGFQSGPKTGAPSRVEQFKEAINEASYFMSTSPVSDNVPMLGWI<br>DQLTGLTRNMKHCGKKLDLVVESIINDHRQKRRFSRTKGGDEKDDEQ<br>DDFIDICLSIMEQPQLPGNNNPSQIPIKSIVLDMIGGGTDTTKLTTIWTLS<br>LLLNNPHVLDKAKQEVDAHFRTKRRSTNDAAAAVVDFDDIRNLVYIQ<br>AIIKESMRLYPASPVVERLSGEDCVVGGFHVPAGTRLWANVWKMQR<br>DPKVWDDPLVFRPDRFLSDEQKMVDVRGQNYELLPFGAGRRVCPGV<br>SFSLDLMQLVLTRLILEFEMKSPSGKVDMTATPGLMSYKVIPLDILLTH<br>RRIKPCVQSAASERDMESSGVPVITLGSGKVMPVLGMGTFEKVGKGS<br>ERERLAILKAIEVGYRYFDTAAAYETEEVLGEAIAEALQLGLVKSRDE<br>LFISSMLWCTDAHADRVLLALQNSLRNLKLEYVDLYMLPFPASLKPG<br>KITMDIPEEDICRMDYRSVWAAMEECQNLGFTKSIGVSNFSCKKLQEL<br>MATANIPPAVNQVEMSPAFQQKKLREYCNANNILVSAISVLGSNGTP<br>WGSNAVLGSEVLKKIAMAKGKSVAQVSMRWVYEQGASLVVKSFSE<br>ERLRENLNIFDWELTKEDHEKIGEIPQCRILSAYFLVSPNGPFKSQEEL<br>WDDEA* | P. somniferum<br>plant source;<br>partial-length<br>amino acid<br>sequence<br>>MIKW-<br>2013651 | SEQ. ID<br>NO. 4 |
| MELQYISYFQPTSSVVALLLALVSILSSVVVLRKTFLNNYSSSPASSTK<br>TAVLSHQRQQSCALPISGLLHIFMNKNGLIHVTLGNMADKYGPIFSFPT<br>GSHRTLVVSSWEMVKECFTGNNDTAFSNRPIPLAFKTIFYACGGIDSY<br>GLSSVPYGKYWRELRKVCVHNLLSNQQLLKFRHLIISQVDTSFNKLYE<br>LCKNSEDNQGNYTTTTTAAGMVRIDDWLAELSFNVIGRIVCGFQSGP<br>KTGAPSRVEQFKEAINEASYFMSTSPVSDNVPMLGWIDQLTGLTRNM | P. setigerum<br>plant source;<br>full-length<br>amino acid<br>sequence<br>>EPRK- | SEQ. ID<br>NO. 5 |

TABLE 1-continued example amino acid sequences of DRS-DRR enzymes, split DRS and DRR enzymes, and other nucleotide sequences.

| Sequence | Description | SEQ. ID NO. |
|---|---|---|
| KHCGKKLDLVVESIINDHRQKRRFSRTKGGDEKDDEQDDFIDICLSIM EQPQLPGNNNPSQIPIKSIVLDMIGGGTDTTKLTTIWTLSLLLNNPHVL DKAKQEVDAHFRTKRRSTNDAAAAVVDFDDIRNLVYIQAIIKESMRL YPASPVVERLSGEDCVVGGFHVPAGTRLWANVWKMQRDPKVWDDDP LVFRPDRFLSDEQKMVDVRGQNYELLPFGAGRRVCPGVSFSLDLMQL VLTRLILEFEMKSPSGKVDMTATPGLMSYKVIPLDILLTHRRIKPCVQS AASERDMESSGVPVITLGSGKVMPVLGMGTFEKVGKGSERERLAILK AIEVGYRYFDTAAAYETEEVLGEAIAEALQLGLVKSRDELFISSMLWC TDAHADRVLLALQNSLRNLKLEYVDLYMLPFPASLKPGKITMDIPEED ICRMDYRSVWAAMEECQNLGFTKSIGVSNFSCKKLQELMATANIPPA VNQVEMSPAFQQKLREYCNANNILVSAISVLGSNGTPWGSNAVLGS EVLKKIAMAKGKSVAQVSMRWVYEQGASLVVKSFSEERLRENLNIFD WELTKEDHEKIGEIPQCRILSAYFLVSPNGPFKSQEELWDDEA* | 2027940 (also FPYZ-2037562, STDO-2019715, FNXH-2029312, MLPX-2016196, MLPX-2016197) | |
| MELQYISYFQPTSSVVALLLALVSILSSVVVLRKTFLNNYSSSPASSTK TAVLSHQRQQSCALPISGLLHIFMNKNGLIHVTLGNMADKYGPIFSFPT GSHRTLVVSSWEMVKECFTGNNDTAFSNRPIPLAFKTIFYACGGIDSY GLSSVPYGKYWRELRKVCVHNLLSNQQLLKFRHLIISQVDTSFNKLYE LCKNSEDNQGNYTTTTTAAGMVRIDDWLAELSFNVIGRIVCGFQSGP KTGAPSRVEQFKEAINEASYFMSTSPVSDNVPMLGWIDQLTGLTRNM KHCGKKLDLVVESIINDHRQKRRFSRTKGGDEKDDEQDDFIDICLSIM EQPQLPGNNNPSQIPIKSIVLDMIGGGTDTTKLTTIWTLSLLLNNPHVL DKAKQEVDAHFRTKRRSTNDAAAAVVDFDDIRNLVYIQALYPASPVV ERLSGEDCVVGGFHVPAGTRLWANVWKMQRDPKVWDDPLVFRPDR FLSDEQKMVDVRGQNYELLPFGAGRRVCPGVSFSLDLMQLVLTRLIL EFEMKSPSGKVDMTATPGLMSYKVIPLDILLTHRRIKPCVQSAASERD MESSGVPVITLGSGKVMPVLGMGTFEKVGKGSERERLAILKAIEVGY RYFDTAAAYETEEVLGEAIAEALQLGLVKSRDELFISSMLWCTDAHA DRVLLALQNSLRNLKLEYVDLYMLPFPASLKPGKITMDIPEEDICRMD YRSVWAAMEE | P. setigerum plant source; partial-length amino acid sequence >QCOU-2000833 | SEQ. ID NO. 6 |
| MELQYFSYFQPTSSVVALLLALVSILFSVVVLRKTFSNNYSSPASSTET AVLCHQRQQSCALPISGLLHVFMNKNGLIHVTLGNMADKYGPIFSFPT GSHRTLVVSSWEMVKECFTGNNDTAFSNRPIPLAFQTIFYACGGIDSY GLSSVPYGKYWRELRKVCVHNLLSNQQLLKFRHLIISQVDTSFNKLYE LCKNSEDNQGMVRMDDWLAQLSFNVIGRIVCGFQSDPKTGAPSRVE QFKEVINEASYFMSTSPVSDNVPMLGWIDQLTGLTRNMKHCGKKLDL VVESIIKDHRQKRRFSRTKGGDEKDDEQDDFIDICLSIMEQPQLPGNNS PPQIPIKSIVLDMIGGGTDTTKLTTIWTLSLLLNNPHVLDKAKQEVDAH FRKKRRSTDDAAAAVVDFDDIRNLVYIQAIIKESMRLYPASPVVERLS GEDCVVGGFHVPAGTRLWANVWKMQRDPKVWDDPLVFRPERFLSD EQKMVDVRGQNYELLPFGAGRRICPGVSFSLDLMQLVLTRLILEFEM KSPSGKVDMTATPGLMSYKVVPLDILLTHRRIKSCVQLASSERDMESS GVPVITLSSGKVMPVLGMGTFEKVGKGSERERLAILKAIEVGYRYFDT AAAYETEEVLGEAIAEALQLGLIESRDELFISSMLWCTDAHPDRVLLA LQNSLRNLKLEYLDLYMLPFPASLKPGKITMDIPEEDICRMDYRSVWS AMEECQNLGFTKSIGVSNFSSKKLQELMATANIPPAVNQVEMSPAFQ QKKLREYCNANNILVSAVSILGSNGTPWGSNAVLGSEVLKQIAMAKG KSVAQVSMRWVYEQGASLVVKSFSEERLRENLNIFDWELTKEDNEKI GEIPQCRILTAYFLVSPNGPFKSQEELWDDKA* | P. bracteatum plant source; full-length amino acid sequence >SSDU-2015634 (also SSDU-2015636, ZSNV-2027701, RRID-2004435) | SEQ. ID NO. 7 |
| MELQYFSYFQPTSSVVALLLALVSILFSVVVLRKTFSNNYSSPASSTET AVLCHQRQQSCALPISGLLHVFMNKNGLIHVTLGNMADKYGPIFSFPT GSHRTLVVSSWEMVKECFTGNNDTAFSNRPIPLAFQTIFYACGGIDSY GLSSVPYGKYWRELRKVCVHNLLSNQQLLKFRHLIISQVDTSFNKLYE LCKNSEDNQGMVRMDDWLAQLSFNVIGRIVCGFQSDPKTGAPSRVE QFKEVINEASYFMSTSPVSDNVPMLGWIDQLTGLTRNMKHCGKKLDL VVESIIKDHRQKRRFSRTKGGDEKDDEQDDFIDICLSIMEQPQLPGNNS PPQIPIKSIVLDMIGGGTDTTKLTTIWTLSLLLNNPHVLDKAKQEVDAH FRKKRRSTDDAAAAVVDFDDIRNLVYIQAIIKESMRLYPASPVVERLS GEDCVVGGFHVPAGTRLWANVWKMQRDPKVWDDPLVFRPERFLSD EQKMVDVRGQNYELLPFGAGRRICPGVSFSLDLMQLVLTRLILEFEM KSPSGKVDMTATPGLMSYKVVPLDILLTHRRIKSCVQLASSERDMESS GVPVITLSSGKVMPVLGMGTFEKVGKGSERERLAILKAIEVGYRYFDT AAAYETEEVLGEAIAEALQLGLIESRDELFISSMLWCTDAHPDRVLLA LQNSLRNLKLEYLDLYMLPFPASLKPGKITMDIPEEDICRMDYRSVWS AMEECQNLGFTKSIGVSNFSCKKLQELMATANIPPAVNQVEMSPAFQ QKKLREYCNANNILVSAVSILGSNGTPWGSNAVLGSEVLKQIAMAKG KSVAQVSMRWVYEQGASLVVKSFSEERLRENLNIFDWELTKEDNEKI GEIPQCRILTAYFLVSPNGPFKSQEELWDDKA* | P. bracteatum plant source; full-length amino acid sequence >TMWO-2027322 (also RRID-2004435) | SEQ. ID NO. 8 |
| SSPASSTETAVLCHQRQQSCALPISGLLHIFMNKNGLIHVTLGNMADK YGPIFSFPTGSHRILVVSSWEMVKECFTGNNDTAFSNRPIPLAFKTIFYA CRGIDSYGLSSVPYGKYWRELRKVCVHNLLSNQQLLKFRHLIISQVDT | P. bracteatum plant source; partial-length | SEQ. ID NO. 9 |

TABLE 1-continued example amino acid sequences of DRS-DRR enzymes, split DRS and DRR enzymes, and other nucleotide sequences.

| Sequence | Description | SEQ. ID NO. |
|---|---|---|
| SFNKLYELCKNSEDNQGMVRMDDWLAQLSFSVIGRIVCGFQSDPKTG APSRVEQFKEAINEASYFMSTSPVSDNVPMLGWIDQLTGLTRNMTHC GKKLDLVVESIINDHRQKRRFSRTKGGDEKDDEQDDFIDICLSIMEQP QLPGNNNPPKIPIKSIVLDMIGAGTDTTKLTIIWTLSLLLNNPNVLAKA KQEVDAHFETKKRSTNEASVVVDFDDIGNLVYIQAIIKESMRLYPVSP VVERLSSEDCVVGGFHVPAGTRLWANVWKMQRDPKVWDDPLVFRP ERFLSDEQKMVDVRGQNYELLPFGAGRRICPGVSFSLDLMQLVLTRLI LEFEMKSPSGKVDMTATPGLMSYKVVPLDILLTHRRIKSCVQLASSER DMESSGVPVITLRSGKVMPVLGMGTFEKAGKGSERERLAILKAIEVG YRYFDTAAAYETEEVLGEAIAEALQLGLIKSRDELFISSMLWCTDAHP DRVLLALQNSLRNLKLEYVDLYMLPFPASLKPGKITMDIPEEDICPMD YRSVWSAMEECQNLGLTKSIGVSNFSCKKLEELMATANIPPAVNQVE MSPAFQQKKLREYCNANNILVSAVSILGSNGTPWGSNAVLGSEVLKKI AMAKGKSVAQVSMRWVYEQGASLVVKSFSEERLRENLNIFDWQLTK EDNEKIGEIPQCRILSAYFLVSPKGPFKSQEELWDDKA* | amino acid sequence >pbr.PBRST1 PF_89405 | |
| SSPASSTETAVLCHQRQQSCALPISGLLHIFMNKNGLIHVTLGNMADK YGPIFSFPTGSHRILVVSSWEMVKECFTGNNDTFFSNRPIPLAFKIIFYA GGVDSYGLALVPYGKYWRELRKICVHNLLSNQQLLKFRHLIISQVDTS FNKLYELCKNSEDNQGMVRMDDWLAQLSFSVIGRIVCGFQSDPKTGA PSRVEQFKEAINEASYFMSTSPVSDNVPMLGWIDQLTGLTRNMTHCG KKLDLVVESIINDHRQKRRFSRTKGGDEKDDEQDDFIDICLSIMEQPQL PGNNNPPKIPIKSIVLDMIGGGTDTTKLTTIWTLSLLLNNPHVLDKAKQ EVDAHFLTKRRSTNDAAVVDFDDIRNLVYIQAIIKESMRLYPASPVVE RLSGEDCVVGGFHVPAGTRLWVNVWKMQRDPNVWADPMVFRPERF LSHGQKKMVDVRGKNYELLPFGAGRRICPGISFSLDLMQLVLTRLILE FEMKSPSGKVDMTATPGLMSYKVVPLDILLTHRRIKSCVQLASSERD MESSGVPVITLRSGKVMPVLGMGTFEKAGKGSERERLAILKAIEVGYR YFDTAAAYETEEVLGEAIAEALQLGLIKSRDELFISSMLWCTDAHPDR VLLALQNSLRNLKLEYVDLYMLPFPASLKPGKITMDIPEEDICPMDYR SVWSAMEECQNLGLTKSIGVSNFSCKKLEELMATANIPPAVNQVEMS PAFQQKKLREYCNANNILVSAVSILGSNGTPWGSNAVLGSEVLKKIA MAKGKSVAQVSMRWVYEQGASLVVKSFSEERLRENLNIFDWQLTKE DNEKIGEIPQCRILSAYFLVSPKGPFKSQEELWDDKA* | P. bracteatum plant source; partial-length amino acid sequence >pbr.PBRST1 PF_4328 | SEQ. ID NO. 10 |
| SSPASSTETAVLCHQRQQSCALPISGLLHIFMNKNGLIHVTLGNMADK YGPIFSFPTGSHRILVVSSWEMVKECFTGNNDTFFSNRPIPLAFKIIFYA GGVDSYGLALVPYGKYWRELRKICVHNLLSNQQLLNFRHLIISQVDTS FNKLYDLSNKKKNTTTDSGTVRMDDWLAQLSFNVIGRIVCGFQTHTE TSATSSVERFTEAIDEASRFMSIATVSDTFPWLGWIDQLTGLTRKMKH YGKKLDLVVESIIEDHRQNRRISGTKQGDDFIDICLSIMEQPQIIPGNND PPRQIPIKSIVLDMIGGGTDTTKLTTTWTLSLLLNNPHVLEKAREEVDA HFGTKRRPTNDDAVMVEFDDIRNLVYIQAIIKESMRLYPASPVVERLS GEDCVVGGFHVPAGTRLWVNVWKMQRDPNVWADPMVFRPERFLSD EQKMVDVRGQNYELLPFGAGRRICPGVSFSLDLMQLVLTRLILEFEM KSPSGKVDMTATPGLMSYKVVPLDILLTHRRIKSCVQLASSERDMESS GVPVITLRSGKVMPVLGMGTFEKAGKGSERERLAILKAIEVGYRYFDT AAAYETEEVLGEAIAEALQLGLIKSRDELFISSMLWCTDAHPDRVLLA LQNSLRNLKLEYVDLYMLPFPASLKPGKITMDIPEEDICPMDYRSVWS AMEECQNLGLTKSIGVSNFSCKKLEELMATANIPPAVNQVEMSPAFQ QKKLREYCNANNILVSAVSILGSNGTPWGSNAVLGSEVLKKIAMAKG KSVAQVSMRWVYEQGASLVVKSFSEERLRENLNIFDWQLTKEDNEKI GEIPQCRILSAYFLVSPKGPFKSQEELWDDKA* | P. bracteatum plant source; partial-length amino acid sequence >pbr.PBRST1 PF_12180 | SEQ. ID NO. 11 |
| VALRKKILKNYYSSSSSTATAVSHQWPKASRALPLIDLLHVFFNKTDL MHVTLGNMADKFGPIFSFPTGSHRTLVVSSWEKAKECFTGNNDIVFS GRPLPLAFKLIFYAGGIDSYGISQVPYGKKWRELRNICVHNILSNQQLL KFRHLMISQVDNSFNKLYEVCNSNKDEGDSATSTTAAGIVRMDDWL GKLAFDVIARIVCGFQSQTETSTTSSMERFTEAMDEASRFMSVTAVSD TVPWLGWIDQLTGLKRNMKHCGKKLNLVVKSIIEDHRQKRRLSSTKK GDENIIDEDEQDDFIDICLSIMEQPQLPGNNNPPKIPIKSIVLDMIGGGTD TTKLTTIWTLSLLLNNPHVLDKAKQEVDAHFLTKRRSTNDAAVVDFD DIRNLVYIQAIIKESMRLYPASPVVERLSGEDCVVGGFHVPAGTRLWV NVWKMQRDPNVWADPMVFRPERFLSDEQKMVDVRGQNYELLPFGA GRRICPGVSFSLDLMQLVLTRLILEFEMKSPSGKVDMTATPGLMSYKV VPLDILLTHRRIKSCVQLASSERDMESSGVPVITLRSGKVMPVLGMGT FEKAGKGSERERLAILKAIEVGYRYFDTAAAYETEEVLGEAIAEALQL GLIKSRDELFISSMLWCTDAHPDRVLLALQNSLRNLKLEYVDLYMLPF PASLKPGKITMDIPEEDICPMDYRSVWSAMEECQNLGLTKSIGVSNFS CKKLEELMATANIPPAVNQVEMSPAFQQKKLREYCNANNILVSAVSIL GSNGTPWGSNAVLGSEVLKKIAMAKGKSVAQVSMRWVYEQGASLV VKSFSEERLRENLNIFDWQLTKEDNEKIGEIPQCRILSAYFLVSPKGPFK SQEELWDDKA* | P. bracteatum plant source; partial-length amino acid sequence >pbr.PBRST1 PF_4329 | SEQ. ID NO. 12 |

TABLE 1-continued example amino acid sequences of DRS-DRR enzymes, split DRS and DRR enzymes, and other nucleotide sequences.

| Sequence | Description | SEQ. ID NO. |
|---|---|---|
| MELQYFSYFQPTSSVVALLLALVSILFSVVVLRKTFSNNYSSPASSTET AVLCHQRQQSCALPISGLLHVFMNKNGLIHVTLGNMADKYGPIFSFPT GSHRTLVVSSWEMVKECFTGNNDTAFSNRPIPLAFQTIFYACGGIDSY GLSSVPYGKYWRELRKVCVHNLLSNQQLLKFRHLIISQVDTSFNKLYE LCKNSEDNQGMVRMDDWLAQLSFNVIGRIVCGFQSDPKTGAPSRVE QFKEVINEASYFMSTSPVSDNVPMLGWIDQLTGLTRNMKHCGKKLDL VVESIIKDHRQKRRFSRTKGGDEKDDEQDDFIDICLSIMEQPQLPGNNS PPQIPIKSIVLDMIGGGTDTTKLTTIWTLSLLLNNPHVLDKAKQEVDAH FRKKRRSTDDAAAAVVDFDDIRNLVYIQAIIKESMRLYPASPVVERLS GEDCVVGGFHVPAGTRLWANVWKMQRDPKVWDDPLVFRPERFLSD EQKMVDVRGQNYELLPFGAGRRICPGVSFSLDLMQLVLTRLILEFEM KSPSGKVDMTATPGLMSYKVVPLDILLTHRRIKSCVQLASSERDMESS GVPVITLSSGKVMPVLGMGTFEKVGKGSERERLAILKAIEVGYRYFDT AAAYETEEVLGEAIAEALQLGLIESRDELFISSMLWCTDAHPDRVLLA LQNSLRNLKLEYLDLYMLPFPASLKPGKITMDIPEEDICRMDYRSVWS AMEECQNLGFTKSIGVSNFSSKKLQELMATANIPPAVNQVEMSPAFQ QKKLREYCNANNILVSAVSILGSNGTPWGSNAVLGSEVLKQIAMAKG KSVAQVSMRWVXKFSAYAIVWSLFFGHRICITLYSFLIRNVAYICITY* | *P. bracteatum* plant source; partial-length amino acid sequence >SSDU-2015635 | SEQ. ID NO. 13 |
| MELQYFSYFQPTSSVVALLLALVSILFSVVVLRKTFSNNYSSPASSTET AVLCHQRQQSCALPISGLLHVFMNKNGLIHVTLGNMADKYGPIFSFPT GSHRTLVVSSWEMVKECFTGNNDTAFSNRPIPLAFQTIFYACGGIDSY GLSSVPYGKYWRELRKVCVHNLLSNQQLLKFRHLIISQVDTSFNKLYE LCKNSEDNQGMVRMDDWLAQLSFNVIGRIVCGFQSDPKTGAPSRVE QFKEVINEASYFMSTSPVSDNVPMLGWIDQLTGLTRNMKHCGKKLDL VVESIIKDHRQKRRFSRTKGGDEKDDEQDDFIDICLSIMEQPQLPGNNS PPQIPIKSIVLDMIGGGTDTTKLTTIWTLSLLLNNPHVLDKAKQEVDAH FRKKRRSTDDAAAAVVDFDDIRNLVYIQAIIKESMRLYPASPVVERLS GEDCVVGGFHVPAGTRLWANVWKMQRDPKVWDDPLVFRPERFLSD EQKMVDVRGQNYELLPFGAGRRICPGVSFSLDLMQLVLTRLILEFEM KSPSGKVDMTATPGLMSYKVVPLDILLTHRRIKSCVQLASSERDMESS GVPVITLSSGKVMPVLGMGTFEKVGKGSERERLAILKAIEVGYRYFDT AAAYETEEVLGEAIAEALQLGLIESRDELFISSMLWCTDAHPDRVLLA LQNSLRQVFLMQIRLIYICTYQQVHLNIYFQINEFVLCDMYRNLKLEY | *P. bracteatum* plant source; partial-length amino acid sequence >SSDU-2015637 | SEQ. ID NO. 14 |
| LNNYSSPASSTKTAVLSHQRQQSCALPISGLLHIFMNKNGLIHVTLGN MADKYGPIFSFPTGSHRTLVVSSWEMVKECFTGNNDTAFSNRPIPLAF KTIFYACGGIDSYGLSSVPYGKYWRELRKVCVHNLLSNQQLLKFRHLI ISQVDTSFNKLYELCKNSEDNQGNYPTTTTAAGMVRIDDWLAELSFN VIGRIVCGFQSGPKTGAPSRVEQFKEAINEASYFMSTSPVSDNVPMLG WIDQLTGLTRNMKHCGKKLDLVVESIINDHRQKRRFSRTKGGDEKDD EQDDFIDICLSIMEQPQLPGNNNPSQIPIKSIVLDMIGGGTDTTKLTTIW TLSLLLNNPHVLDKAKQEVDAHFRTKRRSTNDAAAAVVDFDDIRNLV YIQAIIKESMRLYPASPVVERLSGEDCVVGGFHVPAGTRLWANVWK QRDPKVWDDPLVFRPDRFLSDEQKMVDVRGQNYELLPFGAGRRVCP GVSFSLDLMQLVLTRLILEFEMKSPSGKVDMTATPGLMSYKVIPLDIL LTHRRIKPCVQSAASERDMESSGVPVITLGSGKVMPVLGMGTFEKVG KGSERERLAFLKAIEVGYRYFDTAAAYETEEFLGEAIAEALQLGLIKSR DELFITSKLWPCDAHPDLVVPALQNSLRNLKLEYVDLYMLPFPASLKP GKITMDIPEEDICRMDYRSVWAAMEECQNLGFTKSIGVSNFSCKKLQE LMATANIPPAVNQVEMSPAFQQKKLREYCNANNILVSAISVLGSNGTP WGSNAVLGSEVLKKIAMAKGKSVAQVSMRWVYEQGASLVVKSFSE ERLRENLNIFDWELTKEDHEKIGEIPQCRILSAYFLVSPNGPFKSQEEL WDDEA* | *C. majus* plant source; partial-length amino acid sequence >chm.CMAS T2PF_14984 | SEQ. ID NO. 15 |
| MELQYFSYFQPTSSVVALLLALVSILFSVVVLRKTFSNNYSSPASSTET AVLCHQRQQSCALPISGLLHVFMNKNGLIHVTLGNMADKYGPIFSFPT GSHRTLVVSSWEMVKECFTGNNDTAFSNRPIPLAFQTIFYACGGIDSY GLSSVPYGKYWRELRKVCVHNLLSNQQLLKFRHLIISQVDTSFNKLYE LCKNSEDNQGMVRMDDWLAQLSFNVIGRIVCGFQSDPKTGAPSRVE QFKEVINEASYFMSTSPVSDNVPMLGWIDQLTGLTRNMKHCGKKLDL VVESIIKDHRQKRRFSRTKGGDEKDDEQDDFIDICLSIMEQPQLPGNNS PPQIPIKSIVLDMIGGGTDTTKLTTIWTLSLLLNNPHVLDKAKQEVDAH FRKKRRSTDDAAAAVVDFDDIRNLVYIQAIIKESMRLYPASPVVERLS GEDCVVGGFHVPAGTRLWANVWKMQRDPKVWDDPLVFRPERFLSD EQKMVDVRGQNYELLPFGAGRRICPGVSFSLDLMQLVLTRLILEFEM KSPSGKVDMTATPGLMSYKVVPLDILLTHRRIKSCVQLASSERDMESS GVPVITLSSGKVMPVLGMGTFEKVGKGSERERLAILKAIEVGYRYFDT AAAYETEEVLGEAIAEALQLGLIESRDELFISSMLWCTDAHPDRVLLA LQNSLRNLKLEYLDLYMLPFPASLKPGKITMDIPEEDICRMDYRSVWS AMEECQNLGFTKSIGVSNFSCKKLQELMATANIPPAVNQVEMSPAFQ QKKLREYCNANNILVSAVSILGSNGTPWGSNAVLGSEVLKQIAMAKG KSVAQVSMRWVYEQGASLVVKSFSEERLRENLNIFDWELTKEDNEKI GEIPQCRILTAYFLVSPNGPFKSQEELWDDKA* | *P. bracteatum* DRS-DRR | SEQ. ID NO. 16 |

TABLE 1-continued example amino acid sequences of DRS-DRR enzymes, split DRS and DRR enzymes, and other nucleotide sequences.

| Sequence | Description | SEQ. ID NO. |
|---|---|---|
| MELQYFSYFQPTSSVVALLLALVSILFSVVVLRKTFSNNYSSPASSTET AVLCHQRQQSCALPISGLLHVFMNKNGLIHVTLGNMADKYGPIFSFPT GSHRTLVVSSWEMVKECFTGNNDTAFSNRPIPLAFQTIFYACGGIDSY GLSSVPYGKYWRELRKVCVHNLLSNQQLLKFRHLIISQVDTSFNKLYE LCKNSEDNQGMVRMDDWLAQLSFNVIGRIVCGFQSDPKTGAPSRVE QFKEVINEASYFMSTSPVSDNVPMLGWIDQLTGLTRNMKHCGKKLDL VVESIIKDHRQKRRFSRTKGGDEKDDEQDDFIDICLSIMEQPQLPGNNS PPQIPIKSIVLDMIGGGTDTTKLTTIWTLSLLLNNPHVLDKAKQEVDAH FRKKRRSTDDAAAAVVDFDDIRNLVYIQAIIKESMRLYPASPVVERLS GEDCVVGGFHVPAGTRLWANVWKMQRDPKVWDDPLVFRPERFLSD EQKMVDVRGQNYELLPFGAGRRICPGVSFSLDLMQLVLTRLILEFEM KSPSGKVDMTATPGLMSYKVVPLDILLTHRRIKSCVQLASSERD | P. bracteatum DRS | SEQ. ID NO. 17 |
| MESSGVPVITLSSGKVMPVLGMGTFEKVGKGSERERLAILKAIEVGYR YFDTAAAYETEEVLGEAIAEALQLGLIESRDELFISSMLWCTDAHPDR VLLALQNSLRNLKLEYLDLYMLPFPASLKPGKITMDIPEEDICRMDYR SVWSAMEECQNLGFTKSIGVSNFSCKKLQELMATANIPPAVNQVEMS PAFQQKKLREYCNANNILVSAVSILGSNGTPWGSNAVLGSEVLKQIA MAKGKSVAQVSMRWVYEQGASLVVKSFSEERLRENLNIFDWELTKE DNEKIGEIPQCRILTAYFLVSPNGPFKSQEELWDDKA* | P. bracteatum DRR | SEQ. ID NO. 18 |
| TTCAGTTCGAGTTTATCATTATCAATACTGCCATTTCAAAGAATAC GTAAATAATTAATAGTAGTGATTTTCCTAACTTTATTTAGTCAAAA AATTAGCCTTTTAATTCTGCTGTAACCCGTACATGCCCAAAATAGG GGGCGGGTTACACAGAATATATAACATCGTAGGTGTCTGGGTGAA CAGTTTATTCCTGGCATCCACTAAATATAATGGAGCCCGCTTTTTA AGCTGGCATCCAGAAAAAAAAAGAATCCCAGCACCAAAATATTGT TTTCTTCACCAACCATCAGTTCATAGGTCCATTCTCTTAGCGCAACT ACAGAGAACAGGGGCACAAACAGGCAAAAAACGGGCACAACCTC AATGGAGTGATGCAACCTGCCTGGAGTAAATGATGACACAAGGCA ATTGACCCACGCATGTATCTATCTCATTTTCTTACACCTTCTATTAC CTTCTGCTCTCTCTGATTTGGAAAAAGCTGAAAAAAAAGGTTGAAA CCAGTTCCTGAAATTATTCCCCTACTTGACTAATAAGTATATAAA GACGGTAGGTATTGATTGTAATTCTGTAAATCTATTTCTTAAACTTC TTAAATTCTACTTTTATAGTTAGTCTTTTTTTTAGTTTTAAAACACC AAGAACTTAGTTTCGAATAAACACACATAAACAAACAAA | TDH3 Promoter | SEQ. ID NO. 19 |
| GAGCGTTGGTTGGTGGATCAAGCCCACGCGTAGGCAATCCTCGAG CAGATCCGCCAGGCGTGTATATATAGCGTGGATGGCCAGGCAACT TTAGTGCTGACACATACAGGCATATATATATGTGTGCGACGACACA TGATCATATGGCATGCATGTGCTCTGTATGTATATAAAACTCTTGT TTTCTTCTTTTCTCTAAATATTCTTTCCTTATACATTAGGACCTTTGC AGCATAAATTACTATACTTCTATAGACACACAAACACAAATACAC ACACTAAATTAATA | CYC1 Promoter | SEQ. ID NO. 20 |
| CATAGCTTCAAAATGTTTCTACTCCTTTTTTACTCTTCCAGATTTTC TCGGACTCCGCGCATCGCCGTACCACTTCAAAACACCCAAGCACA GCATACTAAATTTCCCCTCTTTCTTCCTCTAGGGTGTCGTTAATTAC CCGTACTAAAGGTTTGGAAAAGAAAAAAGAGACCGCCTCGTTTCT TTTTCTTCGTCGAAAAAGGCAATAAAAATTTTTATCACGTTTCTTTT TCTTGAAAATTTTTTTTTGATTTTTTTCTCTTTCGATGACCTCCCA TTGATATTTAAGTTAATAAACGGTCTTCAATTTCTCAAGTTTCAGTT TCATTTTCTTGTTCTATTACAACTTTTTTTACTTCTTGCTCATTAGA AAGAAAGCATAGCAATCTAATCTAAGTTTTAATTACAAA | TEF1 Promoter | SEQ. ID NO. 21 |
| ACAGGCCCCTTTTCCTTTGTCGATATCATGTAATTAGTTATGTCACG CTTACATTCACGCCCTCCTCCCACATCCGCTCTAACCGAAAAGGAA GGAGTTAGACAACCTGAAGTCTAGGTCCCTATTTATTTTTTTTAAT AGTTATGTTAGTATTAAGAACGTTATTTATATTTCAAATTTTTCTTT TTTTTCTGTACAAACGCGTGTACGCATGTAACATTACTGAAAAC CTTGCTTGAGAAGGTTTTGGGACGCTCGAAGGCTTTAATTTG | CYC1 Terminator | SEQ. ID NO. 22 |
| GCGAATTTCTTATGATTTATGATTTTTATTATTAAATAAGTTATAAA AAAATAAGTGTATACAAATTTTAAAGTGACTCTTAGGTTTTAAAA CGAAAATTCTTATTCTTGAGTAACTCTTTCCTGTAGGTCAGGTTGCT TTCTCAGGTA | ADH1 Terminator | SEQ. ID NO. 23 |
| CCTCGCCGCAGTTAATTAAAGTCAGTGAGCGAGGAAGCGCGTAAC TATAACGGTCCTAAGGTAGCGAATCCTGATGCGGTATTTTCTCCTT ACGCATCTGTGCGGTATTTCACACCGCATAGATCGGCAAGTGCACA AACAATACTTAAATAAATACTACTCAGTAATAACCTATTTCTTAGC ATTTTTTGACGAAATTTGCTATTTTGTTAGAGTCTTTTACACCATTTG TCTCCACACCTCCGCTTACATCAACACCAATAACGCCATTTAATCT | pDW10 | SEQ. ID NO. 24 |

TABLE 1-continued example amino acid sequences of DRS-DRR enzymes, split DRS and DRR enzymes, and other nucleotide sequences.

| Sequence | Description | SEQ. ID NO. |
|---|---|---|
| AAGCGCATCACCAACATTTTCTGGCGTCAGTCCACCAGCTAACATA<br>AAATGTAAGCTTTCGGGGCTCTCTTGCCTTCCAACCCAGTCAGAAA<br>TCGAGTTCCAATCCAAAAGTTCACCTGTCCCACCTGCTTCTGAATC<br>AAACAAGGGAATAAACGAATGAGGTTTCTGTGAAGCTGCACTGAG<br>TAGTATGTTGCAGTCTTTTGGAAATACGAGTCTTTTAATAACTGGC<br>AAACCGAGGAACTCTTGGTATTCTTGCCACGACTCATCTCCATGCA<br>GTTGGACGATATCAATGCCGTAATCATTGACCAGAGCCAAAACAT<br>CCTCCTTAAGTTGATTACGAAACACGCCAACCAAGTATTTCGGAGT<br>GCCTGAACTATTTTATATGCTTTTACAAGACTTGAAATTTTCCTTG<br>CAATAACCGGGTCAATTGTTCTCTTTCTATTGGGCACACATATAAT<br>ACCCAGCAAGTCAGCATCGGAATCTAGAGCACATTCTGCGGCCTCT<br>GTGCTCTGCAAGCCGCAAACTTTCACCAATGGACCAGAACTACCTG<br>TGAAATTAATAACAGACATACTCCAAGCTGCCTTTGTGTGCTTAAT<br>CACGTATACTCACGTGCTCAATAGTCACCAATGCCCTCCCTCTTGG<br>CCCTCTCCTTTTCTTTTTTCGACCGAATTAATTCTTAATCGGCAAAA<br>AAAGAAAAGCTCCGGATCAAGATTGTACGTAAGGTGACAAGCTAT<br>TTTTCAATAAAGAATATCTTCCACTACTGCCATCTGGCGTCATAAC<br>TGCAAAGTACACATATATTACGATGCTGTTCTATTAAATGCTTCCT<br>ATATTATATATATAGTAATGTCGTGATCTATGGTGCACTCTCAGTA<br>CAATCTGCTCTGATGCCGCATAGTTAAGCCAGCCCCGACACCCGCC<br>AACACCCGCTGACGCGCCCTGACGGGCTTGTCTGCTCCCGGCATCC<br>GCTTACAGACAAGCTGTGACCGTCTCCGGGAGCTGCATGTGTCAG<br>AGGTTTTCACCGTCATCACCGAAACGCGCGAGACGAAAGGGCCTC<br>GTGATACGCCTATTTTTATAGGTTAATGTCATGATAATAATGGTTT<br>CTTAGACGGATCGCTTGCCTGTAACTTACACGCGCCTCGTATCTTTT<br>AATGATGGAATAATTTGGGAATTTACTCTGTGTTTATTTATTTTTAT<br>GTTTTGTATTTGGATTTTAGAAAGTAAATAAAGAAGGTAGAAGAG<br>TTACGGAATGAAGAAAAAAAAATAAACAAAGGTTTAAAAAATTTC<br>AACAAAAAGCGTACTTTACATATATATTTATTAGACAAGAAAAGC<br>AGATTAAATAGATATACATTCGATTAACGATAAGTAAAATGTAAA<br>ATCACAGGATTTTCGTGTGTGGTCTTCTACACAGACAAGGTGAAAC<br>AATTCGGCATTAATACCTGAGAGCAGGAAGAGCAAGATAAAAGGT<br>AGTATTTGTTGGCGATCCCCCTAGAGTCTTTTACATCTTCGGAAAA<br>CAAAAACTATTTTTTCTTTAATTTCTTTTTTTACTTTCTATTTTTAAT<br>TTATATATTTATATTAAAAAATTTAAATTATAATTATTTTTATAGCA<br>CGTGATGAAAAGGACCCAGGTGGCACTTTTCGGGGAAATGTGCGC<br>GGAACCCCTATTTGTTTATTTTTCTAAATACATTCAAATATGTATCC<br>GCTCATGAGACAATAACCCTGATAAATGCTTCAATAATATTGAAA<br>AAGGAAGAGTATGAGTATTCAACATTTCCGTGTCGCCCTTATTCCC<br>TTTTTTGCGGCATTTTGCCTTCCTGTTTTTGCTCACCCAGAAACGCT<br>GGTGAAAGTAAAAGATGCTGAAGATCAGTTGGGACGCGTAGTCTA<br>GACCAGCCAGGACAGAAATGCCTCGACTTCGCTGCTACCCAAGGT<br>TGCCGGGTGACGCACACCGTGGAAACGGATGAAGGCACGAACCCA<br>GTGGACATAAGCCTGTTCGGTTCGTAAGCTGTAATGCAAGTAGCGT<br>ATGCGCTCACGCAACTGGTCCAGAACCTTGACCGAACGCAGCGGT<br>GGTAACGGCGCAGTGGCGGTTTTCATGGCTTGTTATGACTGTTTTT<br>TTGGGGTACAGTCTATGCCTCGGGCATCCAAGCAGCAAGCGCGTT<br>ACGCCGTGGGTCGATGTTTGATGTTATGGAGCAGCAACGATGTTAC<br>GCAGCAGGGCAGTCGCCCTAAAACAAAGTTAAACATTATGAGGGA<br>AGCGGTGATCGCCGAAGTATCGACTCAACTATCAGAGGTAGTTGG<br>CGCCATCGAGCGCCATCTCGAACCGACGTTGCTGGCCGTACATTTG<br>TACGGCTCCGCAGTGGATGGCGGCCTGAAGCCACACAGTGATATT<br>GATTTGCTGGTTACGGTGACCGTAAGGCTTGATGAAACAACGCGG<br>CGAGCTTTGATCAACGACCTTTTGGAAACTTCGGCTTCCCCTGGAG<br>AGAGCGAGATTCTCCGCGCTGTAGAAGTCACCATTGTTGTGCACGA<br>CGACATCATTCCGTGGCGTTATCCAGCTAAGCGCGAACTGCAATTT<br>GGAGAATGGCAGCGCAATGACATTCTTGCAGGTATCTTCGAGCCA<br>GCCACGATCGACATTGATCTGGCTATCTTGCTGACAAAAGCAAGA<br>GAACATAGCGTTGCCTTGGTAGGTCCAGCGGCGGAGGAACTCTTT<br>GATCCGGTTCCTGAACAGGATCTATTTGAGGCGCTAAATGAAACCT<br>TAACGCTATGGAACTCGCCGCCCGACTGGGCTGGCGATGAGCGAA<br>ATGTAGTGCTTACGTTGTCCCGCATTTGGTACAGCGCAGTAACCGG<br>CAAAATCGCGCCGAAGGATGTCGCTGCCGGCTGGGCAATGGAGCG<br>CCTGCCGGCCCAGTATCAGCCCGTCATACTTGAAGCTAGACAGGCT<br>TATCTTGGACAAGAAGAGATCGCTTGGCCTCGCGCGCAGATCAG<br>TTGGAAGAATTTGTCCACTACGTGAAAGGCGAGATCACCAAGGTA<br>GTCGGCAAATAACCCTCGAGCATTCAAGGCGCCTTGATTATTTGAC<br>GTGGTTTGATGGCCTCCACGCACGTTGTGATATGTAGATGATTCAG<br>TTCGAGTTTATCATTATCAATACTGCCATTTCAAAGAATACGTAAA<br>TAATTAATAGTAGTGATTTTCCTAACTTTATTTAGTCAAAAAATTA<br>GCCTTTTAATTCTGCTGTAACCCGTACATGCCCAAAATAGGGGCG<br>GGTTACACAGAATATATAACATCGTAGGTGTCTGGGTGAACAGTTT<br>ATTCCTGGCATCCACTAAATATAATGGAGCCCGCTTTTTAAGCTGG<br>CATCCAGAAAAAAAAAGAATCCCAGCACCAAAATATTGTTTTCTTC | | |

TABLE 1-continued example amino acid sequences of DRS-DRR enzymes, split DRS and DRR enzymes, and other nucleotide sequences.

| Sequence | Description | SEQ. ID NO. |
|---|---|---|
| ACCAACCATCAGTTCATAGGTCCATTCTCTTAGCGCAACTACAGAG AACAGGGGCACAAACAGGCAAAAAACGGGCACAACCTCAATGGA GTGATGCAACCTGCCTGGAGTAAATGATGACACAAGGCAATTGAC CCACGCATGTATCTATCTCATTTTCTTACACCTTCTATTACCTTCTG CTCTCTCTGATTTGGAAAAAGCTGAAAAAAAAGGTTGAAACCAGT TCCCTGAAATTATTCCCCTACTTGACTAATAAGTATATAAAGACGG TAGGTATTGATTGTAATTCTGTAAATCTATTTCTTAAACTTCTTAAA TTCTACTTTTATAGTTAGTCTTTTTTTTAGTTTTAAAACACCAAGAA CTTAGTTTCGAATAAACACACATAAACAAACAAAATGGAACTTCA GTACTTCTCCTATTTTCAACCCACTTCATCTGTCGTAGCCCTACTAC TAGCACTAGTGAGTATTTTATTTAGCGTAGTTGTTTTGAGGAAGAC TTTCAGTAACAATTACTCCAGCCCCGCGTCAAGTACGGAAACCGCT GTGCTGTGTCATCAGAGGCAACAGAGTTGCGCCCTACCTATCAGCG GCCTTCTTCACGTGTTCATGAATAAGAACGGCCTGATTCATGTCAC CTTGGGAAATATGGCTGACAAATATGGCCCTATCTTCAGTTTTCCG ACAGGCAGCCACCGTACTTTAGTAGTCAGTTCCTGGGAAATGGTG AAAGAGTGTTTCACCGGTAATAACGACACGGCATTCTCCAACAGA CCAATCCCTTTGGCTTTTCAAACCATATTCTACGCCTGTGGCGGCA TTGATTCTTACGGTTTAAGTAGTGTCCCGTATGGTAAATACTGGAG GGAGTTGAGAAAGGTGTGTGTTCACAACCTGCTGAGTAATCAGCA ATTGCTGAAGTTCAGACATCTTATAATCTCCCAAGTGGATACGTCT TTTAACAAGTTGTATGAGCTGTGTAAGAACTCTGAAGATAATCAAG GTATGGTAAGGATGGATGATTGGCTAGCTCAACTTTCCTTTAACGT CATCGGTAGGATCGTTTGCGGATTCCAGTCTGACCCAAAGACGGGT GCACCTTCAAGGGTAGAACAGTTTAAGGAAGTCATAAATGAGGCG TCATATTTTATGTCAACAAGTCCAGTCTCCGATAACGTACCAATGT TGGGATGGATCGACCAATTGACCGGTCTGACGAGGAACATGAAGC ATTGTGGGAAGAAGCTTGACTTAGTAGTGGAGTCAATTATCAAGG ACCATAGGCAAAAGAGACGTTTTTCACGTACAAAAGGTGGCGATG AGAAGGATGACGAACAGGACGACTTTATTGATATTTGCTTGAGCA TCATGGAGCAGCCACAGTTGCCCGGGAACAATTCTCCCCCTCAAAT TCCGATCAAATCTATCGTGCTAGACATGATTGGGGGTGGTACCGAC ACTACGAAACTTACAACCATATGGACCCTATCACTTTTGTTGAACA ATCCTCACGTGTTAGATAAAGCTAAACAAGAGGTCGACGCTCACTT TCGTAAAAGAGAAGATCAACAGATGACGCAGCAGCGGCAGTCGT TGATTTTGACGACATAAGAAATTTAGTATACATCCAAGCCATCATT AAAGAAAGTATGAGGCTTTATCCAGCCAGCCCGGTGGTTGAGCGT CTTTCCGGCGAGGATTGCGTTGTTGGAGGTTTTCACGTGCCTGCTG GTACGAGACTATGGGCTAACGTTTGGAAGATGCAAAGAGATCCCA AAGTTTGGGACGATCCTCTAGTATTCAGACCTGAAAGGTTTTTGAG CGACGAGCAAAAGATGGTAGACGTTCGTGGCCAAAACTATGAACT TCTGCCATTCGGCGCAGGAAGAAGAATCTGTCCAGGCGTTTCCTTT AGTCTTGACCTTATGCAACTTGTCCTAACCAGGTTAATCCTAGAGT TCGAAATGAAGTCCCCGTCCGGCAAGGTAGATATGACCGCAACTC CAGGACTAATGTCTTACAAGGTGGTTCCATTGGACATATTGCTGAC TCACCGTCGTATCAAGTCATGCGTTCAATTGGCGTCTTCTGAACGT GATATGGAAAGTTCTGGGGTGCCTGTGATCACATTGTCCTCAGGTA AAGTAATGCCCGTACTGGGCATGGGAACCTTCGAAAAGGTGGGTA AGGGGTCTGAACGTGAGCGTTTAGCCATTCTTAAAGCGATCGAAG TTGGTTACCGTTACTTTGATACCGCAGCGGCATATGAAACGGAAGA AGTTCTAGGGGAAGCCATTGCTGAAGCTTTACAATTGGGTCTGATA GAGAGCCGTGACGAGCTGTTCATCAGCTCAATGCTTTGGTGCACCG ACGCACATCCAGACCGTGTGCTACTTGCTCTGCAAAACAGTCTGAG AAATCTAAAACTTGAATATCTAGACCTATATATGTTGCCGTTTCCT GCCAGCCTTAAGCCGGGCAAAATTACGATGGATATTCCTGAGGAG GATATTTGCCGTATGGATTATCGTTCAGTCTGGAGCGCCATGGAAG AGTGTCAAAACTTAGGATTTACTAAAAGTATTGGTGTAAGCAACTT TTCTTGCAAGAAATTACAAGAATTAATGGCCACTGCAAATATCCCG CCCGCGGTAAATCAAGTAGAGATGTCACCAGCTTTCCAACAGAAA AAACTGAGGGAATATTGTAACGCAAACAACATATTGGTATCCGCA GTAAGCATTCTGGGATCAAACGGGACGCCCTGGGGTAGTAATGCT GTTCTTGGAAGCGAAGTTTTGAAACAGATCGCGATGGCGAAAGGC AAAAGCGTTGCGCAAGTCAGTATGAGGTGGGTCTATGAGCAGGGC GCGTCTTTAGTAGTCAAGAGTTTCTCTGAAGAACGTTTAAGAGAAA ACCTGAATATTTTGACTGGGAGCTTACGAAAGAAGACAATGAGA AGATAGGCGAAATCCCGCAATGTAGAATCCTTACTGCGTACTTCCT TGTCTCCCCGAACGGCCCGTTTAAATCTCAGGAAGAGCTTTGGGAT GACAAGGCAtaaACAGGCCCCTTTTCCTTTGTCGATATCATGTAATT AGTTATGTCACGCTTACATTCACGCCCTCCTCCCACATCCGCTCTA ACCGAAAAGGAAGGAGTTAGACAACCTGAAGTCTAGGTCCCTATT TATTTTTTTAATAGTTATGTTAGTATTAAGAACGTTATTTATATTT CAAATTTTTCTTTTTTTCTGTACAAACGCGTGTACGCATGTAACAT TATACTGAAAACCTTGCTTGAGAAGGTTTTGGGACGCTCGAAGGCT TTAATTTGTAATCATTATCACTTTACGGGTCCTTTCCGGTGATCCGA | | |

TABLE 1-continued example amino acid sequences of DRS-DRR enzymes, split DRS and DRR enzymes, and other nucleotide sequences.

| Sequence | Description | SEQ. ID NO. |
|---|---|---|
| CAGGTTACGGGGCGGCGACCTCGCGGGTTTTCGCTATTTATGAAAA<br>TTTTCCGGTTTAAGGCGTTTCCGTTCTTCTTCGTCATAACTTAATGT<br>TTTTATTTAAAATACCTCGCGAGTGGCAACACTGAAAATACCCATG<br>GAGCGGCGTAACCGTCGCACAGgatctaggtgaagatcctttttgata<br>atctcatgaccaaaatcccttaacgtgagttttcgttccactgagcgt<br>cagaccccgtagaaaagatcaaaggatcttcttgagatccttttttc<br>tgcgcgtaatctgctgcttgcaaacaaaaaaaccaccgctaccagcgg<br>tggtttgtttgccggatcaagagctaccaactcttttccgaaggtaa<br>ctggcttcagcagagcgcagataccaaatactgtccttctagtgtagc<br>cgtagttaggccaccacttcaagaactctgtagcaccgcctacatacc<br>tcgctctgctaatcctgttaccagtggctgctgccagtggcgataagt<br>cgtgtcttaccgggttggactcaagacgatagttaccggataaggcgc<br>agcggtcgggctgaacgggggttcgtgcacacagcccagcttggagc<br>gaacgacctacaccgaactgagatacctacagcgtgagctatgagaaa<br>gcgccacgcttcccgaagggagaaaggcggacaggtatccggtaagcg<br>gcagggtcggaacaggagagcgcacgagggagcttccaggggggaaacg<br>cctggtatctttatagtcctgtcgggtttcgccacctctgacttgagc<br>gtcgattttgtgatgctcgtcaggggggcggagcctatggaaaaacg<br>ccagcaacgcggcagtggaacgTGCATTATGAATTAGTTACGCTAGGG<br>ATAACAGGGTAATATAGAACCCGAACGACCGAGCGCAGCGGCGGCCGC<br>GCTGATACCGCCGC | | |
| CCTCGCCGCAGTTAATTAAAGTCAGTGAGCGAGGAAGCGCGTAAC<br>TATAACGGTCCTAAGGTAGCGAATCCTGATGCGGTATTTTCTCCTT<br>ACGCATCTGTGCGGTATTTCACACCGCATAGATCGGCAAGTGCACA<br>AACAATACTTAAATAAATACTACTCAGTAATAACCTATTTCTTAGC<br>ATTTTTGACGAAATTTGCTATTTTGTTAGAGTCTTTTACACCATTTG<br>TCTCCACACCTCCGCTTACATCAACACCAATAACGCCATTTAATCT<br>AAGCGCATCACCAACATTTTCTGGCGTCAGTCCACCAGCTAACATA<br>AAATGTAAGCTTTCGGGGCTCTCTTGCCTTCCAACCCAGTCAGAAA<br>TCGAGTTCCAATCCAAAAGTTCACCTGTCCCACCTGCTTCTGAATC<br>AAACAAGGGAATAAACGAATGAGGTTTCTGTGAAGCTGCACTGAG<br>TAGTATGTTGCAGTCTTTTGGAAATACGAGTCTTTTAATAACTGGC<br>AAACCGAGGAACTCTTGGTATTCTTGCCACGACTCATCTCCATGCA<br>GTTGGACGATATCAATGCCGTAATCATTGACCAGAGCCAAAACAT<br>CCTCCTTAAGTTGATTACGAAACACGCCAACCAAGTATTTCGGAGT<br>GCCTGAACTATTTTTATATGCTTTTACAAGACTTGAAATTTTCCTTG<br>CAATAACCGGGTCAATTGTTCTCTTTCTATTGGGCACACATATAAT<br>ACCCAGCAAGTCAGCATCGGAATCTAGAGCACATTCTGCGGCCTCT<br>GTGCTCTGCAAGCCGCAAACTTTCACCAATGGACCAGAACTACCTG<br>TGAAATTAATAACAGACATACTCCAAGCTGCCTTTGTGTGCTTAAT<br>CACGTATACTCACGTGCTCAATAGTCACCAATGCCCTCCCTCTTGG<br>CCCTCTCCTTTTCTTTTTTCGACCGAATTAATTCTTAATCGGCAAAA<br>AAAGAAAAGCTCCGGATCAAGATTGTACGTAAGGTGACAAGCTAT<br>TTTTCAATAAAGAATATCTTCCACTACTGCCATCTGGCGTCATAAC<br>TGCAAAGTACACATATATTACGATGCTGTTCTATTAAATGCTTCCT<br>ATATTATATATAGTAATGTCGTGATCTATGGTGCACTCTCAGTA<br>CAATCTGCTCTGATGCCGCATAGTTAAGCCAGCCCCGACACCCGCC<br>AACACCCGCTGACGCGCCCTGACGGGCTTGTCTGCTCCCGGCATCC<br>GCTTACAGACAAGCTGTGACCGTCTCCGGGAGCTGCATGTGTCAG<br>AGGTTTTCACCGTCATCACCGAAACGCGCGAGACGAAAGGGCCTC<br>GTGATACGCCTATTTTTATAGGTTAATGTCATGATAATAATGGTTT<br>CTTAGACGGATCGCTTGCCTGTAACTTACACGCGCCTCGTATCTTTT<br>AATGATGGAATAATTTGGGAATTTACTCTGTGTTTATTTATTTTTAT<br>GTTTTGTATTTGGATTTTAGAAAGTAAATAAAGAAGGTAGAAGAG<br>TTACGGAATGAAGAAAAAAAAATAAACAAAGGTTTAAAAAATTTC<br>AACAAAAAGCGTACTTTACATATATATTTATTAGACAAGAAAAGC<br>AGATTAAATAGATATACATTCGATTAACGATAAGTAAAATGTAAA<br>ATCACAGGATTTTCGTGTGTGGTCTTCTACACAGACAAGGTGAAAC<br>AATTCGGCATTAATACCTGAGAGCAGGAAGAGCAAGATAAAAGGT<br>AGTATTTGTTGGCGATCCCCCTAGAGTCTTTTACATCTTCGGAAAA<br>CAAAAACTATTTTTTCTTTAATTTCTTTTTTTACTTTCTATTTTTAAT<br>TTATATATTTATATTAAAAAATTTAAATTATAATTATTTTTATAGCA<br>CGTGATGAAAAGGACCCAGGTGGCACTTTTCGGGGAAATGTGCGC<br>GGAACCCCTATTTGTTTATTTTTCTAAATACATTCAAATATGTATCC<br>GCTCATGAGACAATAACCCTGATAAATGCTTCAATAATATTGAAA<br>AAGGAAGAGTATGAGTATTCAACATTTCCGTGTCGCCCTTATTCCC<br>TTTTTTGCGGCATTTTGCCTTCCTGTTTTTGCTCACCCAGAAACGCT<br>GGTGAAAGTAAAAGATGCTGAAGATCAGTTGGGACGCGTAGTCTA<br>GACCAGCCAGGACAGAAATGCCTCGACTTCGCTGCTACCCAAGGT<br>TGCCGGGTGACGCACACCGTGGAAACGGATGAAGGCACGAACCCA<br>GTGGACATAAGCCTGTTCGGTTCGTAAGCTGTAATGCAAGTAGCGT<br>ATGCGCTCACGCAACTGGTCCAGAACCTTGACCGAACGCAGCGGT<br>GGTAACGGCGCAGTGGCGGTTTTCATGGCTTGTTATGACTGTTTTT | pDW18 | SEQ. ID NO. 25 |

TABLE 1-continued example amino acid sequences of DRS-DRR enzymes, split DRS and DRR enzymes, and other nucleotide sequences.

| Sequence | Description | SEQ. ID NO. |
|---|---|---|
| TTGGGGTACAGTCTATGCCTCGGGCATCCAAGCAGCAAGCGCGTT ACGCCGTGGGTCGATGTTTGATGTTATGGAGCAGCAACGATGTTAC GCAGCAGGGCAGTCGCCCTAAAACAAAGTTAAACATTATGAGGGA AGCGGTGATCGCCGAAGTATCGACTCAACTATCAGAGGTAGTTGG CGCCATCGAGCGCCATCTCGAACCGACGTTGCTGGCCGTACATTTG TACGGCTCCGCAGTGGATGGCGGCCTGAAGCCACACAGTGATATT GATTTGCTGGTTACGGTGACCGTAAGGCTTGATGAAACAACGCGG CGAGCTTTGATCAACGACCTTTTGGAAACTTCGGCTTCCCCTGGAG AGAGCGAGATTCTCCGCGCTGTAGAAGTCACCATTGTTGTGCACGA CGACATCATTCCGTGGCGTTATCCAGCTAAGCGCGAACTGCAATTT GGAGAATGGCAGCGCAATGACATTCTTGCAGGTATCTTCGAGGCCA GCCACGATCGACATTGATCTGGCTATCTTGCTGACAAAAGCAAGA GAACATAGCGTTGCCTTGGTAGGTCCAGCGGCGGAGGAACTCTTT GATCCGGTTCCTGAACAGGATCTATTTGAGGCGCTAAATGAAACCT TAACGCTATGGAACTCGCCGCCCGACTGGGCTGGCGATGAGCGAA ATGTAGTGCTTACGTTGTCCCGCATTTGGTACAGCGCAGTAACCGG CAAAATCGCGCCGAAGGATGTCGCTGCCGGCTGGGCAATGGAGCG CCTGCCGGCCCAGTATCAGCCCGTCATACTTGAAGCTAGACAGGCT TATCTTGGACAAGAAGAAGATCGCTTGGCCTCGCGCGCAGATCAG TTGGAAGAATTTGTCCACTACGTGAAAGGCGAGATCACCAAGGTA GTCGGCAAATAACCCTCGAGCATTCAAGGCGCCTTGATTATTTGAC GTGGTTTGATGGCCTCCACGCACGTTGTGATATGTAGATGAGAGCG TTGGTTGGTGGATCAAGCCCACGCGTAGGCAATCCTCGAGCAGAT CCGCCAGGCGTGTATATATAGCGTGGATGGCCAGGCAACTTTAGT GCTGACACATACAGGCATATATATATGTGTGCGACGACACATGAT CATATGGCATGCATGTGCTCTGTATGTATATAAAACTCTTGTTTTCT TCTTTTCTCTAAATATTCTTTCCTTATACATTAGGACCTTTGCAGCA TAAATTACTATACTTCTATAGACACACAAACACAAATACACACACT AAATTAATAATGGAACTTCAGTACTTCTCCTATTTTCAACCCACTTC ATCTGTCGTAGCCCTACTACTAGCACTAGTGAGTATTTTATTTAGC GTAGTTGTTTTGAGGAAGACTTTCAGTAACAATTACTCCAGCCCCG CGTCAAGTACGGAAACCGCTGTGCTGTGTCATCAGAGGCAACAGA GTTGCGCCCTACCTATCAGCGGCCTTCTTCACGTGTTCATGAATAA GAACGGCCTGATTCATGTCACCTTGGGAAATATGGCTGACAAATAT GGCCCTATCTTCAGTTTTCCGACAGGCAGCCACCGTACTTTAGTAG TCAGTTCCTGGGAAATGGTGAAAGAGTGTTTCACCGGTAATAACG ACACGGCATTCTCCAACAGACCAATCCCTTTGGCTTTTCAAACCAT ATTCTACGCCTGTGGCGGCATTGATTCTTACGGTTTAAGTAGTGTC CCGTATGGTAAATACTGGAGGGAGTTGAGAAAGGTGTGTGTTCAC AACCTGCTGAGTAATCAGCAATTGCTGAAGTTCAGACATCTTATAA TCTCCCAAGTGGATACGTCTTTTAACAAGTTGTATGAGCTGTGTAA GAACTCTGAAGATAATCAAGGTATGGTAAGGATGGATGATTGGCT AGCTCAACTTTCCTTTAACGTCATCGGTAGGATCGTTTGCGGATTC CAGTCTGACCCAAAGACGGGTGCACCTTCAAGGGTAGAACAGTTT AAGGAAGTCATAAATGAGGCGTCATATTTTATGTCAACAAGTCCA GTCTCCGATAACGTACCAATGTTGGGATGGATCGACCAATTGACCG GTCTGACGAGGAACATGAAGCATTGTGGGAAGAAGCTTGACTTAG TAGTGGAGTCAATTATCAAGGACCATAGGCAAAAGAGACGTTTTT CACGTACAAAAGGTGGCGATGAGAAGGATGACGAACAGGACGAC TTTATTGATATTTGCTTGAGCATCATGGAGCAGCCACAGTTGCCCG GGAACAATTCTCCCCCTCAAATTCCGATCAAATCTATCGTGCTAGA CATGATTGGGGGTGGTACCGACACTACGAAACTTACAACCATATG GACCCTATCACTTTTGTTGAACAATCCTCACGTGTTAGATAAAGCT AAACAAGAGGTCGACGCTCACTTTCGTAAAAAGAGAAGATCAACA GATGACGCAGCAGCGGCAGTCGTTGATTTTGACGACATAAGGAAAT TTAGTATACATCCAAGCCATCATTAAAGAAAGTATGAGGCTTTATC CAGCCAGCCCGGTGGTTGAGCGTCTTTCCGGCGAGGATTGCGTTGT TGGAGGTTTTCACGTGCCTGCTGGTACGAGACTATGGGCTAACGTT TGGAAGATGCAAAGAGATCCCAAAGTTTGGGACGATCCTCTAGTA TTCAGACCTGAAAGGTTTTTGAGCGACGAGCAAAAGATGGTAGAC GTTCGTGGCCAAAACTATGAACTTCTGCCATTCGGCGCAGGAAGA AGAATCTGTCCAGGCGTTTCCTTTAGTCTTGACCTTATGCAACTTGT CCTAACCAGGTTAATCCTAGAGTTCGAAATGAAGTCCCCGTCCGGC AAGGTAGATATGACCGCAACTCCAGGACTAATGTCTTACAAGGTG GTTCCATTGGACATATTGCTGACTCACCGTCGTATCAAGTCATGCG TTCAATTGGCGTCTTCTGAACGTGATATGGAAAGTTCTGGGGTGCC TGTGATCACATTGTCCTCAGGTAAAGTAATGCCCGTACTGGGCATG GGAACCTTCGAAAAGGTGGGTAAGGGGTCTGAACGTGAGCGTTTA GCCATTCTTAAAGCGATCGAAGTTGGTTACCGTTACTTTGATACCG CAGCGGCATATGAAACGGAAGAAGTTCTAGGGGAAGCCATTGCTG AAGCTTTACAATTGGGTCTGATAGAGAGCCGTGACGAGCTGTTCAT CAGCTCAATGCTTTGGTGCACCGACGCACATCCGACCGTGTGCTA CTTGCTCTGCAAAACAGTCTGAGAAATCTAAAACTTGAATATCTAG ACCTATATATGTTGCCGTTTCCTGCCAGCCTTAAGCCGGGCAAAAT | | |

TABLE 1-continued example amino acid sequences of DRS-DRR enzymes, split DRS and DRR enzymes, and other nucleotide sequences.

| Sequence | Description | SEQ. ID NO. |
|---|---|---|
| TACGATGGATATTCCTGAGGAGGATATTTGCCGTATGGATTATCGT<br>TCAGTCTGGAGCGCCATGGAAGAGTGTCAAAACTTAGGATTTACT<br>AAAAGTATTGGTGTAAGCAACTTTTCTTGCAAGAAATTACAAGAAT<br>TAATGGCCACTGCAAATATCCCGCCCGCGGTAAATCAAGTAGAGA<br>TGTCACCAGCTTTCCAACAGAAAAAACTGAGGGAATATTGTAACG<br>CAAACAACATATTGGTATCCGCAGTAAGCATTCTGGGATCAAACG<br>GGACGCCCTGGGGTAGTAATGCTGTTCTTGGAAGCGAAGTTTTGAA<br>ACAGATCGCGATGGCGAAAGGCAAAAGCGTTGCGCAAGTCAGTAT<br>GAGGTGGGTCTATGAGCAGGGCGCGTCTTTAGTAGTCAAGAGTTTC<br>TCTGAAGAACGTTTAAGAGAAAACCTGAATATTTTTGACTGGGAG<br>CTTACGAAAGAAGACAATGAGAAGATAGGCGAAATCCCGCAATGT<br>AGAATCCTTACTGCGTACTTCCTTGTCTCCCCGAACGGCCCGTTTA<br>AATCTCAGGAAGAGCTTTGGGATGACAAGGCAtaaACAGGCCCCTTT<br>TCCTTTGTCGATATCATGTAATTAGTTATGTCACGCTTACATTCACG<br>CCCTCCTCCCACATCCGCTCTAACCGAAAAGGAAGGAGTTAGACA<br>ACCTGAAGTCTAGGTCCCTATTTATTTTTTTAATAGTTATGTTAGT<br>ATTAAGAACGTTATTTATATTTCAAATTTTTCTTTTTTTTCTGTACA<br>AACGCGTGTACGCATGTAACATTATACTGAAAACCTTGCTTGAGAA<br>GGTTTTGGGACGCTCGAAGGCTTTAATTTGTAATCATTATCACTTTT<br>ACGGGTCCTTTCCGGTGATCCGACAGGTTACGGGGCGGCGACCTC<br>GCGGGTTTTCGCTATTTATGAAAATTTTCCGGTTTAAGGCGTTTCCG<br>TTCTTCTTCGTCATAACTTAATGTTTTTATTTAAAATACCTCGCGAG<br>TGGCAACACTGAAAATACCCATGGAGCGGCGTAACCGTCGCACAG<br>gatctaggtgaagatccttttgataatctcatgaccaaaatcccttaacgtgagttttcgttccactgagcgtcagaccccgtagaaaagatcaaaggatcttcttgagatcctttttttctgcgcgtaatctgctgcttgcaaacaaaaaaaccaccgctaccagcggtggtttgtttgccggatcaagagctaccaactctttttccgaaggtaactggcttcagcagagcgcagataccaaatactgtccttctagtgtagccgtagttaggccaccacttcaagaactctgtagcaccgcctacatacctcgctctgctaatcctgttaccagtggctgctgccagtggcgataagtcgtgtcttaccgggttggactcaagacgatagttaccggataaggcgcagcggtcgggctgaacggggttcgtgcacacagcccagcttggagcgaacgacctacaccgaactgagatacctacagcgtgagctatgagaaagcgccacgcttcccgaagggagaaaggcggacaggtatccggtaagcggcagggtcggaacaggagagcgcacgagggagcttccaggggaaacgcctggtatctttatagtcctgtcgggtttcgccacctctgacttgagcgtcgatttttgtgatgctcgtcaggggggcggagcctatggaaaaacgccagcaacgcggcagtggaacgTGCATTATGAATTAGTTACGCTAGGGATAACAGGGTAATATAGAACCCGAACGACCGAGCGCAGCGGCGGCCGCGCTGATACCGCCGC | | |
| CCTCGCCGCAGTTAATTAAAGTCAGTGAGCGAGGAAGCGCGTAACTATAACGGTCCTAAGGTAGCGAATCCTGATGCGGTATTTTCTCCTTACGCATCCTGTGCGGTATTTCACACCGCATAGATCGGCAAGTGCACAAACAATACTTAAATAAATACTACTCAGTAATAACCTATTTCTTAGCATTTTTTGACGAAATTTGCTATTTTGTTAGAGTCTTTTACACCATTTGTCTCCACACCTCCGCTTACATCAACACCAATAACGCCATTTAATCTAAGCGCATCACCAACATTTTCTGGCGTCAGTCCACCAGCTAACATAAAATGTAAGCTTTCGGGGCTCTCTTGCCTTCCAACCCAGTCAGAAATCGAGTTCCAATCCAAAAGTTCACCTGTCCCACCTGCTTCTGAATCAAACAAGGGAATAAACGAATGAGGTTTCTGTGAAGCTGCACTGAGTAGTATGTTGCAGTCTTTTGGAAATACGAGTCTTTTAATAACTGGCAAACCGAGGAACTCTTGGTATTCTTGCCACGACTCATCTCCATGCAGTTGGACGATATCAATGCCGTAATCATTGACCAGAGCCAAAACATCCTCCTTAAGTTGATTACGAAACACGCCAACCAAGTATTTCGGAGTGCCTGAACTATTTTTATATGCTTTTACAAGACTTGAAATTTTCCTTGCAATAACCGGGTCAATTGTTCTCTTTCTATTGGGCACACATATAATACCCAGCAAGTCAGCATCGGAATCTAGAGCACATTCTGCGGCCTCTGTGCTCTGCAAGCCGCAAACTTTCACCAATGGACCAGAACTACCTGTGAAATTAATAACAGACATACTCCAAGCTGCCTTTGTGTGCTTAATCACGTATACTCACGTGCTCAATAGTCACCAATGCCCTCCCTCTTGGCCCTCTCCTTTTCTTTTTTCGACCGAATTAATTCTTAATCGGCAAAAAAAGAAAAGCTCCGGATCAAGATTGTACGTAAGGTGACAAGCTATTTTTCAATAAAGAATATCTTCCACTACTGCCATCTGGCGTCATAACTGCAAAGTACACATATATTACGATGCTGTTCTATTAAATGCTTCCTATATTATATATATAGTAATGTCGTGATCTATGGTGCACTCTCAGTACAATCTGCTCTGATGCCGCATAGTTAAGCCAGCCCCGACACCCGCCAACACCCGCTGACGCGCCCTGACGGGCTTGTCTGCTCCCGGCATCCGCTTACAGACAAGCTGTGACCGTCTCCGGGAGCTGCATGTGTCAGAGGTTTTCACCGTCATCACCGAAACGCGCGAGACGAAAGGGCCTCGTGATACGCCTATTTTTATAGGTTAATGTCATGATAATAATGGTTTCTTAGACGGATCGCTTGCCTGTAACTTACACGCGCCTCGTATCTTTTAATGATGGAATAATTTGGGAATTTACTCTGTGTTTATTTATTTTTATGTTTTGTATTTGGATTTTAGAAAGTAAATAAAGAAGGTAGAAGAG | pDW21 | SEQ. ID NO. 26 |

TABLE 1-continued example amino acid sequences of DRS-DRR enzymes, split DRS and DRR enzymes, and other nucleotide sequences.

| Sequence | Description | SEQ. ID NO. |
|---|---|---|
| TTACGGAATGAAGAAAAAAAAATAAACAAAGGTTTAAAAAATTTC AACAAAAAGCGTACTTTACATATATATTTATTAGACAAGAAAAGC AGATTAAATAGATATACATTCGATTAACGATAAGTAAAATGTAAA ATCACAGGATTTTCGTGTGTGGTCTTCTACACAGACAAGGTGAAAC AATTCGGCATTAATACCTGAGAGCAGGAAGAGCAAGATAAAAGGT AGTATTTGTTGGCGATCCCCCTAGAGTCTTTTACATCTTCGGAAAA CAAAAACTATTTTTTCTTTAATTTCTTTTTTTACTTTCTATTTTTAAT TTATATATTTATATTAAAAAATTTAAATTATAATTATTTTTATAGCA CGTGATGAAAAGGACCCAGGTGGCACTTTTCGGGGAAATGTGCGC GGAACCCCTATTTGTTTATTTTTCTAAATACATTCAAATATGTATCC GCTCATGAGACAATAACCCTGATAAATGCTTCAATAATATTGAAA AAGGAAGAGTATGAGTATTCAACATTTCCGTGTCGCCCTTATTCCC TTTTTTGCGGCATTTTGCCTTCCTGTTTTTGCTCACCCAGAAACGCT GGTGAAAGTAAAAGATGCTGAAGATCAGTTGGGACGCGTAGTCTA GACCAGCCAGGACAGAAATGCCTCGACTTCGCTGCTACCCAAGGT TGCCGGGTGACGCACACCGTGGAAACGGATGAAGGCACGAACCCA GTGGACATAAGCCTGTTCGGTTCGTAAGCTGTAATGCAAGTAGCGT ATGCGCTCACGCAACTGGTCCAGAACCTTGACCGAACGCAGCGGT GGTAACGGCGCAGTGGCGGTTTTCATGGCTTGTTATGACTGTTTTT TTGGGGTACAGTCTATGCCTCGGGCATCCAAGCAGCAAGCGCGTT ACGCCGTGGGTCGATGTTTGATGTTATGGAGCAGCAACGATGTTAC GCAGCAGGGCAGTCGCCCTAAAACAAAGTTAAACATTATGAGGGA AGCGGTGATCGCCGAAGTATCGACTCAACTATCAGAGGTAGTTGG CGCCATCGAGCGCCATCTCGAACCGACGTTGCTGGCCGTACATTTG TACGGCTCCGCAGTGGATGGCGGCCTGAAGCCACACAGTGATATT GATTTGCTGGTTACGGTGACCGTAAGGCTTGATGAAACAACGCGG CGAGCTTTGATCAACGACCTTTTGGAAACTTCGGCTTCCCCTGGAG AGAGCGAGATTCTCCGCGCTGTAGAAGTCACCATTGTTGTGCACGA CGACATCATTCCGTGGCGTTATCCAGCTAAGCGCGAACTGCAATTT GGAGAATGGCAGCGCAATGACATTCTTGCAGGTATCTTCGAGCCA GCCACGATCGACATTGATCTGGCTATCTTGCTGACAAAAGCAAGA GAACATAGCGTTGCCTTGGTAGGTCCAGCGGCGGAGGAACTCTTT GATCCGGTTCCTGAACAGGATCTATTTGAGGCGCTAAATGAAACCT TAACGCTATGGAACTCGCCGCCCGACTGGGCTGGCGATGAGCGAA ATGTAGTGCTTACGTTGTCCCGCATTTGGTACAGCGCAGTAACCGG CAAAATCGCGCCGAAGGATGTCGCTGCCGGCTGGGCAATGGAGCG CCTGCCGGCCCAGTATCAGCCCGTCATACTTGAAGCTAGACAGGCT TATCTTGGACAAGAAGAAGATCGCTTGGCCTCGCGCGCAGATCAG TTGGAAGAATTTGTCCACTACGTGAAAGGCGAGATCACCAAGGTA GTCGGCAAATAACCCTCGAGCATTCAAGGCGCCTTGATTATTTGAC GTGGTTTGATGGCCTCCACGCACGTTGTGATATGTAGATGAGAGCG TTGGTTGGTGGATCAAGCCCACGCGTAGGCAATCCTCGAGCAGAT CCGCCAGGCGTGTATATATAGCGTGGATGGCCAGGCAACTTTAGT GCTGACACATACAGGCATATATATATGTGTGCGACGACACATGAT CATATGGCATGCATGTGCTCTGTATGTATATAAAACTCTTGTTTTCT TCTTTTTCTCTAAATATTCTTTCCTTATACATTAGGACCTTTGCAGCA TAAATTACTATACTTCTATAGACACACAAACACAAATACACACACT AAATTAATAATGGAACTTCAGTACTTCTCCTATTTTCAACCCACTTC ATCTGTCGTAGCCCTACTACTAGCACTAGTGAGTATTTTATTTAGC GTAGTTGTTTTGAGGAAGACTTTCAGTAACAATTACTCCAGCCCCG CGTCAAGTACGGAAACCGCTGTGCTGTGTCATCAGAGGCAACAGA GTTGCGCCCTACCTATCAGCGGCCTTCTTCACGTGTTCATGAATAA GAACGGCCTGATTCATGTCACCTTGGGAAATATGGCTGACAAATAT GGCCCTATCTTCAGTTTTCCGACAGGCAGCCACCGTACTTTAGTAG TCAGTTCCTGGGAAATGGTGAAAGAGTGTTTCACCGGTAATAACG ACACGGCATTCTCCAACAGACCAATCCCTTTGGCTTTTCAAACCAT ATTCTACGCCTGTGGCGGCATTGATTCTTACGGTTTAAGTAGTGTC CCGTATGGTAAATACTGGAGGGAGTTGAGAAAGGTGTGTGTTCAC AACCTGCTGAGTAATCAGCAATTGCTGAAGTTCAGACATCTTATAA TCTCCCAAGTGGATACGTCTTTTAACAAGTTGTATGAGCTGTGTAA GAACTCTGAAGATAATCAAGGTATGGTAAGGATGGATGATTGGCT AGCTCAACTTTCCTTTAACGTCATCGGTAGGATCGTTTGCGGATTC CAGTCTGACCCAAAGACGGGTGCACCTTCAAGGGTAGAACAGTTT AAGGAAGTCATAAATGAGGCGTCATATTTTATGTCAACAAGTCCA GTCTCCGATAACGTACCAATGTTGGGATGGATCGACCAATTGACCG GTCTGACGAGGAACATGAAGCATTGTGGGAAGAAGCTTGACTTAG TAGTGGAGTCAATTATCAAGGACCATAGGCAAAAGAGACGTTTTT CACGTACAAAAGGTGGCGATGAGAAGGATGACGAACAGGACGAC TTTATTGATATTTGCTTGAGCATCATGGAGCAGCCACAGTTGCCCG GGAACAATTCTCCCCCTCAAATTCCGATCAAATCTATCGTGCTAGA CATGATTGGGGGTGGTACCGACACTACGAAACTTACAACCATATG GACCCTATCACTTTTGTTGAACAATCCTCACGTGTTAGATAAAGCT AAACAAGAGGTCGACGCTCACTTTCGTAAAAAGAGAAGATCAACA GATGACGCAGCAGCGGCAGTCGTTGATTTTGACGACATAAGAAAT | | |

TABLE 1-continued example amino acid sequences of DRS-DRR enzymes, split DRS and DRR enzymes, and other nucleotide sequences.

| Sequence | Description | SEQ. ID NO. |
|---|---|---|
| TTAGTATACATCCAAGCCATCATTAAAGAAAGTATGAGGCTTTATC<br>CAGCCAGCCCGGTGGTTGAGCGTCTTTCCGGCGAGGATTGCGTTGT<br>TGGAGGTTTTCACGTGCCTGCTGGTACGAGACTATGGGCTAACGTT<br>TGGAAGATGCAAAGAGATCCCAAAGTTTGGGACGATCCTCTAGTA<br>TTCAGACCTGAAAGGTTTTTGAGCGACGAGCAAAAGATGGTAGAC<br>GTTCGTGGCCAAAACTATGAACTTCTGCCATTCGGCGCAGGAAGA<br>AGAATCTGTCCAGGCGTTTCCTTTAGTCTTGACCTTATGCAACTTGT<br>CCTAACCAGGTTAATCCTAGAGTTCGAAATGAAGTCCCCGTCCGGC<br>AAGGTAGATATGACCGCAACTCCAGGACTAATGTCTTACAAGGTG<br>GTTCCATTGGACATATTGCTGACTCACCGTCGTATCAAGTCATGCG<br>TTCAATTGGCGTCTTCTGAACGTGATtaaGCGAATTTCTTATGATTTA<br>TGATTTTTATTATTAAATAAGTTATAAAAAAAATAAGTGTATACAA<br>ATTTTAAAGTGACTCTTAGGTTTTAAAACGAAAATTCTTATTCTTG<br>AGTAACTCTTTCCTGTAGGTCAGGTTGCTTTCTCAGGTACATAGCTT<br>CAAAATGTTTCTACTCCTTTTTTACTCTTCCAGATTTTCTCGGACTC<br>CGCGCATCGCCGTACCACTTCAAAACACCCAAGCACAGCATACTA<br>AATTTCCCCTCTTTCTTCCTCTAGGGTGTCGTTAATTACCCGTACTA<br>AAGGTTTGGAAAAGAAAAAAGAGACCGCCTCGTTTCTTTTTCTTCG<br>TCGAAAAAGGCAATAAAAATTTTTATCACGTTTCTTTTTCTTGAAA<br>ATTTTTTTTTTTGATTTTTTTCTCTTTCGATGACCTCCCATTGATATT<br>TAAGTTAATAAACGGTCTTCAATTTCTCAAGTTTCAGTTTCATTTTT<br>CTTGTTCTATTACAACTTTTTTTACTTCTTGCTCATTAGAAAGAAAG<br>CATAGCAATCTAATCTAAGTTTTAATTACAAAATGGAAAGTTCTGG<br>GGTGCCTGTGATCACATTGTCCTCAGGTAAAGTAATGCCCGTACTG<br>GGCATGGGAACCTTCGAAAAGGTGGGTAAGGGGTCTGAACGTGAG<br>CGTTTAGCCATTCTTAAAGCGATCGAAGTTGGTTACCGTTACTTTG<br>ATACCGCAGCGGCATATGAAACGGAAGAAGTTCTAGGGGAAGCCA<br>TTGCTGAAGCTTTACAATTGGGTCTGATAGAGAGCCGTGACGAGCT<br>GTTCATCAGCTCAATGCTTTGGTGCACCGACGCACATCCAGACCGT<br>GTGCTACTTGCTCTGCAAAACAGTCTGAGAAATCTAAAACTTGAAT<br>ATCTAGACCTATATATGTTGCCGTTTCCTGCCAGCCTTAAGCCGGG<br>CAAAATTACGATGGATATTCCTGAGGAGGATATTTGCCGTATGGAT<br>TATCGTTCAGTCTGGAGCGCCATGGAAGAGTGTCAAAACTTAGGA<br>TTTACTAAAAGTATTGGTGTAAGCAACTTTTCTTGCAAGAAATTAC<br>AAGAATTAATGGCCACTGCAAATATCCCGCCCGCGGTAAATCAAG<br>TAGAGATGTCACCAGCTTTCCAACAGAAAAAACTGAGGGAATATT<br>GTAACGCAAACAACATATTGGTATCCGCAGTAAGCATTCTGGGAT<br>CAAACGGGACGCCCTGGGGTAGTAATGCTGTTCTTGGAAGCGAAG<br>TTTTGAAACAGATCGCGATGGCGAAAGGCAAAAGCGTTGCGCAAG<br>TCAGTATGAGGTGGGTCTATGAGCAGGGCGCGTCTTTAGTAGTCAA<br>GAGTTTCTCTGAAGAACGTTTAAGAGAAAACCTGAATATTTTTGAC<br>TGGGAGCTTACGAAAGAAGACAATGAGAAGATAGGCGAAATCCC<br>GCAATGTAGAATCCTTACTGCGTACTTCCTTGTCTCCCCGAACGGC<br>CCGTTTAAATCTCAGGAAGAGCTTTGGGATGACAAGGCAtaaACAG<br>GCCCCTTTTCCTTTGTCGATATCATGTAATTAGTTATGTCACGCTTA<br>CATTCACGCCCTCCTCCCACATCCGCTCTAACCGAAAAGGAAGGA<br>GTTAGACAACCTGAAGTCTAGGTCCCTATTTATTTTTTTAATAGTT<br>ATGTTAGTATTAAGAACGTTATTTATATTTCAAATTTTTCTTTTTTT<br>CTGTACAAACGCGTGTACGCATGTAACATTATACTGAAAACCTTGC<br>TTGAGAAGGTTTTGGGACGCTCGAAGGCTTTAATTTGTAATCATTA<br>TCACTTTACGGGTCCTTTCCGGTGATCCGACAGGTTACGGGCGGC<br>GACCTCGCGGGTTTTCGCTATTTATGAAAATTTTCCGGTTTAAGGC<br>GTTTCCGTTCTTCTTCGTCATAACTTAATGTTTTTATTTAAAATACC<br>TCGCGAGTGGCAACACTGAAAATACCCATGGAGCGGCGTAACCGT<br>CGCACAGgatctaggtgaagatcctttttgataatctcatgaccaaaa<br>tcccttaacgtgagttttcgttccactgagcgtcagaccccgtagaaa<br>agatcaaaggatcttcttgagatcctttttttctgcgcgtaatctgct<br>gcttgcaaacaaaaaaaccaccgctaccagcggtggtttgtttgccgg<br>atcaagagctaccaactctttttccgaaggtaactggcttcagcagag<br>cgcagataccaaatactgtccttctagtgtagccgtagttaggccacc<br>acttcaagaactctgtagcaccgcctacatacctcgctctgctaatcc<br>tgttaccagtggctgctgccagtggcgataagtcgtgtcttaccgggt<br>tggactcaagacgatagttaccggataaggcgcagcggtcgggctgaa<br>cggggggttcgtgcacacagcccagcttggagcgaacgacctacaccg<br>aactgagatacctacagcgtgagctatgagaaagcgccacgcttcccg<br>aagggagaaaggcggacaggtatccggtaagcggcagggtcggaacag<br>gagagcgcacgagggagcttccaggggaaacgcctggtatctttata<br>gtcctgtcgggtttcgccacctctgacttgagcgtcgatttttgtgat<br>gctcgtcaggggggcggagcctatggaaaaacgccagcaacgcggcag<br>tggaacgTGCATTATGAATTAGTTACGCTAGGGATAACAGGGTAATAT<br>AGAACCCGAACGACCGAGCGCAGCGGCGGCCCGCGCTGATACCGCCGC | | |
| CCTCGCCGCAGTTAATTAAAGTCAGTGAGCGAGGAAGCGCGTAAC<br>TATAACGGTCCTAAGGTAGCGAATCCTGATGCGGTATTTTCTCCTT | pJL29 | SEQ. ID<br>NO. 27 |

TABLE 1-continued example amino acid sequences of DRS-DRR enzymes, split DRS and DRR enzymes, and other nucleotide sequences.

| Sequence | Description | SEQ. ID NO. |
|---|---|---|
| ACGCATCTGTGCGGTATTTCACACCGCATAGATCGGCAAGTGCACA AACAATACTTAAATAAATACTACTCAGTAATAACCTATTTCTTAGC ATTTTTGACGAAATTTGCTATTTTGTTAGAGTCTTTTACACCATTTG TCTCCACACCTCCGCTTACATCAACACCAATAACGCCATTTAATCT AAGCGCATCACCAACATTTTCTGGCGTCAGTCCACCAGCTAACATA AAATGTAAGCTTTCGGGGCTCTCTTGCCTTCCAACCCAGTCAGAAA TCGAGTTCCAATCCAAAAGTTCACCTGTCCCACCTGCTTCTGAATC AAACAAGGGAATAAACGAATGAGGTTTCTGTGAAGCTGCACTGAG TAGTATGTTGCAGTCTTTTGGAAATACGAGTCTTTTAATAACTGGC AAACCGAGGAACTCTTGGTATTCTTGCCACGACTCATCTCCATGCA GTTGGACGATATCAATGCCGTAATCATTGACCAGAGCCAAAACAT CCTCCTTAAGTTGATTACGAAACACGCCAACCAAGTATTTCGGAGT GCCTGAACTATTTTTATATGCTTTTACAAGACTTGAAATTTTCCTTG CAATAACCGGGTCAATTGTTCTCTTTCTATTGGGCACACATATAAT ACCCAGCAAGTCAGCATCGGAATCTAGAGCACATTCTGCGGCCTCT GTGCTCTGCAAGCCGCAAACTTTCACCAATGGACCAGAACTACCTG TGAAATTAATAACAGACATACTCCAAGCTGCCTTTGTGTGCTTAAT CACGTATACTCACGTGCTCAATAGTCACCAATGCCCTCCCTCTTGG CCCTCTCCTTTTCTTTTTTCGACCGAATTAATTCTTAATCGGCAAAA AAAGAAAAGCTCCGGATCAAGATTGTACGTAAGGTGACAAGCTAT TTTTCAATAAAGAATATCTTCCACTACTGCCATCTGGCGTCATAAC TGCAAAGTACACATATATTACGATGCTGTTCTATTAAATGCTTCCT ATATTATATATATAGTAATGTCGTGATCTATGGTGCACTCTCAGTA CAATCTGCTCTGATGCCGCATAGTTAAGCCAGCCCCGACACCCGCC AACACCCGCTGACGCGCCCTGACGGGCTTGTCTGCTCCCGGCATCC GCTTACAGACAAGCTGTGACCGTCTCCGGGAGCTGCATGTGTCAG AGGTTTTCACCGTCATCACCGAAACGCGCGAGACGAAAGGGCCTC GTGATACGCCTATTTTTATAGGTTAATGTCATGATAATAATGGTTT CTTAGACGGATCGCTTGCCTGTAACTTACACGCGCCTCGTATCTTTT AATGATGGAATAATTTGGGAATTTACTCTGTGTTTATTTATTTTTAT GTTTTGTATTTGGATTTTAGAAAGTAAATAAAGAAGGTAGAAGAG TTACGGAATGAAGAAAAAAAAAATAAACAAAGGTTTAAAAAATTTC AACAAAAAGCGTACTTTACATATATATTTATTAGACAAGAAAAGC AGATTAAATAGATATACATTCGATTAACGATAAGTAAAATGTAAA ATCACAGGATTTTCGTGTGTGGTCTTCTACACAGACAAGGTGAAAC AATTCGGCATTAATACCTGAGAGCAGGAAGAGCAAGATAAAAGGT AGTATTTGTTGGCGATCCCCCTAGAGTCTTTTACATCTTCGGAAAA CAAAAACTATTTTTCTTTAATTTCTTTTTTTACTTTCTATTTTTAAT TTATATATTTATATTAAAAAATTTAAATTATAATTATTTTTATAGCA CGTGATGAAAAGGACCCAGGTGGCACTTTTCGGGGAAATGTGCGC GGAACCCCTATTTGTTTATTTTTCTAAATACATTCAAATATGTATCC GCTCATGAGACAATAACCCTGATAAATGCTTCAATAATATTGAAA AAGGAAGAGTATGAGTATTCAACATTTCCGTGTCGCCCTTATTCCC TTTTTTGCGGCATTTTGCCTTCCTGTTTTTGCTCACCCAGAAACGCT GGTGAAAGTAAAAGATGCTGAAGATCAGTTGGGACGCGTAGTCTA GACCAGCCAGGACAGAAATGCCTCGACTTCGCTGCTACCCAAGGT TGCCGGGTGACGCACACCGTGGAAACGGATGAAGGCACGAACCCA GTGGACATAAGCCTGTTCGGTTCGTAAGCTGTAATGCAAGTAGCGT ATGCGCTCACGCAACTGGTCCAGAACCTTGACCGAACGCAGCGGT GGTAACGGCGCAGTGGCGGTTTTCATGGCTTGTTATGACTGTTTTT TTGGGGTACAGTCTATGCCTCGGGCATCCAAGCAGCAAGCGCGTT ACGCCGTGGGTCGATGTTTGATGTTATGGAGCAGCAACGATGTTAC GCAGCAGGGCAGTCGCCCTAAAACAAAGTTAAACATTATGAGGGA AGCGGTGATCGCCGAAGTATCGACTCAACTATCAGAGGTAGTTGG CGCCATCGAGCGCCATCTCGAACCGACGTTGCTGGCCGTACATTTG TACGGCTCCGCAGTGGATGGCGGCCTGAAGCCACACAGTGATATT GATTTGCTGGTTACGGTGACCGTAAGGCTTGATGAAACAACGCGG CGAGCTTTGATCAACGACCTTTTGGAAACTTCGGCTTCCCCTGGAG AGAGCGAGATTCTCCGCGCTGTAGAAGTCACCATTGTTGTGCACGA CGACATCATTCCGTGGCGTTATCCAGCTAAGCGCGAACTGCAATTT GGAGAATGGCAGCGCAATGACATTCTTGCAGGTATCTTCGAGCCA GCCACGATCGACATTGATCTGGCTATCTTGCTGACAAAAGCAAGA GAACATAGCGTTGCCTTGGTAGGTCCAGCGGCGGAGGAACTCTTT GATCCGGTTCCTGAACAGGATCTATTTGAGGCGCTAAATGAAACCT TAACGCTATGGAACTCGCCGCCCGACTGGGCTGGCGATGAGCGAA ATGTAGTGCTTACGTTGTCCCGCATTTGGTACAGCGCAGTAACCGG CAAAATCGCGCCGAAGGATGTCGCTGCCGACTGGGCAATGGAGCG CCTGCCGGCCCAGTATCAGCCCGTCATACTTGAAGCTAGACAGGCT TATCTTGGACAAGAAGAAGATCGCTTGGCCTCGCGCGCAGATCAG TTGGAAGAATTTGTCCACTACGTGAAAGGCGAGATCACCAAGGTA GTCGGCAAATAACCCTCGAGCATTCAAGGCGCCTTGATTATTTGAC GTGGTTTGATGGCCTCCACGCACGTTGTGATATGTAGATGATTCAG TTCGAGTTTATCATTATCAATACTGCCATTTCAAAGAATACGTAAA TAATTAATAGTAGTGATTTTCCTAACTTTATTTAGTCAAAAAATTA | | |

TABLE 1-continued example amino acid sequences of DRS-DRR enzymes, split DRS and DRR enzymes, and other nucleotide sequences.

| Sequence | Description | SEQ. ID NO. |
|---|---|---|
| GCCTTTTAATTCTGCTGTAACCCGTACATGCCCAAAATAGGGGCG GGTTACACAGAATATATAACATCGTAGGTGTCTGGGTGAACAGTTT ATTCCTGGCATCCACTAAATATAATGGAGCCCGCTTTTTAAGCTGG CATCCAGAAAAAAAAAGAATCCCAGCACCAAAATATTGTTTTCTTC ACCAACCATCAGTTCATAGGTCCATTCTCTTAGCGCAACTACAGAG AACAGGGGCACAAACAGGCAAAAAACGGGCACAACCTCAATGGA GTGATGCAACCTGCCTGGAGTAAATGATGACACAAGGCAATTGAC CCACGCATGTATCTATCTCATTTTCTTACACCTTCTATTACCTTCTG CTCTCTCTGATTTGGAAAAAGCTGAAAAAAAAGGTTGAAACCAGT TCCCTGAAATTATTCCCCTACTTGACTAATAAGTATATAAAGACGG TAGGTATTGATTGTAATTCTGTAAATCTATTTCTTAAACTTCTTAAA TTCTACTTTTATAGTTAGTCTTTTTTTTAGTTTTAAAACACCAAGAA CTTAGTTTCGAATAAACACACATAAACAAACAAAATGGAACTTCA GTACTTCTCCTATTTTCAACCCACTTCATCTGTCGTAGCCCTACTAC TAGCACTAGTGAGTATTTTATTTAGCGTAGTTGTTTTGAGGAAGAC TTTCAGTAACAATTACTCCAGCCCCGCGTCAAGTACGGAAACCGCT GTGCTGTGTCATCAGAGGCAACAGAGTTGCGCCCTACCTATCAGCG GCCTTCTTCACGTGTTCATGAATAAGAACGGCCTGATTCATGTCAC CTTGGGAAATATGGCTGACAAATATGGCCCTATCTTCAGTTTTCCG ACAGGCAGCCACCGTACTTTAGTAGTCAGTTCCTGGGAAATGGTG AAAGAGTGTTTCACCGGTAATAACGACACGGCATTCTCCAACAGA CCAATCCCTTTGGCTTTTCAAACCATATTCTACGCCTGTGGCGGCA TTGATTCTTACGGTTTAAGTAGTGTCCCGTATGGTAAATACTGGAG GGAGTTGAGAAAGGTGTGTGTTCACAACCTGCTGAGTAATCAGCA ATTGCTGAAGTTCAGACATCTTATAATCTCCCAAGTGGATACGTCT TTTAACAAGTTGTATGAGCTGTGTAAGAACTCTGAAGATAATCAAG GTATGGTAAGGATGGATGATTGGCTAGCTCAACTTTCCTTTAACGT CATCGGTAGGATCGTTTGCGGATTCCAGTCTGACCCAAAGACGGGT GCACCTTCAAGGGTAGAACAGTTTAAGGAAGTCATAAATGAGGCG TCATATTTTATGTCAACAAGTCCAGTCTCCGATAACGTACCAATGT TGGGATGGATCGACCAATTGACCGGTCTGACGAGGAACATGAAGC ATTGTGGGAAGAAGCTTGACTTAGTAGTGGAGTCAATTATCAAGG ACCATAGGCAAAAGAGACGTTTTTCACGTACAAAAGGTGGCGATG AGAAGGATGACGAACAGGACGACTTTATTGATATTTGCTTGAGCA TCATGGAGCAGCCACAGTTGCCCGGGAACAATTCTCCCCCTCAAAT TCCGATCAAATCTATCGTGCTAGACATGATTGGGGGTGGTACCGAC ACTACGAAACTTACAACCATATGGACCCTATCACTTTTGTTGAACA ATCCTCACGTGTTAGATAAAGCTAAACAAGAGGTCGACGCTCACTT TCGTAAAAAGAGAAGATCAACAGATGACGCAGCAGCGGCAGTCGT TGATTTTGACGACATAAGAAATTTAGTATACATCCAAGCCATCATT AAAGAAAGTATGAGGCTTTATCCAGCCAGCCCCGGTGGTTGAGCGT CTTTCCGGCGAGGATTGCGTTGTTGGAGGTTTTCACGTGCCTGCTG GTACGAGACTATGGGCTAACGTTTGGAAGATGCAAAGAGATCCCA AAGTTTGGGACGATCCTCTAGTATTCAGACCTGAAAGGTTTTTGAG CGACGAGCAAAAGATGGTAGACGTTCGTGGCCAAAACTATGAACT TCTGCCATTCGGCGCAGGAAGAAGAATCTGTCCAGGCGTTTCCTTT AGTCTTGACCTTATGCAACTTGTCCTAACCAGGTTAATCCTAGAGT TCGAAATGAAGTCCCCGTCCGGCAAGGTAGATATGACCGCAACTC CAGGACTAATGTCTTACAAGGTGGTTCCATTGGACATATTGCTGAC TCACCGTCGTATCAAGTCATGCGTTCAATTGGCGTCTTCTGAACGT GATtaaGCGAATTTCTTATGATTTATGATTTTTATTATTAAATAAGTT ATAAAAAAAATAAGTGTATACAAATTTTAAAGTGACTCTTAGGTTT TAAAACGAAAATTCTTATTCTTGAGTAACTCTTTCCTGTAGGTCAG GTTGCTTTCTCAGGTACATAGCTTCAAAATGTTTCTACTCCTTTTTT ACTCTTCCAGATTTTCTCGGACTCCGCGCATCGCCGTACCACTTCA AAACACCCAAGCACAGCATACTAAATTTCCCCTCTTTCTTCCTCTA GGGTGTCGTTAATTACCCGTACTAAAGGTTTGGAAAAGAAAAAAG AGACCGCCTCGTTTCTTTTTCTTCGTCGAAAAAGGCAATAAAAATT TTTATCACGTTTCTTTTTCTTGAAAATTTTTTTTTTGATTTTTTTCTC TTTCGATGACCTCCCATTGATATTTAAGTTAATAAACGGTCTTCAA TTTCTCAAGTTTCAGTTTCATTTTTCTTGTTCTATTACAACTTTTTTT ACTTCTTGCTCATTAGAAAGAAAGCATAGCAATCTAATCTAAGTTT TAATTACAAAATGGAAAGTTCTGGGGTGCCTGTGATCACATTGTCC TCAGGTAAAGTAATGCCCGTACTGGGCATGGGAACCTTCGAAAAG GTGGGTAAGGGGTCTGAACGTGAGCGTTTAGCCATTCTTAAAGCG ATCGAAGTTGGTTACCGTTACTTTGATACCGCAGCGGCATATGAAA CGGAAGAAGTTCTAGGGGAAGCCATTGCTGAAGCTTTACAATTGG GTCTGATAGAGAGCCGTGACGAGCTGTTCATCAGCTCAATGCTTTG GTGCACCGACGCACATCCAGACCGTGTGCTACTTGCTCTGCAAAAC AGTCTGAGAAATCTAAAACTTGAATATCTAGACCTATATATGTTGC CGTTTCCTGCCAGCCTTAAGCCGGGCAAAATTACGATGGATATTCC TGAGGAGGATATTTGCCGTATGGATTATCGTTCAGTCTGGAGCGCC ATGGAAGAGTGTCAAAACTTAGGGATTTACTAAAAGTATTGGTGTA AGCAACTTTTCTTGCAAGAAATTACAAGAATTAATGGCCACTGCAA | | |

TABLE 1-continued example amino acid sequences of DRS-DRR enzymes, split DRS and DRR enzymes, and other nucleotide sequences.

| Sequence | Description | SEQ. ID NO. |
|---|---|---|
| ATATCCCGCCCGCGGTAAATCAAGTAGAGATGTCACCAGCTTTCCA ACAGAAAAAACTGAGGGAATATTGTAACGCAAACAACATATTGGT ATCCGCAGTAAGCATTCTGGGATCAAACGGGACGCCCTGGGGTAG TAATGCTGTTCTTGGAAGCGAAGTTTTGAAACAGATCGCGATGGCG AAAGGCAAAAGCGTTGCGCAAGTCAGTATGAGGTGGGTCTATGAG CAGGGCGCGTCTTTAGTAGTCAAGAGTTTCTCTGAAGAACGTTTAA GAGAAAACCTGAATATTTTTGACTGGGAGCTTACGAAAGAAGACA ATGAGAAGATAGGCGAAATCCCGCAATGTAGAATCCTTACTGCGT ACTTCCTTGTCTCCCCGAACGGCCCGTTTAAATCTCAGGAAGAGCT TTGGGATGACAAGGCAtaaACAGGCCCCTTTTCCTTTGTCGATATCA TGTAATTAGTTATGTCACGCTTACATTCACGCCCTCCTCCCACATCC GCTCTAACCGAAAAGGAAGGAGTTAGACAACCTGAAGTCTAGGTC CCTATTTATTTTTTTAATAGTTATGTTAGTATTAAGAACGTTATTT ATATTTCAAATTTTTCTTTTTTTTCTGTACAAACGCGTGTACGCATG TAACATTATACTGAAAACCTTGCTTGAGAAGGTTTTGGGACGCTCG AAGGCTTTAATTTGTAATCATTATCACTTTACGGGTCCTTTCCGGTG ATCCGACAGGTTACGGGCGGCGACCTCGCGGGTTTTCGCTATTTA TGAAAATTTTCCGGTTTAAGGCGTTTCCGTTCTTCTTCGTCATAACT TAATGTTTTTATTTAAAATACCTCGCGAGTGGCAACACTGAAAATA CCCATGGAGCGGCGTAACCGTCGCACAGgatctaggtgaagatcctt ttgataatctcatgaccaaaatcccttaacgtgagttttcgttccact gagcgtcagaccccgtagaaaagatcaaaggatcttcttgagatcctt tttttctgcgcgtaatctgctgcttgcaaacaaaaaaaccaccgctac cagcggtggtttgtttgccggatcaagagctaccaactcttttttccga aggtaactggcttcagcagagcgcagataccaaatactgtccttctag tgtagccgtagttaggccaccacttcaagaactctgtagcaccgccta catacctcgctctgctaatcctgttaccagtggctgctgccagtggcg ataagtcgtgtcttaccgggttggactcaagacgatagttaccggata aggcgcagcggtcgggctgaacggggggttcgtgcacacagcccagct tggagcgaacgacctacaccgaactgagatacctacagcgtgagctat gagaaagcgccacgcttcccgaagggagaaaggcggacaggtatccgg taagcggcagggtcggaacaggagagcgcacgagggagcttccagggg gaaacgcctggtatctttatagtcctgtcgggtttcgccacctctgac ttgagcgtcgatttttgtgatgctcgtcaggggggcggagcctatgga aaaacgccagcaacgcggcagtggaacgTGCATTATGAATTAGTTACG CTAGGGATAACAGGGTAATATAGAACCCGAACGACCGAGCGCAGCGGC GGCCGCGCTGATACCGCCGC | | |
| CCTCGCCGCAGTTAATTAAAGTCAGTGAGCGAGGAAGCGCGTAAC TATAACGGTCCTAAGGTAGCGAATCCTGATGCGGTATTTTCTCCTT ACGCATCTGTGCGGTATTTCACACCGCATAGATCGGCAAGTGCACA AACAATACTTAAATAAATACTACTCAGTAATAACCTATTTCTTAGC ATTTTTTGACGAAATTTGCTATTTTGTTAGAGTCTTTTACACCATTTG TCTCCACACCTCCGCTTACATCAACACCAATAACGCCATTTAATCT AAGCGCATCACCAACATTTTCTGGCGTCAGTCCACCAGCTAACATA AAATGTAAGCTTTCGGGGCTCTCTTGCCTTCCAACCCAGTCAGAAA TCGAGTTCCAATCCAAAAGTTCACCTGTCCCACCTGCTTCTGAATC AAACAAGGGAATAAACGAATGAGGTTTCTGTGAAGCTGCACTGAG TAGTATGTTGCAGTCTTTTGGAAATACGAGTCTTTTAATAACTGGC AAACCGAGGAACTCTTGGTATTCTTGCCACGACTCATCTCCATGCA GTTGGACGATATCAATGCCGTAATCATTGACCAGAGCCAAAACAT CCTCCTTAAGTTGATTACGAAACACGCCAACCAAGTATTTCGGAGT GCCTGAACTATTTTTATATGCTTTTACAAGACTTGAAATTTTCCTTG CAATAACCGGGTCAATTGTTCTCTTTCTATTGGGCACACATATAAT ACCCAGCAAGTCAGCATCGGAATCTAGAGCACATTCTGCGGCCTCT GTGCTCTGCAAGCCGCAAACTTTCACCAATGGACCAGAACTACCTG TGAAATTAATAACAGACATACTCCAAGCTGCCTTTGTGTGCTTAAT CACGTATACTCACGTGCTCAATAGTCACCAATGCCCTCCCTCTTGG CCCTCTCCTTTTCTTTTTTCGACCGAATTAATTCTTAATCGGCAAAA AAAGAAAAGCTCCGGATCAAGATTGTACGTAAGGTGACAAGCTAT TTTTCAATAAAGAATATCTTCCACTACTGCCATCTGGCGTCATAAC TGCAAAGTACACATATATTACGATGCTGTTCTATTAAATGCTTCCT ATATTATATATAGTAATGTCGTGATCTATGGTGCACTCTCAGTA CAATCTGCTCTGATGCCGCATAGTTAAGCCAGCCCCGACACCCGCC AACACCCGCTGACGCGCCCTGACGGGCTTGTCTGCTCCCGGCATCC GCTTACAGACAAGCTGTGACCGTCTCCGGGAGCTGCATGTGTCAG AGGTTTTCACCGTCATCACCGAAACGCGCGAGACGAAAGGGCCTC GTGATACGCCTATTTTTATAGGTTAATGTCATGATAATAATGGTTT CTTAGACGGATCGCTTGCCTGTAACTTACACGCGCCTCGTATCTTT AATGATGGAATAATTTGGGAATTTACTCTGTGTTTATTTATTTTTAT GTTTTGTATTTGGATTTTAGAAAGTAAATAAAGAAGGGTAGAAGAG TTACGGAATGAAGAAAAAAAATAAACAAAGGTTTAAAAAATTTC AACAAAAAGCGTACTTTACATATATATTTATTAGACAAGAAAAGC AGATTAAATAGATATACATTCGATTAACGATAAGTAAAATGTAAA | pJL32 | SEQ. ID NO. 28 |

TABLE 1-continued example amino acid sequences of DRS-DRR enzymes, split DRS and DRR enzymes, and other nucleotide sequences.

| Sequence | Description | SEQ. ID NO. |
|---|---|---|
| ATCACAGGATTTTCGTGTGTGGTCTTCTACACAGACAAGGTGAAAC AATTCGGCATTAATACCTGAGAGCAGGAAGAGCAAGATAAAAGGT AGTATTTGTTGGCGATCCCCCTAGAGTCTTTTACATCTTCGGAAAA CAAAAACTATTTTTCTTTAATTTCTTTTTTTACTTTCTATTTTTAAT TTATATATTTATATTAAAAAATTTAAATTATAATTATTTTTATAGCA CGTGATGAAAAGGACCCAGGTGGCACTTTTCGGGGAAATGTGCGC GGAACCCCTATTTGTTTATTTTTCTAAATACATTCAAATATGTATCC GCTCATGAGACAATAACCCTGATAAATGCTTCAATAATATTGAAA AAGGAAGAGTATGAGTATTCAACATTTCCGTGTCGCCCTTATTCCC TTTTTTGCGGCATTTTGCCTTCCTGTTTTTGCTCACCCAGAAACGCT GGTGAAAGTAAAAGATGCTGAAGATCAGTTGGGACGCGTAGTCTA GACCAGCCAGGACAGAAATGCCTCGACTTCGCTGCTACCCAAGGT TGCCGGGTGACGCACACCGTGGAAACGGATGAAGGCACGAACCCA GTGGACATAAGCCTGTTCGGTTCGTAAGCTGTAATGCAAGTAGCGT ATGCGCTCACGCAACTGGTCCAGAACCTTGACCGAACGCAGCGGT GGTAACGGCGCAGTGGCGGTTTTCATGGCTTGTTATGACTGTTTTT TTGGGGTACAGTCTATGCCTCGGGCATCCAAGCAGCAAGCGCGTT ACGCCGTGGGTCGATGTTTGATGTTATGGAGCAGCAACGATGTTAC GCAGCAGGGCAGTCGCCCTAAAACAAAGTTAAACATTATGAGGGA AGCGGTGATCGCCGAAGTATCGACTCAACTATCAGAGGTAGTTGG CGCCATCGAGCGCCATCTCGAACCGACGTTGCTGGCCGTACATTTG TACGGCTCCGCAGTGGATGGCGGCCTGAAGCCACACAGTGATATT GATTTGCTGGTTACGGTGACCGTAAGGCTTGATGAAACAACGCGG CGAGCTTTGATCAACGACCTTTTGGAAACTTCGGCTTCCCCTGGAG AGAGCGAGATTCTCCGCGCTGTAGAAGTCACCATTGTTGTGCACGA CGACATCATTCCGTGGCGTTATCCAGCTAAGCGCGAACTGCAATTT GGAGAATGGCAGCGCAATGACATTCTTGCAGGTATCTTCGAGCCA GCCACGATCGACATTGATCTGGCTATCTTGCTGACAAAAGCAAGA GAACATAGCGTTGCCTTGGTAGGTCCAGCGGCGGAGGAACTCTTT GATCCGGTTCCTGAACAGGATCTATTTGAGGCGCTAAATGAAACCT TAACGCTATGGAACTCGCCGCCCGACTGGGCTGGCGATGAGCGAA ATGTAGTGCTTACGTTGTCCCGCATTTGGTACAGCGCAGTAACCGG CAAAATCGCGCCGAAGGATGTCGCTGCCGGCTGGGCAATGGAGCG CCTGCCGGCCCAGTATCAGCCCGTCATACTTGAAGCTAGACAGGCT TATCTTGGACAAGAAGAAGATCGCTTGGCCTCGCGCGCAGATCAG TTGGAAGAATTTGTCCACTACGTGAAAGGCGAGATCACCAAGGTA GTCGGCAAATAACCCTCGAGCATTCAAGGCGCCTTGATTATTTGAC GTGGTTTGATGGCCTCCACGCACGTTGTGATATGTAGATGAGAGCG TTGGTTGGTGGATCAAGCCCACGCGTAGGCAATCCTCGAGCAGAT CCGCCAGGCGTGTATATATAGCGTGGATGGCCAGGCAACTTTAGT GCTGACACATACAGGCATATATATATGTGTGCGACGACACATGAT CATATGGCATGCATGTGCTCTGTATGTATATAAAACTCTTGTTTTCT TCTTTTCTCTAAATATTCTTTCCTTATACATTAGGACCTTTGCAGCA TAAATTACTATACTTCTATAGACACACAAACACAAATACACACACT AAATTAATAATGGAACTTCAGTACTTCTCCTATTTTCAACCCACTTC ATCTGTCGTAGCCCTACTACTAGCACTAGTGAGTATTTTATTTAGC GTAGTTGTTTTGAGGAAGACTTTCAGTAACAATTACTCCAGCCCCG CGTCAAGTACGGAAAACCGCTGTGCTGTGTCATCAGAGGCAACAGA GTTGCGCCCTACCTATCAGCGGCCTTCTTCACGTGTTCATGAATAA GAACGGCCTGATTCATGTCACCTTGGGAAATATGGCTGACAAATAT GGCCCTATCTTCAGTTTTCCGACAGGCAGCCACCGTACTTTAGTAG TCAGTTCCTGGGAAATGGTGAAAGAGTGTTTCACCGGTAATAACG ACACGGCATTCTCCAACAGACCAATCCCTTTGGCTTTTCAAACCAT ATTCTACGCCTGTGGCGGCATTGATTCTTACGGTTTAAGTAGTGTC CCGTATGGTAAATACTGGAGGGAGTTGAGAAAGGTGTGTGTTCAC AACCTGCTGAGTAATCAGCAATTGCTGAAGTTCAGACATCTTATAA TCTCCCAAGTGGATACGTCTTTTAACAAGTTGTATGAGCTGTGTAA GAACTCTGAAGATAATCAAGGTATGGTAAGGATGGATGATTGGCT AGCTCAACTTTCCTTTAACGTCATCGGTAGGATCGTTTGCGGATTC CAGTCTGACCCAAAGACGGGTGCACCTTCAAGGGTAGAACAGTTT AAGGAAGTCATAAATGAGGCGTCATATTTTATGTCAACAAGTCCA GTCTCCGATAACGTACCAATGTTGGGATGGATCGACCAATTGACCG GTCTGACGAGGAACATGAAGCATTGTGGGAAGAAGCTTGACTTAG TAGTGGAGTCAATTATCAAGGACCATAGGCAAAAGAGACGTTTTT CACGTACAAAAGGTGGCGATGAGAAGGATGACGAACAGGACGAC TTTATTGATATTTGCTTGAGCATCATGGAGCAGCCACAGTTGCCCG GGAACAATTCTCCCCCTCAAATTCCGATCAAATCTATCGTGCTAGA CATGATTGGGGTGGTACCGACACTACGAAACTTACAACCATATG GACCCTATCACTTTTGTTGAACAATCCTCACGTGTTAGATAAAGCT AAACAAGAGGTCGACGCTCACTTTCGTAAAAAGAGAAGATCAACA GATGACGCAGCAGCGGCAGTCGTTGATTTGACGACATAAGAAAT TTAGTATACATCCAAGCCATCATTAAAGAAAGTATGAGGCTTTATC CAGCCAGCCCGTGGTTGAGCGTCTTTCCGGCGAGGATTGCGTTGT TGGAGGTTTTCACGTGCCTGCTGGTACGAGACTATGGGCTAACGTT | | |

TABLE 1-continued example amino acid sequences of DRS-DRR enzymes, split DRS and DRR enzymes, and other nucleotide sequences.

| Sequence | Description | SEQ. ID NO. |
|---|---|---|

TGGAAGATGCAAAGAGATCCCAAAGTTTGGGACGATCCTCTAGTA
TTCAGACCTGAAAGGTTTTTGAGCGACGAGCAAAAGATGGTAGAC
GTTCGTGGCCAAAACTATGAACTTCTGCCATTCGGCGCAGGAAGA
AGAATCTGTCCAGGCGTTTCCTTTAGTCTTGACCTTATGCAACTTGT
CCTAACCAGGTTAATCCTAGAGTTCGAAATGAAGTCCCCGTCCGGC
AAGGTAGATATGACCGCAACTCCAGGACTAATGTCTTACAAGGTG
GTTCCATTGGACATATTGCTGACTCACCGTCGTATCAAGTCATGCG
TTCAATTGGCGTCTTCTGAACGTGATtaaGCGAATTTCTTATGATTTA
TGATTTTTATTATTAAATAAGTTATAAAAAAATAAGTGTATACAA
ATTTTAAAGTGACTCTTAGGTTTTAAAACGAAAATTCTTATTCTTG
AGTAACTCTTTCCTGTAGGTCAGGTTGCTTTCTCAGGTATTCAGTTC
GAGTTTATCATTATCAATACTGCCATTTCAAAGAATACGTAAATAA
TTAATAGTAGTGATTTTCCTAACTTTATTTAGTCAAAAAATTAGCCT
TTTAATTCTGCTGTAACCCGTACATGCCCAAAATAGGGGCGGGTT
ACACAGAATATATAACATCGTAGGTGTCTGGGTGAACAGTTTATTC
CTGGCATCCACTAAATATAATGGAGCCCGCTTTTTAAGCTGGCATC
CAGAAAAAAAAAGAATCCCAGCACCAAAATATTGTTTTCTTCACC
AACCATCAGTTCATAGGTCCATTCTCTTAGCGCAACTACAGAGAAC
AGGGGCACAAACAGGCAAAAAACGGGCACAACCTCAATGGAGTG
ATGCAACCTGCCTGGAGTAAATGATGACACAAGGCAATTGACCCA
CGCATGTATCTATCTCATTTTCTTACACCTTCTATTACCTTCTGCTCT
CTCTGATTTGGAAAAAGCTGAAAAAAAAGGTTGAAACCAGTTCCC
TGAAATTATTCCCCTACTTGACTAATAAGTATATAAAGACGGTAGG
TATTGATTGTAATTCTGTAAATCTATTTCTTAAACTTCTTAAATTCT
ACTTTTATAGTTAGTCTTTTTTTTAGTTTTAAAACACCAAGAACTTA
GTTTCGAATAAACACACATAAACAAACAAAATGGAAAGTTCTGGG
GTGCCTGTGATCACATTGTCCTCAGGTAAAGTAATGCCCGTACTGG
GCATGGGAACCTTCGAAAAGGTGGGTAAGGGGTCTGAACGTGAGC
GTTTAGCCATTCTTAAAGCGATCGAAGTTGGTTACCGTTACTTTGA
TACCGCAGCGGCATATGAAACGGAAGAAGTTCTAGGGGAAGCCAT
TGCTGAAGCTTTACAATTGGGTCTGATAGAGAGCCGTGACGAGCT
GTTCATCAGCTCAATGCTTTGGTGCACCGACGCACATCCAGACCGT
GTGCTACTTGCTCTGCAAAACAGTCTGAGAAATCTAAAACTTGAAT
ATCTAGACCTATATATGTTGCCGTTTCCTGCCAGCCTTAAGCCGGG
CAAAATTACGATGGATATTCCTGAGGAGGATATTGCCGTATGGAT
TATCGTTCAGTCTGGAGCGCCATGGAAGAGTGTCAAAACTTAGGA
TTTACTAAAAGTATTGGTGTAAGCAACTTTTCTTGCAAGAAATTAC
AAGAATTAATGGCCACTGCAAATATCCCGCCCGCGGTAAATCAAG
TAGAGATGTCACCAGCTTTCCAACAGAAAAAACTGAGGGAATATT
GTAACGCAAACAACATATTGGTATCCGCAGTAAGCATTCTGGGAT
CAAACGGGACGCCCTGGGGTAGTAATGCTGTTCTTGGAAGCGAAG
TTTTGAAACAGATCGCGATGGCGAAAGGCAAAAGCGTTGCGCAAG
TCAGTATGAGGTGGGTCTATGAGCAGGGCGCGTCTTTAGTAGTCAA
GAGTTTCTCTGAAGAACGTTTAAGAGAAAACCTGAATATTTTTGAC
TGGGAGCTTACGAAAGAAGACAATGAGAAGATAGGCGAAATCCC
GCAATGTAGAATCCTTACTGCGTACTTCCTTGTCTCCCCGAACGGC
CCGTTTAAATCTCAGGAAGAGCTTTGGGATGACAAGGCAtaaACAG
GCCCCTTTTCCTTTGTCGATATCATGTAATTAGTTATGTCACGCTTA
CATTCACGCCCTCCTCCCACATCCGCTCTAACCGAAAAGGAAGGA
GTTAGACAACCTGAAGTCTAGGTCCCTATTTATTTTTTTAATAGTT
ATGTTAGTATTAAGAACGTTATTTATATTTCAAATTTTTCTTTTTTTT
CTGTACAAACGCGTGTACGCATGTAACATTATACTGAAAACCTTGC
TTGAGAAGGTTTTGGGACGCTCGAAGGCTTTAATTTGTAATCATTA
TCACTTTACGGGTCCTTTCCGGTGATCCGACAGGTTACGGGCGGC
GACCTCGCGGGTTTTCGCTATTTATGAAAATTTTCCGGTTTAAGGC
GTTTCCGTTCTTCTTCGTCATAACTTAATGTTTTTATTTAAAATACC
TCGCGAGTGGCAACACTGAAAATACCCATGGAGCGGCTAACCGT
CGCACAGgatctaggtgaagatcctttttgataatctcatgaccaaaa
tcccttaacgtgagttttcgttccactgagcgtcagaccccgtagaaa
agatcaaaggatcttcttgagatcctttttttctgcgcgtaatctgct
gcttgcaaacaaaaaaaccaccgctaccagcggtggtttgtttgccgg
atcaagagctaccaactctttttccgaaggtaactggcttcagcagag
cgcagataccaaatactgtccttctagtgtagccgtagttaggccacc
acttcaagaactctgtagcaccgcctacatacctcgctctgctaatcc
tgttaccagtggctgctgccagtggcgataagtcgtgtcttaccgggt
tggactcaagacgatagttaccggataaggcgcagcggtcgggctgaa
cggggggttcgtgcacacagcccagcttggagcgaacgacctacaccg
aactgagatacctacagcgtgagctatgagaaagcgccacgcttcccg
aagggagaaaggcggacaggtatccggtaagcggcagggtcggaacag
gagagcgcacgagggagcttccaggggggaaacgcctggtatctttata
gtcctgtcgggtttcgccacctctgacttgagcgtcgatttttgtgat
gctcgtcagggggggcggagcctatggaaaaacgccagcaacgcggcag
tggaacgTGCATTATGAATTAGTTACGCTAGGGATAACAGGGTAATAT
AGAACCCGAACGACCGAGCGCAGCGGCGGCCCGCGCTGATACCGCCGC TABLE 1-continued example amino acid sequences of DRS-DRR enzymes, split DRS and DRR enzymes, and other nucleotide sequences.

| Sequence | Description | SEQ. ID NO. |
|---|---|---|
| CCTCGCCGCAGTTAATTAAAGTCAGTGAGCGAGGAAGCGCGTAAC<br>TATAACGGTCCTAAGGTAGCGAATCCTGATGCGGTATTTTCTCCTT<br>ACGCATCTGTGCGGTATTTCACACCGCATAGATCGGCAAGTGCACA<br>AACAATACTTAAATAAATACTACTCAGTAATAACCTATTTCTTAGC<br>ATTTTTGACGAAATTTGCTATTTTGTTAGAGTCTTTTACACCATTTG<br>TCTCCACACCTCCGCTTACATCAACACCAATAACGCCATTTAATCT<br>AAGCGCATCACCAACATTTTCTGGCGTCAGTCCACCAGCTAACATA<br>AAATGTAAGCTTTCGGGGCTCTCTTGCCTTCCAACCCAGTCAGAAA<br>TCGAGTTCCAATCCAAAAGTTCACCTGTCCCACCTGCTTCTGAATC<br>AAACAAGGGAATAAACGAATGAGGTTTCTGTGAAGCTGCACTGAG<br>TAGTATGTTGCAGTCTTTTGGAAATACGAGTCTTTTAATAACTGGC<br>AAACCGAGGAACTCTTGGTATTCTTGCCACGACTCATCTCCATGCA<br>GTTGGACGATATCAATGCCGTAATCATTGACCAGAGCCAAAACAT<br>CCTCCTTAAGTTGATTACGAAACACGCCAACCAAGTATTTCGGAGT<br>GCCTGAACTATTTTTATATGCTTTTACAAGACTTGAAATTTTCCTTG<br>CAATAACCGGGTCAATTGTTCTCTTTCTATTGGGCACACATATAAT<br>ACCCAGCAAGTCAGCATCGGAATCTAGAGCACATTCTGCGGCCTCT<br>GTGCTCTGCAAGCCGCAAACTTTCACCAATGGACCAGAACTACCTG<br>TGAAATTAATAACAGACATACTCCAAGCTGCCTTTGTGTGCTTAAT<br>CACGTATACTCACGTGCTCAATAGTCACCAATGCCCTCCCTCTTGG<br>CCCTCTCCTTTTCTTTTTTCGACCGAATTAATTCTTAATCGGCAAAA<br>AAAGAAAAGCTCCGGATCAAGATTGTACGTAAGGTGACAAGCTAT<br>TTTTCAATAAAGAATATCTTCCACTACTGCCATCTGGCGTCATAAC<br>TGCAAAGTACACATATATTACGATGCTGTTCTATTAAATGCTTCCT<br>ATATTATATATATAGTAATGTCGTGATCTATGGTGCACTCTCAGTA<br>CAATCTGCTCTGATGCCGCATAGTTAAGCCAGCCCCGACACCCGCC<br>AACACCCGCTGACGCGCCCTGACGGGCTTGTCTGCTCCCGGCATCC<br>GCTTACAGACAAGCTGTGACCGTCTCCGGGAGCTGCATGTGTCAG<br>AGGTTTTCACCGTCATCACCGAAACGCGCGAGACGAAAGGGCCTC<br>GTGATACGCCTATTTTTATAGGTTAATGTCATGATAATAATGGTTT<br>CTTAGACGGATCGCTTGCCTGTAACTTACACGCGCCTCGTATCTTTT<br>AATGATGGAATAATTTGGGAATTTACTCTGTGTTTATTTATTTTTAT<br>GTTTTGTATTTGGATTTTAGAAAGTAAATAAAGAAGGTAGAAGAG<br>TTACGGAATGAAGAAAAAAAAATAAACAAAGGTTTAAAAAATTTC<br>AACAAAAAGCGTACTTTACATATATATTTATTAGACAAGAAAAGC<br>AGATTAAATAGATATACATTCGATTAACGATAAGTAAAATGTAAA<br>ATCACAGGATTTTCGTGTGTGGTCTTCTACACAGACAAGGTGAAAC<br>AATTCGGCATTAATACCTGAGAGCAGGAAGAGCAAGATAAAAGGT<br>AGTATTTGTTGGCGATCCCCCTAGAGTCTTTTACATCTTCGGAAAA<br>CAAAAACTATTTTTTCTTTAATTTCTTTTTTTACTTTCTATTTTTAAT<br>TTATATATTTATATTAAAAAATTTAAATTATAATTATTTTTATAGCA<br>CGTGATGAAAAGGACCCAGGTGGCACTTTTCGGGGAAATGTGCGC<br>GGAACCCCTATTTGTTTATTTTTCTAAATACATTCAAATATGTATCC<br>GCTCATGAGACAATAACCCTGATAAATGCTTCAATAATATTGAAA<br>AAGGAAGAGTATGAGTATTCAACATTTCCGTGTCGCCCTTATTCCC<br>TTTTTTGCGGCATTTTGCCTTCCTGTTTTTGCTCACCCAGAAACGCT<br>GGTGAAAGTAAAAGATGCTGAAGATCAGTTGGGACGCGTAGTCTA<br>GACCAGCCAGGACAGAAATGCCTCGACTTCGCTGCTACCCAAGGT<br>TGCCGGGTGACGCACACCGTGGAAACGGATGAAGGCACGAACCCA<br>GTGGACATAAGCCTGTTCGGTTCGTAAGCTGTAATGCAAGTAGCGT<br>ATGCGCTCACGCAACTGGTCCAGAACCTTGACCGAACGCAGCGGT<br>GGTAACGGCGCAGTGGCGGTTTTCATGGCTTGTTATGACTGTTTTT<br>TTGGGGTACAGTCTATGCCTCGGGCATCCAAGCAGCAAGCGCGTT<br>ACGCCGTGGGTCGATGTTTGATGTTATGGAGCAGCAACGATGTTAC<br>GCAGCAGGGCAGTCGCCCTAAAACAAAGTTAAACATTATGAGGGA<br>AGCGGTGATCGCCGAAGTATCGACTCAACTATCAGAGGTAGTTGG<br>CGCCATCGAGCGCCATCTCGAACCGACGTTGCTGGCCGTACATTTG<br>TACGGCTCCGCAGTGGATGGCGGCCTGAAGCCACACAGTGATATT<br>GATTTGCTGGTTACGGTGACCGTAAGGCTTGATGAAACAACGCGG<br>CGAGCTTTGATCAACGACCTTTTGGAAACTTCGGCTTCCCCTGGAG<br>AGAGCGAGATTCTCCGCGCTGTAGAAGTCACCATTGTTGTGCACGA<br>CGACATCATTCCGTGGCGTTATCCAGCTAAGCGCGAACTGCAATTT<br>GGGAGAATGGCAGCGCAATGACATTCTTGCAGGTATCTTCGAGCCA<br>GCCACGATCGACATTGATCTGGCTATCTTGCTGACAAAAGCAAGA<br>GAACATAGCGTTGCCTTGGTAGGTCCAGCGGCGGAGGAACTCTTT<br>GATCCGGTTCCTGAACAGGATCTATTTGAGGCGCTAAATGAAACCT<br>TAACGCTATGGAACTCGCCGCCCGACTGGGCTGGCGATGAGCGAA<br>ATGTAGTGCTTACGTTGTCCCGCATTTGGTACAGCGCAGTAACCGG<br>CAAAATCGCGCCGAAGGATGTCGCTGCCGGCTGGGCAATGGAGCG<br>CCTGCCGGCCCAGTATCAGCCCGTCATACTTGAAGCTAGACAGGCT<br>TATCTTGGACAAGAAGAAGATCGCTTGGCCTCGCGCGCAGATCAG<br>TTGGAAGAATTTGTCCACTACGTGAAAGGCGAGATCACCAAGGTA<br>GTCGGCAAATAACCCTCGAGCATTCAAGGCGCCTTGATTATTTGAC | PjL35 | SEQ. ID NO. 29 |

TABLE 1-continued example amino acid sequences of DRS-DRR enzymes, split DRS and DRR enzymes, and other nucleotide sequences.

| Sequence | Description | SEQ. ID NO. |
|---|---|---|
| GTGGTTTGATGGCCTCCACGCACGTTGTGATATGTAGATGATTCAG<br>TTCGAGTTTATCATTATCAATACTGCCATTTCAAAGAATACGTAAA<br>TAATTAATAGTAGTGATTTTCCTAACTTTATTTAGTCAAAAAATTA<br>GCCTTTTAATTCTGCTGTAACCCGTACATGCCCAAAATAGGGGGCG<br>GGTTACACAGAATATATAACATCGTAGGTGTCTGGGTGAACAGTTT<br>ATTCCTGGCATCCACTAAATATAATGGAGCCCGCTTTTTAAGCTGG<br>CATCCAGAAAAAAAAAGAATCCCAGCACCAAAATATTGTTTTCTTC<br>ACCAACCATCAGTTCATAGGTCCATTCTCTTAGCGCAACTACAGAG<br>AACAGGGGCACAAACAGGCAAAAAACGGGCACAACCTCAATGGA<br>GTGATGCAACCTGCCTGGAGTAAATGATGACACAAGGCAATTGAC<br>CCACGCATGTATCTATCTCATTTTCTTACACCTTCTATTACCTTCTG<br>CTCTCTCTGATTTGGAAAAAGCTGAAAAAAAAGGTTGAAACCAGT<br>TCCCTGAAATTATTCCCCTACTTGACTAATAAGTATATAAAGACGG<br>TAGGTATTGATTGTAATTCTGTAAATCTATTTCTTAAACTTCTTAAA<br>TTCTACTTTTATAGTTAGTCTTTTTTTTAGTTTTAAAACACCAAGAA<br>CTTAGTTTCGAATAAACACACATAAACAAACAAAATGGAACTTCA<br>GTACTTCTCCTATTTTCAACCCACTTCATCTGTCGTAGCCCTACTAC<br>TAGCACTAGTGAGTATTTTATTTAGCGTAGTTGTTTTGAGGAAGAC<br>TTTCAGTAACAATTACTCCAGCCCCGCGTCAAGTACGGAAACCGCT<br>GTGCTGTGTCATCAGAGGCAACAGAGTTGCGCCCTACCTATCAGCG<br>GCCTTCTTCACGTGTTCATGAATAAGAACGGCCTGATTCATGTCAC<br>CTTGGGAAATATGGCTGACAAATATGGCCCTATCTTCAGTTTTCCG<br>ACAGGCAGCCACCGTACTTTAGTAGTCAGTTCCTGGGAAATGGTG<br>AAAGAGTGTTTCACCGGTAATAACGACACGGCATTCTCCAACAGA<br>CCAATCCCTTTGGCTTTTCAAACCATATTCTACGCCTGTGGCGGCA<br>TTGATTCTTACGGTTTAAGTAGTGTCCCGTATGGTAAATACTGGAG<br>GGAGTTGAGAAAGGTGTGTGTTCACAACCTGCTGAGTAATCAGCA<br>ATTGCTGAAGTTCAGACATCTTATAATCTCCCAAGTGGATACGTCT<br>TTTAACAAGTTGTATGAGCTGTGTAAGAACTCTGAAGATAATCAAG<br>GTATGGTAAGGATGGATGATTGGCTAGCTCAACTTTCCTTTAACGT<br>CATCGGTAGGATCGTTTGCGGATTCCAGTCTGACCCAAAGACGGGT<br>GCACCTTCAAGGGTAGAACAGTTTAAGGAAGTCATAAATGAGGCG<br>TCATATTTTATGTCAACAAGTCCAGTCTCCGATAACGTACCAATGT<br>TGGGATGGATCGACCAATTGACCGGTCTGACGAGGAACATGAAGC<br>ATTGTGGGAAGAAGCTTGACTTAGTAGTGGAGTCAATTATCAAGG<br>ACCATAGGCAAAAGAGACGTTTTTCACGTACAAAAGGTGGCGATG<br>AGAAGGATGACGAACAGGACGACTTTATTGATATTTGCTTGAGCA<br>TCATGGAGCAGCCACAGTTGCCCGGGAACAATTCTCCCCCTCAAAT<br>TCCGATCAAATCTATCGTGCTAGACATGATTGGGGGTGGTACCGAC<br>ACTACGAAACTTACAACCATATGGACCCTATCACTTTTGTTGAACA<br>ATCCTCACGTGTTAGATAAAGCTAAACAAGAGGTCGACGCTCACTT<br>TCGTAAAAAGAGAAGATCAACAGATGACGCAGCAGCGGCAGTCGT<br>TGATTTTGACGACATAAGAAATTTAGTATACATCCAAGCCATCATT<br>AAAGAAAGTATGAGGCTTTATCCAGCCAGCCCGGTGGTTGAGCGT<br>CTTTCCGGCGAGGATTGCGTTGTTGGAGGTTTTCACGTGCCTGCTG<br>GTACGAGACTATGGGCTAACGTTTGGAAGATGCAAAGAGATCCCA<br>AAGTTTGGGACGATCCTCTAGTATTCAGACCTGAAAGGTTTTTGAG<br>CGACGAGCAAAAGATGGTAGACGTTCGTGGCCAAAACTATGAACT<br>TCTGCCATTCGGCGCAGGAAGAAGAATCTGTCCAGGCGTTTCCTTT<br>AGTCTTGACCTTATGCAACTTGTCCTAACCAGGTTAATCCTAGAGT<br>TCGAAATGAAGTCCCCGTCCGGCAAGGTAGATATGACCGCAACTC<br>CAGGACTAATGTCTTACAAGGTGGTTCCATTGGACATATTGCTGAC<br>TCACCGTCGTATCAAGTCATGCGTTCAATTGGCGTCTTCTGAACGT<br>GATtaaGCGAATTTCTTATGATTTATGATTTTTATTATTAAATAAGTT<br>ATAAAAAAAATAAGTGTATACAAATTTTAAAGTGACTCTTAGGTTT<br>TAAAACGAAAATTCTTATTCTTGAGTAACTCTTTCCTGTAGGTCAG<br>GTTGCTTTCTCAGGTAGAGCGTTGGTTGGTGGATCAAGCCCACGCG<br>TAGGCAATCCTCGAGCAGATCCGCCAGGCGTGTATATATAGCGTG<br>GATGGCCAGGCAACTTTAGTGCTGACACATACAGGCATATATATAT<br>GTGTGCGACAACACATGATCATATGGCATGCATGTGCTCTGTATGT<br>ATATAAAACTCTTGTTTTCTTCTTTTCTCTAAATATTCTTTCCTTATA<br>CATTAGGACCTTTTGCAGCATAAATTACTATACTTCTATAGCACAC<br>AAACACAAATACACACACTAAATTAATAATGGAAAGTTCTGGGGT<br>GCCTGTGATCACATTGTCCTCAGGTAAAGTAATGCCCGTACTGGGC<br>ATGGGAACCTTCGAAAAGGTGGGTAAGGGGTCTGAACGTGAGCGT<br>TTAGCCATTCTTAAAGCGATCGAAGTTGGTTACCGTTACTTTGATA<br>CCGCAGCGGCATATGAAACGGAAGAAGTTCTAGGGGAAGCCATTG<br>CTGAAGCTTTACAATTGGGTCTGATAGAGAGCCGTGACGAGCTGTT<br>CATCAGCTCAATGCTTTGGTGCACCGACGCACATCCAGACCGTGTG<br>CTACTTGCTCTGCAAAACAGTCTGAGAAATCTAAAACTTGAATATC<br>TAGACCTATATATGTTGCCGTTTCCTGCCAGCCTTAAGCCGGGCAA<br>AATTACGATGGATATTCCTGAGGAGGATATTTGCCGTATGGATTAT<br>CGTTCAGTCTGGAGCGCCATGGAAGAGTGTCAAAACTTAGGATTT<br>ACTAAAAGTATTGGTGTAAGCAACTTTTCTTGCAAGAAATTACAAG | | |

TABLE 1-continued example amino acid sequences of DRS-DRR enzymes, split DRS and DRR enzymes, and other nucleotide sequences.

| Sequence | Description | SEQ. ID NO. |
|---|---|---|
| AATTAATGGCCACTGCAAATATCCCGCCCGCGGTAAATCAAGTAG AGATGTCACCAGCTTTCCAACAGAAAAAACTGAGGGAATATTGTA ACGCAAACAACATATTGGTATCCGCAGTAAGCATTCTGGGATCAA ACGGGACGCCCTGGGGTAGTAATGCTGTTCTTGGAAGCGAAGTTTT GAAACAGATCGCGATGGCGAAAGGCAAAAGCGTTGCGCAAGTCA GTATGAGGTGGGTCTATGAGCAGGGCGCGTCTTTAGTAGTCAAGA GTTTCTCTGAAGAACGTTTAAGAGAAAACCTGAATATTTTTGACTG GGAGCTTACGAAAGAAGACAATGAGAAGATAGGCGAAATCCCGC AATGTAGAATCCTTACTGCGTACTTCCTTGTCTCCCCGAACGGCCC GTTTAAATCTCAGGAAGAGCTTTGGGATGACAAGGCAtaaACAGGC CCCTTTTCCTTTGTCGATATCATGTAATTAGTTATGTCACGCTTACA TTCACGCCCTCCTCCCACATCCGCTCTAACCGAAAAGGAAGGAGTT AGACAACCTGAAGTCTAGGTCCCTATTTATTTTTTTAATAGTTATG TTAGTATTAAGAACGTTATTTATATTTCAAATTTTTCTTTTTTTCTG TACAAACGCGTGTACGCATGTAACATTATACTGAAAACCTTGCTTG AGAAGGTTTTGGGACGCTCGAAGGCTTTAATTTGTAATCATTATCA CTTTACGGGTCCTTTCCGGTGATCCGACAGGTTACGGGGCGGCGAC CTCGCGGGTTTTCGCTATTTATGAAAATTTTCCGGTTTAAGGCGTTT CCGTTCTTCTTCGTCATAACTTAATGTTTTTATTTAAAATACCTCGC GAGTGGCAACACTGAAAATACCCATGGAGCGGCGTAACCGTCGCA CAGgatctaggtgaagatccttttgataatctcatgaccaaaatccc ttaacgtgagttttcgttccactgagcgtcagacccgtagaaaagat caaaggatcttcttgagatcctttttttctgcgcgtaatctgctgctt gcaaacaaaaaaaccaccgctaccagcggtggtttgtttgccggatca agagctaccaactctttttccgaaggtaactggcttcagcagagcgca gataccaaatactgtccttctagtgtagccgtagttaggccaccactt caagaactctgtagcaccgcctacatacctcgctctgctaatcctgtt accagtggctgctgccagtggcgataagtcgtgtcttaccgggttgga ctcaagacgatagttaccggataaggcgcagcggtcgggctgaacggg gggttcgtgcacacagcccagcttggagcgaacgacctacaccgaact gagatacctacagcgtgagctatgagaaagcgccacgcttcccgaagg gagaaaggcggacaggtatccggtaagcggcagggtcggaacaggaga gcgcacgagggagcttccaggggggaaacgcctggtatctttatagtcc tgtcgggtttcgccacctctgacttgagcgtcgatttttgtgatgctc gtcagggggcggagcctatggaaaaacgccagcaacgcggcagtgga acgTGCATTATGAATTAGTTACGCTAGGGATAACAGGGTAATATAGAA CCCGAACGACCGAGCGCAGCGGCGGCCGCGCTGATACCGCCGC | | |

Morphinan Alkaloid Generating Modifications

Figure 20:
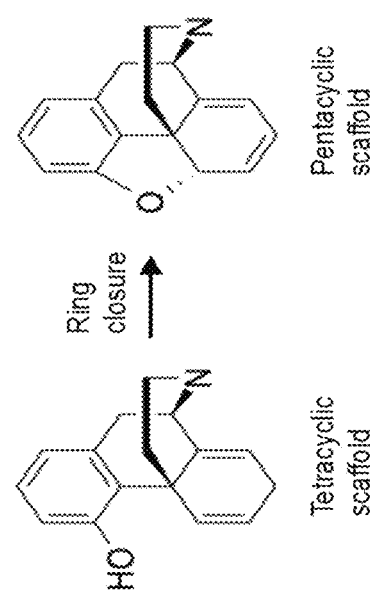
FIG. 20 illustrates the general ring closure reaction converting a tetracyclic scaffold to a pentacyclic scaffold, in accordance with embodiments of the invention.

Some methods, processes, and systems provided herein describe the conversion of promorphinan alkaloids to morphinan alkaloids. Some of the methods, processes, and systems describe the conversion of a tetracyclic scaffold to a pentacyclic scaffold (FIG. 20). Some of the methods, processes, and systems may comprise an engineered host cell. In some examples, the production of pentacyclic thebaine, or a morphinan alkaloid, from a tetracyclic precursor, or a promorphinan alkaloid is described. In some examples, the conversion of promorphinan alkaloids to thebaine are key steps in the conversion of a substrate to a diverse range of benzylisoquinoline alkaloids.

In some examples, the tetracyclic precursor may be salutaridine, salutaridinol, or salutaridinol-7-O-acetate. The tetracyclic precursor may be converted to pentacyclic thebaine by closure of an oxide bridge between C-4 and C-5. In some examples, the tetracyclic precursor salutaridine may be prepared for ring closure by stepwise hydroxylation and O-acetylation at C-7. Ring closure may be activated by elimination of an acetate leaving group. In some examples, the allylic elimination and oxide ring closure that generates thebaine occurs spontaneously. In other examples, the ring closure reaction that generates pentacyclic thebaine is promoted by factors such as pH or solvent. In other examples, the thebaine-generating ring closure reaction is promoted by contact with a protein or enzyme. These conversion steps are provided in FIG. 14 and represented generally in Scheme 2.

$R_1$, $R_2$, and $R_3$ may be H or $CH_3$. $R_4$ may be $CH_3$, $CH_3CH_2$, $CH_3CH_2CH_2$, or other appropriate alkyl group. In some cases, $R_1$, $R_2$, $R_3$, and $R_4$ may be $CH_3$ as provided in FIG. 14.

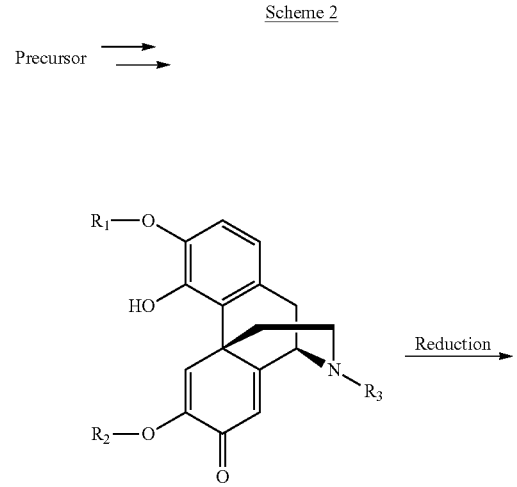

Scheme 2

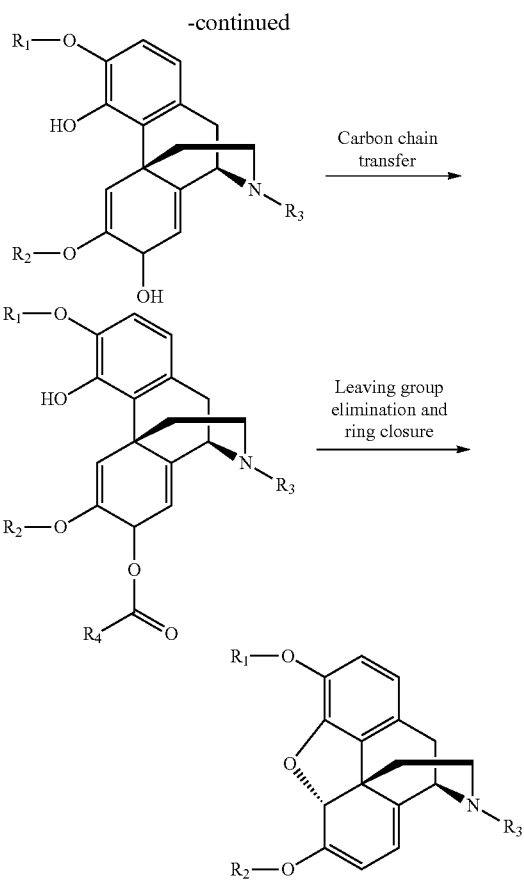

In some examples, the first enzyme that prepares the tetracyclic precursor is salutaridine reductase (SalR). In some cases, SalR hydroxylates the substrate salutaridine at the C-7 position (see Formula III). The product of this reaction may be one or more salutaridinol epimers. In some examples, the product is (7S)-salutaridinol. In some examples, the salutaridine reductase may catalyze the reduction reaction within a host cell, such as an engineered host, as described herein.

In some examples, the second enzyme that prepares the tetracyclic precursor is salutaridinol 7-O-acetyltransferase (SalAT). In some cases, SalAT transfers the acetyl from acetyl-CoA to the 7-OH of salutaridinol (see Formula IV). In other cases, SalAT may utilize a novel cofactor such as n-propionyl-CoA and transfer the propionyl to the 7-OH of salutaridinol. In some examples, the product of SalAT is (7S)-salutaridinol-7-O-acetate. In some examples, the salutaridinol 7-O-acetyltransferase may catalyze the acetyl transfer reaction within a host cell, such as an engineered host, as described herein.

In some examples, the tetracyclic precursor of thebaine is (7S)-salutaridinol-7-O-acetate. In some examples (7S)-salutaridinol-7-O-acetate is unstable and spontaneously eliminates the acetate at C-7 and closes the oxide bridge between C-4 and C-5 to form thebaine (see Formula V). In some examples, the rate of elimination of the acetate leaving group is promoted by pH. In some examples, the allylic elimination and oxide bridge closure is catalyzed by an enzyme with thebaine synthase activity, or a thebaine synthase. In some examples, this enzyme is a Bet v 1-fold protein. In some examples, this enzyme is an engineered thebaine synthase, an engineered SalAT, a dirigent (DIR) protein, or a chalcone isomerase (CHI). In some examples, the enzyme encoding thebaine synthase activity may catalyze the ring closure reaction within a host cell, such as an engineered host, as described herein.

In some examples, the salutaridine reductase enzyme may be SalR or a SalR-like enzyme from plants in the Ranunculales order that biosynthesize thebaine, for example *Papaver somniferum*. In other examples, the enzyme with salutaridine reductase activity may be from mammals or any other vertebrate or invertebrate that biosynthesizes endogenous morphine.

In some examples, the salutaridinol 7-O-acetyltransferase enzyme may be SalAT or a SalAT-like enzyme from plants in the Ranunculales order that biosynthesize thebaine, for example *P. somniferum*. In other examples, the enzyme with salutaridinol 7-O-acetyltransferase activity may be from mammals or any other vertebrate or invertebrate that biosynthesizes endogenous morphine.

In some examples, the thebaine synthase enzyme may be a Bet v 1 fold protein from plants in the Ranunculales order that biosynthesize thebaine, for example *P. somniferum*. In some examples, the Bet v 1 protein includes the following domains in order from the N-terminus to C-terminus: a β-strand, one or two α-helices, six β-strands, and one or two α-helices. The protein is organized such that it has a Bet v 1 fold and an active site that accepts large, bulky, hydrophobic molecules, such as morphinan alkaloids. This protein may be any plant Bet v 1 protein, pathogenesis-related 10 protein (PR-10), a major latex protein (MLP), fruit or pollen allergen, plant hormone binding protein (e.g., binding to cytokinin or brassinosteroids), plant polyketide cyclase-like protein, or norcoclaurine synthase (NCS)-related protein that has a Bet v 1 fold. Other non-plant examples of the Bet v 1 fold protein are polyketide cyclases, activator of Hsp90 ATPase homolog 1 (AHA1) proteins, SMU440-like proteins (e.g., from *Streptococcus mutans*), PA1206-related proteins (e.g., from *Pseudomonas aeruginosa*), CalC calicheamicin resistance protein (e.g., from *Micromonospora echinospora*), and the CoxG protein from carbon monoxide metabolizing *Oligotropha carboxidovorans*. Further examples from Bet v 1-related families include START lipid transfer proteins, phosphatidylinositol transfer proteins, and ring hydroxylases.

In some examples, the thebaine synthase enzyme may be a dirigent protein from plants in the Ranunculales order that biosynthesize thebaine, for example *P. somniferum*. In other examples, the enzyme may be any dirigent protein from plants.

In some examples, the thebaine synthase enzyme may be a chalcone isomerase protein from plants in the Ranunculales order that biosynthesize thebaine, for example *P. somniferum*. In other examples, the enzyme may be any chalcone isomerase protein from plants.

In some examples, the thebaine synthase enzyme may be a SalAT-like enzyme from plants in the Ranunculales order that biosynthesize thebaine, for example *P. somniferum*. In other examples, the enzyme may be any SalAT-like protein from plants.

In some examples, the enzyme with thebaine synthase activity may be from mammals or any other vertebrate or invertebrate that biosynthesizes endogenous morphine.

In some examples, any combination of the above enzymes together with additional accessory proteins may function to convert any tetracyclic precursor into thebaine. In some examples, these enzymes catalyze the reactions within a host cell, such as an engineered host, as described herein.

Examples of amino acid sequences for thebaine synthase activity are set forth in Table 2. An amino acid sequence for a thebaine synthase that is utilized in a tetracyclic precursor to thebaine may be 45% or more identical to a given amino acid sequence as listed in Table 2. For example, an amino acid sequence for such a thebaine synthase may comprise an amino acid sequence that is at least 45% or more, 46% or more, 47% or more, 48% or more, 49% or more, 50% or more, 51% or more, 52% or more, 53% or more, 54% or more, 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to an amino acid sequence as provided herein. Additionally, in certain embodiments, an "identical" amino acid sequence contains at least 80%-99% identity at the amino acid level to the specific amino acid sequence. In some cases an "identical" amino acid sequence contains at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

An engineered host cell may be provided that produces a salutaridine reductase, salutaridinol 7-O-acetyltransferase, and thebaine synthase that converts a tetracyclic precursor into thebaine, wherein the thebaine synthase comprises an amino acid sequence selected from the group consisting of SEQ ID NOs: 30, 31, 32, 33, 34, 35, 36, and 37. In some cases, the thebaine synthase may form a fusion protein with other enzymes. The enzymes that are produced within the engineered host cell may be recovered and purified so as to form a biocatalyst. These one or more enzymes may also be used to catalyze the conversion of a tetracyclic promorphinan precursor to thebaine.

In other examples, the thebaine synthase comprises an amino acid sequence selected from the group consisting of SEQ ID NOs: 38, 39, 40, 41, 42, 43, 44, 45, 46, 47, 48, 49, 50, 51, 52, 53, 54, 55, 56, 57, 58, 59, 60, and 61.

In additional cases, the one or more enzymes that are recovered from the engineered host cell may be used in a process for converting a tetracyclic promorphinan precursor to a thebaine. The process may include contacting the tetracyclic promorphinan precursor with the recovered enzymes in an amount sufficient to convert said tetracyclic promorphinan precursor to thebaine. In examples, the tetracyclic promorphinan precursor may be contacted with a sufficient amount of the one or more enzymes such that at least 5% of said tetracyclic promorphinan precursor is converted to thebaine. In further examples, the tetracyclic promorphinan precursor may be contacted with a sufficient amount of the one or more enzymes such that at least 10%, at least 15%, at least 20%, at least 25%, at least 30%, at least 35%, at least 40%, at least 45%, at least 50%, at least 55%, at least 60%, at least 65%, at least 70%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said tetracyclic promorphinan precursor is converted to thebaine.

In some examples, process conditions are implemented to support the formation of thebaine in engineered host cells. In some cases, engineered host cells are grown at pH 3.3, and once high cell density is reached the pH is adjusted to pH 8.0 to support continued production of thebaine at higher pH. In some cases, the engineered host cells produce additional enzymes to convert sugar and other simple precursors, such as tyrosine, to thebaine. In some cases, the SalAT enzyme has been engineered to exhibit higher activity at pH 8.0 and is expressed from a late stage promoter.

In some examples, one or more of the enzymes converting a tetracyclic promorphinan precursor to a thebaine are localized to cellular compartments. In some examples, SalR, SalAT, and Bet v 1 may be modified such that they encode targeting sequences that localize them to the endoplasmic reticulum membrane of the engineered host cell (see for example WO2014143744). In other examples, SalAT and Bet v 1 may be co-localized in to a single protein fusion. In some examples, the fusion is created between SalAT and Bet v 1 by one of several methods, including, direct fusion, co-localization to a yeast organelle, or by enzyme co-localization tools such as leucine zippers, protein scaffolds that utilize adaptor domains, or RNA scaffolds that utilize aptamers. Co-localizing the thebaine synthesis enzyme may facilitate substrate channeling between the active sites of the enzymes and limit the diffusion of unstable intermediates such as salutaridinol-7-O-acetate.

In some examples, an engineered salutaridinol 7-O-acetyltransferase (SalAT) enzyme is used in converting a tetracyclic promorphinan precursor to a thebaine. In some examples, a SalAT enzyme is engineered to combine two functions: (1) the transfer of an acyl group from acetyl-CoA to the 7-OH of salutaridinol, and (2) the subsequent elimination of the acetyl group and closure of an oxide bridge between carbons C4 and C5 to form thebaine.

In some examples, an enzyme with salutaridinol 7-O-acetyltransferase activity is fused to a peptide with a Bet v 1 fold. In some examples, salutaridinol 7-O-acetyltransferase enzyme and the Bet v 1 fold protein may be fused in any order from N-terminus to C-terminus, C-terminus to N-terminus, N-terminus to N-terminus, or C-terminus to C-terminus. In some examples, the two protein sequences may be fused directly or fused through a peptide linker region.

In some examples, an enzyme with salutaridinol 7-O-acetyltransferase activity is fused to a peptide with a Bet v 1 fold by circular permutation. In some cases, the N- and C-termini of SalAT are fused and the Bet v 1 sequence is then inserted randomly within this sequence. In some cases, the resulting fusion protein library is screened for thebaine production. In other cases, a circular permutation SalAT library is first screened for activity in the absence of Bet v 1. In other cases, the N- and C-termini of SalAT are fused and the enzyme is digested and blunt end cloned. In other cases, this library of circularly permuted SalAT is screened for salutaridinol 7-O-acetyltransferase activity. In other cases, active variants from the circularly permuted SalAT library are then used to design protein fusions with a peptide with a Bet v 1 fold.

The one or more enzymes that may be used to convert a tetracyclic promorphinan precursor to a thebaine may contact the tetracyclic promorphinan precursor in vitro. Additionally, or alternatively, the one or more enzymes that may be used to convert a tetracyclic promorphinan precursor to thebaine may contact the tetracyclic promorphinan precursor in vivo. Additionally, the one or more enzymes that may be used to convert a tetracyclic promorphinan precursor to thebaine may be provided to a cell having the tetracyclic promorphinan precursor within, or may be produced within an engineered host cell.

In some examples, the methods provide for engineered host cells that produce an alkaloid product, wherein the conversion of a tetracyclic promorphinan precursor to a thebaine may comprise a key step in the production of an alkaloid product. In some examples, the alkaloid product is a thebaine. In still other embodiments, the alkaloid product is derived from a thebaine, including for example, downstream morphinan alkaloids. In another embodiment, a tetracyclic promorphinan precursor is an intermediate toward the product in of the engineered host cell. In still other embodiments, the alkaloid product is selected from the group consisting of morphinan, nor-opioid, or nal-opioid alkaloids.

In some examples, the substrate of the reduction reaction is a compound of Formula III:

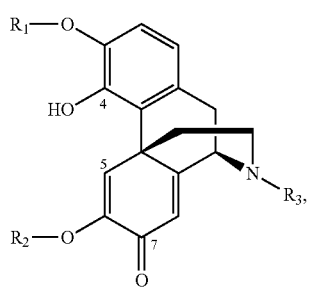

Formula III or a salt thereof, wherein:

$R_1$, $R_2$, and $R_3$ are independently selected from hydrogen and methyl.

In some other examples, $R_1$, $R_2$, and $R_3$ are methyl, and the reduction reaction is catalyzed by a salutaridine reductase.

In some examples, the substrate of the carbon chain transfer reaction is a compound of Formula IV:

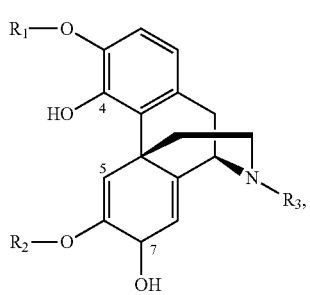

Formula IV or a salt thereof, wherein:

$R_1$, $R_2$, and $R_3$ are independently selected from hydrogen and methyl.

In some other examples, $R_1$, $R_2$, and $R_3$ are methyl, and the carbon chain transfer reaction is catalyzed by a salutaridinol 7-O-acetyltransferase.

In some examples, the substrate of thebaine synthase is a compound of Formula V:

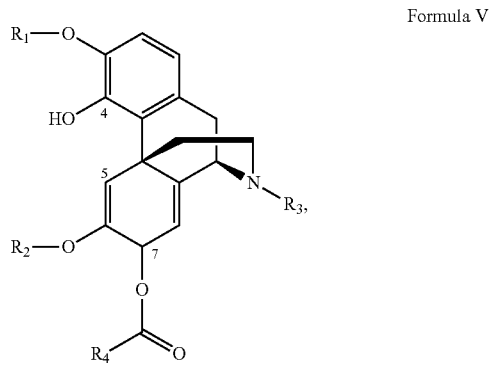

Formula V or a salt thereof, wherein:

$R_1$, $R_2$, and $R_3$ are independently selected from hydrogen and methyl; and $R_4$ is selected from methyl, ethyl, propyl, and other appropriate alkyl group.

In some other examples, $R_1$, $R_2$, $R_3$, and $R_4$ are methyl, and the ring closure reaction is catalyzed by a thebaine synthase. In some examples, the thebaine synthase is a Bet v 1 protein.

In some examples, the methods provide for engineered host cells that produce alkaloid products from salutaridine. The conversion of salutardine to thebaine may comprise a key step in the production of diverse alkaloid products from a precursor. In some examples, the precursor is L-tyrosine or a sugar (e.g., glucose). The diverse alkaloid products can include, without limitation, morphinan, nor-opioid, or nal-opioid alkaloids.

Any suitable carbon source may be used as a precursor toward a pentacyclic morphinan alkaloid. Suitable precursors can include, without limitation, monosaccharides (e.g., glucose, fructose, galactose, xylose), oligosaccharides (e.g., lactose, sucrose, raffinose), polysaccharides (e.g., starch, cellulose), or a combination thereof. In some examples, unpurified mixtures from renewable feedstocks can be used (e.g., cornsteep liquor, sugar beet molasses, barley malt, biomass hydrolysate). In still other embodiments, the carbon precursor can be a one-carbon compound (e.g., methanol, carbon dioxide) or a two-carbon compound (e.g., ethanol). In yet other embodiments, other carbon-containing compounds can be utilized, for example, methylamine, glucosamine, and amino acids (e.g., L-tyrosine). In some examples, a 1-benzylisoquinoline alkaloid may be added directly to an engineered host cell of the invention, including, for example, norlaudanosoline, laudanosoline, norreticuline, and reticuline.

In some examples, the benzylisoquinoline alkaloid product, or a derivative thereof, is recovered. In some examples, the benzylisoquinoline alkaloid product is recovered from a cell culture. In some examples, the benzylisoquinoline alkaloid product is a morphinan, nor-opioid, or nal-opioid alkaloid.

TABLE 2

Example amino acid sequences of morphinan alkaloid generating enzymes.

| Sequence Name | Description | Sequence | SEQ. ID NO. |
|---|---|---|---|
| Bet v1 | | | |
| | P. bracteatum | MAPRGVSGLVGKLSTELDVNCDAEKYYNMYKNGEDVQKA VPHLCMDVKVISGDATRSGCIKEWNVNIDGKTIRSVEETTH NDETKTLRHRVFEGDMMKDYKKFDTIMEVNPKPDGNGCV VTRSIEYEKVNENSPTPFDYLQFGHQAMEDMNKY | SEQ. ID. NO. 30 |
| | P. setigerum | MLVGKLSTELEVDCDAEKYYNMYKHGEDVKKALCVDVKVI SGDPTRSGCIKEWNVNIDGKTIRSVEETTHNDETKTLRHRV FEGDMMKDFKKFDTIMVVNPKPDGNGCVVTRSIEYEKTNE NSPTPFDYLQFGHQAIEDMNKYL | SEQ. ID. NO. 31 |
| | P. setigerum | MLVGKLSTELEVDCDAEKYYNMYKHGEDKRQCVDVKVISG DPTRSGCIKEWNVNIDGKTIRSVEETTHNDETKTLRHRVFE GDMMKDFKKFDTIMVVNPKPDGNGCVVTRSIEYEKTNENS PTPFDYLQFGHQAIEDMNKY | SEQ. ID. NO. 32 |
| | P. setigerum | MLVGKLSTELEVDCDAEKYYNMYKHGEDVKKAVPHLCVDV KIISGDPTSSGCIKEWNVNIDGKTIRSVEETTHDDETKTLRH RVFEGDMVKDFKKFDTIMVVNPKPDGNGCVVTRSIEYEKT NENSPTPFDYLQFGHQAIEDMNKYL | SEQ. ID. NO. 33 |
| | P. setigerum | MVKIISGDPTSSGCIKEWNVNIDGKTIRSVEETTHDDETKTL RHRVFEGDMVKDFKKFDTIMVVNPKPDGNGCVVTRSIEYE KTNENSPTPFDYLQFGHQAIEDMNKYL | SEQ. ID. NO. 34 |
| | P. somniferum | MDSINSSIYFCAYFRELIIKLLMAPPGVSGLVGKLSTELEVNC DAEKYYNMYKHGEDVQKAVPHLCVDVKVISGDPTRSGCIKE WNVNIDGKTIRSVEETTHNDETKTLRHRVFEGDVMKDFKK FDTIMVVNPKPDGNGCVVTRSIEYEKTNDNSPTPFDYLQFG HQAIEDMNKYLRDSE | SEQ. ID. NO. 35 |
| | P. somniferum | MNFFIKDHLYICLVGKLSTELEVDCDAEKYYNMYKHGEDVK KAVPHLCVDVKIISGDPTSSGCIKEWNVNIDGKTIRSVEETT HDDETKTLRHRVFEGDVMKDFKKFDTIMVVNPKPDGNGC VVTRSIEYEKTNENSPTPFDYLQFGHQAIEDMNKYLRDSES N | SEQ. ID. NO. 36 |
| | P. somniferum | MAPLGVSGLVGKLSTELEVDCDAEKYYNMYKHGEDVKKAV PHLCVDVKIISGDPTSSGCIKEWNVNIDGKTIRSVEETTHDD ETKTLRHRVFEGDVMKDFKKFDTIMVVNPKPDGNGCVVTR SIEYEKTNENSPTPFDYLQFGHQAIEDMNKYLRDSESN | SEQ. ID. NO. 37 |
| SalAT | | | |
| | P. somniferum | MMKVCVSSREKIKPSRPTPGHLKTHKLSFLDQVAARIYVPL LLYYAGNKENVDTDTRCNIIKKSLAETLTKFYILAGKIVNDEI ERFVNCNDDGVDFCVTKVSNCQLFQVIKRPDIFDQVTLFLP FDPCDNEITASGDFLLSVQVNVFEDCRGMVIGLCINHKVAD ASSITTFVNYWATIARGLVLNVDDRQIQDPCFQVQSIFPQKE KGIGFKISSSSIDGTLVTKKFGFEASKLAELKERCKFAGATED IRGGYKPNRVEALSTFLWKCFIDIDQAKTKAAAPARVYLAS NAVNIRSRIVPQLPTSSFGNMVAITDAIFTVNSNENNGINDP YYPKLVQKFRDAVKRVDGEYIEALQSTDLLLNNVTKLFKHI LNGQTLSISFTSWCRFPFYDTDLLD | SEQ. ID. NO. 38 |
| | P. somniferum | MKVQVISKELIKPSTPTPPRLRNFKLSLLDQLLPPFYVPIIIFY PANDDHESNNNDQCIKANILKKSLSETLTRFYPIAGRIRDKI LVECNDEGVHYIEAKVNAVMSDFMSLDVIHQLHPSYITLDD LAEEAQLAVQVTMFDCGGIALSICSSHKIIDGCTSTTFLNSW AATARAPSNPEIVYPTFDAAAIFPAQPSGVQVSTLESDDRLQ GENVVTKRFLFSASKITALRARIAESRSSNILSKYPSRSEAVS ALVWKSFMETSRVKVTREHTFSAEASTKPIVRSIANFVVNL RTRLNPPLPNVSFGNIIMDATAESLIIDNGENTLGFVETLDG LISQLRLGVTKMDDEYVRKLREDDVEFLKSLDEASHPSNGE GDGNGERV | SEQ. ID. NO. 39 |
| | P. setigerum | MNDTMKIEVVSKESIKPSYPTPNNLKIHNLSNLDQLIPAFY MDHILYYPSLDSNDSSLGDDEEDKKMIFSASSRHRCDVVKK SLAETLTRYYPLAGRIKDEKSVECNDEGVDYIEARVVGITVS QVIQLASSDIEVMEPFLPYEPYGGTGSAFRRAGIHSNSKPLL KIQVNVFDCGGMVICLSGSHKVIDATSILNFVNDWAATARG GFDTHDDELKVAVVDKPCYIFSSMFPPTSFGNQEEKDTADQ AQLVPDRIEIVTKRFVFKDSSIAKLKKKCIHVNTNNGSDHQV | SEQ. ID. NO. 40 |

TABLE 2-continued

Example amino acid sequences of morphinan alkaloid generating enzymes.

| Sequence Name | Description | Sequence | SEQ. ID NO. |
|---|---|---|---|
| | | DKQEHNMQQMPSRIEALTSLIWMCFMDVDRRFRVKQIDD AVSPVNTVNEVSLPKQVQYVAGFAINLRTRTIQPLPTNSFG NMTDTAIAEVTLNLTGSDHFNNEKGIRDQSQNYPELVSKIK DSIKLVDNKHIEAMKRNLAISCNNIKMHQMMKESTFDQNT RELLMFSSWCRFPIYEADFGWGKPSWASITKLLYKNCVMF LDTSSGDGIEAWVSLKEEDMVEFERHEELVALAS | |
| | P. somniferum | MKVQVISKEIIKPSSPTPPHLRNFKLSLLDQILPPFYVPIVMF YPAGDDYVTNNNIHDQSSKSEFLKKSLSETLTRFYPIAGRIK DNILIDCNNEGVDYIEAKVNGIMSDFMSVDVVHQLHPSHIM LDDVAKEAQLAVQVNLFDCGGIAISISMSHKIVDACTAITFIN GWAATARAAPKQEIVCPTFDSAAIFPALPPGVQVSSLESDDS VQGVNVVTKMFAFTAPKIASLRARIAELRSSSDGLSKYPTRT EALSALVWKSFIRTSRVKAARKYSLSPASTKPVIKSVANYAV NLRTRLNPPLPQVSFGNILMDATAESTTTIDDDDSHEFADT LAGLIGQLRLGVSRINGDYIRKLQEGDLAFLKSLDEASHDSN GEKVQICWISSLCRFPPYEADFGWGKPSWVALNTNAEYKN SLFLMDTKCGTGIEAWVSLEEDDMAIFEEDQDLLQCVKSIN | SEQ. ID. NO. 41 |
| | P. setigerum | MENMKVEVVLKQTIKPSTQTPLHSKTFNLSFLDQHLGPPIYI PFTLYYESGDVNNKNNHCDGYKNNLEEACEHRVSVIKQSLS ETLARYYPLAGRMKEDNLAVECNDEGVEYFETRVSDVRLS QVIKRSPNHNSVLRKFLPPCISSCDNSMSIPFDYGFKSKTLLA IQVNIFECGGIVIGMCMAHRLADASTMFTFITDWAATARGA IEDIKGPSFDFSYTLFPQKDVINNFKPFDPMLTREEDLVTKY FVFPASKIVELKRRNVNNIVCQDTSQQNTSPCTRVEAVTSF MWKRYMDSVRAKNQTQATSVEKYGALYTVNLRSRITPPLP ANSFGNIYTFTIALSTPSDENDIDDGLRKDVSSPNDLNLVGK VRDAIKKIDDKYTRKLQSSEDELVNDVKPLTSGEAIFLGFSS WCRFPIYEADFGWGKPTWVSIGTMALRNTVFLMDTKSGD GIEAFVNMAKEDMDNFEVKLLADQ | SEQ. ID. NO. 42 |
| | P. setigerum | MENMKVEVVLEQTIKPSTQTPLHSKTFNLSFLDQHLGPPIYI PFTLYYESGDVNNKNNHCDGYKNNLEEVCEHRVSVIKQSLS ETLARYYPLAGRMKEDNLAVECNDEGVEYFETRVSDVRLS QVIKRSPNHNSVLRKFLPPCISSCDNSMSIPFDYGFKSKTLLA IQVNIFECGGIVIGMCMAHRLADASTMFTFITDWAATARGA IEDIKGPSFDFSYTLFPQKDVINNFKPFDPMLTREEDLVTKY FVFPASKIVELKRRNVNNIVCQDTSQQNTSPCTRVEAVTSF MWKRYMDSVRAKNQTQATSVEKYGALYTVNLRSRITPPLP ANSFGNIYTFTIALSTPSDENDIDDGLRKDVSSPNDLNLVGK VRDAIKKIDDKYTRKLQSSEDELVNDVKPLTSGEAIFLGFSS WCRFPIYEADFGWGKPTWVSIGTMALRNTVFLMDTKSGD GIEAFVNMAKEDMDNFEVKLLADQLLHVPTV | SEQ. ID. NO. 43 |
| | P. setigerum | MSSTVEVISKQTIKPSTPTPIQRKNHSLSLIDQHFAPIYIPIVL FYPAAAVNDTGNVQHGDNTCVLKRSLSETLVHFYPLAGRM KDNIVVDCNDQGVEFTEVKVSGTMCDFLMKPDEQLSGLLP SEAVCMNFVREAQVMIQVNTFDCGSKAISLCVSHKIADASTI TTFSRCWAETTIAVSKSTSAVTPIVSSKFHPTFDAASLFPPIK QLISPSGVTPALPELIPSEESKFGKIISKRFLFSATTINSVREKL SALMADKLKYRRLTRVEVVSALIWNSFDKLATTGSVAVMV KHAVNLRKRIDPPLPDVSFGNILEFTKAVVGEAAANTTTQG TVGSSSKLLEELSEFAGQLREPVSKMNKGDHDFDMENTDY EERDLWMSSWCNYGLYDIDFGCGKPVWVTTVATMYPYSD GFFMNDTRCGQGIEVWGNLVEEDMANFQLNLSELLDRI | SEQ. ID. NO. 44 |
| | P. somniferum | MMKVCVSSREKIKPSRPTPGHLKTHKLSFLDQVAARIYVPL LLYYAGNKENVDTDTRCNIIKKSLAETLTKFYILAGKIVNDEI ERFVNCNDDGVDFCVTKVSNCQLFQVIKRPDIFDQVTLFLP FDPCDNEITASGDFLLSVQVNVFEDCRGMVIGLCINHKVAD ASSITTFVNYWATIARGLVLNVDDRQIQDPCFQVQSIFPQKE KGIGFKISSSSIDGTLVTKKFGFEASKLAELKERCKFTTEPED GYKPTRVEALSAFLWKCFIDIDQAKLKGVARTKVYLATNAV NMRSRMVPQLPTSSFGNIISITDAVFSINNDDSTGINDPYYP KLVRKFRDAIKKIDRDYIEALRSTDLLLNNMMKLIEHVLSG HTLSIYFSSWCRFPLYETDFGWGKPIWVSTCTIPQKNVIVL MDSNSSADGIEAYVTLAKEDMGELEHHEELLALIS | SEQ. ID. NO. 45 |

TABLE 2-continued

Example amino acid sequences of morphinan alkaloid generating enzymes.

| Sequence Name | Description | Sequence | SEQ. ID NO. |
|---|---|---|---|
| Dirigent proteins | | | |
| | P. somniferum | MGAMKFFSFLAVAMVLSLAHIQAQQGNWGDETVPYTMGP EKITKLRFYFHDIVTGNNPTAVQIAQATGTNSSSTLFGALFM IDDPLTEGPDPDSRLVGRAQGFYGSAGQNEAALILGMSLVF TGNEKFNGSTISVLSRNPVTHTEREFAIVGGTGYFQFARGFI SAKTYSLVGPNAVVEYNCTIVHPSSVSESGKSNSSPGKSDSN SGSQISLGSNLVFVSVIAYVTIILSL | SEQ. ID. NO. 46 |
| | P. setigerum | MVLSMSHSQAQEGNWGDESVPYTMGPEKMTKLRFYFHDII TGNSPTAVQIAQATGTNTSATMFGALMMIDDPLTEGPDPN SRLVGRAQGFYGSAGQNELALILGMSLVFTGNEKFNGSTISV LSRNPVMHTEREFAIVGGTGYFQFARGFISAKTYSLVGPNA VVEYNCTIVHPSSVSESGKSDSSSGKSDSSSGSQISLGTNLVF LSVIAFVTIIVSPQHFSW | SEQ. ID. NO. 47 |
| Chalcone isomerase | | | |
| | P. somniferum | MTKTVLVDDIPFPPQNITTVTTEKQLPLLGQGITDMEIH FLQIKFTAIGTAIGVYLEPEIASHLQQWKGKTGAELSQ DDEFFAAVVSASVEKYVRVVVIKEIKGSQYMLQLES WVRDELAAADKYEDEEEESLDKVIEFFQSKYLKQLSF IPSHFSATTPAVAEIGLEIEGQKDLKIKVENGNVIEMIQ KWYLGGTRGVSPSTTQSLATSL | SEQ. ID. NO. 48 |
| | P. somniferum | MPFLKAIEIEGCKFRPFVTPPGSTQILFLAGSGVKEEFG DSKSMKYSSCAIYLQPTCILYLAKAWAQKSVVDITQS LNFFMDIATGPFEKYCRITMLETAKGEDYAAMITKNC EEMLTNSKRYSETAKAALTKESEAFNGRTLASGSSIH VTVSTSNSVTLAFTEDGSTPKQGDVTLDCKEVGEAFL MSTISLHTTIRESMGSRISGLYK | SEQ. ID. NO. 49 |
| | P. setigerum | MAPMAQLSEIQVEQFVFPPTMTPPSSTESLFLGGAGVR GLQIQDRFIKFTAIGVYLAEEAIPSLSPKWKSKSPEELT DDVEFFMDIVTGPFEKFVKITMILPLTGDQYAEKVTEN CIQYLKSKDMYTDAEAKAVERFIEIFKNEMFPPASSIL FTISPAGSLTVGF* | SEQ. ID. NO. 50 |
| | P. rhoeas | MVYLEPEIATHLKQWKGKTGAELSQDDDFFSAVVSA PVEKYVRVVVIKEIKGSQYMLQLESWVRDELAAADK YEDEEEESLDKVIEFFQSKYLKQHSVIITFHFSATTPAV AEIGLEIEGQKDLKIKVENGNVVEMIQKWYLGGTRGV SPSTTQSLATSL | SEQ. ID. NO. 51 |
| | P. bracteatum | MTKMVLVDDIPFPPQNITTATTAKQLPLLGQGITDMEIH FLQIKFTAIGVYLEPEIASHLKQWKGKTGAELSQDDEF FSAIVSAPVEKYVRVVVIKEIKGSQYMLQLESWVRDE LAAADKYEDEEEESLEKVIEFFQSKYLKQHSVIPFHFS ATTPAVAEIGLEIEGHKDLKMKVENGNVVEMIQKWY LAGTRGVSPSTTQSLATSL | SEQ. ID. NO. 52 |
| | P. bracteatum | MAPMAQLSEIQVEQFVFPPTMTPPSSTESLFLGGAGVR GLQIQDRFIKFTAIGVYLAEEAIPSLSPKWKSKTPEELT NDVEFFMDIVTGPFEKFVKITMILPLTGDQYAEKVTEN CVEYLKSKDLYTDAEAKAVERFIEIFKNEMFPPASSIL FTISPTGSLTVGFSKDTSIPEARNAVIENKALSESILESII GKNGVSPAAKQSLAERISELLK | SEQ. ID. NO. 53 |

TABLE 2-continued

Example amino acid sequences of morphinan alkaloid generating enzymes.

| Sequence Name | Description | Sequence | SEQ. ID NO. |
|---|---|---|---|
| Other | | | |
| | P. ginseng | MGLTGKLICQTGIKSDGDVFHELFGTRPHHVPNITPANIQGC DLHEGEFGKVGSVVIWNYSIDGNAMIAKEEIVAIDEEDKSVT FKVVEGHLFEEFKSIVFSVHVDTKGEDNLVTWSIDYEKLNE SVKDPTSYLDFLLSVTRDIEAHHLPK | SEQ. ID. NO. 54 |
| | A. hypogaea | MGVFTFEDEITSTVPPAKLYNAMKDADSITPKIIDDVKSVEI VEGNGGPGTIKKLTIVEDGETKFILHKVESIDEANYAYNYSV VGGVALPPTAEKITFETKLVEGPNGGSIGKLTLKYHTKGDA KPDEEELKKGKAKGEGLFRAIEGYVLANPTQY | SEQ. ID. NO. 55 |
| | H. perforatum | MGIDPFTMAAYTIVKEEESPIAPHRLFKALVLERHQVLVKA QPHVFKSGEIIEGDGGVGTVTKITFVDGHPLTYMLHKFDEID AANFYCKYTLFEGDVLRDNIEKVVYEVKLEAVGGGSKGKIT VTYHPKPGCTVNEEEVKIGEKKAYEFYKQVEEYLAANPEVF A | SEQ. ID. NO. 56 |
| | L. luteus | MGVFTFQDEYTSTIAPAKLYKALVTDADIIIPKAVETIQSVEI VEGNGGPGTIKKLTFIEGGESKYVLHKIEAIDEANLGYNYSIV GGVGLPDTIEKISFETKLVEGANGGSIGKVTIKIETKGDAQPN EEEGKAAKARGDAFFKAIESYLSAHPDYN | SEQ. ID. NO. 57 |
| | Strawberry (Fragaria x ananassa) | MAGVFTYETEFTSVIPPPRLFKAFILDADNLIPKIAPQAVKC AEIIEGDGGVGTIKKITFGEGSQFGSVTHKIDGIDKENFVYSY SLIEGDALSDKIEKISYETKLVSSSDGGSIIKSTSNYHTKGDVE IKEEHVKAGKEKFSHLFKLVEGYLLANPNEYC | SEQ. ID. NO. 58 |
| | A. deliciosa | MDLSGKMVKQVEILSDGIVFYEIFRYRLYLISEMSPVNIQGV DLLEGNWGTVGSVIFFKYTIDGKEKTAKDIVEAIDEETKSVT FKIVEGDLMELYKTFIIIVQVDTKGEHNSVTWTFHYEKLKE DVEEPNTLMNFCIEITKDIETYHLK | SEQ. ID. NO. 59 |
| | T. flavum | MGIINQVSTVTKVIHHELEVAASADDIWTVYSWPGLAKHLP DLLPGAFEKLEIIGDGGVGTILDMTFVPGEFPHEYKEKFILV DNEHRLKKVQMIEGGYLDLGVTYYMDTIHVVPTGKDSCVIK SSTEYHVKPEFVKIVEPLITTGPLAAMADAISKLVLEHKS | SEQ. ID. NO. 60 |
| | V. radiata | MVKEFNTQTELSVRLEALWAVLSKDFITVVPKVLPHIVKDV QLIEGDGGVGTILIFNFLPEVSPSYQREEITEFDESSHEIGLQV IEGGYLSQGLSYYKTTFKLSEIEEDKTLVNVKISYDHDSDIEE KVTPTKTSQSTLMYLRRLERYLSNGSA | SEQ. ID. NO. 61 |

BIA Generating Modifications

Once BIAs are formed, the BIAs may be further derivatized or modified. The BIAs may be derivatized or modified utilizing one or more enzymes that are produced by the engineered host cell. In particular, the BIAs may be derivatized or modified by contacting the BIAs with one or more enzymes that are produced by the engineered host cell. Additionally or alternatively, the BIAs may be derivatized or modified by contacting the BIAs with one or more enzymes that are provided to the BIAs from a source that is external to the engineered host cell. The one or more enzymes that may be used to derivatize or modify the BIAs may be used to perform tailoring reactions. Examples of tailoring reactions include oxidation, reduction, O-methylation, N-methylation, O-demethylation, acetylation, methylenedioxybridge formation, and O,O-demethylation. A BIA may be derivatized or modified using one or more tailoring reactions.

Examples of tailoring reactions are provided in Table 9. In some examples, tailoring enzymes may be used to catalyze carbon-carbon coupling reactions performed on a BIA, or a derivative thereof. Examples of tailoring enzymes that may be used to catalyze carbon-carbon coupling reactions include a Berberine bridge enzyme (BBE) from *Papaver somniferum, Eschscholzia californica, Coptis japonica, Berberis stolonifer, Thalictrum flavum*, or another species; Salutaridine synthase (SalSyn) from *Papaver somniferum* or another species; and Corytuberine synthase (CorSyn) from *Coptis japonica* or another species. Non-limiting examples of reactions that can be catalyzed by tailoring enzymes are shown in Scheme 3, wherein $R^a$, $R^b$, $R^c$, and $R^d$ are independently selected from hydrogen, hydroxy, fluoro, chloro, bromo, carboxaldehyde, $C_1$-$C_4$ acyl, $C_1$-$C_4$ alkyl, and $C_1$-$C_4$ alkoxy. In some examples, $R^a$, $R^b$, and the carbon atoms to which they are attached optionally form a carbocycle or heterocycle. In some examples, $R^c$, $R^d$, and the carbon atoms to which they are attached optionally form a carbocycle or heterocycle.

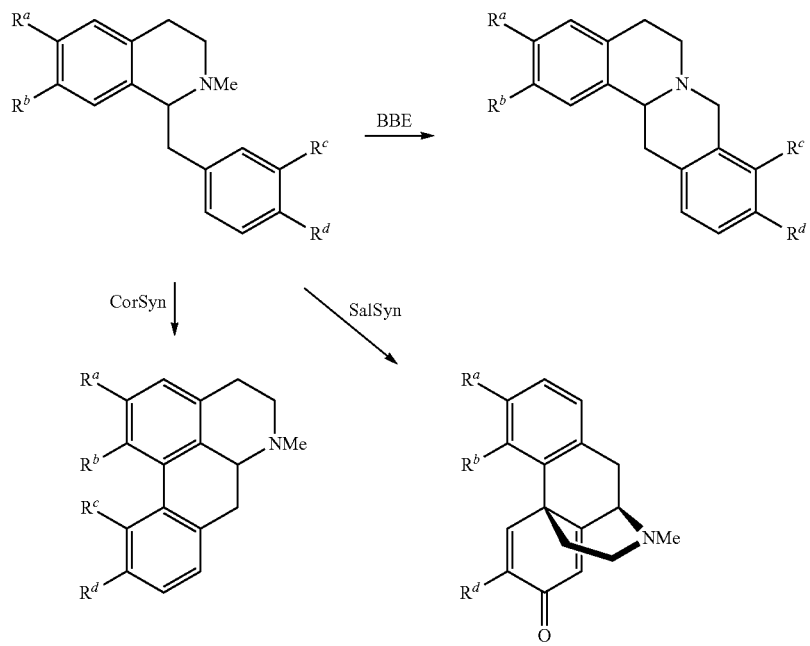

Scheme 3

In some examples, tailoring enzymes may be used to catalyze oxidation reactions performed on a BIA, or a derivative thereof. Examples of tailoring enzymes that may be used to catalyze oxidation reactions include a Tetrahydroprotoberberine oxidase (STOX) from *Coptis japonica, Argemone mexicana, Berberis wilsonae*, or another species; Dihydrobenzophenanthridine oxidase (DBOX) from *Papaver somniferum* or another species; Methylstylopine hydroxylase (MSH) from *Papaver somniferum* or another species; and Protopine 6-hydroxylase (P6H) from *Papaver somniferum, Eschscholzia californica*, or another species.

Tailoring enzymes may also be used to catalyze methylenedioxy bridge formation reactions performed on a BIA, or a derivative thereof. Examples of tailoring enzymes that may be used to catalyze methylenedioxy bridge formation reactions include a Stylopine synthase (StySyn) from *Papaver somniferum, Eschscholzia californica, Argemone mexicana*, or another species; Cheilanthifoline synthase (CheSyn) from *Papaver somniferum, Eschscholzia californica, Argemone mexicana*, or another species; and Canadine synthase (CAS) from *Thalictrum flavum, Coptis chinensis*, or another species.

In other examples, tailoring enzymes may be used to catalyze O-methylation reactions performed on a BIA, or a derivative thereof. Examples of tailoring enzymes that may be used to catalyze O-methylation reactions include a Norcoclaurine 6-O-methyltransferase (6OMT) from *Papaver somniferum, Thalictrum flavum, Coptis japonica, Papaver bracteatum*, or another species; 3'hydroxy-N-methylcoclaurine 4'-O-methyltransferase (4'OMT) from *Papaver somniferum, Thalictrum flavum, Coptis japonica, Coptis chinensis*, or another species; Reticuline 7-O-methyltransferase (7OMT) from *Papaver somniferum, Eschscholzia californica*, or another species; and Scoulerine 9-O-methyltransferase (9OMT) from *Papaver somniferum, Thalictrum flavum, Coptis japonica, Coptis chinensis*, or another species.

Additionally, tailoring enzymes may be used to catalyze N-methylation reactions performed on a BIA, or a derivative thereof. Examples of tailoring enzymes that may be used to catalyze N-methylation reactions include Coclaurine N-methyltransferase (CNMT) from *Papaver somniferum, Thalictrum flavum, Coptis japonica*, or another species; Tetrahydroprotoberberine N-methyltransferase (TNMT) from *Papaver somniferum, Eschscholzia californica, Papaver bracteatum*, or another species.

Further, tailoring enzymes may be used to catalyze O-demethylation reactions performed on a BIA, or a derivative thereof. Examples of tailoring enzymes that may be used to catalyze O-demethylation reactions include Thebaine demethylase (T6ODM) from *Papaver somniferum* or another species; and Codeine demethylase (CODM) from *Papaver somniferum*, or another species.

Tailoring enzymes may also be used to catalyze reduction reactions performed on a BIA, or a derivative thereof. Examples of tailoring enzymes that may be used to catalyze reduction reactions include Salutaridine reductase (SalR) from *Papaver somniferum, Papaver bracteatum*, or another species; Codeinone reductase (COR) from *Papaver somniferum* or another species; and Sanguinarine reductase (SanR) from *Eschscholzia californica* or another species. In other examples, tailoring enzymes may be used to catalyze acetylation reactions performed on a BIA, or a derivative thereof. An example of a tailoring enzyme that may be used to catalyze acetylation reactions includes Salutaridine acetyltransferase (SalAT) from *Papaver somniferum* or another species.

O-Demethylation Modifications

Some methods, processes, and systems provided herein describe the conversion of a first benzylisoquinoline alkaloid to a second benzylisoquinoline alkaloid by the removal of an O-linked methyl group. Some of these methods, processes, and systems may comprise an engineered host cell. In some examples, the conversion of a first benzylisoquinoline alkaloid to a second benzylisoquinoline alkaloid is a key step in the conversion of a substrate to a nor-opioids or nal-opioids.

In some examples, the conversion of a first alkaloid to a second alkaloid comprises a demethylase reaction.

Figure 6:
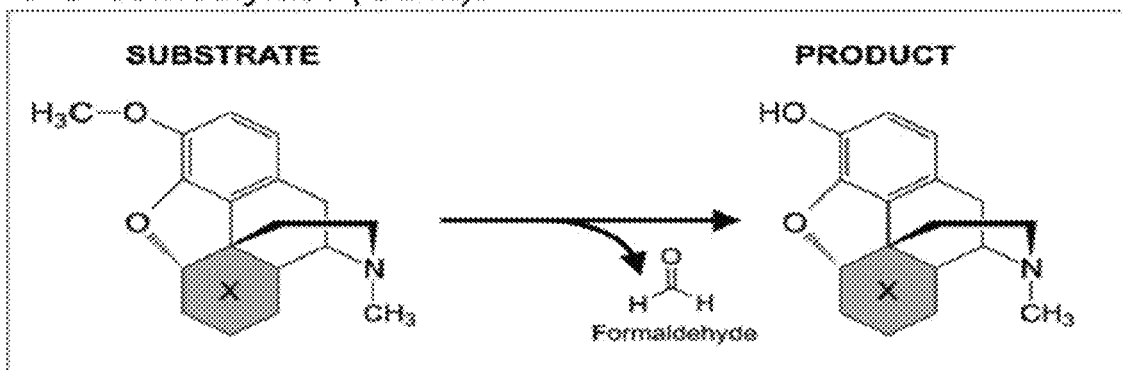
FIG. 6 illustrates an enzyme having opioid 3-O-demethylase activity, in accordance with embodiments of the invention.

FIG. 6 illustrates an enzyme having opioid 3-O-demethylase activity, in accordance with embodiments of the invention. Specifically, the enzyme may act on any morphinan alkaloid structure to remove the methyl group from the oxygen bound to carbon 3.

Examples of amino acid sequences of ODM enzymes are set forth in Table 4. An amino acid sequence for an ODM that is utilized in converting a first alkaloid to a second alkaloid may be 75% or more identical to a given amino acid sequence as listed in Table 4. For example, an amino acid sequence for such an epimerase may comprise an amino acid sequence that is at least 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to an amino acid sequence as provided herein. Additionally, in certain embodiments, an "identical" amino acid sequence contains at least 80%-99% identity at the amino acid level to the specific amino acid sequence. In some cases an "identical" amino acid sequence contains at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

An engineered host cell may be provided that produces an ODM that converts a first alkaloid to a second alkaloid, wherein the ODM comprises a given amino acid sequence as listed in Table 4. An engineered host cell may be provided that produces one or more ODM enzymes. The ODM that is produced within the engineered host cell may be recovered and purified so as to form a biocatalyst. The process may include contacting the first alkaloid with an ODM in an amount sufficient to convert said first alkaloid to a second alkaloid. In examples, the first alkaloid may be contacted with a sufficient amount of the one or more enzymes such that at least 5% of said first alkaloid is converted to a second alkaloid. In further examples, the first alkaloid may be contacted with a sufficient amount of the one or more enzymes such that at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said first alkaloid is converted to a second alkaloid.

The one or more enzymes that may be used to convert a first alkaloid to a second alkaloid may contact the first alkaloid in vitro. Additionally, or alternatively, the one or more enzymes that may be used to convert a first alkaloid to a second alkaloid may contact the first alkaloid in vivo. In some examples, the one or more enzymes that may be used to convert a first alkaloid to a second alkaloid may be provided to a cell having the first alkaloid within. In some examples, the one or more enzymes that may be used to convert a first alkaloid to a second alkaloid may be produced within an engineered host cell.

In some examples, the methods provide for engineered host cells that produce an alkaloid product, wherein the O-demethylation of a substrate to a product may comprise a key step in the production of an alkaloid product. In some examples, the alkaloid produced is a nor-opioid or a nal-opioid. In still other embodiments, the alkaloid produced is derived from a nor-opioid or a nal-opioid. In another embodiment, a first alkaloid is an intermediate toward the product of the engineered host cell. In still other embodiments, the alkaloid product is selected from the group consisting of morphine, oxymorphine, oripavine, hydromorphone, dihydromorphine, 14-hydroxymorphine, morphinone, and 14-hydroxymorphinone.

In some examples, the substrate alkaloid is an opioid selected from the group consisting of codeine, oxycodone, thebaine, hydrocodone, dihydrocodeine, 14-hydroxycodeine, codeinone, and 14-hydroxycodeinone.

N-Demethylation Modifications

Some methods, processes, and systems provided herein describe the conversion of a first alkaloid to a second alkaloid by the removal of an N-linked methyl group. Some of these methods, processes, and systems may comprise an engineered host cell. In some examples, the conversion of a first alkaloid to a second alkaloid is a key step in the conversion of a substrate to a nor-opioids or nal-opioids. In some examples, the conversion of a first alkaloid to a second alkaloid comprises a demethylase reaction.

Figure 7:
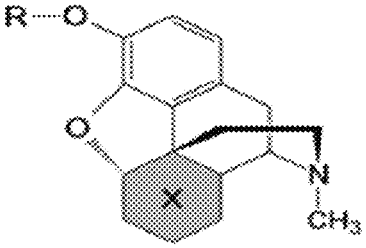
FIG. 7 illustrates an enzyme having opioid N-demethylase activity, in accordance with embodiments of the invention.

FIG. 7 illustrates an enzyme having opioid N-demethylase activity, in accordance with embodiments of the invention. Specifically, the enzyme may act on any morphinan alkaloid structure to remove the methyl group from the nitrogen.

Examples of an amino acid sequence of an N-demethylase enzyme that may be used to perform the conversion a first alkaloid to a second alkaloid are provided in Table 5. An amino acid sequence for an NDM that is utilized in converting a first alkaloid to a second alkaloid may be 75% or more identical to a given amino acid sequence as listed in Table 5. For example, an amino acid sequence for such an epimerase may comprise an amino acid sequence that is at least 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to an amino acid sequence as provided herein. Additionally, in certain embodiments, an "identical" amino acid sequence contains at least 80%-99% identity at the amino acid level to the specific amino acid sequence. In some cases an "identical" amino acid sequence contains at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

An engineered host cell may be provided that produces an NDM that converts a first alkaloid to a second alkaloid, wherein the NDM comprises an amino acid sequence as listed in Table 5. An engineered host cell may be provided that produces one or more NDM enzymes. The NDM that is produced within the engineered host cell may be recovered and purified so as to form a biocatalyst. The process may include contacting the first alkaloid with an NDM in an amount sufficient to convert said first alkaloid to a second alkaloid. In examples, the first alkaloid may be contacted with a sufficient amount of the one or more enzymes such that at least 5% of said first alkaloid is converted to a second alkaloid. In further examples, the first alkaloid may be contacted with a sufficient amount of the one or more enzymes such that at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said first alkaloid is converted to a second alkaloid.

The one or more enzymes that may be used to convert a first alkaloid to a second alkaloid may contact the first alkaloid in vitro. Additionally, or alternatively, the one or more enzymes that may be used to convert a first alkaloid to a second alkaloid may contact the first alkaloid in vivo. In some examples, the one or more enzymes that may be used to convert a first alkaloid to a second alkaloid may be provided to a cell having the first alkaloid within. In some examples, the one or more enzymes that may be used to convert a first alkaloid to a second alkaloid may be produced within an engineered host cell.

In some examples, the methods provide for engineered host cells that produce an alkaloid product, wherein the N-demethylation of a substrate to a product may comprise a key step in the production of an alkaloid product. In some examples, the alkaloid produced is a nor-opioid or a nal-opioid. In still other embodiments, the alkaloid produced is derived from a nor-opioid or a nal-opioid. In another embodiment, a first alkaloid is an intermediate toward the product of the engineered host cell. In still other embodiments, the alkaloid product is selected from the group consisting of norcodeine, noroxycodone, northebaine, nor-hydrocodone, nordihydro-codeine, nor-14-hydroxy-codeine, norcodeinone, nor-14-hydroxy-codeinone, normorphine, noroxymorphone, nororipavine, norhydro-morphone, nordihydro-morphine, nor-14-hydroxy-morphine, normorphinone, and nor-14-hydroxy-morphinone.

In some examples, the substrate alkaloid is an opioid selected from the group consisting of codeine, oxycodone, thebaine, hydrocodone, dihydrocodeine, 14-hydroxycodeine, codeinone, and 14-hydroxycodeinone, morphine, oxymorphone, oripavine, hydromorphone, dihydromorphine, 14-hydroxy-morphine, morphinone, or 14-hydroxy-morphinone.

N-Linked Modifications

Some methods, processes, and systems provided herein describe the conversion of a first alkaloid to a second alkaloid by the addition of an N-linked sidechain group. Some methods, processes, and systems provided herein describe the conversion of a first alkaloid to a second alkaloid by the transfer of a sidechain group from a cosubstrate to the first alkaloid. Some of these methods, processes, and systems may comprise an engineered host cell. In some examples, the conversion of a first alkaloid to a second alkaloid is a key step in the conversion of a substrate to a nal-opioid. In some examples, the conversion of a first alkaloid to a second alkaloid comprises a methyltransferase reaction.

Figure 8:
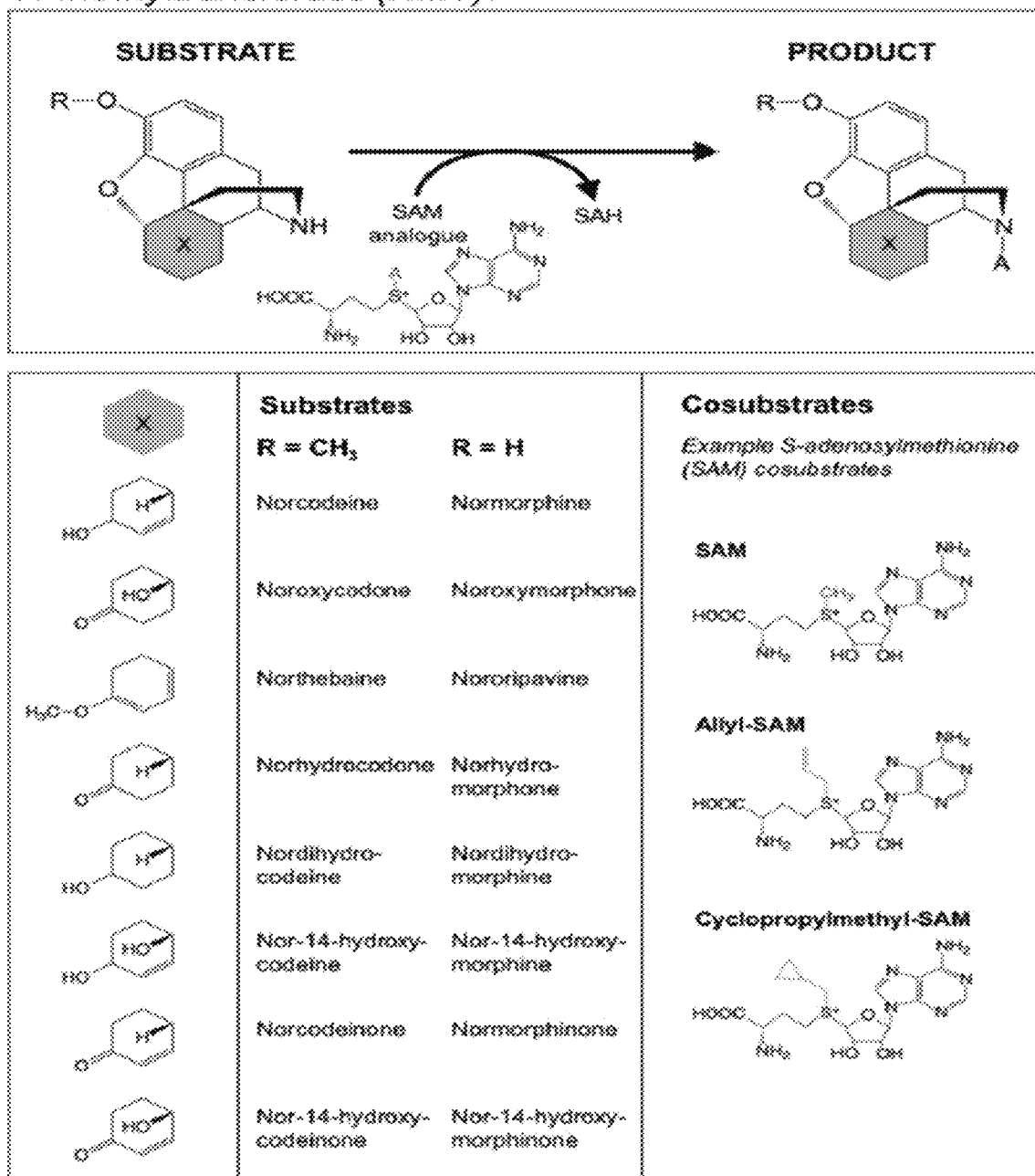
FIG. 8 illustrates an enzyme having N-methyltransferase activity, in accordance with embodiments of the invention.

FIG. 8 illustrates an enzyme having N-methyltransferase activity, in accordance with embodiments of the invention. Specifically, the enzyme may act on any morphinan alkaloid structure to add a methyl group or other carbon moiety to the nitrogen. S-Adenosyl methionine (SAM) may act as the donor of the functional group (methyl, allyl, cyclopropylmethyl, or other).

Examples of amino acid sequences of NMT enzymes are set forth in Table 6. An amino acid sequence for an NMT that is utilized in converting a first alkaloid to a second alkaloid may be 75% or more identical to a given amino acid sequence as listed in Table 6. For example, an amino acid sequence for such an epimerase may comprise an amino acid sequence that is at least 75% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to an amino acid sequence as provided herein. Additionally, in certain embodiments, an "identical" amino acid sequence contains at least 80%-99% identity at the amino acid level to the specific amino acid sequence. In some cases an "identical" amino acid sequence contains at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

An engineered host cell may be provided that produces an NMT that converts a first alkaloid to a second alkaloid, wherein the NMT comprises an amino acid sequence as provided in Table 6. An engineered host cell may be provided that produces one or more NMT enzymes. The NMT that is produced within the engineered host cell may be recovered and purified so as to form a biocatalyst. The process may include contacting the first alkaloid with an NMT in an amount sufficient to convert said first alkaloid to a second alkaloid. In examples, the first alkaloid may be contacted with a sufficient amount of the one or more enzymes such that at least 5% of said first alkaloid is converted to a second alkaloid. In further examples, the first alkaloid may be contacted with a sufficient amount of the one or more enzymes such that at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99%, at least 99.5%, at least 99.7%, or 100% of said first alkaloid is converted to a second alkaloid.

The one or more enzymes that may be used to convert a first alkaloid to a second alkaloid may contact the first alkaloid in vitro. Additionally, or alternatively, the one or more enzymes that may be used to convert a first alkaloid to a second alkaloid may contact the first alkaloid in vivo. In some examples, the one or more enzymes that may be used to convert a first alkaloid to a second alkaloid may be provided to a cell having the first alkaloid within. In some examples, the one or more enzymes that may be used to convert a first alkaloid to a second alkaloid may be produced within an engineered host cell.

In some examples, the methods provide for engineered host cells that produce an alkaloid product, wherein the N-methyltransferase of a substrate to a product may comprise a key step in the production of an alkaloid product. In some examples, the alkaloid produced is a nal-opioid. In still other embodiments, the alkaloid produced is derived from a nor-opioid or a nal-opioid. In another embodiment, a first alkaloid is an intermediate toward the product of the engineered host cell. In still other embodiments, the alkaloid product is selected from the group including naloxone, naltrexone, and nalmefene.

In some examples, the substrate alkaloid is an opioid selected from the group consisting of norcodeine, noroxycodone, northebaine, norhydrocodone, nordihydro-codeine, nor-14-hydroxy-codeine, norcodeinone, nor-14-hydroxycodeinone, normorphine, noroxymorphone, nororipavine, norhydro-morphine, nordihydro-morphine, nor-14-hydroxy-morphine, normorphinone, and nor-14-hydroxy-morphinone. In some examples, the cosubstrate is S-adenosyl-methionine, Allyl-S-adenosylmethionine, or cyclopropylmethyl-S-adenosylmethionine.

Heterologous Coding Sequences

In some instances, the engineered host cells harbor one or more heterologous coding sequences (such as two or more, three or more, four or more, five or more) which encode activity(ies) that enable the engineered host cells to produce desired enzymes of interest and/or BIAs of interest, e.g., as described herein. As used herein, the term "heterologous coding sequence" is used to indicate any polynucleotide that codes for, or ultimately codes for, a peptide or protein or its equivalent amino acid sequence, e.g., an enzyme, that is not normally present in the host organism and may be expressed in the host cell under proper conditions. As such, "heterologous coding sequences" includes multiple copies of coding sequences that are normally present in the host cell, such that the cell is expressing additional copies of a coding sequence that are not normally present in the cells. The heterologous coding sequences may be RNA or any type thereof, e.g., mRNA, DNA or any type thereof, e.g., cDNA, or a hybrid of RNA/DNA. Coding sequences of interest include, but are not limited to, full-length transcription units that include such features as the coding sequence, introns, promoter regions, 3'-UTRs, and enhancer regions.

In examples, the engineered host cells may comprise a plurality of heterologous coding sequences each encoding an enzyme, such as an enzyme listed in Table 3. In some examples, the plurality of enzymes encoded by the plurality of heterologous coding sequences may be distinct from each other. In some examples, some of the plurality of enzymes encoded by the plurality of heterologous coding sequences may be distinct from each other and some of the plurality of enzymes encoded by the plurality of heterologous coding sequences may be duplicate copies.

In some examples, the heterologous coding sequences may be operably connected. Heterologous coding sequences that are operably connected may be within the same pathway of producing a particular benzylisoquinoline alkaloid product and/or thebaine synthase product. In some examples, the operably connected heterologous coding sequences may be directly sequential along the pathway of producing a particular benzylisoquinoline alkaloid product and/or thebaine synthase product. In some examples, the operably connected heterologous coding sequences may have one or more native enzymes between one or more of the enzymes encoded by the plurality of heterologous coding sequences. In some examples, the heterologous coding sequences may have one or more heterologous enzymes between one or more of the enzymes encoded by the plurality of heterologous coding sequences. In some examples, the heterologous coding sequences may have one or more non-native enzymes between one or more of the enzymes encoded by the plurality of heterologous coding sequences.

The engineered host cells may also be modified to possess one or more genetic alterations to accommodate the heterologous coding sequences. Alterations of the native host genome include, but are not limited to, modifying the genome to reduce or ablate expression of a specific protein that may interfere with the desired pathway. The presence of such native proteins may rapidly convert one of the intermediates or final products of the pathway into a metabolite or other compound that is not usable in the desired pathway. Thus, if the activity of the native enzyme were reduced or altogether absent, the produced intermediates would be more readily available for incorporation into the desired product.

Heterologous coding sequences include but are not limited to sequences that encode enzymes, either wild-type or equivalent sequences, that are normally responsible for the production of BIAs of interest in plants. In some cases, the enzymes for which the heterologous sequences code may be any of the enzymes in the 1-BIA pathway, and may be from any convenient source. The choice and number of enzymes encoded by the heterologous coding sequences for the particular synthetic pathway may be selected based upon the desired product. In certain embodiments, the host cells of the invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more heterologous coding sequences, such as 1, 2, 3, 4, 5, 6, 7, 8, 9, 10, 11, 12, 13, 14, or 15 heterologous coding sequences.

As used herein, the term "heterologous coding sequences" also includes the coding portion of the peptide or enzyme, i.e., the cDNA or mRNA sequence, of the peptide or enzyme, as well as the coding portion of the full-length transcriptional unit, i.e., the gene including introns and exons, as well as "codon optimized" sequences, truncated sequences or other forms of altered sequences that code for the enzyme or code for its equivalent amino acid sequence, provided that the equivalent amino acid sequence produces a functional protein. Such equivalent amino acid sequences may have a deletion of one or more amino acids, with the deletion being N-terminal, C-terminal, or internal. Truncated forms are envisioned as long as they have the catalytic capability indicated herein. Fusions of two or more enzymes are also envisioned to facilitate the transfer of metabolites in the pathway, provided that catalytic activities are maintained.

Operable fragments, mutants, or truncated forms may be identified by modeling and/or screening. In some cases, this is achieved by deletion of, for example, N-terminal, C-terminal, or internal regions of the protein in a step-wise fashion, followed by analysis of the resulting derivative with regard to its activity for the desired reaction compared to the original sequence. If the derivative in question operates in this capacity, it is considered to constitute an equivalent derivative of the enzyme proper.

In examples, some heterologous proteins may show occurrences where they are incorrectly processed when expressed in a recombinant host. For example, plant proteins such as cytochrome P450 enzymes expressed in microbial production hosts may have occurrences of incorrect processing. In particular, salutaridine synthase may undergo N-linked glycosylation when heterologously expressed in yeast. This N-linked glycosylation may not be observed in plants, which may be indicative of incorrect N-terminal sorting of the nascent SalSyn transcript so as to reduce the activity of the enzyme in the heterologous microbial host. In such examples, protein engineering directed at correcting N-terminal sorting of the nascent transcript so as to remove the N-linked glycosylation pattern may result in improved activity of the salutaridine synthase enzyme in the recombinant production host, see for example WO2016183023A1.

Some aspects of the invention also relate to heterologous coding sequences that code for amino acid sequences that are equivalent to the native amino acid sequences for the various enzymes. An amino acid sequence that is "equivalent" is defined as an amino acid sequence that is not identical to the specific amino acid sequence, but rather contains at least some amino acid changes (deletions, substitutions, inversions, insertions, etc.) that do not essentially affect the biological activity of the protein as compared to a similar activity of the specific amino acid sequence, when used for a desired purpose. The biological activity refers to, in the example of a thebaine synthase, its catalytic activity. Equivalent sequences are also meant to include those which have been engineered and/or evolved to have properties different from the original amino acid sequence. Mutable properties of interest include catalytic activity, substrate specificity, selectivity, stability, solubility, localization, etc.

In some instances, the expression of each type of enzyme is increased through additional gene copies (i.e., multiple copies), which increases intermediate accumulation and/or BIA of interest production. Some embodiments of the invention include increased BIA of interest production in a host cell through simultaneous expression of multiple species variants of a single or multiple enzymes. In some cases, additional gene copies of a single or multiple enzymes are included in the host cell. Any convenient methods may be utilized including multiple copies of a heterologous coding sequence for an enzyme in the host cell.

In some examples, the engineered host cell includes multiple copies of a heterologous coding sequence for an enzyme, such as 2 or more, 3 or more, 4 or more, 5 or more, or even 10 or more copies. In certain embodiments, the engineered host cell includes multiple copies of heterologous coding sequences for one or more enzymes, such as multiple copies of two or more, three or more, four or more, etc. In some cases, the multiple copies of the heterologous coding sequence for an enzyme are derived from two or more different source organisms as compared to the host cell. For example, the engineered host cell may include multiple copies of one heterologous coding sequence, where each of the copies is derived from a different source organism. As such, each copy may include some variations in explicit sequences based on inter-species differences of the enzyme of interest that is encoded by the heterologous coding sequence.

In certain embodiments, the engineered host cell includes multiple copies of heterologous coding sequences for one or more enzymes, such as multiple copies of two or more, three or more, four or more, etc. In some cases, the multiple copies of the heterologous coding sequence for an enzyme are derived from two or more different source organisms as compared to the host cell. For example, the engineered host cell may include multiple copies of one heterologous coding sequence, where each of the copies is derived from a different source organism. As such, each copy may include some variations in explicit sequences based on inter-species differences of the enzyme of interest that is encoded by the heterologous coding sequence.

The engineered host cell medium may be sampled and monitored for the production of BIAs of interest. The BIAs of interest may be observed and measured using any convenient methods. Methods of interest include, but are not limited to, LC-MS methods (e.g., as described herein) where a sample of interest is analyzed by comparison with a known amount of a standard compound. Additionally, there are other ways that BIAs of interest may be observed and/or measured. Examples of alternative ways of observing and/or measuring BIAs include GC-MS, UV-vis spectroscopy, NMR, LC-NMR, LC-UV, TLC, capillary electrophoresis, among others. Identity may be confirmed, e.g., by m/z and MS/MS fragmentation patterns, and quantitation or measurement of the compound may be achieved via LC trace peaks of know retention time and/or EIC MS peak analysis by reference to corresponding LC-MS analysis of a known amount of a standard of the compound.

Additionally, a culture of the engineered host cell may be sampled and monitored for the production of enzymes of interest, such as a thebaine synthase enzyme. The enzymes of interest may be observed and measured using any convenient methods. Methods of interest include enzyme activity assays, polyacrylamide gel electrophoresis, carbon monoxide spectroscopy, and western blot analysis.

Methods

Methods for Culturing Host Cells for BIA production

As summarized above, some aspects of the invention include methods of preparing benzylisoquinoline alkaloids (BIAs) of interest. Additionally, some aspects of the invention include methods of preparing enzymes of interest. As such, some aspects of the invention include culturing an engineered host cell under conditions in which the one or more host cell modifications (e.g., as described herein) are functionally expressed such that the cell converts starting compounds of interest into product enzymes and/or BIAs of interest. Also provided are methods that include culturing an engineered host cell under conditions suitable for protein production such that one or more heterologous coding sequences are functionally expressed and convert starting compounds of interest into product enzymes or BIAs of interest. In examples, the method is a method of preparing a benzylisoquinoline alkaloid (BIA) that includes culturing an engineered host cell (e.g., as described herein); adding a starting compound to the cell culture; and recovering the BIA from the cell culture. In some examples, the method is a method of preparing an enzyme that includes culturing an engineered host cell (e.g., as described herein); adding a starting compound to the cell culture; and recovering the enzyme from the cell culture.

Fermentation media may contain suitable carbon substrates. The source of carbon suitable to perform the methods of this disclosure may encompass a wide variety of carbon containing substrates. Suitable substrates may include, without limitation, monosaccharides (e.g., glucose, fructose, galactose, xylose), oligosaccharides (e.g., lactose, sucrose, raffinose), polysaccharides (e.g., starch, cellulose), or a combination thereof. In some cases, unpurified mixtures from renewable feedstocks may be used (e.g., cornsteep liquor, sugar beet molasses, barley malt). In some cases, the carbon substrate may be a one-carbon substrate (e.g., methanol, carbon dioxide) or a two-carbon substrate (e.g., ethanol). In other cases, other carbon containing compounds may be utilized, for example, methylamine, glucosamine, and amino acids.

Any convenient methods of culturing engineered host cells may be employed for producing the enzymes and/or BIAs of interest. The particular protocol that is employed may vary, e.g., depending on the engineered host cell, the heterologous coding sequences, the enzymes of interest, the BIAs of interest, etc. The cells may be present in any convenient environment, such as an environment in which the cells are capable of expressing one or more functional heterologous enzymes. In some embodiments, the cells are cultured under conditions that are conducive to enzyme expression and with appropriate substrates available to allow production of enzymes and/or BIAs of interest in vivo. In some embodiments, the functional enzymes are extracted from the engineered host for production of enzymes and/or BIAs of interest under in vitro conditions. In some instances, the engineered host cells are placed back into a multicellular host organism. The engineered host cells are in any phase of growth, including, but not limited to, stationary phase and log-growth phase, etc. In addition, the cultures themselves may be continuous cultures or they may be batch cultures.

Cells may be grown in an appropriate fermentation medium at a temperature between 14-40° C. Cells may be grown with shaking at any convenient speed (e.g., 200 rpm). Cells may be grown at a suitable pH. Suitable pH ranges for the fermentation may be between pH 5-9. Fermentations may be performed under aerobic, anaerobic, or microaerobic conditions. Any suitable growth medium may be used. Suitable growth media may include, without limitation, common commercially prepared media such as synthetic defined (SD) minimal media or yeast extract peptone dextrose (YEPD) rich media. Any other rich, defined, or synthetic growth media appropriate to the microorganism may be used.

Cells may be cultured in a vessel of essentially any size and shape. Examples of vessels suitable to perform the methods of this disclosure may include, without limitation, multi-well shake plates, test tubes, flasks (baffled and non-baffled), and bioreactors. The volume of the culture may range from 10 microliters to greater than 10,000 liters.

The addition of agents to the growth media that are known to modulate metabolism in a manner desirable for the production of alkaloids may be included. In a non-limiting example, cyclic adenosine 2'3'-monophosphate may be added to the growth media to modulate catabolite repression.

Any convenient cell culture conditions for a particular cell type may be utilized. In certain embodiments, the host cells that include one or more modifications are cultured under standard or readily optimized conditions, with standard cell culture media and supplements. As one example, standard growth media when selective pressure for plasmid maintenance is not required may contain 20 g/L yeast extract, 10 g/L peptone, and 20 g/L dextrose (YPD). Host cells containing plasmids are grown in synthetic complete (SC) media containing 1.7 g/L yeast nitrogen base, 5 g/L ammonium sulfate, and 20 g/L dextrose supplemented with the appropriate amino acids required for growth and selection. Alternative carbon sources which may be useful for inducible enzyme expression include, but are not limited to, sucrose, raffinose, and galactose. Cells are grown at any convenient temperature (e.g., 30° C.) with shaking at any convenient rate (e.g., 200 rpm) in a vessel, e.g., in test tubes or flasks in volumes ranging from 1-1000 mL, or larger, in the laboratory.

Culture volumes may be scaled up for growth in larger fermentation vessels, for example, as part of an industrial process. The industrial fermentation process may be carried out under closed-batch, fed-batch, or continuous chemostat conditions, or any suitable mode of fermentation. In some cases, the cells may be immobilized on a substrate as whole cell catalysts and subjected to fermentation conditions for alkaloid production.

A batch fermentation is a closed system, in which the composition of the medium is set at the beginning of the fermentation and not altered during the fermentation process. The desired organism(s) are inoculated into the medium at the beginning of the fermentation. In some instances, the batch fermentation is run with alterations made to the system to control factors such as pH and oxygen concentration (but not carbon). In this type of fermentation system, the biomass and metabolite compositions of the system change continuously over the course of the fermentation. Cells typically proceed through a lag phase, then to a log phase (high growth rate), then to a stationary phase (growth rate reduced or halted), and eventually to a death phase (if left untreated).

A continuous fermentation is an open system, in which a defined fermentation medium is added continuously to the bioreactor and an equal amount of fermentation media is continuously removed from the vessel for processing. Continuous fermentation systems are generally operated to maintain steady state growth conditions, such that cell loss due to medium being removed must be balanced by the growth rate in the fermentation. Continuous fermentations are generally operated at conditions where cells are at a constant high cell density. Continuous fermentations allow for the modulation of one or more factors that affect target product concentration and/or cell growth.

The liquid medium may include, but is not limited to, a rich or synthetic defined medium having an additive component described above. Media components may be dissolved in water and sterilized by heat, pressure, filtration, radiation, chemicals, or any combination thereof. Several media components may be prepared separately and sterilized, and then combined in the fermentation vessel. The culture medium may be buffered to aid in maintaining a constant pH throughout the fermentation.

Process parameters including temperature, dissolved oxygen, pH, stirring, aeration rate, and cell density may be monitored or controlled over the course of the fermentation. For example, temperature of a fermentation process may be monitored by a temperature probe immersed in the culture medium. The culture temperature may be controlled at the set point by regulating the jacket temperature. Water may be cooled in an external chiller and then flowed into the bioreactor control tower and circulated to the jacket at the temperature required to maintain the set point temperature in the vessel.

Additionally, a gas flow parameter may be monitored in a fermentation process. For example, gases may be flowed into the medium through a sparger. Gases suitable for the methods of this disclosure may include compressed air, oxygen, and nitrogen. Gas flow may be at a fixed rate or regulated to maintain a dissolved oxygen set point.

The pH of a culture medium may also be monitored. In examples, the pH may be monitored by a pH probe that is immersed in the culture medium inside the vessel. If pH control is in effect, the pH may be adjusted by acid and base pumps which add each solution to the medium at the required rate. The acid solutions used to control pH may be sulfuric acid or hydrochloric acid. The base solutions used to control pH may be sodium hydroxide, potassium hydroxide, or ammonium hydroxide.

Further, dissolved oxygen may be monitored in a culture medium by a dissolved oxygen probe immersed in the culture medium. If dissolved oxygen regulation is in effect, the oxygen level may be adjusted by increasing or decreasing the stirring speed. The dissolved oxygen level may also be adjusted by increasing or decreasing the gas flow rate. The gas may be compressed air, oxygen, or nitrogen.

Stir speed may also be monitored in a fermentation process. In examples, the stirrer motor may drive an agitator. The stirrer speed may be set at a consistent rpm throughout the fermentation or may be regulated dynamically to maintain a set dissolved oxygen level.

Additionally, turbidity may be monitored in a fermentation process. In examples, cell density may be measured using a turbidity probe. Alternatively, cell density may be measured by taking samples from the bioreactor and analyzing them in a spectrophotometer. Further, samples may be removed from the bioreactor at time intervals through a sterile sampling apparatus. The samples may be analyzed for alkaloids produced by the host cells. The samples may also be analyzed for other metabolites and sugars, the depletion of culture medium components, or the density of cells.

In another example, a feed stock parameter may be monitored during a fermentation process. In particular, feed stocks including sugars and other carbon sources, nutrients, and cofactors that may be added into the fermentation using an external pump. Other components may also be added during the fermentation including, without limitation, anti-foam, salts, chelating agents, surfactants, and organic liquids.

Any convenient codon optimization techniques for optimizing the expression of heterologous polynucleotides in host cells may be adapted for use in the subject host cells and methods, see e.g., Gustafsson, C. et al. (2004) *Trends Biotechnol*, 22, 346-353, which is incorporated by reference in its entirety.

The subject method may also include adding a starting compound to the cell culture. Any convenient methods of addition may be adapted for use in the subject methods. The cell culture may be supplemented with a sufficient amount of the starting materials of interest (e.g., as described herein), e.g., a mM to μM amount such as between about 1-5 mM of a starting compound. It is understood that the amount of starting material added, the timing and rate of addition, the form of material added, etc., may vary according to a variety of factors. The starting material may be added neat or pre-dissolved in a suitable solvent (e.g., cell culture media, water, or an organic solvent). The starting material may be added in concentrated form (e.g., 10× over desired concentration) to minimize dilution of the cell culture medium upon addition. The starting material may be added in one or more batches, or by continuous addition over an extended period of time (e.g., hours or days).

Methods for Isolating Products from the Fermentation Medium

The subject methods may also include recovering the enzymes and/or BIAs of interest from the cell culture. Any convenient methods of separation and isolation (e.g., chromatography methods or precipitation methods) may be adapted for use in the subject methods to recover the enzymes and/or BIAs of interest from the cell culture. Filtration methods may be used to separate soluble from insoluble fractions of the cell culture. In some cases, liquid chromatography methods (e.g., reverse phase HPLC, size exclusion, normal phase chromatography) may be used to separate the BIA of interest from other soluble components of the cell culture. In some cases, extraction methods (e.g., liquid extraction, pH based purification, solid phase extraction, affinity chromatography, ion exchange, etc.) may be used to separate the enzymes and/or BIAs of interest from other components of the cell culture.

The produced alkaloids may be isolated from the fermentation medium using methods known in the art. A number of recovery steps may be performed immediately after (or in some instances, during) the fermentation for initial recovery of the desired product. Through these steps, the alkaloids (e.g., BIAs) may be separated from the cells, cellular debris and waste, and other nutrients, sugars, and organic molecules may remain in the spent culture medium. This process may be used to yield a BIA-enriched product.

In an example, a product stream having a benzylisoquinoline alkaloid (BIA) product is formed by providing engineered yeast cells and a feedstock including nutrients and water to a batch reactor. In particular, the engineered yeast cells may be subjected to fermentation by incubating the engineered yeast cells for a time period of at least about 5 minutes to produce a solution comprising the BIA product and cellular material. Once the engineered yeast cells have been subjected to fermentation, at least one separation unit may be used to separate the BIA product from the cellular material to provide the product stream comprising the BIA product. In particular, the product stream may include the BIA product as well as additional components, such as a clarified yeast culture medium. Additionally, a BIA product may comprise one or more BIAs of interest, such as one or more BIA compounds.

Different methods may be used to remove cells from a bioreactor medium that include an enzyme and/or BIA of interest. In examples, cells may be removed by sedimentation over time. This process of sedimentation may be accelerated by chilling or by the addition of fining agents such as silica. The spent culture medium may then be siphoned from the top of the reactor or the cells may be decanted from the base of the reactor. Alternatively, cells may be removed by filtration through a filter, a membrane, or other porous material. Cells may also be removed by centrifugation, for example, by continuous flow centrifugation or by using a continuous extractor.

If some valuable enzymes and/or BIAs of interest are present inside the cells, the cells may be permeabilized or lysed and the cell debris may be removed by any of the methods described above. Agents used to permeabilize the cells may include, without limitation, organic solvents (e.g., DMSO) or salts (e.g., lithium acetate). Methods to lyse the cells may include the addition of surfactants such as sodium dodecyl sulfate, or mechanical disruption by bead milling or sonication.

Enzymes and/or BIAs of interest may be extracted from the clarified spent culture medium through liquid-liquid extraction by the addition of an organic liquid that is immiscible with the aqueous culture medium. In examples, the use of liquid-liquid extraction may be used in addition to other processing steps. Examples of suitable organic liquids include, but are not limited to, isopropyl myristate, ethyl acetate, chloroform, butyl acetate, methylisobutyl ketone, methyl oleate, toluene, oleyl alcohol, ethyl butyrate. The organic liquid may be added to as little as 10% or as much as 100% of the volume of aqueous medium.

In some cases, the organic liquid may be added at the start of the fermentation or at any time during the fermentation. This process of extractive fermentation may increase the yield of enzymes and/or BIAs of interest from the host cells by continuously removing enzymes and/or BIAs to the organic phase.

Agitation may cause the organic phase to form an emulsion with the aqueous culture medium. Methods to encourage the separation of the two phases into distinct layers may include, without limitation, the addition of a demulsifier or a nucleating agent, or an adjustment of the pH. The emulsion may also be centrifuged to separate the two phases, for example, by continuous conical plate centrifugation.

Alternatively, the organic phase may be isolated from the aqueous culture medium so that it may be physically removed after extraction. For example, the solvent may be encapsulated in a membrane.

In examples, enzymes and/or BIAs of interest may be extracted from a fermentation medium using adsorption methods. In examples, BIAs of interest may be extracted from clarified spent culture medium by the addition of a resin such as Amberlite® XAD4 or another agent that removes BIAs by adsorption. The BIAs of interest may then be released from the resin using an organic solvent. Examples of suitable organic solvents include, but are not limited to, methanol, ethanol, ethyl acetate, or acetone.

BIAs of interest may also be extracted from a fermentation medium using filtration. At high pH, the BIAS of interest may form a crystalline-like precipitate in the bioreactor. This precipitate may be removed directly by filtration through a filter, membrane, or other porous material. The precipitate may also be collected by centrifugation and/or decantation.

The extraction methods described above may be carried out either in situ (in the bioreactor) or ex situ (e.g., in an external loop through which media flows out of the bioreactor and contacts the extraction agent, then is recirculated back into the vessel). Alternatively, the extraction methods may be performed after the fermentation is terminated using the clarified medium removed from the bioreactor vessel.

Methods for Purifying Products from Alkaloid-Enriched Solutions

Subsequent purification steps may involve treating the post-fermentation solution enriched with BIA product(s) of interest using methods known in the art to recover individual product species of interest to high purity.

In one example, BIAs of interest extracted in an organic phase may be transferred to an aqueous solution. In some cases, the organic solvent may be evaporated by heat and/or vacuum, and the resulting powder may be dissolved in an aqueous solution of suitable pH. In a further example, the BIAs of interest may be extracted from the organic phase by addition of an aqueous solution at a suitable pH that promotes extraction of the BIAs of interest into the aqueous phase. The aqueous phase may then be removed by decantation, centrifugation, or another method.

The BIA-containing solution may be further treated to remove metals, for example, by treating with a suitable chelating agent. The BIA of interest-containing solution may be further treated to remove other impurities, such as proteins and DNA, by precipitation. In one example, the BIA of interest-containing solution is treated with an appropriate precipitation agent such as ethanol, methanol, acetone, or isopropanol. In an alternative example, DNA and protein may be removed by dialysis or by other methods of size exclusion that separate the smaller alkaloids from contaminating biological macromolecules.

In further examples, the solution containing BIAs of interest may be extracted to high purity by continuous cross-flow filtration using methods known in the art.

If the solution contains a mixture of BIAs of interest, it may be subjected to acid-base treatment to yield individual BIA of interest species using methods known in the art. In this process, the pH of the aqueous solution is adjusted to precipitate individual BIAs.

For high purity, small-scale preparations, the BIAs may be purified in a single step by liquid chromatography.

Liquid Chromatography Mass Spectrometry (LCMS) Method

The BIA compounds of interest, including morphinan, nal-opioids, and nor-opioids, may be separated using liquid chromatography, and detected and quantified using mass spectrometry. Compound identity may be confirmed by characteristic elution time, mass-to-charge ratio (m/z) and fragmentation patterns (MS/MS). Quantitation may be performed by comparison of compound peak area to a standard curve of a known reference standard compound. Additionally, BIAs of interest may be detected by alternative methods such as GC-MS, UV-vis spectroscopy, NMR, LC-NMR, LC-UV, TLC, and capillary electrophoresis.

Purpald Assay Method

For high throughput screening of demethylation reactions a purpald assay may be used. For example, demethylation catalyzed by 2-oxoglutarate dependent dioxygenases produces formaldehyde a as product as shown in the generalized chemical equation: [substrate]+2-oxoglutarate+$O_2$⇌[product]+formaldehyde+succinate+$CO_2$. Purpald reagent in alkaline conditions undergoes a color change in the presence of formaldehyde that can be quantified to concentrations as low as 1 nM with a spectrophotometer at 510 nm.

Yeast-Derived Alkaloid APIs Versus Plant-Derived APIs

The clarified yeast culture medium (CYCM) may contain a plurality of impurities. The clarified yeast culture medium may be dehydrated by vacuum and/or heat to yield an alkaloid-rich powder. This product is analogous to the concentrate of poppy straw (CPS) or opium, which is exported from poppy-growing countries and purchased by API manufacturers. For the purposes of this invention, CPS is a representative example of any type of purified plant extract from which the desired alkaloids product(s) may ultimately be further purified. Table 10 and Table 11 highlight the impurities in these two products that may be specific to either CYCM or CPS or may be present in both. While some BIAs may have a pigment as an impurity, other BIAs may be categorized as pigments themselves. Accordingly, these BIAs may be assessed for impurities based on non-pigment impurities. By analyzing a product of unknown origin for a subset of these impurities, a person of skill in the art could determine whether the product originated from a yeast or plant production host.

API-grade pharmaceutical ingredients are highly purified molecules. As such, impurities that could indicate the plant- or yeast-origin of an API (such as those listed in Table 10 and Table 11) may not be present at the API stage of the product. Indeed, many of the API products derived from yeast strains of the present invention may be largely indistinguishable from the traditional plant-derived APIs. In some cases, however, conventional alkaloid compounds may be subjected to chemical modification using chemical synthesis approaches, which may show up as chemical impurities in plant-based products that require such chemical modifications. For example, chemical derivatization may often result in a set of impurities related to the chemical synthesis processes. In certain situations, these modifications may be performed biologically in the yeast production platform, thereby avoiding some of the impurities associated with chemical derivation from being present in the yeast-derived product. In particular, these impurities from the chemical derivation product may be present in an API product that is produced using chemical synthesis processes but may be absent from an API product that is produced using a yeast-derived product. Alternatively, if a yeast-derived product is mixed with a chemically-derived product, the resulting impurities may be present but in a lesser amount than would be expected in an API that only or primarily contains chemically-derived products. In this example, by analyzing the API product for a subset of these impurities, a person of skill in the art could determine whether the product originated from a yeast production host or the traditional chemical derivatization route.

Non-limiting examples of impurities that may be present in chemically-derivatized morphinan APIs but not in biosynthesized APIs include a codeine-O(6)-methyl ether impurity in API codeine; 8,14-dihydroxy-7,8-dihydrocodeinone in API oxycodone; and tetrahydrothebaine in API hydrocodone. The codeine-O(6)-methyl ether may be formed by chemical over-methylation of morphine. The 8,14-dihydroxy-7,8-dihydrocodeinone in API oxycodone may be formed by chemical over-oxidation of thebaine. Additionally, the tetrahydrothebaine in API hydrocodone may be formed by chemical over-reduction of thebaine.

However, in the case where the yeast-derived compound and the plant-derived compound are both subjected to chemical modification through chemical synthesis approaches, the same impurities associated with the chemical synthesis process may be expected in the products. In such a situation, the starting material (e.g., CYCM or CPS) may be analyzed as described above.

Host Cell Derived Nal-Opioids Vs Chemically Derived Nal-Opioids

Nal-opioids produced by chemical synthesis may contain a plurality of impurities. These impurities may arise from many different causes, for example, unreacted starting materials, incomplete reactions, the formation of byproducts, persistence of intermediates, dimerization, or degradation. An example of an unreacted starting material could be oxymorphone remaining in a preparation of naltrexone. An example of an impurity arising from an incomplete reaction could be 3-O-Methylbuprenorphine resulting from the incomplete 3-O-demethylation of thebaine. Chemical modification can result in the addition or removal of functional groups at off-target sites. For example, the oxidation of C10 to create 10-hydroxynaltrexone and 10-ketonaltrexone during naltrexone synthesis, or the removal of the 6-O-methyl group to give 6-O-desmethylbuprenorphine during buprenorphine synthesis. Impurites may arise from the persistence of reaction intermediates, for example the persistence of N-oxides like oxymorphone N-oxide formed during the N-demethylation process. Another source of impurities is dimerization, the conjugation of two opioid molecules, for example two buprenorphine molecules (2,2'-bisbuprenorphine), two naltrexone molecules (2,2'-bisnaltrexone), or two naloxone molecules (2,2'-bisnaloxone). Impurities may arise from degradation of starting materials, reaction intermediates, or reaction products. The extreme physical conditions used in chemical syntheses may make the presence of degradation more likely. An example of an impurity that may arise from degradation is dehydrobuprenorphine produced by oxidizing conditions during buprenorphine synthesis.

Nal-opioids produced by enzyme catalysis in a host cell may contain different impurities than nal-opioids produced by chemical synthesis. Nal-opioids produced by enzyme catalysis in a host cell may contain fewer impurities than nal-opioids produced by chemical synthesis. Nal-opioids produced by enzyme catalysis in a host cell may lack certain impurities that are found in nal-opioids produced by chemical synthesis. In examples, key features of enzyme synthesis may include, (1) enzymes target a specific substrate and residue with high fidelity; (2) enzymes perform reactions in the mild physiological conditions within the cell which do not compromise the stability of the molecules; and (3) enzymes are engineered to be efficient catalysts that drive reactions to completion.

Table 12 highlights some of the impurities that may be specific to chemically produced nal-opioids. Accordingly, nal-opioids may be assessed for impurities to determine the presence or absence of any impurity from Table 12. By analyzing a product of unknown origin for a subset of these impurities, a person of skill in the art could determine whether the product originated from a chemical or enzymatic synthesis.

Methods of Engineering Host Cells

Also included are methods of engineering host cells for the purpose of producing enzymes and/or BIAs of interest. Inserting DNA into host cells may be achieved using any convenient methods. The methods are used to insert the heterologous coding sequences into the engineered host cells such that the host cells functionally express the enzymes and convert starting compounds of interest into product enzymes and/or BIAs of interest.

Any convenient promoters may be utilized in the subject engineered host cells and methods. The promoters driving expression of the heterologous coding sequences may be constitutive promoters or inducible promoters, provided that the promoters are active in the engineered host cells. The heterologous coding sequences may be expressed from their native promoters, or non-native promoters may be used. Such promoters may be low to high strength in the host in which they are used. Promoters may be regulated or constitutive. In certain embodiments, promoters that are not glucose repressed, or repressed only mildly by the presence of glucose in the culture medium, are used. Promoters of interest include but are not limited to, promoters of glycolytic genes such as the promoter of the $B.$ $subtilis$ tsr gene (encoding the promoter region of the fructose bisphosphate aldolase gene) or the promoter from yeast $S.$ $cerevisiae$ gene coding for glyceraldehyde 3-phosphate dehydrogenase (GPD, GAPDH, or TDH3), the ADH1 promoter of baker's yeast, the phosphate-starvation induced promoters such as the PHO5 promoter of yeast, the alkaline phosphatase promoter from $B.$ $licheniformis$, yeast inducible promoters such as Gal1-10, Gal1, GalL, GalS, repressible promoter Met25, tetO, and constitutive promoters such as glyceraldehyde 3-phosphate dehydrogenase promoter (GPD), alcohol dehydrogenase promoter (ADH), translation-elongation factor-1-α promoter (TEF), cytochrome c-oxidase promoter (CYC1), MRP7 promoter, etc. Autonomously replicating yeast expression vectors containing promoters inducible by hormones such as glucocorticoids, steroids, and thyroid hormones may also be used and include, but are not limited to, the glucorticoid responsive element (GRE) and thyroid hormone responsive element (TRE). These and other examples are described U.S. Pat. No. 7,045,290, which is incorporated by reference, including the references cited therein. Additional vectors containing constitutive or inducible promoters such as a factor, alcohol oxidase, and PGH may be used. Additionally any promoter/enhancer combination (as per the Eukaryotic Promoter Data Base EPDB) could also be used to drive expression of genes. Any convenient appropriate promoters may be selected for the host cell, e.g., $E.$ $coli$. One may also use promoter selection to optimize transcript, and hence, enzyme levels to maximize production while minimizing energy resources.

Figure 11:
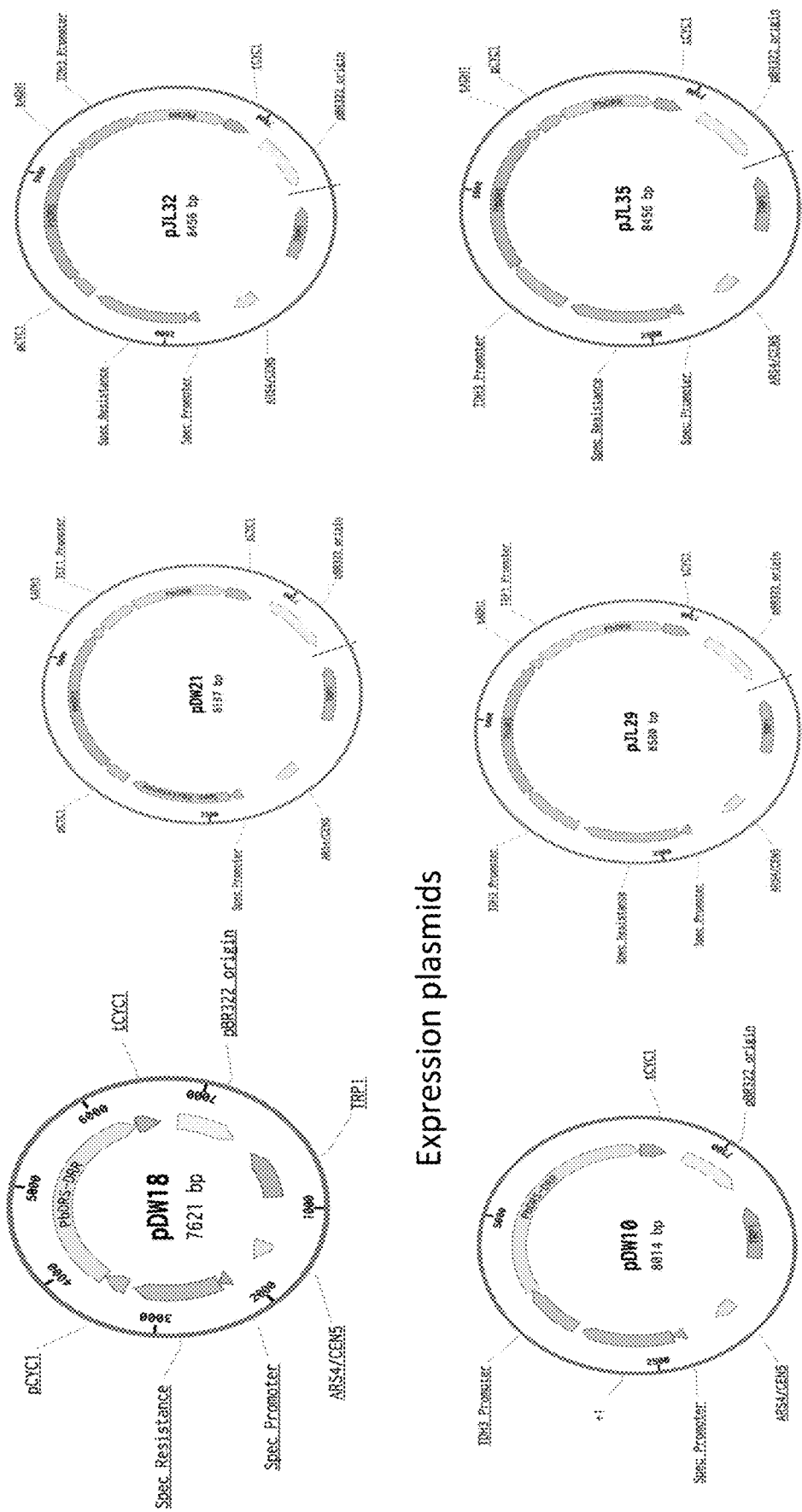
FIG. 11 illustrates plasmid/YAC vectors for enzyme expression and engineering, in accordance with embodiments of the invention.

Any convenient vectors may be utilized in the subject engineered host cells and methods. Vectors of interest include vectors for use in yeast and other cells. The types of yeast vectors may be broken up into 4 general categories: integrative vectors (YIp), autonomously replicating high copy-number vectors (YEp or 2μ plasmids), autonomously replicating low copy-number vectors (YCp or centromeric plasmids) and vectors for cloning large fragments (YACs). Vector DNA is introduced into prokaryotic or eukaryotic cells via any convenient transformation or transfection techniques. DNA of another source (e.g. PCR-generated double stranded DNA product, or synthesized double stranded or single stranded oligonucleotides) may be used to engineer the yeast by integration into the genome. Any single transformation event may include one or several nucleic acids (vectors, double stranded or single stranded DNA fragments) to genetically modify the host cell. FIG. 11 illustrates examples of convenient vectors.

Utility

The engineered host cells and methods of the invention, e.g., as described above, find use in a variety of applications. Applications of interest include, but are not limited to: research applications and therapeutic applications. Methods of the invention find use in a variety of different applications including any convenient application where the production of enzymes and/or BIAs is of interest.

The subject engineered host cells and methods find use in a variety of therapeutic applications. Therapeutic applications of interest include those applications in which the preparation of pharmaceutical products that include BIAs is of interest. The engineered host cells described herein produce BIAs of interest and enzymes of interest. Reticuline is a major branch point intermediate of interest in the synthesis of BIAs including engineering efforts to produce end products such as opioid products. The subject host cells may be utilized to produce BIAs of interest from simple and inexpensive starting materials that may find use in the production of BIAs of interest, including reticuline, and BIA end products. As such, the subject host cells find use in the supply of therapeutically active BIAs of interest.

In some instances, the engineered host cells and methods find use in the production of commercial scale amounts of BIAs thereof where chemical synthesis of these compounds is low yielding and not a viable means for large-scale production. In certain cases, the host cells and methods are utilized in a fermentation facility that would include bioreactors (fermenters) of e.g., 5,000-200,000 liter capacity allowing for rapid production of BIAs of interest thereof for therapeutic products. Such applications may include the industrial-scale production of BIAs of interest from fermentable carbon sources such as cellulose, starch, and free sugars.

The subject engineered host cells and methods find use in a variety of research applications. The subject host cells and methods may be used to analyze the effects of a variety of enzymes on the biosynthetic pathways of a variety of enzymes and/or BIAs of interest. In addition, the engineered host cells may be engineered to produce enzymes and/or BIAs of interest that find use in testing for bioactivity of interest in as yet unproven therapeutic functions. In some cases, the engineering of host cells to include a variety of heterologous coding sequences that encode for a variety of enzymes elucidates the high yielding biosynthetic pathways towards enzymes and/or BIAs of interest. In certain cases, research applications include the production of enzymes and/or BIAs of interest for therapeutic molecules of interest that may then be further chemically modified or derivatized to desired products or for screening for increased therapeutic activities of interest. In some instances, host cell strains are used to screen for enzyme activities that are of interest in such pathways, which may lead to enzyme discovery via conversion of BIA metabolites produced in these strains.

The subject engineered host cells and methods may be used as a production platform for plant specialized metabolites. The subject host cells and methods may be used as a platform for drug library development as well as plant enzyme discovery. For example, the subject engineered host cells and methods may find use in the development of natural product based drug libraries by taking yeast strains producing interesting scaffold molecules, such as protopine, and further functionalizing the compound structure through combinatorial biosynthesis or by chemical means. By producing drug libraries in this way, any potential drug hits are already associated with a production host that is amenable to large-scale culture and production. As another example, these subject engineered host cells and methods may find use in plant enzyme discovery. The subject host cells provide a clean background of defined metabolites to express plant EST libraries to identify new enzyme activities. The subject host cells and methods provide expression methods and culture conditions for the functional expression and increased activity of plant enzymes in yeast.

Kits and Systems

Aspects of the invention further include kits and systems, where the kits and systems may include one or more components employed in methods of the invention, e.g., engineered host cells, starting compounds, heterologous coding sequences, vectors, culture medium, etc., as described herein. In some embodiments, the subject kit includes an engineered host cell (e.g., as described herein), and one or more components selected from the following: starting compounds, a heterologous coding sequence and/or a vector including the same, vectors, growth feedstock, components suitable for use in expression systems (e.g., cells, cloning vectors, multiple cloning sites (MCS), bi-directional promoters, an internal ribosome entry site (IRES), etc.), and a culture medium.

Any of the components described herein may be provided in the kits, e.g., host cells including one or more modifications, starting compounds, culture medium, etc. A variety of components suitable for use in making and using heterologous coding sequences, cloning vectors and expression systems may find use in the subject kits. Kits may also include tubes, buffers, etc., and instructions for use. The various reagent components of the kits may be present in separate containers, or some or all of them may be pre-combined into a reagent mixture in a single container, as desired.

Also provided are systems for producing enzymes and/or BIAs of interest, where the systems may include engineered host cells including one or more modifications (e.g., as described herein), starting compounds, culture medium, a fermenter and fermentation equipment, e.g., an apparatus suitable for maintaining growth conditions for the host cells, sampling and monitoring equipment and components, and the like. A variety of components suitable for use in large scale fermentation of yeast cells may find use in the subject systems.

In some cases, the system includes components for the large scale fermentation of engineered host cells, and the monitoring and purification of enzymes and/or BIA compounds produced by the fermented host cells. In certain embodiments, one or more starting compounds (e.g., as described herein) are added to the system, under conditions by which the engineered host cells in the fermenter produce one or more desired BIA products of interest. In some instances, the host cells produce a BIA of interest (e.g., as described herein). In certain cases, the BIA products of interest are opioid products, such as thebaine, codeine, neopine, morphine, neomorphine, hydrocodone, oxycodone, hydromorphone, dihydrocodeine, 14-hydroxycodeine, dihydromorphine, or oxymorphone.

In some cases, the system includes processes for monitoring and or analyzing one or more enzymes and/or BIAs of interest compounds produced by the subject host cells. For example, a LC-MS analysis system as described herein, a chromatography system, or any convenient system where the sample may be analyzed and compared to a standard, e.g., as described herein. The fermentation medium may be monitored at any convenient times before and during fermentation by sampling and analysis. When the conversion of starting compounds to enzymes and/or BIA products of interest is complete, the fermentation may be halted and purification of the BIA products may be done. As such, in some cases, the subject system includes a purification component suitable for purifying the enzymes and/or BIA products of interest from the host cell medium into which it is produced. The purification component may include any convenient means that may be used to purify the enzymes and/or BIA products of interest produced by fermentation, including but not limited to, silica chromatography, reverse-phase chromatography, ion exchange chromatography, HIC chromatography, size exclusion chromatography, liquid extraction, and pH extraction methods. In some cases, the subject system provides for the production and isolation of enzyme and/or BIA fermentation products of interest following the input of one or more starting compounds to the system.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.), but some experimental errors and deviations should be accounted for. Unless indicated otherwise, parts are parts by weight, molecular weight is weight average molecular weight, temperature is in degrees Centigrade, and pressure is at or near atmospheric.

Discussion of Enzyme List

The host cells may be engineered to include one or more modifications (such as two or more, three or more, four or more, five or more, or even more modifications) that provide for the production of BIAs of interest and/or enzymes of interest. Table 3 provides a list of exemplary genes that may be acted upon by one or more modifications so as to provide for the production of BIAs of interest and/or enzymes of interest in an engineered host cell.

Modifications of genes as provided in Table 3 may be used to produce BIAs of interest from engineered host cells that are supplied with a medium containing the minimal nutrients required for growth. This minimal medium may contain a carbon source, a nitrogen source, amino acids, vitamins, and salts. For example, modifications of genes as provided in Table 3 may be used to produce BIAs of interest from engineered host cells that are fed sugar. Additionally, modifications of one or more genes as provided in Table 3 may be used to augment the biosynthetic processes of host cells that may be engineered for drug production.

Additionally, the use of these modifications to provide for the production of BIAs of interest and/or enzymes of interest in engineered host cells is not readily apparent from the mere identification of enzymes that may be produced by the genes. In particular, synthetic pathways that have been reconstructed in host cells, such as yeast cells, as described herein comprise a variety of enzymes that do not act together in nature within a single organism. Additionally, some of the enzymes discussed herein do not act for BIA biosynthesis in their natural context. Further, some of the enzymes described herein are not evolved to function in particular host cells, such as yeast cells, and are not evolved to function together. In these cases, it would not be obvious that the enzymes would exhibit sufficient activity in the context of the synthetic BIA pathway in a host cell, such as yeast, to have sufficient flux through the pathway to produce downstream BIA end products.

For example, plant enzymes are often difficult to functionally express in heterologous microbial hosts, such as yeast. In many cases the enzymes may be misfolded, not correctly localized within the host cell, and/or incorrectly processed. The differences in protein translation and processing between yeast and plants can lead to these enzymes exhibiting substantially reduced to no detectable activities in the yeast host. These challenges arise commonly for endomembrane localized enzymes, such as cytochrome P450s, which are strongly represented in the BIA pathways. Even reduced enzyme activities may pose a substantial challenge to engineering yeast to produce complex BIAs, which requires sufficient activity at each step to ensure high-level accumulation of the desired BIA products.

Additionally, there are endogenous enzymes/pathways in some host cells, such as yeast, that may act on many of the early precursors in the BIA pathway (i.e., intermediates from tyrosine to norcoclaurine), and thus it may not be readily apparent that there would be sufficient flux through the heterologous pathway to achieve substantial BIA production given these competing endogenous pathways. For example, the Erlich pathway (Hazelwood, et al. 2008. Appl. Environ. Microbiol. 74: 2259-66; Larroy, et al. 2003. Chem. Biol. Interact. 143-144: 229-38; Larroy, et al. 2002. Eur. J. Biochem. 269: 5738-45) in yeast is the main endogenous pathway that would act to convert many of the intermediates in the early BIA pathway to undesired products and divert flux from the synthetic pathway.

Further, many of the enzymes as discussed herein, and as provided in Table 3, may function under very specific regulation strategies, including spatial regulation, in the native plant hosts, which may be lost upon transfer to the heterologous yeast host. In addition, plants present very different biochemical environments than yeast cells under which the enzymes are evolved to function, including pH, redox state, and substrate, cosubstrate, coenzyme, and cofactor availabilities. Given the differences in biochemical environments and regulatory strategies between the native hosts and the heterologous yeast hosts, it is not obvious that the enzymes would exhibit substantial activities when in the context of the yeast environment and further not obvious that they would work together to direct simple precursors such as sugar to complex BIA compounds. Maintaining the activities of the enzymes in the yeast host is particularly important as many of the pathways have many reaction steps (>10), such that if these steps are not efficient then one would not expect accumulation of desired downstream products.

In addition, in the native plant hosts, the associated metabolites in these pathways may be localized across different cell and tissue types. In several examples, there are cell types that may be specialized for biosynthesis and cell types that may be synthesized for metabolite accumulation. This type of cell specialization may be lost when expressing the pathways within a heterologous yeast host, and may play an important role in controlling the toxicity of these metabolites on the cells. Thus, it is not obvious that yeast could be successfully engineered to biosynthesize and accumulate these metabolites without being harmed by the toxicity of these compounds.

As one example, in the native plant hosts, the enzyme BBE is reported to have dynamic subcellular localization. In particular, the enzyme BBE initially starts in the ER and then is sorted to the vacuole (Bird and Facchini. 2001. Planta.

213: 888-97). It has been suggested that the ER-association of BBE in plants (Alcantara, et al. 2005. Plant Physiol. 138: 173-83) provides the optimal basic pH (pH~8.8) for BBE activity (Ziegler and Facchini. 2008. Annu. Rev. Plant Biol. 59: 735-69). As another example, there is evidence that sanguinarine biosynthesis occurs in specialized vesicles within plant cells (Amann, et al. 1986. Planta. 167: 310-20), but only some of the intermediates accumulate in the vesicles. This may occur so as to sequester them from other enzyme activities and/or toxic effects.

As another example, the biosynthetic enzymes in the morphinan pathway branch are all localized to the phloem, which is part of the vascular tissue in plants. In the phloem, the pathway enzymes may be further divided between two cell types: the sieve elements common to all plants, and the laticifer which is a specialized cell type present only in certain plants which make specialized secondary metabolites. The upstream enzymes (i.e., from NCS through to SalAT) are predominantly in the sieve elements, and the downstream enzymes (i.e., T6ODM, COR, CODM) are mostly in the laticifer (Onoyovwe, et al. 2013. Plant Cell. 25: 4110-22). Additionally, it was discovered that the final steps in the noscapine biosynthetic pathway take place in the laticifer (Chen and Facchini. 2014. Plant J. 77: 173-84). This compartmentalization is thought to be highly important for regulating biosynthesis by isolating or trafficking intermediates, providing optimal pH, enhancing supply of cofactors, although the nature of the poppy laticifer microenvironment is still under investigation (Ziegler and Facchini. 2008. Annu. Rev. Plant Biol. 59: 735-69). Further, it is predicted that several of the enzymes may function as multi-enzyme complexes or metabolic channels common to plant secondary metabolism (Kempe, et al. 2009. Phytochemistry. 70: 579-89; Allen, et al. 2004. Nat. Biotechnol. 22: 1559-66). When biosynthetic enzymes are combined from different hosts and/or expressed recombinantly in a heterologous yeast cell it is not clear that these complexes or channels will form as they would in the native host. In an additional example, in *Coptis japonica*, berberine is biosynthesized in root tissues and then accumulated within the rhizome via the action of specialized ATP-binding cassette transport proteins (Shitan, et al. 2013. Phytochemistry. 91: 109-16). In opium poppy, morphinan alkaloids are accumulated within the latex (cytoplasm of laticifer cells) (Martin, et al. 1967. Biochemistry. 6: 2355-63).

Further, even without these considerations, it is also the case that the plant enzymes for several of the steps in the pathways described herein have not yet been characterized. For example, the conversion of tyrosine to the early benzylisoquinoline alkaloid scaffold norcoclaurine has not yet been characterized. Additionally, the conversion of (S)-reticuline to (R)-reticuline has only recently been characterized as described herein. Thus, for several of the steps in the pathways described herein, alternative biosynthetic scheme were produced by bringing together enzyme activities that do not normally occur together in nature for the biosynthesis of BIAs or identifying new enzyme activities from genome sequence information to use in the reconstructed pathways.

For example, the two-step conversion of tyrosine to dopamine may be achieved by combining at least 5 mammalian enzymes and 1 bacterial enzyme, which do not naturally occur together and were not evolved to function in the context of this pathway or with plant enzymes. In these instances, it may not be obvious to utilize these enzymes for the biosynthesis of compounds they were not evolved for in nature and that they would function effectively in the context of a heterologous microbial host and this pathway. In these instances, it may not be obvious to utilize these enzymes for the biosynthesis of compounds they were not evolved for in nature and that they would function effectively in the context of a heterologous microbial host and this pathway.

As another example, until recent years the enzyme responsible for the conversion of (S)-reticuline to (R)-reticuline was unknown. Even when a fused epimerase enzyme was discovered, evolutionary analysis suggested that morphine-producing poppies evolved a fusion enzyme between the oxidase and reductase for an epimerase reaction, which was in contrast to non-morphine producing poppies where the epimerase enzymes were non-fused. Based on this analysis, some scholars believed the fusion of the oxidase and reductase portions was necessary to efficiently catalyze the conversion of (S)-Reticuline to (R)-Reticuline. Novel methods of using engineered split epimerases as discussed herein may perform this epimerization reaction in yeast and in the context of the synthetic BIA pathway, and may perform this epimerization with greater efficiency than performing an epimerization with a wild-type epimerase.

Examples of the genes that are the object of modifications so as to produce BIAs of interest and/or enzymes of interest are discussed below. Additionally, the genes are discussed in the context of a series of Figures that illustrate pathways that are used in generating BIAs of interest and/or enzymes of interest.

[TKL1] In some examples, the engineered host cell may modify the expression of the enzyme transketolase. Transketolase is encoded by the TKL1 gene. In examples, transketolase catalyzes the reaction of fructose-6-phosphate+glyceraldehyde-3-phosphate↔xylulose-5-phosphate+erythrose-4-phosphate, as referenced in FIG. 2. An engineered host cell may be modified to include constitutive overexpression of the TKL1 gene in the engineered host cell. Additionally or alternatively, the engineered host cell may be modified to synthetically regulate the expression of the TKL1 gene in the engineered host cell. In examples, the engineered host cell may be modified to incorporate a copy, copies, or additional copies, of the TKL1 gene. Additionally or alternatively, the engineered host cell may be modified to incorporate the introduction of a strong promoter element for the overexpression of the TKL1 gene within the engineered host cell. The TKL1 gene may be derived from *Saccharomyces cerevisiae* or another species. In some examples, the TKL1 gene may be 100% similar to the naturally occurring gene.

[ZWF1] In some examples, the engineered host cell may modify the expression of the enzyme glucose-6-phosphate dehydrogenase. Glucose-6-phosphate dehydrogenase is encoded by the ZWF1 gene. In examples, glucose-6-phosphate dehydrogenase catalyzes the reaction of glucose-6-phosphate→6-phosphogluconolactone, as referenced in FIG. 2. An engineered host cell may be modified to delete the coding region of the ZWF1 gene in the engineered host cell. Alternatively, the engineered host cell may be modified to disable the functionality of the ZWF1 gene, such as by introducing an inactivating mutation.

[ARO4] In some examples, the engineered host cell may modify the expression of the enzyme 3-deoxy-D-arabino-heptulosonate-7-phosphate (DAHP) synthase. DAHP synthase is encoded by the ARO4 gene. In examples, DAHP synthase catalyzes the reaction of erythrose-4-phosphate+phosphoenolpyruvic acid→DAHP, as referenced in FIG. 2. An engineered host cell may modify the ARO4 gene to incorporate one or more feedback inhibition alleviating mutations. In particular, a feedback inhibition alleviating mutation (e.g., ARO4$^{FBR}$) may be incorporated as a directed mutation to a native ARO4 gene at the original locus; as an additional copy introduced as a genetic integration at a separate locus; or as an additional copy on an episomal vector such as a 2 μm or centromeric plasmid. The identifier "FBR" in the mutation ARO4$^{FBR}$ refers to feedback resistant mutants and mutations. The feedback inhibited copy of the DAHP synthase enzyme may be under a native yeast transcriptional regulation, such as when the engineered host cell is a yeast cell. Alternatively, the feedback inhibited copy of the DAHP synthase enzyme may be introduced to the engineered host cell with engineered constitutive or dynamic regulation of protein expression by placing it under the control of a synthetic promoter. In some cases, the ARO4 gene may be derived from *Saccharomyces cerevisiae*. In some cases, the ARO4 gene may be 100% similar to the naturally occurring gene. Examples of modifications to the ARO4 gene include a feedback inhibition resistant mutation, K229L, or Q166K.

[ARO7] In some examples, the engineered host cell may modify the expression of the enzyme chorismate mutase. Chorismate mutase is encoded by the ARO7 gene. In examples, chorismate mutase catalyzes the reaction of chorismate→prephenate, as referenced in FIG. 2. An engineered host cell may modify the ARO7 gene to incorporate one or more feedback inhibition alleviating mutations. In particular, a feedback inhibition alleviating mutation (e.g., ARO7$^{FBR}$) may be incorporated as a directed mutation to a native ARO7 gene at the original locus; as an additional copy introduced as a genetic integration at a separate locus; or as an additional copy on an episomal vector such as a 2-μm or centromeric plasmid. The identifier "FBR" in the mutation ARO7$^{FBR}$ refers to feedback resistant mutants and mutations. The feedback inhibited copy of the chorismate mutase enzyme may be under a native yeast transcriptional regulation, such as when the engineered host cell is a yeast cell. Alternatively, the feedback inhibited copy of the chorismate mutase enzyme may be introduced to the engineered host cell with engineered constitutive or dynamic regulation of protein expression by placing it under the control of a synthetic promoter. In some cases, the ARO7 gene may be derived from *Saccharomyces cerevisiae*. In some cases, the ARO7 gene may be 100% similar to the naturally occurring gene. Examples of modifications to the ARO7 gene include a feedback inhibition resistant mutation or T226I.

[ARO10] In some examples, the engineered host cell may modify the expression of the enzyme phenylpyruvate decarboxylase. Phenylpyruvate decarboxylase is encoded by the ARO10 gene. In examples, phenylpyruvate decarboxylase catalyzes the reaction of hydroxyphenylpyruvate→4-hydroxyphenylacetate (4HPA), as referenced in FIG. 2. An engineered host cell may be modified to include constitutive overexpression of the ARO10 gene in the engineered host cell. Additionally or alternatively, the engineered host cell may be modified to synthetically regulate the expression of the ARO10 gene in the engineered host cell. In examples, the engineered host cell may be modified to incorporate a copy, copies, or additional copies, of the ARO10 gene. Additionally or alternatively, the engineered host cell may be modified to incorporate the introduction of a strong promoter element for the overexpression of the ARO10 gene within the engineered host cell. The ARO10 gene may be derived from *Saccharomyces cerevisiae* or another species. In some examples, the ARO10 gene may be 100% similar to the naturally occurring gene.

[ADH2-7, SFA1] In some examples, the engineered host cell may modify the expression of alcohol dehydrogenase enzymes. Alcohol dehydrogenase enzymes may be encoded by one or more of the ADH2, ADH3, ADH4, ADH5, ADH6, ADH7, and SFA1 genes. In examples, alcohol dehydrogenase catalyzes the reaction of 4HPA→tyrosol. An engineered host cell may be modified to delete the coding region of one or more of the ADH2, ADH3, ADH4, ADH5, ADH6, ADH7, and SFA1 genes in the engineered host cell. Alternatively, the engineered host cell may be modified to disable the functionality of one or more of the ADH2, ADH3, ADH4, ADH5, ADH6, ADH7, and SFA1 genes, such as by introducing an inactivating mutation.

[ALD2-6] In some examples, the engineered host cell may modify the expression of aldehyde oxidase enzymes. Aldehyde oxidase enzymes may be encoded by one or more of the ALD2, ALD3, ALD4, ALD5, and ALD6 genes. In examples, aldehyde oxidase catalyzes the reaction of 4HPA→4 hydroxyphenylacetic acid. An engineered host cell may be modified to delete the coding region of one or more of the ALD2, ALD3, ALD4, ALD5, and ALD6 genes in the engineered host cell. Alternatively, the engineered host cell may be modified to disable the functionality of one or more of the ALD2, ALD3, ALD4, ALD5, and ALD6 genes, such as by introducing an inactivating mutation.

[ARO9] In some examples, the engineered host cell may modify the expression of the enzyme aromatic aminotransferase. Aromatic aminotransferase is encoded by the ARO9 gene. In examples, aromatic aminotransferase catalyzes the reaction of hydroxyphenylpyruvate+L-alanine↔tyrosine↔pyruvate, as referenced in FIG. 2. An engineered host cell may be modified to include constitutive overexpression of the ARO9 gene in the engineered host cell. Additionally or alternatively, the engineered host cell may be modified to synthetically regulate the expression of the ARO9 gene in the engineered host cell. In examples, the engineered host cell may be modified to incorporate a copy, copies, or additional copies, of the ARO9 gene. Additionally or alternatively, the engineered host cell may be modified to incorporate the introduction of a strong promoter element for the overexpression of the ARO9 gene within the engineered host cell. The ARO9 gene may be derived from *Saccharomyces cerevisiae* or another species. In some examples, the ARO9 gene may be 100% similar to the naturally occurring gene.

[ARO8] In some examples, the engineered host cell may modify the expression of the enzyme aromatic aminotransferase. Aromatic aminotransferase is encoded by the ARO8 gene. In examples, aromatic aminotransferase catalyzes the reaction of hydroxyphenylpyruvate+glutamate↔tyrosine+alpha-ketogluterate, as referenced in FIG. 2. An engineered host cell may be modified to include constitutive overexpression of the ARO8 gene in the engineered host cell. Additionally or alternatively, the engineered host cell may be modified to synthetically regulate the expression of the ARO8 gene in the engineered host cell. In examples, the engineered host cell may be modified to incorporate a copy, copies, or additional copies, of the ARO8 gene. Additionally or alternatively, the engineered host cell may be modified to incorporate the introduction of a strong promoter element for the overexpression of the ARO8 gene within the engineered host cell. The ARO8 gene may be derived from *Saccharomyces cerevisiae* or another species. In some examples, the ARO8 gene may be 100% similar to the naturally occurring gene.

[TYR1] In some examples, the engineered host cell may modify the expression of the enzyme prephenate dehydrogenase. Prephenate dehydrogenase is encoded by the TYR1 gene. In examples, prephenate dehydrogenase catalyzes the reaction of prephenate+$NADP^+$→4-hydroxyphenylpyruvate+$CO_2$+NADPH, as referenced in FIG. 2. An engineered host cell may be modified to include constitutive overexpression of the TYR1 gene in the engineered host cell. Additionally or alternatively, the engineered host cell may be modified to synthetically regulate the expression of the TYR1 gene in the engineered host cell. In examples, the engineered host cell may be modified to incorporate a copy, copies, or additional copies, of the TYR1 gene. Additionally or alternatively, the engineered host cell may be modified to incorporate the introduction of a strong promoter element for the overexpression of the TYR1 gene within the engineered host cell. The TYR1 gene may be derived from *Saccharomyces cerevisiae* or another species. In some examples, the TYR1 gene may be 100% similar to the naturally occurring gene.

[TYR] In some examples, the engineered host cell may modify the expression of the enzyme tyrosinase. Tyrosinase is encoded by the TYR gene. In examples, tyrosinase catalyzes the reaction of tyrosine→L-DOPA, as referenced in FIGS. 2, 12, and 13. In other examples, tyrosinase catalyzes the reaction of L-DOPA→dopaquinone. An engineered host cell may be modified to include constitutive expression of the TYR gene in the engineered host cell. Additionally or alternatively, the engineered host cell may be modified to synthetically regulate the expression of the TYR gene in the engineered host cell. In examples, the engineered host cell may be modified to incorporate a copy, copies, or additional copies, of the TYR gene. Additionally or alternatively, the engineered host cell may be modified to incorporate the introduction of a strong promoter element for the overexpression of the TYR gene within the engineered host cell. The TYR gene may be derived from *Ralstonia solanacearum, Agaricus bisporus*, or another species. In some examples, the TYR gene may be 100% similar to the naturally occurring gene.

[TyrH] In some examples, the engineered host cell may modify the expression of the enzyme tyrosine hydroxylase. Tyrosine hydroxylase is encoded by the TyrH gene. In examples, tyrosine hydroxylase catalyzes the reaction of tyrosine→L-DOPA, as referenced in FIGS. 2, 12, and 13. An engineered host cell may be modified to include constitutive expression of the TyrH gene in the engineered host cell. Additionally or alternatively, the engineered host cell may be modified to synthetically regulate the expression of the TyrH gene in the engineered host cell. In examples, the engineered host cell may be modified to incorporate a copy, copies, or additional copies, of the TyrH gene. Additionally or alternatively, the engineered host cell may be modified to incorporate the introduction of a strong promoter element for the overexpression of the TyrH gene within the engineered host cell. The TyrH gene may be derived from *Homo sapiens, Rattus norvegicus, Mus musculus*, or another species. In some examples, the TyrH gene may be 100% similar to the naturally occurring gene.

[DODC] In some examples, the engineered host cell may modify the expression of the enzyme L-DOPA decarboxylase. L-DOPA decarboxylase is encoded by the DODC gene. In examples, L-DOPA decarboxylase catalyzes the reaction of L-DOPA→dopamine, as referenced in FIGS. 2, 12, and 13. An engineered host cell may be modified to include constitutive expression of the DODC gene in the engineered host cell. Additionally or alternatively, the engineered host cell may be modified to synthetically regulate the expression of the DODC gene in the engineered host cell. In examples, the engineered host cell may be modified to incorporate a copy, copies, or additional copies, of the DODC gene. Additionally or alternatively, the engineered host cell may be modified to incorporate the introduction of a strong promoter element for the overexpression of the DODC gene within the engineered host cell. The DODC gene may be derived from *Pseudomonas putida, Rattus norvegicus*, or another species. In some examples, the DODC gene may be 100% similar to the naturally occurring gene.

[TYDC] In some examples, the engineered host cell may modify the expression of the enzyme tyrosine/DOPA decarboxylase. Tyrosine/DOPA decarboxylase is encoded by the TYDC gene. In examples, tyrosine/DOPA decarboxylase catalyzes the reaction of L-DOPA→dopamine, as referenced in FIGS. 2, 12, and 13. An engineered host cell may be modified to include constitutive expression of the TYDC gene in the engineered host cell. Additionally or alternatively, the engineered host cell may be modified to synthetically regulate the expression of the TYDC gene in the engineered host cell. In examples, the engineered host cell may be modified to incorporate a copy, copies, or additional copies, of the TYDC gene. Additionally or alternatively, the engineered host cell may be modified to incorporate the introduction of a strong promoter element for the overexpression of the TYDC gene within the engineered host cell. The TYDC gene may be derived from *Papaver somniferum* or another species. In some examples, the TYDC gene may be 100% similar to the naturally occurring gene.

[MAO] In some examples, the engineered host cell may modify the expression of the enzyme monoamine oxidase. Monoamine oxidase is encoded by the MAO gene. In examples, monoamine oxidase catalyzes the reaction of dopamine 3,4-DHPA, as referenced in FIGS. 2 and 13. An engineered host cell may be modified to include constitutive expression of the MAO gene in the engineered host cell. Additionally or alternatively, the engineered host cell may be modified to synthetically regulate the expression of the MAO gene in the engineered host cell. In examples, the engineered host cell may be modified to incorporate a copy, copies, or additional copies, of the MAO gene. Additionally or alternatively, the engineered host cell may be modified to incorporate the introduction of a strong promoter element for the overexpression of the MAO gene within the engineered host cell. In some cases, the MAO gene may be codon optimized for expression in *Saccharomyces cerevisiae*. The MAO gene may be derived from *Escherichia coli, Homo sapiens, Micrococcus luteus*, or another species. In some examples, the MAO gene may be 77% similar to the naturally occurring gene.

Figure 12:
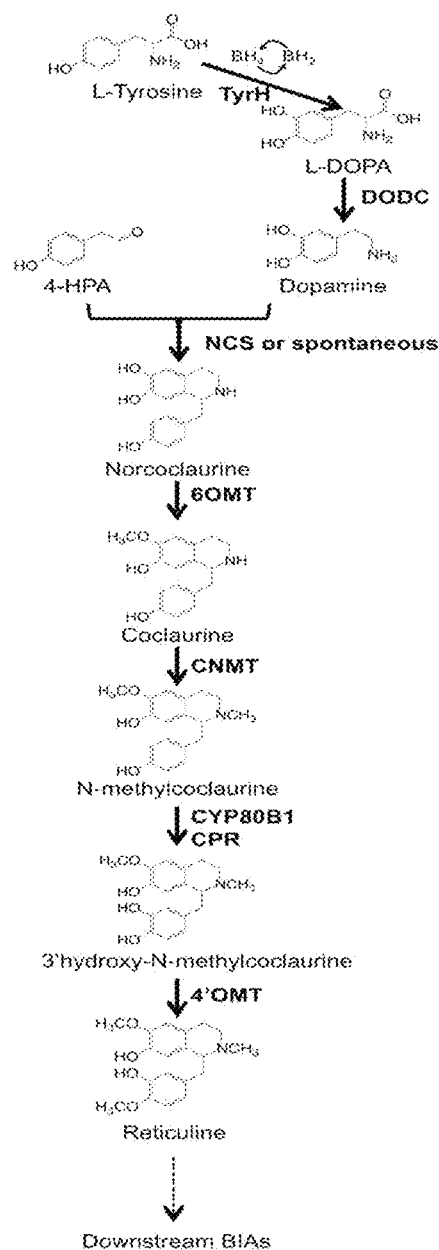
FIG. 12 illustrates a biosynthetic scheme for conversion of L-tyrosine to reticuline via norcoclaurine, in accordance with embodiments of the invention.

[NCS] In some examples, the engineered host cell may modify the expression of the enzyme norcoclaurine synthase. Norcoclaurine synthase is encoded by the NCS gene. In examples, norcoclaurine synthase catalyzes the reaction of 4HPA+dopamine→(S)-norcoclaurine, as referenced in FIGS. 12 and 13. In particular, FIG. 12 illustrates a biosynthetic scheme for conversion of L-tyrosine to reticuline via norcoclaurine, in accordance with embodiments of the invention. FIG. 12 provides the use of the enzymes TyrH, tyrosine hydroxylase; DODC, DOPA decarboxylase; NCS, norcoclaurine synthase, as discussed herein; 6OMT, 6-O-methyltransferase; CNMT, coclaurine N-methyltransferase; CYP80B1, cytochrome P450 80B1; CPR, cytochrome P450 NADPH reductase; 4'OMT, 3'hydroxy-N-methylcoclaurine 4'-O-methyltransferase. L-DOPA, L-3,4-dihydroxyphenylalanine; and 4-HPA, 4-hydroxyphenylacetylaldehyde. Of the enzymes that are illustrated in FIG. 12, 4-HPA and L-tyrosine are naturally synthesized in yeast. All other metabolites shown are not naturally produced in yeast. Additionally, although TyrH is depicted as catalyzing the conversion of L-tyrosine to L-DOPA, other enzymes may also be used to perform this step as described in the specification. For example, tyrosinases may also be used to perform the conversion of L-tyrosine to L-DOPA. In addition, other enzymes such as cytochrome P450 oxidases may also be used to perform the conversion of L-tyrosine to L-DOPA. Such enzymes may exhibit oxidase activity on related BIA precursor compounds including L-DOPA and L-tyrosine.

Figure 13:
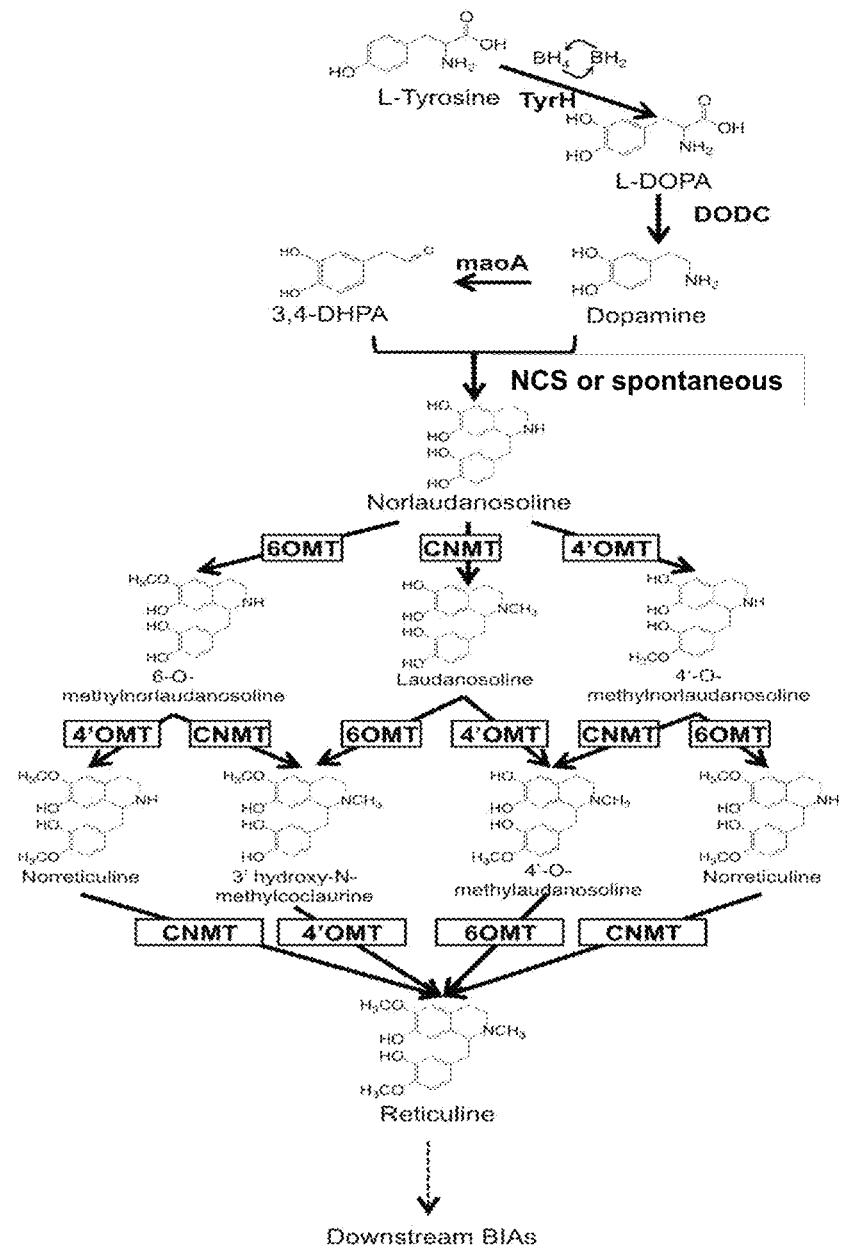
FIG. 13 illustrates a biosynthetic scheme for conversion of L-tyrosine to reticuline via norlaudanosoline, in accordance with embodiments of the invention.

Additionally, norcoclaurine synthase catalyzes the reaction of 3,4-DHPA+dopamine→(S)-norlaudanosoline, as referenced in FIG. 13. In particular, FIG. 13 illustrates a biosynthetic scheme for conversion of L-tyrosine to reticuline via norlaudanosoline, in accordance with embodiments of the invention. FIG. 13 provides the use of the enzymes TyrH, tyrosine hydroxylase; DODC, DOPA decarboxylase; maoA, monoamine oxidase; NCS, norcoclaurine synthase; 6OMT, 6-O-methyltransferase; CNMT, coclaurine N-methyltransferase; 4'OMT, 3'hydroxy-N-methylcoclaurine 4'-O-methyltransferase. L-DOPA, L-3,4-dihydroxyphenylalanine; and 3,4-DHPA, 3,4-dihydroxyphenylacetaldehyde. Of the enzymes that are illustrated in FIG. 13, L-tyrosine is naturally synthesized in yeast. Other metabolites that are shown in FIG. 13 are not naturally produced in yeast.

An engineered host cell may be modified to include constitutive expression of the NCS gene in the engineered host cell. Additionally or alternatively, the engineered host cell may be modified to synthetically regulate the expression of the NCS gene in the engineered host cell. In examples, the engineered host cell may be modified to incorporate a copy, copies, or additional copies, of the NCS gene. Additionally or alternatively, the engineered host cell may be modified to incorporate the introduction of a strong promoter element for the overexpression of the NCS gene within the engineered host cell. Additionally, the norcoclaurine synthase may have an N-terminal truncation. In some cases, the NCS gene may be codon optimized for expression in *Saccharomyces cerevisiae*. The NCS gene may be derived from *Coptis japonica, Papaver somniferum, Papver bracteatum, Thalicitum flavum, Corydalis saxicola*, or another species. In some examples, the NCS gene may be 80% similar to the naturally occurring gene.

[6OMT] In some examples, the engineered host cell may modify the expression of the enzyme norcoclaurine 6-O-methyltransferase. Norcoclaurine 6-O-methyltransferase is encoded by the 6OMT gene. In some examples, norcoclaurine 6-O-methyltransferase catalyzes the reaction of norcoclaurine→coclaurine, as referenced in FIG. 12. In other examples, norcoclaurine 6-O-methyltransferase catalyzes the reaction of norlaudanosoline→3'hydroxycoclaurine, as well as other reactions detailed herein, such as those provided in FIG. 13. Additionally, the engineered host cell may be modified to include constitutive expression of the 6OMT gene in the engineered host cell. Additionally or alternatively, the engineered host cell may be modified to synthetically regulate the expression of the 6OMT gene in the engineered host cell. In examples, the engineered host cell may be modified to incorporate a copy, copies, or additional copies, of the 6OMT gene. Additionally or alternatively, the engineered host cell may be modified to incorporate the introduction of a strong promoter element for the overexpression of the 6OMT gene within the engineered host cell. The 6OMT gene may be derived from *P. somniferum, T. flavum, Coptis japonica*, or another species. In some examples, the 6OMT gene may be 100% similar to the naturally occurring gene.

[CNMT] In some examples, the engineered host cell may modify the expression of the enzyme coclaurine-N-methyltransferase. Coclaurine-N-methyltransferase is encoded by the CNMT gene. In some examples, coclaurine-N-methyltransferase catalyzes the reaction of coclaurine→N-methylcoclaurine, as referenced in FIG. 12. In other examples, the coclaurine-N-methyltransferase enzyme may catalyze the reaction of 3'hydroxycoclaurine→3'hydroxy-N-methylcoclaurine. In other examples, coclaurine-N-methyltransferase may catalyze other reactions detailed herein, such as those provided in FIG. 13. Additionally, the engineered host cell may be modified to include constitutive expression of the CNMT gene in the engineered host cell. Additionally or alternatively, the engineered host cell may be modified to synthetically regulate the expression of the CNMT gene in the engineered host cell. In examples, the engineered host cell may be modified to incorporate a copy, copies, or additional copies, of the CNMT gene. Additionally or alternatively, the engineered host cell may be modified to incorporate the introduction of a strong promoter element for the overexpression of the CNMT gene within the engineered host cell. The CNMT gene may be derived from *P. somniferum, T. flavum, Coptis japonica*, or another species. In some examples, the CNMT gene may be 100% similar to the naturally occurring gene.

[4'OMT] In some examples, the engineered host cell may modify the expression of the enzyme 4'-O-methyltransferase. 4'-O-methyltransferase is encoded by the 4'OMT gene. In some examples, 4'-O-methyltransferase catalyzes the reaction of 3'-hydroxy-N-methylcoclaurine→reticuline, as referenced in FIG. 12. In other examples, 4'-O-methyltransferase catalyzes other reactions detailed herein, such as those provided in FIG. 13. Additionally, the engineered host cell may be modified to include constitutive expression of the 4'OMT gene in the engineered host cell. Additionally or alternatively, the engineered host cell may be modified to synthetically regulate the expression of the 4'OMT gene in the engineered host cell. In examples, the engineered host cell may be modified to incorporate a copy, copies, or additional copies, of the 4'OMT gene. Additionally or alternatively, the engineered host cell may be modified to incorporate the introduction of a strong promoter element for the overexpression of the 4'OMT gene within the engineered host cell. The 4'OMT gene may be derived from *P. somniferum, T. flavum, Coptis japonica*, or another species. In some examples, the 4'OMT gene may be 100% similar to the naturally occurring gene.

[CYP80B1] In some examples, the engineered host cell may modify the expression of the enzyme cytochrome P450 80B1. Cytochrome P450 80B1 is encoded by the CYP80B1 gene. In examples, cytochrome P450 80B1 catalyzes the reaction of N-methylcoclaurine→3'-hydroxy-N-methylcoclaurine, as referenced in FIG. 12. An engineered host cell may be modified to include constitutive expression of the cytochrome P450 80B1 gene in the engineered host cell. Additionally or alternatively, the engineered host cell may be modified to synthetically regulate the expression of the cytochrome P450 80B1 gene in the engineered host cell. In examples, the engineered host cell may be modified to incorporate a copy, copies, or additional copies, of the cytochrome P450 80B1 gene. Additionally or alternatively, the engineered host cell may be modified to incorporate the introduction of a strong promoter element for the overexpression of the cytochrome P450 80B1 gene within the engineered host cell. In some cases, the CYP80B1 gene may be codon optimized for expression in *Saccharomyces cerevisiae*. The cytochrome P450 80B1 gene may be derived from *P. somniferum, E. californica, T. flavum*, or another species. In some examples, the P450 80B1 gene may be 77% similar to the naturally occurring gene.

[FOL2] In some examples, the engineered host cell may modify the expression of the enzyme GTP cyclohydrolase. GTP cyclohydrolase is encoded by the FOL2 gene. In some examples, GTP cyclohydrolase catalyzes the reaction of GTP→dihydroneopterin triphosphate, as referenced in FIG. 1. The engineered host cell may be modified to include constitutive overexpression of the FOL2 gene in the engineered host cell. The engineered host cell may also be modified to include native regulation. Additionally or alternatively, the engineered host cell may be modified to synthetically regulate the expression of the FOL2 gene in the engineered host cell. In examples, the engineered host cell may be modified to incorporate a copy, copies, or additional copies, of the FOL2 gene. Additionally or alternatively, the engineered host cell may be modified to incorporate the introduction of a strong promoter element for the overexpression of the FOL2 gene within the engineered host cell. The FOL2 gene may be derived from *Saccharomyces cerevisiae, Homo sapiens, Mus musculus*, or another species. In some examples, the FOL2 gene may be 100% similar to the naturally occurring gene.

[PTPS] In some examples, the engineered host cell may modify the expression of the enzyme 6-pyruvoyl tetrahydrobiopterin (PTP) synthase. Pyruvoyl tetrahydrobiopterin synthase is encoded by the PTPS gene. In some examples, 6-pyruvoyl tetrahydrobiopterin synthase catalyzes the reaction of dihydroneopterin triphosphate→PTP, as referenced in FIG. 1. The engineered host cell may be modified to include constitutive expression of the PTPS gene in the engineered host cell. Additionally or alternatively, the engineered host cell may be modified to synthetically regulate the expression of the PTPS gene in the engineered host cell. In examples, the engineered host cell may be modified to incorporate a copy, copies, or additional copies, of the PTPS gene. Additionally or alternatively, the engineered host cell may be modified to incorporate the introduction of a strong promoter element for the overexpression of the PTPS gene within the engineered host cell. In some cases, the PTPS gene may be codon optimized for expression in *Saccharomyces cerevisiae*. The PTPS gene may be derived from *Rattus norvegicus, Homo sapiens, Mus musculus*, or another species. In some examples, the PTPS gene may be 80% similar to the naturally occurring gene.

[SepR] In some examples, the engineered host cell may modify the expression of the enzyme sepiapterin reductase. Sepiapterin reductase is encoded by the SepR gene. In some examples, sepiapterin reductase catalyzes the reaction of PTP→$BH_4$, as referenced in FIG. 1. The engineered host cell may be modified to include constitutive expression of the SepR gene in the engineered host cell. Additionally or alternatively, the engineered host cell may be modified to synthetically regulate the expression of the SepR gene in the engineered host cell. In examples, the engineered host cell may be modified to incorporate a copy, copies, or additional copies, of the SepR gene. Additionally or alternatively, the engineered host cell may be modified to incorporate the introduction of a strong promoter element for the overexpression of the SepR gene within the engineered host cell. In some cases, the SepR gene may be codon optimized for expression in *Saccharomyces cerevisiae*. The SepR gene may be derived from *Rattus norvegicus, Homo sapiens, Mus musculus*, or another species. In some examples, the SepR gene may be 72% similar to the naturally occurring gene.

[PCD] In some examples, the engineered host cell may modify the expression of the enzyme 4a-hydroxytetrahydrobiopterin (pterin-4α-carbinolamine) dehydratase. 4a-hydroxytetrahydrobiopterin dehydratase is encoded by the PCD gene. In some examples, 4a-hydroxytetrahydrobiopterin dehydratase catalyzes the reaction of 4a-hydroxytetrahydrobiopterin→$H_2O$+quinonoid dihydropteridine, as referenced in FIG. 1. The engineered host cell may be modified to include constitutive expression of the PCD gene in the engineered host cell. Additionally or alternatively, the engineered host cell may be modified to synthetically regulate the expression of the PCD gene in the engineered host cell. In examples, the engineered host cell may be modified to incorporate a copy, copies, or additional copies, of the PCD gene. Additionally or alternatively, the engineered host cell may be modified to incorporate the introduction of a strong promoter element for the overexpression of the PCD gene within the engineered host cell. In some cases, the PCD gene may be codon optimized for expression in *Saccharomyces cerevisiae*. The PCD gene may be derived from *Rattus norvegicus, Homo sapiens, Mus musculus*, or another species. In some examples, the PCD gene may be 79% similar to the naturally occurring gene.

[QDHPR] In some examples, the engineered host cell may modify the expression of the enzyme quinonoid dihydropteridine reductase. Quinonoid dihydropteridine reductase is encoded by the QDHPR gene. In some examples, quinonoid dihydropteridine reductase catalyzes the reaction of quinonoid dihydropteridine→$BH_4$, as referenced in FIG. 1. The engineered host cell may be modified to include constitutive expression of the QDHPR gene in the engineered host cell. Additionally or alternatively, the engineered host cell may be modified to synthetically regulate the expression of the QDHPR gene in the engineered host cell. In examples, the engineered host cell may be modified to incorporate a copy, copies, or additional copies, of the QDHPR gene. Additionally or alternatively, the engineered host cell may be modified to incorporate the introduction of a strong promoter element for the overexpression of the QDHPR gene within the engineered host cell. In some cases, the QDHPR gene may be codon optimized for expression in *Saccharomyces cerevisiae*. The QDHPR gene may be derived from *Rattus norvegicus, Homo sapiens, Mus musculus*, or another species. In some examples, the QDHPR gene may be 75% similar to the naturally occurring gene.

[DHFR] In some examples, the engineered host cell may modify the expression of the enzyme dihydrofolate reductase. Dihydrofolate reductase is encoded by the DHFR gene. In some examples, dihydrofolate reductase catalyzes the reaction of 7,8-dihydrobiopterin ($BH_2$)→5,6,7,8-tetrahydrobiopterin ($BH_4$), as referenced in FIG. 1. This reaction may be useful in recovering $BH_4$ as a co-substrate for the conversation of tyrosine to L-DOPA, as illustrated in FIG. 12. The engineered host cell may be modified to include constitutive expression of the DHFR gene in the engineered host cell. Additionally or alternatively, the engineered host cell may be modified to synthetically regulate the expression of the DHFR gene in the engineered host cell. In examples, the engineered host cell may be modified to incorporate a copy, copies, or additional copies, of the DHFR gene. Additionally or alternatively, the engineered host cell may be modified to incorporate the introduction of a strong promoter element for the overexpression of the DHFR gene within the engineered host cell. In some cases, the DHFR gene may be codon optimized for expression in *Saccharo-

*myces cerevisiae*. The DHFR gene may be derived from *Rattus norvegicus, Homo sapiens*, or another species. In some examples, the DHFR gene may be 77% similar to the naturally occurring gene.

Figure 14:
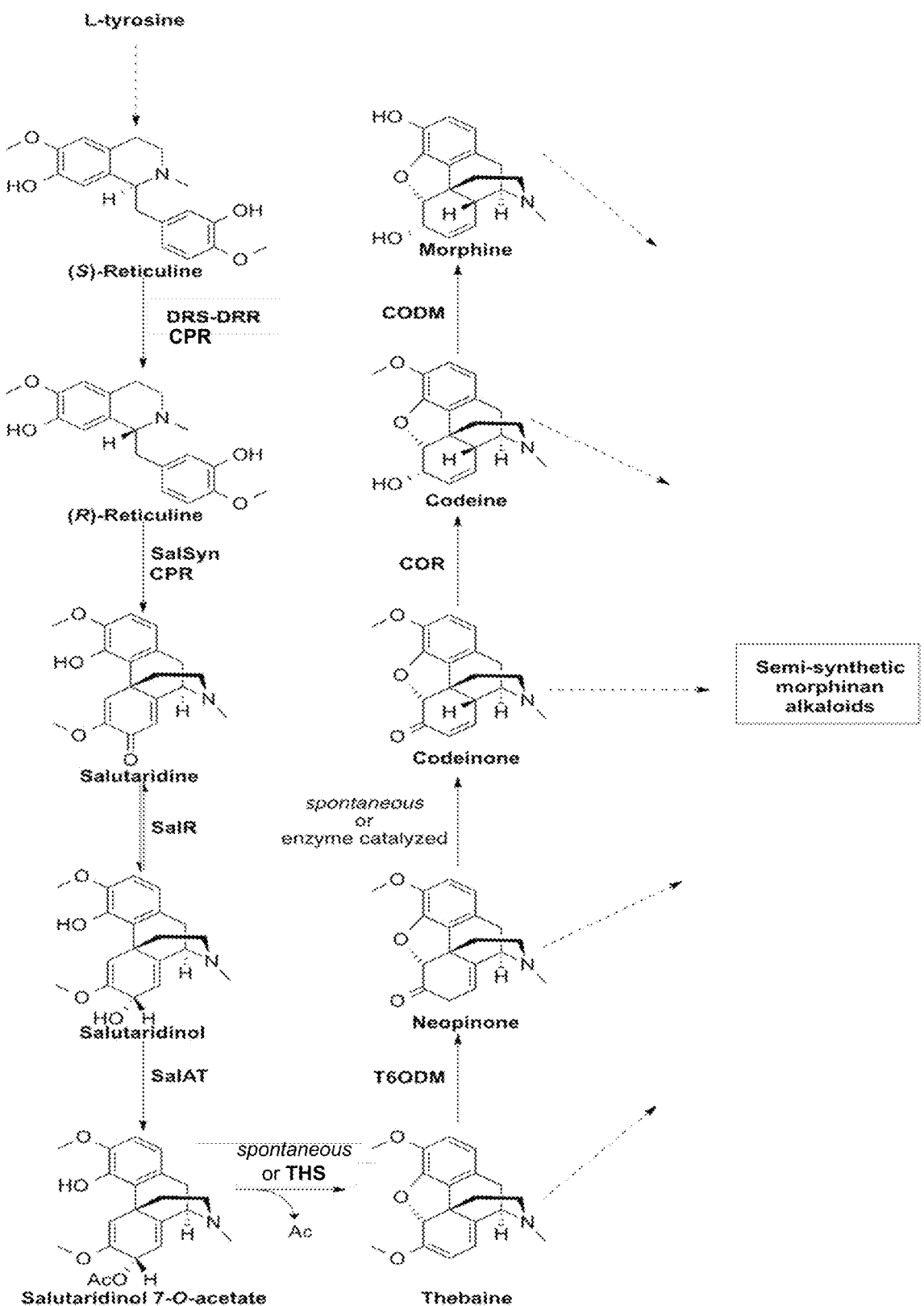
FIG. 14 illustrates a biosynthetic scheme for conversion of L-tyrosine to morphinan alkaloids, in accordance with embodiments of the invention.

[DRS-DRR] As discussed above with regard to epimerizing 1-BIAs, the engineered host cell may modify the expression of a BIA epimerase. The BIA epimerase is encoded by the DRS-DRR gene. In some examples, DRS-DRR may also be referred to as CYP-COR. In some examples, the BIA epimerase, or an engineered split version or an engineered fused version of the BIA epimerase, catalyzes the conversion of (S)-1-BIA→(R)-1-BIA, as referenced in FIG. 14. In particular, FIG. 14 illustrates a biosynthetic scheme for conversion of L-tyrosine to morphinan alkaloids, in accordance with embodiments of the invention. FIG. 14 provides the use of the enzymes CPR, cytochrome P450 reductase; DRS-DRR, dehydroreticuline synthase and dehydroreticuline reductase; SalSyn, salutaridine synthase; SalR, salutaridine reductase; SalAT, salutaridinol 7-O-acetyltransferase; TS, thebaine synthase; T6ODM, thebaine 6-O-demethylase; COR, codeinone reductase; and CODM, codeine-O-demethylase.

The engineered host cell may be modified to include constitutive expression of the DRS-DRR gene or the engineered DRS-DRR gene in the engineered host cell. In some cases, the engineered DRS-DRR gene may encode an engineered fusion epimerase. In some cases, the engineered DRS-DRR gene may encode an engineered split epimerase. Additionally or alternatively, the engineered host cell may be modified to synthetically regulate the expression of the DRS-DRR gene in the engineered host cell. In examples, the engineered host cell may be modified to incorporate a copy, copies, or additional copies, of the DRS-DRR gene. Additionally or alternatively, the engineered host cell may be modified to incorporate the introduction of a strong promoter element for the overexpression of the DRS-DRR gene within the engineered host cell. The DRS-DRR gene may be derived from *Papaver bracteatum, Papaver somniferum, Papaver setigerum, Chelidonium majus*, or another species. In some examples, the DRS-DRR gene may be 77% similar to the naturally occurring gene.

[CPR] In some examples, the engineered host cell may modify the expression of the enzyme cytochrome P450 reductase. The cytochrome P450 reductase is encoded by the CPR gene. In some examples, the cytochrome P450 reductase catalyzes the reaction of (R)-reticuline salutaridine, as referenced in FIG. 14. Additionally, the cytochrome P450 reductase catalyzes other reactions such as those described in FIGs. throughout the application. The engineered host cell may be modified to include constitutive expression of the CPR gene in the engineered host cell. Additionally or alternatively, the engineered host cell may be modified to synthetically regulate the expression of the CPR gene in the engineered host cell. In examples, the engineered host cell may be modified to incorporate a copy, copies, or additional copies, of the CPR gene. Additionally or alternatively, the engineered host cell may be modified to incorporate the introduction of a strong promoter element for the overexpression of the CPR gene within the engineered host cell. The CPR gene may be derived from *E. californica, P. somniferum, H sapiens, S. cerevisiae, A. thaliana*, or another species. In some examples, the CPR gene may be 100% similar to the naturally occurring gene.

[SalSyn] In some examples, the engineered host cell may modify the expression of the enzyme salutaridine synthase. The salutaridine synthase is encoded by the SalSyn gene. In some examples, the salutaridine synthase catalyzes the reaction of (R)-reticuline salutaridine, as referenced in FIG. 14. The engineered host cell may be modified to include constitutive expression of the SalSyn gene in the engineered host cell. Additionally or alternatively, the engineered host cell may be modified to synthetically regulate the expression of the SalSyn gene in the engineered host cell. In examples, the engineered host cell may be modified to incorporate a copy, copies, or additional copies, of the SalSyn gene. Additionally or alternatively, the engineered host cell may be modified to incorporate the introduction of a strong promoter element for the overexpression of the SalSyn gene within the engineered host cell. In some cases, the SalSyn gene may be codon optimized for expression in *Saccharomyces cerevisiae*. In some examples the SalSyn may be modified at the N-terminus. The SalSyn gene may be derived from *Papaver somniferum, Papaver* spp, *Chelidonium majus*, or another species. In some examples, the SalSyn gene may be 78% similar to the naturally occurring gene.

[SalR] In some examples, the engineered host cell may modify the expression of the enzyme salutaridine reductase. Salutaridine reductase is encoded by the SalR gene. In some examples, salutaridine reductase reversibly catalyzes the reaction of salutaridinol→salutaridine, as referenced in FIG. 14. The engineered host cell may be modified to include constitutive expression of the SalR gene in the engineered host cell. Additionally or alternatively, the engineered host cell may be modified to synthetically regulate the expression of the SalR gene in the engineered host cell. In examples, the engineered host cell may be modified to incorporate a copy, copies, or additional copies, of the SalR gene. Additionally or alternatively, the engineered host cell may be modified to incorporate the introduction of a strong promoter element for the overexpression of the SalR gene within the engineered host cell. In some cases, the SalR gene may be codon optimized for expression in *Saccharomyces cerevisiae*. The SalR gene may be derived from *Papaver somniferum, Papaver bracteatum, Papaver* spp., *Chelidonium majus*, or another species. In some examples, the SalR gene may be 80-100% similar to the naturally occurring gene.

[SalAT] In some examples, the engineered host cell may modify the expression of the enzyme acetyl-CoA:salutaridinol 7-O-acetyltransferase. Acetyl-CoA:salutaridinol 7-O-acetyltransferase is encoded by the SalAT gene. In some examples, acetyl-CoA:salutaridinol 7-O-acetyltransferase catalyzes the reaction of acetyl-CoA+salutaridinol→CoA+ 7-O-acetylsalutaridinol, as referenced in FIG. 14. The engineered host cell may be modified to include constitutive expression of the SalAT gene in the engineered host cell. Additionally or alternatively, the engineered host cell may be modified to synthetically regulate the expression of the SalAT gene in the engineered host cell. In examples, the engineered host cell may be modified to incorporate a copy, copies, or additional copies, of the SalAT gene. Additionally or alternatively, the engineered host cell may be modified to incorporate the introduction of a strong promoter element for the overexpression of the SalAT gene within the engineered host cell. In some cases, the SalAT gene may be codon optimized for expression in *Saccharomyces cerevisiae*. The SalAT gene may be derived from *Papaver somniferum, Papaver bracteatum, Papaver orientale, Papaver* spp., or another species. In some examples, the SalAT gene may be 77-80% similar to the naturally occurring gene.

[TS] In some examples, the engineered host cell may modify the expression of the enzyme thebaine synthase. Thebaine synthase is encoded by the TS gene. In some examples, a thebaine synthase or an engineered thebaine synthase catalyzes the reaction of 7-O-acetylsalutaridinol→thebaine+acetate, as referenced in FIG. 14. In some examples, the reaction of 7-O-acetylsalutaridinol→thebaine+acetate occurs spontaneously, but thebaine synthase catalyzes some portion of this reaction. In particular, FIG. 14 illustrates a biosynthetic scheme for conversion of L-tyrosine to morphinan alkaloids, in accordance with embodiments of the invention. FIG. 14 provides the use of the enzymes CPR, cytochrome P450 reductase; DRS-DRR, dehydroreticuline synthase and dehydroreticuline reductase; SalSyn, salutaridine synthase; SalR, salutaridine reductase; SalAT, salutaridinol 7-O-acetyltransferase; TS, thebaine synthase; T6ODM, thebaine 6-O-demethylase; COR, codeinone reductase; and CODM, codeine-O-demethylase.

The engineered host cell may be modified to include constitutive expression of the TS gene or the engineering TS gene in the engineered host cell. In some cases, the engineered TS gene may encode an engineered fusion enzyme. Additionally or alternatively, the engineered host cell may be modified to synthetically regulate the expression of the TS gene in the engineered host cell. In examples, the engineered host cell may be modified to incorporate a copy, copies, or additional copies, of the TS gene. Additionally or alternatively, the engineered host cell may be modified to incorporate the introduction of a strong promoter element for the overexpression of the TS gene within the engineered host cell. In some cases, the TS gene may be codon optimized for expression in *Saccharomyces cerevisiae*. The TS gene may be derived from *Papaver somniferum, Papaver bracteatum, Papaver orientale, Papaver* spp., or another species. In some examples, the TS gene may be 75-80% similar to the naturally occurring gene.

[T6ODM] In some examples, the engineered host cell may modify the expression of the enzyme thebaine 6-O-demethylase. Thebaine 6-0 demethylase is encoded by the T6ODM gene. In some examples, thebaine 6-O-demethylase catalyzes the reaction of thebaine→neopinone, as referenced in FIGS. 14, 15, and 16. Once the neopinone has been produced, the neopinone may be converted to codeinone. The conversion of neopinone→codeinone may occur spontaneously. Alternatively, the conversion of neopinone→codeinone may occur as a result of a catalyzed reaction. In other examples, the T6ODM enzyme may catalyze the O-demethylation of substrates other than thebaine. For example, T6ODM may O-demethylate oripavine to produce morphinone. Alternatively, T6ODM may catalyze the O-demethylation of BIAs within the 1-benzylisoquinoline, protoberberine, or protopine classes such as papaverine, canadine, and allocryptopine, respectively. The engineered host cell may be modified to include constitutive expression of the T6ODM gene in the engineered host cell. Additionally or alternatively, the engineered host cell may be modified to synthetically regulate the expression of the T6ODM gene in the engineered host cell. In examples, the engineered host cell may be modified to incorporate a copy, copies, or additional copies, of the T6ODM gene. Additionally or alternatively, the engineered host cell may be modified to incorporate the introduction of a strong promoter element for the overexpression of the T6ODM gene within the engineered host cell. In some cases, the T6ODM gene may be codon optimized for expression in *Saccharomyces cerevisiae*. The T6ODM gene may be derived from *Papaver somniferum*, or another species. In some examples, the T6ODM gene may be 76.2% similar to the naturally occurring gene.

[COR] In some examples, the engineered host cell may modify the expression of the enzyme codeinone reductase. Codeinone reductase is encoded by the COR gene. In some examples, codeinone reductase catalyzes the reaction of codeinone to codeine, as referenced in FIGS. 14, 15, and 16. In some cases, codeinone reductase can catalyze the reaction of neopinone to neopine. In other examples, COR can catalyze the reduction of other morphinans including hydrocodone→dihydrocodeine, 14-hydroxycodeinone→14-hydroxycodeine, and hydromorphone→dihydromorphine. The engineered host cell may be modified to include constitutive expression of the COR gene in the engineered host cell. Additionally or alternatively, the engineered host cell may be modified to synthetically regulate the expression of the COR gene in the engineered host cell. In examples, the engineered host cell may be modified to incorporate a copy, copies, or additional copies, of the COR gene. Additionally or alternatively, the engineered host cell may be modified to incorporate the introduction of a strong promoter element for the overexpression of the COR gene within the engineered host cell. In some cases, the COR gene may be codon optimized for expression in *Saccharomyces cerevisiae*. Additionally or alternatively, the COR gene may be modified with the addition of targeting sequences for mitochondria, vacuole, endoplasmic reticulum, or a combination thereof. The COR gene may be derived from *Papaver somniferum*, or another species. In some examples, the COR gene may be 76-78% similar to the naturally occurring gene. In examples, the COR gene may be 76.8%, 77.0%, 77.3%, or 77.7% similar to the naturally occurring gene.

[CODM] In some examples, the engineered host cell may modify the expression of the enzyme codeine O-demethylase. Codeine O-demethylase is encoded by the CODM gene. In some examples, codeine O-demethylase catalyzes the reaction of codeine to morphine, as referenced in FIGS. 14, 15, and 16. Codeine O-demethylase can also catalyze the reaction of neopine to neomorphine. Codeine O-demethylase can also catalyze the reaction of thebaine to oripavine. In other examples, CODM may catalyze the O-demethylation of BIAs within the 1-benzylisoquinoline, aporphine, and protoberberine classes such as reticuline, isocorydine, and scoulerine, respectively. In other examples, the CODM enzyme may catalyze an O,O-demethylenation reaction to cleave the methylenedioxy bridge structures in protopines. The engineered host cell may be modified to include constitutive expression of the CODM gene in the engineered host cell. Additionally or alternatively, the engineered host cell may be modified to synthetically regulate the expression of the CODM gene in the engineered host cell. In examples, the engineered host cell may be modified to incorporate a copy, copies, or additional copies, of the CODM gene. Additionally or alternatively, the engineered host cell may be modified to incorporate the introduction of a strong promoter element for the overexpression of the CODM gene within the engineered host cell. In some cases, the CODM gene may be codon optimized for expression in *Saccharomyces cerevisiae*. Additionally or alternatively, the CODM gene may be modified with the addition of targeting sequences for mitochondria. The CODM gene may be derived from *Papaver somniferum, Papaver* spp., or another species. In some examples, the CODM gene may be 75% similar to the naturally occurring gene. In examples, the CODM gene may be 75.2% similar to the naturally occurring gene.

[BBE] In some examples, the engineered host cell may modify the expression of the enzyme berberine bridge enzyme. The berberine bridge enzyme is encoded by the BBE gene. In some examples, berberine bridge enzyme catalyzes the reaction of (S)-reticuline (S)-scoulerine. The engineered host cell may be modified to include constitutive expression of the BBE gene in the engineered host cell. Additionally or alternatively, the engineered host cell may be modified to synthetically regulate the expression of the BBE gene in the engineered host cell. In examples, the engineered host cell may be modified to incorporate a copy, copies, or additional copies, of the BBE gene. Additionally or alternatively, the engineered host cell may be modified to incorporate the introduction of a strong promoter element for the overexpression of the BBE gene within the engineered host cell. The BBE gene may be derived from *Papaver somniferum, Argemone mexicana, Eschscholzia californica, Berberis stolonifera, Thalictrum flavum* subsp. *glaucum, Coptis japonica, Papaver* spp., or another species. In some examples, the BBE gene may be 99% similar to the naturally occurring gene.

[S9OMT] In some examples, the engineered host cell may modify the expression of the enzyme S-adenosyl-L-methionine:(S)-scoulerine 9-O-methyltransferase. S-adenosyl-L-methionine:(S)-scoulerine 9-O-methyltransferase is encoded by the S9OMT gene. In some examples, S-adenosyl-L-methionine:(S)-scoulerine 9-O-methyltransferase catalyzes the reaction of S-adenosyl-L-methionine+(S)-scoulerine→S-adenosyl-L-homocysteine+(S)-tetrahydrocolumbamine. The engineered host cell may be modified to include constitutive expression of the S9OMT gene in the engineered host cell. Additionally or alternatively, the engineered host cell may be modified to synthetically regulate the expression of the S9OMT gene in the engineered host cell. In examples, the engineered host cell may be modified to incorporate a copy, copies, or additional copies, of the S9OMT gene. Additionally or alternatively, the engineered host cell may be modified to incorporate the introduction of a strong promoter element for the overexpression of the S9OMT gene within the engineered host cell. In some cases, the S9OMT gene may be codon optimized for expression in *Saccharomyces cerevisiae*. The S9OMT gene may be derived from *Thalictrum flavum* subsp. *glaucum, Coptis japonica, Coptis chinensis, Papaver somniferum, Thalictrum* spp., *Coptis* spp., *Papaver* spp., or another species. In some examples, the S9OMT gene may be 100% similar to the naturally occurring gene. In examples, the S9OMT gene may be 80% similar to the naturally occurring gene.

[CAS] In some examples, the engineered host cell may modify the expression of the enzyme (S)-canadine synthase. (S)-canadine synthase is encoded by the CAS gene. In some examples, (S)-canadine synthase catalyzes the reaction of (S)-tetrahydrocolumbamine→(S)-canadine. The engineered host cell may be modified to express the CAS gene in the engineered host cell. The engineered host cell may be modified to include constitutive expression of the CAS gene in the engineered host cell. Additionally or alternatively, the engineered host cell may be modified to synthetically regulate the expression of the CAS gene in the engineered host cell. In examples, the engineered host cell may be modified to incorporate a copy, copies, or additional copies, of the CAS gene. Additionally or alternatively, the engineered host cell may be modified to incorporate the introduction of a strong promoter element for the overexpression of the CAS gene within the engineered host cell. The CAS gene may be derived from *Thalictrum flavum* subsp. *glaucum, Coptis japonica, Thalictrum* spp., *Coptis* spp., or another species. In some examples, the CAS gene may be 100% similar to the naturally occurring gene.

[STOX] In some examples, the engineered host cell may modify the expression of the enzyme (S)-tetrahydroprotoberberine oxidase. (S)-tetrahydroprotoberberine oxidase is encoded by the STOX gene. In some examples, (S)-tetrahydroprotoberberine oxidase catalyzes the reaction of (S)-tetrahydroberberine+2 $O_2$→berberine+2 $H_2O_2$. The engineered host cell may be modified to include constitutive expression of the STOX gene in the engineered host cell. Additionally or alternatively, the engineered host cell may be modified to synthetically regulate the expression of the STOX gene in the engineered host cell. In examples, the engineered host cell may be modified to incorporate a copy, copies, or additional copies, of the STOX gene. Additionally or alternatively, the engineered host cell may be modified to incorporate the introduction of a strong promoter element for the overexpression of the STOX gene within the engineered host cell. In some examples the STOX may be modified at the N-terminus. In some cases, the STOX gene may be codon optimized for expression in *Saccharomyces cerevisiae*. The STOX gene may be derived from *Berberis wilsonae, Coptis japonica, Berberis* spp., *Coptis* spp., or another species. In some examples, the STOX gene may be 78% similar to the naturally occurring gene.

[TNMT] In some examples, the engineered host cell may modify the expression of the enzyme tetrahydroprotoberberine-N-methyltransferase. Tetrahydroprotoberberine-N-methyltransferase is encoded by the TNMT gene. In some examples, tetrahydroprotoberberine-N-methyltransferase catalyzes the reaction of canadine→N-methylcanadine. In some examples, tetrahydroprotoberberine-N-methyltransferase catalyzes the reaction of noroxymorphone→naloxone.

In other examples, tetrahydroprotoberberine-N-methyltransferase catalyzes the reaction of stylopine→cis-N-methylstylopine. The engineered host cell may be modified to include constitutive expression of the TNMT gene in the engineered host cell. Additionally or alternatively, the engineered host cell may be modified to synthetically regulate the expression of the TNMT gene in the engineered host cell. In examples, the engineered host cell may be modified to incorporate a copy, copies, or additional copies, of the TNMT gene. Additionally or alternatively, the engineered host cell may be modified to incorporate the introduction of a strong promoter element for the overexpression of the TNMT gene within the engineered host cell. In some cases, the TNMT gene may be codon optimized for expression in *Saccharomyces cerevisiae*. The TNMT gene may be derived from *Papaver somniferum, Eschscholzia californica, Papaver bracteatuin, Argemone mexicana*, or another species. In some examples, the TNMT gene may be 100% similar to the naturally occurring gene. In examples, the TNMT gene may be 81% similar to the naturally occurring gene.

[CFS] In some examples, the engineered host cell may modify the expression of the enzyme cheilanthifoline synthase. Cheilanthifoline synthase is encoded by the CFS gene. In examples, cheilanthifoline synthase catalyzes the reaction of scoulerine→cheilanthifoline. An engineered host cell may be modified to include constitutive expression of the CFS gene in the engineered host cell. Additionally or alternatively, the engineered host cell may be modified to synthetically regulate the expression of the CFS gene in the engineered host cell. In examples, the engineered host cell may be modified to incorporate a copy, copies, or additional copies, of the CFS gene. Additionally or alternatively, the engineered host cell may be modified to incorporate the introduction of a strong promoter element for the overexpression of the CFS gene within the engineered host cell. The CFS gene may be derived from *P. somniferum, E. californica, A. mexicana*, or another species. In some examples, the CFS gene may be 77%, 78%, or 79% similar to the naturally occurring gene. Additionally, the CFS gene may be codon optimized for expression in *Saccharomyces cerevisiae*.

In some examples, the engineered host cell may modify the expression of the enzyme stylopine synthase. Stylopine synthase is encoded by the STS gene. In examples, stylopine synthase catalyzes the reaction of cheilanthifoline→stylopine. An engineered host cell may be modified to include constitutive expression of the STS gene in the engineered host cell. Additionally or alternatively, the engineered host cell may be modified to synthetically regulate the expression of the STS gene in the engineered host cell. In examples, the engineered host cell may be modified to incorporate a copy, copies, or additional copies, of the STS gene. Additionally or alternatively, the engineered host cell may be modified to incorporate the introduction of a strong promotor element for the overexpression of the STS gene within the engineered host cell. The STS gene may be derived from *P. somniferum, E. californica, A. mexicana*, or another species. In some examples, the STS gene may be 76%, 78%, or 79% similar to the naturally occurring gene. Additionally, the STS gene may be codon optimized for expression in *Saccharomyces cerevisiae*.

[MSH] In some examples, the engineered host cell may modify the expression of the enzyme cis-N-methylstylopine 14-hydroxylase. Cis-N-methylstylopine 14-hydroxylase is encoded by the MSH gene. In examples, cis-N-methylstylopine 14-hydroxylase catalyzes the reaction of cis-N-methylstylopine→protopine. An engineered host cell may be modified to include constitutive expression of the MSH gene in the engineered host cell. Additionally or alternatively, the engineered host cell may be modified to synthetically regulate the expression of the MSH gene in the engineered host cell. In examples, the engineered host cell may be modified to incorporate a copy, copies, or additional copies, of the MSH gene. Additionally or alternatively, the engineered host cell may be modified to incorporate the introduction of a strong promotor element for the overexpression of the MSH gene within the engineered host cell. The MSH gene may be derived from *P. somniferum* or another species. In some examples, the MSH gene may be 79% similar to the naturally occurring gene. Additionally, the MSH gene may be codon optimized for expression in *Saccharomyces cerevisiae*.

[P6H] In some examples, the engineered host cell may modify the expression of the enzyme protopine-6-hydroxylase. Protopine-6-hydroxylase is encoded by the P6H gene. In examples, protopine-6-hydroxylase catalyzes the reaction of Protopine→6-hydroxyprotopine. An engineered host cell may be modified to include constitutive expression of the P6H gene in the engineered host cell. Additionally or alternatively, the engineered host cell may be modified to synthetically regulate the expression of the P6H gene in the engineered host cell. In examples, the engineered host cell may be modified to incorporate a copy, copies, or additional copies, of the P6H gene. Additionally or alternatively, the engineered host cell may be modified to incorporate the introduction of a strong promoter element for the overexpression of the CFS gene within the engineered host cell. The P6H gene may be derived from *P. somniferum, E. californica*, or another species. In some examples, the P6H gene may be 79% similar to the naturally occurring gene. Additionally, the P6H gene may be codon optimized for expression in *Saccharomyces cerevisiae*.

[DBOX] In some examples, the engineered host cell may modify the expression of the enzyme dihydrobenzophenanthridine oxidase. Dihydrobenzophenanthridine oxidase is encoded by the DBOX gene. In examples, dihydrobenzophenanthridine oxidase catalyzes the reaction of dihydrosanguinarine→sanguinarine. An engineered host cell may be modified to include constitutive expression of the DBOX gene in the engineered host cell. Additionally or alternatively, the engineered host cell may be modified to synthetically regulate the expression of the DBOX gene in the engineered host cell. In examples, the engineered host cell may be modified to incorporate a copy, copies, or additional copies, of the DBOX gene. Additionally or alternatively, the engineered host cell may be modified to incorporate the introduction of a strong promotor element for the overexpression of the DBOX gene within the engineered host cell. The DBOX gene may be derived from *P. somniferum* or another species. In some examples, the DBOX gene may be 100% similar to the naturally occurring gene. Additionally, the DBOX gene may be codon optimized for expression in *Saccharomyces cerevisiae*.

Figure 15:
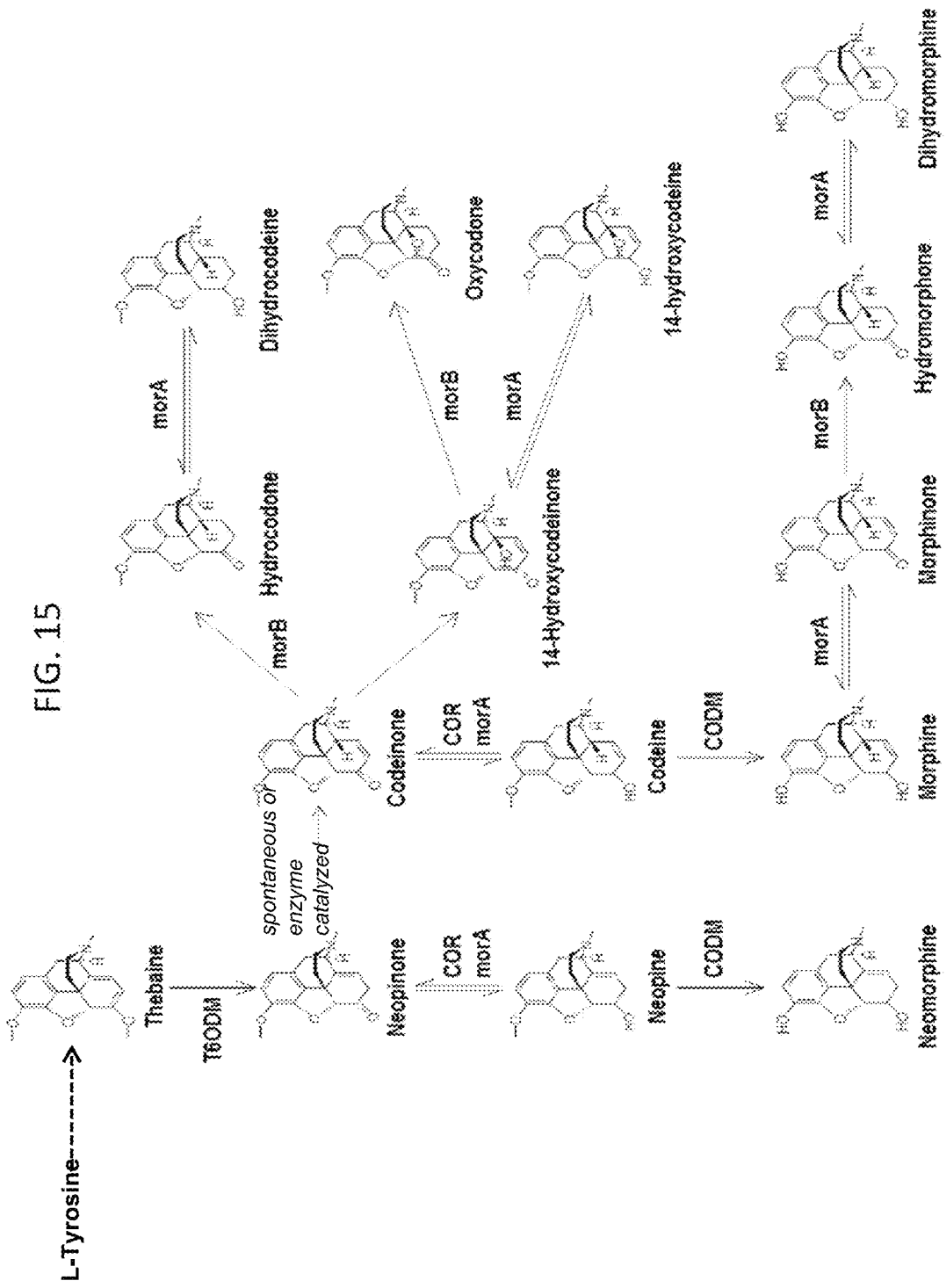
FIG. 15 illustrates a biosynthetic scheme for production of semi-synthetic opioids, in accordance with embodiments of the invention.
Figure 16:
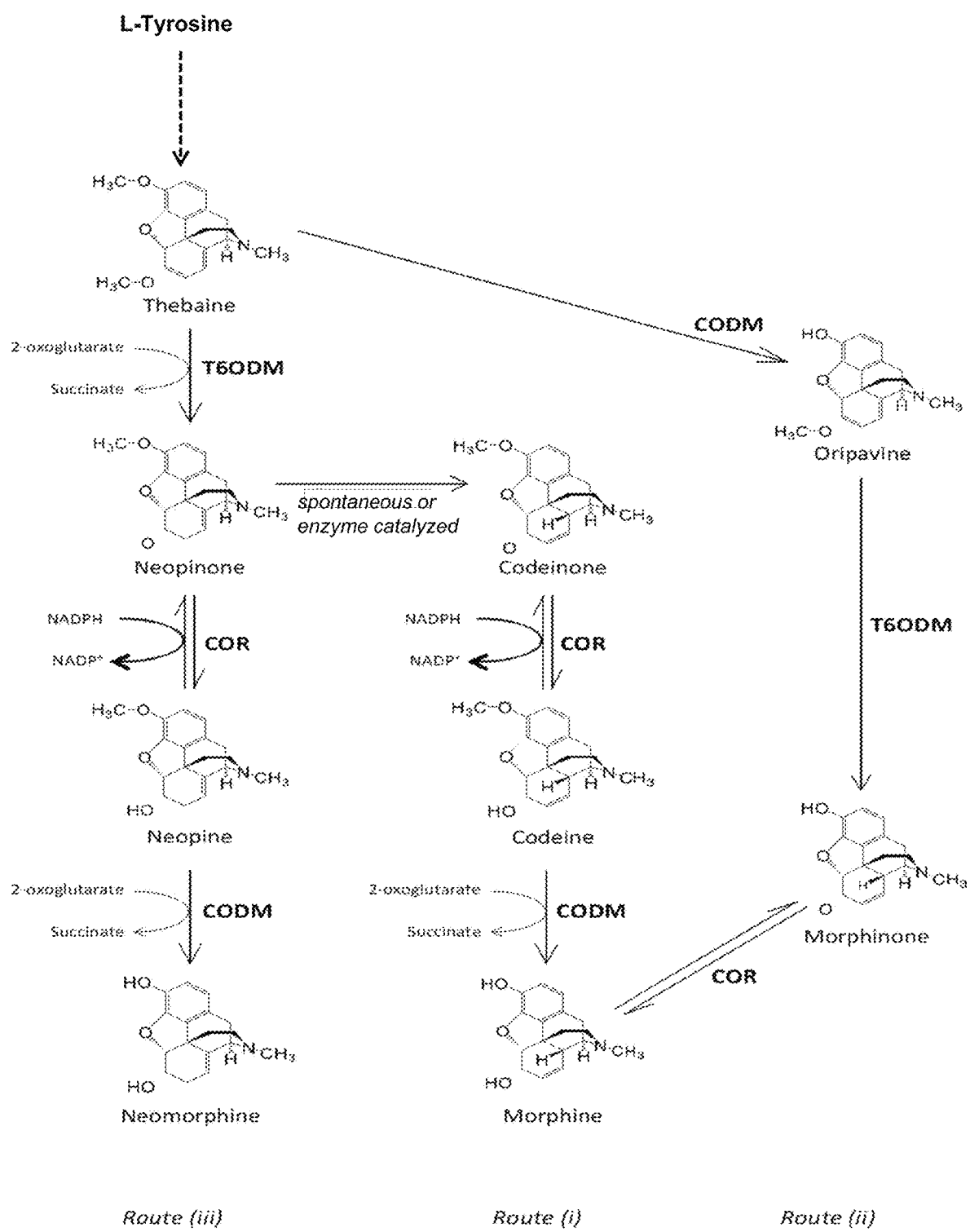
FIG. 16 illustrates a biosynthetic scheme for production of opioids, in accordance with embodiments of the invention.

[morA] In some examples, the engineered host cell may modify the expression of the enzyme morphine dehydrogenase. Morphine dehydrogenase is encoded by the morA gene. In some examples, morphine dehydrogenase catalyzes the reaction of morphine→morphinone, as referenced in FIG. 15. In other examples, morphine dehydrogenase catalyzes the reaction of codeinone→codeine, also as referenced in FIG. 15. FIG. 15 illustrates a biosynthetic scheme for production of semi-synthetic opioids, in accordance with embodiments of the invention. In particular, FIG. 15 illustrates extended transformations of thebaine in yeast by incorporating morA, morphine dehydrogenase; and morB, morphine reductase.

The engineered host cell may be modified to include constitutive expression of the morA gene in the engineered host cell. Additionally or alternatively, the engineered host cell may be modified to synthetically regulate the expression of the morA gene in the engineered host cell. In examples, the engineered host cell may be modified to incorporate a copy, copies, or additional copies, of the morA gene. Additionally or alternatively, the engineered host cell may be modified to incorporate the introduction of a strong promoter element for the overexpression of the morA gene within the engineered host cell. In some cases, the morA gene may be codon optimized for expression in *Saccharomyces cerevisiae*. The morA gene may be derived from *Pseudomonas putida* or another species. In some examples, the morA gene may be 73.7% similar to the naturally occurring gene.

[morB] In some examples, the engineered host cell may modify the expression of the enzyme morphinone reductase. Morphinone reductase is encoded by the morB gene. In some examples, morphinone reductase catalyzes the reaction of codeinone hydrocodone, as referenced in FIG. 15. In other examples, morphinone reductase catalyzes the reaction of morphinone hydromorphone, also as referenced in FIG. 15. In other examples, morphinone reductase catalyzes the reaction 14-hydroxycodeinone oxycodone. The engineered host cell may be modified to include constitutive expression of the morB gene in the engineered host cell. Additionally or alternatively, the engineered host cell may be modified to synthetically regulate the expression of the morB gene in the engineered host cell. In examples, the engineered host cell may be modified to incorporate a copy, copies, or additional copies, of the morB gene. Additionally or alternatively, the engineered host cell may be modified to incorporate the introduction of a strong promoter element for the overexpression of the morB gene within the engineered host cell.

In some cases, the morB gene may be codon optimized for expression in *Saccharomyces cerevisiae*. The morB gene may be derived from *Pseudomonas putida* or another species. In some examples, the morB gene may be 67.2% similar to the naturally occurring gene.

[CYP80A1] In some examples, the engineered host cell may express the enzyme berbamunine synthase. Berbamunine synthase is encoded by the gene for cytochrome P450 enzyme 80A1 (CYP80A1). In some examples, CYP80A1 catalyzes the reaction (S)—N-methylcoclaurine+(R)—N-methylcoclaurine→berbamunine. In other examples, CYP80A1 catalyzes the reaction (R)—N-methylcoclaurine+(R)—N-methylcoclaurine→guattegaumerine. In other examples, CYP80A1 catalyzes the reaction (R)—N-methylcoclaurine+(S)-coclaurine→2'norberbamunine. The engineered host cell may be modified to include constitutive expression of the CYP80A1 gene in the engineered host cell. Additionally or alternatively, the engineered host cell may be modified to synthetically regulate the expression of the CYP80A1 gene in the engineered host cell. In examples, the engineered host cell may be modified to incorporate a copy, copies, or additional copies, of the CYP80A1 gene. Additionally or alternatively, the engineered host cell may be modified to incorporate the introduction of a strong promoter element for the overexpression of the CYP80A1 gene within the engineered host cell. In some cases, the CYP80A1 gene may be codon optimized for expression in *Saccharomyces cerevisiae*. The CYP80A1 gene may be derived from Berber's *stolonifera* or another species. In some examples, the CYP80A1 gene may be 76% similar to the naturally occurring gene.

[PODA] In some example, the engineered host cell may express the enzyme protopine O-dealkylase. Protopine O-dealkylase is encoded by the gene PODA. In some examples, PODA catalyzes the 0, O-demethylenation of protoberberines and protopines such as canadine, stylopine, berberine, cryptopine, allocryptopine, and protopine. In some examples, PODA catalyzes the O-demethylation of BIAs including tetrahydropapaverine, tetrahydropalmatine, and cryptopine. The engineered host cell may be modified to include constitutive expression of the PODA gene in the engineered host cell. Additionally or alternatively, the engineered host cell may be modified to synthetically regulate the expression of the PODA gene in the engineered host cell. In examples, the engineered host cell may be modified to incorporate a copy, copies, or additional copies, of the PODA gene. Additionally or alternatively, the engineered host cell may be modified to incorporate the introduction of a strong promoter element for the overexpression of the PODA gene within the engineered host cell. In some cases, the PODA gene may be codon optimized for expression in *Saccharomyces cerevisiae*. The PODA gene may be derived from *Papaver somniferum* or other species. In some examples, the PODA gene may be 70-100% similar to the naturally occurring gene.

[BM3] In some examples, the engineered host cell may express the enzyme BM3. BM3 is a *Bacillus megaterium* cytochrome P450 involved in fatty acid monooxygenation in its native host. In some cases BM3 N-demethylates an opioid to produce a nor-opioid, as referenced in FIG. 9. In some cases the host cell is modified to express BM3 in addition to other heterologous enzymes for the production of a nal-opioid or nor-opioid, as referenced in FIG. 10. The engineered host cell may be modified to include constitutive expression of the BM3 gene in the engineered host cell. Additionally or alternatively, the engineered host cell may be modified to synthetically regulate the expression of the BM3 gene in the engineered host cell. In examples, the engineered host cell may be modified to incorporate a copy, copies, or additional copies, of the BM3 gene. Additionally or alternatively, the engineered host cell may be modified to incorporate the introduction of a strong promoter element for the overexpression of the BM3 gene within the engineered host cell. BM3 has several advantages as a biosynthetic enzyme including that it is soluble, comes with a fused reductase partner protein, and can readily be engineered to accept new substrates. Additionally, Table 8 illustrates variants of BM3 N-demethylase.

Examples of the aforementioned genes can be expressed from a number of different platforms in the host cell, including plasmid (2μ, ARS/CEN), YAC, or genome. In addition, examples of the aforementioned gene sequences can either be native or codon optimized for expression in the desired heterologous host (e.g., *Saccharomyces cerevisiae*).

EXAMPLES

The following examples are given for the purpose of illustrating various embodiments of the invention and are not meant to limit the invention in any fashion. Where indicated, expression constructs are understood to incorporate a suitable promoter, gene, and terminator, even if the exact terminator sequence used is not specified. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Figures 1, 21:
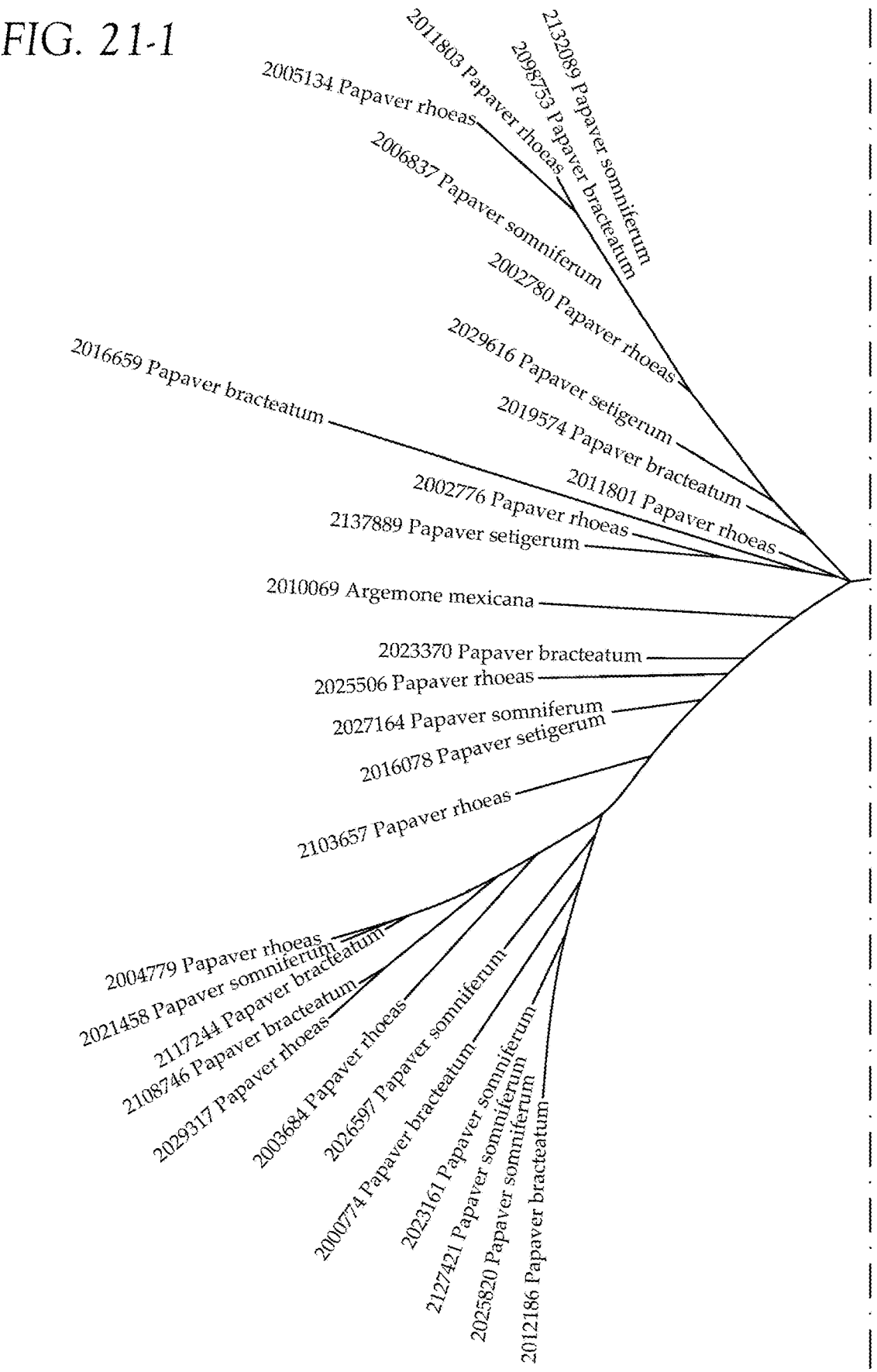
FIG. 21 illustrates a phylogenetic tree generated through a bioinformatic search for morphinan alkaloid generating enzymes, in accordance with embodiments of the invention.
Figures 2, 21:
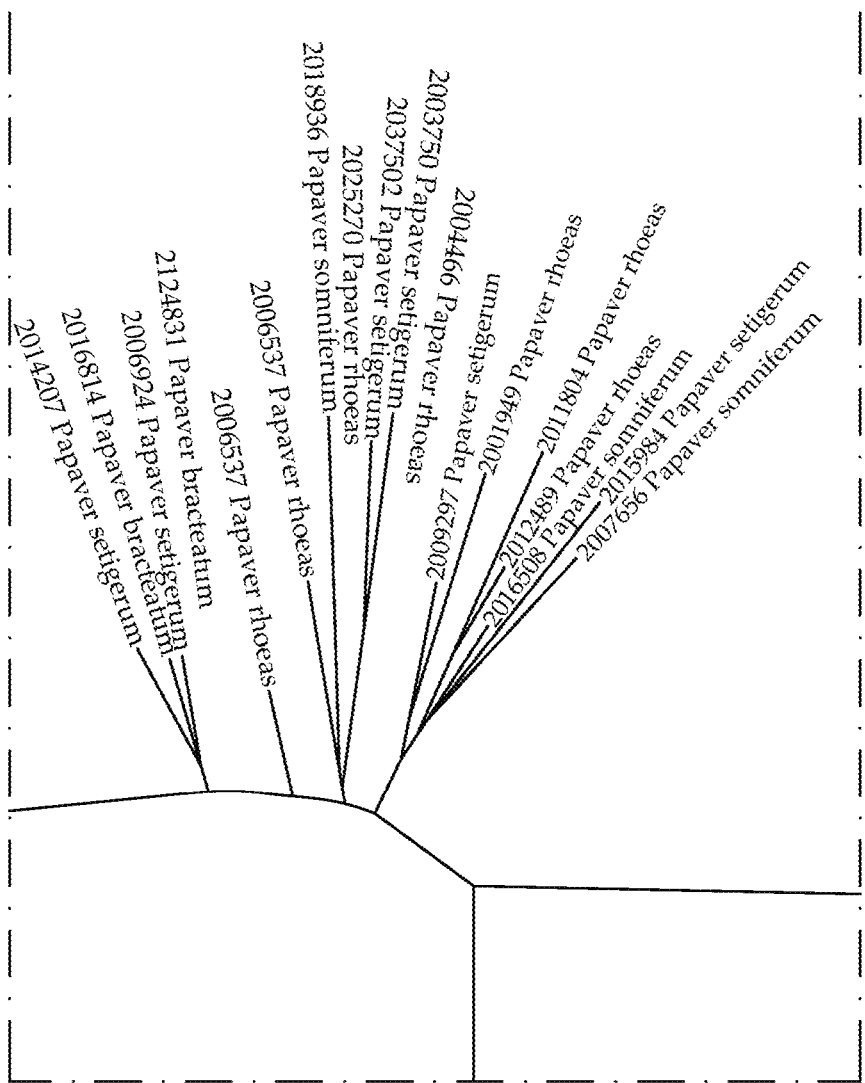
Figures 3, 21:
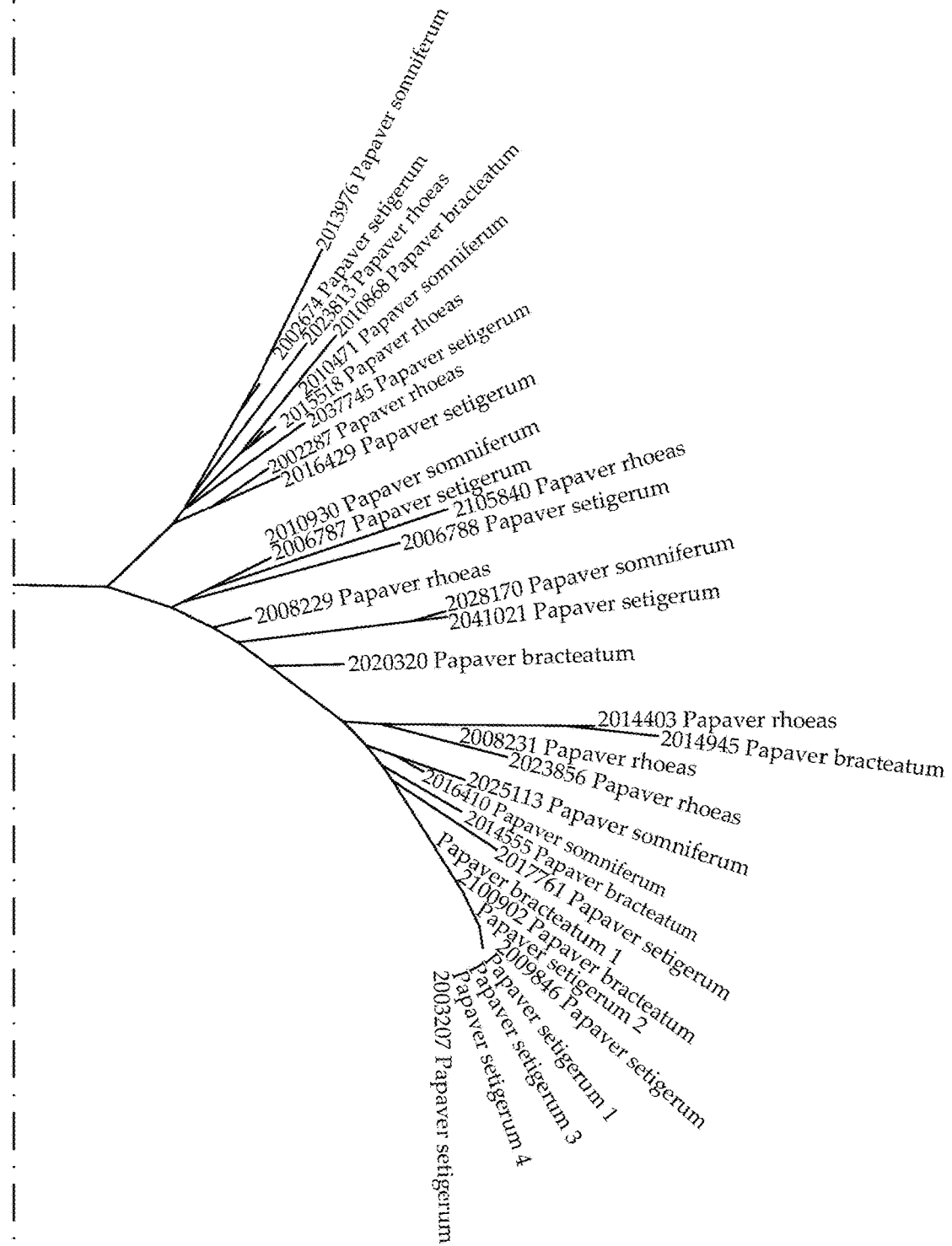
Figure 21A:
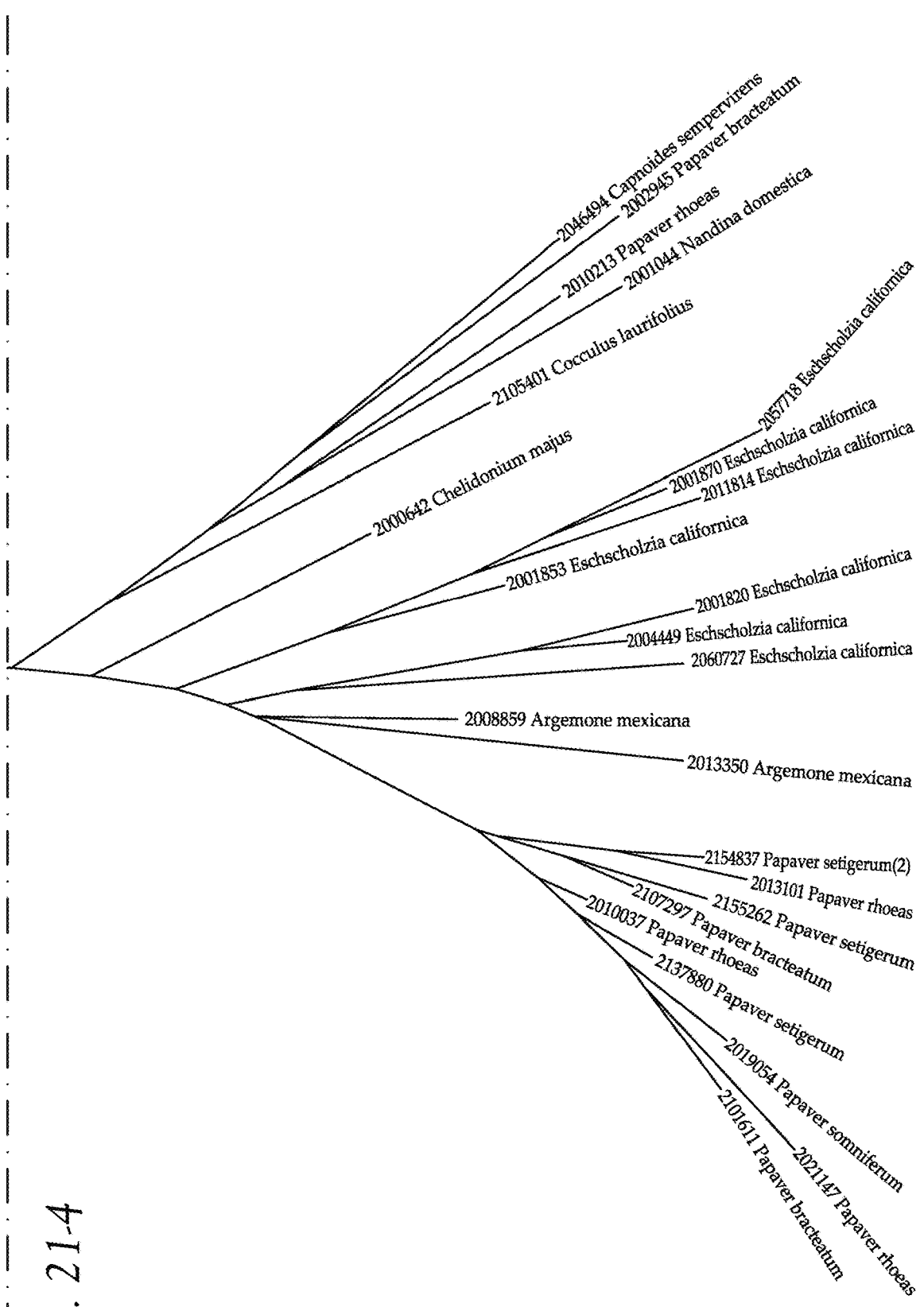

Example 1: Bioinformatic Identification of Enzymes for Morphinan Alkaloid Production The OneKP (Matasci N et al. 2014. Data access for the 1,000 Plants (1KP) project. Gigascience 3:17) and Phytometasyn (Xiao M et al. 2013. Transcriptome analysis based on next-generation sequencing of non-model plants producing specialized metabolites of biotechnological interest. J Biotechnol 166:122-34) plant transcriptome databases were queried with amino acid sequences of representative variants from each of the hypothesized classes of enzymes. In particular, the basal eudicot Glade, which includes many plant species that produce benzylisoquinoline alkaloids of interest, were searched. A large number of sequences were identified from these searches and the list of candidate sequences were narrowed down by building phylogenetic trees. In building the trees, sequences were included from similar known and characterized enzymes from plant species that produce morphinan alkaloids. These reference sequences helped to develop an understanding of the relationships between sequences and further constrain the sequence space for identifying the candidates most likely to exhibit desired activities. An example of a phylogenetic tree generated for the Bet v 1/PR10/major latex protein class of enzymes using this approach is show in FIG. 21.

Example 2: The Amino Acid Positions at which DRS-DRR can be Truncated to Form Separate DRS and DRR Enzymes An alignment of the primary amino acid sequence of PbDRS-DRR versus dehydroreticuline synthase (DRS) and dehydroreticuline reductase (DRR) from *P. rhoeas* was generated using the Clustal Omega (http://www.ebi.ac.uk/

Tools/msa/clustalo/). Based on the alignment with DRR from *P. rhoeas*, we identified a truncation point at which to separate PbDRS-DRR into DRS and DRR enzymes, where a conserved methionine residue at position M569 is found (SEQ ID NO. 16). This residue corresponds to position 1 of SEQ ID NO. 18. In FIG. 17, the black arrow, between residues D568 and M569, represents the site at which PbDRS-DRR was truncated. The separate DRS enzyme based on PbDRS-DRR was designed to end at position D568. The dashed arrow points to a region of PbDRS-DRR that is not conserved with or homologous to either DRS or DRR from *P. rhoeas*. Truncations after each of these non-conservative residues, the sequence starting at K557 and ending at D568 within the black box, were generated, and the activity of each successive truncation of DRS was assayed in a vector backbone identical to pDW21 (with DRR under the control of the TEF1 promoter). These plasmids were separately transformed in to the reporter yeast strain YA106 harboring PbSalSyn on a separate plasmid (DW24).

For propagation of yeast strains harboring engineered DRS-DRR (or separate DRS and DRR) enzymes, the reporter strain was transformed with expression plasmids using standard molecular biology techniques, and single colonies of yeast were isolated from solid agar medium plates under selective conditions (such as synthetic complete 2% dextrose without tryptophan). Colonies were inoculated into liquid culture medium and grown for 2 days at 30° C. Cultures were then subcultured into fresh medium of the same composition, or in some cases into synthetic complete liquid medium containing 8% maltodextrin. To release monosaccharide from the maltodextrin polymer, amyloglucosidase from *A. niger* (Sigma) was added at a concentration of approximately 3 U/L. Yeast strains were grown for an additional 3 or 4 days at 30° C., cultures were separated by centrifugation, and salutaridine concentration was measured directly in the supernatant by LC-MS.

Plasmids and Strains

| Plasmid/Strain | Genotype |
|---|---|
| pDW10 | Spec$^R$, TRP, P$_{TDH3}$-PbDRS-DRR-T$_{CYC1}$ |
| pDW18 | Spec$^R$, TRP, P$_{CYC1}$-PbDRS-DRR-T$_{CYC1}$ |
| pDW21 | Spec$^R$, TRP, P$_{CYC1}$-PbDRS-T$_{ADH1}$-P$_{TEF1}$-PbDRR-T$_{CYC1}$ |
| pJL29 | Spec$^R$, TRP, P$_{TDH3}$-PbDRS-T$_{ADH1}$-P$_{TEF1}$-PbDRR-T$_{CYC1}$ |
| pJL32 | Spec$^R$, TRP, P$_{CYC1}$-PbDRS-T$_{ADH1}$-P$_{TDH3}$-PbDRR-T$_{CYC1}$ |
| pJL35 | Spec$^R$, TRP, P$_{TDH3}$-PbDRS-T$_{ADH1}$-P$_{CYC1}$-PbDRR-T$_{CYC1}$ |
| YA106 | *S. cerevisiae* Cen. PK, BIA pathway = CjNCS, PsCNMT, Ps6OMT, PbCYP80B1, PsCPR, Ps4OMT (complete genotype in Galanie et al. 2015) |
| DW6 | YA106, PbSalSyn (LEU+) |
| DW24 | YA106, PbSalSyn (LEU+), ΔTRP(URA3+) |

Figure 18:
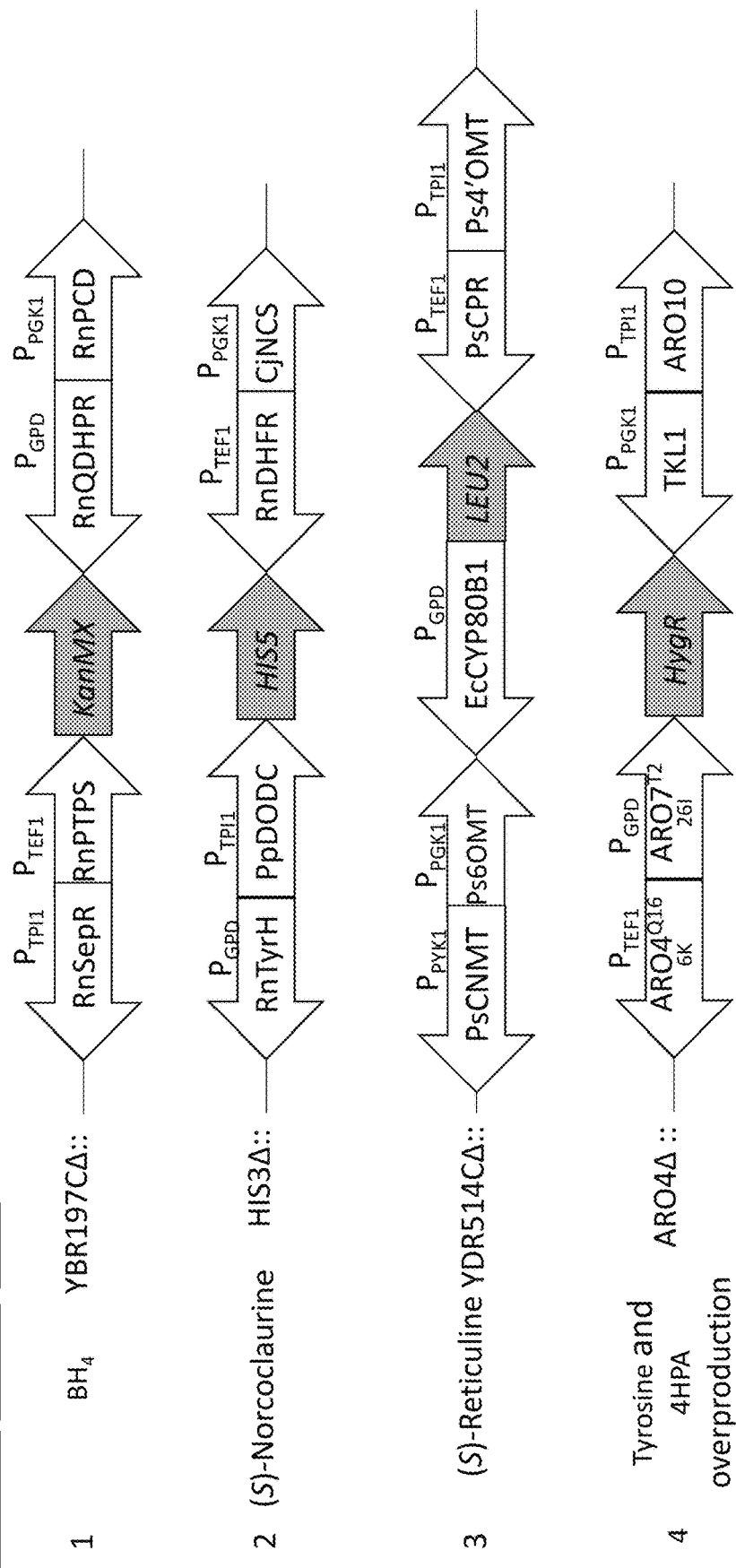
FIG. 18 illustrates yeast platform strains for the production of reticuline from L-tyrosine, in accordance with embodiments of the invention.

Example 3: Platform Yeast Strains Engineered to Produce (S)-Reticuline from Glucose and Simple Nitrogen Sources A platform yeast strain that produces the key branch point BIA intermediate (S)-reticuline from L-tyrosine was constructed (FIG. 12). Specifically, four multi-gene expression constructs were integrated into the genome of a yeast strain. The composition of the four constructs is indicated in FIG. 18. Each construct is comprised of 4 or 5 genes expressed from yeast promoters. Genes are positioned at each locus as complete expression cassettes comprising a promoter, gene open reading frame, and terminator as specified in the annotations above the schematic. The schematic shows the orientation of each expression cassette by the direction of the arrow representing a given gene. Selectable markers are italicized in the annotation and represented by grey arrows in the schematic. Each selection marker is flanked by loxP sites to allow removal of the marker from the locus. Additionally, each construct has a selectable marker flanked by loxP sites so that it can be removed by Cre recombinase.

In the first integration construct, four heterologous genes from *Rattus norvegicus* are integrated into the YBR197C locus together with a G418 selection marker (KanMX). RnPTPS, RnSepR, RnPCD, and RnQDHPR are required to synthesize and regenerate tetrahydrobiopterin (BH$_4$) from the yeast endogenous folate synthesis pathway as indicated in FIG. 1. Each gene is codon optimized for expression in yeast.

In the second integration construct, four heterologous genes are integrated into the HIS5 locus together with the HIS5 selection marker. *Rattus norvegicus* tyrosine hydroxylase (RnTyrH) converts tyrosine to L-DOPA using the cosubstrate BH$_4$ generated by the preceding integration construct. The RnTyrH gene can be any of the wild-type or improved mutants which confer enhanced activity (e.g., W166Y, R37E, and R38E). A second *Rattus norvegicus* gene, RnDHFR, encodes an enzyme that reduces dihydrobiopterin (an oxidation product of BH$_4$) to BH$_4$, in this way increasing the availability of this cosubstrate. Also included in the third construct is PpDODC from *Pseudomonas putida*, an enzyme that converts L-DOPA to dopamine. The fourth enzyme is CjNCS from *Coptis japonica*, which condenses 4-HPA and dopamine to make norcoclaurine. Each gene is codon optimized for expression in yeast.

In the third integration construct, five heterologous genes from plants and the LEU2 selection marker are integrated into the locus YDR514C. Ps6OMT, Ps4'OMT, and PsCNMT are methyltransferases from *Papaver somniferum* and are expressed as native plant nucleotide sequences. A fourth *P. somniferum* gene, yPsCPRv2, is codon optimized for yeast and encodes a reductase that supports the activity of a cytochrome P450 from *Eschscholzia californica*, EcCYP80A1. The enzymes encoded in this construct perform two O-methylations, an N-methylation, and a hydroxylation to produce reticuline from the norcoclaurine produced by the preceding integration construct. Each gene is codon optimized for expression in yeast.

In the final integration construct, additional copies of *Saccharomyces cerevisiae* endogenous genes ARO4$^{Q166K}$, ARO7$^{T226I}$, TYR1, and ARO10 are integrated into the ARO4 locus together with a hygromycin resistance selection marker. ARO4$^{Q166K}$ and ARO7$^{T226I}$ are feedback-resistant mutants of ARO4 and ARO10 which each encode a single base pair substitution relative to the wild-type sequence. TYR1 and ARO10 are identical to the native yeast genes, but are expressed behind strong promoters. Aro4p and Aro7p are enzymes in the biosynthesis of aromatic amino acids including tyrosine. Removing feedback inhibition from these enzymes results in upregulation of endogenous tyrosine biosynthesis. Overexpression of Tyr1p upregulates tyrosine biosynthesis and thus production of tyrosine. Overexpression of Aro10p increases the production of 4-HPA.

Platform yeast strains can be constructed with any number of the four expression cassettes. Specifically, platform yeast strains were constructed with integration constructs 1-4 and integration constructs 1-3. In the latter strain in which the tyrosine over-production construct (construct 4) is excluded, additional tyrosine may be supplied in the culture medium to support the biosynthesis of reticuline. Additional genetic modifications may be incorporated into the platform strains to support production of downstream BIAs and increased flux to BIA biosynthesis.

The yeast strains were grown in synthetic complete media with the appropriated amino acid drop out solution at 30° C. BIA metabolites in the media supernatant were analyzed after 48 and 96 hours of growth by LC-MS/MS analysis.

Example 4A: Platform Yeast Strains Engineered to Produce Thebaine from Glucose and Simple Nitrogen Sources Yeast strains can be engineered for the production of the morphinan alkaloid thebaine from early precursors such as tyrosine. As an example, the platform yeast strains described in Example 3 can be further engineered to produce the morphinan alkaloid products from L-tyrosine (FIG. 14).

Figure 19:
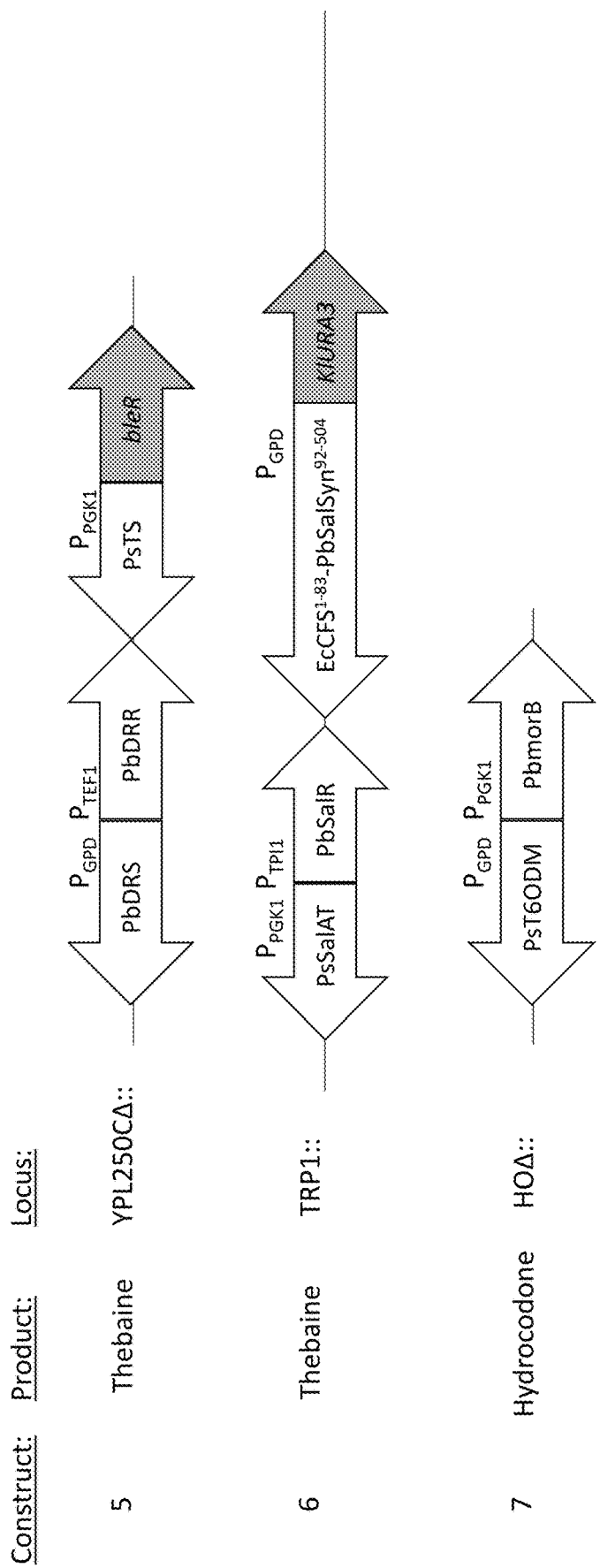
FIG. 19 illustrates yeast strains for the production of thebaine and hydrocodone from L-tyrosine, in accordance with embodiments of the invention.

The platform yeast strain producing (S)-reticuline from L-tyrosine (see description in Example 3) was further engineered to incorporate an engineered split epimerase DRS-DRR, an engineered salutaridine synthase, salutaridine reductase, salutaridinol acetyltransferase, and thebaine synthase to convert the biosynthesized (S)-reticuline to the first morphinan alkaloid thebaine (FIG. 14). Three expression cassettes ($P_{TDH3}$-yEcCFS$^{1-26}$-yPbSS$^{33-504}$, $P_{TP11}$-yPbSalR, $P_{TEF1}$-yPsSalAT) were assembled into an integration construct with a bleR selective marker and integrated into the locus TRP1 in the platform yeast strain. An additional three expression cassettes ($P_{TDH3}$-yPhDRS, $P_{TEF1}$-yPbDRR, $P_{PGK1}$-yPsTS) were assembled into an integration construct with a URA3 selective marker and integrated into the locus YPL250CΔ in the platform yeast strain. The composition of the two constructs is indicated in FIG. 19.

The yeast strains harboring the integrated cassettes were grown in synthetic complete media with the appropriated drop out solution at 30° C. After 96 hours of growth, the media was analyzed for BIA metabolites by LC-MS/MS analysis.

Example 4B: Production of Thebaine from Glucose and Simple Nitrogen Sources Via Engineered Yeast Strains Yeast strains were engineered as described in Examples 3 and 4 to produce the pentacyclic morphinan alkaloid thebaine directly from simple sugars (e.g., glucose) and nitrogen sources present in standard growth media. Specifically, a CEN.PK strain of Saccharomyces cerevisiae was engineered to express the following heterologous enzymes via integration into the yeast chromosome: TyrH, DODC, PTPS, SepR, PCD, QDHPR, NCS, 6OMT, CNMT, CYP80B1, CPR, 4OMT, DRS, DRR, SalSyn, SalR, SalAT, and TS. In this example, the SalSyn enzyme is engineered to have its leader sequence replaced with 83 amino acids from the N-terminus of Eschscholzia californica chelanthifoline synthase (EcCFS). Additional modifications were made to the strain to increase BIA precursor accumulation, including: overexpression of ARO10, overexpression of TYR1, expression of a feedback resistant ARO4 (ARO4$^{Q166K}$) and expression of a feedback resistant ARO7 (ARO7$^{T226I}$). Separate engineered yeast strains were made as described, harboring different variants of enzymes encoding thebaine synthase activity (TS), including SEQ ID NOs. 35 (i.e., TS1), 37 (i.e., TS2), and a variant of 35 with a N-terminal truncation of the first 22 amino acids (i.e., tTS1), and no thebaine synthase enzyme (YA397). The sequences of the enzyme variants are provided in Table 2.

Figure 22:
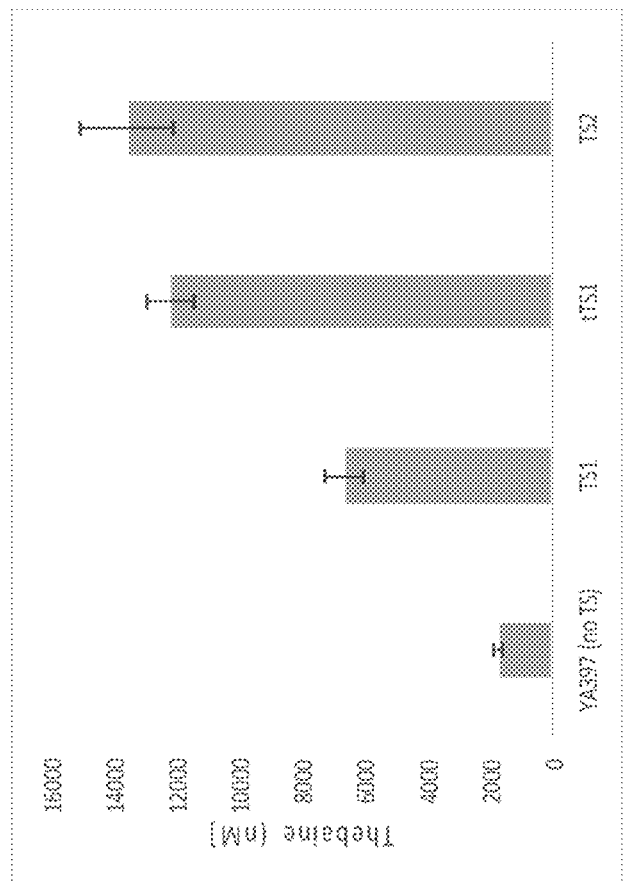
FIG. 22 illustrates the production of the morphinan alkaloid thebaine from sugar and L-tyrosine from an engineered yeast strain, in accordance with embodiments of the invention.
Figure 23:
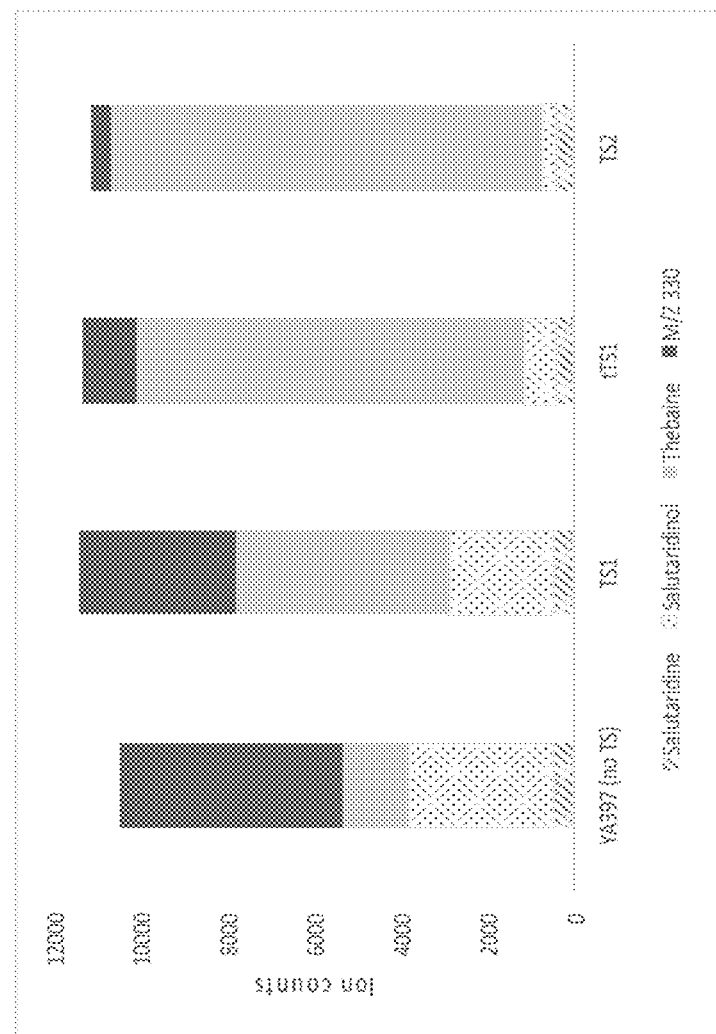
FIG. 23 illustrates the production of promorphinan alkaloids and a morphinan alkaloid thebaine from sugar and L-tyrosine from an engineered yeast strain, in accordance with embodiments of the invention.

The described yeast strains were inoculated into 2 ml of synthetic complete media (yeast nitrogen base and amino acids) with 2% glucose and grown for approximately 4 hours at 30° C. Then, 10 uL of each culture was transferred to 400 uL of fresh media in a 96-well plate in replicates of 4 and grown for an additional 48 hours at 30° C. The production media contains 1× yeast nitrogen broth and amino acids, 20 mM ascorbic acid, 300 mg/L tyrosine, 40 g/L maltodextrin, and 2 units/L amylase. The amylase is used to mimic a fed-batch process and gradually releases glucose from maltodextrin polymer so that the yeast can use it as a carbon source. The cells were separated from the media by centrifugation, and thebaine concentration was measured directly in the supernatant by LC-MS/MS analysis. All engineered yeast strains produced thebaine from glucose and simple nitrogen sources present in the growth media (FIGS. 22 and 23). Strains harboring a thebaine synthase activity produced higher levels of thebaine relative to strains not harboring this activity under the described fermentation conditions.

Example 5: Yeast Strains Engineered to Produce Downstream Morphinan Alkaloids from Glucose and Simple Nitrogen Sources Yeast strains can be engineered for the production of the downstream morphinan alkaloids from early precursors such as tyrosine. As an example, the platform yeast strains described in Example 4 can be further engineered to produce the downstream morphinan alkaloid products from L-tyrosine (FIG. 14).

The platform yeast strain producing thebaine from L-tyrosine (see description in Example 5) was further engineered to incorporate thebaine 6-O-demethylase, codeinone reductase, and codeinone-O-demethylase to convert the biosynthesized thebaine to the downstream morphinan alkaloids including morphine (FIG. 14). Three expression cassettes ($P_{ADH1}$-T6DM-T$_{ADH1}$, $P_{HX77}$-COR-T$_{PGK1}$, $P_{TEF1}$-CODM-T$_{CYC1}$) were directly assembled with a TRP1 selective marker and integrated into the trpl locus in the thebaine platform yeast strain (Thodey et al., 2014).

The yeast strains harboring the integrated cassettes were grown in synthetic complete media with the appropriated drop out solution at 30° C. After 96 hours of growth, the media was analyzed for BIA metabolites by LC-MS/MS analysis.

Example 6: Yeast Strains Engineered to Produce Semi-Synthetic Opioids from Glucose and Simple Nitrogen Sources Yeast strains can be engineered for the production of the downstream morphinan alkaloids from early precursors such as tyrosine. As an example, the yeast strains described in Examples 4 and 5 can be further engineered to produce the semi-synthetic opioid products from L-tyrosine (FIG. 15).

The yeast strains producing downstream morphinan alkaloids from L-tyrosine (see description in Example 4) were further engineered to incorporate morphine dehydrogenase and morphinone reductase to convert the biosynthesized thebaine to the downstream morphinan alkaloids including morphine (FIG. 15). Two expression cassettes ($P_{GPD}$-morA-T$_{CYC1}$, $P_{PGK1}$-morB-T$_{PHO5}$) were directly assembled with a KanMX selective marker and integrated into the HO locus in the downstream morphinan alkaloids producing yeast strains (Thodey et al., 2014).

The yeast strains harboring the integrated cassettes were grown in synthetic complete media with the appropriated drop out solution at 30° C. After 96 hours of growth, the media was analyzed for BIA metabolites by LC-MS/MS analysis.

Example 7: Microbial Strains Engineered to Produce 0-Demethylated Opioid Compounds from Glucose and Simple Nitrogen Sources Enzymes listed in Table 4 that displayed O-demethylase activity on morphinan alkaloids, were incorporated into a microbial strain (either *Saccharomyces cerevisiae* or *Escherichia coli*) which biosynthesizes morphinan alkaloids de novo (as described in Example 5). The complete BIA biosynthetic pathway uses L-tyrosine produced by the host cell and/or supplemented in the culture medium. Two molecules of tyrosine are modified and condensed to form the first benzylisoquinoline structure, which may be either norcoclaurine or norlaudanosoline. The benzylisoquinoline is further modified to form (S)-reticuline and then stereochemically inverted by the activity of an epimerase enzyme to yield (R)-reticuline. (R)-reticuline undergoes a carbon-carbon coupling reaction to form the first promorphinan, salutaridine, and is further modified before undergoing an oxygen-carbon coupling reaction catalyzed by a thebaine synthase to arrive at the first morphinan alkaloid structure, thebaine (see FIG. 14). Table 3 lists enzymes and activities in the complete pathway.

Figure 10:
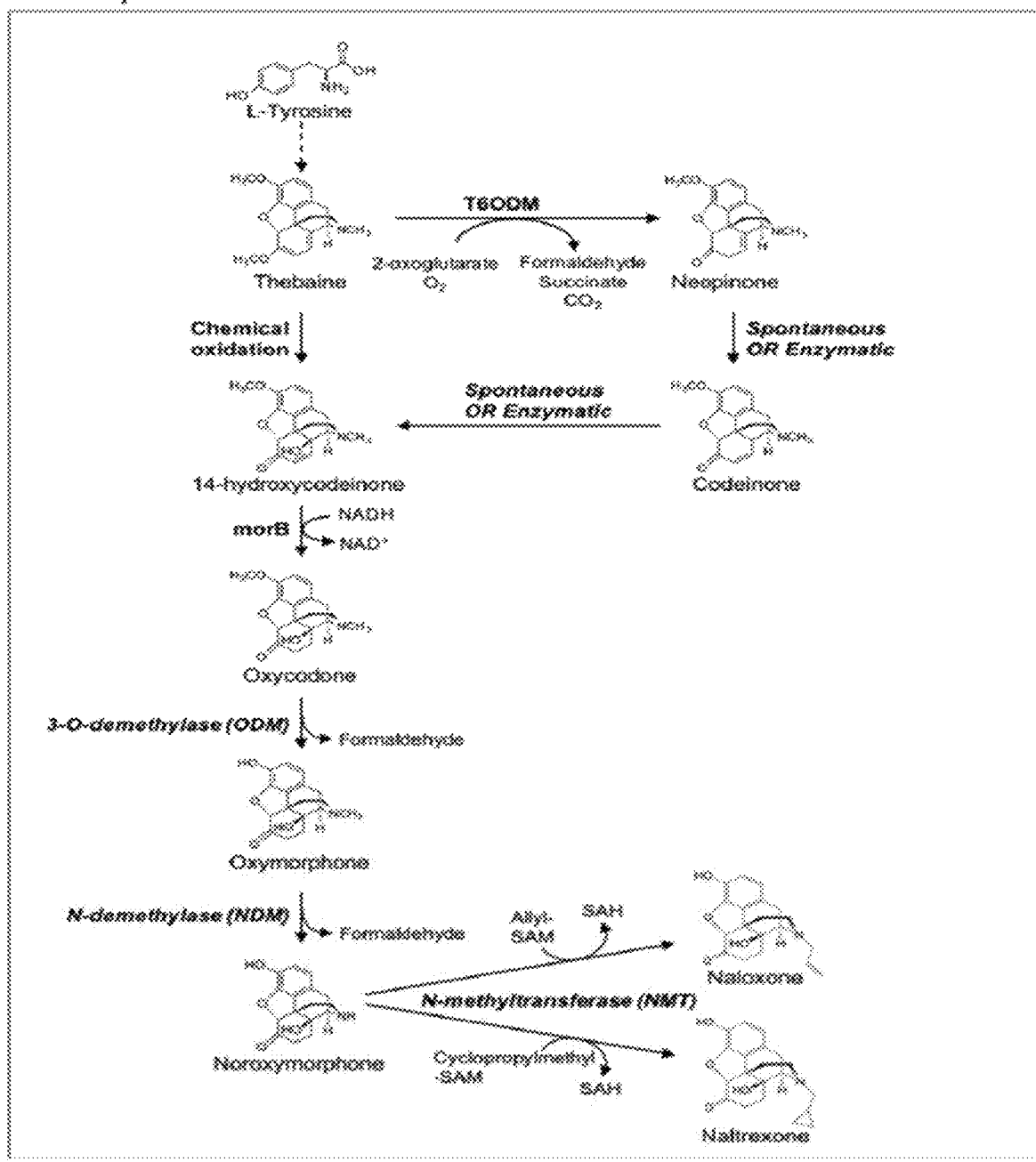
FIG. 10 illustrates a biosynthesis scheme for conversion of L-tyrosine to a nor-opioid or nal-opioid in a microbial cell, in accordance with embodiments of the invention.

FIG. 10 illustrates a biosynthesis scheme in a microbial cell, in accordance with embodiments of the invention. Tyrosine produced endogenously by the cell and/or supplied in the culture medium is converted to oxycodone (broken arrows represent multiple enzymatic steps). The oxycodone is then 3-O-demethylated to oxymorphone and N-demethylated to noroxymorphone. Finally, an N-methyltransferase accepts allyl and cyclopropylmethyl carbon moieties from SAM analogues to produce naloxone and naltrexone, respectively.

To detect O-demethylase activity in strains producing morphinan alkaloid molecules, cells expressing candidate enzymes, either from plasmid vectors or chromosomally-integrated cassettes, were propagated by fermentation and cell supernatants were collected to analyze the total opioid profile (as described above). O-demethylation of opioid molecules in strains harboring the complete BIA pathway was detected by LC-MS (as described above). Specifically, the conversion of oxycodone to oxymorphone was detected. To detect 0-demethylation activity via biocatalysis, strains were cultured in selective medium and then lysed by glass bead disruption. Cell lysates were supplied exogenously with opioid substrates (see FIG. 6), and other cofactors necessary for enzyme function. O-demethylation of opioid molecules was detected by LC-MS.

Example 8: Microbial Strains Engineered to Produce N-Demethylated Opioid Compounds from Glucose and Simple Nitrogen Sources Enzymes listed in Table 5, that displayed N-demethylase activity on morphinan alkaloids, were incorporated into a microbial strain (either *Saccharomyces cerevisiae* or *Escherichia coli*) which biosynthesizes morphinan alkaloids de novo (as described in Example 6). The complete BIA biosynthetic pathway uses L-tyrosine produced by the host cell and/or supplemented in the culture medium. Two molecules of tyrosine are modified and condensed to form the first benzylisoquinoline structure which may be either norcoclaurine or norlaudanosoline. The benzylisoquinoline is further modified to form (S)-reticuline and then stereochemically inverted by the activity of an epimerase enzyme to yield (R)-reticuline. (R)-reticuline undergoes a carbon-carbon coupling reaction to form the first promorphinan, salutaridine, and is further modified before undergoing an oxygen-carbon coupling reaction catalyzed by a thebaine synthase to arrive at the first morphinan alkaloid structure, thebaine (see FIG. 14). Table 3 lists enzymes and activities in the complete pathway.

To detect N-demethylase activity in strains producing morphinan alkaloid molecules, cells expressing candidate enzymes, either from plasmid vectors or chromosomally-integrated cassettes, were propagated by fermentation and cell supernatants were collected to analyze the total opioid profile (as described above). N-demethylation of opioid molecules in strains harboring the complete BIA pathway was detected by LC-MS (as described above). Specifically, the conversion of oxymorphone to noroxymorphone was detected. To detect N-demethylation activity via biocatalysis, strains were cultured in selective medium and then lysed by glass bead disruption. Cell lysates were supplied exogenously with opioid substrates (see FIG. 7), and other cofactors necessary for enzyme function. N-demethylation of opioid molecules was detected by LC-MS.

Example 9: Microbial Strains Engineered to Produce Nal-Opioid Compounds from Glucose and Simple Nitrogen Sources Enzymes listed in Table 6, that displayed N-methylase activity on morphinan alkaloids, were incorporated into a microbial strain (either *Saccharomyces cerevisiae* or *Escherichia coli*) which biosynthesizes morphinan alkaloids de novo (as described in Example 6). FIG. 10 shows an example of the complete reaction scheme from the precursor molecule thebaine to the final nal-opioid compounds naloxone and naltrexone. These strains additionally express enzymes from Examples 8 and 9 and Table 3, that are responsible for generating nor-opioid compounds from the complete BIA pathway. N-methylase enzymes were also expressed in a microbial strain (either Cen.PK2 for *S. cerevisiae* or BL21 for *E. coli*, for example) lacking the biosynthetic pathway, to generate a strain that is capable of biocatalysis of several different exogenously-supplied substrate molecules. The complete BIA biosynthetic pathway uses tyrosine produced by the host cell and/or supplemented in the culture medium. Two molecules of tyrosine are modified and condensed to form the first benzylisoquinoline structure which may be either norcoclaurine or norlaudanosoline. The benzylisoquinoline is further modified to form (S)-reticuline and then stereochemically inverted by the activity of an epimerase enzyme to yield (R)-reticuline. (R)-reticuline undergoes a carbon-carbon coupling reaction to form the first promorphinan, salutaridine, and is further modified before undergoing an oxygen-carbon coupling reaction catalyzed by a thebaine synthase to arrive at the first morphinan alkaloid structure, thebaine (see FIG. 14). Table 3 lists enzymes and activities in the complete pathway.

To detect N-modifying activity in strains with the complete BIA pathway to nor-opioids (see FIG. 10), cells expressing candidate enzymes were propagated by fermentation (as described above) and incubated with SAM or SAM analogs, such as those listed in FIG. 8. Enzymatic modification of nor-opioid or other BIA molecules in strains harboring the complete BIA pathway was detected in supernatants by LC-MS (as described above). To detect N-modifying activity via biocatalysis, strains were cultured in selective medium and then lysed by glass bead disruption. Cell lysates were supplied exogenously with SAM or SAM analogs, and other cofactors necessary for enzyme function. Specifically, the conversion of noroxymorphone to naloxone and naltrexone (using the SAM analogs allyl-SAM or cyclopropane-SAM, as shown in FIG. 8) was detected. Modification of nor-opioid or other BIA molecules was detected by LC-MS. To detect N-modifying activity by biocatalysis in a strain that does not have the complete BIA pathway, Cen.PK2 strains expressing the described heterologous enzymes were grown in selective medium and lysed by glass bead disruption. Cell lysates were supplied exogenously with SAM or SAM analogs, cofactors necessary for enzyme function, and nor-opioid molecules such as those listed in FIG. 8 and Table 3. Modification of these compounds was detected by LC-MS.

TABLE 3

Enzyme list

| Enzyme | Abbrev | Catalyzed Reactions | Source organisms | Genbank # |
|---|---|---|---|---|
| 3-deoxy-d-arabinose-heptulosonate-7-phosphate synthase | ARO4, DHAP synthase | erythrose-4-phosphate + PEP → DHAP (EC 2.5.1.54) | Saccharomyces cerevisiae | CAA85212.1 |
| Chorismate mutase | ARO7 | chorismate → prephenate (EC 5.4.99.5) | Saccharomyces cerevisiae | NP_015385.1 |
| Phenylpyruvate decarboxylase | ARO10 | hydroxyphenylpyruvate → 4HPA (EC 4.1.1.80) | Saccharomyces cerevisiae | NP_010668.3 |
| Aromatic aminotransferase | ARO9 | hydroxyphenylpyruvate + L-alanine ↔ tyrosine + pyruvate (EC 2.6.1.58) | Saccharomyces cerevisiae | AEC14313.1 |
| Aromatic aminotransferase | ARO8 | hydroxyphenylpyruvate + glutamate ↔ tyrosine + alpha-ketogluterate (EC 2.6.1.5) | Saccharomyces cerevisiae | KZV11.027.1 |
| Transketolase | TKL1 | fructose-6-phosphate + glyceraldehyde-3-phosphate↔ xylulose-5-phosphate + erythrose-4-phosphate (EC 2.2.1.1) | Saccharomyces cerevisiae | NP_015399.1 |
| Glucose-6-phosphate dehydrogenase | ZWF1 | glucose-6-phosphate → 6-phosphogluconolactone (EC 1.1.1.49) | Saccharomyces cerevisiae | CAA96146.1 |
| Prephenate dehydrogenase | TYR1 | prephenate + $NADP^+$ → 4-hydroxyphenylpyruvate + $CO_2$ + NADPH (EC1.3.1.13) | Saccharomyces cerevisiae | CAA85127.1 |
| Alcohol dehydrogenase | ADH2-7, SFA1 | 4HPA → tyrosol (EC 1.1.1.90) | Saccharomyces cerevisiae | NP_014032.1, AAT93007.1, NP_011258.2, NP_009703.3, NP_014051.3, NP_010030.1, NP_010113.1 |
| Aldehyde oxidase | ALD2-6 | 4HPA → hydroxyphenylacetic acid (EC 1.2.1.39) | Saccharomyces cerevisiae | NP_013893.1, NP_013892.1, NP_015019.1, NP_010996.2, NP_015264.1 |
| Tyrosinase | TYR | tyrosine → L-DOPA, L-DOPA → dopaquinone (EC 1.14.18.1) | Ralstonia solonacearum, Agaricus bisporus | NP_518458.1, AJ223816, |
| Tyrosine hydroxylase | TyrH | tyrosine → L-DOPA (EC 1.14.16.2) | Homo sapiens, Rattus norvegicus, Mus musculus | NM 012740, NM 000240, |
| GTP cyclohydrolase | FOL2 | GTP → dihydroneopterin triphosphate (EC 3.5.4.16) | Saccharomyces cerevisiae, Homo sapiens, Mus musculus | CAA97297.1, NP_001019195.1, NP_032128.1 |
| 6-pyruvoyl tetrahydrobiopterin (PTP) synthase | PTPS | dihydroneopterin triphosphate → PTP (EC 4.2.3.12) | Rattus norvegicus, Homo sapiens, Mus musculus | AAH59140.1, BAA04224.1, AAH29013.1 |

TABLE 3-continued

Enzyme list

| Enzyme | Abbrev | Catalyzed Reactions | Source organisms | Genbank # |
|---|---|---|---|---|
| Sepiapterin reductase | SepR | PTP → BH4 (EC 1.1.1.153) | Rattus norvegicus, Homo sapiens, Mus musculus | NP_062054.1, NP_003115.1, NP_035597.2 |
| 4a-hydroxytetrahydrobiopterin (pterin-4α-carbinolamine) dehydratase | PCD | 4a-hydroxytetrahydrobiopterin → H2O + quinoiddihydropteridine (EC 4.2.1.96) | Rattus norvegicus, Homo sapiens, Mus musculus | NP_001007602.1, AAB25581.1, NP_079549.1 |
| Quinoid dihydropteridine reductase | QDHPR | quinoiddihydropteridine → BH4 (EC 1.5.1.34) | Rattus norvegicus, Homo sapiens, Mus musculus | AAH72536.1, NP_000311.2, AAH02107.1 |
| L-DOPA decarboxylase | DODC | L-DOPA → dopamine (EC 4.1.1.28) | Pseudomonas putida, Rattus norvegicus | AE015451.1, NP_001257782.1 |
| Tyrosine/DOPA decarboxylase | TYDC | L-DOPA → dopamine (EC 4.1.1.28) | Papaver somniferum | AAA97535.1, CAB56038.1 |
| Monoamine oxidase | MAO | dopamine → 3,4-DHPA (EC 1.4.3.4) | E. coli, Homo sapiens, Micrococcus luteus | 103792, D2367, AB010716.1 |
| Dihydrofolate reductase | DHFR | 7,8-Dihydrobiopterin → 5,6,7,8-Tetrahydrobiopterin (BH4) EC 1.5.1.3 | Rattus norvegicus, Homo sapiens | AF318150.1 |
| Norcoclaurine 6-O-methyltransferase | 6OMT | Norcoclaurine → coclaurine Norlaudanosoline → 3'hydroxycoclaurine EC 2.1.1.128 | P. somniferum T. flovum Coptis japonica* | AY268894 AY610507 D29811 |
| Coclaurine-N-methyltransferase | CNMT | Coclaurine → N-methylcoclaurine 3'hydroxycoclaurine → 3'-hydroxy-N-methylcoclaurine EC 2.1.1.140 | P. somniferum T. flovum Coptis japonica* | AY217336 AY610508 AB061863 |
| 4'-O-methyltransferase | 4'OMT | 3'-hydroxy-N-methylcoclaurine → Reticuline EC 2.1.1.116 | P. somniferum T. flovum Coptis japonica* | AY217333, AY217334 AY610510 D29812 |
| Norcoclaurine synthase | NCS | 4HPA + dopamine → S-norcoclaurine (EC 4.2.1.78) 3,4-DHPA + dopamine → S-norlaudanosoline | Coptis japonica, Papaver somniferum, Papver bracteatum, Thalicitum flavum, Corydalis saxicola | BAF45337.1, ACI45396.1, AC090258.1, AC090247.1, AEB71889.1 |
| Cytochrome P450 80B1 | CYP80B1 | N-methylcoclaurine → 3'-hydroxy-N-methylcoclaurine (EC 1.14.13.71) | P. somniferum, E. californica, T. flavum | AAF61400.1, AAC39453.1, AAU20767.1 |
| Cheilanthifoline synthase | CFS | Scoulerine → cheilanthifoline EC1.14.21.2 | P. somniferum E. californica A. mexicana | GU325749 AB434654 EF451152 |
| Stylopine synthase | STS | Cheilanthifoline → stylopine EC1.14.21.1 | P. somniferum E. californica A. mexicana | GU325750 AB126257 EF451151 |
| Tetrahydroprotoberberine-N-methyltransferase | TNMT | Stylopine → cis-N-methylstylopine EC2.1.1.122 | P. somniferum E. californica P. bracteatum A. mexicana | DQ028579 EU882977 EU882994 HQ116698 |
| Cis-N-methylstylopine 14-hydroxylase | MSH | cis-N-methylstylopine → protopine EC1.14.13.37 | P. somniferum | KC154003 |
| Protopine-6-hydroxylase | P6H | Protopine → 6-hydroxyprotopine EC1.14.13.55 | E. californica P. somniferum | AB598834 AGC92397 |
| Dihydrobenzophenanthridine oxidase | DBOX | Dihydrosanguinarine → sanguinarine EC 1.5.3.12 | P. somniferum | [not in genbank] |

TABLE 3-continued

Enzyme list

| Enzyme | Abbrev | Catalyzed Reactions | Source organisms | Genbank # |
|---|---|---|---|---|
| (S)-tetrahydroprotoberberine oxidase | STOX | (S)-tetrahydroberberine + 2 $O_2$ → berberine + 2 $H_2O_2$<br>EC 1.3.3.8 | Berberis wilsonae, Coptis japonica, Berberis spp, Coptis spp | HQ116697, AB564543 |
| S-adenosyl-L-methionine: (S)-scoulerine 9-O-methyltransferase | S9OMT | S-adenosyl-L-methionine + (S)-scoulerine → S-adenosyl-L-homocysteine + (S)-tetrahydrocolumbamine<br>EC 2.1.1.117 | Thalictrum flavum subsp. glaucum, Coptis japonica, Coptis chinensis, Papaver somniferum, Thalictrum spp, Coptis spp, Papaver spp | AY610512, D29809, EU980450, JN185323 |
| (S)-tetrahydrocolumbamine, NAD PH: oxygen oxidoreductase (methylenedioxy-bridge-forming), also known as (S)-canadine synthase | CAS | (S)-tetrahydrocolumbamine + NADPH + H+ + O2 → (S)-canadine + NADP+ + 2 H2O<br>EC 1.14.21.5 | Thalictrum flavum subsp. glaucum, Coptis japonica, Thalictrum spp, Coptis spp | AY610513, AB026122, AB374407, AB374408 |
| (S)-reticuline: oxygen oxidoreductase (methylene-bridge-forming), also known as berberine bridge enzyme | BBE | (S)-reticuline + O2 → (S)-scoulerine + H2O2<br>EC 1.21.3.3 | Papaver somniferum, Argemone mexicana, Eschscholzia californica, Berberis stolonifera, Thalictrum flavum subsp. glaucum, Coptis japonica, Papaver spp, Eschscholzia spp, Berberis spp, Thalictrum spp, Coptis spp | AF025430, EU881889, EU881890, S65550 AF005655, AF049347, AY610511, AB747097 |
| NADPH: hemoprotein oxidoreductase, also known as cytochrome P450 reductase | ATR1, CPR | NADPH + H+ + n oxidized hemoprotein → NADP+ + n reduced hemoprotein<br>EC 1.6.2.4 | Arabidopsis thaliana, Eschscholzia californica, Papaver somniferum, Homo sapiens, Saccharomyces cerevisiae, Papaver bracteatum, Papaver spp, all plants | CAB58576.1, CAB58575.1, AAC05021.1, AAC05022.1, NM118585, many others (Ref PMID 19931102) |
| salutaridinol: NADP+ 7-oxidoreductase, also known as salutaridine reductase | SalR | salutaridinol + NADP+ → salutaridine + NADPH + H+<br>EC 1.1.1.248 | Papaver somniferum, Papaver bracteatum, Papaver spp Chelidonium majus | DQ316261, EF184229 (Ref PMID 22424601) |
| acetyl-CoA: salutaridinol 7-O-acetyltransferase, also known as salutaridinol 7-O-acetyltransferase | SalAT | acetyl-CoA + salutaridinol → CoA + 7-O-acetylsalutaridinol<br>EC 2.3.1.150 | Papaver somniferum, Papaver bracteatum, Papaver orientale, Papaver spp | AF339913, FJ200355, FJ200358, FJ200356, JQ659008 |
| thebaine synthase | TS | 7-O-acetylsalutaridinol → thebaine + acetate | Papaver somniferum, Papaver bracteatum, Papaver orientale, Papaver spp | [not in genebank] |

TABLE 3-continued

Enzyme list

| Enzyme | Abbrev | Catalyzed Reactions | Source organisms | Genbank # |
|---|---|---|---|---|
| (R)-reticuline, NADPH: oxygen oxidoreductase (C—C phenol-coupling), also known as salutaridine synthase | SalSyn | (R)-reticuline + NADPH + H+ + O2 → salutaridine + NADP+ + 2 H2O EC 1.14.21.4 | *Papaver somniferum*, *Papaver* spp *Chelidonium majus* | EF451150 (Ref PMID 22424601) |
| 1-benzylisoquinoline alkaloid epimerase (cytochrome P450 82Y1-like codeinone reductase-like) | DRS-DRR (or CYP-COR) | (S)-reticuline -> (R)-reticuline (S)-1-benzylisoquinoline -> (R)-1-benzylisoquinoline EC 1.5.1.27 | *Papaver bracteatum*, *Papaver somniferum*, *Papaver setigerum*, *Chelidonium majus* | P0DKI7.1, AK060175.1, AK060180.1, AK060179.1, AK060175.1 |
| Cytochrome P450, family 2, subfamily D, polypeptide 6 | CYP2D6 | Promiscuous oxidase, can perform (R)-reticuline + NADPH + H+ + O2 → salutaridine + NADP+ + 2 H2O among other reactions EC 1.14.14.1 | *Homo sapiens* | BC067432 |
| Thebaine 6-O demethylase | T6ODM | thebaine → neopinone EC 1.14.11.31 | *Papaver somniferum*, *Papaver* spp. | GQ500139.1 |
| Codeinone reductase | COR | codeinone → codeine EC 1.1.1.247, neopinone → neopine | *Papaver somniferum*, *Papaver* spp. | AF108432.1 AF108433.1 AF108434.1 AF108435.1 |
| Codeine O-demethylase | CODM | codeine → morphine EC 1.14.11.32, neopine → neomorphine | *Papaver somniferum*, *Papaver* spp. | GQ500141.1 |
| Morphine dehydrogenase | morA | morphine → morphinone EC 1.1.1.218, codeinone → codeine EC 1.1.1.247 | *Pseudomonas putida* | M94775.1 |
| Morphinone reductase | morB | codeinone → hydrocodone morphinone → hydromorphone EC 1.3.1.- | *Pseudomonas putida* | U37350.1 |
| Reticuline N-methyltransferase | RNMT | reticuline → tembetarine | *Papaver somniferum*, *Papaver* spp. | KX369612.1 |
| Papaverine 7-O-demethylase | P7OMT | papaverine → pacodine | *Papaver somniferum*, *Papaver* spp. | KT159979.1 |
| 3-O-demethylase | 3ODM | oxycodone → oxymorphone hydrocodone → hydromorphone dihydrocodeine → dihydromorphine 14-hydroxycodeine → 14-hydroxymorphine codeinone-morphinone 14-hydroxycodeinone → 14-hydroxymorphinone | *Papaver somniferum*, *Papaver bracteatum*, *Papaver rhoeas*, *Papaver* spp. | |
| N-demethylase | NDM | Codeine → Norcodeine Morphine→Normorphine Oxycodone → Noroxycodone Oxymorphone → Noroxymorphone Thebaine → Northebaine Oripavine → Nororipavine Hydrocodone → Norhydrocodone Hydromorphone → Norhydromorphone Dihydrocodeine → Nordihydrocodeine | *Bacillus megaterium*, *Homo sapiens*, *Papaver somniferum*, *Papaver* spp., *Chelidonium majus*, *Stylophorum diphyllum*, *Nigella sativa*, *Hydrastis canadensis*, | |

TABLE 3-continued

Enzyme list

| Enzyme | Abbrev | Catalyzed Reactions | Source organisms | Genbank # |
|---|---|---|---|---|
| | | Dihydromorphine → Nordihydromorphine<br>14-hydroxycodeine → Nor-14-hydroxycodeine<br>14-hydroxymorphine → Nor-14-hydroxymorphine<br>Codeinone → Norcodeinone<br>Morphinone → Normorphinone<br>14-hydroxycodeinone → Nor-14-hydroxycodeinone<br>14-hydroxymorphinone → Nor-14-hydroxymorphinone | *Glaucium flavum, Eschscholzia californica, Menispermum canadense, Papaver bracteatum* | |
| N-methyltransferase | NMT | Norcodeine → codeine<br>Normorphine → morphine<br>Noroxycodone → oxycodone<br>Noroxymorphone → noroxymorphone<br>Northebaine → thebaine<br>Nororipavine → oripavine<br>Norhydrocodone → hydrocodone<br>Norhydromorphone → Hydromorphone<br>Nordihydrocodeine → Dihydrocodeine<br>Nordihydromorphine → Dihydromorphine<br>Nor-14-hydroxycodeine → 14-hydroxycodeine<br>Nor-14-hydroxymorphine → 14-hydroxymorphine<br>Norcodeineone → Codeineone<br>Normorphinone → Morphinone<br>Nor-14-hydroxy-codeinone → 14-hydroxycodeinone<br>Nor-14-hydroxy-morphinone → 14-hydroxymorphinone | *Papaver* spp., *Chelidonium majus, Thalictrum flavum, Coptis japonica, Papaver somniferum, Eschscholzia californica, Papaver bracteatum, Argenome mexicana, Glaucium flavum, Sanguinaria canadensis, Corydalis chelanthifolia, Nigella saliva, Jeffersonia diphylla, Berberis thunbergii, Mahonia aquifolium, Menispermum canadense, Tinospora cordifolia, Cissampelos mucronata, Cocculus trilobus* | |
| N-allyltransferase | NAT | Norcodeine → N-allyl-norcodeine<br>Normorphine → N-allyl-normorphine<br>Noroxycodone → N-allyl-noroxycodone<br>Noroxymorphone → N-allyl-nornoroxymorphone<br>Northebaine → N-allyl-northebaine<br>Nororipavine → N-allyl-nororipavine<br>Norhydrocodone → N-allyl-norhydrocodone<br>Norhydromorphone → N-allyl-norhydromorphone<br>Nordihydrocodeine → N-allyl-nordihydrocodeine<br>Nordihydromorphine- N-allyl-nordihydromorphine<br>Nor-14-hydroxycodeine → N-allyl-nor-14-hydroxycodeine<br>Nor-14-hydroxymorphine → N-allyl-nor-14-hydroxymorphine | *Papaver* spp., *Chelidonium majus, Thalictrum flavum, Coptis japonica, Papaver somniferum, Eschscholzia californica, Papaver bracteatum, Argenome mexicana, Glaucium flavum, Sanguinaria canadensis, Corydalis chelanthifolia, Nigella sativa, Jeffersonia diphylla, Berberis thunbergii, Mahonia* | |

TABLE 3-continued

Enzyme list

| Enzyme | Abbrev | Catalyzed Reactions | Source organisms | Genbank # |
|---|---|---|---|---|
| | | Norcodeineone → N-allyl-norcodeineone<br>Normorphinone → N-allyl-normorphinone<br>Nor-14-hydroxy-codeinone → N-allyl-nor-14-hydroxycodeinone<br>Nor-14-hydroxy-morphinone → N-allyl-nor-14-hydroxymorphinone | *aquifolium,*<br>*Menispermum*<br>*canadense,*<br>*Tinospora*<br>*cordifolia,*<br>*Cissampelos*<br>*mucronata,*<br>*Cocculus trilobus* | |
| N-cyclopropylmethyltransferase | NCPMT | Norcodeine-N-(Cyclopropylmethyl) norcodeine<br>Normorphine-N-(Cyclopropylmethyl) normorphine<br>Noroxycodone → N-(Cyclopropylmethyl) noroxycodone<br>Noroxymorphone → N-(Cyclopropylmethyl) nornoroxymorphone<br>Northebaine → N-(Cyclopropylmethyl) northebaine<br>Nororipavine → N-(Cyclopropylmethyl) nororipavine<br>Norhydrocodone → N-(Cyclopropylmethyl) norhydrocodone<br>Nordihydrocodeine → N-(Cyclopropylmethyl) nordihydrocodeine<br>Nordihydromorphine-N-(Cyclopropylmethyl) nordihydromorphine<br>Nor-14-hydroxycodeine → N-(Cyclopropylmethyl) nor-14-hydroxycodeine<br>Nor-14-hydroxymorphine → N-(Cyclopropylmethyl) nor-14-hydroxymorphine<br>Norcodeineone → N-(Cyclopropylmethyl) norcodeineone<br>Normorphinone → N-(Cyclopropylmethyl) normorphinone<br>Nor-14-hydroxy-codeinone → N-(Cyclopropylmethyl) nor-14-hydroxycodeinone<br>Nor-14-hydroxy-morphinone → N-(Cyclopropylmethyl) nor-14-hydroxymorphinone | *Papaver* spp.,<br>*Chelidonium*<br>*majus,*<br>*Thalictrum*<br>*flavum, Coptis*<br>*japonica,*<br>*Papaver*<br>*somniferum,*<br>*Eschscholzia*<br>*californica,*<br>*Papaver*<br>*bracteatum,*<br>*Argenome*<br>*mexicana,*<br>*Glaucium*<br>*flavum,*<br>*Sanguinaria*<br>*canadensis,*<br>*Corydalis*<br>*chelanthifolia,*<br>*Nigella sativa,*<br>*Jeffersonia*<br>*diphylla,*<br>*Berberis*<br>*thunbergii,*<br>*Mahonia*<br>*aquifolium,*<br>*Menispermum*<br>*canadense,*<br>*Tinospora*<br>*cordifolia,*<br>*Cissampelos*<br>*mucronata,*<br>*Cocculus trilobus* | |

TABLE 4

O-demethylase candidate enzymes

| Name | Sequence |
|---|---|
| T6ODM | MEKAKLMKLGNGMEIPSVQELAKLTLAEIPSRYVCANENLLLPMGASVINDHETIPVIDIE<br>NLLSPEPIIGKLELDRLHFACKEWGFFQVVNHGVDASLVDSVKSEIQGFFNLSMDEKTKY<br>EQEDGDVEGFGQGFIESEDQTLDWADIFMMFTLPLHLRKPHLFSKLPVPLRETIESYSSEM<br>KKLSMVLFNKMEKALQVQAAEIKGMSEVFIDGTQAMRMNYYPPCPQPNLAIGLTSHSDF |

TABLE 4-continued

O-demethylase candidate enzymes

| Name | Sequence |
|---|---|
| | GGLTILLQINEVEGLQIKREGTWISVKPLPNAFVVNVGDILEIMTNGIYHSVDHRAVVNST<br>NERLSIATFHDPSLESVIGPISSLITPETPALFKSGSTYGDLVEECKTRKLDGKSFLDSMRI |
| CODM | METPILIKLGNGLSIPSVQELAKLTLAEIPSRYTCTGESPLNNIGASVTDDETVPVIDLQNLL<br>SPEPVVGKLELDKLHSACKEWGFFQLVNHGVDALLMDNIKSEIKGFFNLPMNEKTKYGQ<br>QDGDFEGFGQPYIESEDQRLDWTEVFSMLSLPLHLRKPHLFPELPLPFRETLESYLSKMKK<br>LSTVVFEMLEKSLQLVEIKGMTDLFEDGLQTMRMNYYPPCPRPELVLGLTSHSDFSGLTIL<br>LQLNEVEGLQIRKEERWISIKPLPDAFIVNVGDILEIMTNGIYRSVEHRAVVNSTKERLSIA<br>TFHDSKLESEIGPISSLVTPETPALFKRGRYEDILKENLSRKLDGKSFLDYMRM |
| PsP7ODM | MEKAKLMKLGNGLSIPSVQELAELTFAEVPSRYVCTNDENLLLMTMGASEIDDETVPVID<br>LQNLLSPEPAIGKSELDWLHYSCKEWGFFQLVNHGVDALLVDHVKSEIHSFFNLPLNEKT<br>KYGQRDGDVEGFGQAFLVSENQKLDWADMFFINTLPLHLRKPHLFPNLPLPLRETIESYSS<br>EMKKLSMVLFEMMGKAIEVIDIKEAITEMFEDGMQSMRMNYYPPCPQPERVIGITPHSDF<br>DGLTILLQLNEVEGLQIRKEDKWISIKPLPDAFIVNVGDIWEIMTNGVHRSVDHRGVINST<br>KERLSIATFHSPKLELEIGPISSLIRPETPAVFKSAGRFEDLLKEGLSRKLDGKSFLDCMRM |
| PsoDIOX1 | MEKAKLMKLGNGMEIPSVQELAKLTLAEIPSRYVCANENLLLPMGASVINDHETIPVIDIE<br>NLLSPEPIIGKLELDRLHFACKEWGFFQVVNHGVDASLVDSVKSEIQGFFNLSMDEKTKY<br>EQEDGDVEGFGQGFIESEDQTLDWADIFMMFTLPLHLRKPHLFSKLPVPLRETIESYSSEM<br>KKLSMVLFNKMEKALQVQAAEIKGMSEVFIDGTQAMRMNYYPPCPQPNLAIGLTSHSDF<br>GGLTILLQINEVEGLQIKREGTWISVKPLPNAFVVNVGDILEIMTNGIYHSVD |
| PsoDIOX2 | METAKLMKLGNGMSIPSVQELAKLTLAEIPSRYICTVENLQLPVGASVIDDHETVPVIDIE<br>NLISSEPVIEKLELDRLHSACKEWGFFQVVNHGVDTSLVDNVKSDIQGFFNLSMNEKIKY<br>GQKDGDVEGFGQAFVASEDQTLDWADIFMILTLPLHLRKPHLFSKLPLPLRETIESYSSEM<br>KKLSMVLFEKMEKALQVQAVEIKEISEVFKDMTQVMRMNYYPPCPQPELAIGLTPHSDF<br>GGLTILLQLNEVEGLQIKNEGRWISVKPLPNAFVVNVGDVLEIMTNGMYRSVDHRAVVN<br>STKERLSIATFHDPNLESEIGPISSLITPNTPALFRSGSTYGELVEEFHSRKLDGKSFLDSRM<br>M |
| PbrDIOX2 | METPKSIKLGGSLLVPSVQELAQQSFAEVPARYVRDDLEPLTDLSGVSMIDQTIPVIDLQK<br>LQSPVPIIRELESEKLHSACKEWGFFQVVNHGVDILLVEKTKSEIKDFFNLPMDEKKKFWQ<br>EEGDIQGFGQAFVQSEDQKLDWADIFLMVTLPRHTRNPRLFPKLPLPLRNTMDSYSSKLS<br>KLASTLIEMMGKALHMETSVLAELFEDGRQTMRINYYPPCPQPKDVIGLTPHSDGGGLTI<br>LLQLNEVDGLQIRKEKIWIPIKPLPNAFVVNIGNILEIMTNGIYRSVEHRATIHSTKERLSVA<br>AFHNPKVGVEIGPIVSMITPESPALFRTIEYDDYGKKYFSRKLDGKSSLDFMRIGEGDEEN<br>KAT |
| PbrDIOX3 | METPKLIKLGGSLLVPSVLELTKQSPAEVPARYIRNDLEPMTDLSSASLTDQTIPVIDLQNL<br>LSPEPELELEKLHSGCKEWGFFQVMNHGVDILLVEKVKSEIQGFFNLPIDEKNKFWQEEG<br>DLEGYGKAFVHSEDEKLDWADMFFILTQPQYMRKPRVFPKLPLRLRETIESYSLELSKLG<br>LTLLLDLMGKALQIETGVMSELFEDGRQTMRMNYYPPCPQPEHVIGLTPHSDGGALTILLQ<br>LNQVDGLQIRKEEIWVPIKPLPNAFVVNIGDILEIMSNGVYRSVEHRATINSSKERLSVAIF<br>QSPKHGTEIGPILSMITPEAPALFKTIPYEDYLRKFFSRKLGGKSFVDSMRIGESDEDNNTA |
| PbrDIOX4 | METQKQENFGASLSVPNVQELAKQSPEQVPDRYIRSDQDSSTNISCPSMTDQIPVIDLQSL<br>LSPDPIIGELELERLHSACKEWGFFQVVNHGVDNLLVEKVKSEIQGFFNLPMDEKKKFWQ<br>EEGDFEGFGQAFVFSEDQKLDWGDVFFILTQPQHMRKPRLFPKLPLPFRKTIESYSLETNK<br>LSMTLLELMEKALKIETGVMTELFEGGIQRMRMTYYPPCPQPKHVIGLTPHSDPDALTILL<br>QLNEVDGLQIRKEKIWVPIKPLSNAFVVNIGDILEIMSNGIYRSVEHRATVNSTKERLSVAT<br>FHSPRKDTEIGPILITPETPALFRTSGFEDYFRKFFAHKLNGKSFLSSIRIGETDEGNNAT |
| PbrDIOX5 | MEAPKLIMLGGSLFVPSVQELAKQSLAEVPVRYVRDDQDTLGNNINITPMSMIDQSIPVID<br>LEKLLSPEPIVGELELERLHSACKEWGFFQVVNHGVDSLLVEKVKSEIEGFFKLPMDEKTK<br>FWQEEGDIEGFGQVFVHSQDQKLDWGDMFLMQTLPRHTRKPRLFPNLPLPLRQTIESYSS<br>ELSKLVLTLVDLMGKALQMESGVLIELFENGIQRMRMNYYPPCPQPEQVIGLTPHSDVG<br>GLTILLQLNEVDGLQIKKDKVWVPIKPLANAFVVNVGDALEIMSNGIYRSVEHRATINST<br>KERLSIATFHNPRADREIGPIPSMISPETPALFKTTGYEEYFKKFFSRKLEGKSFLDSLRIREG<br>DEHCGRLDVKGPCN |
| PbrDIOX6 | MEIPNPIKIGSSLLVPSVQELAKQSFAEVPARYIRNDVDPLITKLSDVSLIDQTVPVIDLQKL<br>LSPEPIVGELELERLHSACKEWGFFQVVNHGVDNLLVEKVKSEIQGFFNLPMEEKKKFWQ<br>EEGDFEGFGQMFVQSEEQKLDWGDMFFILTQPQHMRKPRLFSKLPLPLRETIESYSLELIK<br>LGLTIIKLMEKALQIDAGVMAELFEDGIHTMRMNYYPPCPQPEHVIGLTPHSDGGGLTILL<br>QLNEVDGLQIRRENIWVPIKPLPNAFVVNIGDILEILSNGIYRSVEHRSTVNATKERLSVAT<br>FQNPKQESVIGPNMITPERPALFRKIVYKDYMKKLFSRKLDGKSFLDSLRIGEGDERP |
| PbrDIOX8 | METLKTVKPGGSLFIPNGQELAKQSLEEVYVGNDQDTMLLIGQTIPVIDLQKLLSPEPITG<br>DMELDKLHSACKEWGFFQVVNHGVDILLVEKVKSEVHDFFNIPMDEKKPFWQEEGDLE<br>GFGQVFITSEDQQLDWGDMFFMVTLPKHMRKPRLFLKLPLPLRETIESYSLKLSKLGVTL<br>VELMGKALQMEDRIMSELFDDGRQTMRMNYYPPCPQPEQVIGLTPHSDPGGLTILLELNE<br>VNGLIRKENIWPIIPLPNAFIVNIGDILEIMSNGIYHSVEHRATINSTKERLSVAMFNSPKV<br>DTEIGPIHSMITPETPALFRTIGYDEYLKIFFSRKLDGKSLLESMKI |

TABLE 4-continued

O-demethylase candidate enzymes

| Name | Sequence |
|---|---|
| PbrDIOX10 | MEAPKLIMLGGSLFVPSVQELAKQSLAEVPVRYVRDDQDTLGNNINITPMSMIDQSIPVID LEKLLSPEPIVGELELERLHSACKEWGFFQVVNHGVDSLLVEKVKSEIEGFFELPVDEKKK FWQEEGDIEGFGQIFVHSEDQKLDWADMFYMLTLPPNMRKPRLFPNLPLPLRQTIDSYSS ELSKLVLTLVDLMGKALQMESGVLTELFENGIQRMRMNYYPPCPQPEQVIGLTPHSDVG GLTILLQLNEVDGLQIKKDKIWVPIKPLRNAFVVNVGDALEIMSNGIYRSVEHRATINSTK ERLSIATFHNPRADREIGPIPSMISPETPALFKTTGYEEYFKKFFSRKLEGKSFLDSLRIGEG DEHCGRLXVKGXCN |
| PbrDIOX11 | METPKLMKLGGSLFVPSVQELAKQSLAEVPARYVRDDRDMVGNIINVTPMSMIDQSIPVI DLEKLLSPDLIVGELELERLHSACKEWGFFQVVNHGVDSLLVEKVKSEIEGFFELPMDEK KKFWQEEGDAEGFAQFFVQSEDQKLDYSGDMFFMLNLPQHMRKPRLFLKLPLPLRETIES YSLKLSKLGVTLVELMGKALQMEDRIMSELFDDGRQTMRMNYYPPCPQPEQVIGLTPHS DPGGLTILLELNEVNGLIRKENIWVPIIPLPNAFIVNIGDILEIMSNGIYHSVEHRATINSTKE RLSVAMFNSPKVDTEIGPIHSMITPETPALFRTIGYDEYLKIFFSRKLDGKSLLESMKI |
| PbrDIOX13 | METPKLRDFGSFLPVPSVQELAKQVLTEIPPRYIRTDLEALNKLSCASNTDQTVPIIDMQCL LSAEPEMELEKLHSACKEWGFFPRVMVNHGVDNLESVKSEIESFLNLPVNAKNKYGQKQGD DQGFGSRFVLSEEQKLDWGDFFYMVTRPLYLRKPHLFPELPLPLRETIESYSSEVSKLAMA LFEMMGKALKIETGVMTEIFEGGMQAMRMNYYPPCPRPDLVIGLNAHSDFGGLTILLQL NEVEGLEIRNKGEWVSVKPLANAFVVNVGDVMEILTNGIYHSVEHRATINSSKERLSVAT FHYPKLETGIGPLPCMITPKTPALFGRIERYELLLRKYYARKLNGKSTLDCMRIGNGFEDD NTA |
| PbrDIOX18 | MEAPKLIMLGGSLFVPSVQELAKQSLAEVPARYVRDDQDTLGNNINITPMSMIDQSIPVID LEKLLSPEPIVGELELERLHSACKEWGFFQVVNHGVDSLLVEKVKSEIEGFFELPVDEKKK FWQEEGDIEGFGQIFVHSEDQKLDWADMFYMLTLPPNMRKPRLFPNLPLPLRQTIDSYSS ELSKLVLTLVDLMGKALQMESGVLTELFENGIQRMRMNYYPPCPQPEQVIGLTPHSEVG GLTILLQLNEVDGLQIRKEKIWVPIKPLSNAFIVNIGDILEIMSNGIYRSVEHRATVNSTKER LSVATFHSPRKDTEIGPILITPETPALFRTSGFEDYFRKFFAHKLNGKSFLSSIRIGETDEGNN AT |
| PbrDIOX19 | MSMIDQSIPVIDLEKLLSPEPIVGELELERLHSACKEWGFFQVVNHGVDSLLVEKVKSEIE GFFELPVDEKKKFWQEEGDIEGFGQIFVHSEDQKLDWADMFYMLTLPPNMRKPRLFPNL PLPLRQTIDSYSSELSKLVLTLVDLMGKALQMESGVLTELFENGIQRMRMNYYPPCPQPE QVIGLTPHSDVGGLTILLQLNEVDGLQIRKEKIWVPIKPLSNAFIVNIGDILEIMSNGIYHSV EHRATINSTKERLSVAMFNSPKVDTEIGPIHSMITPETPALFRTIGYDEYLKIFFSRKLDGKS LLESMKI |
| PbrDIOX21 | METPKLVKSSGSSLFLSTSVQELAKQSLPEVPARYIRTNLEPLSNVGDSQSVPIDLQKLL SSEPIIGELELDKLHSACKEWGFFQVVNHGVDNLVMEKIKTIEIQGFFNLSLDEKQKFWKK EGDAEGFGQNFIESEDQKLDWGDTFGMFTLPIHMRNPRLFPELPLPLRETIESYSLDVRKL ALALIGLMEKALKIKTSAMSELFEDGGQAMRMNYYPPCPQPEHVIGLTPHSDAGGLTILL QLNEVDGLQIKKDKIWVPIKPLPNAFVVNIGDILEIMTNGIYRSVEHRATINSSKERLSVAA FHSPKGDTLIGPMVSLITPETPALFRTIGYQDYMKKFMSRKLDGKSLVNSMRIGEGDEDK |
| PbrDIOX-ZSNV-2004018 | METPTLMKLGNGLSVPSVQELAKATLAEIPSRYICTDENLLTMGASTTDNETVPVIDLQNL LSPEPVIGMLELDRLHSACKEWGFFQLVNHGVDALLVDNEVQGFFNLPMDEKTKYGQK DGDDEGFGQFFVISEDQKLDWADVFYMSTLPLHSRKPHLFPELPLPLRETMESYSSEMKK LSMVLFDMMGKALQVVEIKGITELFEDGAQQIRMNYYPPCPQPELVFGLTSHSDFDGLTI LLQLGEVEGLQIKKEERWISIKPLPDAFIVNVGDILEIMTNGIYRSVDHRAVVNSIKERLTIA TFHDPRLEAEIGPISSLITPETPALFKRGVFEDLLKEMFLRKLDGKSFLDCMRM |
| PrhDIOX-MVTX-2001522 | GNGLSVPSVQELAKQTLAEIPSRYICTDENPLITGASVVDDETVPVINLQNLLSPEPVIGKL ELDKLHSACKEWGFFQVVNHGVNDSLVDSVKSEIEGFFNLPANEKLKYGQKDGDVEGFG QHFVVSEDQKLDWADVFYMVTLPVRLRKPHLFPELPLPLRDTLDSYSSELNKLSMVLLE MMEKALKLVECKGITDFFEDGQQMRMNYYPPCPRPELVTGLTSHSDFGGLTILLQLND VEGLQIKKEERWISIKPLPNAFIVNIGDVLEIMSNGIYRSVDHRAVINSTKVRMSVATFHDP RLEAVIGPISSLITPETPALFKRGVFEDLLKEMFLRKLDGKSFLDCMRI |
| PseDIOX-JSVC-2005842 | LMKLANGMSVPIVQELAKLTVGEIPSRYICTDGNLLTMGASVIDYETVPVIDLQNLQSREP VIEKLELDRLHSACKEWGFFQLLNHGVDASLMDNVRSEIRGFFNLPISDKMKYGQKDGD EEGFGQHFIVSEDQKLDWVDAFMMFTLPLHSRNPRLTPEFPQPLRETVESYSSEMKKLSV LLFELMEKALQVKGITEMFEDGLQSIRMNYYPPCPRPELAIGLTSHSDFDGLTILLQLNEV EGLQIKKEERWISIKPLPNAFIVNVGDVLEVMTNGIYRSVDHRAVVNSTKERLSIATFHDP ELESEIGPIASLITPETPALFKRGRFKDLLKENLSTKLDGKSFLDCIRM |
| CYP2D6 | MGLEALVPLAVIVAIFLLLVDLMHRRQRWAARYSPGPLPLPGLGNLLHVDFQNTPYCFD QLRRRFGDVFSLQLAWTPVVVLNGLAAVREALVTHGEDTADRPPVPITQILGFGPRSQGV FLARYGPAWREQRRFSVSTLRNLGLGKKSLEQWVTEEAACLCAAFANHSGRPFRPNGLL DKAVSNVIASLTCGRRFEYDDPRFLRLLDLAQEGLKEESGFLREVLNAVPVLLHIPALAG KVLRFQKAFLTQLDELLTEHRMTWDPAQPPRDLTEAFLAEMEKAKGNPESSFNDENLRIV VADLFSAGMVTTSTTLAWGLLLMILHPDVQRRVQQEIDDVIGQVRRPEMGDQAHMPYT TAVIHEVQRFGDIVPLGVTHMTSRDIEVQGFRIPKGTTLITNLSSVLKDEAVWEKPPRFHPE HFLDAQGHFVKPEAFLPFSAGRRACLGEPLARMELFLFFTSLLQHFSFSVPTGQPRSHHG VFAFLVTPSPYELCAVPR |

TABLE 5

N-demethylase candidate enzymes

| Name | Sequence |
|---|---|
| BM3 | MTIKEMPQPKTFGELKNLPLLNTDKPVQALMKIADELGEIFKFEAPGRVTRYLSSQRLI<br>KEACDESRFDKNLSQAAKFARDFAGDGLVTSWTHEKNWKKAHNILLPSFSQQAMKG<br>YHAMMVDIAVQLVQKWERLNADEHIEVSEDMTRLTLDTIGLCGFNYRFNSFYRDQPH<br>PFIISMVRAADEVMNKLQRANPDDPAYDENKRQFQEDIKVMNDLVDKIIADRKARGEQ<br>SDDLLTQMLNGKDPETGEPLDDGNIRYQIITFLIAGHETTSGLLSFALYFLVKNPHVLQK<br>VAEEAARVLVDPVPSYKQVKQLKYVGMVLNEALRLWPTAPAFSLYAKEDTVLGGEY<br>PLEKGDEVMVLIPQLHRDKTVWGDDVEEFRPERFENPSAIPQHAFKPFGNGQRACIGQ<br>QFALHEATLVLGMMLKHFDFEDHTNYELDIKETLTLKPKGFVVKAKSKKIPLGGIPSPS<br>TEQSAKKVRKKAENAHNTPLLVLYGSNMGTAEGTARDLADIAMSKGFAPQVATLDSH<br>AGNLPREGAVLIVTASYNGHPPDNAKQFVDWLDQASADEVKGVRYSVFGCGDKNWA<br>TTYQKVPAFIDETLAAKGAENIADRGEADASDDFEGTYEEWREHMWSDVAAYFNLDI<br>ENSEDNKSTLSLQFVDSAADMPLAKMHGAFSTNVVASKELQQPGSARSTRHLEIELPK<br>EASYQEGDHLGVIPRNYEGIVNRVTARFGLDASQQIRLEAEEEKLAHLPLAKTVSVEEL<br>LQYVELQDPVTRTQLRAMAAKTVCPPHKVELEALLEKQAYKEQVLAKRLTMLELLEK<br>YPACEMKFSEFIALLPSIRPRYYSISSSPRVDEKQASITVSVVSGEAWSGYGEYKGIASN<br>YLAELQEGDTITCFISTPQSEFTLPKDPETPLIMVGPGTGVAPFRGFVQARKQLKEQGQS<br>LGEAHLYFGCRSPHEDYLYQEELENAQSEGIITLHTAFSRMPNQPKTYVQHVMEQDGK<br>KLIELLDQGAHFYICGDGSQMAPAVEATLMKSYADVHQVSEADARLWLQQLEEKGRY<br>AKDVWAG |
| CYP3A4-1 | MALIPDLAMETWLLLAVSLVLLYLYGTHSHGLFKKLGIPGPTPLPFLGNILSYHKGFCM<br>FDMECHKKYGKVWGFYDGQQPVLAITDPDMIKTVLVKECYSVFTNRRPFGPVGFMKS<br>AISIAEDEEWKRLRSLLSPTFTSGKLKEMVPIIAQYGDVLVRNLRREAETGKPVTLKDVF<br>GAYSMDVITSTSFGVNIDSLNNPQDPFVENTKKLLRFDFLDPPFLSITVFPFLIPILEVLNI<br>CVFPREVTNFLRKSVKRMKESRLEDTQKHRVDFLQLMIDSQNSKETESHKALSLDELV<br>AQSIIFIFAGYETTSSVLSFIMYELATHPDVQQKLQEEIDAVLPNKAPPTYDTVLQMEYL<br>DMVVNETLRLFPIAMRLERVCKKDVEINGMFIPKGVVVMIPSYALHRDPKYWTEPEKF<br>LPERFSKKNKDNIDPYIYTPFGSGPRNCIGMRFALMNMKLALIRVLQNFSFKPCKETQIP<br>LKLSLGGLLQPEKPVVLKVESRDGTVSGA |
| CYP3A4-2 | MALIPDLAMETWLLLAVSLVLLYLYGTHSHGLFKKLGIPGPTPLPFLGNILSYHKGFCM<br>FDMECHKKYGKVWGFYDGQQPVLAITDPDMIKTVLVKECYSVFTNRRPFGPVGFMKS<br>AISIAEDEEWKRLRSLLSPTFTSGKLKEMVPIIAQYGDVLVRNLRREAETGKPVTLKDVF<br>GAYSMDVITSTSFGVNIDSLNNPQDPFVENTKKLLRFDFLDPPFLSIIFPFLIPILEVLNICV<br>FPREVTNFLRKSVKRMKESRLEDTQKHRVDFLQLMIDSQNSKETESHKALSDLELVAQ<br>SIIFIFAGYETTSSVLSFIMYELATHPDVQQKLQEEIDAVLPNKAPPTYDTVLQMEYLDM<br>VVNETLRLFPIAMRLERVCKKDVEINGMFIPKGVVVMIPSYALHRDPKYWTEPEKFLPE<br>RFSKKNKDNIDPYIYTPFGSGPRNCIGMRFALMNMKLALIRVLQNFSFKPCKETQIPLKL<br>SLGGLLQPEKPVVLKVESRDGTVSGA |
| McaCYP82-4 | MIMMFIDYYSSWLPQTLLLQSILLAVSLVIFINLFLTRRRSYSSKSHTNIIHPPKAAGALP<br>VIGHLYTLFRGLSAGVPLYRQLDAMADRYGPAFIIHLGVPTLVVTCRELAKECFTTND<br>QTFATRPSTCAGKYIGYNYAFFGFAPYGPYWREARKIATVELLSNYRLDSLRHVREAE<br>VGRNVDELYALHASSSTNKQNMMKIDMKQWFDQVTLNVILMMVVGKRCVTTGGNE<br>EEVRVVKVLHEFFKHLGTLSVSDVVPYVEWMDLDGNIGRMKSTAKELDCILGRWLEE<br>HRRERRSDPMDAMLAMVEGIKIPYYDSDTVIKAICLNLLNAGSDTLGITMTWALSLLL<br>NNRHVLKKVKDELDVHVGKNRQVEELDVKNLVYLHAVVKETLRLFPPAPLGVPHEA<br>MEDCVVGGFHVAKGTRLVVNVWKLHRDPSVWSDPLAFKPERFLDNNTVDVRGQHFQ<br>LLPFGSGRRGCPGITFALQVAHLTLARLLHGFEWDTPDGAPVDMSEVSVLTTAKKNPV<br>EVLFTPRLPAEVYTQN |
| NsaCYP82-4 | MLSIHDSTMVFLQLQAICGIFGFIFIITWWTRWKSSNKMKAPEVAGAWPVIGHLHLLGG<br>GRPLYQLLGDMSDKYGPAFTLRMGIQKALVVSSWEVAKECLTTNDRALATRPSSAGG<br>KYMGYNNALIPFSPYGPYWRDMRKIATLELLSNHRLEELKHVREMEINTCISDMYKLC<br>QVEDGVEIKPISVDLSQWFADLTFNVVVMMITGKRYIGSTDAGDMNEIRHFQAALVKF<br>MRLLRISLLVDVFPVLQWINYGGFKGVMKSTARDIDSVLENWLQEHQRKRLSPDFNGN<br>HDFIDVMISTLEGTEFSDYDHNTIIKAISMAMVVGGTDTTTTTLIWAISLLLNNPNAMK<br>KVQEELEIHVGKERNVDGSDIQHLVYLQAVVKETLRLYPPVPLSVMHQAMEDCVIGSY<br>NIQAGTRVLFNLWKLHRDSSVWSDPLEFRPERFLTSHVDVDVRGQHFELIPFGSGRRSC<br>PGISFALQVIHLTIARLFHGFNLTTPGNSSVDMSEISGATLSKVTPLEVLVTPRLSSKLYN |
| HcaCYP82-10 | MDSLLQLQIIGALAALIFTYKLLKVICRSPMTDGMEAPEPPGAWPIIGHLHLLGGQDPIA<br>RTLGVMTDKYGPILKLRLGVHTGLVVSNWELAKECFTTNDRVLASRPMGAAGKYLG<br>YNYAIFGLAPHGPYWSEVRKIVLRELLSNQSLEKKHVRISEINTCLKNLFSLNNGNTPI<br>KVDMKQWFERPMFNVVTMMIAGKRYFSMENDNEAMNFRKVATEFMYLTGVFVVSD<br>ALPYLEWLDLQGHVSAMKRTAKELDIHVGKWLEEHRRAKLLGETKNEDDFVDLLTI<br>LPEDLKDNQTYIHDRDTIIKATALALFLAASDTTAITLTWALSLILNNPDVLKRAQDELD<br>KHVGKEKLVKESDIIINLVYLQAIIKETLRLYPAAPLLLPHEAMEDCTVGGYHVPKGTRI<br>FVNIWKLQRDPRVWFDPNEFRPERFLTTHANVDFKGQHFEYIPFSSGRRVCPGITFSTQI<br>MHLTLAHLLHEFNIVTPTKSNAGVDMTESLGITMPKATPLEVLLTPRLPSNLYNQYRD |
| EcaCYP82-7 | MNLLIFFQFLLQFQVLVGLSVLLAFSYYLWVSKNPKINKFKGKGALLAPQAAGAWPIV<br>GHLPQLVGPKPLFRILGAMADNYGPIFMLRFGVHPTVVVSSWEMTKECFTTNDRHLAS<br>RPSNAASQYLIYEVYALFGFSLYGSSYWRDARKIATLELLSHRRLELLKHVPYTEIDTCI<br>KQLHRLWTKNNKQNNPELKVEMNQFFTDLTMNVILKLVVGKRFFNVDDAADHEKE<br>EARKIQGTIFEFFKLTEGSVSAGALPLLNWLDLNGQKRAMKRTAKKMDSIAEKLLDEH |

TABLE 5-continued

N-demethylase candidate enzymes

| Name | Sequence |
|---|---|
| | RQKRLSKEGVKGTHDHNDFMDVLLSILDADQGDYSHHPFNYSRDHVIKATTLSMILSS<br>MSISVSLSWALSLLLNNRHVLKKAQDELDMNVGKDRQVEEGDIKNLVYLQAIVKETF<br>RMYPANPLLLPHEAIEDCKIGGFNVPAGTRVVVNAWKLQHDPRVWSNPSEFKPERFLN<br>DQAAKVVDVRGQNFEYLPFGSGRRVCPGISFSLQTIHMSLARLVQAFELGTPSNERIDM<br>TEGSGLTMPKTTPLHVLLNPRLPLYE |
| GflCYP82-8 | MELINSLEIQPITISILALLTVSILLYKIIWNHGSRKNNKSNKNNRKTSSSAGVVEIPGAWP<br>IIGHLHLFNGSEQMFHKLGSLADQYGPAPFFIRFGSRKYVVVSNWELVKTCFTAQSQIF<br>VSRPPMLAMNILFFPKDSLSYIQHGDHWRELRKISSTKLLSSHRVETQKHLIASEVDYCF<br>KQLYKLSNNGEFTLVRLNTWCEDMALNVHVRMIAGMKNYVAAPGSGEYGGQARRY<br>RKALEEALDLLNQFTITDVVPWLGWLDHFRDVVGRMKRCGAELDSIFATWVEEHRVK<br>RASGKGGDVEPDFIDLCWESMEQLPGNDPATVIKLMCKEHIFNGSGTSSLTLAWILSLI<br>MNNPYVIKKAREELEKHVGNHRQVEESDLPNLLYIQAIIKEGMRLYTPGPFIDRNTTED<br>YEINGVHIPAGTCLYVNLWKIHRDPNVYEDPLEFKPERFLKNNSDLDLKGQNYQLLPF<br>GAGRRICPGVSLALPLMYLTVSRLIHGFDMKLPKGVEKADMTAHGGVINQRAYPLEVL<br>LKPRLTFQQA |
| SdiCYP82-3 | MTIGALALLSFIYFLRVSVIKRTKYTNTAVTATNKLENDEDEANHSKRVVAPPEVAGA<br>WPILGHLPQLVGLKQPLFRVLGDMADKYGPIFIVRFGMYPTLVVSSWEMAKECFTTND<br>RVLASRPASASGKYLTYNYAMFGFTNGPYWREIRKISMLELLSHRRVELLKHVPSTEID<br>SSIKQLYHLWVENQNQMKQGDHQVKVDMSQLLRDLTLNIVLKLVVGKRLFNNNDMD<br>HEQDEAARKLQKTMVELIKVAGASVASDALPFLGWLDVDGLKRTMKRIAKEIDVIAE<br>RWLQEHRQKKLTSNDKGGSNNIQGGGGDNDFMDVMLSILDDDSNFFINYNRDTVIKA<br>TSLTMILAGSDTTTLSLTWALTLLATNPGALRKAQDELDTKVGRDRQVDERDIKNLVY<br>LQAIVKETLRMYPAAPLAIPHEATQDCIVGGYHVTAGTRVWVNLWKLQRDPHAWPNP<br>SEFRPERFLAVENDCKQQGTCDGEAANMDFRGQHFEYMPFGSGRRMCPGINFAIQIIH<br>MTLARLLHSFELRVPEEEVIDMAEDSGLTISKVTPLELLLTPRLPLYI |
| SdiCYP82-6 | FCQFQGIVGILLAFLTFLYYLWRASITGLRTKPKHNDFKVTKAAPEADGAWPIVGHFAQ<br>FIGPRPLFRILGDMADKYGSIFMVRFGMYPTLVVSSWEMAKECFTTNDRFLASRPASAA<br>GKYLTYDFAMLSFSFYGPYWREIRKISMLELLSHRRVELLKHVPSTEIDSSIKQLYHLW<br>VENQNQNKQGDHQVKVDMSQLLRDLTLNIVLKLVVGKRLFNNNDMDHEQDEAARK<br>LQKTMVELIKVAGASVASDALPFLGWLDVDGLKRTMKRIAKEIDVIAERWLQEHRQK<br>KLTSNDKGGSNNIQGGGGDNDFMDVMLSILDDDSNFFINYNRDTVIKATSLTMILAGS<br>DTTTLSLTWALTLLATYPLCALRKAQDELDTKVGRDRQVDERDIKNLVYLQAIVKETL<br>RMYPAAPLAIPHEATQDCIVGGYHVTAGTRVWVNLWKLQRDPHAWPNPSEFRPERFL<br>AVENDCKQQGTCDGEAANMDFRGQHFEYMPFGSGRRMCPGINFAIQIIHMTLARLLHS<br>FELRVPEEEVIDMAEDSGLTISKVTPLELLLTPRLPLYI |
| CmaCYP82-6 | MDLFIFFSRFQYIVGLLAFLTFFYYLWRVSITGTRIKTNQNIMNGTNMMAPEAAGAWPI<br>VGHLPQLVGPQPLFKILGDMADKYGSIFMVRFGMHPTLVVSSWEMAKECFTTNDKFL<br>ASRPTSAGGKYLTYDFAMFGFSFYGPYWREIRKISTLELLSHRRVELLKHVPYIEIGGSI<br>KQLYKLWMETQNQNKQRDDHQVKVDMSQVFGYLTLNTVLKLVVGKGLFNNNDMN<br>HEQEEGRKLHETVLEFFKLAGVSVASDALPFLGWLDVDGQKRSMKRIAKEMDLIAER<br>WLQEHRQKRLTSNNKASSGHDDFMSVLLSILDDDSNFFYNYNRDTVIKATSLNLILAASD<br>TTSVSLTWVLSLLVTNPGALKKVQDELDTKVGRNRHVEERDIEKLVYLQATVKETLR<br>MYPAGPLSVPHEATQDCTVGGYQVTAGTRLVVNVWKLQRDPRVWPNPSEFKPERFLP<br>DGCEVGCGEAANMDFRGQHFEYIPFGSGRRMCPGIDFAIQIHMTLACLLHAFEFQVPS<br>SLDKHLVPAVIDMSEGSGLTMPKVTPLEVLLNPRLPLYEL |
| EcaCYP82-5 | MEKPILLQLQPGILGLLALMCFLYYVIKVSLSTRNCQLVRHPPEAAGSWPIVGHLPQL<br>VGSGKPLFRVLGDMADKFGPIFMVRFGHPTLVVSSWEMAKECFTSNDKFLASRPPSA<br>ASIYMAYDHAMLGFSSYGPYWREIRKISTLHLLSHRRLELLKHVPHLEIHNFIKGLYGI<br>WKDHQKQQQPTARDDQDSVMLEMSQLFGYLTLNIVLSLVVGKRVCNYHADGHLDD<br>GEEAGQGQKLHQTITDFFKLSGVSVASDALPFLGLFDLDGQKKIMKRVAKEMDFVAER<br>WLQDKKSSLLLSSKSNNKQNEAGEGDVDDFMDVLMSTLPDDDDSFFTKYSRDTVIKA<br>NSLSMVVAGSDTTSVSLTWALSLLLNNIQVLRKAQDELDTKVGRDRHVEEKDIDNLV<br>YLQAIVKETLRMYPAGPLSVPHEAIEDCNVGGYHIKTGTRLLVNIWKLQRDPRVWSNP<br>SEFRPERFLDNQSNGTLLDFRGQHFEYIPFGSGRRMCPGVNLATPILHMTLARLLQSFDL<br>TTPSSSPVDMTEGSGLTMPKVTPLKVLLTPRLPLYDY |
| PbrCYP82-5 | MDVAIIVDHHYLQPFVSIAGLLALLSFFYCIWVFIIRPRIIKSNLDERKLSPSSPPEVAGA<br>WPIVGHLPQLIGSTPLFKILADMSNKYGPIFMVRFGMYPTLVVSSWEMSKECFTTNDRL<br>FATRPPSAAGKYLTKALFAFSVYGPYWREIRKISTIHLLSLRRLELLKHGRYLEIDKCMK<br>RLFEYWMEHHKNIISTTSSVKVNMSQVFAELSLNVVLKIIVGKTLFIKNGNEDYTKEEE<br>EGQKLHKTILKFMELAGVSVASDVLPFLGWLDVDGQKKQMKRVYKEMNLIASKWLG<br>EHRERKRLQIIQKRGAARGSNYDDGNDFMDVLMSILDEENDDLFFGYSRDTVIKSTCL<br>QLIVAASDTTSLAMTWALSLLLTNPNVLQKAQDELDTKVGRDRIIEEHDIECLVYLQAI<br>VKETLRLYPPAPLSLPHEAMEDCTVGGYQVKAGTRLVVNLWKLQRDPRVWSNPLEFK<br>PERFLPQSDGGFGGEEARMDFRGQHFEYTPFGSGRRICPGIDFFLQTVHMALARLLQAF<br>DFNTAGGLVIDMVEGPGLTMPKVTPLEVHLNP<br>RLPVTLY |
| PbrCYP82-6 | MQVDWPNILQKYYPIITCSLLTLLSFYYIWVSITKPSRNSKTKLPPPEVAGSWPIVGHLP<br>QLVGSTPLFKILANMSDKYGPIFMVRFGMHPTLVVSSWEMSKECFTTNDKFLASRPPSA<br>SAKYLGYDNAMFVFSDYGPYWREIRKISTLQLLTHKRLDSLKNIPYLEINSCVKTLYTR |

TABLE 5-continued

N-demethylase candidate enzymes

| Name | Sequence |
|---|---|
| | WAKTQSQIKQNVGGAADDFVKVDMTEMFGHLNLNVVLRLVVGKPIFIQKDNADEDY<br>TKDGHNKEELGQKLHKTIIEFFELAGASVASDVLPYLGWLDVDGQKKRMKKIAMEMD<br>LFAQKWLEEHRQKGINHDNENDFMAVLISVLGEGKDDHIFGYSRDTVIKATCLTLIVA<br>ATDTTLVSLTWALSLLLTNPRVLSKAQDELDTVVGKERNVEDRDVNHLVYLQAVIKE<br>TLRLYPPSPLAVPHEAIENCNVGGYEVKARTRLLVNLWKIHRDPRVVSNPLEFKPERFL<br>PKLDGGTGEASKLDFKGQDFVYTPFGSGRRMCPGINFASQTLHMTLARLLHAFDFDIES<br>NGLVIDMTEGSGLTMPKVTPLQVHLRPRLPATLY |
| McaCYP82-4 | MIMMFIDYYSSWLPQTLLLQSILLAVSLVIFINLFLTRRRSYSSKSHTNIIHPPKAAGALP<br>VIGHLYTLFRGLSAGVPLYRQLDAMADRYGPAFIIHLGVYPTLVVTCRELAKECFTTND<br>QTFATRPSTCAGKYIGYNYAFFGFAPYGPYWREARKIATVELLSNYRLDSLRHVREAE<br>VGRNVDELYALHASSSTNKQNMMKIDMKQWFDQVTLNVILMMVVGKRCVTTGGNE<br>EEVRVVKVLHEFFKHLGTLSVSDVVPYVEWMDLDGNIGRMKSTAKELDCILGRWLEE<br>HRRERRSDFMDAMLAMVEGIKIPYYDSDTVIKAICLNLLNAGSDTLGITMTWALSLLL<br>NNRHVLKKVKDELDVHVGKNRQVEELDVKNLVYLHAVVKETLRLFPPAPLGVPHEA<br>MEDCVVGGFHVAKGTRLVVNVWKLHRDPSVWSDPLAFKPERFLDNNTVDVRGQHFQ<br>LLPFGSGRRGCPGITFALQVAHLTLARLLHGFEWDTPDGAPVDMSEVSVLTTAKKNPV<br>EVLFTPRLPAEVYTQN |
| NsaCYP82-4 | MLSIHDSTMVFLQLQAICGIFGFIFIITWWTRWKSSNKMKAPEVAGAWPVIGHLHLLGG<br>GRPLYQLLGDMSDKYGPAFTLRMGIQKALVVSSWEVAKECLTTNDRALATRPSSAGG<br>KYMGYNNALIPFSPYGPYWRDMRKIATLELLSNHRLEELKHVREMEINTCISDMYKLC<br>QVEDGVEIKPISVDLSQWFADLTFNVVVMMITGKRYIGSTDAGDMNEIRHFQAALVKF<br>MRLLRISLLVDVFPVLQWINYGGFKGVMKSTARDIDSVLENWLQEHQRKLSPDFNGN<br>HDFIDVMISTLEGTEFSDYDHNTIIKAISMAMVVGGTDTTTTLIWAISLLLNNPNAMK<br>KVQEEELEIHVGKERNVDGSDIQHLVYLQAVVKETLRLYPPVPLSVMHQAMEDCVIGSY<br>NIQAGTRVLFNLWKLHRDSSVWSDPLEFRPERFLTSHVDVDVRGQHFELIPFGSGRRSC<br>PGISFALQVIHLTIARLFHGFNLTTPGNSSVDMSEISGATLSKVTPLEVLVTPRLSSKLYN |
| HcaCYP82-10 | MDSLLQLQIIGALAALIFTYKLLKVICRSPMTDGMEAPEPPGAWPIIGHLHLLGGQDPIA<br>RTLGVMTDKYGPILKLRLGVHTGLVVSNWELAKECFTTNDRVLASRPMGAAGKYLG<br>YNYAIFGLAPHGPYWSEVRKIVLRELLSNQSLEKLKHVRISEINTCLKNLFSLNNGNTPI<br>KVDMKQWFERPMFNVVTMMIAGKRYFSMENDNEAMNFRKVATEFMYLTGVFVVSD<br>ALPYLEWLDLQGHVSAMKRTAKELDIHVGKWLEEHRRAKLLGETKNEDDFVDVLLTI<br>LPEDLKDNQTYIHDRDTIIKATALALFLAASDTTAITLTWALSLILNNPDVLKRAQDELD<br>KHVGKEKLVKESDIINLVYLQAIIKETLRLYPAAPLLLPHEAMEDCTVGGYHVPKGTRI<br>FVNIWKLQRDPRVWFDPNEFRPERFLTTHANVDFKGQHFEYIPFSSGRRVCPGITFSTQI<br>MHLTLAHLLHEFNIVTPTKSNAGVDM1ESLGITMPKATPLEVLLTPRLPSNLYNQYRD |
| EcaCYP82-7 | MNLLIFFQFLLQFQVLVGLSVLLAFSYYLWVSKNPKINKFKGKGALLAPQAAGAWPIV<br>GHLPQLVGPKPLFRILGAMADNYGPIFMLRFGVHPTVVVSSWEMTKECFTTNDRHLAS<br>RPSNAASQYLIYEVYALFGFSLYGSSYWRDARKIATLELLSHRRLELLKHVPYTEIDTCI<br>KQLHRLWTKNNKNQNNPELKVEMNQFFTDLTMNVILKLVVGKRFFNVDDAADHEKE<br>EARKIQGTIFEFFKLTEGSVSAGALPLLNWLDLNGQKRAMKRTAKKMDSIAEKLLDEH<br>RQKRLSKEGVKGTHDHNDFMDVLLSILDADQGDYSHHPFNYSRDHVIKATTLSMILSS<br>MSISVSLSWALSLLLNNRHVLKKAQDELDMNVGKDRQVEEGDIKNLVYLQAIVKETF<br>RMYPANPLLLPHEAIEDCKIGGFNVPAGTRVVVNAWKLQHDPRVWSNPSEFKPERFLN<br>DQAAKVVDVRGQNFEYLPFGSGRRVCPGISFSLQTIHMSLARLVQAFELGTPSNERIDM<br>TEGSGLTMPKTTPLHVLLNPRLPLPLYE |
| GflCYP82-8 | MELINSLEIQPITISILALLTVSILLYKIIWNHGSRKNNKSNKNNRKTSSSAGVVEIPGAWP<br>IIGHLHLFNGSEQMFHKLGSLADQYGPAPFFIRFGSRKYVVVSNWELVKTCFTAQSQIF<br>VSRPPMLAMNILFFPKDSLSYIQHGDHWRELRKISSTKLLSSHRVETQKHLIASEVDYCF<br>KQLYKLSNNGEFTLVRLNTWCEDMALNVHVRMIAGMKNYVAAPGSGEYGGQARRY<br>RKALEEALDLLNQFTITDVVPWLGWLDHFRDVVGRMKRCGAELDSIFATWVEEHRVK<br>RASGKGGDVEPDFIDLCWESMEQLPGNDPATVIKLMCKEHIFNGSGTSSLTLAWILSLI<br>MNNPYVIKKAREELEKHVGNHRQVEESDLPNLLYIQAIIKEGMRLYTGPFIDRNTTED<br>YEINGVHIPAGTCLYVNLWKIHRDPNVYEDPLEFKPERFLKNNSDLDLKGQNYQLLPF<br>GAGRRICPGVSLALPLMYLTVSRLIHGFDMKLPKGVEKADMTAHGGVINQRAYPLEVL<br>LKPRLTFQQA |
| SdiCYP82-3 | MTIGALALLSFIYFLRVSVIKRTKYTNTAVTATNKLENDEDEANHSKRVVAPPEVAGA<br>WPILGHLPQLVGLKQPLFRVLGDMADKYGPIFIVRFGMYPTLVVSSWEMAKECFTTND<br>RVLASRPASASGKYLTYNYAMFGFTNGPYWREIRKISMLELLSHRRVELLKHVPSTEID<br>SSIKQLYHLWVENQNQNKQGDHQVKVDMSQLLRDLTLNIVLKLVVGKRLFNNNDMD<br>HEQDEAARKLQKTMVELIKVAGASVASDALPFLGWLDVDGLKRTMKRIAKEIDVIAE<br>RWLQEHRQKKLTSNDKGGSNNIQGGGGDNDFMDVMLSILDDDSNFFINYNRDTVIKA<br>TSLTMILAGSDTTTLSLTWALTLLATNPGALRKAQDELDTKVGRDRQVDERDIKNLVY<br>LQAIVKETLRMYPAAPLAIPHEATQDCIVGGYHVTAGTRVWVNLWKLQRDPHAWPNP<br>SEFRPERFLAVENDCKQQGTCDGEAANMDFRGQHFEYMPFGSGRRMCPGINFAIQIIH<br>MTLARLLHSFELRVPEEEVIDMAEDSGLTISKVTPLELLLTPRLPLPLYI |
| SdiCYP82-6 | FCQFQGIVGILLAFLTFYYLWRASITGLRTKPKHNDFKVTKAAPEADGAWPIVGHFAQ<br>FIGPRPLFRILGDMADKYGSIFMVRFGMYPTLVVSSWEMAKECFTTNDRFLASRPASAA<br>GKYLTYDFAMLSFSFYGPYWREIRKISMLELLSHRRVELLKHVPSTEIDSSIKQLYHLW<br>VENQNQNKQGDHQVKVDMSQLLRDLTLNIVLKLVVGKRLFNNNDMDHEQDEAARK |

TABLE 5-continued

N-demethylase candidate enzymes

| Name | Sequence |
|---|---|
| | LQKTMVELIKVAGASVASDALPFLGWLDVDGLKRTMKRIAKEIDVIAERWLQEHRQK<br>KLTSNDKGGSNNIQGGGGDNDFMDVMLSILDDDSNFFINYNRDTVIKATSLTMILAGS<br>DTTTLSLTWALTLLATYPLCALRKAQDELDTKVGRDRQVDERDIKNLVYLQAIVKETL<br>RMYPAAPLAIPHEATQDCIVGGYHVTAGTRVWVNLWKLQRDPHAWPNPSEFRPERFL<br>AVENDCKQQGTCDGEAANMDFRGQHFEYMPFGSGRRMCPGINFAIQIIHMTLARLLHS<br>FELRVPEEEVIDMAEDSGLTISKVTPLELLLTPRLPLPLYI |
| CmaCYP82-6 | MDLFIFFSRFQYIVGLLAFLTFFYYLWRVSITGTRIKTNQNIMNGTNMMAPEAAGAWPI<br>VGHLPQLVGPQPLFKILGDMADKYGSIFMVRFGMHPTLVVSSWEMAKECFTTNDKFL<br>ASRPTSAGGKYLTYDFAMFGFSFYGPYWREIRKISTLELLSHRRVELLKHVPYIEIGGSI<br>KQLYKLWMETQNQNKQRDDHQVKVDMSQVFGYLTLNTVLKLVVGKGLFNNNDMN<br>HEQEEGRKLHETVLEFFKLAGVSVASDALPFLGWLDVDGQKRSMKRIAKEMDLIAER<br>WLQEHRQKRLTSNNKASSGHDDFMSVLLSILDDDSNFFNYNRDTVIKATSLNLILAASD<br>TTSVSLTWVLSLLVTNPGALKKVQDELDTKVGRNRHVEERDIEKLVYLQATVKETLR<br>MYPAGPLSVPHEATQDCTVGGYQVTAGTRLVVNVWKLQRDPRVWPNPSEFKPERFLP<br>DGCEVGCGEAANMDFRGQHFEYIPFGSGRRMCPGIDFAIQIIHMTLACLLHAFEFQVPS<br>SLDKHLVPAVIDMSEGSGLTMPKVTPLEVLLNPRLPLPLYEL |
| EcaCYP82-5 | MEKPILLQLQPGILGLLALMCFLYYVIKVSLSTRNCNQLVRHPPEAAGSWPIVGHLPQL<br>VGSGKPLFRVLGDMADKFGPIFMVRFGVHPTLVVSSWEMAKECFTSNDKFLASRPPSA<br>ASIYMAYDHAMLGFSSYGPYWREIRKISTLHLLSHRRLELLKHVPHLEIHNFIKGLYGI<br>WKDHQKQQQQPTARDDQDSVMLEMSQLFGYLTLNIVLSLVVGKRVCNYHADGHLDD<br>GEEAGQGQKLHQTITDFFKLSGVSVASDALPFLGLFDLDGQKIMKRVAKEMDFVAER<br>WLQDKKSSLLLSSKSNNKQNEAGEGDVDDFMDVLMSTLPDDDDSFFTKYSRDTVIKA<br>NSLSMVVAGSDTTSVSLTWALSLLLNNIQVLRKAQDELDTKVGRDRHVEEKDIDNLV<br>YLQAIVKETLRMYPAGPLSVPHEAIEDCNVGGYHIKTGTRLLVNIWKLQRDPRVWSNP<br>SEFRPERFLDNQSNGTLLDFRGQHFEYIPFGSGRRMCPGVNLATPILHMTLARLLQSFDL<br>TTPSSSPVDMTEGSGLTMPKVTPLKVLLTPRLPLPLYDY |
| PbrCYP82-5 | MDVAIIVDHHYLQPFVSIAGLLALLSFFYCIWVFIIRPRIIKSNLDERKLSPSSPPEVAGA<br>WPIVGHLPQLIGSTPLFKILADMSNKYGPIFMVRFGMYPTLVVSSWEMSKECFTTNDRL<br>FATRPPSAAGKYLTKALFAFSVYGPYWREIRKISTIHLLSLRRLELLKHGRYLEIDKCMK<br>RLFEYWMEHHKNIISTTSSVKVNMSQVFAELSLNVVLKIIVGKTLFIKNGNEDYTKEEE<br>EGQKLHKTILKFMELAGVSVASDVLPFLGWLDVDGQKKQMKRVYKEMNLIASKWLG<br>EHRERKRLQIIQKRGAARGSNYDDGNDFMDVLMSILDEENDDLFFGYSRDTVIKSTCL<br>QLIVAASDTTSLAMTWALSLLLTNPNVLQKAQDELDTKVGRDRIIEEHDIECLVYLQAI<br>VKETLRLYPPAPLSLPHEAMEDCTVGGYQVKAGTRLVVNLWKLQRDPRVWSNPLEFK<br>PERFLPQSDGGFGGEEARMDFRGQHFEYTPFGSGRRICPGIDFFLQTVHMALARLLQAF<br>DFNTAGGLVIDMVEGPGLTMPKVTPLEVHLNPRLPVTLY |
| PbrCYP82-6 | MQVDWPNILQKYYPIITCSLLTLLSFYYIWVSITKPSRNSKTKLPPPEVAGSWPIVGHLP<br>QLVGSTPLFKILANMSDKYGPIFMVRFGMHPTLVVSSWEMSKECFTTNDKFLASRPPSA<br>SAKYLGYDNAMFVFSDYGPYWREIRKISTLQLLTHKRLDSLKNIPYLEINSCVKTLYTR<br>WAKTQSQIKQNVGGAADDFVKVDMTEMFGHLNLNVVLRLVVGKPIFIQKDNADEDY<br>TKDGHNKEELGQKLHKTIIEFFELAGASVASDVLPYLGWLDVDGQKKRMKKIAMEMD<br>LFAQKWLEEHRQKGINHDNENDFMAVLISVLGEGKDDHIFGYSRDTVIKATCLTLIVA<br>ATDTTLVSLTWALSLLLTNPRVLSKAQDELDTVVGKERNVEDRDVNHLVYLQAVIKE<br>TLRLYPPSPLAVPHEAIENCNVGGYEVKARTRLLVNLWKIHRDPRVWSNPLEFKPERFL<br>PKLDGGTGEASKLDFKGQDFVYTPFGSGRRMCPGINFASQTLHMTLARLLHAFDFDIES<br>NGLVIDMIEGSGLTMPKVTPLQVHLRPRLPATLY |
| PbrCYP82-7 | MMDLAMFIDQYFSLAKIAGLLALLSFFYYLWISTLWSPRNPKLSSVSPPEVAGAWPILG<br>HLPQLLGSRPLFKILADMSDNYGPIFMVRFGMHPTLVVSSWEMAKECFTTNDRFLAGR<br>PSGAANKYLTFALFGFSTYGPYWREIRKIATLHLLSHRRLELLKHVPDLEVTNCMKHL<br>HRRWIDSQNQIKQNDAAAGSVKVDMGRVFGELTLNVVLKLVAGKSIFFKNDNTRQYD<br>SKDGHNKEEEEGKKLHKTIIDFYSLAGASVASDVLPFLGWLDVDGQKKRMKRVAKD<br>MDFIAAKWLEEHRHQKRQTVLSSSATLGSSNHDDAKDFMDVLMSILDGENDDLFFGY<br>SRDTVIKTTCLQLIAAAADTTSVTMTWALALLITNPTILRKAQDELDTKVGKDRNIEER<br>DINDLVYLQAIVKETLRMYPAGPLNVPHEAIADCNIGGYEVRAGTRLLVNLWKMHRD<br>PRVWSNPSEFKPERFLPQLDGGSGGEANLDFRGQDFEYLPFSAGRRMCPGIDFSLQTL<br>HMTLARLLHGFDFNNDSAGIIIDMEEGSGLTMPKLTPLEIYLCPRLPAKLY |

TABLE 6

N-methyltransferase and N-modifying candidate enzymes

| Name | Sequence |
|---|---|
| TfCNMT | MAVEGKQVAPKKAIIVELLKKLELGLVPDDEIKKLIRIQLGRRLQWGCKSTYEEQIAQLVNLTHSLRQMKIATEVE<br>TLDDQMYEVPIDFLKIMNGSNLKGSCCYFKNDSTTLDEAEIAMLELYCERAQIKDGHSVLDLGCGQGALTLYVA<br>QKYKNSRVTAVTNSVSQKEFIEEESRKRNLSNVEVLLADITTHKMPDTYDRILVVELFEHMKNYELLLRKIKEWM<br>AKDGLLFVEHICHKTFAYHYEPIDEDDWFTEYVFPAGTMIIPSASFFLYFQDDVSVVNHWTLSGKHFSRTNEEWL<br>KRLDANVELIKPMFVTITGQCRQEAMKLINYWRGFCLSGMEMFGYNNGEEWMASHVLFKKK |

TABLE 6-continued

N-methyltransferase and N-modifying candidate enzymes

| Name | Sequence |
|---|---|
| CjCNMT | MAVEAKQTKKAAIVELLKQLELGLVPYDDIKQLIRRELARRLQWGYKPTYEEQIAEIQNLTHSLRQMKIATEVETL<br>DSQLYEIPIEFLKIMNGSNLKGSCCYFKEDSTTLDEAEIAMLDLYCERAQIQDGQSVLDLGCGQGALTLHVAQKY<br>KNCRVTAVTNSVSQKEYIEEESRRRNLLNVEVKLADITTHEMAETYDRILVIELFEHMKNYELLLRKISEWISKDG<br>LLFLEHICHKTFAYHYEPLDDDDWFTEYVFPAGTMIIPSASFFLYFQDDVSVVNHWTLSGKHFSRTNEEWLKRLD<br>ANLDVIKPMFETLMGNEEEAVKLINYWRGFCLSGMEMFGYNNGEEWMASHVLFKKK |
| PsCNMT | MQLKAKEELLRNMELGLIPDQEIRQLIRVELEKRLQWGYKETHEEQLSQLLDLVHSLKGMKMATEMENLDLKLY<br>EAPMEFLKIQHGSNMKQSAGYYTDESTTLDEAEIAMLDLYMERAQILSDGQSVLDLGCGLGAVALFGANKFKKC<br>QFTGVTSSVEQKDYIEGKCKELKLTNVKVLLADITTYETEERFDRIFAVELIEHMKNYQLLLKKISEWMKDDGLLF<br>VEHVCHKTLAYHYEPVDAEDWYTNYIFPAGTLTLSSASMLLYFQDDVSVVNQWTLSGKHYSRSHEEWLKNMDK<br>NIVEFKEIMRSITKTEKEAIKLLNFWRIFCMCGAELFGYKNGEEWMLTHLLFKKK |
| PsTNMT | MGSIDEVKKESAGETLGRLLKGEIKDEELKKLIKFQFEKRLQWGYKSSHQEQLSFNLDFIKSLKKMEMSGEIETMN<br>KETYELPSEFLEAVFGKTVKQSMCYFTHESATIDEAEEAAHELYCERAQIKDGQTVLDIGCGQGGLVLYIAQKYKN<br>CHVTGLTNSKAQVNYLLKQAEKLGLTNVDAILADVTQYESDKTYDRLLMIEAIEHMKNLQLFMKKLSTWMTKES<br>LLFVDHVCHKTFAHFFEAVDEDDWYSGFIFPPGCATILAANSLLYFQDDVSVVDHWVVNGMHHMARSVDIWRK<br>ALDKNMEAAKEILLPGLGGSHETVNGVVTHIRTFCMGGYEQFSMNNGDEWMVAQLLFKKK |
| EcTNMT | MGSSAGEIMGRLLMKGEIEDEELKKLIRHQWDRRIEWGYKPTHEKQLAFNLDFIKGLKEMVMSGEIDTMNKETY<br>ELPTAFLEAVFGKTVKQSCCYFKDENSTIDEAEEAAHELYCERAQIKDGQTVLDIGCGQGGLVLYIAEKYKNCHVT<br>GLTNSKAQANYIEQQAEKLELTNVDVIFADVTKFDTDKTYDRILVVETIEHMKNIQLFMKKLSTWMTEDSLLFVD<br>HISHKTFNHNFEALDEDDWYSGFIFPKGCVTILSSSTLLYFQDDVSALDHWVVNGMHHMARSVEAWRKKLDETI<br>EAAREILEPGLGSKEAVNQVITHIRTFCIGGYEQFSYNNGEEWMITQILFKKK |
| PsRNMT | MSTTMETTKISQQDDLWKNMELGQISDEEVRRLMKIGIEKRIKWGTKPTQQEQLAQLLDFNKSLRGMKMATE<br>IDTLENHKIYETPESFNQIIGGKESAGLFTDETTTTMEEANTKMMDLYCERAGLKDGHTILDLGCGAGLLVLHLAK<br>KYKKSKITGITNTSSHKEYILKQCKNLNLSNVEIILADVTKVDIESTFDRVFVIGLIEHMKNFELFLRKISKWMKD<br>DGLLLLEHLCHKSFSDHWEPLSEDDWYAKNFFPSGTLVIPSATCLLYFQEDVTVIDHWILSGNNFARSNEVILKRI<br>DGKIEEVKDIFMSFYGIGREEEAVKLINWWRLLCITANELFKYNNGEEWLISQLLFKKKLMTCI |
| TfPNMT | METKQTKKEAVANLIKRIEHGEVSDEEIRGMMKIQVQKRLKWGYKPTHEQQLAQLVTFAQSLKGMEMAEEVD<br>TLDAELYEIPLPFLHIMCGKTLKFSPGYFKDESTTLDESEVYMMDLYCERAQIKDGQSILDLGCGHGSLTLHVAQK<br>YRGCKVTGITNSVSQKEFIMDQCKKLDLSNVEIILEDVTKFETEITYDRIFAVALIEHMKNYELFLKKVSTWIAQY<br>GLLFVEHHCHKVFAYQYEPLDEDDWYTEYIFPSGTLVMSSSSILLYFQEDVSVVNHWTLSGKHPSLGFKQWLKRLD<br>DNIDEVKEIFESFYGSKEKAMKFITYWRVFCIAHSQMYSTNNGEEWMLSQVLFKKK |
| PbrTNMT1 | MGSIDEVKKESAGETLGRLLKGEIKDEELKKLIKFQFEKRLQWGYKSSHQEQLSFNLDFIKSLKKMEMSGEIETMN<br>KETYELPSEFLEAVFGKTVKQSMCYFKHESATIDEAEEAAHELYCERAQIKDGQTVLDIGCGQGGLVLYIARKYKK<br>CHVTGLTNSKAQVNYLLKQAEKLGLTNVDAILADVTQYESDKTYDRLLMIEAIEHMKNLQLFMKKLSTWMTEES<br>LLFVDHVCHKTFAHFFEAVDEDDWYSGFIFPPGCATILAANSLLYFQDDVSVVDHWVVNGMHHMARSVDIWRK<br>ALDKNMEAAKEILLPGLGGSHEAVNGVVTHIRTFCMGGYEQFSMNDGDEWMVAQLLFKKK |
| PbrTNMT2 | MGSIEEVKKESAEETLGRLLRGEINDEELKKLIKYQLEKRLQWGYKSSHQEQLSFNLDFINSLKKMGMSGQVEAF<br>TNEVYELPTECFEAAYGKSMKLSGCYFKHESSTIDEAEEASHELYCERAQIKDGQTVLDIGCGQGGLVLYVAQKY<br>KNCHVTGLTNSKEQVNYILKQAEKLGLRNVDVILADVTQYESDKTYDRILVIGVVEHMKNMQLFIKKLSTWMAE<br>DSLLFVDHSCHKTFNHFFEALDEDDWYSGYIFPPGCATFLSADSLLYFQDDSVVVDHWVVNGMHFARTVDAW<br>RKKLDKNMEAVKEILPGLGGNHEAVNGVITHIRTCCVGGYVQFSLNDGDEWMNAQLLFKKK |
| AmeNMT1 | MCLFFAEKMGLMAEANNQQQLKKEDLLKNMELGLIPDEEIRKLIRVQLEKRLNWGYKSTHEQQLSQLLHLVHS<br>LKKMKIATEMENLDLKLYEAPFSFVQIQHGSTIKESSGLFKDESTTLDEAEIAMLDLYTKRAKIEDGQSVLDLGCG<br>LGAVTLYVAQKFKNCYVTGITSSVEQKDFIEGRCKELKLSNVKVILADITTYETEEKYNRIFAVELIEHMKNYELL<br>LRKISEWMKQDGLLFIEHVCHKTLAYHYEPLDEEDWYTNYIFPAGTLTLSSATLLLYFQDDVAVVDQWTLSGKHYS<br>RSHEEWLKRIDGNIEEVKEIMKSITKSEEEAKKLLNFWRIFCMCGAELFGYKNGEEWMMTHILFKKK |
| GfINMT1 | MDLMATSKQVKKKEELLKNMELGLVPDEEIRRLIRIELEKRLKWGYKPTHQQQLAQLLDLVHSLKKMKIATEME<br>SLDLKLYEAPFSFVQIKHGSTIKESSSYFKDESMTLDEAEIAMLDLYVERAQIEDGQSVLDLGCGLGAVTLHVAKK<br>YKNCHVTGLTNSVEQKDFIEGKCKELNLSNVKVILADVTSHEMEDKFDRIFAVELIEHMKNYELLLRRISKWMKDD<br>GLLFIEHVCHKTLAYHYEPIDEDDWYTEYIFPAGTLTLSSASLLLYFQDDVSVVNHWTLSGKHYSRSHEEWLKRID<br>GNMDAVKEIMKSITKTEEEAVKLINFWRIFCMCGAELFGYKDGEEWMMSHVLFKKKQLLQQC |
| EcaNMT1 | MVDLKVEKEELLKSMELGLVPDEDIRKHIRSQLEKRLWGYKPNHEQQLAQLLDVIHSLKKMKISKEYESFDLRLY<br>EAPFDFHKIQLGTHLKESCSYYKDESTTLDEAEGAMLDLYTQKAKIEDGQSILDLGCGHGSILTLFVANKYKNCKV<br>TGITSCQWQKDFIENKCKELNLTNVRVIIGDVTAYEMEETFDRIFAIELIEHMKNYELLLRKISKWMKDDGLLFIE<br>HVCHKILAYPYEPIDEEDWFTEYIFPGGTLTLSSASLLLYFQDDVSVVEHSSLNGKHYSRSHGEWLKNIDANIDEV<br>KGIMRSITKTEEEAVRLVNFWRIFCMCGIELFGYNNGEEWMVSHILLKKK |
| EcaNMT2 | MAADLVVKKWNNKKELIDEMELGLVPDEEIRELIRNDLEKRLKWGYKSNHEQQLAQLLHFVHSLRGMKIAADE<br>VESFNIKVYEAPFSFNKIQLGSSLKESSCYYKHDETTLDEGEIAMMELYTEKAQIKDGQSVLDLGCGLGSLTYVA<br>NKYPNCKVTGTTASLWHKDFIESKCKEQELTNVKIVLGDATTHEMEERFDRILAIGLIEHLKNYGLLLGRISKWLK<br>DDGFLFIQHVCHKTLAYPLVPVDEEDWIGEYIFPGGTLTMPSASLLLYFQDELSVVDHSTLNGKHFSRTHEEWLKN<br>IDAKIDEVKEILKSVTKTEEEVVRLTNFWRIFCMFGVEMFGYNEGEEWMLSQILFKKK |
| CmaNMT4 | MASGKVVDLLKRLDSGLVSDEELRRVIRFELERRLKWGYKPTHEQQLAELLNLAHATKQMEIATKIDTLNSTMYE<br>VPNSFLEIQLGSTLKESCLYFKDESTTVDEAEIAMMDLYLERAQIKDGQIILDLGCGLGALAFHIAQKYTNCVTS<br>VTNSVKQKEFIEEKCKILNVSNVKVILTDICTLEMEATFDRIFAIGLIEHMKNYELLLRKFSAWMKDGLLFIEHL |

TABLE 6-continued

N-methyltransferase and N-modifying candidate enzymes

| Name | Sequence |
|---|---|
| | CHKTLGYHNEPIDEDDWYTAYFFPAGTLTFIPSSFLLYFQDDVSVVNHWTLSGKHFSRSNEEWLKRMDNKIDEVKE<br>IYKAAASETKDDDIMKLIRLWRFLSISAAEMFGYKDGEEWMISQVLFKKK |
| EcNMT3 | MASLVEEGSFVNNKESVKERVSELVKRLKNGLVSDEELRKLMRVELEKRLEWGYKSTHEQQLSQLIDLAHSMKK<br>MEIAMEIDALNSTVYEVPLSFLQIIHGTTIKESCLYFKDESTTVDEAEIAMMDLYLERAQIKDGQSILDLGCGLGG<br>FSFHIASKFTGCNITAVTNSVQKEFIEEKCKTLNVPNIKVILADICTTEIENVFDRIIAIGLIEHMKNYELLLKK<br>FSKWMTQDGLLFIEHLCHKTFGYHNEPLDEDDWYTTYFFPAGTLTFIPSSFLLYFQDDVSVVDHWTLNGKHFARSN<br>EEWLKRMDEKMDEVKQIFRSNLKSENEVTKTIGEWRFLSMSAAEMFGYNNGEEWMVSQLLFKKK |
| GflNMT5 | MGSNETNGELKTKEMVPDLLKRLESGLVADEELRKLIRFELERRLKWGYKPTHEQQLAELLKLAHSTKQMKIATE<br>TDSLNSTMYEVPIPFLQLQFGSAIKESCCYFKDESTTLDEAEVAMMDLYLERTQIKDGQSILDLGCGLGALAFHIV<br>QKYPNCNVLAITNSVEQKEFIEEKCKIRKVENVKVSLADICTLEMKTTFDRIFAIGLLEHMKNYQLLLKKFSNWMK<br>QDGLLFIEHLCHKTLAYHYEPLDEDDWYTEYFFPAGTLTIISSSFLLYFQDDVSIVNHWSLSGKHFSRSNEEWLKR<br>MDMKIDEVKEILEAAFENKDHDITKLINHWRFLAINATEMFGYNNGEEWMVSQVLFKKK |
| ScaNMT1 | MASDHEVSNKELKKKKEVITELLKRLESGLVSDEELRGLIRFELERRLRWGYKPTHEQQLAQLLNLAHSMKQMKI<br>ATEIDALNSTMYEVPIPFLQIQLGSTLKESCCYFKDESTTVDEAEIAMMDLYLERAQIKDGQSILDLGCGLGALAF<br>HIAQKYTNCNITAITNSVRQKEFIEEKCKILNVSNVKVSLADICTLEMEATFDRIFAIGLIEHMKNYELLLKKFSE<br>WMKQDGLIFIEHLCHKTLAYHEPLDEDDWYTEYFFPAGTLTLISSSFLLYFQDDVSVVDHWTLSGKHFSRSNEEW<br>LKRMDEKIDEVKEIFESVSDSKDDDVTKLINHWRFFCISSAEMFGYNNGEEWMISQVLFKKK |
| CchNMT3 | MIKKSKIMAFSDHHHEVVKNHSKKEMIADLLKRLEAGLVPDEEMRNLFRFELERRLQWGYKSIHQEQLSQLLKL<br>AHSTKEMTIVAEMDALNSSMYELPISFLQIQLGSNLKQSSLYFKDELTTVDEAEVAIMDLYLERAQIEDGQSILDL<br>GCGLGAFSFHVARKYTNCNITAVTNSLTQKEFIEKKSKILNIQNVKVIFADVTTVEMETTFDRVFAIGLIEHMQNY<br>ELFLKKLSKWMKQDGLLFIEHFCHKTLAYHYKPIDEDDWFTNLLYPNGTVISSSLLLYFQDDVSVVDHWSLSGKH<br>FSRASEESLKRMDAKMDEMKEIFESITDSKEEAMKLINQWRIFCISCAEMFGYNNGEEWMTSHFLFKKKL |
| CchNMT6 | MGSSTASDHEMVIMENDSKNKQVVIADLLKRLVGGLVPDEEMRNMFRFELEKRLKWGYKSTHQQQLSQLLNL<br>VELNKGIAKIAPEMDALNSAMYEVPIPYLKLMLGSTLKQSCLYFKDESTTLDEAEIEMMDLYLERADIQDGQSILD<br>LGCGLGGLGFHIAQKYISCNITALTNSLTQKEFIEEKCKTLNIPNVKVILADVTTVEIETTFDRLFAIGLVEHMEN<br>YELFLRKLSKWMKQDGLLFIEHLCHKTLAYHYKPIDEDDWYSNLLYPTGTLTSASFLLYFQDDLSVVDHWSLSGKH<br>FSRATEEWLKMIDANMDKIREIYESVTESKEEATRSINQWRIFCISCAEMFGYNDGEEWMISHFLFKNKKQIE |
| CchNMT1 | MATSDQEVKTSKMEMIADLLKRLEAGLVPDDEIRSLIRVELERRLKWGYKSTHQEQLDQLLNLAHSIKKMKIAST<br>EMDGLTSTMYEVPISLVQIQLGSHLKESCLYFKDETTTVDEAEIAMMDLYLERAQIKDGQSILDLGCGLGAVSFHI<br>AQKYTSCNITAVTNSVRQKEFIEEKSKTLNVPNVKVLLADITTLEMEHTFDRLFAISLIEHMENYELLLRKLSEWM<br>KQDGLLFIEHLCHKTLSYHFEPMDEDDWYTNLLFPAGTLTLVSASFLLYFQDDLSVVNQWVMSGKHFSRANEEW<br>LKNMDAKMDEMREIFESITDSEEEVVKLINHWRIFCISSAEMFAYNDGEEWMNSHVLFKKKKQIQ |
| CchNMT2 | MAGSGANKEMIADLLKRLEVGLVPDEEIRSLIRFQLKRRLKWGYKTTHQEQLEQLLSLAHSIRKMKIATEMDALN<br>STMYEVPISFMQIVFGSTLKESCLYFKDEATTVNEAEIAMMDLYLERAQIKDGQSILDLGCGMGSLCFHIARKYT<br>NCNITAVTNSVSQKEFIEEKSKTLNLPNVKVILADITTLEMDDTFDCLFAIGLIEHMKNYELLLRKLSNWMKQDSL<br>LFIDHVCHKTLAYHYEPIDEDDWYTNLLFPAGTLTLVSASFLLYFQDDLSLVDHWSMSGKHFSRTNKEWLKNID<br>GKMDKIREIVKSITDSEEEVVKLINHWRMLCINSSEMFGFNDGEEWMNSHVLFKKKKQI |
| ScaNMT2 | MEMIADLLKRLEAGLVPDDEIRSLIRVELERRLKWGYKSTHQEQLDQLLNLAHSIKKMKIASTEMDGLTSTMYEV<br>PISLVQIQLGSHLKESCLYFKDETTTVDEAEIAMMDLYLERAQIKDGQSILDLGCGLGSVCFHIARKYTSCNITAV<br>TNSVSQKEFIEEKSKTLNVPNVKVLLADITTLEMDDTFDCLFAIGLIEHMENYELLLRKLSDWMKQDGLLFIDHVC<br>HKTLSYHFEPMDEDDWYTNLLFPAGTLTLVSASFLLYFQDDLSLVDHWSMSGKHFSRTNKEWLKNIDGKMDKIR<br>EIVKSITDSEEEVVKLINHWRMLCINSSEMFGFNDGEEWMNSHVLFKKKKQI |
| PbrNMT2 | MCTTMDTTKISQQDDLWKNMELGLISDEEVRRLMKIETEKRIKWGTKPTQQEQLAQLLDFNKSLRGMKMATE<br>VHALENHKIYEIPDSFNQIIGGKESAGLFTDEATTTIEEANTKMMDLYCERAGLKDGQTILDIGCGAGLLVLHLAK<br>KYKNCKITGVTNTSWHKEHILEQCKNLNLSNVEVILADVTTVDIERTFDRVFVIGLIEHMKNFELFLRKISKWMKD<br>DGLLFLEHLCHKSFSDHWEPLSEDDWYAKNFFPSGTLVIPSATCLLYFQEDVTVKDHWLLSGNNFARSNEAILKR<br>IDSKIEEVKDIFMSFYGIGEEEAVKLINWWRLLCITANELFKYNNGEEWLISQLLFKKKLMTCI |
| PbrNMT1 | MVKGDQFQTTTMEETKISQENDLWTNMELGLIPDEEVRRLMKIEIEKRIEWGMKPTQHQQLAQLLDFTKSLR<br>GMKMATELDKLDSKLYETPHSFNQIVNGSTLKESSGLYTDVTTTMDEASIKMMDLYCERANIKDGQTILDLGCG<br>PGPLVLHIAKKYSNCKITGVTNAFSQREYILEECKKLSLSNVEIILADVTSLDLETTFDRVFVIGFIEHMKNFELF<br>LRKISKWMKDDAVLFLEHFCHKSFSYHGEPLSEDDWYAKNFFAPGTLVIPSATCLLYFQEDLAVIDHWFLSGNHFA<br>RTNEEMLKGIDGKIEEIKDIFMSFYGINEAEAVKLINWWRLFCITGAEMFSYNNGEEWFISQLLFKKK |
| EcaNMT4 | MALEQEDSMSVPERNEGVADLIKRMELGLVNDEEIRRLMRIQIENRLKWGYKPTHDQQLAQHLHFINSLKEMK<br>MATEMDSLDSQVYESPNSFQQIMCGRSMKESAGLFMDDVTTVEEAHIRMMDLYCDKATFEDGQKILDLGCG<br>HGSVVLHVAQKYKGCQVTGVTNSSAQKQYILEQCKKLDLSNVEIILADVTTLEMEEKFDRVIIGLIEHMKNFKLF<br>FQKVSKWMKEGGLLFLENYFHKDFAYHCEKIDEDDWYDGYIFPPGSLLMPSASTLLYFQEDLTVADHWVLPGTH<br>FAKTFEEFLKKIDLRIEEVREIFEAFYGISKEEAMKLSNYWRNFCISAMEIFNYNNGQEWMISHLLYTKK |
| CmaNMT5 | METGKNNQNMKTTIDDLWNQMMLGIVPDKEIRRLMKIELKKRLDWGYRPTHQQQLSQLLDFAKGLCNYCW<br>TALRCMKMSAEFDTLDSKVYETPKSFQQIMCGTTIKESSGLFMNESTTLDQAQISMLDLYFDKAKIKDGQSILDL<br>GCGHGALILYLAQKYQNCITGVTNSLSQKEFIVEKCKKLGLSNVEILLADVTKLEMEDMFDRVFVIGIEHMKNF<br>ELFLRKISEWMKPDGLLFLEHYCHKSFAHQWEPIDEEDWFSKYIFPPGTVIIPSASFLLYFQEDVKVIDHWTLSGN<br>HFARTQEEWLKGIDGHIDEVEKTFESFYGISKEEAVKLINFWRVFCLSGVEMFGYNNGEEWMISHLLFKKK |

TABLE 6-continued

N-methyltransferase and N-modifying candidate enzymes

| Name | Sequence |
|---|---|
| GflNMT4 | MTMEANNAKKEAIENLWEQMMMGLVPDHEITRLMKSELQKRLNWGYKPTHQQQISQLLDFAKSLRRMEM<br>SLDFDNLELDTKMYETPESFQLIMSGTTLKESSGLFTDETATLDQTQIRMMDLYLEKAKIKDGQSILDLGCGHGA<br>LILHVAQKYRNCNVTGVTNSIAQKEFIFKQCKKLGLSNVEMVLADVTKCEMKATFDHIFVIGLIEHMKNFELFLRK<br>VSEWMKSDGLLFMEHYCHKSFAYQWEPMDDDDLFSKYVFPPGSAIIPSASFLLYFQDDLTVVDHWTLSGNHF<br>ARTHQEWLKRIDSQSDEIKGIFESFYGISKEEAVKLINYWRVFCLFGVEMFGYNNGEEWMISHLLFKKK |
| CchNMT5 | MEVVATSSARNPKKEIVDLWKRMELGLIPDEEIRDLMKIGLEKRLKWGYKPTHEQQLSQLLHFAKSLRSMKMA<br>SEMETLDDQMYETPTAFQQLMCGSTIKESAGFFKDESTTLDEAEIKMLDLYCEKARIEDGQKILDLGCGHGAVM<br>LHIAQKYKNCNVTGVTNSISQQQFIVQRSKELNLSNVNMILADVTMLEMDATYDRIFIIGLIEHMKNFELFLRKIS<br>KWITKEGLLFLEHYCHKTFAYQCEPVDEDDWYNMFIFPPGTLILPSASFLLYFQDDLIVVDRWTLNGNHYARTQE<br>EWLKRIDANVDGVKQMFESVCDGNKEEAVKLMNFWRIFCISGAEMLAYNNGEEWMISHYLFKKRN |
| NsNMT2 | MEATQITKKQGVAELIKRIENGQVPDEEITRMMKIQIQKRLKLGYKSTHEQQLAQLLHFVHSLQKMEMAEEVD<br>TLDSELYEIPLPFLHIMCGKALKFSPGYFKDESTTLDESEVNMLDLYCERAQIEDGQTILDLGCGHGSLTLHVAKK<br>YRGCKVTGITNSVSQKDFIMEECKKLNLSNVEIILEDVTKFETGTTYDRIFAVALIEHMKNYELFLKKVSAWMAQD<br>GLLFVEHHCHKVFAYKYEPIDDDDWYTEYIFPTGTLVMSSSSILLYFQEDVSVVNHWTLSGKHPSLGFKQWLKRI<br>DDNIDEIKEIFESFYGSKEKATKFITYWRVFCIAHSEMYATNGGEEWMLSQVLFKRK |
| ScaNMT5 | MGGVADLLKKMELGLVPEEEIRRLMRIIIEKRLEWGYKPTHAEQLDHLTNFIQCLRGMKMADEIDALDAKMYEI<br>PLPFMQTICGSTLKFSPGYFKDESTTLDESEIHMMDLYCERAEVKDGHSILDLGCGHGGFVLHVAQKYKNSIVTG<br>VTNSVAEKEFIMTQCKKLCLSNVEIILADVTKFEPETTYDRVFAIALIEHMKNYELVLEKLSKWVAQDGFLFVEHH<br>CHKVFPPYKYEPLDEDDWYTEYIFPGGTIVLPSASILLYFQKDVSVVNHWSLNGKHPARGFKEWLKRLDENMDAV<br>KAIFEPFYGSKEEAMKWITYWRVFCITHSEMYAYNNGEEWMLSQVLFKRK |
| JdiNMT1 | MSKGVAKLVERMELGLVSDDEVRRLMRILIEKRLKWGYKPTHEEQLTYLTNFIQGLKGMKIAEEIDALDAKMYEI<br>PIAFMQILCGYSLKFSPGFFEDESTTLDESETIMMDLYCERAQVQDGQSILDLGCGHGGFVLHVAQKYKNCKVT<br>GVTNSVSETEYIMEQCKKLGLSNVEIIADVTKFEPEVTYDRVFAIALIEHMKNYELVLQKLSKWVAQDGFLFVDH<br>HCHKVFPYKYEPIDEDDWYTQYIFPGGTLVLPSASILLYFQEDVSIVNHWTLSGNHPARGFKEWLKRLDDNMDE<br>IKAIFEPFYGSKEEAMKWITYWRVFCITHSEMYAYNGGEEWMISQVLFKRK |
| BthNMT1 | MEVKQAGKEGVTELLVKRMELGLVPEEEIRRLMRIQIQKRLDWGYKPTHEEQLAHLTKFIQNIRGMKMADEID<br>ALDAKMYEIPLPFLQTICGKTLKFSPGYFKDESTTLDESETLMMDLYCERAQVKDGQSILDLGCGHGGFVLHLAQ<br>KYRNSVVTGVTNSVSETEYIKEQCKKLGLSNVEIIIADVTKFEPEVTYDRVFAIALIEHMKNYALVLNKISKWVAQ<br>DGYLFVEHHCHKVFPYKYEPLDEDDWYTNYIFPGGTLILPSASILLYFQEDVTVLNHWSLSGKHPSRGFIEWLKRL<br>DENIDVIMGIFEPFYGSKEEATKWINYWRVFCMTHSEMYAYGNGEEWMLSQVLFKRK |
| MaqNMT3 | MELGLVPEKEIRRLMRIQIQKRLEWGYKPTHEEQLAHLTKFIQNIRGMKMADEIDALDAKMYEIPLPFLQTICGK<br>TLKFSPGYFKDESTTLDESETLMMDLYCERAQVKDGQSILDLGCGHGGFVLHLAQKYRNSIVTGVTNSVSETEYI<br>KEQCKKLGLSNVEIIIADVTKFEPEVTYDRVFAIALIEHMKNYALVLNKISKWVAQDGYLFVEHHCHKVFPYKYEP<br>LDEDDWYTNYIFPGGTLILPSASILLYFQEDVTVLNHWSLSGKHPSRGFIEWLKRLDENIDVIMGIFEPFYGSKEE<br>ATKWINYWRVFCITHSEMYAYGNGEEWMLSQVLLKRK |
| McaNMT4 | MDKANERELKRAELFKKLEDDLVTYDEIKQVMRTELAKRLEWGYKPTHQQQLAHLLDFAHALEGMKIANEVET<br>LASEVYETPLPFXEIVLGPAKKXSSCLFEDESTTLEQAEIAMLDLYFERAQIRXGMSVLDLGCGXGSVGLHIARKY<br>KNCXVTCITNSISQKQYIENQCKLYNLSNVKIILADIVAHDTDDTFDVVLVIGVIEHMKNYALLLNKISKWMAKDG<br>LLFVEHLCHKTFPYHFEPLDEDDWYSNFVFPTGTLTMPSVSFLLYFQADVSILNHWILSGKNFSRTXEEFLKRIDA<br>NVDAIKDGLKPSLGSEGVAKLISYWRGFCLTGMEMFGYNNGEEWMVSQVLFKNK |
| TcoNMT3 | MEDNNNLLQEEMNVVELLQRPELGLVPDEKIRKLTRLQLQKRLWGYKPTHEAQLSHLFQFIHSLPSLNMESED<br>ENPKSWLYETPTSFLQLLYGDCIKESDTYYKEDTATLEEAVINMLELYCERARITEGLSVLDLGCGYGALTLHVAQ<br>KYKSCVTGVTSSISQKQYIMEKCKKLNLTNVEIILADVATIEIEAASYDRIFALGIFEHVNDYKLFLGKLSKWMK<br>QDGLLFVEYLCHKTFPYQNKPLDKGDKWYNEYVFPSGGLIIPSASFILYFQNDVSVVRQWTQGGQHSARTFEELLK<br>RIDGNIDKIKEIFIESYGSKEDAVRFINYWRVFLITGVEMFSYNDGEEWMGAHFLFKKKFIMQE |
| CmuNMT4 | MEVKQSKGDELRSRVAELLERPELGLVPDEEIRRLAKARLEKRLWGYKATHGEQLSSLLQFVESLPSLNMASED<br>DSPKAWLYETPTSFLQLIYGDIIKESGSYYKDESTTLEEAMIHNMNLCCERANIKEGQSVVDLGCGYGAFILHVAQ<br>KYKTCRVTGITSSISQKHYIMEQCKKLNLSNVEVILADVATIKLDATFDRVFAAGMFEHVNDYKSFLRKITNWMK<br>PDGRLFVEHLCNKTFPYQNKPLDDGDNWGEYVFPSGGLIIPSASLLLYFQEDVSIVNHWTFSGKHAANKFEELLK<br>RIDAKIDAIKRIFNECYGSKDSIRFINYWRVFLITAAEMFGYNNGEEWMGVHLLFKKK |
| CtrNMT2 | GLKSSVAELLERPELGLVPDGEIRKLTKTRLAKRLEWGYKATHEDQLSHLLRFIHSLPSLNMASEDDSPKAWLYET<br>PTSFLQLIYGDIIKESGTYYKDESSTLEEAIIHNMDLCCERARIKEGQSVLDLGCGYGAFTLHVAQKYKSCSVTGI<br>TSSISQKDYIMEQCKKLNLSNVEVILADVATIKMNTTFDRVFALGMFEHINDYKLFLRRISNWMKHDGLLFVEHLC<br>NKTFAYQNKPLDDGDDWFNEYVFPSAGLIIPSASLLLYFQEDVSIVHHWTFSGKHAAYKFEELLERIDAKIEAIKE<br>IFIECYGSKEDAIRFINYWRVFLITAAEMFAYRDGEEWMGSHVLFKKK |
| CmuNMT5 | MEAKQHESNNNIDEELKNRVNIGEQEERPGFEDEEIRRLAKAQLAKRLWGYKPTHEQQLSHLLQFLQSLPSLN<br>MASEDESSKAWLYETPTSFLQLLFGNVIKFSGYYYKHESSTFEESMIHNMDLCCERANIKEGQNVIDLGCGYGAF<br>VLHVAQKYKSCSVTGITCSITQKHHIMEECKKLNLCNVKVILADVATIELGTAFDRVFAFGMFEEINDYKLILRKI<br>SNWMKPDGLFFVEHLCHKTLAYQNKLIDDQDWYEEYIFPSGGLIVPSASLLLYFQDDLSVVYHWTYNGKHGARS<br>FEKMLERTDANIDTIKDMFTEFYGSKEKAIKFINYWRVFFITAAEMFAYNDGEEWMCSQLLFKKK |

TABLE 6-continued

N-methyltransferase and N-modifying candidate enzymes

| Name | Sequence |
|---|---|
| CmuNMT8 | MEHKIEDIRKLKSRVEEQLERPELGLVKDEDIKTLAKAKLEKRLKWGYKPTYAEQLSNLLQFAQSLPSLKMENVDD<br>QGSSKQWLYGVPSEFLQIIYGGIIKMSGSYYEDESTTLEESMIKDMDSCCEKANVKEGHSVLDIGCGYGSLIIHIA<br>KKYRTCNVTGITNFVEQKQYIMEECKKLNLSNVEVIVGDGTTINLNTTTFDRVFVTGMLEEINDYKLFLKSVSDWM<br>KPDGLLLVTHFCHKTFAYQNNKALDDEDWHNEYIFPSGNLIVPSASLLLYFQEDLSVVSHWATNGTHTGRTCKK<br>LVERIDANIEKIKEIFSEFYGSKEDAIRMINYWRVLCITGAEMYTCKDGEEWMDVYYLFKKK |

TABLE 7

Variants of BM3 N-demethylase

BM3 variant

| | Genotype |
|---|---|
| 8F11 | L437A |
| 4H9 | L181A, T260A, L437A |
| 8C7 | L75A, L181A |
| 4H5 | L75A, M177A, L181A |
| 7A1 | L75A, M177A, L181A, T260A |

| | Amino Acid Sequence |
|---|---|
| 8F11 | MTIKEMPQPKTFGELKNLPLLNTDKPVQALMKIADELGEIFKFEAPGRVTRY<br>LSSQRLIKEACDESRFDKNLSQALKFARDFAGDGLVTSWTHEKNWKKAHNI<br>LLPSFSQQAMKGYHAMMVDIAVQLVQKWERLNADEHIEVSEDMTRLTLDT<br>IGLCGFNYRFNSFYRDQPHPFIISMVRALDEVMNKLQRANPDDPAYDENKR<br>QFQEDIKVMNDLVDKIIADRKARGEQSDDLLTQMLNGKDPETGEPLDDGNI<br>RYQIITFLIAGHETTSGLLSFALYFLVKNPHVLQKVAEEEAARVLVDPVPSYKQ<br>VKQLKYVGMVLNEALRLWPTAPAFSLYAKEDTVLGGEYPLEKGDEVMVLI<br>PQLHRDKTVWGDDVEEFRPERFENPSAIPQHAFKPFGNGQRACIGQQFALHE<br>ATLVLGMMLKHFDFEDHTNYELDIKETATLKPKGFVVKAKSKKIPLGGIPSP<br>STEQSAKKVRKKAENAHNTPLLVLYGSNMGTAEGTARDLADIAMSKGFAP<br>QVATLDSHAGNLPREGAVLIVTASYNGHPPDNAKQFVDWLDQASADEVKG<br>VRYSVFGCGDKNWATTYQKVPAFIDETLAAKGAENIADRGEADASDDFEG<br>TYEEWREHMWSDVAAYFNLDIENSEDNKSTLSLQFVDSAADMPLAKMHGA<br>FSTNVVASKELQQPGSARSTRHLEIELPKEASYQEGDHLGVIPRNYEGIVNRV<br>TARFGLDASQQIRLEAEEEKLAHLPLAKTVSVEELLQYVELQDPVTRQLRA<br>MAAKTVCPPHKVELEALLEKQAYKEQVLAKRLTMLELLEKYPACEMKFSE<br>FIALLPSIRPRYYSISSSPRVDEKQASITVSVVSGEAWSGYGEYKGIASNYLAE<br>LQEGDTITCFISTPQSEFTLPKDPETPLIMVGPGTGVAPFRGFVQARKQLKEQ<br>GQSLGEAHLYFGCRSPHEDYLYQEELENAQSEGIITLHTAFSRMPNQPKTYV<br>QHVMEQDGKKLIELLDQGAHFYICGDGSQMAPAVEATLMKSYADVHQVSE<br>ADARLWLQQLEEKGRYAKDVWAG |
| 4H9 | MTIKEMPQPKTFGELKNLPLLNTDKPVQALMKIADELGEIFKFEAPGRVTRY<br>LSSQRLIKEACDESRFDKNLSQALKFARDFAGDGLVTSWTHEKNWKKAHNI<br>LLPSFSQQAMKGYHAMMVDIAVQLVQKWERLNADEHIEVSEDMTRLTLDT<br>IGLCGFNYRFNSFYRDQPHPFIISMVRAADEVMNKLQRANPDDPAYDENKR<br>QFQEDIKVMNDLVDKIIADRKARGEQSDDLLTQMLNGKDPETGEPLDDGNI<br>RYQIIAFLIAGHETTSGLLSFALYFLVKNPHVLQKVAEEEAARVLVDPVPSYK<br>QVKQLKYVGMVLNEALRLWPTAPAFSLYAKEDTVLGGEYPLEKGDEVMVL<br>IPQLHRDKTVWGDDVEEFRPERFENPSAIPQHAFKPFGNGQRACIGQQFALH<br>EATLVLGMMLKHFDFEDHTNYELDIKETATLKPKGFVVKAKSKKIPLGGIPS<br>PSTEQSAKKVRKKAENAHNTPLLVLYGSNMGTAEGTARDLADIAMSKGFA<br>PQVATLDSHAGNLPREGAVLIVTASYNGHPPDNAKQFVDWLDQASADEVK<br>GVRYSVFGCGDKNWATTYQKVPAFIDETLAAKGAENIADRGEADASDDFE<br>GTYEEWREHMWSDVAAYFNLDIENSEDNKSTLSLQFVDSAADMPLAKMHG<br>AFSTNVVASKELQQPGSARSTRHLEIELPKEASYQEGDHLGVIPRNYEGIVNR<br>VTARFGLDASQQIRLEAEEEKLAHLPLAKTVSVEELLQYVELQDPVTRTQLR<br>AMAAKTVCPPHKVELEALLEKQAYKEQVLAKRLTMLELLEKYPACEMKFS<br>EFIALLPSIRPRYYSISSSPRVDEKQASITVSVVSGEAWSGYGEYKGIASNYLA<br>ELQEGDTITCFISTPQSEFTLPKDPETPLIMVGPGTGVAPFRGFVQARKQLKE<br>QGQSLGEAHLYFGCRSPHEDYLYQEELENAQSEGIITLHTAFSRMPNQPKTY<br>VQHVMEQDGKKLIELLDQGAHFYICGDGSQMAPAVEATLMKSYADVHQVS<br>EADARLWLQQLEEKGRYAKDVWAG |
| 8C7 | MTIKEMPQPKTFGELKNLPLLNTDKPVQALMKIADELGEIFKFEAPGRVTRY<br>LSSQRLIKEACDESRFDKNLSQAAKFARDFAGDGLVTSWTHEKNWKKAHNI<br>LLPSFSQQAMKGYHAMMVDIAVQLVQKWERLNADEHIEVSEDMTRLTLDT |

TABLE 7-continued

Variants of BM3 N-demethylase

BM3 variant

IGLCGFNYRFNSFYRDQPHPFIISMVRAADEVMNKLQRANPDDPAYDENKR
QFQEDIKVMNDLVDKIIADRKARGEQSDDLLTQMLNGKDPETGEPLDDGNI
RYQIITFLIAGHETTSGLLSFALYFLVKNPHVLQKVAEEAARVLVDPVPSYKQ
VKQLKYVGMVLNEALRLWPTAPAFSLYAKEDTVLGGEYPLEKGDEVMVLI
PQLHRDKTVWGDDVEEFRPERFENPSAIPQHAFKPFGNGQRACIGQQFALHE
ATLVLGMMLKHFDFEDHTNYELDIKETLTLKPKGFVVKAKSKKIPLGGIPSP
STEQSAKKVRKKAENAHNTPLLVLYGSNMGTAEGTARDLADIAMSKGFAP
QVATLDSHAGNLPREGAVLIVTASYNGHPPDNAKQFVDWLDQASADEVKG
VRYSVFGCGDKNWATTYQKVPAFIDETLAAKGAENIADRGEADASDDFEG
TYEEWREHMWSDVAAYFNLDIENSEDNKSTLSLQFVDSAADMPLAKMHGA
FSTNVVASKELQQPGSARSTRHLEIELPKEASYQEGDHLGVIPRNYEGIVNRV
TARFGLDASQQIRLEAEEEKLAHLPLAKTVSVEELLQYVELQDPVTRTQLRA
MAAKTVCPPHKVELEALLEKQAYKEQVLAKRLTMLELLEKYPACEMKFSE
FIALLPSIRPRYYSISSSPRVDEKQASITVSVVSGEAWSGYGEYKGIASNYLAE
LQEGDTITCFISTPQSEFTLPKDPETPLIMVGPGTGVAPFRGFVQARKQLKEQ
GQSLGEAHLYFGCRSPHEDYLYQEELENAQSEGIITLHTAFSRMPNQPKTYV
QHVMEQDGKKLIELLDQGAHFYICGDGSQMAPAVEATLMKSYADVHQVSE
ADARLWLQQLEEKGRYAKDVWAG

4H5    MTIKEMPQPKTFGELKNLPLLNTDKPVQALMKIADELGEIFKFEAPGRVTRY
LSSQRLIKEACDESRFDKNLSQAAKFARDFAGDGLVTSWTHEKNWKKAHNI
LLPSFSQQAMKGYHAMMVDIAVQLVQKWERLNADEHIEVSEDMTRLTLDT
IGLCGFNYRFNSFYRDQPHPFIISAVRAADEVMNKLQRANPDDPAYDENKR
QFQEDIKVMNDLVDKIIADRKARGEQSDDLLTQMLNGKDPETGEPLDDGNI
RYQIITFLIAGHETTSGLLSFALYFLVKNPHVLQKVAEEAARVLVDPVPSYKQ
VKQLKYVGMVLNEALRLWPTAPAFSLYAKEDTVLGGEYPLEKGDEVMVLI
PQLHRDKTVWGDDVEEFRPERFENPSAIPQHAFKPFGNGQRACIGQQFALHE
ATLVLGMMLKHFDFEDHTNYELDIKETLTLKPKGFVVKAKSKKIPLGGIPSP
STEQSAKKVRKKAENAHNTPLLVLYGSNMGTAEGTARDLADIAMSKGFAP
QVATLDSHAGNLPREGAVLIVTASYNGHPPDNAKQFVDWLDQASADEVKG
VRYSVFGCGDKNWATTYQKVPAFIDETLAAKGAENIADRGEADASDDFEG
TYEEWREHMWSDVAAYFNLDIENSEDNKSTLSLQFVDSAADMPLAKMHGA
FSTNVVASKELQQPGSARSTRHLEIELPKEASYQEGDHLGVIPRNYEGIVNRV
TARFGLDASQQIRLEAEEEKLAHLPLAKTVSVEELLQYVELQDPVTRTQLRA
MAAKTVCPPHKVELEALLEKQAYKEQVLAKRLTMLELLEKYPACEMKFSE
FIALLPSIRPRYYSISSSPRVDEKQASITVSVVSGEAWSGYGEYKGIASNYLAE
LQEGDTITCFISTPQSEFTLPKDPETPLIMVGPGTGVAPFRGFVQARKQLKEQ
GQSLGEAHLYFGCRSPHEDYLYQEELENAQSEGIITLHTAFSRMPNQPKTYV
QHVMEQDGKKLIELLDQGAHFYICGDGSQMAPAVEATLMKSYADVHQVSE
ADARLWLQQLEEKGRYAKDVWAG

7A1    MTIKEMPQPKTFGELKNLPLLNTDKPVQALMKIADELGEIFKFEAPGRVTRY
LSSQRLIKEACDESRFDKNLSQAAKFARDFAGDGLVTSWTHEKNWKKAHNI
LLPSFSQQAMKGYHAMMVDIAVQLVQKWERLNADEHIEVSEDMTRLTLDT
IGLCGFNYRFNSFYRDQPHPFIISAVRAADEVMNKLQRANPDDPAYDENKR
QFQEDIKVMNDLVDKIIADRKARGEQSDDLLTQMLNGKDPETGEPLDDGNI
RYQIIAFLIAGHETTSGLLSFALYFLVKNPHVLQKVAEEAARVLVDPVPSYK
QVKQLKYVGMVLNEALRLWPTAPAFSLYAKEDTVLGGEYPLEKGDEVMVL
IPQLHRDKTVWGDDVEEFRPERFENPSAIPQHAFKPFGNGQRACIGQQFALH
EATLVLGMMLKHFDFEDHTNYELDIKETLTLKPKGFVVKAKSKKIPLGGIPS
PSTEQSAKKVRKKAENAHNTPLLVLYGSNMGTAEGTARDLADIAMSKGFA
PQVATLDSHAGNLPREGAVLIVTASYNGHPPDNAKQFVDWLDQASADEVK
GVRYSVFGCGDKNWATTYQKVPAFIDETLAAKGAENIADRGEADASDDFE
GTYEEWREHMWSDVAAYFNLDIENSEDNKSTLSLQFVDSAADMPLAKMHG
AFSTNVVASKELQQPGSARSTRHLEIELPKEASYQEGDHLGVIPRNYEGIVNR
VTARFGLDASQQIRLEAEEEKLAHLPLAKTVSVEELLQYVELQDPVTRTQLR
AMAAKTVCPPHKVELEALLEKQAYKEQVLAKRLTMLELLEKYPACEMKFS
EFIALLPSIRPRYYSISSSPRVDEKQASITVSVVSGEAWSGYGEYKGIASNYLA
ELQEGDTITCFISTPQSEFTLPKDPETPLIMVGPGTGVAPFRGFVQARKQLKE
QGQSLGEAHLYFGCRSPHEDYLYQEELENAQSEGIITLHTAFSRMPNQPKTY
VQHVMEQDGKKLIELLDQGAHFYICGDGSQMAPAVEATLMKSYADVHQVS
EADARLWLQQLEEKGRYAKDVWAG

Nucleotide Sequence

8F11   ATGACCATCAAAGAAATGCCACAACCTAAGACTTTCGGTGAATTGAAGA
ATTTGCCTTTGTTGAACACCGATAAGCCAGTTCAAGCTTTGATGAAGATT
GCTGATGAATTGGGTGAAATCTTCAAGTTTGAAGCTCCAGGTAGAGTCAC
TAGATACTTGTCATCTCAAAGATTGATCAAGAAGCCTGCGACGAATCC
AGATTTGATAAGAATTTGTCTCAAGCTTTGAAGTTCGCTAGAGATTTTGC
TGGTGATGGTTTGGTTACTTCTTGGACTCACGAAAAGAATTGGAAGAAG
GCCCATAACATTTTGTTGCCATCTTTCTCACAACAAGCCATGAAGGGTTA
TCATGCTATGATGGTTGATATCGCCGTTCAATTGGTTCAAAGTGGGAAA
GATTGAACGCCGATGAACATATCGAAGTCTCTGAAGATATGACCAGATT
GACCTTGGATACCATTGGTTTGTGTGGTTTCAACTACAGATTCAACTCCTT
CTACAGAGATCAACCACATCCATTCATCATCTCTATGGTTAGAGCTTTGG

TABLE 7-continued

Variants of BM3 N-demethylase

| BM3 variant | |
|---|---|
| | ATGAAGTCATGAACAAATTGCAAAGAGCTAATCCAGACGATCCAGCTTA
TGACGAAAACAAGAGACAATTCCAAGAAGATATCAAGGTCATGAACGAT
TTGGTCGATAAGATTATCGCTGATAGAAAGGCTAGAGGTGAACAATCTG
ATGATTTGTTGACCCAAATGTTGAACGGTAAGGATCCAGAAACTGGTGA
ACCATTGGATGATGGTAACATCAGATACCAAATTATCACCTTCTTGATTG
CTGGTCACGAAACTACATCTGGTTTGTTGTCTTTTGCCTTGTACTTTTTGG
TTAAGAACCCACACGTCTTGCAAAAGGTTGCTGAAGAAGCTGCAAGAGT
TTTGGTTGATCCAGTTCCATCTTACAAGCAAGTCAAGCAATTGAAGTACG
TTGGTATGGTTTTGAACGAAGCTTTGAGATTGTGGCCAACTGCTCCAGCT
TTTTCATTATACGCTAAAGAAGATACCGTCTTGGGTGGTAATATCCATT
GGAAAAAGGTGATGAAGTTATGGTCTTGATCCCACAATTGCATAGAGAT
AAGACTGTTTGGGGTGATGATGTCGAAGAATTCAGACCAGAAAGATTCG
AAAACCCATCTGCTATTCCACAACATGCTTTTAAGCCATTTGGTAACGGT
CAAAGAGCTTGCATTGGTCAACAATTCGCTTTACATGAAGCTACCTTGGT
TTTGGGTATGATGTTGAAACACTTCGACTTCGAAGATCACACCAACTACG
AATTGGATATCAAAGAAACCGCTACCTTGAAGCCAAAGGGTTTTGTTGTT
AAGGCTAAGTCCAAAAAGATTCCATTGGGTGGTATTCCATCTCCATCTAC
TGAACAATCCGCTAAGAAGGTTAGAAAGAAAGCTGAAAACGCTCATAAC
ACACCTTTGTTGGTCTTGTACGGTTCTAATATGGGTACTGCTGAAGGTAC
AGCAAGAGATTTGGCAGATATTGCTATGTCTAAAGGTTTCGCTCCACAAG
TTGCTACTTTGGATTCTCATGCTGGTAATTTGCCAAGAGAAGGTGCTGTT
TTGATAGTTACTGCTTCTTACAATGGTCACCCACCAGATAATGCTAAGCA
ATTCGTTGATTGGTTGGATCAAGCTTCAGCTGATGAAGTAAAAGGTGTTA
GATACTCTGTTTTCGGTTGCGGTGACAAAAATTGGGCTACTACTTATCAA
AAGGTTCCAGCCTTTATTGACGAAACTTTGGCTGCTAAAGGTGCTGAAAA
CATTGCTGACAGAGGTGAAGCTGATGCCTCCGACGACTTCGAAGGTACT
TACGAAGAATGGAGAGAACACATGTGGTCTGACGTTGCTGCTTACTTCA
ACTTGGACATCGAAAACTCTGAAGACAACAAGTCCACTTTGTCTTTGCAA
TTCGTTGACTCCGCTGCTGACATGCCATTGGCTAAGATGCACGGTGCTTT
CTCTACCAACGTCGTTGCCTCCAAGGAATTGCAACAACCAGGTTCTGCTA
GATCTACTAGACACTTGGAAATCGAATTGCCAAAGGAAGCTTCCTACCA
AGAAGGTGACCACTTGGGCGTTATTCCAAGAAACTACGAAGGTATCGTC
AACAGAGTTACTGCTAGATTCGGTTTGGATGCTTCTCAACAAATCAGATT
AGAAGCTGAAGAAGAAAAAGTTGGCTCACTTGCCATTAGCTAAGACTGTC
TCCGTTGAAGAATTGTTGCAATACGTCGAATTGCAAGACCCAGTTACCAG
AACCCAATTGAGAGCCATGGCTGCCAAGACCGTCTGTCCACCACACAAG
GTTGAATTGGAAGCCTTGTTGGAAAAGCAAGCCTACAAGGAACAAGTTT
TGGCTAAGAGATTGACCATGTTGGAATTGTTGGAAAAGTACCCAGCCTG
CGAAATGAAGTTCTCTGAATTTATCGCCTTGTTGCCATCTATCAGACCAC
GTTACTACTCTATTTCTTCCTCTCCACGTGTTGACGAAAAGCAAGCTTCTA
TTACTGTTTCCGTTGTCTCCGGTGAAGCTTGGTCCGGTTACGGTGAATAC
AAGGGTATTGCTTCTAACTACTTGGCTGAATTGCAAGAAGGTGACACCAT
TACTTGTTTCATCTCTACTCCACAATCCGAATTTACTTTGCCAAAGGACCC
AGAAACTCCATTGATCATGGTTGGTCCAGGTACTGGTGTCGCTCCATTCA
GAGGTTTCGTTCAAGCTAGAAAACAATTGAAGGAACAAGGTCAATCTTT
GGGTGAAGCTCACTTGTACTTCGGTTGTAGATCTCCACACGAAGACTACT
TATACCAAGAAGAATTGGAAAACGCTCAATCCGAAGGTATTATCACTTTT
GCACACCGCTTTCTCCAGAATGCCAAACCAACCAAAGACTTACGTCCAA
CACGTTATGGAACAAGACGGTAAGAAGTTGATTGAATTGTTGGACCAAG
GTGCTCACTTCTACATTTGTGGTGATGGTTCTCAAATGGCTCCAGCCGTT
GAAGCCACTTTGATGAAGTCTTACGCTGATGTTCACCAAGTTTCCGAAGC
CGATGCTAGATTATGGTTGCAACAATTGGAAGAAAAAGGTCGTTACGCT
AAGGATGTCTGGGCCGGTTGA |
| 4H9 | ATGACCATCAAAGAAATGCCACAACCTAAGACTTTCGGTGAATTGAAGA
ATTTGCCTTTGTTGAACACCGATAAGCCAGTTCAAGCTTTGATGAAGATT
GCTGATGAATTGGGTGAAATCTTCAAGTTTGAAGCTCCAGGTAGAGTCAC
TAGATACTTGTCATCTCAAAGATTGATCAAAGAAGCCTGCGACGAATCC
AGATTTGATAAGAATTTGTCTCAAGCTTTGAAGTTCGCTAGAGATTTTGC
TGGTGATGGTTTGGTTACTTCTTGGACTCACGAAAAGAATTGGAAGAAG
GCCCATAACATTTTGTTGCCATCTTTCTCACAACAAGCCATGAAGGGTTA
TCATGCTATGATGGTTGATATCGCCGTTCAATTGGTTCAAAAGTGGGAAA
GATTGAACGCCGATGAACATATCGAAGTCTCTGAAGATATGACCAGATT
GACCTTGGATACCATTGGTTTGTGTGGTTTCAACTACAGATTCAACTCCTT
CTACAGAGATCAACCACATCCATTCATCATCTCTATGGTTAGAGCTGCAG
ATGAAGTCATGAACAAATTGCAAAGAGCTAATCCAGACGATCCAGCTTA
TGACGAAAACAAGAGACAATTCCAAGAAGATATCAAGGTCATGAACGAT
TTGGTCGATAAGATTATCGCTGATAGAAAGGCTAGAGGTGAACAATCTG
ATGATTTGTTGACCCAAATGTTGAACGGTAAGGATCCAGAAACTGGTGA
ACCATTGGATGATGGTAACATCAGATACCAAATTATCGCTTTCTTGATTG
CTGGTCACGAAACTACATCTGGTTTGTTGTCTTTTGCCTTGTACTTTTTGG
TTAAGAACCCACACGTCTTGCAAAAGGTTGCTGAAGAAGCTGCAAGAGT
TTTGGTTGATCCAGTTCCATCTTACAAGCAAGTCAAGCAATTGAAGTACG
TTGGTATGGTTTTGAACGAAGCTTTGAGATTGTGGCCAACTGCTCCAGCT
TTTTCATTATACGCTAAAGAAGATACCGTCTTGGGTGGTAATATCCATT
GGAAAAAGGTGATGAAGTTATGGTCTTGATCCCACAATTGCATAGAGAT |

TABLE 7-continued

Variants of BM3 N-demethylase

| BM3 variant | |
|---|---|
| | AAGACTGTTTGGGGTGATGATGTCGAAGAATTCAGACCAGAAAGATTCG
AAAACCCATCTGCTATTCCACAACATGCTTTTAAGCCATTTGGTAACGGT
CAAAGAGCTTGCATTGGTCAACAATTCGCTTTACATGAAGCTACCTTGGT
TTTGGGTATGATGTTGAAACACTTCGACTTCGAAGATCACACCAACTACG
AATTGGATATCAAAGAAACCGCTACCTTGAAGCCAAAGGGTTTTGTTGTT
AAGGCTAAGTCCAAAAAGATTCCATTGGGTGGTATTCCATCTCCATCTAC
TGAACAATCCGCTAAGAAGGTTAGAAAGAAAGCTGAAAACGCTCATAAC
ACACCTTTGTTGGTCTTGTACGGTTCTAATATGGGTACTGCTGAAGGTAC
AGCAAGAGATTTGGCAGATATTGCTATGTCTAAAGGTTTCGCTCCACAAG
TTGCTACTTTGGATTCTCATGCTGGTAATTTGCCAAGAGAAGGTGCTGTT
TTGATAGTTACTGCTTCTTACAATGGTCACCCACCAGATAATGCTAAGCA
ATTCGTTGATTGGTTGGATCAAGCTTCAGCTGATGAAGTAAAAGGTGTTA
GATACTCTGTTTTCGGTTGCGGTGACAAAAATTGGGCTACTACTTATCAA
AAGGTTCCAGCCTTTATTGACGAAACTTTGGCTGCTAAAGGTGCTGAAAA
CATTGCTGACAGAGGTGAAGCTGATGCCTCCGACGACTTCGAAGGTACT
TACGAAGAATGGAGAGAACACATGTGGTCTGACGTTGCTGCTTACTTCA
ACTTGGACATCGAAAACTCTGAAGACAACAAGTCCACTTTGTCTTTGCAA
TTCGTTGACTCCGCTGCTGACATGCCATTGGCTAAGATGCACGGTGCTTT
CTCTACCAACGTCGTTGCCTCCAAGGAATTGCAACAACCAGGTTCTGCTA
GATCTACTAGACACTTGGAAATCGAATTGCCAAAGGAAGCTTCCTACCA
AGAAGGTGACCACTTGGGCGTTATTCCAAGAAACTACGAAGGTATCGTC
AACAGAGTTACTGCTAGATTCGGTTTGGATGCTTCTCAACAAATCAGATT
AGAAGCTGAAGAAGAAAAGTTGGCTCACTTGCCATTAGCTAAGACTGTC
TCCGTTGAAGAATTGTTGCAATACGTCGAATTGCAAGACCCAGTTACCAG
AACCCAATTGAGAGCCATGGCTGCCAAGACCGTCTGTCCACCACACAAG
GTTGAATTGGAAGCCTTGTTGGAAAAGCAAGCCTACAAGGAACAAGTTT
TGGCTAAGAGATTGACCATGTTGGAATTGTTGGAAAAGTACCCAGCCTG
CGAAATGAAGTTCTCTGAATTTATCGCCTTGTTGCCATCTATCAGACCAC
GTTACTACTCTATTTCTTCCTCTCCACGTGTTGACGAAAAGCAAGCTTCTA
TTACTGTTTCCGTTGTCTCCGGTGAAGCTTGGTCCGGTTACGGTGAATAC
AAGGGTATTGCTTCTAACTACTTGGCTGAATTGCAAGAAGGTGACACCAT
TACTTGTTTCATCTCTACTCCACAATCCGAATTTACTTTGCCAAAGGACCC
AGAAACTCCATTGATCATGGTTGGTCCAGGTACTGGTGTCGCTCCATTCA
GAGGTTTCGTTCAAGCTAGAAAACAATTGAAGGAACAAGGTCAATCTTT
GGGTGAAGCTCACTTGTACTTCGGTTGTAGATCTCCACACGAAGACTACT
TATACCAAGAAGAATTGGAAAACGCTCAATCCGAAGGTATTATCACTTTT
GCACACCGCTTTCTCCAGAATGCCAAACCAACCAAAGACTTACGTCCAA
CACGTTATGGAACAAGACGGTAAGAAGTTGATTGAATTGTTGGACCAAG
GTGCTCACTTCTACATTTGTGGTGATGGTTCTCAAATGGCTCCAGCCGTT
GAAGCCACTTTGATGAAGTCTTACGCTGATGTTCACCAAGTTTCCGAAGC
CGATGCTAGATTATGGTTGCAACAATTGGAAGAAAAAGGTCGTTACGCT
AAGGATGTCTGGGCCGGTTGA |
| 8C7 | ATGACCATCAAAGAAATGCCACAACCTAAGACTTTCGGTGAATTGAAGA
ATTTGCCTTTGTTGAACACCGATAAGCCAGTTCAAGCTTTTGATGAAGATT
GCTGATGAATTGGGTGAAATCTTCAAGTTTGAAGCTCCAGGTAGAGTCAC
TAGATACTTGTCATCTCAAAGATTGATCAAAGAAGCCTGCGACGAATCC
AGATTTGATAAGAATTTGTCTCAAGCTGCTAAGTTCGCTAGAGATTTTGC
TGGTGATGGTTTGGTTACTTCTTGGACTCACGAAAAGAATTGGAAGAAG
GCCCATAACATTTTGTTGCCATCTTTCTCACAACAAGCCATGAAGGGTTA
TCATGCTATGATGGTTGATATCGCCGTTCAATTGGTTCAAAAGTGGGAAA
GATTGAACGCCGATGAACATATCGAAGTCTCTGAAGATATGACCAGATT
GACCTTGGATACCATTGGTTTGTGTGGTTTCAACTACAGATTCAACTCCTT
CTACAGAGATCAACCACATCCATTCATCATCTCTATGGTTAGAGCTGCAG
ATGAAGTCATGAACAAATTGCAAAGAGCTAATCCAGACGATCCAGCTTA
TGACGAAAACAAGAGACAATTCCAAGAAGATATCAAGGTCATGAACGAT
TTGGTCGATAAGATTATCGCTGATAGAAAGGCTAGAGGTGAACAATCTG
ATGATTTGTTGACCCAAATGTTGAACGGTAAGGATCCAGAAACTGGTGA
ACCATTGGATGATGGTAACATCAGATACCAAATTATCACCTTCTTGATTG
CTGGTCACGAAACTACATCTGGTTTGTTGTCTTTTGCCTTGTACTTTTGG
TTAAGAACCCACACGTCTTGCAAAAGGTTGCTGAAGAAGCTGCAAGAGT
TTTGGTTGATCCAGTTCCATCTTACAAGCAAGTCAAGCAATTGAAGTACG
TTGGTATGGTTTTTGAACGAAGCTTTGAGATTGTGGCCAACTGCTCCAGCT
TTTTCATTATACGCTAAAGAAGATACCGTCTTGGGTGGTAATATCCATT
GGAAAAAGGTGATGAAGTTATGGTCTTGATCCCACAATTGCATAGAGAT
AAGACTGTTTGGGGTGATGATGTCGAAGAATTCAGACCAGAAAGATTCG
AAAACCCATCTGCTATTCCACAACATGCTTTTAAGCCATTTGGTAACGGT
CAAAGAGCTTGCATTGGTCAACAATTCGCTTTACATGAAGCTACCTTGGT
TTTGGGTATGATGTTGAAACACTTCGACTTCGAAGATCACACCAACTACG
AATTGGATATCAAAGAAACCTTGACCTTGAAGCCAAAGGGTTTTGTTGTT
AAGGCTAAGTCCAAAAAGATTCCATTGGGTGGTATTCCATCTCCATCTAC
TGAACAATCCGCTAAGAAGGTTAGAAAGAAAGCTGAAAACGCTCATAAC
ACACCTTTGTTGGTCTTGTACGGTTCTAATATGGGTACTGCTGAAGGTAC
AGCAAGAGATTTGGCAGATATTGCTATGTCTAAAGGTTTCGCTCCACAAG
TTGCTACTTTGGATTCTCATGCTGGTAATTTGCCAAGAGAAGGTGCTGTT
TTGATAGTTACTGCTTCTTACAATGGTCACCCACCAGATAATGCTAAGCA |

TABLE 7-continued

Variants of BM3 N-demethylase

| BM3 variant | |
|---|---|
| | ATTCGTTGATTGGTTGGATCAAGCTTCAGCTGATGAAGTAAAAGGTGTTA<br>GATACTCTGTTTTCGGTTGCGGTGACAAAAATTGGGCTACTACTTATCAA<br>AAGGTTCCAGCCTTTATTGACGAAACTTTGGCTGCTAAAGGTGCTGAAAA<br>CATTGCTGACAGAGGTGAAGCTGATGCCTCCGACGACTTCGAAGGTACT<br>TACGAAGAATGGAGAGAACACATGTGGTCTGACGTTGCTGCTTACTTCA<br>ACTTGGACATCGAAAACTCTGAAGACAACAAGTCCACTTTGTCTTTGCAA<br>TTCGTTGACTCCGCTGCTGACATGCCATTGGCTAAGATGCACGGTGCTTT<br>CTCTACCAACGTCGTTGCCTCCAAGGAATTGCAACAACCAGGTTCTGCTA<br>GATCTACTAGACACTTGGAAATCGAATTGCCAAAGGAAGCTTCCTACCA<br>AGAAGGTGACCACTTGGGCGTTATTCCAAGAAACTACGAAGGTATCGTC<br>AACAGAGTTACTGCTAGATTCGGTTTGGATGCTTCTCAACAAATCAGATT<br>AGAAGCTGAAGAAGAAAAGTTGGCTCACTTGCCATTAGCTAAGACTGTC<br>TCCGTTGAAGAATTGTTGCAATACGTCGAATTGCAAGACCCAGTTACCAG<br>AACCCAATTGAGAGCCATGGCTGCCAAGACCGTCTGTCCACCACACAAG<br>GTTGAATTGGAAGCCTTGTTGGAAAAGCAAGCCTACAAGGAACAAGTTT<br>TGGCTAAGAGATTGACCATGTTGGAATTGTTGGAAAAGTACCCAGCCTG<br>CGAAATGAAGTTCTCTGAATTTATCGCCTTGTTGCCATCTATCAGACCAC<br>GTTACTACTCTATTTCTTCCTCTCCACGTGTTGACGAAAAGCAAGCTTCTA<br>TTACTGTTTCCGTTGTCTCCGGTGAAGCTTGGTCCGGTTACGGTGAATAC<br>AAGGGTATTGCTTCTAACTACTTGGCTGAATTGCAAGAAGGTGACACCAT<br>TACTTGTTTCATCTCTACTCCACAATCGGAATTTACTTTGCCAAAGGACCC<br>AGAAACTCCATTGATCATGGTTGGTCCAGGTACTGGTGTCGCTCCATTCA<br>GAGGTTTCGTTCAAGCTAGAAAACAATTGAAGGAACAAGGTCAATCTTT<br>GGGTGAAGCTCACTTGTACTTCGGTTGTAGATCTCCACACGAAGACTACT<br>TATACCAAGAAGAATTGGAAAACGCTCAATCCGAAGGTATTATCACTTT<br>GCACACCGCTTTCTCCAGAATGCCAAACCAACCAAAGACTTACGTCCAA<br>CACGTTATGGAACAAGACGGTAAGAAGTTGATTGAATTGTTGGACCAAG<br>GTGCTCACTTCTACATTTGTGGTGATGGTTCTCAAATGGCTCCAGCCGTT<br>GAAGCCACTTTGATGAAGTCTTACGCTGATGTTCACCAAGTTTCCGAAGC<br>CGATGCTAGATTATGGTTGCAACAATTGGAAGAAAAAGGTCGTTACGCT<br>AAGGATGTCTGGGCCGGTTGA |
| 4H5 | ATGACCATCAAAGAAATGCCACAACCTAAGACTTTCGGTGAATTGAAGA<br>ATTTGCCTTTGTTGAACACCGATAAGCCAGTTCAAGCTTTGATGAAGATT<br>GCTGATGAATTGGGTGAAATCTTCAAGTTTGAAGCTCCAGGTAGAGTCAC<br>TAGATACTTGTCATCTCAAAGATTGATCAAAGAAGCCTGCGACGAATCC<br>AGATTTGATAAGAATTTGTCTCAAGCTGCTAAGTTCGCTAGAGATTTTGC<br>TGGTGATGGTTTGGTTACTTCTTGGACTCACGAAAAGAATTGGAAGAAG<br>GCCCATAACATTTTGTTGCCATCTTTCTCACAACAAGCCATGAAGGGTTA<br>TCATGCTATGATGGTTGATATCGCCGTTCAATTGGTTCAAAAGTGGGAAA<br>GATTGAACGCCATGAACATATCGAAGTCTCTGAAGATATGACCAGATT<br>GACCTTGGATACCATTGGTTTGTGTGGTTTCAACTACAGATTCAACTCCTT<br>CTACAGAGATCAACCACATCCATTCATCATCTCTGCTGTTAGAGCTGCAG<br>ATGAAGTCATGAACAAATTGCAAAGAGCTAATCCAGACGATCCAGCTTA<br>TGACGAAAACAAGAGACAATTCCAAGAAGATATCAAGGTCATGAACGAT<br>TTGGTCGATAAGATTATCGCTGATAGAAAGGCTAGAGGTGAACAATCTG<br>ATGATTTGTTGACCCAAATGTTGAACGGTAAGGATCCAGAAACTGGTGA<br>ACCATTGGATGATGGTAACATCAGATACCAAATTATCACCTTCTTGATTG<br>CTGGTCACGAAACTACATCTGGTTTGTTGTCTTTTGCCTTGTACTTTTTGG<br>TTAAGAACCCACACGTCTTGCAAAAGGTTGCTGAAGAAGCTGCAAGAGT<br>TTTGGTTGATCCAGTTCCATCTTACAAGCAAGTCAAGCAATTGAAGTACG<br>TTGGTATGGTTTTGAACGAAGCTTTGAGATTGTGGCCAACTGCTCCAGCT<br>TTTTCATTATACGCTAAAGAAGATACCGTCTTGGGTGGTAATATCCATT<br>GGAAAAAGGTGATGAAGTTATGGTCTTGATCCCACAATTGCATAGAGAT<br>AAGACTGTTTGGGGTGATGATGTCGAAGAATTCAGACCAGAAAGATTCG<br>AAAACCCATCTGCTATTCCACAACATGCTTTTAAGCCATTTGGTAACGGT<br>CAAAGAGCTTGCATTGGTCAACAATTCGCTTTACATGAAGCTACCTTGGT<br>TTTGGGTATGATGTTGAAACACTTCGACTTCGAAGATCACACCAACTACG<br>AATTGGATATCAAAGAAACCTTGACCTTGAAGCCAAAGGGTTTTGTTGTT<br>AAGGCTAAGTCCAAAAAGATTCCATTGGGTGGTATTCCATCTCCATCTAC<br>TGAACAATCCGCTAAGAAGGTTAGAAAGAAAGCTGAAAACGCTCATAAC<br>ACACCTTTGTTGGTCTTGTACGGTTCTAATATGGGTACTGCTGAAGGTAC<br>AGCAAGAGATTTGGCAGATATTGCTATGTCTAAAGGTTTCGCTCCACAAG<br>TTGCTACTTTGGATTCTCATGCTGGTAATTTGCCAAGAGAAGGTGCTGTT<br>TTGATAGTTACTGCTTCTTACAATGGTCACCCACCAGATAATGCTAAGCA<br>ATTCGTTGATTGGTTGGATCAAGCTTCAGCTGATGAAGTAAAAGGTGTTA<br>GATACTCTGTTTTCGGTTGCGGTGACAAAAATTGGGCTACTACTTATCAA<br>AAGGTTCCAGCCTTTATTGACGAAACTTTGGCTGCTAAAGGTGCTGAAAA<br>CATTGCTGACAGAGGTGAAGCTGATGCCTCCGACGACTTCGAAGGTACT<br>TACGAAGAATGGAGAGAACACATGTGGTCTGACGTTGCTGCTTACTTCA<br>ACTTGGACATCGAAAACTCTGAAGACAACAAGTCCACTTTGTCTTTGCAA<br>TTCGTTGACTCCGCTGCTGACATGCCATTGGCTAAGATGCACGGTGCTTT<br>CTCTACCAACGTCGTTGCCTCCAAGGAATTGCAACAACCAGGTTCTGCTA<br>GATCTACTAGACACTTGGAAATCGAATTGCCAAAGGAAGCTTCCTACCA<br>AGAAGGTGACCACTTGGGCGTTATTCCAAGAAACTACGAAGGTATCGTC<br>AACAGAGTTACTGCTAGATTCGGTTTGGATGCTTCTCAACAAATCAGATT |

TABLE 7-continued

Variants of BM3 N-demethylase

BM3 variant

AGAAGCTGAAGAAGAAAAGTTGGCTCACTTGCCATTAGCTAAGACTGTC
TCCGTTGAAGAATTGTTGCAATACGTCGAATTGCAAGACCCAGTTACCAG
AACCCAATTGAGAGCCATGGCTGCCAAGACCGTCTGTCCACCACACAAG
GTTGAATTGGAAGCCTTGTTGGAAAAGCAAGCCTACAAGGAACAAGTTT
TGGCTAAGAGATTGACCATGTTGGAATTGTTGGAAAAGTACCCAGCCTG
CGAAATGAAGTTCTCTGAATTTATCGCCTTGTTGCCATCTATCAGACCAC
GTTACTACTCTATTTCTTCCTCTCCACGTGTTGACGAAAGCAAGCTTCTA
TTACTGTTTCCGTTGTCTCCGGTGAAGCTTGGTCCGGTTACGGTGAATAC
AAGGGTATTGCTTCTAACTACTTGGCTGAATTGCAAGAAGGTGACACCAT
TACTTGTTTCATCTCTACTCCACAATCCGAATTTACTTTGCCAAAGGACCC
AGAAACTCCATTGATCATGGTTGGTCCAGGTACTGGTGTCGCTCCATTCA
GAGGTTTCGTTCAAGCTAGAAAACAATTGAAGGAACAAGGTCAATCTTT
GGGTGAAGCTCACTTGTACTTCGGTTGTAGATCTCCACACGAAGACTACT
TATACCAAGAAGAATTGGAAAACGCTCAATCCGAAGGTATTATCACTTTT
GCACACCGCTTTCTCCAGAATGCCAAACCAACCAAAGACTTACGTCCAA
CACGTTATGGAACAAGACGGTAAGAAGTTGATTGAATTGTTGGACCAAG
GTGCTCACTTCTACATTTGTGGTGATGGTTCTCAAATGGCTCCAGCCGTT
GAAGCCACTTTGATGAAGTCTTACGCTGATGTTCACCAAGTTTCCGAAGC
CGATGCTAGATTATGGTTGCAACAATTGGAAGAAAAAGGTCGTTACGCT
AAGGATGTCTGGGCCGGTTGA

7A1

ATGACCATCAAAGAAATGCCACAACCTAAGACTTTCGGTGAATTGAAGA
ATTTGCCTTTGTTGAACACCGATAAGCCAGTTCAAGCTTTGATGAAGATT
GCTGATGAATTGGGTGAAATCTTCAAGTTTGAAGCTCCAGGTAGAGTCAC
TAGATACTTGTCATCTCAAAGATTGATCAAAGAAGCCTGCGACGAATCC
AGATTTGATAAGAATTTGTCTCAAGCTGCTAAGTTCGCTAGAGATTTTGC
TGGTGATGGTTTGGTTACTTCTTGGACTCACGAAAAGAATTGGAAGAAG
GCCCATAACATTTTGTTGCCATCTTTCTCACAACAAGCCATGAAGGGTTA
TCATGCTATGATGGTTGATATCGCCGTTCAATTGGTTCAAAAGTGGGAAA
GATTGAACGCCGATGAACATATCGAAGTCTCTGAAGATATGACCAGATT
GACCTTGGATACCATTGGTTTGTGTGGTTTCAACTACAGATTCAACTCCTT
CTACAGAGATCAACCACATCCATTCATCATCTCTGCTGTTAGAGCTGCAG
ATGAAGTCATGAACAAATTGCAAAGAGCTAATCCAGACGATCCAGCTTA
TGACGAAAACAAGAGACAATTCCAAGAAGATATCAAGGTCATGAACGAT
TTGGTCGATAAGATTATCGCTGATAGAAAGGCTAGAGGTGAACAATCTG
ATGATTTGTTGACCCAAATGTTGAACGGTAAGGATCCAGAAACTGGTGA
ACCATTGGATGATGGTAACATCAGATACCAAATTATCGCTTTCTTGATTG
CTGGTCACGAAACTACATCTGGTTTGTTGTCTTTTGCCTTGTACTTTTGG
TTAAGAACCCACACGTCTTGCAAAAGGTTGCTGAAGAAGCTGCAAGAGT
TTTGGTTGATCCAGTTCCATCTTACAAGCAAGTCAAGCAATTGAAGTACG
TTGGTATGGTTTTGAACGAAGCTTTGAGATTGTGGCCAACTGCTCCAGCT
TTTTCATTATACGCTAAAGAAGATACCGTCTTGGGTGGTGAATATCCATT
GGAAAAAGGTGATGAAGTTATGGTCTTGATCCCACAATTGCATAGAGAT
AAGACTGTTTGGGGTGATGATGTCGAAGAATTCAGACCAGAAAGATTCG
AAAACCCATCTGCTATTCCACAACATGCTTTTAAGCCATTTGGTAACGGT
CAAAGAGCTTGCATTGGTCAACAATTCGCTTTACATGAAGCTACCTTGGT
TTTGGGTATGATGTTGAAACACTTCGACTTCGAAGATCACACCAACTACG
AATTGGATATCAAAGAAACCTTGACCTTGAAGCCAAAGGGTTTTGTTGTT
AAGGCTAAGTCCAAAAAGATTCCATTGGGTGGTATTCCATCTCCATCTAC
TGAACAATCCGCTAAGAAGGTTAGAAAGAAAGCTGAAAACGCTCATAAC
ACACCTTTGTTGGTCTTGTACGGTTCTAATATGGGTACTGCTGAAGGTAC
AGCAAGAGATTTGGCAGATATTGCTATGTCTAAAGGTTTCGCTCCACAAG
TTGCTACTTTGGATTCTCATGCTGGTAATTTGCCAAGAGAAGGTGCTGTT
TTGATAGTTACTGCTTCTTACAATGGTCACCCACCAGATAATGCTAAGCA
ATTCGTTGATTGGTTGGATCAAGCTTCAGCTGATGAAGTAAAAGGTGTTA
GATACTCTGTTTTCGGTTGCGGTGACAAAAATTGGGCTACTACTTATCAA
AAGGTTCCAGCCTTTATTGACGAAACTTTGGCTGCTAAAGGTGCTGAAAA
CATTGCTGACAGAGGTGAAGCTGATGCCTCCGACGACTTCGAAGGTACT
TACGAAGAATGGAGAGAACACATGTGGTCTGACGTTGCTGCTTACTTCA
ACTTGGACATCGAAAACTCTGAAGACAACAAGTCCACTTTGTCTTTGCAA
TTCGTTGACTCCGCTGCTGACATGCCATTGGCTAAGATGCACGGTGCTTT
CTCCTACCAACGTCGTTGCCTCCAAGGAATTGCAACAACCAGGTTCTGCTA
GATCTACTAGACACTTGGAAATCGAATTGCAAAGGAAGCTTCCTACCA
AGAAGGTGACCACTTGGGCGTTATTCCAAGAAACTACGAAGGTATCGTC
AACAGAGTTACTGCTAGATTCGGTTTGGATGCTTCTCAACAAATCAGATT
AGAAGCTGAAGAAGAAAAGTTGGCTCACTTGCCATTAGCTAAGACTGTC
TCCGTTGAAGAATTGTTGCAATACGTCGAATTGCAAGACCCAGTTACCAG
AACCCAATTGAGAGCCATGGCTGCCAAGACCGTCTGTCCACCACACAAG
GTTGAATTGGAAGCCTTGTTGGAAAAGCAAGCCTACAAGGAACAAGTTT
TGGCTAAGAGATTGACCATGTTGGAATTGTTGGAAAAGTACCCAGCCTG
CGAAATGAAGTTCTCTGAATTTATCGCCTTGTTGCCATCTATCAGACCAC
GTTACTACTCTATTTCTTCCTCTCCACGTGTTGACGAAAGCAAGCTTCTA
TTACTGTTTCCGTTGTCTCCGGTGAAGCTTGGTCCGGTTACGGTGAATAC
AAGGGTATTGCTTCTAACTACTTGGCTGAATTGCAAGAAGGTGACACCAT
TACTTGTTTCATCTCTACTCCACAATCCGAATTTACTTTGCCAAAGGACCC
AGAAACTCCATTGATCATGGTTGGTCCAGGTACTGGTGTCGCTCCATTCA

TABLE 7-continued

Variants of BM3 N-demethylase

BM3 variant

```
GAGGTTTCGTTCAAGCTAGAAAACAATTGAAGGAACAAGGTCAATCTTT
GGGTGAAGCTCACTTGTACTTCGGTTGTAGATCTCCACACGAAGACTACT
TATACCAAGAAGAATTGGAAAACGCTCAATCCGAAGGTATTATCACTTT
GCACACCGCTTTCTCCAGAATGCCAAACCAACCAAAGACTTACGTCCAA
CACGTTATGGAACAAGACGGTAAGAAGTTGATTGAATTGTTGGACCAAG
GTGCTCACTTCTACATTTGTGGTGATGGTTCTCAAATGGCTCCAGCCGTT
GAAGCCACTTTGATGAAGTCTTACGCTGATGTTCACCAAGTTTCCGAAGC
CGATGCTAGATTATGGTTGCAACAATTGGAAGAAAAAGGTCGTTACGCT
AAGGATGTCTGGGCCGGTTGA
```

TABLE 8 pA24, pA25, and pA26 sequences

| | |
|---|---|
| pA24 Sequence | cctcgccgcagttaattaaagtcagtgagcgaggaagcgcgtaactataacggtcctaaggtagcgaatcct gatgcggtattttctccttacgcatctgtgcggtatttcacaccgcatagatcggcaagtgcacaaacaata cttaaataaatactactcagtaataacctatttcttagcattttgacgaaatttgctattttgttagagtc ttttacaccatttgtctccacacctccgcttacatcaacaccaataacgccatttaatctaagcgcatcacc aacattttctggcgtcagtccaccagctaacataaaatgtaagctttcggggctctcttgccttccaaccca gtcagaaatcgagttccaatccaaaagttcacctgtcccacctgcttctgaatcaaacaagggaataaacga atgaggtttctgtgaagctgcactgagtagtatgttgcagtcttttggaaatacgagtcttttaataactgg caaaccgaggaactcttggtattcttgccacgactcatctccatgcagtggagccaatcaattcttgcggtc aactttggacgatatcaatgccgtaatcattgaccagagccaaaacatcctccttaagttgattacgaaaca cgccaaccaagtatttcggagtgcctgaactatttttatatgcttttacaagacttgaaattttccttgcaa taaccgggtcaattgttctcttctattgggcacacatataatacccagcaagtcagcatcggaatctagag cacattctgcggcctctgtgctctgcaagccgcaaactttcaccaatggaccagaactacctgtgaaattaa taacagacatactccaagctgcctttgtgtgcttaatcacgtatactcacgtgctcaatagtcaccaatgcc ctccctcttggccctctccttttcttttttcgaccgaattaattcttaatcggcaaaaaaagaaaagctccg gatcaagattgtacgtaaggtgacaagctatttttcaataaagaatatcttccactactgccatctggcgtc ataactgcaaagtacacatatattacgatgctgttctattaaatgcttcctatattatatatagtaatgt cgtgatctatggtgcactctcagtacaatctgctctgatgccgcatagttaagccagccccgacacccgcca acacccgctgacgcgccctgacgggcttgtctgctcccggcatccgcttacagacaagctgtgaccgtctcc gggagctgcatgtgtcagaggttttcaccgtcatcaccgaaacgcgcgagacgaaagggcctcgtgatacgc ctatttttataggttaatgtcatgataataatggtttcttagacggatcgcttgcctgtaacttacacgcgc ctcgtatctctttaatgatggaataatttgggaatttactctgtgtttattttttatgttttgtatttgg attttagaaagtaaataaggaaggtagaagagttacggaatgaagaaaaaaaataaacaaaggtttaaaaa atttcaacaaaaagcgtactttacatatatatttattagacaagaaaagcagattaaatagatatacattcg attaacgataagtaaaatgtaaaatcacaggattttcgtgtgtggtcttctacacagacaaggtgaaacaat tcggcattaatacctgagagcaggaagagcaagataaaaggtagtatttgttggcgatccccctagagtctt ttacatcttcggaaaacaaaaactattttttcttttaatttcttttttttactttctatttttaatttatatat ttatattaaaaaatttaaattataattatttttatagcacgtgatgaaaaggaccaggtggcacttttcgg ggaaatgtgcgcggaacccctattgtttatttttctaaatacattcaaatatgtatccgctcatgagacaa taaccctgataaatgcttcaataatattgaaaaaggaagagtatgagtattcaacatttccgtgtcgccctt attccctttttttgcggcattttgccttcctgttttgctcacccagaaacgctggtgaaagtaaaagatgct gaagatcagttgggacgcgtagtctagaccagccaggacagaaatgcctcgacttcgctgctacccaaggtt gccgggtgacgcacaccgtggaaacggatgaaggcacgaacccagtggacataagcctgttcggttcgtaag ctgtaatgcaagtagcgtatgcgctcacgcaactggtccagaaccttgaccgaacgcagcggtggtaacggc gcagtggcggttttcatggcttgttatgactgtttttttggggtacagtctatgcctcgggcatccaagcag caagcgcgttacgccgtgggtcgatgtttgatgtttatggagcagcaacgatgttacgcagcagggcagtcgc cctaaaacaaagttaaacattatgagggaagcggtgatcgccgaagtatcgactcaactatcagaggtagtt ggcgccatcgagcgccatctcgaaccgacgttgctggccgtacatttgtacggctccgcagtggatggcggc ctgaagccacacagtgatattgatttgctggttacggtgaccgtaaggcttgatgaaacaacgcggcagct tgatcaacgacctttggaaacttcggcttcccctggagagagcgagattctccgcgctgtagaagtcacc attgttgtgcacgacgacatcattccgtggcgttatccagctaagcgcgaactgcaatttggagaatggcag cgcaatgacattcttgcaggtatcttcgagccagccacgatcgacattgatctggctatcttgctgacaaaa gcaagagaacatagcgttgccttggtaggtccagcggcggagaactctttgatccggttcctgaacaggat ctatttgaggcgctaaatgaaaccttaacgctatggaactcgccgcccgactgggctggcgatgagcgaaat gtagtgcttacgttgtcccgcatttggtacagcgcagtaaccggcaaaatcgcgccgaaggatgtcgctgcc ggctgggcaatggagcgcctgccggcccagtatcagcccgtcatacttgaagctagacaggcttatcttgga caagaagaagatcgcttggcctcgcgcgcagatcagttggaagaatttgtccactacgtgaaaggcgagatc accaaggtagtcggcaaataaccctcgagcattcaaggcgccttgattatttgacgtggtttgatgcctcc acgcacgttgtgatatgtagatgattcagttcgagtttatcattatcaatactgccatttcaaagaatacgt aaataattaatagtagtgattttcctaacttatttagtcaaaaaattagccttttaattctgctgtaaccc gtacatgcccaaaataggggggcgggttacacagaatatataacatcgtaggtgtctgggtgaacagtttatt cctggcatccactaaatataatggagcccgctttttaagctggcatccagaaaaaaaagaatcccagcact aaaatattgttttcttcaccaaccatcagttcataggtccattctcttagcgcaactacagagaacagggc acaaacaggcaaaaaacgggcacaacctcaatggagtgatgcaacctgcctggagtaaatgatgacacaagg caattgacccacgcatgtatctatctcattttcttacaccttctattaccttctgctctctctgatttggaa aagctgaaaaaaaaggttgaaaccagttccctgaaattattccccctacttgactaataagtatataaagag ggtaggtattgattgtaattctgtaaatctatttcttaaactttcttaaattctacttttatagttagtcttt ttttagttttaaaacaccaagaacttagtttcgaatcaaacacacataaacaaacaaaacaggccccttttc ctttgtcgatatcatgtaattagttatgtcacgcttacattcacgccctcctcccacatccgctctaaccga aaaggaaggagttagacaacctgaagtctaggtccctatttattttttttaatagttatgttagtattaaga |

TABLE 8-continued pA24, pA25, and pA26 sequences

|   |   |
|---|---|
|   | acgttatttatatttcaaattttctttttttctgtacaaacgcgtgtacgcatgtaacattatactgaaa<br>accttgcttgagaaggttttgggacgctcgaaggctttaatttgtaatcattatcactttacgggtcctttc<br>cggtgatccgacaggttacggggcggcgacctcgcgggttttcgctatttatgaaaattttccggtttaagg<br>cgtttccgttcttcttcgtcataacttaatgttttttatttaaaatacctcgcgagtggcaacactgaaaata<br>cccatggagcggcgtaaccgtcgcacaggatctaggtgaagatcctttttgataatctcatgaccaaaatcc<br>cttaacgtgagttttcgttccactgagcgtcagaccccgtagaaaagatcaaaggatcttcttgagatcctt<br>tttttctgcgcgtaatctgctgcttgcaaacaaaaaaaccaccgctaccagcggtggtttgtttgccggatc<br>aagagctaccaactctctttccgaaggtaactggcttcagcagagcgcagataccaaatactgtccttctagt<br>gtagccgtagttaggccaccacttcaagaactctgtagcaccgcctacatacctcgctctgctaatcctgtt<br>accagtggctgctgccagtggcgataagtcgtgtcttaccgggttggactcaagacgatagttaccggataa<br>ggcgcagcggtcgggctgaacggggggttcgtgcacacagcccagcttggagcgaacgacctacaccgaact<br>gagatacctacagcgtgagctatgagaaagcgccacgcttcccgaagggagaaaggcggacaggtatccggt<br>aagcggcagggtcggaacaggagagcgcacgagggagcttccaggggaaacgcctggtatctttatagtcc<br>tgtcgggtttcgccacctctgacttgagcgtcgatttttgtgatgctcgtcagggggcggagcctatggaa<br>aaacgccagcaacgcggcagtggaacgtgcattatgaattagttacgctagggataacagggtaatatagaa<br>cccgaacgaccgagcgcagcggcggccgcgctgataccgccgc |
| pA25<br>sequence | aacgacctacaccgaactgagatacctacagcgtgagctatgagaaagcgccacgcttcccgaagggagaaa<br>ggcggacaggtatccggtaagcggcagggtcggaacaggagagcgcacgagggagcttccaggggaaacgc<br>ctggtatctttatagtcctgtcgggtttcgccacctctgacttgagcgtcgatttttgtgatgctcgtcagg<br>ggggcggagcctatggaaaaacgccagcaacgcggcagtggaacgtgcattatgaattagttacgctaggga<br>taacagggtaatatagaacccgaacgaccgagcgcagcggcggccgcgctgataccgccgcctcgccgcag<br>ttaattaaagtcagtgagcgaggaagcgcgtaactataacggtcctaaggtagcgaatcctgatcgcggtatt<br>ttctccttacgcatctgtgcggtatttcacaccgcatagatcggcaagtgcacaaacaatacttaaataaat<br>actactcagtaataacctatttcttagcatttttgacgaaatttgctattttgttagagtcttttacaccat<br>ttgtctccacacctccgcttacatcaacaccaataacgccatttaatctaagcgcatcaccaacatttctg<br>gcgtcagtccaccagctaacataaaatgtaagattcggggctctcttgccttccaaccagtcagaaatcga<br>gttccaatccaaaagttcacctgtcccacctgcttctgaatcaaacaagggaataaacgaatgaggtttctg<br>tgaagctgcactgagtagtatgttgcagtcttttggaaatacgagtcttttaataactggcaaaccgaggaa<br>ctcttggtattcttgccacgactcatctccatgcagtggagccaatcaattcttgcggtcaactttggacga<br>tatcaatgccgtaatcattgaccagagccaaaacatcctccttaagttgattacgaaacacgccaaccaagt<br>atttcggagtgcctgaactattttttatatgcttttacaagacttgaaattttccttgcaataaccgggtcaa<br>ttgttctctttctattgggcacacatataatacccagcaagtcagcatcggaatctagaacacattctgcgg<br>cctctgtgctctgcaagccgcaaactttcaccaatggaccagaactacctgtgaaattaataacagacatac<br>tccaagctgcctttgtgtgcttaatcacgtatactcacgtgctcaatagtcaccaatgccctccctcttggc<br>cctctcctttttcttttttcgaccgaattaattcttaatcggcaaaaaaagaaaagctccggatcaagattgt<br>acgtaaggtgacaagctatttttcaataaagaatatcttccactactgccatctggcgtcataactgcaaag<br>tacacatatattacgatgctgttctattaaatgcttcctatattatatatagtaatgtcgtgatctatgg<br>tgcactctcagtacaatctgctctgatgccgcatagttaagccagccccgacacccgccaacacccgctgac<br>gcgccctgacgggcttgtctgctcccggcatccgcttacagacaagctgtgaccgtctccgggagctgcatg<br>tgtcagaggttttcaccgtcatcaccgaaacgcgcgagacgaaagggcctcgtgatacgcctatttttatag<br>gttaatgtcatgataataatggtttcttagacggatcgcttgcctgtaacttacacgcgcctcgtatctttt<br>aatgatggaataatttgggaatttactctgtgtttatttattttatgttttgtatttggattttagaaagt<br>aaataaagaaggtagaagagttacggaatgaagaaaaaaaataaaggttttaaaaaatttcaacaaaa<br>agcgtactttacatatatatttattagacaagaaaagcagattaaatagatatacattcgattaacgataag<br>taaaatgtaaaatcacaggattttcgtgtgtggtcttctacacagacaaggtgaaacaattcggcattaata<br>cctgagagcaggaagagcaagataaaaggtagtatttgttggcgatcccctagagtcttttacatcttcgg<br>aaaacaaaaactattttttctttaatttctttttttactttctattttttaattttatataattatattaaaaa<br>atttaaattataatttatttttatagcacgtgatgaaaaggaccccaggtggcacttttcggggaaatgtgcgc<br>ggaacccctatttgttttatttttctaaatacattcaaatatgtatccgctcatgagacaataaccctgataa<br>atgcttcaataatattgaaaaaggaagagtatgagtattcaacatttccgtgtcgcccttattccctttttt<br>gcggcattttgccttcctgttttgctcacccagaaacgctggtgaaagtaaaagatgctgaagatcagttg<br>ggacgcgtagtctagaccagccaggacagaaatgcctgcacttcgctgctacccaaggttgccgggtgacgc<br>acaccgtggaaacggatgaaggcacgaacccagtggacataagcctgttccggttcgtaagctgtaatgcaag<br>tagcgtatgcgctcacgcaactggtccagaaccttgaccgaacgcagcggtggtaacggcgcagtggcggtt<br>ttcatggcttgttatgactgttttttggggtacagtctatgcctcgggcatccaagcagcaagcgcgttac<br>gccgtgggtcgatgtttgatgttatgagcagcaacgatgttacgcagcagggcagtcgccctaaaacaaag<br>ttaaacattatgagggaagcggtgatcgccgaagtatcgactcaactatcagaggtagttggcgccatcgag<br>cgccatctcgaaccgacgttgctggccgtacattgtacggctccgcagtggatggcggcctgaagccacac<br>agtgatattgatttgctggttacggtgaccgtaaggcttgatgaaacaacgcggcgagctttgatcaacgac<br>cttttggaaacttcggcttccctggagagagcgagattctccgcgtctgtagaagtcaccatttgttgtgcac<br>gacgacatcattccgtggcgttatccagctaagcgcgaactgcaattggagaatggcagcgcaatgacatt<br>cttgcaggtatcttcgagccagccacgatcgacattgatctggctatcttgctgacaaaagcaagagaacat<br>agcgttgccttggtaggtccagcggcggaggaactctttgatccggttcctgaacaggatctatttgaggcg<br>ctaaatgaaaccttaacgctatggaactcgccgcccgactgggctggcgatgagcgaaatgtagtgcttacg<br>ttgtcccgcatttggtacagcgcagtaaccggcaaaatcgcgccgaaggatgtcgctgccggctgggcaatg<br>gagcgcctgccggcccagtatcagcccgtcatacttgaagctagacaggcttatcttggacaagaagaagat<br>cgcttggcctcgcgcgcagatcagttggaagaatttgtccactacgtgaaaggcgagatcaccaaggtagtc<br>ggcaaataaccctcgagcattcaaggccttgattatttgacgtggtttgatggcctccacgcacgttgtg<br>atatgtagatgagagcgttggttggtggatcaagcccacgcgtaggcaatcctcgagcagatccgccaggcg<br>tgtatatatagcgtggatggccaggcaacttagtgctgacacatacaggcatatatatgtgtgcgacaa<br>cacatgatcatatggcatgcatgtgctctgtatgtatataaaactcttgttttcttcttttctctaaatatt<br>ctttccttatacattaggacctttgcagcataaattactatacttctatagacacaaacaacaaatacaca<br>cactaaattaataacaggcccttttccttttgtcgatatcatgtaattagttatgtcacgcttacattcacg<br>ccctccccccacatccgctctaaccgaaaaggaaggagttagacaacctgaagtctaggtccctatttattt<br>ttttatagttatgttagtattaagaacgttatttatatttcaaatttttctttttttctgtacaaacgcgt<br>gtacgcatgtaacattatactgaaaaccttgcttgagaaggttttgggacgctcgaaggctttaatttgtaa<br>tcattatcactttacgggtccttttccggtgatccgacaggttacggggcggcgacctcgcgggttttcgcta |

TABLE 8-continued pA24, pA25, and pA26 sequences tttatgaaaattttccggtttaaggcgtttccgttcttcttcgtcataacttaatgtttttatttaaaatac
ctcgcgagtggcaacactgaaaatacccatggagcggcgtaaccgtcgcacaggatctaggtgaagatcctt
tttgataatctcatgaccaaaatcccttaacgtgagtttttcgttccactgagcgtcagacccccgtagaaaag
atcaaaggatcttcttgagatcctttttttctgcgcgtaatctgctgcttgcaaacaaaaaaaccaccgcta
ccagcggtggtttgtttgccggatcaagagctaccaactcttttttccgaaggtaactggcttcagcagagcg
cagataccaaatactgtccttctagtgtagccgtagttaggccaccacttcaagaactctgtagcaccgcct
acatacctcgctctgctaatcctgttaccagtggctgctgccagtggcgataagtcgtgtcttaccgggttg
gactcaagacgatagttaccggataaggcgcagcggtcgggctgaacggggggttcgtgcacacagcccagc
ttggagcg pA26 sequence
acgacctacaccgaactgagatacctacagcgtgagctatgagaaagcgccacgcttcccgaagggagaaag
gcggacaggtatccggtaagcggcagggtcggaacaggagagcgcacgagggagcttccaggggggaaacgcc
tggtatctttatagtcctgtcgggtttcgccacctctgacttgagcgtcgatttttgtgatgctcgtcaggg
gggcggagcctatggaaaaacgccagcaacgcggcagtggaacgtgcattatgaattagttacgctagggat
aacagggtaatatagaacccgaacgaccgagcgcagcggcggccgcgctgataccgccgccctcgccgcagt
taattaaagtcagtgagcgaggaagcgcgtaactataacggtcctaaggtagcgaatcctgatgcggtattt
tctccttacgcatctgtgcggtatttcacaccgcatagatcggcaagtgcacaaacaatacttaaataaata
ctactcagtaataacctatttcttagcattttttgacgaaatttgctattttgttagagtcttttacaccatt
tgtctccacacctccgcttacatcaacaccaataacgccatttaatctaagcgcatcaccaacattttctgg
cgtcagtccaccagctaacataaaatgtaagctttcggggctctcttgccttccaacccagtcagaaatcga
gttccaatccaaaagttcacctgtcccacctgcttctgaatcaaacaagggaataaacgaatgaggtttctg
tgaagctgcactgagtagtatgttgcagtcttttggaaatacgagtcttttaataactggcaaaccgaggaa
ctcttggtattcttgccacgactcatctccatgcagtggagccaatcaattcttgcggtcaacttttggacga
tatcaatgccgtaatcattgaccagagccaaaacatcctccttaagttgattacgaaacacgccaaccaagt
atttcggagtgcctgaactattttttatatgcttttacaagacttgaaattttccttgcaataaccgggtcaa
ttgttctctttctattgggcacacatataatacccagcaagtcagcatcggaatctagagcacattctgcgg
cctctgtgctctgcaagccgcaaactttcaccaatggaccagaactacctgtgaaattaataacagacatac
tccaagctgcctttgtgtgcttaatcacgtatactcacgtgctcaatagtcaccaatgccctccctcttggc
cctctccttttcttttttcgaccgaattaattcttaatcggcaaaaaaagaaaagctccggatcaagattgt
acgtaaggtgacaagctatttttcaataaagaatatcttccactactgccatctggcgtcataactgcaaag
tacacatatattacgatgctgttctattaaatgcttcctatattatatatagtaatgtcgtgatctatgg
tgcactctcagtacaatctgctctgatgccgcatagttaagccagccccgacacccgccaacacccgctgac
gcgcccctgacgggcttgtctgctcccggcatccgcttacagacaagctgtgaccgtctccgggagctgcatg
tgtcagaggttttcaccgtcatcaccgaaacgcgcgagacgaaagggcctcgtgatacgcctatttttatag
gttaatgtcatgataataatggtttcttagacggatcgcttgcctgtaacttacacgcgcctcgtatcttt
aatgatggaataatttgggaatttactctgtgtttatttatttttatgttttgtatttggatttttagaaagt
aaataaagaaggtagaagagttacggaatgaagaaaaaaaataaacaaaggtttaaaaaatttcaacaaaa
agcgtactttacatatatatttattagacaagaaaagcagattaaatagatacattcgattaacgataag
taaaatgtaaaatcacaggattttcgtgtgtggtcttctacacagacaaggtgaaacaattcggcattaata
cctgagagcaggaagagcaagataaaaggtagtattttgtggcgatcccctagagtctttttacatcttcgg
aaaacaaaaactatttttttctttaatttcttttttttacttttctattttttaatttatatatttatattaaaaa
atttaaattataattattttatagcacgtgatgaaaaggaccaggtggcacttttcggggaaatgtgcgc
ggaaccccctatttgttttattttttctaaatacattcaaatatgtatccgctcatgagacaataaccctgataa
atgcttcaataatattgaaaaaggaagagtatgagtattcaacattcccgtgtcgcccttattcccttttttt
gcggcattttgccttcctgtttttgctcacccagaaacgctggtgaaagtaaaagatgctgaagatcagttg
ggacgcgtagtctagaccagccaggacagaaatgcctcgacttcgctgctacccaaggttgccgggtgacgc
acaccgtggaaacggatgaaggcacgaacccagtggacataagcctgttcggttcgtaagctgtaatgcaag
tagcgtatgcgctcacgcaactgtccagaaaccttgaccgaacgcagcggtggtaacggcgcagtggcggtt
ttcatggcttgttatgactgtttttttggggtacagtctatgcctcgggcatccaagcagcaagcggcgttac
gccgtgggtcgatgtttgatgttatggagcagcaacgatgttacgcagcagggcagtcgccctaaaacaaag
ttaaacattatgagggaagcggtgatcgccgaagtatcgactcaactatcagaggtagttggcgccatcgag
cgccatctcgaaccgacgttgctggccgtacatttgtacggctccgcagtggatggcggcctgaagccacac
agtgatattgatttgctggttacggtgaccgtaaggcttgatgaaacaacgcggcgagcttttgatcaacgac
cttttggaaacttcggcttcccctggagagagcgagattctccgcgctgtagaagtcaccattgttgtgcac
gacgacatcattccgtggcgttatccagctaagcgcgaactgcaatttggagaatggcagcgcaatgacatt
cttgcaggtatcttcgagccagccacgatcgacattgatctggctatcttgctgacaaaagcaagagaacat
agcgttgccttggtaggtccagcggcggaggaactctttgactccggttcctgaacaggatctatttgaggcg
ctaaatgaaaccttaacgctatggaactcgccgcccgactgggctggcgatgagcgaaatgtagtgcttacg
ttgtcccgcatttggtacagcgcagtaaccggcaaaatcgcgccgaaggatgtcgctgccggctgggcaatg
gagcgcctgccggcccagtatcagcccgtcatacttgaagctagacaggcttatcttggacaagaagaagat
cgcttggcctcgcgcgcagatcgttggaagaatttgtccactacgtgaaaggcgagatcaccaaggtagtc
ggcaaataaccctcgagcattcaaggcgccttgattatttgacgtggtttgatggcctccacgcacgttgtg
atatgtagatgactcgtaggaacaatttcgggcccctgcgtgttcttctgaggttcatcttttacatttgct
tctgctggataattttcagaggcaacaaggaaaaattagatggcaaaaagtcgtctttcaaggaaaaatccc
caccatctttcgagatcccctgtaacttattggcaaactaaaatgaggaaatacaaaatatac
tagaactgaaaaaaaaaagtataaatagagacgatatatgccaatacttcacaatgttcgaatctattctt
catttgcagctattgtaaaataataaaacatcaagaacaaacaagctcaacttgtcttttctaagaacaaag
aataaacacaaaaacaaaagtttttttaattttaatcaaaaaacaggccccttttcctttgtcgatatcat
gtaattagttatgtcacgcttacattcacgccctccccccacatccgctctaaccgaaaaggaaggagttag
acaacctgaagtctaggtccctatttatttttttatagttatgttagtattaagaacgttatttatatttca
aatttttcttttttttctgtacaaacgcgtgtacgcatgtaacattatactgaaaaccttgcttgagaaggt
tttgggacgctcgaaggctttaatttgtaatcattatcactttacgggtccttttccggtgatccgacaggtt
acggggcggcgacctcgcgggttttcgctatttatgaaaattttccggtttaaggcgtttccgttcttcttc
gtcataacttaatgtttttatttaaaatacctcgcgagtggcaacactgaaaatacccatggagcggcgtaa
ccgtcgcacaggatctaggtgaagatccttttgataatctcatgaccaaaatcccttaacgtgagttttcg
ttccactgagcgtcagaccccgtagaaaagatcaaaggatcttcttgagatcctttttttctgcgcgtaatc
tgctgcttgcaaacaaaaaaaccaccgctaccagcggtggtttgtttgccggatcaagagctaccaactctct
tttccgaaggtaactggcttcagcagagcgcagataccaaatactgtccttctagtgtagccgtagttaggc

TABLE 8-continued pA24, pA25, and pA26 sequences caccacttcaagaactctgtagcaccgcctacatacctcgctctgctaatcctgttaccagtggctgctgcc
agtggcgataagtcgtgtcttaccgggttggactcaagacgatagttaccggataaggcgcagcggtcgggc
tgaacgggggttcgtgcacacagcccagcttggagcga

TABLE 9

| Tailoring enzymes | | |
| --- | --- | --- |
| Reaction Catalyzed | Enzyme | Species |
| Carbon-carbon coupling | Berberine bridge enzyme (BBE) | Ps, Ec, Cj, Bs, Tf |
|  | Salutaridine synthase (SalSyn) | Ps |
|  | Corytuberine synthase (CorSyn) | Cj |
| Oxidation | Tetrahydroprotoberberine oxidase (STOX) | Cj, Am, Bw |
|  | Dihydrobenzophenanthridine oxidase (DBOX) | Ps |
|  | Methylstylopine hydroxylase (MSH) | Ps |
|  | Protopine 6-hydroxylase (P6H) | Ps, Ec |
| Methylenedioxy bridge formation | Stylopine synthase (StySyn) | Ps, Ec, Am |
|  | Cheilanthifoline synthase (CheSyn) | Ps, Ec, Am |
|  | Canadine synthase (CAS) | Tf, Cc |
| O-methylation | Norcoclaurine 6-O-methyltransferase (6OMT) | Ps, Tf, Cj, Pb |
|  | 3'hydroxy-N-methylcoclaurine 4'-O-methyltransferase (4'OMT) | Ps, Tf, Cj, Cc |
|  | Reticuline 7-O-methyltransferase (7OMT) | Ps, Ec |
|  | Scoulerine 9-O-methyltransferase (9OMT) | Ps, Tf, Cj, Cc |
| N-methylation | Coclaurine N-methyltransferase (CNMT) | Ps, Tf, Cj |
|  | Tetrahydroprotoberberine N-methyltransferase (TMNT) | Ps, Ec, Pb |
| O-demethylation | Thebaine demthylase (T6ODM) | Ps |
|  | Codeine demthylase (CODM) | Ps, Ga |
| Reduction | Salutaridine reductase (SalR) | Ps, Pb, Ga |
|  | Codeinone reductase (COR) | Ps |
|  | Sanguinarine reductase (SanR) | Ec |
| Acetylation | Salutaridine acetyltransferase (SalAT) | Ps |

TABLE 10 comparison of impurities that may be present in concentrate of poppy straw and clarified yeast culture medium.

| Impurities: | | Concentrate of Poppy Straw | Clarified Yeast Culture Medium |
| --- | --- | --- | --- |
| Inorganic | Sodium | ✓ | ✓ |
|  | Magnesium | ✓ | ✓ |
|  | Silicon | ✓ |  |
|  | Phosphorus | ✓ | ✓ |
|  | Sulfur | ✓ | ✓ |
|  | Chloride | ✓ | ✓ |
|  | Potassium | ✓ | ✓ |
|  | Calcium | ✓ | ✓ |
|  | Copper | ✓ | ✓ |
|  | Zinc | ✓ | ✓ |
|  | Molybdenum | ✓ |  |
|  | Iron | ✓ | ✓ |
|  | Manganese | ✓ | ✓ |
|  | Ammonium | ✓ | ✓ |
|  | Boron | ✓ | ✓ |
| Organic | Polysaccharide (starch, cellulose, xylan) | ✓ |  |
|  | Lignin (p-courmaryl, coniferyl, sinapyl alcohols) | ✓ |  |
|  | Pigments (chlorophyll, anthocyanins, carotenoids) | ✓ |  |
|  | Flavonoids | ✓ |  |
|  | Phenantheroids | ✓ |  |
|  | Latex, gum and wax | ✓ |  |
|  | Rubisco |  | ✓ |

TABLE 10-continued comparison of impurities that may be present in concentrate of poppy straw and clarified yeast culture medium.

| Impurities: | | Concentrate of Poppy Straw | Clarified Yeast Culture Medium |
|---|---|---|---|
| Other | Meconic acid | ✓ | |
| | Pseudomorphine | ✓ | |
| | Narceine | ✓ | |
| | Thebaol | ✓ | |
| | Pesticides | ✓ | |
| | Pollen | ✓ | |

15

TABLE 11

Distinct groups of molecules present in clarified yeast culture medium (CYCM). Unlike concentrate of poppy straw (CPS), yeast host strains may be engineered to produce molecules of a predetermined class of alkaloids (i.e., only one biosynthesis pathway per strain) such that other classes of alkaloids are not present. Therefore, the CYCM may contain molecules within a single biosynthesis pathway including a subset of molecules spanning one or two columns, whereas the CPS may contain a subset of molecules across many columns.

| 1-Benzylisoquinoline | Protoberberine and Phihalideisoquinoline | Morphinan | Isopavine | Aporphine | BisBIA |
|---|---|---|---|---|---|
| Tetrahydropapaverine | Scoulene | Saluterdine | | Magnolonine | Daurince |
| Dihydropapaverine | Chelanthiloline | Salutaridinol | Caryachine | Corytuberine | Berbamonine |
| Papavierine | Styopine | Salutaridine-7-O-acetate | Biso | Apimorphine | |
| | Cis-N-methylstylopine | Thebane | Isonaremonine | Boldine | Fang |
| | Protopine | Codeinone | | | Tetracrine |
| | Dihydrosanguinrine | Oripavine | | | Curine |
| | Sanguinarine | Morphinone | | | Cepharanthine |
| | Tetrahydro Canadine | Neopinone | | | Berbamine |
| | N-methylcandine | Neopine | | | |
| | Noscapine | Codeine | | | |
| | Berberine | Morphine | | | |
| | | Neomorphine | | | |
| | | Hydrocodone | | | |
| | | Oxycodone | | | |
| | | 14-hydroxycodenone | | | |
| | | 14-hydroxycodeine | | | |
| | | Dihydromorphine | | | |
| | | Dihydrocodeine | | | |

TABLE 12

Impurities that may be present in chemical synthesis preparations of compounds

| Compound | Impurities |
|---|---|
| Buprenorphine | 15,16-Dehydrobuprenolphine, 17,18-Dehydrobuprenmphine, 18,19-demethylbuprenolphine, 19,19'-Ethylbuprenotphine, 2,2'-Bisbuprenorphine, 3-Deshydroxybuprenorphine, 3-O-Methylbuprenorphine, 3-O-Methyl-N-cyanonorbuprenorphine, 3-O-Methyl-N-methylnorbuprenolphine, 6-O-Desmethylbuprenorphine, Buprenorphine N-oxide, N-But-3-enylnorbuprenorphine, N-But-3-enylnormethylbuprenorphine, N-Butylnorbuprenorphine, N-Methylbuprenorphine, Norbuprenorphine, Tetramethylfuran buprenorphine |
| Oxymorphone | 1-Bromooxymorphone, 6-Beta oxymorphol, 10-Alpha-hydroxyoxymorphone, 10-Ketooxymorphone, 2,2-Bisoxymorphone, Noroxymorphone, Oxymorphone N-oxide, 10-Hydroxyoxymorphone, 4-Hydroxyoxymorphone, 8-Hydroxyoxymolphone, Hydromorphinol. |
| Naltrexone | 10-Hydroxynaltrexone, 10-Ketonaltrexone, 14-Hydroxy-17-cyclopropylmethylnormorphinone, 2,2'-Bisnaltrexone, 3-Cyclopropylmethylnaltrexone, 3-O-Methylnaltrexone, 8-Hydroxynaltrexone, N-(3-Butenyl)-noroxymolphone, Naltrexone aldol dimer, N-Formyl-noroxymorphone |

TABLE 12-continued

Impurities that may be present in chemical synthesis preparations of compounds

| Compound | Impurities |
|---|---|
| Naloxone | 10-Alpha-hydroxynaloxone, 10-Beta-hydroxynaloxone, 10-Ketonaloxone, 3-O-Allylnaloxone, 7,8-Didehydronaloxone, 2,2'-Bisnaloxone, Naloxone N-oxide |
| Nalbuphine | Beta-epimer of nalbuphine, 2,2'-Bisnalbuphine, 6-Ketonalbuphine, 10-Ketonalbuphine, Alpha-noroxymorphol, N-(Cyclobutylcarbonyl)-alpha-noroxymorphol, N-Formyl-6-alpha-noroxymophol. |

While preferred embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An engineered microbial cell, comprising:
   i) an engineered epimerase, wherein the engineered epimerase converts an (S)-1-benzylisoquinoline precursor to an (R)-1-benzylisoquinoline product within the engineered microbial cell;
   ii) a thebaine synthase, wherein the thebaine synthase has measurable activity within the engineered microbial cell; and
   iii) at least one modification selected from the group consisting of: a) a substrate inhibition alleviating mutation, b) a product inhibition alleviating mutation, c) a cofactor recovery promoting mechanism, d) a feedback inhibition alleviating mutation, e) transcriptional modulation modification, and f) an inactivating mutation; and
   iv) wherein the cell further comprises the enzymes of:
      (a) tyrosinase or tyrosine hydroxylase (TYR or TyrH), L-DOPA decarboxylase (DODC), 6-O-methyltransferase (6OMT), coclaurine-N-methyltransferase (CNMT), cytochrome P450 80B1 (CYP80B1), (4'-O-methyltransferase) (4'OMT), dehydroreticuline synthase and dehydroreticuline reductase (DRS-DRR), salutaridine synthase (SalSyn), salutaridine reductase SalR), and salutaridinol 7-O-acetyltransferase (SalAT); or
      (b) TYR or TyrH, DODC, monoamine oxidase (maoA), 6OMT, CNMT, 4'OMT, DRS-DRR, SalSyn, SalR, and SalAT, and
   wherein, within the engineered microbial cell, the engineered microbial cell converts a plurality of tetracyclic promorphinan precursor molecules to a category of alkaloid products selected from the group consisting of: i) a morphinan alkaloid, ii) a nal-opioid alkaloid, and iii) a nor-opioid alkaloid, and
   wherein the engineered microbial cell produces at least 10% more thebaine relative to a same microbial cell that lacks the thebaine synthase.

2. The engineered microbial cell of claim 1, wherein the engineered epimerase is a split epimerase.

3. The engineered microbial cell of claim 1, wherein the engineered epimerase converts (S)-reticuline to (R)-reticuline.

4. The engineered microbial cell of claim 3, wherein at least 50% of the (S)-1-benzylisoquinoline alkaloid molecules within the engineered microbial cell are converted to the (R)-1-benzylisoquinoline product.

5. The engineered microbial cell of claim 1, wherein the thebaine synthase is an engineered thebaine synthase.

6. The engineered microbial cell of claim 1, wherein the plurality of tetracyclic promorphinan precursor molecules are fed to the engineered microbial cell.

7. The engineered microbial cell of claim 1, wherein the plurality of tetracyclic promorphinan precursor molecules are produced within the engineered microbial cell.

8. The engineered microbial cell of claim 1, wherein the plurality of tetracyclic promorphinan precursor molecules are selected from the group consisting of reticuline, 3'hydroxy-N-methylcoclaurine, coclaurine, norcoclaurine, norlaudanosoline, methylnorlaudanosoline, laudanosoline, methylnorlaudanosoline, norreticuline, 3'hydroxy-N-methylcoclaurine, 4'-O'-methylaudanosoline, L-Dopa, tyrosine, dopamine, 3,4-dihydroxyphenylacetaldehyde (3,4-DHPA), hydroxyphenylpyruvate, prephenate, chorismate, 5-enolpyruvylshikimate-3-phosphate (EPSP), 3-deoxy-D-arabinoheptulosonate-7-phosphate (DAHP), erythrose-4-phosphate (E4P), phosphoenolpyruvate (PEP), and glucose.

9. The engineered microbial cell of claim 1, wherein at least 50% of the tetracyclic promorphinan precursor molecules within the engineered microbial cell are converted to thebaine.

10. The engineered microbial cell of claim 9, wherein the tetracyclic promorphinan molecules are selected from the group consisting of salutaridine, salutaridinol, or salutaridinol-7-O-acetate.

11. The engineered microbial cell of claim 1, wherein the plurality of tetracyclic promorphinan precursor molecules are an (S)-substrate of Formula I:

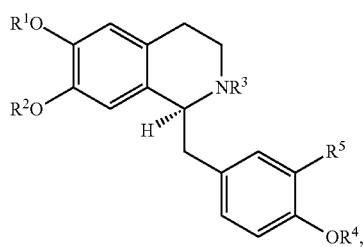

Formula I or a salt thereof, wherein:
$R^1$, $R^2$, $R^3$, and $R^4$ are independently selected from hydrogen and methyl; and
$R^5$ is selected from hydrogen, hydroxy, and methoxy.

12. The engineered microbial cell of claim 11, wherein at least one of $R^1$, $R^2$, $R^3$, $R^4$, and $R^5$ is hydrogen.

13. The engineered microbial cell of claim 1, wherein a precursor of a promorphinan molecule is (S)-substrate is a compound of Formula II:

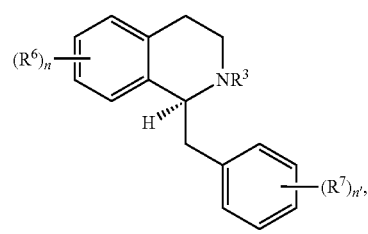

Formula II or a salt thereof, wherein:
$R^3$ is selected from hydrogen and $C_1$-$C_4$ alkyl;
$R^6$ and $R^7$ are independently selected at each occurrence from hydroxy, fluoro, chloro, bromo, carboxaldehyde, $C_1$-$C_4$ acyl, $C_1$-$C_4$ alkyl, and $C_1$-$C_4$ alkoxy;
n is 0, 1, 2, 3, or 4; and
n' is 0, 1, 2, 3, 4 or 5.

14. The engineered microbial cell of claim 1, wherein the plurality of tetracyclic promorphinan precursor molecules are tyrosine.

15. The engineered microbial cell of claim 1, wherein the plurality of tetracyclic promorphinan precursor molecules are sugar.

16. The engineered microbial cell of claim 1, further comprising at least one modification selected from the group consisting of: i) a BIA-generating modification, ii) an O-demethylation modification, iii) an N-demethylation modification, and iv) an N-linked modification.

17. The engineered microbial cell of claim 1, wherein the morphinan alkaloid product is a thebaine, codeinone, codeine, morphine, morphinone, oripavine, neopinone, neopine, neomorphine, hydrocodone, dihydrocodeine, 14-hydroxycodeinone, oxycodone, 14-hydroxycodeine, morphinone, hydromorphone, dihydromorphine, dihydroetorphine, ethylmorphine, etorphine, metopon, buprenorphine, pholcodine, heterocodeine, or oxymorphone.

18. The engineered microbial cell of claim 1, wherein the nal-opioid alkaloid product is a naltrexone, naloxone, nalmefene, nalorphine, nalorphine, nalodeine, naldemedine, naloxegol, 6β-naltrexol, naltrindole, methylnaltrexone, methylsamidorphan, alvimopan, axelopran, bevenpran, dinicotinate, levallorphan, samidorphan, buprenorphine, dezocine, eptazocine, butorphanol, levorphanol, nalbuphine, pentazocine, phenazocine, norbinaltorphimine, or diprenorphine.

19. The engineered microbial cell of claim 1, wherein (a) and (b) further comprise norcoclaurine synthase (NCS).

* * * * *

```
                         SEQUENCE LISTING

<160> NUMBER OF SEQ ID NOS: 153

<210> SEQ ID NO 1
<211> LENGTH: 901
<212> TYPE: PRT
<213> ORGANISM: Papaver somniferum

<400> SEQUENCE: 1

Met Glu Leu Gln Tyr Ile Ser Tyr Phe Gln Pro Thr Ser Ser Val Val
1               5                   10                  15

Ala Leu Leu Leu Ala Leu Val Ser Ile Leu Ser Ser Val Val Val Leu
                20                  25                  30

Arg Lys Thr Phe Leu Asn Asn Tyr Ser Ser Ser Pro Ala Ser Ser Thr
            35                  40                  45

Lys Thr Ala Val Leu Ser His Gln Arg Gln Gln Ser Cys Ala Leu Pro
        50                  55                  60

Ile Ser Gly Leu Leu His Ile Phe Met Asn Lys Asn Gly Leu Ile His
65                  70                  75                  80

Val Thr Leu Gly Asn Met Ala Asp Lys Tyr Gly Pro Ile Phe Ser Phe
                85                  90                  95

Pro Thr Gly Ser His Arg Thr Leu Val Val Ser Ser Trp Glu Met Val
                100                 105                 110

Lys Glu Cys Phe Thr Gly Asn Asn Asp Thr Ala Phe Ser Asn Arg Pro
            115                 120                 125

Ile Pro Leu Ala Phe Lys Thr Ile Phe Tyr Ala Cys Gly Gly Ile Asp
        130                 135                 140

Ser Tyr Gly Leu Ser Ser Val Pro Tyr Gly Lys Tyr Trp Arg Glu Leu
145                 150                 155                 160

Arg Lys Val Cys Val His Asn Leu Leu Ser Asn Gln Gln Leu Leu Lys
                165                 170                 175

Phe Arg His Leu Ile Ile Ser Gln Val Asp Thr Ser Phe Asn Lys Leu
            180                 185                 190

Tyr Glu Leu Cys Lys Asn Ser Glu Asp Asn His Gly Asn Tyr Thr Thr
        195                 200                 205

Thr Thr Thr Thr Ala Ala Gly Met Val Arg Ile Asp Asp Trp Leu Ala
    210                 215                 220

Glu Leu Ser Phe Asn Val Ile Gly Arg Ile Val Cys Gly Phe Gln Ser
225                 230                 235                 240
```

```
Gly Pro Lys Thr Gly Ala Pro Ser Arg Val Glu Gln Phe Lys Glu Ala
                245                 250                 255
Ile Asn Glu Ala Ser Tyr Phe Met Ser Thr Ser Pro Val Ser Asp Asn
            260                 265                 270
Val Pro Met Leu Gly Trp Ile Asp Gln Leu Thr Gly Leu Thr Arg Asn
        275                 280                 285
Met Lys His Cys Gly Lys Lys Leu Asp Leu Val Val Glu Ser Ile Ile
    290                 295                 300
Asn Asp His Arg Gln Lys Arg Arg Phe Ser Arg Thr Lys Gly Gly Asp
305                 310                 315                 320
Glu Lys Asp Asp Glu Gln Asp Phe Ile Asp Ile Cys Leu Ser Ile
                325                 330                 335
Met Glu Gln Pro Gln Leu Pro Gly Asn Asn Asn Pro Ser Gln Ile Pro
                340                 345                 350
Ile Lys Ser Ile Val Leu Asp Met Ile Gly Gly Thr Asp Thr Thr
            355                 360                 365
Lys Leu Thr Thr Ile Trp Thr Leu Ser Leu Leu Asn Asn Pro His
    370                 375                 380
Val Leu Asp Lys Ala Lys Gln Glu Val Asp Ala His Phe Arg Thr Lys
385                 390                 395                 400
Arg Arg Ser Thr Asn Asp Ala Ala Ala Val Val Asp Phe Asp Asp
                405                 410                 415
Ile Arg Asn Leu Val Tyr Ile Gln Ala Ile Ile Lys Glu Ser Met Arg
                420                 425                 430
Leu Tyr Pro Ala Ser Pro Val Val Glu Arg Leu Ser Gly Glu Asp Cys
                435                 440                 445
Val Val Gly Gly Phe His Val Pro Ala Gly Thr Arg Leu Trp Ala Asn
450                 455                 460
Val Trp Lys Met Gln Arg Asp Pro Lys Val Trp Asp Asp Pro Leu Val
465                 470                 475                 480
Phe Arg Pro Asp Arg Phe Leu Ser Asp Glu Gln Lys Met Val Asp Val
                485                 490                 495
Arg Gly Gln Asn Tyr Glu Leu Leu Pro Phe Gly Ala Gly Arg Arg Val
                500                 505                 510
Cys Pro Gly Val Ser Phe Ser Leu Asp Leu Met Gln Leu Val Leu Thr
                515                 520                 525
Arg Leu Ile Leu Glu Phe Glu Met Lys Ser Pro Ser Gly Lys Val Asp
                530                 535                 540
Met Thr Ala Thr Pro Gly Leu Met Ser Tyr Lys Val Ile Pro Leu Asp
545                 550                 555                 560
Ile Leu Leu Thr His Arg Arg Ile Lys Pro Cys Val Gln Ser Ala Ala
                565                 570                 575
Ser Glu Arg Asp Met Glu Ser Ser Gly Val Pro Val Ile Thr Leu Gly
                580                 585                 590
Ser Gly Lys Val Met Pro Val Leu Gly Met Gly Thr Phe Glu Lys Val
                595                 600                 605
Gly Lys Gly Ser Glu Arg Glu Arg Leu Ala Ile Leu Lys Ala Ile Glu
            610                 615                 620
Val Gly Tyr Arg Tyr Phe Asp Thr Ala Ala Ala Tyr Glu Thr Glu Glu
625                 630                 635                 640
Val Leu Gly Glu Ala Ile Ala Glu Ala Leu Gln Leu Gly Leu Val Lys
                645                 650                 655
Ser Arg Asp Glu Leu Phe Ile Ser Ser Met Leu Trp Cys Thr Asp Ala
```

```
            660             665             670
His Ala Asp Arg Val Leu Leu Ala Leu Gln Asn Ser Leu Arg Asn Leu
        675                 680                 685

Lys Leu Glu Tyr Val Asp Leu Tyr Met Leu Pro Phe Pro Ala Ser Leu
    690                 695                 700

Lys Pro Gly Lys Ile Thr Met Asp Ile Pro Glu Asp Ile Cys Arg
705                 710                 715                 720

Met Asp Tyr Arg Ser Val Trp Ala Ala Met Glu Glu Cys Gln Asn Leu
            725                 730                 735

Gly Phe Thr Lys Ser Ile Gly Val Ser Asn Phe Ser Cys Lys Lys Leu
        740                 745                 750

Gln Glu Leu Met Ala Thr Ala Asn Ile Pro Pro Ala Val Asn Gln Val
    755                 760                 765

Glu Met Ser Pro Ala Phe Gln Gln Lys Leu Arg Glu Tyr Cys Asn
770                 775                 780

Ala Asn Asn Ile Leu Val Ser Ala Ile Ser Val Leu Gly Ser Asn Gly
785                 790                 795                 800

Thr Pro Trp Gly Ser Asn Ala Val Leu Gly Ser Glu Val Leu Lys Lys
            805                 810                 815

Ile Ala Met Ala Lys Gly Lys Ser Val Ala Gln Val Ser Met Arg Trp
        820                 825                 830

Val Tyr Glu Gln Gly Ala Ser Leu Val Val Lys Ser Phe Ser Glu Glu
    835                 840                 845

Arg Leu Arg Glu Asn Leu Asn Ile Phe Asp Trp Glu Leu Thr Lys Glu
850                 855                 860

Asp His Glu Lys Ile Gly Glu Ile Pro Gln Cys Arg Ile Leu Ser Ala
865                 870                 875                 880

Tyr Phe Leu Val Ser Pro Asn Gly Pro Phe Lys Ser Gln Glu Glu Leu
            885                 890                 895

Trp Asp Asp Glu Ala
            900

<210> SEQ ID NO 2
<211> LENGTH: 919
<212> TYPE: PRT
<213> ORGANISM: Papaver somniferum
<220> FEATURE:
<221> NAME/KEY: MOD_RES
<222> LOCATION: (209)..(209)
<223> OTHER INFORMATION: Any amino acid
<220> FEATURE:
<221> NAME/KEY: MOD_RES
<222> LOCATION: (226)..(226)
<223> OTHER INFORMATION: Any amino acid

<400> SEQUENCE: 2

Met Glu Leu Gln Tyr Ile Ser Tyr Phe Gln Pro Thr Ser Ser Val Val
1               5                   10                  15

Ala Leu Leu Leu Ala Leu Val Ser Ile Leu Ser Ser Val Val Leu
            20                  25                  30

Arg Lys Thr Phe Leu Asn Asn Tyr Ser Ser Pro Ala Ser Ser Thr
        35                  40                  45

Lys Thr Ala Val Leu Ser His Gln Arg Gln Gln Ser Cys Ala Leu Pro
    50                  55                  60

Ile Ser Gly Leu Leu His Ile Phe Met Asn Lys Asn Gly Leu Ile His
65                  70                  75                  80

Val Thr Leu Gly Asn Met Ala Asp Lys Tyr Gly Pro Ile Phe Ser Phe
```

-continued

```
                85                  90                  95
Pro Thr Gly Ser His Arg Thr Leu Val Val Ser Ser Trp Glu Met Val
            100                 105                 110
Lys Glu Cys Phe Thr Gly Asn Asn Asp Thr Ala Phe Ser Asn Arg Pro
            115                 120                 125
Ile Pro Leu Ala Phe Lys Thr Ile Phe Tyr Ala Cys Gly Gly Ile Asp
            130                 135                 140
Ser Tyr Gly Leu Ser Ser Val Pro Tyr Gly Lys Tyr Trp Arg Glu Leu
145                 150                 155                 160
Arg Lys Val Cys Val His Asn Leu Leu Ser Asn Gln Gln Leu Leu Lys
                165                 170                 175
Phe Arg His Leu Ile Ile Ser Gln Val Asp Thr Ser Phe Asn Lys Leu
                180                 185                 190
Tyr Glu Leu Cys Lys Asn Ser Glu Asp Asn His Gly Asn Tyr Thr Thr
                195                 200                 205
Xaa Leu Leu Leu Pro Gln Leu Ala Trp Arg Gln Pro Trp Lys Leu Tyr
                210                 215                 220
Tyr Xaa Thr Thr Thr Ala Ala Gly Met Val Arg Ile Asp Asp Trp
225                 230                 235                 240
Leu Ala Glu Leu Ser Phe Asn Val Ile Gly Arg Ile Val Cys Gly Phe
                245                 250                 255
Gln Ser Gly Pro Lys Thr Gly Ala Pro Ser Arg Val Glu Gln Phe Lys
                260                 265                 270
Glu Ala Ile Asn Glu Ala Ser Tyr Phe Met Ser Thr Ser Pro Val Ser
                275                 280                 285
Asp Asn Val Pro Met Leu Gly Trp Ile Asp Gln Leu Thr Gly Leu Thr
                290                 295                 300
Arg Asn Met Lys His Cys Gly Lys Lys Leu Asp Leu Val Val Glu Ser
305                 310                 315                 320
Ile Ile Asn Asp His Arg Gln Lys Arg Phe Ser Arg Thr Lys Gly
                325                 330                 335
Gly Asp Glu Lys Asp Asp Glu Gln Asp Asp Phe Ile Asp Ile Cys Leu
                340                 345                 350
Ser Ile Met Glu Gln Pro Gln Leu Pro Gly Asn Asn Asn Pro Ser Gln
                355                 360                 365
Ile Pro Ile Lys Ser Ile Val Leu Asp Met Ile Gly Gly Gly Thr Asp
                370                 375                 380
Thr Thr Lys Leu Thr Thr Ile Trp Thr Leu Ser Leu Leu Asn Asn
385                 390                 395                 400
Pro His Val Leu Asp Lys Ala Lys Gln Glu Val Asp Ala His Phe Arg
                405                 410                 415
Thr Lys Arg Arg Ser Thr Asn Asp Ala Ala Ala Val Val Asp Phe
                420                 425                 430
Asp Asp Ile Arg Asn Leu Val Tyr Ile Gln Ala Ile Ile Lys Glu Ser
                435                 440                 445
Met Arg Leu Tyr Pro Ala Ser Pro Val Val Glu Arg Leu Ser Gly Glu
                450                 455                 460
Asp Cys Val Val Gly Gly Phe His Val Pro Ala Gly Thr Arg Leu Trp
465                 470                 475                 480
Ala Asn Val Trp Lys Met Gln Arg Asp Pro Lys Val Trp Asp Pro
                485                 490                 495
Leu Val Phe Arg Pro Asp Arg Phe Leu Ser Asp Glu Gln Lys Met Val
                500                 505                 510
```

```
Asp Val Arg Gly Gln Asn Tyr Glu Leu Leu Pro Phe Gly Ala Gly Arg
            515                 520                 525

Arg Val Cys Pro Gly Val Ser Phe Ser Leu Asp Leu Met Gln Leu Val
        530                 535                 540

Leu Thr Arg Leu Ile Leu Glu Phe Glu Met Lys Ser Pro Ser Gly Lys
545                 550                 555                 560

Val Asp Met Thr Ala Thr Pro Gly Leu Met Ser Tyr Lys Val Ile Pro
                565                 570                 575

Leu Asp Ile Leu Leu Thr His Arg Arg Ile Lys Pro Cys Val Gln Ser
            580                 585                 590

Ala Ala Ser Glu Arg Asp Met Glu Ser Ser Gly Val Pro Val Ile Thr
        595                 600                 605

Leu Gly Ser Gly Lys Val Met Pro Val Leu Gly Met Gly Thr Phe Glu
    610                 615                 620

Lys Val Gly Lys Gly Ser Glu Arg Glu Arg Leu Ala Ile Leu Lys Ala
625                 630                 635                 640

Ile Glu Val Gly Tyr Arg Tyr Phe Asp Thr Ala Ala Tyr Glu Thr
                645                 650                 655

Glu Glu Val Leu Gly Glu Ala Ile Ala Glu Ala Leu Gln Leu Gly Leu
            660                 665                 670

Val Lys Ser Arg Asp Glu Leu Phe Ile Ser Ser Met Leu Trp Cys Thr
        675                 680                 685

Asp Ala His Ala Asp Arg Val Leu Leu Ala Leu Gln Asn Ser Leu Arg
    690                 695                 700

Asn Leu Lys Leu Glu Tyr Val Asp Leu Tyr Met Leu Pro Phe Pro Ala
705                 710                 715                 720

Ser Leu Lys Pro Gly Lys Ile Thr Met Asp Ile Pro Glu Glu Asp Ile
                725                 730                 735

Cys Arg Met Asp Tyr Arg Ser Val Trp Ala Ala Met Glu Glu Cys Gln
            740                 745                 750

Asn Leu Gly Phe Thr Lys Ser Ile Gly Val Ser Asn Phe Ser Cys Lys
        755                 760                 765

Lys Leu Gln Glu Leu Met Ala Thr Ala Asn Ile Pro Pro Ala Val Asn
    770                 775                 780

Gln Val Glu Met Ser Pro Ala Phe Gln Gln Lys Lys Leu Arg Glu Tyr
785                 790                 795                 800

Cys Asn Ala Asn Asn Ile Leu Val Ser Ala Ile Ser Val Leu Gly Ser
                805                 810                 815

Asn Gly Thr Pro Trp Gly Ser Asn Ala Val Leu Gly Ser Glu Val Leu
            820                 825                 830

Lys Lys Ile Ala Met Ala Lys Gly Lys Ser Val Ala Gln Val Ser Met
        835                 840                 845

Arg Trp Val Tyr Glu Gln Gly Ala Ser Leu Val Val Lys Ser Phe Ser
    850                 855                 860

Glu Glu Arg Leu Arg Glu Asn Leu Asn Ile Phe Asp Trp Glu Leu Thr
865                 870                 875                 880

Lys Glu Asp His Glu Lys Ile Gly Glu Ile Pro Gln Cys Arg Ile Leu
                885                 890                 895

Ser Ala Tyr Phe Leu Val Ser Pro Asn Gly Pro Phe Lys Ser Gln Glu
            900                 905                 910

Glu Leu Trp Asp Asp Glu Ala
        915
```

```
<210> SEQ ID NO 3
<211> LENGTH: 732
<212> TYPE: PRT
<213> ORGANISM: Papaver somniferum
<220> FEATURE:
<221> NAME/KEY: MOD_RES
<222> LOCATION: (725)..(725)
<223> OTHER INFORMATION: Any amino acid

<400> SEQUENCE: 3
```

```
Met Glu Leu Gln Tyr Ile Ser Tyr Phe Gln Pro Thr Ser Ser Val Val
1               5                   10                  15

Ala Leu Leu Leu Ala Leu Val Ser Ile Leu Ser Ser Val Val Val Leu
            20                  25                  30

Arg Lys Thr Phe Leu Asn Asn Tyr Ser Ser Ser Pro Ala Ser Ser Thr
        35                  40                  45

Lys Thr Ala Val Leu Ser His Gln Arg Gln Gln Ser Cys Ala Leu Pro
    50                  55                  60

Ile Ser Gly Leu Leu His Ile Phe Met Asn Lys Asn Gly Leu Ile His
65                  70                  75                  80

Val Thr Leu Gly Asn Met Ala Asp Lys Tyr Gly Pro Ile Phe Ser Phe
                85                  90                  95

Pro Thr Gly Ser His Arg Thr Leu Val Val Ser Ser Trp Glu Met Val
            100                 105                 110

Lys Glu Cys Phe Thr Gly Asn Asp Thr Ala Phe Ser Asn Arg Pro
        115                 120                 125

Ile Pro Leu Ala Phe Lys Thr Ile Phe Tyr Ala Cys Gly Gly Ile Asp
130                 135                 140

Ser Tyr Gly Leu Ser Ser Val Pro Tyr Gly Lys Tyr Trp Arg Glu Leu
145                 150                 155                 160

Arg Lys Val Cys Val His Asn Leu Leu Ser Asn Gln Gln Leu Leu Lys
                165                 170                 175

Phe Arg His Leu Ile Ile Ser Gln Val Asp Thr Ser Phe Asn Lys Leu
            180                 185                 190

Tyr Glu Leu Cys Lys Asn Ser Glu Asp Asn His Gly Asn Tyr Thr Thr
        195                 200                 205

Thr Thr Thr Thr Ala Ala Gly Met Val Arg Ile Asp Asp Trp Leu Ala
    210                 215                 220

Glu Leu Ser Phe Asn Val Ile Gly Arg Ile Val Cys Gly Phe Gln Ser
225                 230                 235                 240

Gly Pro Lys Thr Gly Ala Pro Ser Arg Val Glu Gln Phe Lys Glu Ala
                245                 250                 255

Ile Asn Glu Ala Ser Tyr Phe Met Ser Thr Ser Pro Val Ser Asp Asn
            260                 265                 270

Val Pro Met Leu Gly Trp Ile Asp Gln Leu Thr Gly Leu Thr Arg Asn
        275                 280                 285

Met Lys His Cys Gly Lys Lys Leu Asp Leu Val Val Glu Ser Ile Ile
    290                 295                 300

Asn Asp His Arg Gln Lys Arg Arg Phe Ser Arg Thr Lys Gly Gly Asp
305                 310                 315                 320

Glu Lys Asp Asp Glu Gln Asp Asp Phe Ile Asp Cys Leu Ser Ile
                325                 330                 335

Met Glu Gln Pro Gln Leu Pro Gly Asn Asn Asn Pro Ser Gln Ile Pro
            340                 345                 350

Ile Lys Ser Ile Val Leu Asp Met Ile Gly Gly Gly Thr Asp Thr Thr
```

```
                355                 360                 365
Lys Leu Thr Thr Ile Trp Thr Leu Ser Leu Leu Asn Asn Pro His
370                 375                 380
Val Leu Asp Lys Ala Lys Gln Glu Val Asp Ala His Phe Arg Thr Lys
385                 390                 395                 400
Arg Arg Ser Thr Asn Asp Ala Ala Ala Val Val Asp Phe Asp Asp
            405                 410                 415
Ile Arg Asn Leu Val Tyr Ile Gln Ala Ile Lys Glu Ser Met Arg
            420                 425                 430
Leu Tyr Pro Ala Ser Pro Val Glu Arg Leu Ser Gly Glu Asp Cys
            435                 440                 445
Val Val Gly Gly Phe His Val Pro Ala Gly Thr Arg Leu Trp Ala Asn
450                 455                 460
Val Trp Lys Met Gln Arg Asp Pro Lys Val Trp Asp Pro Leu Val
465                 470                 475                 480
Phe Arg Pro Asp Arg Phe Leu Ser Asp Glu Gln Lys Met Val Asp Val
            485                 490                 495
Arg Gly Gln Asn Tyr Glu Leu Leu Pro Phe Gly Ala Gly Arg Arg Val
            500                 505                 510
Cys Pro Gly Val Ser Phe Ser Leu Asp Leu Met Gln Leu Val Leu Thr
            515                 520                 525
Arg Leu Ile Leu Glu Phe Glu Met Lys Ser Pro Ser Gly Lys Val Asp
            530                 535                 540
Met Thr Ala Thr Pro Gly Leu Met Ser Tyr Lys Val Ile Pro Leu Asp
545                 550                 555                 560
Ile Leu Leu Thr His Arg Arg Ile Lys Pro Cys Val Gln Ser Ala Ala
            565                 570                 575
Ser Glu Arg Asp Met Glu Ser Ser Gly Val Pro Val Ile Thr Leu Gly
            580                 585                 590
Ser Gly Lys Val Met Pro Val Leu Gly Met Gly Thr Phe Glu Lys Val
            595                 600                 605
Gly Lys Gly Ser Glu Arg Glu Arg Leu Ala Ile Leu Lys Ala Ile Glu
610                 615                 620
Val Gly Tyr Arg Tyr Phe Asp Thr Ala Ala Ala Tyr Glu Thr Glu Glu
625                 630                 635                 640
Val Leu Gly Glu Ala Ile Ala Glu Ala Leu Gln Leu Gly Leu Val Lys
            645                 650                 655
Ser Arg Asp Glu Leu Phe Ile Ser Ser Met Leu Trp Cys Thr Asp Ala
            660                 665                 670
His Ala Asp Arg Val Leu Leu Ala Leu Gln Asn Ser Leu Arg Asn Leu
            675                 680                 685
Lys Leu Glu Tyr Val Asp Leu Tyr Met Leu Pro Phe Pro Ala Ser Leu
            690                 695                 700
Lys Pro Gly Lys Ile Thr Met Asp Ile Pro Glu Glu Asp Ile Cys Arg
705                 710                 715                 720
Met Asp Tyr Arg Xaa Val Ser Lys Pro Trp Leu His
            725                 730

<210> SEQ ID NO 4
<211> LENGTH: 764
<212> TYPE: PRT
<213> ORGANISM: Papaver somniferum
<220> FEATURE:
<221> NAME/KEY: MOD_RES
<222> LOCATION: (6)..(6)
```

<223> OTHER INFORMATION: Any amino acid

<400> SEQUENCE: 4

```
Met Arg Trp His Arg Xaa Ile Asp Ser Tyr Gly Leu Ser Ser Val Pro
1               5                   10                  15

Tyr Gly Lys Tyr Trp Arg Glu Leu Arg Lys Val Cys Val His Asn Leu
            20                  25                  30

Leu Ser Asn Gln Gln Leu Leu Lys Phe Arg His Leu Ile Ile Ser Gln
        35                  40                  45

Val Asp Thr Ser Phe Asn Lys Leu Tyr Glu Leu Cys Lys Asn Ser Glu
    50                  55                  60

Asp Asn Gln Gly Asn Tyr Pro Thr Thr Thr Ala Ala Gly Met Val
65                  70                  75                  80

Arg Ile Asp Asp Trp Leu Ala Glu Leu Ser Phe Asn Val Ile Gly Arg
                85                  90                  95

Ile Val Cys Gly Phe Gln Ser Gly Pro Lys Thr Gly Ala Pro Ser Arg
            100                 105                 110

Val Glu Gln Phe Lys Glu Ala Ile Asn Glu Ala Ser Tyr Phe Met Ser
        115                 120                 125

Thr Ser Pro Val Ser Asp Asn Val Pro Met Leu Gly Trp Ile Asp Gln
    130                 135                 140

Leu Thr Gly Leu Thr Arg Asn Met Lys His Cys Gly Lys Lys Leu Asp
145                 150                 155                 160

Leu Val Val Glu Ser Ile Ile Asn Asp His Arg Gln Lys Arg Arg Phe
                165                 170                 175

Ser Arg Thr Lys Gly Gly Asp Glu Lys Asp Glu Gln Asp Phe
            180                 185                 190

Ile Asp Ile Cys Leu Ser Ile Met Glu Gln Pro Gln Leu Pro Gly Asn
            195                 200                 205

Asn Asn Pro Ser Gln Ile Pro Ile Lys Ser Ile Val Leu Asp Met Ile
    210                 215                 220

Gly Gly Gly Thr Asp Thr Thr Lys Leu Thr Thr Ile Trp Thr Leu Ser
225                 230                 235                 240

Leu Leu Leu Asn Asn Pro His Val Leu Asp Lys Ala Lys Gln Glu Val
                245                 250                 255

Asp Ala His Phe Arg Thr Lys Arg Arg Ser Thr Asn Asp Ala Ala Ala
            260                 265                 270

Ala Val Val Asp Phe Asp Asp Ile Arg Asn Leu Val Tyr Ile Gln Ala
        275                 280                 285

Ile Ile Lys Glu Ser Met Arg Leu Tyr Pro Ala Ser Pro Val Val Glu
    290                 295                 300

Arg Leu Ser Gly Glu Asp Cys Val Val Gly Phe His Val Pro Ala
305                 310                 315                 320

Gly Thr Arg Leu Trp Ala Asn Val Trp Lys Met Gln Arg Asp Pro Lys
                325                 330                 335

Val Trp Asp Asp Pro Leu Val Phe Arg Pro Asp Arg Phe Leu Ser Asp
            340                 345                 350

Glu Gln Lys Met Val Asp Val Arg Gly Gln Asn Tyr Glu Leu Leu Pro
        355                 360                 365

Phe Gly Ala Gly Arg Arg Val Cys Pro Gly Val Ser Phe Ser Leu Asp
    370                 375                 380

Leu Met Gln Leu Val Leu Thr Arg Leu Ile Leu Glu Phe Glu Met Lys
385                 390                 395                 400
```

```
Ser Pro Ser Gly Lys Val Asp Met Thr Ala Thr Pro Gly Leu Met Ser
            405                 410                 415

Tyr Lys Val Ile Pro Leu Asp Ile Leu Leu Thr His Arg Arg Ile Lys
            420                 425                 430

Pro Cys Val Gln Ser Ala Ala Ser Glu Arg Asp Met Glu Ser Ser Gly
            435                 440                 445

Val Pro Val Ile Thr Leu Gly Ser Gly Lys Val Met Pro Val Leu Gly
            450                 455                 460

Met Gly Thr Phe Glu Lys Val Gly Lys Gly Ser Glu Arg Glu Arg Leu
465                 470                 475                 480

Ala Ile Leu Lys Ala Ile Glu Val Gly Tyr Arg Tyr Phe Asp Thr Ala
            485                 490                 495

Ala Ala Tyr Glu Thr Glu Glu Val Leu Gly Glu Ala Ile Ala Glu Ala
            500                 505                 510

Leu Gln Leu Gly Leu Val Lys Ser Arg Asp Glu Leu Phe Ile Ser Ser
            515                 520                 525

Met Leu Trp Cys Thr Asp Ala His Ala Asp Arg Val Leu Leu Ala Leu
            530                 535                 540

Gln Asn Ser Leu Arg Asn Leu Lys Leu Glu Tyr Val Asp Leu Tyr Met
545                 550                 555                 560

Leu Pro Phe Pro Ala Ser Leu Lys Pro Gly Lys Ile Thr Met Asp Ile
            565                 570                 575

Pro Glu Glu Asp Ile Cys Arg Met Asp Tyr Arg Ser Val Trp Ala Ala
            580                 585                 590

Met Glu Glu Cys Gln Asn Leu Gly Phe Thr Lys Ser Ile Gly Val Ser
            595                 600                 605

Asn Phe Ser Cys Lys Lys Leu Gln Glu Leu Met Ala Thr Ala Asn Ile
            610                 615                 620

Pro Pro Ala Val Asn Gln Val Glu Met Ser Pro Ala Phe Gln Gln Lys
625                 630                 635                 640

Lys Leu Arg Glu Tyr Cys Asn Ala Asn Asn Ile Leu Val Ser Ala Ile
            645                 650                 655

Ser Val Leu Gly Ser Asn Gly Thr Pro Trp Gly Ser Asn Ala Val Leu
            660                 665                 670

Gly Ser Glu Val Leu Lys Lys Ile Ala Met Ala Lys Gly Lys Ser Val
            675                 680                 685

Ala Gln Val Ser Met Arg Trp Val Tyr Glu Gln Gly Ala Ser Leu Val
            690                 695                 700

Val Lys Ser Phe Ser Glu Glu Arg Leu Arg Glu Asn Leu Asn Ile Phe
705                 710                 715                 720

Asp Trp Glu Leu Thr Lys Glu Asp His Glu Lys Ile Gly Glu Ile Pro
            725                 730                 735

Gln Cys Arg Ile Leu Ser Ala Tyr Phe Leu Val Ser Pro Asn Gly Pro
            740                 745                 750

Phe Lys Ser Gln Glu Glu Leu Trp Asp Asp Glu Ala
            755                 760

<210> SEQ ID NO 5
<211> LENGTH: 900
<212> TYPE: PRT
<213> ORGANISM: Papaver setigerum

<400> SEQUENCE: 5

Met Glu Leu Gln Tyr Ile Ser Tyr Phe Gln Pro Thr Ser Ser Val Val
1               5                   10                  15
```

```
Ala Leu Leu Leu Ala Leu Val Ser Ile Leu Ser Ser Val Val Leu
            20                  25                  30

Arg Lys Thr Phe Leu Asn Asn Tyr Ser Ser Pro Ala Ser Ser Thr
            35                  40                  45

Lys Thr Ala Val Leu Ser His Gln Arg Gln Ser Cys Ala Leu Pro
 50                  55                  60

Ile Ser Gly Leu Leu His Ile Phe Met Asn Lys Asn Gly Leu Ile His
 65                  70                  75                  80

Val Thr Leu Gly Asn Met Ala Asp Lys Tyr Gly Pro Ile Phe Ser Phe
                 85                  90                  95

Pro Thr Gly Ser His Arg Thr Leu Val Val Ser Ser Trp Glu Met Val
            100                 105                 110

Lys Glu Cys Phe Thr Gly Asn Asn Asp Thr Ala Phe Ser Asn Arg Pro
            115                 120                 125

Ile Pro Leu Ala Phe Lys Thr Ile Phe Tyr Ala Cys Gly Gly Ile Asp
130                 135                 140

Ser Tyr Gly Leu Ser Ser Val Pro Tyr Gly Lys Tyr Trp Arg Glu Leu
145                 150                 155                 160

Arg Lys Val Cys Val His Asn Leu Leu Ser Asn Gln Gln Leu Leu Lys
                165                 170                 175

Phe Arg His Leu Ile Ile Ser Gln Val Asp Thr Ser Phe Asn Lys Leu
            180                 185                 190

Tyr Glu Leu Cys Lys Asn Ser Glu Asp Asn Gln Gly Asn Tyr Thr Thr
            195                 200                 205

Thr Thr Thr Ala Ala Gly Met Val Arg Ile Asp Asp Trp Leu Ala Glu
210                 215                 220

Leu Ser Phe Asn Val Ile Gly Arg Ile Val Cys Gly Phe Gln Ser Gly
225                 230                 235                 240

Pro Lys Thr Gly Ala Pro Ser Arg Val Glu Gln Phe Lys Glu Ala Ile
            245                 250                 255

Asn Glu Ala Ser Tyr Phe Met Ser Thr Ser Pro Val Ser Asp Asn Val
            260                 265                 270

Pro Met Leu Gly Trp Ile Asp Gln Leu Thr Gly Leu Thr Arg Asn Met
            275                 280                 285

Lys His Cys Gly Lys Lys Leu Asp Leu Val Val Glu Ser Ile Ile Asn
            290                 295                 300

Asp His Arg Gln Lys Arg Arg Phe Ser Arg Thr Lys Gly Gly Asp Glu
305                 310                 315                 320

Lys Asp Asp Glu Gln Asp Asp Phe Ile Asp Ile Cys Leu Ser Ile Met
                325                 330                 335

Glu Gln Pro Gln Leu Pro Gly Asn Asn Asn Pro Ser Gln Ile Pro Ile
            340                 345                 350

Lys Ser Ile Val Leu Asp Met Ile Gly Gly Gly Thr Asp Thr Thr Lys
            355                 360                 365

Leu Thr Thr Ile Trp Thr Leu Ser Leu Leu Leu Asn Asn Pro His Val
            370                 375                 380

Leu Asp Lys Ala Lys Gln Glu Val Asp Ala His Phe Arg Thr Lys Arg
385                 390                 395                 400

Arg Ser Thr Asn Asp Ala Ala Ala Val Val Asp Phe Asp Asp Ile
                405                 410                 415

Arg Asn Leu Val Tyr Ile Gln Ala Ile Ile Lys Glu Ser Met Arg Leu
            420                 425                 430
```

-continued

```
Tyr Pro Ala Ser Pro Val Val Glu Arg Leu Ser Gly Glu Asp Cys Val
            435                 440                 445

Val Gly Gly Phe His Val Pro Ala Gly Thr Arg Leu Trp Ala Asn Val
450                 455                 460

Trp Lys Met Gln Arg Asp Pro Lys Val Trp Asp Pro Leu Val Phe
465                 470                 475                 480

Arg Pro Asp Arg Phe Leu Ser Asp Glu Gln Lys Met Val Asp Val Arg
                485                 490                 495

Gly Gln Asn Tyr Glu Leu Leu Pro Phe Gly Ala Gly Arg Arg Val Cys
                500                 505                 510

Pro Gly Val Ser Phe Ser Leu Asp Leu Met Gln Leu Val Leu Thr Arg
            515                 520                 525

Leu Ile Leu Glu Phe Glu Met Lys Ser Pro Ser Gly Lys Val Asp Met
530                 535                 540

Thr Ala Thr Pro Gly Leu Met Ser Tyr Lys Val Ile Pro Leu Asp Ile
545                 550                 555                 560

Leu Leu Thr His Arg Arg Ile Lys Pro Cys Val Gln Ser Ala Ala Ser
                565                 570                 575

Glu Arg Asp Met Glu Ser Ser Gly Val Pro Val Ile Thr Leu Gly Ser
            580                 585                 590

Gly Lys Val Met Pro Val Leu Gly Met Gly Thr Phe Glu Lys Val Gly
            595                 600                 605

Lys Gly Ser Glu Arg Glu Arg Leu Ala Ile Leu Lys Ala Ile Glu Val
            610                 615                 620

Gly Tyr Arg Tyr Phe Asp Thr Ala Ala Ala Tyr Glu Thr Glu Glu Val
625                 630                 635                 640

Leu Gly Glu Ala Ile Ala Glu Ala Leu Gln Leu Gly Leu Val Lys Ser
                645                 650                 655

Arg Asp Glu Leu Phe Ile Ser Ser Met Leu Trp Cys Thr Asp Ala His
                660                 665                 670

Ala Asp Arg Val Leu Leu Ala Leu Gln Asn Ser Leu Arg Asn Leu Lys
            675                 680                 685

Leu Glu Tyr Val Asp Leu Tyr Met Leu Pro Phe Pro Ala Ser Leu Lys
690                 695                 700

Pro Gly Lys Ile Thr Met Asp Ile Pro Glu Glu Asp Ile Cys Arg Met
705                 710                 715                 720

Asp Tyr Arg Ser Val Trp Ala Ala Met Glu Glu Cys Gln Asn Leu Gly
                725                 730                 735

Phe Thr Lys Ser Ile Gly Val Ser Asn Phe Ser Cys Lys Lys Leu Gln
            740                 745                 750

Glu Leu Met Ala Thr Ala Asn Ile Pro Pro Ala Val Asn Gln Val Glu
            755                 760                 765

Met Ser Pro Ala Phe Gln Gln Lys Lys Leu Arg Glu Tyr Cys Asn Ala
770                 775                 780

Asn Asn Ile Leu Val Ser Ala Ile Ser Val Leu Gly Ser Asn Gly Thr
785                 790                 795                 800

Pro Trp Gly Ser Asn Ala Val Leu Gly Ser Glu Val Leu Lys Lys Ile
                805                 810                 815

Ala Met Ala Lys Gly Lys Ser Val Ala Gln Val Ser Met Arg Trp Val
            820                 825                 830

Tyr Glu Gln Gly Ala Ser Leu Val Val Lys Ser Phe Ser Glu Glu Arg
            835                 840                 845

Leu Arg Glu Asn Leu Asn Ile Phe Asp Trp Glu Leu Thr Lys Glu Asp
```

```
                  850                 855                 860
His Glu Lys Ile Gly Glu Ile Pro Gln Cys Arg Ile Leu Ser Ala Tyr
865                 870                 875                 880

Phe Leu Val Ser Pro Asn Gly Pro Phe Lys Ser Gln Glu Glu Leu Trp
                885                 890                 895

Asp Asp Glu Ala
            900

<210> SEQ ID NO 6
<211> LENGTH: 724
<212> TYPE: PRT
<213> ORGANISM: Papaver setigerum

<400> SEQUENCE: 6

Met Glu Leu Gln Tyr Ile Ser Tyr Phe Gln Pro Thr Ser Ser Val Val
1               5                   10                  15

Ala Leu Leu Leu Ala Leu Val Ser Ile Leu Ser Ser Val Val Val Leu
                20                  25                  30

Arg Lys Thr Phe Leu Asn Asn Tyr Ser Ser Pro Ala Ser Ser Thr
                35                  40                  45

Lys Thr Ala Val Leu Ser His Gln Arg Gln Ser Cys Ala Leu Pro
50                  55                  60

Ile Ser Gly Leu Leu His Ile Phe Met Asn Lys Asn Gly Leu Ile His
65                  70                  75                  80

Val Thr Leu Gly Asn Met Ala Asp Lys Tyr Gly Pro Ile Phe Ser Phe
                85                  90                  95

Pro Thr Gly Ser His Arg Thr Leu Val Val Ser Ser Trp Glu Met Val
                100                 105                 110

Lys Glu Cys Phe Thr Gly Asn Asn Asp Thr Ala Phe Ser Asn Arg Pro
            115                 120                 125

Ile Pro Leu Ala Phe Lys Thr Ile Phe Tyr Ala Cys Gly Gly Ile Asp
130                 135                 140

Ser Tyr Gly Leu Ser Ser Val Pro Tyr Gly Lys Tyr Trp Arg Glu Leu
145                 150                 155                 160

Arg Lys Val Cys Val His Asn Leu Leu Ser Asn Gln Gln Leu Leu Lys
                165                 170                 175

Phe Arg His Leu Ile Ile Ser Gln Val Asp Thr Ser Phe Asn Lys Leu
            180                 185                 190

Tyr Glu Leu Cys Lys Asn Ser Glu Asp Asn Gln Gly Asn Tyr Thr Thr
        195                 200                 205

Thr Thr Thr Ala Ala Gly Met Val Arg Ile Asp Asp Trp Leu Ala Glu
210                 215                 220

Leu Ser Phe Asn Val Ile Gly Arg Ile Val Cys Gly Phe Gln Ser Gly
225                 230                 235                 240

Pro Lys Thr Gly Ala Pro Ser Arg Val Glu Gln Phe Lys Glu Ala Ile
            245                 250                 255

Asn Glu Ala Ser Tyr Phe Met Ser Thr Ser Pro Val Ser Asp Asn Val
            260                 265                 270

Pro Met Leu Gly Trp Ile Asp Gln Leu Thr Gly Leu Thr Arg Asn Met
            275                 280                 285

Lys His Cys Gly Lys Lys Leu Asp Leu Val Val Glu Ser Ile Ile Asn
        290                 295                 300

Asp His Arg Gln Lys Arg Phe Ser Arg Thr Lys Gly Gly Asp Glu
305                 310                 315                 320
```

Lys Asp Asp Glu Gln Asp Asp Phe Ile Asp Ile Cys Leu Ser Ile Met
               325                 330                 335

Glu Gln Pro Gln Leu Pro Gly Asn Asn Asn Pro Ser Gln Ile Pro Ile
            340                 345                 350

Lys Ser Ile Val Leu Asp Met Ile Gly Gly Thr Asp Thr Thr Lys
        355                 360                 365

Leu Thr Thr Ile Trp Thr Leu Ser Leu Leu Asn Asn Pro His Val
    370                 375                 380

Leu Asp Lys Ala Lys Gln Glu Val Asp Ala His Phe Arg Thr Lys Arg
385                 390                 395                 400

Arg Ser Thr Asn Asp Ala Ala Ala Val Val Asp Phe Asp Asp Ile
            405                 410                 415

Arg Asn Leu Val Tyr Ile Gln Ala Leu Tyr Pro Ala Ser Pro Val Val
            420                 425                 430

Glu Arg Leu Ser Gly Glu Asp Cys Val Val Gly Gly Phe His Val Pro
        435                 440                 445

Ala Gly Thr Arg Leu Trp Ala Asn Val Trp Lys Met Gln Arg Asp Pro
    450                 455                 460

Lys Val Trp Asp Asp Pro Leu Val Phe Arg Pro Asp Arg Phe Leu Ser
465                 470                 475                 480

Asp Glu Gln Lys Met Val Asp Val Arg Gly Gln Asn Tyr Glu Leu Leu
            485                 490                 495

Pro Phe Gly Ala Gly Arg Arg Val Cys Pro Gly Val Ser Phe Ser Leu
        500                 505                 510

Asp Leu Met Gln Leu Val Leu Thr Arg Leu Ile Leu Glu Phe Glu Met
    515                 520                 525

Lys Ser Pro Ser Gly Lys Val Asp Met Thr Ala Thr Pro Gly Leu Met
530                 535                 540

Ser Tyr Lys Val Ile Pro Leu Asp Ile Leu Leu Thr His Arg Arg Ile
545                 550                 555                 560

Lys Pro Cys Val Gln Ser Ala Ala Ser Glu Arg Asp Met Glu Ser Ser
            565                 570                 575

Gly Val Pro Val Ile Thr Leu Gly Ser Gly Lys Val Met Pro Val Leu
        580                 585                 590

Gly Met Gly Thr Phe Glu Lys Val Gly Lys Gly Ser Glu Arg Glu Arg
    595                 600                 605

Leu Ala Ile Leu Lys Ala Ile Glu Val Gly Tyr Arg Tyr Phe Asp Thr
610                 615                 620

Ala Ala Ala Tyr Glu Thr Glu Glu Val Leu Gly Glu Ala Ile Ala Glu
625                 630                 635                 640

Ala Leu Gln Leu Gly Leu Val Lys Ser Arg Asp Glu Leu Phe Ile Ser
            645                 650                 655

Ser Met Leu Trp Cys Thr Asp Ala His Ala Asp Arg Val Leu Leu Ala
        660                 665                 670

Leu Gln Asn Ser Leu Arg Asn Leu Lys Leu Glu Tyr Val Asp Leu Tyr
    675                 680                 685

Met Leu Pro Phe Pro Ala Ser Leu Lys Pro Gly Lys Ile Thr Met Asp
    690                 695                 700

Ile Pro Glu Glu Asp Ile Cys Arg Met Asp Tyr Arg Ser Val Trp Ala
705                 710                 715                 720

Ala Met Glu Glu

<210> SEQ ID NO 7

```
<211> LENGTH: 889
<212> TYPE: PRT
<213> ORGANISM: Papaver bracteatum

<400> SEQUENCE: 7
```

| | | | | | | | | | | | | | | |
|---|---|---|---|---|---|---|---|---|---|---|---|---|---|---|
| Met | Glu | Leu | Gln | Tyr | Phe | Ser | Tyr | Phe | Gln | Pro | Thr | Ser | Val | Val |
| 1 | | | | 5 | | | | | 10 | | | | | 15 |
| Ala | Leu | Leu | Leu | Ala | Leu | Val | Ser | Ile | Leu | Phe | Ser | Val | Val | Leu |
| | | | 20 | | | | | 25 | | | | | 30 | |
| Arg | Lys | Thr | Phe | Ser | Asn | Asn | Tyr | Ser | Ser | Pro | Ala | Ser | Ser | Thr | Glu |
| | | 35 | | | | | 40 | | | | | 45 | | |
| Thr | Ala | Val | Leu | Cys | His | Gln | Arg | Gln | Gln | Ser | Cys | Ala | Leu | Pro | Ile |
| 50 | | | | | 55 | | | | | 60 | | | | |
| Ser | Gly | Leu | Leu | His | Val | Phe | Met | Asn | Lys | Asn | Gly | Leu | Ile | His | Val |
| 65 | | | | | 70 | | | | | 75 | | | | | 80 |
| Thr | Leu | Gly | Asn | Met | Ala | Asp | Lys | Tyr | Gly | Pro | Ile | Phe | Ser | Phe | Pro |
| | | | | 85 | | | | | 90 | | | | | 95 | |
| Thr | Gly | Ser | His | Arg | Thr | Leu | Val | Val | Ser | Ser | Trp | Glu | Met | Val | Lys |
| | | | 100 | | | | | 105 | | | | | 110 | | |
| Glu | Cys | Phe | Thr | Gly | Asn | Asn | Asp | Thr | Ala | Phe | Ser | Asn | Arg | Pro | Ile |
| | | 115 | | | | | 120 | | | | | 125 | | | |
| Pro | Leu | Ala | Phe | Gln | Thr | Ile | Phe | Tyr | Ala | Cys | Gly | Gly | Ile | Asp | Ser |
| 130 | | | | | 135 | | | | | 140 | | | | | |
| Tyr | Gly | Leu | Ser | Ser | Val | Pro | Tyr | Gly | Lys | Tyr | Trp | Arg | Glu | Leu | Arg |
| 145 | | | | | 150 | | | | | 155 | | | | | 160 |
| Lys | Val | Cys | Val | His | Asn | Leu | Leu | Ser | Asn | Gln | Gln | Leu | Leu | Lys | Phe |
| | | | | 165 | | | | | 170 | | | | | 175 | |
| Arg | His | Leu | Ile | Ile | Ser | Gln | Val | Asp | Thr | Ser | Phe | Asn | Lys | Leu | Tyr |
| | | | 180 | | | | | 185 | | | | | 190 | | |
| Glu | Leu | Cys | Lys | Asn | Ser | Glu | Asp | Asn | Gln | Gly | Met | Val | Arg | Met | Asp |
| | | 195 | | | | | 200 | | | | | 205 | | | |
| Asp | Trp | Leu | Ala | Gln | Leu | Ser | Phe | Asn | Val | Ile | Gly | Arg | Ile | Val | Cys |
| 210 | | | | | 215 | | | | | 220 | | | | | |
| Gly | Phe | Gln | Ser | Asp | Pro | Lys | Thr | Gly | Ala | Pro | Ser | Arg | Val | Glu | Gln |
| 225 | | | | | 230 | | | | | 235 | | | | | 240 |
| Phe | Lys | Glu | Val | Ile | Asn | Glu | Ala | Ser | Tyr | Phe | Met | Ser | Thr | Ser | Pro |
| | | | | 245 | | | | | 250 | | | | | 255 | |
| Val | Ser | Asp | Asn | Val | Pro | Met | Leu | Gly | Trp | Ile | Asp | Gln | Leu | Thr | Gly |
| | | | 260 | | | | | 265 | | | | | 270 | | |
| Leu | Thr | Arg | Asn | Met | Lys | His | Cys | Gly | Lys | Lys | Leu | Asp | Leu | Val | Val |
| | | 275 | | | | | 280 | | | | | 285 | | | |
| Glu | Ser | Ile | Ile | Lys | Asp | His | Arg | Gln | Lys | Arg | Phe | Ser | Arg | Thr |
| 290 | | | | | 295 | | | | | 300 | | | | | |
| Lys | Gly | Gly | Asp | Glu | Lys | Asp | Glu | Gln | Asp | Asp | Phe | Ile | Asp | Ile |
| 305 | | | | 310 | | | | | 315 | | | | | 320 |
| Cys | Leu | Ser | Ile | Met | Glu | Gln | Pro | Gln | Leu | Pro | Gly | Asn | Asn | Ser | Pro |
| | | | | 325 | | | | | 330 | | | | | 335 | |
| Pro | Gln | Ile | Pro | Ile | Lys | Ser | Ile | Val | Leu | Asp | Met | Ile | Gly | Gly | Gly |
| | | | 340 | | | | | 345 | | | | | 350 | | |
| Thr | Asp | Thr | Thr | Lys | Leu | Thr | Thr | Ile | Trp | Thr | Leu | Ser | Leu | Leu | Leu |
| | | 355 | | | | | 360 | | | | | 365 | | | |
| Asn | Asn | Pro | His | Val | Leu | Asp | Lys | Ala | Lys | Gln | Glu | Val | Asp | Ala | His |
| 370 | | | | | 375 | | | | | 380 | | | | | |
| Phe | Arg | Lys | Lys | Arg | Arg | Ser | Thr | Asp | Asp | Ala | Ala | Ala | Ala | Val | Val |

-continued

```
            385                 390                 395                 400
    Asp Phe Asp Asp Ile Arg Asn Leu Val Tyr Ile Gln Ala Ile Ile Lys
                        405                 410                 415

Glu Ser Met Arg Leu Tyr Pro Ala Ser Pro Val Val Glu Arg Leu Ser
                    420                 425                 430

Gly Glu Asp Cys Val Val Gly Phe His Val Pro Ala Gly Thr Arg
                    435                 440                 445

Leu Trp Ala Asn Val Trp Lys Met Gln Arg Asp Pro Lys Val Trp Asp
                450                 455                 460

Asp Pro Leu Val Phe Arg Pro Glu Arg Phe Leu Ser Asp Glu Gln Lys
    465                 470                 475                 480

Met Val Asp Val Arg Gly Gln Asn Tyr Glu Leu Leu Pro Phe Gly Ala
                        485                 490                 495

Gly Arg Arg Ile Cys Pro Gly Val Ser Phe Ser Leu Asp Leu Met Gln
                    500                 505                 510

Leu Val Leu Thr Arg Leu Ile Leu Glu Phe Glu Met Lys Ser Pro Ser
                515                 520                 525

Gly Lys Val Asp Met Thr Ala Thr Pro Gly Leu Met Ser Tyr Lys Val
            530                 535                 540

Val Pro Leu Asp Ile Leu Leu Thr His Arg Arg Ile Lys Ser Cys Val
    545                 550                 555                 560

Gln Leu Ala Ser Ser Glu Arg Asp Met Glu Ser Ser Gly Val Pro Val
                        565                 570                 575

Ile Thr Leu Ser Ser Gly Lys Val Met Pro Val Leu Gly Met Gly Thr
                    580                 585                 590

Phe Glu Lys Val Gly Lys Gly Ser Glu Arg Glu Arg Leu Ala Ile Leu
                595                 600                 605

Lys Ala Ile Glu Val Gly Tyr Arg Tyr Phe Asp Thr Ala Ala Ala Tyr
            610                 615                 620

Glu Thr Glu Glu Val Leu Gly Glu Ala Ile Ala Glu Ala Leu Gln Leu
    625                 630                 635                 640

Gly Leu Ile Glu Ser Arg Asp Glu Leu Phe Ile Ser Ser Met Leu Trp
                        645                 650                 655

Cys Thr Asp Ala His Pro Asp Arg Val Leu Leu Ala Leu Gln Asn Ser
                    660                 665                 670

Leu Arg Asn Leu Lys Leu Glu Tyr Leu Asp Leu Tyr Met Leu Pro Phe
                675                 680                 685

Pro Ala Ser Leu Lys Pro Gly Lys Ile Thr Met Asp Ile Pro Glu Glu
            690                 695                 700

Asp Ile Cys Arg Met Asp Tyr Arg Ser Val Trp Ser Ala Met Glu Glu
    705                 710                 715                 720

Cys Gln Asn Leu Gly Phe Thr Lys Ser Ile Gly Val Ser Asn Phe Ser
                        725                 730                 735

Ser Lys Lys Leu Gln Glu Leu Met Ala Thr Ala Asn Ile Pro Pro Ala
                    740                 745                 750

Val Asn Gln Val Glu Met Ser Pro Ala Phe Gln Gln Lys Lys Leu Arg
                755                 760                 765

Glu Tyr Cys Asn Ala Asn Asn Ile Leu Val Ser Ala Val Ser Ile Leu
            770                 775                 780

Gly Ser Asn Gly Thr Pro Trp Gly Ser Asn Ala Val Leu Gly Ser Glu
    785                 790                 795                 800

Val Leu Lys Gln Ile Ala Met Ala Lys Gly Lys Ser Val Ala Gln Val
                        805                 810                 815
```

Ser Met Arg Trp Val Tyr Glu Gln Gly Ala Ser Leu Val Val Lys Ser
            820                 825                 830

Phe Ser Glu Glu Arg Leu Arg Glu Asn Leu Asn Ile Phe Asp Trp Glu
        835                 840                 845

Leu Thr Lys Glu Asp Asn Glu Lys Ile Gly Glu Ile Pro Gln Cys Arg
850                 855                 860

Ile Leu Thr Ala Tyr Phe Leu Val Ser Pro Asn Gly Pro Phe Lys Ser
865                 870                 875                 880

Gln Glu Glu Leu Trp Asp Asp Lys Ala
                885

<210> SEQ ID NO 8
<211> LENGTH: 889
<212> TYPE: PRT
<213> ORGANISM: Papaver bracteatum

<400> SEQUENCE: 8

Met Glu Leu Gln Tyr Phe Ser Tyr Phe Gln Pro Thr Ser Ser Val Val
1               5                   10                  15

Ala Leu Leu Leu Ala Leu Val Ser Ile Leu Phe Ser Val Val Val Leu
            20                  25                  30

Arg Lys Thr Phe Ser Asn Asn Tyr Ser Ser Pro Ala Ser Ser Thr Glu
        35                  40                  45

Thr Ala Val Leu Cys His Gln Arg Gln Gln Ser Cys Ala Leu Pro Ile
    50                  55                  60

Ser Gly Leu Leu His Val Phe Met Asn Lys Asn Gly Leu Ile His Val
65                  70                  75                  80

Thr Leu Gly Asn Met Ala Asp Lys Tyr Gly Pro Ile Phe Ser Phe Pro
                85                  90                  95

Thr Gly Ser His Arg Thr Leu Val Val Ser Ser Trp Glu Met Val Lys
            100                 105                 110

Glu Cys Phe Thr Gly Asn Asn Asp Thr Ala Phe Ser Asn Arg Pro Ile
        115                 120                 125

Pro Leu Ala Phe Gln Thr Ile Phe Tyr Ala Cys Gly Gly Ile Asp Ser
    130                 135                 140

Tyr Gly Leu Ser Ser Val Pro Tyr Gly Lys Tyr Trp Arg Glu Leu Arg
145                 150                 155                 160

Lys Val Cys Val His Asn Leu Leu Ser Asn Gln Leu Leu Lys Phe
                165                 170                 175

Arg His Leu Ile Ile Ser Gln Val Asp Thr Ser Phe Asn Lys Leu Tyr
            180                 185                 190

Glu Leu Cys Lys Asn Ser Glu Asp Asn Gln Gly Met Val Arg Met Asp
        195                 200                 205

Asp Trp Leu Ala Gln Leu Ser Phe Asn Val Ile Gly Arg Ile Val Cys
    210                 215                 220

Gly Phe Gln Ser Asp Pro Lys Thr Gly Ala Pro Ser Arg Val Glu Gln
225                 230                 235                 240

Phe Lys Glu Val Ile Asn Glu Ala Ser Tyr Phe Met Ser Thr Ser Pro
                245                 250                 255

Val Ser Asp Asn Val Pro Met Leu Gly Trp Ile Asp Gln Leu Thr Gly
            260                 265                 270

Leu Thr Arg Asn Met Lys His Cys Gly Lys Lys Leu Asp Leu Val Val
        275                 280                 285

Glu Ser Ile Ile Lys Asp His Arg Gln Lys Arg Arg Phe Ser Arg Thr

```
            290                 295                 300
Lys Gly Asp Glu Lys Asp Glu Gln Asp Asp Phe Ile Asp Ile
305                 310                 315                 320

Cys Leu Ser Ile Met Glu Gln Pro Gln Leu Pro Gly Asn Asn Ser Pro
                325                 330                 335

Pro Gln Ile Pro Ile Lys Ser Ile Val Leu Asp Met Ile Gly Gly
                340                 345                 350

Thr Asp Thr Thr Lys Leu Thr Thr Ile Trp Thr Leu Ser Leu Leu Leu
                355                 360                 365

Asn Asn Pro His Val Leu Asp Lys Ala Lys Gln Glu Val Asp Ala His
        370                 375                 380

Phe Arg Lys Lys Arg Ser Thr Asp Asp Ala Ala Ala Val Val
385                 390                 395                 400

Asp Phe Asp Asp Ile Arg Asn Leu Val Tyr Ile Gln Ala Ile Ile Lys
                405                 410                 415

Glu Ser Met Arg Leu Tyr Pro Ala Ser Pro Val Val Glu Arg Leu Ser
                420                 425                 430

Gly Glu Asp Cys Val Val Gly Phe His Val Pro Ala Gly Thr Arg
        435                 440                 445

Leu Trp Ala Asn Val Trp Lys Met Gln Arg Asp Pro Lys Val Trp Asp
        450                 455                 460

Asp Pro Leu Val Phe Arg Pro Glu Arg Phe Leu Ser Asp Glu Gln Lys
465                 470                 475                 480

Met Val Asp Val Arg Gly Gln Asn Tyr Glu Leu Leu Pro Phe Gly Ala
                485                 490                 495

Gly Arg Arg Ile Cys Pro Gly Val Ser Phe Ser Leu Asp Leu Met Gln
                500                 505                 510

Leu Val Leu Thr Arg Leu Ile Leu Glu Phe Glu Met Lys Ser Pro Ser
                515                 520                 525

Gly Lys Val Asp Met Thr Ala Thr Pro Gly Leu Met Ser Tyr Lys Val
        530                 535                 540

Val Pro Leu Asp Ile Leu Leu Thr His Arg Arg Ile Lys Ser Cys Val
545                 550                 555                 560

Gln Leu Ala Ser Ser Glu Arg Asp Met Glu Ser Ser Gly Val Pro Val
                565                 570                 575

Ile Thr Leu Ser Ser Gly Lys Val Met Pro Val Leu Gly Met Gly Thr
                580                 585                 590

Phe Glu Lys Val Gly Lys Gly Ser Glu Arg Glu Arg Leu Ala Ile Leu
                595                 600                 605

Lys Ala Ile Glu Val Gly Tyr Arg Tyr Phe Asp Thr Ala Ala Ala Tyr
610                 615                 620

Glu Thr Glu Glu Val Leu Gly Glu Ala Ile Glu Ala Leu Gln Leu
625                 630                 635                 640

Gly Leu Ile Glu Ser Arg Asp Glu Leu Phe Ile Ser Ser Met Leu Trp
                645                 650                 655

Cys Thr Asp Ala His Pro Asp Arg Val Leu Leu Ala Leu Gln Asn Ser
                660                 665                 670

Leu Arg Asn Leu Lys Leu Glu Tyr Leu Asp Leu Tyr Met Leu Pro Phe
        675                 680                 685

Pro Ala Ser Leu Lys Pro Gly Lys Ile Thr Met Asp Ile Pro Glu Glu
        690                 695                 700

Asp Ile Cys Arg Met Asp Tyr Arg Ser Val Trp Ser Ala Met Glu Glu
705                 710                 715                 720
```

```
Cys Gln Asn Leu Gly Phe Thr Lys Ser Ile Gly Val Ser Asn Phe Ser
                725                 730                 735

Cys Lys Lys Leu Gln Glu Leu Met Ala Thr Ala Asn Ile Pro Pro Ala
            740                 745                 750

Val Asn Gln Val Glu Met Ser Pro Ala Phe Gln Lys Lys Leu Arg
            755                 760                 765

Glu Tyr Cys Asn Ala Asn Asn Ile Leu Val Ser Ala Val Ser Ile Leu
770                 775                 780

Gly Ser Asn Gly Thr Pro Trp Gly Ser Asn Ala Val Leu Gly Ser Glu
785                 790                 795                 800

Val Leu Lys Gln Ile Ala Met Ala Lys Gly Lys Ser Val Ala Gln Val
                805                 810                 815

Ser Met Arg Trp Val Tyr Glu Gln Gly Ala Ser Leu Val Val Lys Ser
                820                 825                 830

Phe Ser Glu Glu Arg Leu Arg Glu Asn Leu Asn Ile Phe Asp Trp Glu
                835                 840                 845

Leu Thr Lys Glu Asp Asn Glu Lys Ile Gly Glu Ile Pro Gln Cys Arg
                850                 855                 860

Ile Leu Thr Ala Tyr Phe Leu Val Ser Pro Asn Gly Pro Phe Lys Ser
865                 870                 875                 880

Gln Glu Glu Leu Trp Asp Asp Lys Ala
                885
```

<210> SEQ ID NO 9
<211> LENGTH: 848
<212> TYPE: PRT
<213> ORGANISM: Papaver bracteatum

<400> SEQUENCE: 9

```
Ser Ser Pro Ala Ser Ser Thr Glu Thr Ala Val Leu Cys His Gln Arg
1               5                   10                  15

Gln Gln Ser Cys Ala Leu Pro Ile Ser Gly Leu Leu His Ile Phe Met
                20                  25                  30

Asn Lys Asn Gly Leu Ile His Val Thr Leu Gly Asn Met Ala Asp Lys
            35                  40                  45

Tyr Gly Pro Ile Phe Ser Phe Pro Thr Gly Ser His Arg Ile Leu Val
50                  55                  60

Val Ser Ser Trp Glu Met Val Lys Glu Cys Phe Thr Gly Asn Asn Asp
65                  70                  75                  80

Thr Ala Phe Ser Asn Arg Pro Ile Pro Leu Ala Phe Lys Thr Ile Phe
                85                  90                  95

Tyr Ala Cys Arg Gly Ile Asp Ser Tyr Gly Leu Ser Ser Val Pro Tyr
                100                 105                 110

Gly Lys Tyr Trp Arg Glu Leu Arg Lys Val Cys Val His Asn Leu Leu
            115                 120                 125

Ser Asn Gln Gln Leu Leu Lys Phe Arg His Leu Ile Ile Ser Gln Val
130                 135                 140

Asp Thr Ser Phe Asn Lys Leu Tyr Glu Leu Cys Lys Asn Ser Glu Asp
145                 150                 155                 160

Asn Gln Gly Met Val Arg Met Asp Asp Trp Leu Ala Gln Leu Ser Phe
                165                 170                 175

Ser Val Ile Gly Arg Ile Val Cys Gly Phe Gln Ser Asp Pro Lys Thr
                180                 185                 190

Gly Ala Pro Ser Arg Val Glu Gln Phe Lys Glu Ala Ile Asn Glu Ala
```

```
            195                 200                 205
Ser Tyr Phe Met Ser Thr Ser Pro Val Ser Asp Asn Val Pro Met Leu
210                 215                 220

Gly Trp Ile Asp Gln Leu Thr Gly Leu Thr Arg Asn Met Thr His Cys
225                 230                 235                 240

Gly Lys Lys Leu Asp Leu Val Val Glu Ser Ile Ile Asn Asp His Arg
                245                 250                 255

Gln Lys Arg Arg Phe Ser Arg Thr Lys Gly Asp Glu Lys Asp Asp
                260                 265                 270

Glu Gln Asp Asp Phe Ile Asp Ile Cys Leu Ser Ile Met Glu Gln Pro
                275                 280                 285

Gln Leu Pro Gly Asn Asn Pro Lys Ile Pro Ile Lys Ser Ile
290                 295                 300

Val Leu Asp Met Ile Gly Ala Gly Thr Asp Thr Thr Lys Leu Thr Ile
305                 310                 315                 320

Ile Trp Thr Leu Ser Leu Leu Asn Asn Pro Asn Val Leu Ala Lys
                325                 330                 335

Ala Lys Gln Glu Val Asp Ala His Phe Glu Thr Lys Lys Arg Ser Thr
                340                 345                 350

Asn Glu Ala Ser Val Val Asp Phe Asp Ile Gly Asn Leu Val
                355                 360                 365

Tyr Ile Gln Ala Ile Ile Lys Glu Ser Met Arg Leu Tyr Pro Val Ser
370                 375                 380

Pro Val Val Glu Arg Leu Ser Ser Glu Asp Cys Val Val Gly Gly Phe
385                 390                 395                 400

His Val Pro Ala Gly Thr Arg Leu Trp Ala Asn Val Trp Lys Met Gln
                405                 410                 415

Arg Asp Pro Lys Val Trp Asp Pro Leu Val Phe Arg Pro Glu Arg
                420                 425                 430

Phe Leu Ser Asp Glu Gln Lys Met Val Asp Val Arg Gly Gln Asn Tyr
                435                 440                 445

Glu Leu Leu Pro Phe Gly Ala Gly Arg Arg Ile Cys Pro Gly Val Ser
450                 455                 460

Phe Ser Leu Asp Leu Met Gln Leu Val Leu Thr Arg Leu Ile Leu Glu
465                 470                 475                 480

Phe Glu Met Lys Ser Pro Ser Gly Lys Val Asp Met Thr Ala Thr Pro
                485                 490                 495

Gly Leu Met Ser Tyr Lys Val Val Pro Leu Asp Ile Leu Leu Thr His
                500                 505                 510

Arg Arg Ile Lys Ser Cys Val Gln Leu Ala Ser Ser Glu Arg Asp Met
                515                 520                 525

Glu Ser Ser Gly Val Pro Val Ile Thr Leu Arg Ser Gly Lys Val Met
530                 535                 540

Pro Val Leu Gly Met Gly Thr Phe Glu Lys Ala Gly Lys Gly Ser Glu
545                 550                 555                 560

Arg Glu Arg Leu Ala Ile Leu Lys Ala Ile Glu Val Gly Tyr Arg Tyr
                565                 570                 575

Phe Asp Thr Ala Ala Ala Tyr Glu Thr Glu Val Leu Gly Glu Ala
                580                 585                 590

Ile Ala Glu Ala Leu Gln Leu Gly Leu Ile Lys Ser Arg Asp Glu Leu
                595                 600                 605

Phe Ile Ser Ser Met Leu Trp Cys Thr Asp Ala His Pro Asp Arg Val
610                 615                 620
```

-continued

Leu Leu Ala Leu Gln Asn Ser Leu Arg Asn Leu Lys Leu Glu Tyr Val
625                 630                 635                 640

Asp Leu Tyr Met Leu Pro Phe Pro Ala Ser Leu Lys Pro Gly Lys Ile
            645                 650                 655

Thr Met Asp Ile Pro Glu Glu Asp Ile Cys Pro Met Asp Tyr Arg Ser
        660                 665                 670

Val Trp Ser Ala Met Glu Glu Cys Gln Asn Leu Gly Leu Thr Lys Ser
        675                 680                 685

Ile Gly Val Ser Asn Phe Ser Cys Lys Lys Leu Glu Glu Leu Met Ala
    690                 695                 700

Thr Ala Asn Ile Pro Pro Ala Val Asn Gln Val Glu Met Ser Pro Ala
705                 710                 715                 720

Phe Gln Gln Lys Lys Leu Arg Glu Tyr Cys Asn Ala Asn Asn Ile Leu
                725                 730                 735

Val Ser Ala Val Ser Ile Leu Gly Ser Asn Gly Thr Pro Trp Gly Ser
            740                 745                 750

Asn Ala Val Leu Gly Ser Glu Val Leu Lys Lys Ile Ala Met Ala Lys
        755                 760                 765

Gly Lys Ser Val Ala Gln Val Ser Met Arg Trp Val Tyr Glu Gln Gly
    770                 775                 780

Ala Ser Leu Val Val Lys Ser Phe Ser Glu Glu Arg Leu Arg Glu Asn
785                 790                 795                 800

Leu Asn Ile Phe Asp Trp Gln Leu Thr Lys Glu Asp Asn Glu Lys Ile
                805                 810                 815

Gly Glu Ile Pro Gln Cys Arg Ile Leu Ser Ala Tyr Phe Leu Val Ser
            820                 825                 830

Pro Lys Gly Pro Phe Lys Ser Gln Glu Glu Leu Trp Asp Asp Lys Ala
        835                 840                 845

<210> SEQ ID NO 10
<211> LENGTH: 847
<212> TYPE: PRT
<213> ORGANISM: Papaver bracteatum

<400> SEQUENCE: 10

Ser Ser Pro Ala Ser Ser Thr Glu Thr Ala Val Leu Cys His Gln Arg
1               5                   10                  15

Gln Gln Ser Cys Ala Leu Pro Ile Ser Gly Leu Leu His Ile Phe Met
                20                  25                  30

Asn Lys Asn Gly Leu Ile His Val Thr Leu Gly Asn Met Ala Asp Lys
            35                  40                  45

Tyr Gly Pro Ile Phe Ser Phe Pro Thr Gly Ser His Arg Ile Leu Val
        50                  55                  60

Val Ser Ser Trp Glu Met Val Lys Glu Cys Phe Thr Gly Asn Asn Asp
65                  70                  75                  80

Thr Phe Phe Ser Asn Arg Pro Ile Pro Leu Ala Phe Lys Ile Ile Phe
                85                  90                  95

Tyr Ala Gly Gly Val Asp Ser Tyr Gly Leu Ala Leu Val Pro Tyr Gly
            100                 105                 110

Lys Tyr Trp Arg Glu Leu Arg Lys Ile Cys Val His Asn Leu Leu Ser
        115                 120                 125

Asn Gln Gln Leu Leu Lys Phe Arg His Leu Ile Ile Ser Gln Val Asp
    130                 135                 140

Thr Ser Phe Asn Lys Leu Tyr Glu Leu Cys Lys Asn Ser Glu Asp Asn

-continued

```
            145                 150                 155                 160
        Gln Gly Met Val Arg Met Asp Asp Trp Leu Ala Gln Leu Ser Phe Ser
                            165                 170                 175
        Val Ile Gly Arg Ile Val Cys Gly Phe Gln Ser Asp Pro Lys Thr Gly
                        180                 185                 190
        Ala Pro Ser Arg Val Glu Gln Phe Lys Glu Ala Ile Asn Glu Ala Ser
                    195                 200                 205
        Tyr Phe Met Ser Thr Ser Pro Val Ser Asp Asn Val Pro Met Leu Gly
                210                 215                 220
        Trp Ile Asp Gln Leu Thr Gly Leu Thr Arg Asn Met Thr His Cys Gly
        225                 230                 235                 240
        Lys Lys Leu Asp Leu Val Val Glu Ser Ile Ile Asn Asp His Arg Gln
                            245                 250                 255
        Lys Arg Arg Phe Ser Arg Thr Lys Gly Gly Asp Glu Lys Asp Asp Glu
                        260                 265                 270
        Gln Asp Asp Phe Ile Asp Ile Cys Leu Ser Ile Met Glu Gln Pro Gln
                    275                 280                 285
        Leu Pro Gly Asn Asn Asn Pro Pro Lys Ile Pro Ile Lys Ser Ile Val
                290                 295                 300
        Leu Asp Met Ile Gly Gly Thr Asp Thr Thr Lys Leu Thr Thr Ile
        305                 310                 315                 320
        Trp Thr Leu Ser Leu Leu Leu Asn Asn Pro His Val Leu Asp Lys Ala
                            325                 330                 335
        Lys Gln Glu Val Asp Ala His Phe Leu Thr Lys Arg Arg Ser Thr Asn
                        340                 345                 350
        Asp Ala Ala Val Val Asp Phe Asp Asp Ile Arg Asn Leu Val Tyr Ile
                    355                 360                 365
        Gln Ala Ile Ile Lys Glu Ser Met Arg Leu Tyr Pro Ala Ser Pro Val
                370                 375                 380
        Val Glu Arg Leu Ser Gly Glu Asp Cys Val Val Gly Phe His Val
        385                 390                 395                 400
        Pro Ala Gly Thr Arg Leu Trp Val Asn Val Trp Lys Met Gln Arg Asp
                            405                 410                 415
        Pro Asn Val Trp Ala Asp Pro Met Val Phe Arg Pro Glu Arg Phe Leu
                        420                 425                 430
        Ser His Gly Gln Lys Met Val Asp Val Arg Gly Lys Asn Tyr Glu
                    435                 440                 445
        Leu Leu Pro Phe Gly Ala Gly Arg Arg Ile Cys Pro Gly Ile Ser Phe
                450                 455                 460
        Ser Leu Asp Leu Met Gln Leu Val Leu Thr Arg Leu Ile Leu Glu Phe
        465                 470                 475                 480
        Glu Met Lys Ser Pro Ser Gly Lys Val Asp Met Thr Ala Thr Pro Gly
                            485                 490                 495
        Leu Met Ser Tyr Lys Val Val Pro Leu Asp Ile Leu Leu Thr His Arg
                        500                 505                 510
        Arg Ile Lys Ser Cys Val Gln Leu Ala Ser Ser Glu Arg Asp Met Glu
                    515                 520                 525
        Ser Ser Gly Val Pro Val Ile Thr Leu Arg Ser Gly Lys Val Met Pro
                530                 535                 540
        Val Leu Gly Met Gly Thr Phe Glu Lys Ala Gly Lys Gly Ser Glu Arg
        545                 550                 555                 560
        Glu Arg Leu Ala Ile Leu Lys Ala Ile Glu Val Gly Tyr Arg Tyr Phe
                            565                 570                 575
```

```
Asp Thr Ala Ala Ala Tyr Glu Thr Glu Glu Val Leu Gly Glu Ala Ile
            580                 585                 590

Ala Glu Ala Leu Gln Leu Gly Leu Ile Lys Ser Arg Asp Glu Leu Phe
        595                 600                 605

Ile Ser Ser Met Leu Trp Cys Thr Asp Ala His Pro Asp Arg Val Leu
    610                 615                 620

Leu Ala Leu Gln Asn Ser Leu Arg Asn Leu Lys Leu Glu Tyr Val Asp
625                 630                 635                 640

Leu Tyr Met Leu Pro Phe Pro Ala Ser Leu Lys Pro Gly Lys Ile Thr
                645                 650                 655

Met Asp Ile Pro Glu Glu Asp Ile Cys Pro Met Asp Tyr Arg Ser Val
            660                 665                 670

Trp Ser Ala Met Glu Glu Cys Gln Asn Leu Gly Leu Thr Lys Ser Ile
        675                 680                 685

Gly Val Ser Asn Phe Ser Cys Lys Lys Leu Glu Glu Leu Met Ala Thr
    690                 695                 700

Ala Asn Ile Pro Pro Ala Val Asn Gln Val Glu Met Ser Pro Ala Phe
705                 710                 715                 720

Gln Gln Lys Lys Leu Arg Glu Tyr Cys Asn Ala Asn Asn Ile Leu Val
                725                 730                 735

Ser Ala Val Ser Ile Leu Gly Ser Asn Gly Thr Pro Trp Gly Ser Asn
            740                 745                 750

Ala Val Leu Gly Ser Glu Val Leu Lys Lys Ile Ala Met Ala Lys Gly
        755                 760                 765

Lys Ser Val Ala Gln Val Ser Met Arg Trp Val Tyr Glu Gln Gly Ala
    770                 775                 780

Ser Leu Val Val Lys Ser Phe Ser Glu Glu Arg Leu Arg Glu Asn Leu
785                 790                 795                 800

Asn Ile Phe Asp Trp Gln Leu Thr Lys Glu Asp Asn Glu Lys Ile Gly
                805                 810                 815

Glu Ile Pro Gln Cys Arg Ile Leu Ser Ala Tyr Phe Leu Val Ser Pro
            820                 825                 830

Lys Gly Pro Phe Lys Ser Gln Glu Glu Leu Trp Asp Asp Lys Ala
        835                 840                 845

<210> SEQ ID NO 11
<211> LENGTH: 845
<212> TYPE: PRT
<213> ORGANISM: Papaver bracteatum

<400> SEQUENCE: 11

Ser Ser Pro Ala Ser Ser Thr Glu Thr Ala Val Leu Cys His Gln Arg
1               5                   10                  15

Gln Gln Ser Cys Ala Leu Pro Ile Ser Gly Leu Leu His Ile Phe Met
            20                  25                  30

Asn Lys Asn Gly Leu Ile His Val Thr Leu Gly Asn Met Ala Asp Lys
        35                  40                  45

Tyr Gly Pro Ile Phe Ser Phe Pro Thr Gly Ser His Arg Ile Leu Val
    50                  55                  60

Val Ser Ser Trp Glu Met Val Lys Glu Cys Phe Thr Gly Asn Asn Asp
65                  70                  75                  80

Thr Phe Phe Ser Asn Arg Pro Ile Pro Leu Ala Phe Lys Ile Ile Phe
                85                  90                  95

Tyr Ala Gly Gly Val Asp Ser Tyr Gly Leu Ala Leu Val Pro Tyr Gly
```

```
            100                 105                 110
Lys Tyr Trp Arg Glu Arg Lys Ile Cys Val His Asn Leu Leu Ser
            115                 120                 125

Asn Gln Gln Leu Leu Asn Phe Arg His Leu Ile Ile Ser Gln Val Asp
            130                 135                 140

Thr Ser Phe Asn Lys Leu Tyr Asp Leu Ser Asn Lys Lys Lys Asn Thr
145                 150                 155                 160

Thr Thr Asp Ser Gly Thr Val Arg Met Asp Asp Trp Leu Ala Gln Leu
                165                 170                 175

Ser Phe Asn Val Ile Gly Arg Ile Val Cys Gly Phe Gln Thr His Thr
                180                 185                 190

Glu Thr Ser Ala Thr Ser Ser Val Glu Arg Phe Thr Glu Ala Ile Asp
                195                 200                 205

Glu Ala Ser Arg Phe Met Ser Ile Ala Thr Val Ser Asp Thr Phe Pro
                210                 215                 220

Trp Leu Gly Trp Ile Asp Gln Leu Thr Gly Leu Thr Arg Lys Met Lys
225                 230                 235                 240

His Tyr Gly Lys Lys Leu Asp Leu Val Val Glu Ser Ile Ile Glu Asp
                245                 250                 255

His Arg Gln Asn Arg Arg Ile Ser Gly Thr Lys Gln Gly Asp Asp Phe
                260                 265                 270

Ile Asp Ile Cys Leu Ser Ile Met Glu Gln Pro Gln Ile Ile Pro Gly
                275                 280                 285

Asn Asn Asp Pro Pro Arg Gln Ile Pro Ile Lys Ser Ile Val Leu Asp
                290                 295                 300

Met Ile Gly Gly Gly Thr Asp Thr Thr Lys Leu Thr Thr Thr Trp Thr
305                 310                 315                 320

Leu Ser Leu Leu Leu Asn Asn Pro His Val Leu Glu Lys Ala Arg Glu
                325                 330                 335

Glu Val Asp Ala His Phe Gly Thr Lys Arg Arg Pro Thr Asn Asp Asp
                340                 345                 350

Ala Val Met Val Glu Phe Asp Asp Ile Arg Asn Leu Val Tyr Ile Gln
                355                 360                 365

Ala Ile Ile Lys Glu Ser Met Arg Leu Tyr Pro Ala Ser Pro Val Val
                370                 375                 380

Glu Arg Leu Ser Gly Glu Asp Cys Val Val Gly Gly Phe His Val Pro
385                 390                 395                 400

Ala Gly Thr Arg Leu Trp Val Asn Val Trp Lys Met Gln Arg Asp Pro
                405                 410                 415

Asn Val Trp Ala Asp Pro Met Val Phe Arg Pro Glu Arg Phe Leu Ser
                420                 425                 430

Asp Glu Gln Lys Met Val Asp Val Arg Gly Gln Asn Tyr Glu Leu Leu
                435                 440                 445

Pro Phe Gly Ala Gly Arg Arg Ile Cys Pro Gly Val Ser Phe Ser Leu
                450                 455                 460

Asp Leu Met Gln Leu Val Leu Thr Arg Leu Ile Leu Glu Phe Glu Met
465                 470                 475                 480

Lys Ser Pro Ser Gly Lys Val Asp Met Thr Ala Thr Pro Gly Leu Met
                485                 490                 495

Ser Tyr Lys Val Val Pro Leu Asp Ile Leu Leu Thr His Arg Arg Ile
                500                 505                 510

Lys Ser Cys Val Gln Leu Ala Ser Ser Glu Arg Asp Met Glu Ser Ser
                515                 520                 525
```

```
Gly Val Pro Val Ile Thr Leu Arg Ser Gly Lys Val Met Pro Val Leu
            530                 535                 540

Gly Met Gly Thr Phe Glu Lys Ala Gly Lys Gly Ser Glu Arg Glu Arg
545                 550                 555                 560

Leu Ala Ile Leu Lys Ala Ile Glu Val Gly Tyr Arg Tyr Phe Asp Thr
                565                 570                 575

Ala Ala Ala Tyr Glu Thr Glu Glu Val Leu Gly Glu Ala Ile Ala Glu
            580                 585                 590

Ala Leu Gln Leu Gly Leu Ile Lys Ser Arg Asp Glu Leu Phe Ile Ser
            595                 600                 605

Ser Met Leu Trp Cys Thr Asp Ala His Pro Asp Arg Val Leu Leu Ala
            610                 615                 620

Leu Gln Asn Ser Leu Arg Asn Leu Lys Leu Glu Tyr Val Asp Leu Tyr
625                 630                 635                 640

Met Leu Pro Phe Pro Ala Ser Leu Lys Pro Gly Lys Ile Thr Met Asp
                645                 650                 655

Ile Pro Glu Glu Asp Ile Cys Pro Met Asp Tyr Arg Ser Val Trp Ser
                660                 665                 670

Ala Met Glu Glu Cys Gln Asn Leu Gly Leu Thr Lys Ser Ile Gly Val
            675                 680                 685

Ser Asn Phe Ser Cys Lys Lys Leu Glu Glu Leu Met Ala Thr Ala Asn
            690                 695                 700

Ile Pro Pro Ala Val Asn Gln Val Glu Met Ser Pro Ala Phe Gln Gln
705                 710                 715                 720

Lys Lys Leu Arg Glu Tyr Cys Asn Ala Asn Ile Leu Val Ser Ala
                725                 730                 735

Val Ser Ile Leu Gly Ser Asn Gly Thr Pro Trp Gly Ser Asn Ala Val
            740                 745                 750

Leu Gly Ser Glu Val Leu Lys Lys Ile Ala Met Ala Lys Gly Lys Ser
            755                 760                 765

Val Ala Gln Val Ser Met Arg Trp Val Tyr Glu Gln Gly Ala Ser Leu
770                 775                 780

Val Val Lys Ser Phe Ser Glu Glu Arg Leu Arg Glu Asn Leu Asn Ile
785                 790                 795                 800

Phe Asp Trp Gln Leu Thr Lys Glu Asp Asn Glu Lys Ile Gly Glu Ile
                805                 810                 815

Pro Gln Cys Arg Ile Leu Ser Ala Tyr Phe Leu Val Ser Pro Lys Gly
            820                 825                 830

Pro Phe Lys Ser Gln Glu Glu Leu Trp Asp Asp Lys Ala
            835                 840                 845

<210> SEQ ID NO 12
<211> LENGTH: 869
<212> TYPE: PRT
<213> ORGANISM: Papaver bracteatum

<400> SEQUENCE: 12

Val Ala Leu Arg Lys Lys Ile Leu Lys Asn Tyr Tyr Ser Ser Ser Ser
1               5                   10                  15

Ser Thr Ala Thr Ala Val Ser His Gln Trp Pro Lys Ala Ser Arg Ala
            20                  25                  30

Leu Pro Leu Ile Asp Leu Leu His Val Phe Phe Asn Lys Thr Asp Leu
        35                  40                  45

Met His Val Thr Leu Gly Asn Met Ala Asp Lys Phe Gly Pro Ile Phe
```

```
              50                  55                  60
Ser Phe Pro Thr Gly Ser His Arg Thr Leu Val Val Ser Ser Trp Glu
 65                  70                  75                  80

Lys Ala Lys Glu Cys Phe Thr Gly Asn Asn Asp Ile Val Phe Ser Gly
                     85                  90                  95

Arg Pro Leu Pro Leu Ala Phe Lys Leu Ile Phe Tyr Ala Gly Gly Ile
                100                 105                 110

Asp Ser Tyr Gly Ile Ser Gln Val Pro Tyr Gly Lys Lys Trp Arg Glu
                115                 120                 125

Leu Arg Asn Ile Cys Val His Asn Ile Leu Ser Asn Gln Gln Leu Leu
                130                 135                 140

Lys Phe Arg His Leu Met Ile Ser Gln Val Asp Asn Ser Phe Asn Lys
145                 150                 155                 160

Leu Tyr Glu Val Cys Asn Ser Asn Lys Asp Glu Gly Asp Ser Ala Thr
                165                 170                 175

Ser Thr Thr Ala Ala Gly Ile Val Arg Met Asp Asp Trp Leu Gly Lys
                180                 185                 190

Leu Ala Phe Asp Val Ile Ala Arg Ile Val Cys Gly Phe Gln Ser Gln
                195                 200                 205

Thr Glu Thr Ser Thr Thr Ser Ser Met Glu Arg Phe Thr Glu Ala Met
210                 215                 220

Asp Glu Ala Ser Arg Phe Met Ser Val Thr Ala Val Ser Asp Thr Val
225                 230                 235                 240

Pro Trp Leu Gly Trp Ile Asp Gln Leu Thr Gly Leu Lys Arg Asn Met
                245                 250                 255

Lys His Cys Gly Lys Lys Leu Asn Leu Val Val Lys Ser Ile Ile Glu
                260                 265                 270

Asp His Arg Gln Lys Arg Leu Ser Ser Thr Lys Lys Gly Asp Glu
                275                 280                 285

Asn Ile Ile Asp Glu Asp Glu Gln Asp Asp Phe Ile Asp Ile Cys Leu
                290                 295                 300

Ser Ile Met Glu Gln Pro Gln Leu Pro Gly Asn Asn Asn Pro Pro Lys
305                 310                 315                 320

Ile Pro Ile Lys Ser Ile Val Leu Asp Met Ile Gly Gly Gly Thr Asp
                325                 330                 335

Thr Thr Lys Leu Thr Thr Ile Trp Thr Leu Ser Leu Leu Leu Asn Asn
                340                 345                 350

Pro His Val Leu Asp Lys Ala Lys Gln Glu Val Asp Ala His Phe Leu
                355                 360                 365

Thr Lys Arg Arg Ser Thr Asn Asp Ala Ala Val Val Asp Phe Asp Asp
                370                 375                 380

Ile Arg Asn Leu Val Tyr Ile Gln Ala Ile Ile Lys Glu Ser Met Arg
385                 390                 395                 400

Leu Tyr Pro Ala Ser Pro Val Val Glu Arg Leu Ser Gly Glu Asp Cys
                405                 410                 415

Val Val Gly Gly Phe His Val Pro Ala Gly Thr Arg Leu Trp Val Asn
                420                 425                 430

Val Trp Lys Met Gln Arg Asp Pro Asn Val Trp Ala Asp Pro Met Val
                435                 440                 445

Phe Arg Pro Glu Arg Phe Leu Ser Asp Glu Gln Lys Met Val Asp Val
                450                 455                 460

Arg Gly Gln Asn Tyr Glu Leu Leu Pro Phe Gly Ala Gly Arg Arg Ile
465                 470                 475                 480
```

-continued

Cys Pro Gly Val Ser Phe Ser Leu Asp Leu Met Gln Leu Val Leu Thr
            485                 490                 495

Arg Leu Ile Leu Glu Phe Glu Met Lys Ser Pro Ser Gly Lys Val Asp
            500                 505                 510

Met Thr Ala Thr Pro Gly Leu Met Ser Tyr Lys Val Val Pro Leu Asp
            515                 520                 525

Ile Leu Leu Thr His Arg Arg Ile Lys Ser Cys Val Gln Leu Ala Ser
            530                 535                 540

Ser Glu Arg Asp Met Glu Ser Ser Gly Val Pro Val Ile Thr Leu Arg
545                 550                 555                 560

Ser Gly Lys Val Met Pro Val Leu Gly Met Gly Thr Phe Glu Lys Ala
            565                 570                 575

Gly Lys Gly Ser Glu Arg Glu Arg Leu Ala Ile Leu Lys Ala Ile Glu
            580                 585                 590

Val Gly Tyr Arg Tyr Phe Asp Thr Ala Ala Ala Tyr Glu Thr Glu Glu
            595                 600                 605

Val Leu Gly Glu Ala Ile Ala Glu Ala Leu Gln Leu Gly Leu Ile Lys
            610                 615                 620

Ser Arg Asp Glu Leu Phe Ile Ser Ser Met Leu Trp Cys Thr Asp Ala
625                 630                 635                 640

His Pro Asp Arg Val Leu Leu Ala Leu Gln Asn Ser Leu Arg Asn Leu
            645                 650                 655

Lys Leu Glu Tyr Val Asp Leu Tyr Met Leu Pro Phe Pro Ala Ser Leu
            660                 665                 670

Lys Pro Gly Lys Ile Thr Met Asp Ile Pro Glu Glu Asp Ile Cys Pro
            675                 680                 685

Met Asp Tyr Arg Ser Val Trp Ser Ala Met Glu Glu Cys Gln Asn Leu
            690                 695                 700

Gly Leu Thr Lys Ser Ile Gly Val Ser Asn Phe Ser Cys Lys Lys Leu
705                 710                 715                 720

Glu Glu Leu Met Ala Thr Ala Asn Ile Pro Pro Ala Val Asn Gln Val
            725                 730                 735

Glu Met Ser Pro Ala Phe Gln Gln Lys Lys Leu Arg Glu Tyr Cys Asn
            740                 745                 750

Ala Asn Asn Ile Leu Val Ser Ala Val Ser Ile Leu Gly Ser Asn Gly
            755                 760                 765

Thr Pro Trp Gly Ser Asn Ala Val Leu Gly Ser Glu Val Leu Lys Lys
            770                 775                 780

Ile Ala Met Ala Lys Gly Lys Ser Val Ala Gln Val Ser Met Arg Trp
785                 790                 795                 800

Val Tyr Glu Gln Gly Ala Ser Leu Val Val Lys Ser Phe Ser Glu Glu
            805                 810                 815

Arg Leu Arg Glu Asn Leu Asn Ile Phe Asp Trp Gln Leu Thr Lys Glu
            820                 825                 830

Asp Asn Glu Lys Ile Gly Glu Ile Pro Gln Cys Arg Ile Leu Ser Ala
            835                 840                 845

Tyr Phe Leu Val Ser Pro Lys Gly Pro Phe Lys Ser Gln Glu Glu Leu
            850                 855                 860

Trp Asp Asp Lys Ala
865

<210> SEQ ID NO 13
<211> LENGTH: 858

```
<212> TYPE: PRT
<213> ORGANISM: Papaver bracteatum
<220> FEATURE:
<221> NAME/KEY: MOD_RES
<222> LOCATION: (822)..(822)
<223> OTHER INFORMATION: Any amino acid

<400> SEQUENCE: 13
```

Met Glu Leu Gln Tyr Phe Ser Tyr Phe Gln Pro Thr Ser Ser Val Val
1               5                   10                  15

Ala Leu Leu Leu Ala Leu Val Ser Ile Leu Phe Ser Val Val Val Leu
            20                  25                  30

Arg Lys Thr Phe Ser Asn Asn Tyr Ser Ser Pro Ala Ser Ser Thr Glu
        35                  40                  45

Thr Ala Val Leu Cys His Gln Arg Gln Gln Ser Cys Ala Leu Pro Ile
    50                  55                  60

Ser Gly Leu Leu His Val Phe Met Asn Lys Asn Gly Leu Ile His Val
65                  70                  75                  80

Thr Leu Gly Asn Met Ala Asp Lys Tyr Gly Pro Ile Phe Ser Phe Pro
                85                  90                  95

Thr Gly Ser His Arg Thr Leu Val Val Ser Ser Trp Glu Met Val Lys
            100                 105                 110

Glu Cys Phe Thr Gly Asn Asn Asp Thr Ala Phe Ser Asn Arg Pro Ile
        115                 120                 125

Pro Leu Ala Phe Gln Thr Ile Phe Tyr Ala Cys Gly Gly Ile Asp Ser
    130                 135                 140

Tyr Gly Leu Ser Ser Val Pro Tyr Gly Lys Tyr Trp Arg Glu Leu Arg
145                 150                 155                 160

Lys Val Cys Val His Asn Leu Leu Ser Asn Gln Gln Leu Leu Lys Phe
                165                 170                 175

Arg His Leu Ile Ile Ser Gln Val Asp Thr Ser Phe Asn Lys Leu Tyr
            180                 185                 190

Glu Leu Cys Lys Asn Ser Glu Asp Asn Gln Gly Met Val Arg Met Asp
        195                 200                 205

Asp Trp Leu Ala Gln Leu Ser Phe Asn Val Ile Gly Arg Ile Val Cys
    210                 215                 220

Gly Phe Gln Ser Asp Pro Lys Thr Gly Ala Pro Ser Arg Val Glu Gln
225                 230                 235                 240

Phe Lys Glu Val Ile Asn Glu Ala Ser Tyr Phe Met Ser Thr Ser Pro
                245                 250                 255

Val Ser Asp Asn Val Pro Met Leu Gly Trp Ile Asp Gln Leu Thr Gly
            260                 265                 270

Leu Thr Arg Asn Met Lys His Cys Gly Lys Lys Leu Asp Leu Val Val
        275                 280                 285

Glu Ser Ile Ile Lys Asp His Arg Gln Lys Arg Arg Phe Ser Arg Thr
    290                 295                 300

Lys Gly Gly Asp Glu Lys Asp Glu Gln Asp Phe Ile Asp Ile
305                 310                 315                 320

Cys Leu Ser Ile Met Glu Gln Pro Gln Leu Pro Gly Asn Asn Ser Pro
                325                 330                 335

Pro Gln Ile Pro Ile Lys Ser Ile Val Leu Asp Met Ile Gly Gly Gly
            340                 345                 350

Thr Asp Thr Thr Lys Leu Thr Thr Ile Trp Thr Leu Ser Leu Leu Leu
        355                 360                 365

Asn Asn Pro His Val Leu Asp Lys Ala Lys Gln Glu Val Asp Ala His

```
            370                 375                 380
Phe Arg Lys Lys Arg Arg Ser Thr Asp Asp Ala Ala Ala Val Val
385                 390                 395                 400

Asp Phe Asp Asp Ile Arg Asn Leu Val Tyr Ile Gln Ala Ile Ile Lys
                405                 410                 415

Glu Ser Met Arg Leu Tyr Pro Ala Ser Pro Val Val Glu Arg Leu Ser
            420                 425                 430

Gly Glu Asp Cys Val Val Gly Gly Phe His Val Pro Ala Gly Thr Arg
            435                 440                 445

Leu Trp Ala Asn Val Trp Lys Met Gln Arg Asp Pro Lys Val Trp Asp
            450                 455                 460

Asp Pro Leu Val Phe Arg Pro Glu Arg Phe Leu Ser Asp Glu Gln Lys
465                 470                 475                 480

Met Val Asp Val Arg Gly Gln Asn Tyr Glu Leu Leu Pro Phe Gly Ala
                485                 490                 495

Gly Arg Arg Ile Cys Pro Gly Val Ser Phe Ser Leu Asp Leu Met Gln
                500                 505                 510

Leu Val Leu Thr Arg Leu Ile Leu Glu Phe Glu Met Lys Ser Pro Ser
            515                 520                 525

Gly Lys Val Asp Met Thr Ala Thr Pro Gly Leu Met Ser Tyr Lys Val
530                 535                 540

Val Pro Leu Asp Ile Leu Leu Thr His Arg Arg Ile Lys Ser Cys Val
545                 550                 555                 560

Gln Leu Ala Ser Ser Glu Arg Asp Met Glu Ser Ser Gly Val Pro Val
                565                 570                 575

Ile Thr Leu Ser Ser Gly Lys Val Met Pro Val Leu Gly Met Gly Thr
            580                 585                 590

Phe Glu Lys Val Gly Lys Gly Ser Glu Arg Glu Arg Leu Ala Ile Leu
            595                 600                 605

Lys Ala Ile Glu Val Gly Tyr Arg Tyr Phe Asp Thr Ala Ala Ala Tyr
610                 615                 620

Glu Thr Glu Glu Val Leu Gly Glu Ala Ile Ala Glu Ala Leu Gln Leu
625                 630                 635                 640

Gly Leu Ile Glu Ser Arg Asp Glu Leu Phe Ile Ser Ser Met Leu Trp
                645                 650                 655

Cys Thr Asp Ala His Pro Asp Arg Val Leu Leu Ala Leu Gln Asn Ser
                660                 665                 670

Leu Arg Asn Leu Lys Leu Glu Tyr Leu Asp Leu Tyr Met Leu Pro Phe
            675                 680                 685

Pro Ala Ser Leu Lys Pro Gly Lys Ile Thr Met Asp Ile Pro Glu Glu
690                 695                 700

Asp Ile Cys Arg Met Asp Tyr Arg Ser Val Trp Ser Ala Met Glu Glu
705                 710                 715                 720

Cys Gln Asn Leu Gly Phe Thr Lys Ser Ile Gly Val Ser Asn Phe Ser
                725                 730                 735

Ser Lys Lys Leu Gln Glu Leu Met Ala Thr Ala Asn Ile Pro Pro Ala
                740                 745                 750

Val Asn Gln Val Glu Met Ser Pro Ala Phe Gln Gln Lys Lys Leu Arg
            755                 760                 765

Glu Tyr Cys Asn Ala Asn Asn Ile Leu Val Ser Ala Val Ser Ile Leu
            770                 775                 780

Gly Ser Asn Gly Thr Pro Trp Gly Ser Asn Ala Val Leu Gly Ser Glu
785                 790                 795                 800
```

```
Val Leu Lys Gln Ile Ala Met Ala Lys Gly Lys Ser Val Ala Gln Val
            805                 810                 815

Ser Met Arg Trp Val Xaa Lys Phe Ser Ala Tyr Ala Ile Val Trp Ser
            820                 825                 830

Leu Phe Phe Gly His Arg Ile Cys Ile Thr Leu Tyr Ser Phe Leu Ile
            835                 840                 845

Arg Asn Val Ala Tyr Ile Cys Ile Thr Tyr
            850                 855

<210> SEQ ID NO 14
<211> LENGTH: 716
<212> TYPE: PRT
<213> ORGANISM: Papaver bracteatum

<400> SEQUENCE: 14

Met Glu Leu Gln Tyr Phe Ser Tyr Phe Gln Pro Thr Ser Ser Val Val
1               5                   10                  15

Ala Leu Leu Leu Ala Leu Val Ser Ile Leu Phe Ser Val Val Val Leu
            20                  25                  30

Arg Lys Thr Phe Ser Asn Asn Tyr Ser Ser Pro Ala Ser Ser Thr Glu
        35                  40                  45

Thr Ala Val Leu Cys His Gln Arg Gln Ser Cys Ala Leu Pro Ile
    50                  55                  60

Ser Gly Leu Leu His Val Phe Met Asn Lys Asn Gly Leu Ile His Val
65                  70                  75                  80

Thr Leu Gly Asn Met Ala Asp Lys Tyr Gly Pro Ile Phe Ser Phe Pro
            85                  90                  95

Thr Gly Ser His Arg Thr Leu Val Val Ser Ser Trp Glu Met Val Lys
            100                 105                 110

Glu Cys Phe Thr Gly Asn Asn Asp Thr Ala Phe Ser Asn Arg Pro Ile
        115                 120                 125

Pro Leu Ala Phe Gln Thr Ile Phe Tyr Ala Cys Gly Gly Ile Asp Ser
    130                 135                 140

Tyr Gly Leu Ser Ser Val Pro Tyr Gly Lys Tyr Trp Arg Glu Leu Arg
145                 150                 155                 160

Lys Val Cys Val His Asn Leu Leu Ser Asn Gln Gln Leu Leu Lys Phe
            165                 170                 175

Arg His Leu Ile Ile Ser Gln Val Asp Thr Ser Phe Asn Lys Leu Tyr
            180                 185                 190

Glu Leu Cys Lys Asn Ser Glu Asp Asn Gln Gly Met Val Arg Met Asp
        195                 200                 205

Asp Trp Leu Ala Gln Leu Ser Phe Asn Val Ile Gly Arg Ile Val Cys
    210                 215                 220

Gly Phe Gln Ser Asp Pro Lys Thr Gly Ala Pro Ser Arg Val Glu Gln
225                 230                 235                 240

Phe Lys Glu Val Ile Asn Glu Ala Ser Tyr Phe Met Ser Thr Ser Pro
            245                 250                 255

Val Ser Asp Asn Val Pro Met Leu Gly Trp Ile Asp Gln Leu Thr Gly
            260                 265                 270

Leu Thr Arg Asn Met Lys His Cys Gly Lys Lys Leu Asp Leu Val Val
        275                 280                 285

Glu Ser Ile Ile Lys Asp His Arg Gln Lys Arg Phe Ser Arg Thr
    290                 295                 300

Lys Gly Gly Asp Glu Lys Asp Asp Glu Gln Asp Asp Phe Ile Asp Ile
```

```
              305                 310                 315                 320
        Cys Leu Ser Ile Met Glu Gln Pro Gln Leu Pro Gly Asn Asn Ser Pro
                            325                 330                 335
        Pro Gln Ile Pro Ile Lys Ser Ile Val Leu Asp Met Ile Gly Gly Gly
                            340                 345                 350
        Thr Asp Thr Thr Lys Leu Thr Thr Ile Trp Thr Leu Ser Leu Leu Leu
                            355                 360                 365
        Asn Asn Pro His Val Leu Asp Lys Ala Lys Gln Glu Val Asp Ala His
                            370                 375                 380
        Phe Arg Lys Lys Arg Arg Ser Thr Asp Ala Ala Ala Val Val
        385                 390                 395                 400
        Asp Phe Asp Asp Ile Arg Asn Leu Val Tyr Ile Gln Ala Ile Ile Lys
                            405                 410                 415
        Glu Ser Met Arg Leu Tyr Pro Ala Ser Pro Val Val Glu Arg Leu Ser
                            420                 425                 430
        Gly Glu Asp Cys Val Val Gly Gly Phe His Val Pro Ala Gly Thr Arg
                            435                 440                 445
        Leu Trp Ala Asn Val Trp Lys Met Gln Arg Asp Pro Lys Val Trp Asp
                            450                 455                 460
        Asp Pro Leu Val Phe Arg Pro Glu Arg Phe Leu Ser Asp Glu Gln Lys
        465                 470                 475                 480
        Met Val Asp Val Arg Gly Gln Asn Tyr Glu Leu Leu Pro Phe Gly Ala
                            485                 490                 495
        Gly Arg Arg Ile Cys Pro Gly Val Ser Phe Ser Leu Asp Leu Met Gln
                            500                 505                 510
        Leu Val Leu Thr Arg Leu Ile Leu Glu Phe Glu Met Lys Ser Pro Ser
                            515                 520                 525
        Gly Lys Val Asp Met Thr Ala Thr Pro Gly Leu Met Ser Tyr Lys Val
                            530                 535                 540
        Val Pro Leu Asp Ile Leu Leu Thr His Arg Arg Ile Lys Ser Cys Val
        545                 550                 555                 560
        Gln Leu Ala Ser Ser Glu Arg Asp Met Glu Ser Ser Gly Val Pro Val
                            565                 570                 575
        Ile Thr Leu Ser Ser Gly Lys Val Met Pro Val Leu Gly Met Gly Thr
                            580                 585                 590
        Phe Glu Lys Val Gly Lys Gly Ser Glu Arg Glu Arg Leu Ala Ile Leu
                            595                 600                 605
        Lys Ala Ile Glu Val Gly Tyr Arg Tyr Phe Asp Thr Ala Ala Ala Tyr
                            610                 615                 620
        Glu Thr Glu Glu Val Leu Gly Glu Ala Ile Ala Glu Ala Leu Gln Leu
        625                 630                 635                 640
        Gly Leu Ile Glu Ser Arg Asp Glu Leu Phe Ile Ser Ser Met Leu Trp
                            645                 650                 655
        Cys Thr Asp Ala His Pro Asp Arg Val Leu Leu Ala Leu Gln Asn Ser
                            660                 665                 670
        Leu Arg Gln Val Phe Leu Met Gln Ile Arg Leu Ile Tyr Ile Cys Thr
                            675                 680                 685
        Tyr Gln Gln Val His Leu Asn Ile Tyr Phe Gln Ile Asn Glu Phe Val
                            690                 695                 700
        Leu Cys Asp Met Tyr Arg Asn Leu Lys Leu Glu Tyr
        705                 710                 715

<210> SEQ ID NO 15
```

<211> LENGTH: 864
<212> TYPE: PRT
<213> ORGANISM: Chelidonium majus

<400> SEQUENCE: 15

```
Leu Asn Asn Tyr Ser Ser Pro Ala Ser Ser Thr Lys Thr Ala Val
1               5                   10                  15

Leu Ser His Gln Arg Gln Gln Ser Cys Ala Leu Pro Ile Ser Gly Leu
            20                  25                  30

Leu His Ile Phe Met Asn Lys Asn Gly Leu Ile His Val Thr Leu Gly
        35                  40                  45

Asn Met Ala Asp Lys Tyr Gly Pro Ile Phe Ser Phe Pro Thr Gly Ser
    50                  55                  60

His Arg Thr Leu Val Val Ser Ser Trp Glu Met Val Lys Glu Cys Phe
65              70                  75                  80

Thr Gly Asn Asn Asp Thr Ala Phe Ser Asn Arg Pro Ile Pro Leu Ala
            85                  90                  95

Phe Lys Thr Ile Phe Tyr Ala Cys Gly Gly Ile Asp Ser Tyr Gly Leu
        100                 105                 110

Ser Ser Val Pro Tyr Gly Lys Tyr Trp Arg Glu Leu Arg Lys Val Cys
    115                 120                 125

Val His Asn Leu Leu Ser Asn Gln Gln Leu Leu Lys Phe Arg His Leu
130                 135                 140

Ile Ile Ser Gln Val Asp Thr Ser Phe Asn Lys Leu Tyr Glu Leu Cys
145                 150                 155                 160

Lys Asn Ser Glu Asp Asn Gln Gly Asn Tyr Pro Thr Thr Thr Thr Ala
            165                 170                 175

Ala Gly Met Val Arg Ile Asp Asp Trp Leu Ala Glu Leu Ser Phe Asn
        180                 185                 190

Val Ile Gly Arg Ile Val Cys Gly Phe Gln Ser Gly Pro Lys Thr Gly
    195                 200                 205

Ala Pro Ser Arg Val Glu Gln Phe Lys Glu Ala Ile Asn Glu Ala Ser
    210                 215                 220

Tyr Phe Met Ser Thr Ser Pro Val Ser Asp Asn Val Pro Met Leu Gly
225                 230                 235                 240

Trp Ile Asp Gln Leu Thr Gly Leu Thr Arg Asn Met Lys His Cys Gly
            245                 250                 255

Lys Lys Leu Asp Leu Val Val Glu Ser Ile Ile Asn Asp His Arg Gln
        260                 265                 270

Lys Arg Arg Phe Ser Arg Thr Lys Gly Gly Asp Glu Lys Asp Asp Glu
    275                 280                 285

Gln Asp Asp Phe Ile Asp Ile Cys Leu Ser Ile Met Glu Gln Pro Gln
    290                 295                 300

Leu Pro Gly Asn Asn Asn Pro Ser Gln Ile Pro Ile Lys Ser Ile Val
305                 310                 315                 320

Leu Asp Met Ile Gly Gly Gly Thr Asp Thr Thr Lys Leu Thr Thr Ile
            325                 330                 335

Trp Thr Leu Ser Leu Leu Leu Asn Asn Pro His Val Leu Asp Lys Ala
        340                 345                 350

Lys Gln Glu Val Asp Ala His Phe Arg Thr Lys Arg Arg Ser Thr Asn
    355                 360                 365

Asp Ala Ala Ala Ala Val Val Asp Phe Asp Asp Ile Arg Asn Leu Val
    370                 375                 380

Tyr Ile Gln Ala Ile Ile Lys Glu Ser Met Arg Leu Tyr Pro Ala Ser
```

```
            385                 390                 395                 400
        Pro Val Val Glu Arg Leu Ser Gly Glu Asp Cys Val Val Gly Phe
                        405                 410                 415
        His Val Pro Ala Gly Thr Arg Leu Trp Ala Asn Val Trp Lys Met Gln
                        420                 425                 430
        Arg Asp Pro Lys Val Trp Asp Pro Leu Val Phe Arg Pro Asp Arg
                        435                 440                 445
        Phe Leu Ser Asp Glu Gln Lys Met Val Asp Val Arg Gly Gln Asn Tyr
        450                 455                 460
        Glu Leu Leu Pro Phe Gly Ala Gly Arg Arg Val Cys Pro Gly Val Ser
        465                 470                 475                 480
        Phe Ser Leu Asp Leu Met Gln Leu Val Leu Thr Arg Leu Ile Leu Glu
                        485                 490                 495
        Phe Glu Met Lys Ser Pro Ser Gly Lys Val Asp Met Thr Ala Thr Pro
                        500                 505                 510
        Gly Leu Met Ser Tyr Lys Val Ile Pro Leu Asp Ile Leu Leu Thr His
                        515                 520                 525
        Arg Arg Ile Lys Pro Cys Val Gln Ser Ala Ala Ser Glu Arg Asp Met
        530                 535                 540
        Glu Ser Ser Gly Val Pro Val Ile Thr Leu Gly Ser Gly Lys Val Met
        545                 550                 555                 560
        Pro Val Leu Gly Met Gly Thr Phe Glu Lys Val Gly Lys Gly Ser Glu
                        565                 570                 575
        Arg Glu Arg Leu Ala Phe Leu Lys Ala Ile Glu Val Gly Tyr Arg Tyr
                        580                 585                 590
        Phe Asp Thr Ala Ala Ala Tyr Glu Thr Glu Glu Phe Leu Gly Glu Ala
                        595                 600                 605
        Ile Ala Glu Ala Leu Gln Leu Gly Leu Ile Lys Ser Arg Asp Glu Leu
                        610                 615                 620
        Phe Ile Thr Ser Lys Leu Trp Pro Cys Asp Ala His Pro Asp Leu Val
        625                 630                 635                 640
        Val Pro Ala Leu Gln Asn Ser Leu Arg Asn Leu Lys Leu Glu Tyr Val
                        645                 650                 655
        Asp Leu Tyr Met Leu Pro Phe Pro Ala Ser Leu Lys Pro Gly Lys Ile
                        660                 665                 670
        Thr Met Asp Ile Pro Glu Glu Asp Ile Cys Arg Met Asp Tyr Arg Ser
                        675                 680                 685
        Val Trp Ala Ala Met Glu Glu Cys Gln Asn Leu Gly Phe Thr Lys Ser
        690                 695                 700
        Ile Gly Val Ser Asn Phe Ser Cys Lys Lys Leu Gln Glu Leu Met Ala
        705                 710                 715                 720
        Thr Ala Asn Ile Pro Pro Ala Val Asn Gln Val Glu Met Ser Pro Ala
                        725                 730                 735
        Phe Gln Gln Lys Lys Leu Arg Glu Tyr Cys Asn Ala Asn Asn Ile Leu
                        740                 745                 750
        Val Ser Ala Ile Ser Val Leu Gly Ser Asn Gly Thr Pro Trp Gly Ser
                        755                 760                 765
        Asn Ala Val Leu Gly Ser Glu Val Leu Lys Lys Ile Ala Met Ala Lys
        770                 775                 780
        Gly Lys Ser Val Ala Gln Val Ser Met Arg Trp Val Tyr Glu Gln Gly
        785                 790                 795                 800
        Ala Ser Leu Val Val Lys Ser Phe Ser Glu Glu Arg Leu Arg Glu Asn
                        805                 810                 815
```

-continued

```
Leu Asn Ile Phe Asp Trp Glu Leu Thr Lys Glu Asp His Glu Lys Ile
            820                 825                 830

Gly Glu Ile Pro Gln Cys Arg Ile Leu Ser Ala Tyr Phe Leu Val Ser
            835                 840                 845

Pro Asn Gly Pro Phe Lys Ser Gln Glu Glu Leu Trp Asp Asp Glu Ala
            850                 855                 860

<210> SEQ ID NO 16
<211> LENGTH: 889
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Glu Leu Gln Tyr Phe Ser Tyr Phe Gln Pro Thr Ser Ser Val Val
1               5                   10                  15

Ala Leu Leu Ala Leu Val Ser Ile Leu Phe Ser Val Val Val Val Leu
            20                  25                  30

Arg Lys Thr Phe Ser Asn Asn Tyr Ser Ser Pro Ala Ser Ser Thr Glu
        35                  40                  45

Thr Ala Val Leu Cys His Gln Arg Gln Ser Cys Ala Leu Pro Ile
50                  55                  60

Ser Gly Leu Leu His Val Phe Met Asn Lys Asn Gly Leu Ile His Val
65                  70                  75                  80

Thr Leu Gly Asn Met Ala Asp Lys Tyr Gly Pro Ile Phe Ser Phe Pro
                85                  90                  95

Thr Gly Ser His Arg Thr Leu Val Val Ser Ser Trp Glu Met Val Lys
            100                 105                 110

Glu Cys Phe Thr Gly Asn Asn Asp Thr Ala Phe Ser Asn Arg Pro Ile
        115                 120                 125

Pro Leu Ala Phe Gln Thr Ile Phe Tyr Ala Cys Gly Gly Ile Asp Ser
    130                 135                 140

Tyr Gly Leu Ser Ser Val Pro Tyr Gly Lys Tyr Trp Arg Glu Leu Arg
145                 150                 155                 160

Lys Val Cys Val His Asn Leu Leu Ser Asn Gln Gln Leu Leu Lys Phe
                165                 170                 175

Arg His Leu Ile Ile Ser Gln Val Asp Thr Ser Phe Asn Lys Leu Tyr
            180                 185                 190

Glu Leu Cys Lys Asn Ser Glu Asp Asn Gln Gly Met Val Arg Met Asp
        195                 200                 205

Asp Trp Leu Ala Gln Leu Ser Phe Asn Val Ile Gly Arg Ile Val Cys
    210                 215                 220

Gly Phe Gln Ser Asp Pro Lys Thr Gly Ala Pro Ser Arg Val Glu Gln
225                 230                 235                 240

Phe Lys Glu Val Ile Asn Glu Ala Ser Tyr Phe Met Ser Thr Ser Pro
                245                 250                 255

Val Ser Asp Asn Val Pro Met Leu Gly Trp Ile Asp Gln Leu Thr Gly
            260                 265                 270

Leu Thr Arg Asn Met Lys His Cys Gly Lys Lys Leu Asp Leu Val Val
        275                 280                 285

Glu Ser Ile Ile Lys Asp His Arg Gln Lys Arg Arg Phe Ser Arg Thr
    290                 295                 300

Lys Gly Gly Asp Glu Lys Asp Asp Glu Gln Asp Asp Phe Ile Asp Ile
```

```
305                 310                 315                 320
Cys Leu Ser Ile Met Glu Gln Pro Gln Leu Pro Gly Asn Asn Ser Pro
                325                 330                 335

Pro Gln Ile Pro Ile Lys Ser Ile Val Leu Asp Met Ile Gly Gly Gly
            340                 345                 350

Thr Asp Thr Thr Lys Leu Thr Thr Ile Trp Thr Leu Ser Leu Leu Leu
        355                 360                 365

Asn Asn Pro His Val Leu Asp Lys Ala Lys Gln Glu Val Asp Ala His
    370                 375                 380

Phe Arg Lys Lys Arg Arg Ser Thr Asp Ala Ala Ala Val Val
385                 390                 395                 400

Asp Phe Asp Asp Ile Arg Asn Leu Val Tyr Ile Gln Ala Ile Ile Lys
                405                 410                 415

Glu Ser Met Arg Leu Tyr Pro Ala Ser Pro Val Val Glu Arg Leu Ser
            420                 425                 430

Gly Glu Asp Cys Val Val Gly Gly Phe His Val Pro Ala Gly Thr Arg
        435                 440                 445

Leu Trp Ala Asn Val Trp Lys Met Gln Arg Asp Pro Lys Val Trp Asp
    450                 455                 460

Asp Pro Leu Val Phe Arg Pro Glu Arg Phe Leu Ser Asp Glu Gln Lys
465                 470                 475                 480

Met Val Asp Val Arg Gly Gln Asn Tyr Glu Leu Leu Pro Phe Gly Ala
                485                 490                 495

Gly Arg Arg Ile Cys Pro Gly Val Ser Phe Ser Leu Asp Leu Met Gln
            500                 505                 510

Leu Val Leu Thr Arg Leu Ile Leu Glu Phe Glu Met Lys Ser Pro Ser
        515                 520                 525

Gly Lys Val Asp Met Thr Ala Thr Pro Gly Leu Met Ser Tyr Lys Val
    530                 535                 540

Val Pro Leu Asp Ile Leu Leu Thr His Arg Arg Ile Lys Ser Cys Val
545                 550                 555                 560

Gln Leu Ala Ser Ser Glu Arg Asp Met Glu Ser Ser Gly Val Pro Val
                565                 570                 575

Ile Thr Leu Ser Ser Gly Lys Val Met Pro Val Leu Gly Met Gly Thr
            580                 585                 590

Phe Glu Lys Val Gly Lys Gly Ser Glu Arg Glu Arg Leu Ala Ile Leu
        595                 600                 605

Lys Ala Ile Glu Val Gly Tyr Arg Tyr Phe Asp Thr Ala Ala Ala Tyr
    610                 615                 620

Glu Thr Glu Glu Val Leu Gly Glu Ala Ile Ala Glu Ala Leu Gln Leu
625                 630                 635                 640

Gly Leu Ile Glu Ser Arg Asp Glu Leu Phe Ile Ser Ser Met Leu Trp
                645                 650                 655

Cys Thr Asp Ala His Pro Asp Arg Val Leu Leu Ala Leu Gln Asn Ser
            660                 665                 670

Leu Arg Asn Leu Lys Leu Glu Tyr Leu Asp Leu Tyr Met Leu Pro Phe
        675                 680                 685

Pro Ala Ser Leu Lys Pro Gly Lys Ile Thr Met Asp Ile Pro Glu Glu
    690                 695                 700

Asp Ile Cys Arg Met Asp Tyr Arg Ser Val Trp Ser Ala Met Glu Glu
705                 710                 715                 720

Cys Gln Asn Leu Gly Phe Thr Lys Ser Ile Gly Val Ser Asn Phe Ser
                725                 730                 735
```

```
Cys Lys Lys Leu Gln Glu Leu Met Ala Thr Ala Asn Ile Pro Pro Ala
                740                 745                 750

Val Asn Gln Val Glu Met Ser Pro Ala Phe Gln Gln Lys Lys Leu Arg
        755                 760                 765

Glu Tyr Cys Asn Ala Asn Asn Ile Leu Val Ser Ala Val Ser Ile Leu
        770                 775                 780

Gly Ser Asn Gly Thr Pro Trp Gly Ser Asn Ala Val Leu Gly Ser Glu
785                 790                 795                 800

Val Leu Lys Gln Ile Ala Met Ala Lys Gly Lys Ser Val Ala Gln Val
                805                 810                 815

Ser Met Arg Trp Val Tyr Glu Gln Gly Ala Ser Leu Val Val Lys Ser
                820                 825                 830

Phe Ser Glu Glu Arg Leu Arg Glu Asn Leu Asn Ile Phe Asp Trp Glu
                835                 840                 845

Leu Thr Lys Glu Asp Asn Glu Lys Ile Gly Glu Ile Pro Gln Cys Arg
                850                 855                 860

Ile Leu Thr Ala Tyr Phe Leu Val Ser Pro Asn Gly Pro Phe Lys Ser
865                 870                 875                 880

Gln Glu Glu Leu Trp Asp Asp Lys Ala
                885

<210> SEQ ID NO 17
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Glu Leu Gln Tyr Phe Ser Tyr Phe Gln Pro Thr Ser Ser Val Val
1               5                   10                  15

Ala Leu Leu Leu Ala Leu Val Ser Ile Leu Phe Ser Val Val Val Leu
                20                  25                  30

Arg Lys Thr Phe Ser Asn Asn Tyr Ser Ser Pro Ala Ser Ser Thr Glu
                35                  40                  45

Thr Ala Val Leu Cys His Gln Arg Gln Gln Ser Cys Ala Leu Pro Ile
        50                  55                  60

Ser Gly Leu Leu His Val Phe Met Asn Lys Asn Gly Leu Ile His Val
65                  70                  75                  80

Thr Leu Gly Asn Met Ala Asp Lys Tyr Gly Pro Ile Phe Ser Phe Pro
                85                  90                  95

Thr Gly Ser His Arg Thr Leu Val Val Ser Ser Trp Glu Met Val Lys
                100                 105                 110

Glu Cys Phe Thr Gly Asn Asn Asp Thr Ala Phe Ser Asn Arg Pro Ile
        115                 120                 125

Pro Leu Ala Phe Gln Thr Ile Phe Tyr Ala Cys Gly Gly Ile Asp Ser
        130                 135                 140

Tyr Gly Leu Ser Ser Val Pro Tyr Gly Lys Tyr Trp Arg Glu Leu Arg
145                 150                 155                 160

Lys Val Cys Val His Asn Leu Leu Ser Asn Gln Gln Leu Leu Lys Phe
                165                 170                 175

Arg His Leu Ile Ile Ser Gln Val Asp Thr Ser Phe Asn Lys Leu Tyr
                180                 185                 190

Glu Leu Cys Lys Asn Ser Glu Asp Asn Gln Gly Met Val Arg Met Asp
```

```
                195                 200                 205
Asp Trp Leu Ala Gln Leu Ser Phe Asn Val Ile Gly Arg Ile Val Cys
210                 215                 220
Gly Phe Gln Ser Asp Pro Lys Thr Gly Ala Pro Ser Arg Val Glu Gln
225                 230                 235                 240
Phe Lys Glu Val Ile Asn Glu Ala Ser Tyr Phe Met Ser Thr Ser Pro
                245                 250                 255
Val Ser Asp Asn Val Pro Met Leu Gly Trp Ile Asp Gln Leu Thr Gly
                260                 265                 270
Leu Thr Arg Asn Met Lys His Cys Gly Lys Lys Leu Asp Leu Val Val
                275                 280                 285
Glu Ser Ile Ile Lys Asp His Arg Gln Lys Arg Arg Phe Ser Arg Thr
                290                 295                 300
Lys Gly Gly Asp Glu Lys Asp Asp Glu Gln Asp Asp Phe Ile Asp Ile
305                 310                 315                 320
Cys Leu Ser Ile Met Glu Gln Pro Gln Leu Pro Gly Asn Asn Ser Pro
                325                 330                 335
Pro Gln Ile Pro Ile Lys Ser Ile Val Leu Asp Met Ile Gly Gly Gly
                340                 345                 350
Thr Asp Thr Thr Lys Leu Thr Thr Ile Trp Thr Leu Ser Leu Leu Leu
                355                 360                 365
Asn Asn Pro His Val Leu Asp Lys Ala Lys Gln Glu Val Asp Ala His
370                 375                 380
Phe Arg Lys Lys Arg Ser Thr Asp Ala Ala Ala Val Val
385                 390                 395                 400
Asp Phe Asp Asp Ile Arg Asn Leu Val Tyr Ile Gln Ala Ile Ile Lys
                405                 410                 415
Glu Ser Met Arg Leu Tyr Pro Ala Ser Pro Val Val Glu Arg Leu Ser
                420                 425                 430
Gly Glu Asp Cys Val Val Gly Gly Phe His Val Pro Ala Gly Thr Arg
                435                 440                 445
Leu Trp Ala Asn Val Trp Lys Met Gln Arg Asp Pro Lys Val Trp Asp
450                 455                 460
Asp Pro Leu Val Phe Arg Pro Glu Arg Phe Leu Ser Asp Glu Gln Lys
465                 470                 475                 480
Met Val Asp Val Arg Gly Gln Asn Tyr Glu Leu Leu Pro Phe Gly Ala
                485                 490                 495
Gly Arg Arg Ile Cys Pro Gly Val Ser Phe Ser Leu Asp Leu Met Gln
                500                 505                 510
Leu Val Leu Thr Arg Leu Ile Leu Glu Phe Glu Met Lys Ser Pro Ser
                515                 520                 525
Gly Lys Val Asp Met Thr Ala Thr Pro Gly Leu Met Ser Tyr Lys Val
                530                 535                 540
Val Pro Leu Asp Ile Leu Leu Thr His Arg Arg Ile Lys Ser Cys Val
545                 550                 555                 560
Gln Leu Ala Ser Ser Glu Arg Asp
                565

<210> SEQ ID NO 18
<211> LENGTH: 321
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 18

```
Met Glu Ser Ser Gly Val Pro Val Ile Thr Leu Ser Ser Gly Lys Val
1               5                   10                  15

Met Pro Val Leu Gly Met Gly Thr Phe Glu Lys Val Gly Lys Gly Ser
            20                  25                  30

Glu Arg Glu Arg Leu Ala Ile Leu Lys Ala Ile Glu Val Gly Tyr Arg
        35                  40                  45

Tyr Phe Asp Thr Ala Ala Ala Tyr Glu Thr Glu Glu Val Leu Gly Glu
    50                  55                  60

Ala Ile Ala Glu Ala Leu Gln Leu Gly Leu Ile Glu Ser Arg Asp Glu
65                  70                  75                  80

Leu Phe Ile Ser Ser Met Leu Trp Cys Thr Asp Ala His Pro Asp Arg
                85                  90                  95

Val Leu Leu Ala Leu Gln Asn Ser Leu Arg Asn Leu Lys Leu Glu Tyr
            100                 105                 110

Leu Asp Leu Tyr Met Leu Pro Phe Pro Ala Ser Leu Lys Pro Gly Lys
        115                 120                 125

Ile Thr Met Asp Ile Pro Glu Glu Asp Ile Cys Arg Met Asp Tyr Arg
    130                 135                 140

Ser Val Trp Ser Ala Met Glu Glu Cys Gln Asn Leu Gly Phe Thr Lys
145                 150                 155                 160

Ser Ile Gly Val Ser Asn Phe Ser Cys Lys Lys Leu Gln Glu Leu Met
                165                 170                 175

Ala Thr Ala Asn Ile Pro Pro Ala Val Asn Gln Val Glu Met Ser Pro
            180                 185                 190

Ala Phe Gln Gln Lys Lys Leu Arg Glu Tyr Cys Asn Ala Asn Asn Ile
        195                 200                 205

Leu Val Ser Ala Val Ser Ile Leu Gly Ser Asn Gly Thr Pro Trp Gly
    210                 215                 220

Ser Asn Ala Val Leu Gly Ser Glu Val Leu Lys Gln Ile Ala Met Ala
225                 230                 235                 240

Lys Gly Lys Ser Val Ala Gln Val Ser Met Arg Trp Val Tyr Glu Gln
                245                 250                 255

Gly Ala Ser Leu Val Val Lys Ser Phe Ser Glu Glu Arg Leu Arg Glu
            260                 265                 270

Asn Leu Asn Ile Phe Asp Trp Glu Leu Thr Lys Glu Asp Asn Glu Lys
        275                 280                 285

Ile Gly Glu Ile Pro Gln Cys Arg Ile Leu Thr Ala Tyr Phe Leu Val
    290                 295                 300

Ser Pro Asn Gly Pro Phe Lys Ser Gln Glu Glu Leu Trp Asp Asp Lys
305                 310                 315                 320

Ala
```

<210> SEQ ID NO 19
<211> LENGTH: 682
<212> TYPE: DNA
<213> ORGANISM: Saccharomyces cerevisiae

<400> SEQUENCE: 19

```
ttcagttcga gtttatcatt atcaatactg ccatttcaaa gaatacgtaa ataattaata      60
gtagtgattt tcctaacttt atttagtcaa aaaattagcc ttttaattct gctgtaaccc     120
gtacatgccc aaaatagggg gcgggttaca cagaatatat aacatcgtag gtgtctgggt     180
```

```
gaacagttta ttcctggcat ccactaaata taatggagcc cgcttttta gctggcatcc     240 agaaaaaaaa agaatcccag caccaaaata ttgttttctt caccaaccat cagttcatag     300
gtccattctc ttagcgcaac tacagagaac aggggcacaa acaggcaaaa aacgggcaca     360
acctcaatgg agtgatgcaa cctgcctgga gtaaatgatg acacaaggca attgacccac     420
gcatgtatct atctcatttt cttacacctt ctattacctt ctgctctctc tgatttggaa     480
aaagctgaaa aaaaggttg aaaccagttc cctgaaatta ttcccctact tgactaataa     540
gtatataaag acggtaggta ttgattgtaa ttctgtaaat ctatttctta aacttcttaa     600
attctacttt tatagttagt cttttttta gttttaaaac accaagaact tagtttcgaa     660
taaacacaca taaacaaaca aa                                              682

<210> SEQ ID NO 20
<211> LENGTH: 289
<212> TYPE: DNA
<213> ORGANISM: Saccharomyces cerevisiae

<400> SEQUENCE: 20
gagcgttggt tggtggatca agcccacgcg taggcaatcc tcgagcagat ccgccaggcg     60
tgtatatata gcgtggatgg ccaggcaact ttagtgctga cacatacagg catatatata     120
tgtgtgcgac gacacatgat catatggcat gcatgtgctc tgtatgtata taaaactctt     180
gttttcttct tttctctaaa tattcttcc ttatacatta ggacctttgc agcataaatt     240
actatacttc tatagacaca caaacacaaa tacacacact aaattaata                 289

<210> SEQ ID NO 21
<211> LENGTH: 413
<212> TYPE: DNA
<213> ORGANISM: Saccharomyces cerevisiae

<400> SEQUENCE: 21
catagcttca aaatgtttct actccttttt tactcttcca gatttctcg gactccgcgc      60 atcgccgtac cacttcaaaa cacccaagca cagcatacta aatttcccct ctttcttcct     120
ctagggtgtc gttaattacc cgtactaaag gtttggaaaa gaaaaaagag accgcctcgt     180
ttctttttct tcgtcgaaaa aggcaataaa aatttttatc acgtttcttt tcttgaaaa      240 tttttttttt tgattttttt ctctttcgat gacctcccat tgatatttaa gttaataaac     300
ggtcttcaat ttctcaagtt tcagtttcat ttttcttgtt ctattacaac ttttttact      360 tcttgctcat tagaaagaaa gcatagcaat ctaatctaag ttttaattac aaa            413

<210> SEQ ID NO 22
<211> LENGTH: 274
<212> TYPE: DNA
<213> ORGANISM: Saccharomyces cerevisiae

<400> SEQUENCE: 22
acaggcccct tttcctttgt cgatatcatg taattagtta tgtcacgctt acattcacgc      60
cctcctccca catccgctct aaccgaaaag gaaggagtta gacaacctga agtctaggtc     120
cctatttatt ttttttaata gttatgttag tattaagaac gttatttata tttcaaattt     180 ttctttttt tctgtacaaa cgcgtgtacg catgtaacat tatactgaaa accttgcttg     240
agaaggtttt gggacgctcg aaggctttaa tttg                                 274

<210> SEQ ID NO 23
<211> LENGTH: 150
```

<212> TYPE: DNA
<213> ORGANISM: Saccharomyces cerevisiae

<400> SEQUENCE: 23

```
gcgaatttct tatgatttat gatttttatt attaaataag ttataaaaaa aataagtgta    60
tacaaatttt aaagtgactc ttaggtttta aaacgaaaat tcttattctt gagtaactct   120
ttcctgtagg tcaggttgct ttctcaggta                                    150
```

<210> SEQ ID NO 24
<211> LENGTH: 8014
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

```
cctcgccgca gttaattaaa gtcagtgagc gaggaagcgc gtaactataa cggtcctaag    60
gtagcgaatc ctgatgcggt attttctcct tacgcatctg tgcggtattt cacaccgcat   120
agatcggcaa gtgcacaaac aatacttaaa taaatactac tcagtaataa cctatttctt   180
agcattttg acgaaatttg ctattttgtt agagtctttt acaccattg tctccacacc    240
tccgcttaca tcaacaccaa taacgccatt aatctaagc gcatcaccaa cattttctgg   300
cgtcagtcca ccagctaaca taaaatgtaa gctttcgggg ctctcttgcc ttccaaccca   360
gtcagaaatc gagttccaat ccaaaagttc acctgtccca cctgcttctg aatcaaacaa   420
gggaataaac gaatgaggtt tctgtgaagc tgcactgagt agtatgttgc agtcttttgg   480
aaatacgagt cttttaataa ctggcaaacc gaggaactct tggtattctt gccacgactc   540
atctccatgc agttggacga tatcaatgcc gtaatcattg accagagcca aaacatcctc   600
cttaagttga ttacgaaaca cgccaaccaa gtatttcgga gtgcctgaac tatttttata   660
tgcttttaca agacttgaaa ttttccttgc aataaccggg tcaattgttc tctttctatt   720
gggcacacat ataatacccca gcaagtcagc atcggaatct agagcacatt ctgcggcctc   780
tgtgctctgc aagccgcaaa cttttcaccaa tggaccagaa ctacctgtga aattaataac   840
agacatactc caagctgcct ttgtgtgctt aatcacgtat actcacgtgc tcaatagtca   900
ccaatgccct ccctcttggc cctctccttt tcttttttcg accgaattaa ttcttaatcg   960
gcaaaaaaag aaaagctccg gatcaagatt gtacgtaagg tgacaagcta ttttttcaata  1020
aagaatatct tccactactg ccatctggcg tcataactgc aaagtacaca tatattcga   1080
tgctgttcta ttaaatgctt cctatattat atatatagta atgtcgtgat ctatggtgca  1140
ctctcagtac aatctgctct gatgccgcat agttaagcca gccccgacac ccgccaacac  1200
ccgctgacgc gccctgacgg gcttgtctgc tcccggcatc cgcttacaga caagctgtga  1260
ccgtctccgg gagctgcatg tgtcagaggt tttcaccgtc atcaccgaaa cgcgcgagac  1320
gaaagggcct cgtgatacgc ctatttttat aggttaatgt catgataata atggtttctt  1380
agacggatcg cttgcctgta acttacacgc gcctcgtatc ttttaatgat ggaataattt  1440
gggaatttac tctgtgttta tttattttta tgttttgtat ttggatttta aaagtaaat   1500
aaagaaggta gaagagttac ggaatgaaga aaaaaaaata aacaaggtt taaaaatttt  1560
caacaaaaag cgtactttac atatatattt attagacaag aaaagcgat taaatagata  1620
tacattcgat taacgataag taaaatgtaa aatcacagga ttttcgtgtg tggtcttcta  1680
cacagacaag gtgaaacaat tcggcattaa tacctgagag caggaagagc aagataaaag  1740
```

```
gtagtatttg ttggcgatcc ccctagagtc ttttacatct tcggaaaaca aaaactatttt   1800 tttctttaat ttcttttttt actttctatt tttaatttat atatttatat taaaaaattt   1860
aaattataat tatttttata gcacgtgatg aaaaggaccc aggtggcact tttcggggaa   1920
atgtgcgcgg aacccctatt tgtttatttt tctaaataca ttcaaatatg tatccgctca   1980
tgagacaata accctgataa atgcttcaat aatattgaaa aaggaagagt atgagtattc   2040
aacatttccg tgtcgccctt attcccttttt ttgcggcatt ttgccttcct gttttttgctc  2100 acccagaaac gctggtgaaa gtaaaagatg ctgaagatca gttgggacgc gtagtctaga   2160
ccagccagga cagaaatgcc tcgacttcgc tgctacccaa ggttgccggg tgacgcacac   2220
cgtggaaacg gatgaaggca cgaacccagt ggacataagc ctgttcggtt cgtaagctgt   2280
aatgcaagta gcgtatgcgc tcacgcaact ggtccagaac cttgaccgaa cgcagcggtg   2340
gtaacggcgc agtggcggtt ttcatggctt gttatgactg ttttttttggg gtacagtcta   2400 tgcctcgggc atccaagcag caagcgcgtt acgccgtggg tcgatgtttg atgttatgga   2460
gcagcaacga tgttacgcag cagggcagtc gccctaaaac aaagttaaac attatgaggg   2520
aagcggtgat cgccgaagta tcgactcaac tatcagaggt agttggcgcc atcgagcgcc   2580
atctcgaacc gacgttgctg gccgtacatt tgtacggctc cgcagtggat ggcggcctga   2640
agccacacag tgatattgat ttgctggtta cggtgaccgt aaggcttgat gaaacaacgc   2700
ggcgagcttt gatcaacgac cttttggaaa cttcggcttc ccctggagag agcgagattc   2760
tccgcgctgt agaagtcacc attgttgtgc acgacgacat cattccgtgg cgttatccag   2820
ctaagcgcga actgcaattt ggagaatggc agcgcaatga cattcttgca ggtatcttcg   2880
agccagccac gatcgacatt gatctggcta tcttgctgac aaaagcaaga gaacatagcg   2940
ttgccttggt aggtccagcg gcggaggaac tctttgatcc ggttcctgaa caggatctat   3000
ttgaggcgct aaatgaaacc ttaacgctat ggaactcgcc gcccgactgg gctggcgatg   3060
agcgaaatgt agtgcttacg ttgtcccgca tttggtacag cgcagtaacc ggcaaaatcg   3120
cgccgaagga tgtcgctgcc ggctgggcaa tggagcgcct gccggcccag tatcagcccg   3180
tcatacttga agctagacag gcttatcttg acaagaaga agatcgcttg gcctcgcgcg   3240
cagatcagtt ggaagaattt gtccactacg tgaaaggcga gatcaccaag gtagtcggca   3300 ataaccctc gagcattcaa ggcgccttga ttatttgacg tggtttgatg gcctccacgc   3360
acgttgtgat atgtagatga ttcagttcga gtttatcatt atcaatactg ccatttcaaa   3420
gaatacgtaa ataattaata gtagtgatttt tcctaacttt atttagtcaa aaaattagcc   3480
ttttaattct gctgtaaccc gtacatgccc aaaatagggg gcgggttaca cagaatatat   3540
aacatcgtag gtgtctgggt gaacagttta ttcctggcat ccactaaata taatggagcc   3600
cgctttttaa gctggcatcc agaaaaaaaa agaatcccag caccaaaata ttgttttctt   3660
caccaaccat cagttcatag gtccattctc ttagcgcaac tacagagaac aggggcacaa   3720
acaggcaaaa aacgggcaca acctcaatgg agtgatgcaa cctgcctgga gtaaatgatg   3780
acacaaggca attgacccac gcatgtatct atctcatttt cttacacctt ctattacctt   3840
ctgctctctc tgatttggaa aaagctgaaa aaaaggttg aaaccagttc cctgaaatta   3900
ttcccctact tgactaataa gtatataaag acggtaggta ttgattgtaa ttctgtaaat   3960
ctatttctta aacttcttaa attctacttt tatagttagt cttttttttta gttttaaaac   4020 accaagaact tagtttcgaa taaacacaca taaacaaaca aaatgaaact tcagtacttc   4080
```

```
tcctattttc aacccacttc atctgtcgta gccctactac tagcactagt gagtatttta   4140
tttagcgtag ttgttttgag gaagactttc agtaacaatt actccagccc cgcgtcaagt   4200
acggaaaccg ctgtgctgtg tcatcagagg caacagagtt gcgccctacc tatcagcggc   4260
cttcttcacg tgttcatgaa taagaacggc ctgattcatg tcaccttggg aaatatggct   4320
gacaaatatg gccctatctt cagttttccg acaggcagcc accgtacttt agtagtcagt   4380
tcctgggaaa tggtgaaaga gtgtttcacc ggtaataacg cacggcatt ctccaacaga    4440
ccaatcccct tggcttttca aaccatattc tacgcctgtg gcggcattga ttcttacggt   4500
ttaagtagtg tcccgtatgg taaatactgg agggagttga gaaaggtgtg tgttcacaac   4560
ctgctgagta atcagcaatt gctgaagttc agacatctta taatctccca agtggatacg   4620
tcttttaaca agttgtatga gctgtgtaag aactctgaag ataatcaagg tatggtaagg   4680
atggatgatt ggctagctca actttccttt aacgtcatcg gtaggatcgt ttgcggattc   4740
cagtctgacc caaagacggg tgcaccttca agggtagaac agtttaagga agtcataaat   4800
gaggcgtcat attttatgtc aacaagtcca gtctccgata acgtaccaat gttgggatgg   4860
atcgaccaat tgaccggtct gacgaggaac atgaagcatt gtgggaagaa gcttgactta   4920
gtagtggagt caattatcaa ggaccatagg caaaagagac gttttttcacg tacaaaaggt   4980
ggcgatgaga aggatgacga acaggacgac tttattgata tttgcttgag catcatggag   5040
cagccacagt tgcccgggaa caattctccc cctcaaattc cgatcaaatc tatcgtgcta   5100
gacatgattg ggggtggtac cgacactacg aaacttacaa ccatatggac cctatcactt   5160
ttgttgaaca atcctcacgt gttagataaa gctaaacaag aggtcgacgc tcactttcgt   5220
aaaaagagaa gatcaacaga tgacgcagca gcggcagtcg ttgattttga cgacataaga   5280
aatttagtat acatccaagc catcattaaa gaaagtatga ggctttatcc agccagcccg   5340
gtggttgagc gtcttttccgg cgaggattgc gttgttggag gttttcacgt gcctgctggt   5400
acgagactat gggctaacgt ttggaagatg caaagagatc ccaaagtttg gacgatcct    5460
ctagtattca gacctgaaag gttttttgagc gacgagcaaa agatggtaga cgttcgtggc   5520
caaaactatg aacttctgcc attcggcgca ggaagaagaa tctgtccagg cgtttccttt   5580
agtcttgacc ttatgcaact tgtcctaacc aggttaatcc tagagttcga aatgaagtcc   5640
ccgtccggca aggtagatat gaccgcaact ccaggactaa tgtcttacaa ggtggttcca   5700
ttggacatat tgctgactca ccgtcgtatc aagtcatgcg ttcaattggc gtcttctgaa   5760
cgtgatatgg aaagttctgg ggtgcctgtg atcacattgt cctcaggtaa agtaatgccc   5820
gtactgggca tgggaacctt cgaaaaggtg ggtaagggtt ctgaacgtga gcgtttagcc   5880
attcttaaag cgatcgaagt tggttaccgt tactttgata ccgcagcggc atatgaaacg   5940
gaagaagttc taggggaagc cattgctgaa gctttacaat tgggtctgat agagagccgt   6000
gacgagctgt tcatcagctc aatgctttgg tgcaccgacg cacatccaga ccgtgtgcta   6060
cttgctctgc aaaacagtct gagaaatcta aaacttgaat atctagacct atatatgttg   6120
ccgtttcctg ccagccttaa gccgggcaaa attacgatgg atattcctga ggaggatatt   6180
tgccgtatgg attatcgttc agtctggagc gccatgaag agtgtcaaaa cttaggattt    6240
actaaaagta ttggtgtaag caacttttct tgcaagaaat tacaagaatt aatggccact   6300
gcaaatatcc cgccgcggt aaatcaagta gagatgtcac cagctttcca acagaaaaaa    6360
ctgagggaat attgtaacgc aaacaacata ttggtatccg cagtaagcat tctgggatca   6420
aacgggacgc cctggggtag taatgctgtt cttggaagcg aagttttgaa acagatcgcg   6480
```

```
atggcgaaag gcaaaagcgt tgcgcaagtc agtatgaggt gggtctatga gcagggcgcg    6540
tctttagtag tcaagagttt ctctgaagaa cgtttaagag aaaacctgaa tattttgac    6600 tgggagctta cgaaagaaga caatgagaag ataggcgaaa tcccgcaatg tagaatcctt    6660
actgcgtact tccttgtctc cccgaacggc ccgtttaaat ctcaggaaga gctttgggat    6720
gacaaggcat aaacaggccc cttttccttt gtcgatatca tgtaattagt tatgtcacgc    6780
ttacattcac gccctcctcc cacatccgct ctaaccgaaa aggaaggagt tagacaacct    6840
gaagtctagg tccctattta tttttttaa tagttatgtt agtattaaga cgttattta    6900 tatttcaaat ttttcttttt tttctgtaca aacgcgtgta cgcatgtaac attatactga    6960
aaaccttgct tgagaaggtt ttgggacgct cgaaggcttt aatttgtaat cattatcact    7020
ttacgggtcc tttccggtga tccgacaggt tacgggcgg cgacctcgcg gttttcgct    7080 atttatgaaa attttccggt ttaaggcgtt tccgttcttc ttcgtcataa cttaatgttt    7140
ttatttaaaa tacctcgcga gtggcaacac tgaaaatacc catggagcgg cgtaaccgtc    7200
gcacaggatc taggtgaaga tccttttga taatctcatg accaaaatcc cttaacgtga    7260
gttttcgttc cactgagcgt cagacccgt agaaaagatc aaaggatctt cttgagatcc    7320 ttttttctg cgcgtaatct gctgcttgca acaaaaaaa ccaccgctac cagcggtggt    7380
ttgtttgccg gatcaagagc taccaactct ttttccgaag gtaactggct tcagcagagc    7440
gcagatacca atactgtcc ttctagtgta gccgtagtta ggccaccact tcaagaactc    7500
tgtagcaccg cctacatacc tcgctctgct aatcctgtta ccagtggctg ctgccagtgg    7560
cgataagtcg tgtcttaccg ggttggactc aagacgatag ttaccggata aggcgcagcg    7620
gtcgggctga acggggggtt cgtgcacaca gcccagcttg gagcgaacga cctacaccga    7680
actgagatac ctacagcgtg agctatgaga aagcgccacg cttcccgaag ggagaaaggc    7740
ggacaggtat ccggtaagcg gcagggtcgg aacaggagag cgcacgaggg agcttccagg    7800
gggaaacgcc tggtatcttt atagtcctgt cgggtttcgc cacctctgac ttgagcgtcg    7860
atttttgtga tgctcgtcag ggggggggag cctatggaaa aacgccagca acgcggcagt    7920
ggaacgtgca ttatgaatta gttacgctag ggataacagg gtaatataga acccgaacga    7980
ccgagcgcag cggcggccgc gctgataccg ccgc                               8014
```

<210> SEQ ID NO 25
<211> LENGTH: 7621
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

```
cctcgccgca gttaattaaa gtcagtgagc gaggaagcgc gtaactataa cggtcctaag      60
gtagcgaatc ctgatgcggt attttctcct tacgcatctg tgcggtattt cacaccgcat     120
agatcggcaa gtgcacaaac aatacttaaa taaatactac tcagtaataa cctatttctt     180 agcattttg acgaaatttg ctattttgtt agagtctttt acaccatttg tctccacacc     240
tccgcttaca tcaacaccaa taacgccatt taatctaagc gcatcaccaa cattttctgg     300
cgtcagtcca ccagctaaca taaaatgtaa gctttcgggg ctctcttgcc ttccaaccca     360
gtcagaaatc gagttccaat ccaaaagttc acctgtccca cctgcttctg aatcaaacaa     420
gggaataaac gaatgaggtt tctgtgaagc tgcactgagt agtatgttgc agtcttttgg     480
```

```
aaatacgagt cttttaataa ctggcaaacc gaggaactct tggtattctt gccacgactc    540
atctccatgc agttggacga tatcaatgcc gtaatcattg accagagcca aaacatcctc    600
cttaagttga ttacgaaaca cgccaaccaa gtatttcgga gtgcctgaac tatttttata    660
tgcttttaca agacttgaaa ttttccttgc ataaccggg tcaattgttc tctttctatt    720
gggcacacat ataatacca gcaagtcagc atcggaatct agagcacatt ctgcggcctc    780
tgtgctctgc aagccgcaaa cttcaccaa tggaccagaa ctacctgtga aattaataac    840
agacatactc caagctgcct ttgtgtgctt aatcacgtat actcacgtgc tcaatagtca    900
ccaatgccct ccctcttggc cctctccttt tcttttttcg accgaattaa ttcttaatcg    960
gcaaaaaaag aaaagctccg gatcaagatt gtacgtaagg tgacaagcta ttttcaata    1020
aagaatatct tccactactg ccatctggcg tcataactgc aaagtacaca tatattcga    1080
tgctgttcta ttaaatgctt cctatatat atatatagta atgtcgtgat ctatggtgca    1140
ctctcagtac aatctgctct gatgccgcat agttaagcca gccccgacac cgccaacac    1200
ccgctgacgc gccctgacgg gcttgtctgc tcccggcatc cgcttacaga caagctgtga    1260
ccgtctccgg gagctgcatg tgtcagaggt tttcaccgtc atcaccgaaa cgcgcgagac    1320
gaaagggcct cgtgatacgc ctatttttat aggttaatgt catgataata atggtttctt    1380
agacggatcg cttgcctgta acttacacgc gcctcgtatc ttttaatgat ggaataattt    1440
gggaatttac tctgtgttta tttattttta tgttttgtat ttggatttta gaaagtaaat    1500
aagaaggta gaagagttac ggaatgaaga aaaaaaata acaaaggtt taaaaatt    1560
caacaaaaag cgtactttac atatatattt attagacaag aaaagcagat taaatagata    1620
tacattcgat taacgataag taaaatgtaa aatcacagga ttttcgtgtg tggtcttcta    1680
cacagacaag gtgaaacaat tcggcattaa tacctgagag caggaagagc aagataaaag    1740
gtagtatttg ttggcgatcc ccctagagtc ttttacatct tcggaaaaca aaactattt    1800
tttctttaat ttctttttt actttctatt tttaatttat atatttatat taaaaatttt    1860
aaattataat tatttttata gcacgtgatg aaaaggaccc aggtggcact tttcggggaa    1920
atgtgcgcgg aacccctatt tgtttatttt tctaaataca ttcaaatatg tatccgctca    1980
tgagacaata accctgataa atgcttcaat aatattgaaa aaggaagagt atgagtattc    2040
aacatttccg tgtcgccctt attccctttt ttgcggcatt ttgccttcct gttttgctc    2100
acccagaaac gctggtgaaa gtaaagatg ctgaagatca gttgggacgc gtagtctaga    2160
ccagccagga cagaaatgcc tcgacttcgc tgctacccaa ggttgccggg tgacgcacac    2220
cgtggaaacg gatgaaggca cgaacccagt ggacataagc ctgttcggtt cgtaagctgt    2280
aatgcaagta gcgtatgcgc tcacgcaact ggtccagaac cttgaccgaa cgcagcggtg    2340
gtaacggcgc agtggcggtt ttcatggctt gttatgactg tttttttggg gtacagtcta    2400
tgcctcgggc atccaagcag caagcgcgtt acgccgtggg tcgatgtttg atgttatgga    2460
gcagcaacga tgttacgcag cagggcagtc gccctaaaac aaagttaaac attatgaggg    2520
aagcggtgat cgccgaagta tcgactcaac tatcagaggt agttggcgcc atcgagcgcc    2580
atctcgaacc gacgttgctg gccgtacatt tgtacggctc cgcagtggat ggcggcctga    2640
agccacacag tgatattgat ttgctggtta cggtgaccgt aaggcttgat gaaacaacgc    2700
ggcgagcttt gatcaacgac cttttggaaa cttcggcttc cctggagag agcgagattc    2760
tccgcgctgt agaagtcacc attgttgtgc acgacgacat cattccgtgg cgttatccag    2820
```

```
ctaagcgcga actgcaattt ggagaatggc agcgcaatga cattcttgca ggtatcttcg    2880
agccagccac gatcgacatt gatctggcta tcttgctgac aaaagcaaga gaacatagcg    2940
ttgccttggt aggtccagcg gcggaggaac tctttgatcc ggttcctgaa caggatctat    3000
ttgaggcgct aaatgaaacc ttaacgctat ggaactcgcc gcccgactgg gctggcgatg    3060
agcgaaatgt agtgcttacg ttgtcccgca tttggtacag cgcagtaacc ggcaaaatcg    3120
cgccgaagga tgtcgctgcc ggctgggcaa tggagcgcct gccggcccag tatcagcccg    3180
tcatacttga agctagacag gcttatcttg acaagaaga agatcgcttg gcctcgcgcg    3240
cagatcagtt ggaagaattt gtccactacg tgaaaggcga gatcaccaag gtagtcggca    3300
aataaccctc gagcattcaa ggcgccttga ttatttgacg tggtttgatg gcctccacgc    3360
acgttgtgat atgtagatga gagcgttggt tggtggatca agcccacgcg taggcaatcc    3420
tcgagcagat ccgccaggcg tgtatatata gcgtggatgg ccaggcaact ttagtgctga    3480
cacatacagg catatatata tgtgtgcgac gacacatgat catatggcat gcatgtgctc    3540
tgtatgtata taaaactctt gttttcttct tttctctaaa tattctttcc ttatacatta    3600
ggaccttgc agcataaatt actatacttc tatagacaca caaacacaaa tacacacact    3660
aaattaataa tggaacttca gtacttctcc tattttcaac ccacttcatc tgtcgtagcc    3720
ctactactag cactagtgag tattttattt agcgtagttg ttttgaggaa gactttcagt    3780
aacaattact ccagccccgc gtcaagtacg gaaaccgctg tgctgtgtca tcagaggcaa    3840
cagagttgcg ccctacctat cagcggcctt cttcacgtgt tcatgaataa gaacggcctg    3900
attcatgtca ccttgggaaa tatggctgac aaatatggcc ctatcttcag ttttccgaca    3960
ggcagccacc gtactttagt agtcagttcc tgggaaatgg tgaaagagtg tttcaccggt    4020
aataacgaca cggcattctc caacagacca atccctttgg cttttcaaac catattctac    4080
gcctgtggcg gcattgattc ttacggttta agtagtgtcc cgtatggtaa atactggagg    4140
gagttgagaa aggtgtgtgt tcacaacctg ctgagtaatc agcaattgct gaagttcaga    4200
catcttataa tctcccaagt ggatacgtct tttaacaagt tgtatgagct gtgtaagaac    4260
tctgaagata atcaaggtat ggtaaggatg gatgattggc tagctcaact ttcctttaac    4320
gtcatcggta ggatcgtttg cggattccag tctgacccaa agacgggtgc accttcaagg    4380
gtagaacagt ttaaggaagt cataaatgag gcgtcatatt ttatgtcaac aagtccagtc    4440
tccgataacg taccaatgtt gggatggatc gaccaattga ccggtctgac gaggaacatg    4500
aagcattgtg ggaagaagct tgacttagta gtggagtcaa ttatcaagga ccataggcaa    4560
aagagacgtt tttcacgtac aaaaggtggc gatgagaagg atgacgaaca ggacgacttt    4620
attgatattt gcttgagcat catggagcag ccacagttgc ccgggaacaa ttctccccct    4680
caaattccga tcaaatctat cgtgctagac atgattgggg gtggtaccga cactacgaaa    4740
cttacaacca tatggaccct atcacttttg ttgaacaatc ctcacgtgtt agataaagct    4800
aaacaagagg tcgacgctca ctttcgtaaa aagagaagat caacagatga cgcagcagcg    4860
gcagtcgttg attttgacga cataagaaat ttagtataca tccaagccat cattaaagaa    4920
agtatgaggc tttatccagc cagcccggtg gttgagcgtc tttccggcga ggattgcgtt    4980
gttggaggtt ttcacgtgcc tgctggtacg agactatggg ctaacgtttg gaagatgcaa    5040
agagatccca aagtttggga cgatcctcta gtattcagac ctgaaaggtt tttgagcgac    5100
gagcaaaaga tggtagacgt tcgtggccaa aactatgaac ttctgccatt cggcgcagga    5160
agaagaatct gtccaggcgt ttcctttagt cttgacctta tgcaacttgt cctaaccagg    5220
```

```
ttaatcctag agttcgaaat gaagtccccg tccggcaagg tagatatgac cgcaactcca    5280
ggactaatgt cttacaaggt ggttccattg gacatattgc tgactcaccg tcgtatcaag    5340
tcatgcgttc aattggcgtc ttctgaacgt gatatggaaa gttctggggt gcctgtgatc    5400
acattgtcct caggtaaagt aatgcccgta ctgggcatgg gaaccttcga aaaggtgggt    5460
aaggggtctg aacgtgagcg tttagccatt cttaaagcga tcgaagttgg ttaccgttac    5520
tttgataccg cagcggcata tgaaacggaa gaagttctag gggaagccat tgctgaagct    5580
ttacaattgg gtctgataga gagccgtgac gagctgttca tcagctcaat gctttggtgc    5640
accgacgcac atccagaccg tgtgctactt gctctgcaaa acagtctgag aaatctaaaa    5700
cttgaatatc tagacctata tatgttgccg tttcctgcca gccttaagcc gggcaaaatt    5760
acgatggata ttcctgagga ggatatttgc cgtatggatt atcgttcagt ctggagcgcc    5820
atggaagagt gtcaaaactt aggatttact aaaagtattg gtgtaagcaa cttttcttgc    5880
aagaaattac aagaattaat ggccactgca aatatcccgc ccgcggtaaa tcaagtagag    5940
atgtcaccag ctttccaaca gaaaaaactg agggaatatt gtaacgcaaa caacatattg    6000
gtatccgcag taagcattct gggatcaaac gggacgccct ggggtagtaa tgctgttctt    6060
ggaagcgaag ttttgaaaca gatcgcgatg gcgaaaggca aaagcgttgc gcaagtcagt    6120
atgaggtggg tctatgagca gggcgcgtct ttagtagtca agagtttctc tgaagaacgt    6180
ttaagagaaa acctgaatat ttttgactgg gagcttacga aagaagacaa tgagaagata    6240
ggcgaaatcc cgcaatgtag aatccttact gcgtacttcc ttgtctcccc gaacggcccg    6300
tttaaatctc aggaagagct ttgggatgac aaggcataaa caggccccct tccctttgtc    6360
gatatcatgt aattagttat gtcacgctta cattcacgcc ctcctcccac atccgctcta    6420
accgaaaagg aaggagttag acaacctgaa gtctaggtcc ctatttattt ttttttaatag    6480
ttatgttagt attaagaacg ttatttatat tcaaattttt cttttttttt ctgtacaaac    6540
gcgtgtacgc atgtaacatt atactgaaaa ccttgcttga aaggttttg ggacgctcga    6600
aggctttaat ttgtaatcat tatcacttta cgggtccttt ccggtgatcc gacaggttac    6660
ggggcggcga cctcgcgggt tttcgctatt tatgaaaatt ttccggttta aggcgtttcc    6720
gttcttcttc gtcataactt aatgttttta tttaaaatac ctcgcgagtg caacactga    6780
aaatacccat ggagcggcgt aaccgtcgca caggatctag gtgaagatcc ttttgataa    6840
tctcatgacc aaaatccctt aacgtgagtt ttcgttccac tgagcgtcag accccgtaga    6900
aaagatcaaa ggatcttctt gagatccttt ttttctgcgc gtaatctgct gcttgcaaac    6960
aaaaaaacca ccgctaccag cggtggtttg tttgccggat caagagctac caactctttt    7020
tccgaaggta actggcttca gcagagcgca gataccaaat actgtccttc tagtgtagcc    7080
gtagttaggc caccacttca agaactctgt agcaccgcct acatacctcg ctctgctaat    7140
cctgttacca gtggctgctg ccagtggcga taagtcgtgt cttaccgggt tggactcaag    7200
acgatagtta ccggataagg cgcagcggtc gggctgaacg ggggggttcgt gcacacagcc    7260
cagcttggag cgaacgacct acaccgaact gagataccta cagcgtgagc tatgagaaag    7320
cgccacgctt cccgaaggga gaaaggcgga caggtatccg gtaagcggca gggtcggaac    7380
aggagagcgc acgagggagc ttccaggggg aaacgcctgg tatctttata gtcctgtcgg    7440
gtttcgccac ctctgacttg agcgtcgatt tttgtgatgc tcgtcagggg ggcggagcct    7500
atggaaaaac gccagcaacg cggcagtgga acgtgcatta tgaattagtt acgctaggga    7560
```

-continued

```
taacagggta atatagaacc cgaacgaccg agcgcagcgg cggccgcgct gataccgccg    7620
c                                                                   7621

<210> SEQ ID NO 26
<211> LENGTH: 8187
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
cctcgccgca gttaattaaa gtcagtgagc gaggaagcgc gtaactataa cggtcctaag     60
gtagcgaatc ctgatgcggt attttctcct tacgcatctg tgcggtattt cacaccgcat    120
agatcggcaa gtgcacaaac aatacttaaa taaatactac tcagtaataa cctatttctt    180 agcattttg acgaaatttg ctattttgtt agagtctttt acaccatttg tctccacacc     240
tccgcttaca tcaacaccaa taacgccatt taatctaagc gcatcaccaa cattttctgg    300
cgtcagtcca ccagctaaca taaaatgtaa gctttcgggg ctctcttgcc ttccaaccca    360
gtcagaaatc gagttccaat ccaaaagttc acctgtccca cctgcttctg aatcaaacaa    420
gggaataaac gaatgaggtt tctgtgaagc tgcactgagt agtatgttgc agtcttttgg    480
aaatacgagt cttttaataa ctggcaaacc gaggaactct tggtattctt gccacgactc    540
atctccatgc agttggacga tatcaatgcc gtaatcattg accagagcca aacatcctc     600 cttaagttga ttacgaaaca cgccaaccaa gtatttcgga gtgcctgaac tatttttata    660
tgcttttaca agacttgaaa ttttccttgc aataaccggg tcaattgttc tctttctatt    720
gggcacacat ataatacccca gcaagtcagc atcggaatct agagcacatt ctgcggcctc    780
tgtgctctgc aagccgcaaa cttttaccaa tggaccagaa ctacctgtga aattaataac    840
agacatactc caagctgcct ttgtgtgctt aatcacgtat actcacgtgc tcaatagtca    900
ccaatgccct ccctcttggc cctctccttt tcttttttcg accgaattaa ttcttaatcg    960
gcaaaaaaag aaaagctccg gatcaagatt gtacgtaagg tgacaagcta ttttcaata   1020 aagaatatct tccactactg ccatctggcg tcataactgc aaagtacaca tatattacga   1080
tgctgttcta ttaaatgctt cctatattat atatatagta atgtcgtgat ctatggtgca   1140
ctctcagtac aatctgctct gatgccgcat agttaagcca gccccgacac ccgccaacac   1200
ccgctgacgc gccctgacgg gcttgtctgc tcccggcatc cgcttacaga caagctgtga   1260
ccgtctccgg gagctgcatg tgtcagaggt tttcaccgtc atcaccgaaa cgcgcgagac   1320
gaaagggcct cgtgatacgc ctatttttat aggttaatgt catgataata atggtttctt   1380
agacggatcg cttgcctgta acttacacgc gcctcgtatc ttttaatgat ggaataattt   1440
gggaatttac tctgtgttta tttattttta tgttttgtat ttggattta gaaagtaaat   1500 aaagaaggta gaagttac ggaatgaaga aaaaaaata aacaaggtt taaaaattt   1560 caacaaaaag cgtactttac atatatattt attagacaag aaaagcagat taaatagata   1620
tacattcgat taacgataag taaaatgtaa aatcacagga ttttcgtgtg tggtcttcta   1680
cacagacaag gtgaaacaat tcggcattaa tacctgagag caggaagagc aagataaaag   1740
gtagtatttg ttggcgatcc ccctagagtc ttttacatct tcggaaaaca aaaactattt   1800
tttctttaat ttcttttttt actttctatt tttaatttat atatttatat taaaaaatt   1860 aaattataat tatttttata gcacgtgatg aaaaggaccc aggtggcact tttcggggaa   1920
```

```
atgtgcgcgg aaccoctatt tgtttatttt tctaaataca ttcaaatatg tatccgctca    1980
tgagacaata accctgataa atgcttcaat aatattgaaa aaggaagagt atgagtattc    2040
aacatttccg tgtcgccctt attccctttt ttgcggcatt ttgccttcct gttttgctc    2100 acccagaaac gctggtgaaa gtaaaagatg ctgaagatca gttgggacgc gtagtctaga    2160
ccagccagga cagaaatgcc tcgacttcgc tgctacccaa ggttgccggg tgacgcacac    2220
cgtggaaacg gatgaaggca cgaacccagt ggacataagc ctgttcggtt cgtaagctgt    2280
aatgcaagta gcgtatgcgc tcacgcaact ggtccagaac cttgaccgaa cgcagcggtg    2340
gtaacggcgc agtggcggtt ttcatggctt gttatgactg ttttttttggg gtacagtcta    2400 tgcctcgggc atccaagcag caagcgcgtt acgccgtggg tcgatgtttg atgttatgga    2460
gcagcaacga tgttacgcag cagggcagtc gccctaaaac aaagttaaac attatgaggg    2520
aagcggtgat cgccgaagta tcgactcaac tatcagaggt agttggcgcc atcgagcgcc    2580
atctcgaacc gacgttgctg gccgtacatt tgtacggctc cgcagtggat ggcggcctga    2640
agccacacag tgatattgat ttgctggtta cggtgaccgt aaggcttgat gaaacaacgc    2700
ggcgagcttt gatcaacgac cttttggaaa cttcggcttc ccctggagag agcgagattc    2760
tccgcgctgt agaagtcacc attgttgtgc acgacgacat cattccgtgg cgttatccag    2820
ctaagcgcga actgcaattt ggagaatggc agcgcaatga cattcttgca ggtatcttcg    2880
agccagccac gatcgacatt gatctggcta tcttgctgac aaaagcaaga gaacatagcg    2940
ttgccttggt aggtccagcg gcggaggaac tctttgatcc ggttcctgaa caggatctat    3000
ttgaggcgct aaatgaaacc ttaacgctat ggaactcgcc gcccgactgg gctggcgatg    3060
agcgaaatgt agtgcttacg ttgtcccgca tttggtacag cgcagtaacc ggcaaaatcg    3120
cgccgaagga tgtcgctgcc ggctgggcaa tggagcgcct gccggcccag tatcagcccg    3180
tcatacttga agctagacag gcttatcttg acaagaaga gatcgcttg cctcgcgcg    3240 cagatcagtt ggaagaattt gtccactacg tgaaaggcga gatcaccaag gtagtcggca    3300
aataaccctc gagcattcaa ggcgccttga ttatttgacg tggtttgatg gcctccacgc    3360
acgttgtgat atgtagatga gagcgttggt tggtggatca agcccacgcg taggcaatcc    3420
tcgagcagat ccgccaggcg tgtatatata gcgtggatgg ccaggcaact ttagtgctga    3480
cacatacagg catatatata tgtgtgcgac gacacatgat catatggcat gcatgtgctc    3540
tgtatgtata taaaactctt gttttcttct tttctctaaa tattctttcc ttatacatta    3600
ggacctttgc agcataaatt actatacttc tatagacaca caaacacaaa tacacacact    3660
aaattaataa tggaacttca gtacttctcc tattttcaac ccacttcatc tgtcgtagcc    3720
ctactactag cactagtgag tatttttattt agcgtagttg ttttgaggaa gactttcagt    3780
aacaattact ccagccccgc gtcaagtacg gaaaccgctg tgctgtgtca tcagaggcaa    3840
cagagttgcg ccctacctat cagcggcctt cttcacgtgt tcatgaataa gaacggcctg    3900
attcatgtca ccttgggaaa tatggctgac aaatatggcc ctatcttcag ttttccgaca    3960
ggcagccacc gtactttagt agtcagttcc tgggaaatgg tgaaagagtg tttcaccggt    4020
aataacgaca cggcattctc caacagacca atcccttggg cttttcaaac catattctac    4080
gcctgtggcg gcattgattc ttacggttta agtagtgtcc cgtatggtaa atactggagg    4140
gagttgagaa aggtgtgtgt tcacaacctg ctgagtaatc agcaattgct gaagttcaga    4200
catcttataa tctcccaagt ggatacgtct tttaacaagt tgtatgagct gtgtaagaac    4260
tctgaagata atcaaggtat ggtaaggatg gatgattggc tagctcaact ttcctttaac    4320
```

```
gtcatcggta ggatcgtttg cggattccag tctgacccaa agacgggtgc accttcaagg    4380
gtagaacagt ttaaggaagt cataaatgag gcgtcatatt ttatgtcaac aagtccagtc    4440
tccgataacg taccaatgtt gggatggatc gaccaattga ccggtctgac gaggaacatg    4500
aagcattgtg ggaagaagct tgacttagta gtggagtcaa ttatcaagga ccataggcaa    4560
aagagacgtt tttcacgtac aaaaggtggc gatgagaagg atgacgaaca ggacgacttt    4620
attgatattt gcttgagcat catggagcag ccacagttgc ccgggaacaa ttctccccct    4680
caaattccga tcaaatctat cgtgctagac atgattgggg gtggtaccga cactacgaaa    4740
cttacaacca tatggaccct atcacttttg ttgaacaatc ctcacgtgtt agataaagct    4800
aaacaagagg tcgacgctca ctttcgtaaa aagagaagat caacagatga cgcagcagcg    4860
gcagtcgttg attttgacga cataagaaat ttagtataca tccaagccat cattaaagaa    4920
agtatgaggc tttatccagc cagcccggtg gttgagcgtc tttccggcga ggattgcgtt    4980
gttggaggtt tcacgtgcc tgctggtacg agactatggg ctaacgtttg gaagatgcaa    5040
agagatccca agtttggga cgatcctcta gtattcagac ctgaaaggtt tttgagcgac    5100
gagcaaaaga tggtagacgt tcgtggccaa aactatgaac ttctgccatt cggcgcagga    5160
agaagaatct gtccaggcgt ttcctttagt cttgacctta tgcaacttgt cctaaccagg    5220
ttaatcctag agttcgaaat gaagtccccg tccggcaagg tagatatgac cgcaactcca    5280
ggactaatgt cttacaaggt ggttccattg gacatattgc tgactcaccg tcgtatcaag    5340
tcatgcgttc aattggcgtc ttctgaacgt gattaagcga atttcttatg atttatgatt    5400
tttattatta aataagttat aaaaaaaata agtgtataca aattttaaag tgactcttag    5460
gttttaaaac gaaaattctt attcttgagt aactcttttcc tgtaggtcag gttgctttct    5520
caggtacata gcttcaaaat gtttctactc ctttttttact cttccagatt ttctcggact    5580
ccgcgcatcg ccgtaccact tcaaaacacc aagcacagc atactaaatt tcccctcttt    5640
cttcctctag ggtgtcgtta attcccgta ctaaaggttt ggaaaagaaa aaagagaccg    5700
cctcgtttct ttttcttcgt cgaaaaaggc aataaaaatt tttatcacgt ttcttttttct    5760 tgaaaatttt ttttttttgat tttttttctct ttcgatgacc tcccattgat atttaagtta    5820
ataaacggtc ttcaatttct caagtttcag tttcattttt cttgttctat tacaactttt    5880
tttacttctt gctcattaga aagaaagcat agcaatctaa tctaagtttt aattacaaaa    5940
tggaaagttc tggggtgcct gtgatcacat tgtcctcagg taaagtaatg cccgtactgg    6000
gcatgggaac cttcgaaaag gtgggtaagg ggtctgaacg tgagcgttta gccattctta    6060
aagcgatcga agttggttac cgttactttg ataccgcagc ggcatatgaa acggaagaag    6120
ttctagggga agccattgct gaagctttac aattgggtct gatagagagc cgtgacgagc    6180
tgttcatcag ctcaatgctt tggtgcaccg acgcacatcc agaccgtgtg ctacttgctc    6240
tgcaaaacag tctgagaaat ctaaaacttg aatatctaga cctatatatg ttgccgtttc    6300
ctgccagcct taagccgggc aaaattacga tggatattcc tgaggaggat atttgccgta    6360
tggattatcg ttcagtctgg agcgccatgg aagagtgtca aaacttagga tttactaaaa    6420
gtattggtgt aagcaacttt tcttgcaaga aattacaaga attaatgcc actgcaaata    6480 tcccgcccgc ggtaaatcaa gtagagatgt caccagcttt ccaacagaaa aaactgaggg    6540
aatattgtaa cgcaaacaac atattggtat ccgcagtaag cattctggga tcaaacggga    6600
cgccctgggg tagtaatgct gttcttggaa gcgaagtttt gaaacagatc gcgatggcga    6660
```

```
aaggcaaaag cgttgcgcaa gtcagtatga ggtgggtcta tgagcagggc gcgtctttag    6720
tagtcaagag tttctctgaa gaacgtttaa gagaaaacct gaatatttttt gactgggagc    6780 ttacgaaaga agacaatgag aagataggcg aaatcccgca atgtagaatc cttactgcgt    6840
acttccttgt ctccccgaac ggcccgttta atctcagga agagctttgg gatgacaagg    6900
cataaacagg ccccttttcc tttgtcgata tcatgtaatt agttatgtca cgcttacatt    6960
cacgccctcc tcccacatcc gctctaaccg aaaaggaagg agttagacaa cctgaagtct    7020
aggtccctat ttatttttttt taatagttat gttagtatta agaacgttat ttatatttca    7080 aattttttctt tttttttctgt acaaacgcgt gtacgcatgt aacattatac tgaaaacctt    7140
gcttgagaag gttttgggac gctcgaaggc tttaatttgt aatcattatc actttacggg    7200
tcctttccgg tgatccgaca ggttacgggg cggcgacctc gcgggttttc gctatttatg    7260
aaaattttcc ggtttaaggc gtttccgttc ttcttcgtca taacttaatg tttttattta    7320
aaatacctcg cgagtggcaa cactgaaaat acccatggag cggcgtaacc gtcgcacagg    7380
atctaggtga agatcctttt tgataatctc atgaccaaaa tcccttaacg tgagttttcg    7440
ttccactgag cgtcagaccc cgtagaaaag atcaaaggat cttcttgaga tccttttttt    7500
ctgcgcgtaa tctgctgctt gcaaacaaaa aaaccaccgc taccagcggt ggtttgtttg    7560
ccggatcaag agctaccaac tcttttttccg aaggtaactg gcttcagcag agcgcagata    7620
ccaaatactg tccttctagt gtagccgtag ttaggccacc acttcaagaa ctctgtagca    7680
ccgcctacat acctcgctct gctaatcctg ttaccagtgg ctgctgccag tggcgataag    7740
tcgtgtctta ccgggttgga ctcaagacga tagttaccgg ataaggcgca gcggtcgggc    7800
tgaacggggg gttcgtgcac acagcccagc ttggagcgaa cgacctacac cgaactgaga    7860
tacctacagc gtgagctatg agaaagcgcc acgcttcccg aagggagaaa ggcggacagg    7920
tatccggtaa gcggcagggt cggaacagga gagcgcacga gggagcttcc agggggaaac    7980
gcctggtatc tttatagtcc tgtcgggttt cgccacctct gacttgagcg tcgatttttg    8040
tgatgctcgt caggggggcg gagcctatgg aaaaacgcca gcaacgcggc agtggaacgt    8100
gcattatgaa ttagttacgc tagggataac agggtaatat agaacccgaa cgaccgagcg    8160
cagcggcggc cgcgctgata ccgccgc                                        8187
```

<210> SEQ ID NO 27
<211> LENGTH: 8580
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27

```
cctcgccgca gttaattaaa gtcagtgagc gaggaagcgc gtaactataa cggtcctaag     60
gtagcgaatc ctgatgcggt attttctcct tacgcatctg tgcggtattt cacaccgcat    120
agatcggcaa gtgcacaaac aatacttaaa taaatactac tcagtaataa cctatttctt    180 agcattttttg acgaaatttg ctattttgtt agagtctttt acaccatttg tctccacacc    240
tccgcttaca tcaacaccaa taacgccatt taatctaagc gcatcaccaa catttctctgg    300 cgtcagtcca ccagctaaca taaaatgtaa gctttcgggg ctctcttgcc ttccaaccca    360
gtcagaaatc gagttccaat ccaaaagttc acctgtccca cctgcttctg aatcaaacaa    420
gggaataaac gaatgaggtt tctgtgaagc tgcactgagt agtatgttgc agtcttttgg    480
```

```
aaatacgagt cttttaataa ctggcaaacc gaggaactct tggtattctt gccacgactc    540
atctccatgc agttggacga tatcaatgcc gtaatcattg accagagcca aaacatcctc    600
cttaagttga ttacgaaaca cgccaaccaa gtatttcgga gtgcctgaac tatttttata    660
tgcttttaca agacttgaaa ttttccttgc aataaccggg tcaattgttc tctttctatt    720
gggcacacat ataatacccca gcaagtcagc atcggaatct agagcacatt ctgcggcctc    780
tgtgctctgc aagccgcaaa cttccaccaa tggaccagaa ctacctgtga aattaataac    840
agacatactc caagctgcct tgtgtgctt aatcacgtat actcacgtgc tcaatagtca    900
ccaatgccct ccctcttggc cctctccttt tctttttcg accgaattaa ttcttaatcg    960
gcaaaaaaag aaaagctccg gatcaagatt gtacgtaagg tgacaagcta ttttcaata   1020 aagaatatct tccactactg ccatctggcg tcataactgc aaagtacaca tatattacga   1080
tgctgttcta ttaaatgctt cctatattat atatatagta atgtcgtgat ctatggtgca   1140
ctctcagtac aatctgctct gatgccgcat agttaagcca gccccgacac ccgccaacac   1200
ccgctgacgc gccctgacgg gcttgtctgc tcccggcatc cgcttacaga caagctgtga   1260
ccgtctccgg gagctgcatg tgtcagaggt tttcaccgtc atcaccgaaa cgcgcgagac   1320
gaaagggcct cgtgatacgc ctattttat aggttaatgt catgataata atggtttctt   1380
agacggatcg cttgcctgta acttacacgc gcctcgtatc ttttaatgat ggaataattt   1440
gggaatttac tctgtgttta tttatttta tgttttgtat ttggatttta aaagtaaat   1500 aaagaaggta gaagagttac ggaatgaaga aaaaaaaata aacaaaggtt taaaaaattt   1560
caacaaaaag cgtactttac atatatatt attagacaag aaaagcagat taaatagata   1620
tacattcgat taacgataag taaaatgtaa aatcacagga ttttcgtgtg tggtcttcta   1680
cacagacaag gtgaaacaat tcggcattaa tacctgagag caggaagagc aagataaaag   1740
gtagtatttg ttggcgatcc ccctagagtc ttttacatct tcggaaaaca aaaactattt   1800
tttctttaat ttcttttttt actttctatt tttaatttat atatttatat taaaaaattt   1860
aaattataat tattttttata gcacgtgatg aaaaggaccc aggtggcact tttcggggaa   1920
atgtgcgcgg aaccccctatt tgtttatttt tctaaataca ttcaaatatg tatccgctca   1980
tgagacaata acccctgataa atgcttcaat aatattgaaa aaggaagagt atgagtattc   2040
aacatttccg tgtcgccctt attccctttt tgcggcatt tgccttcct gttttgctc   2100 acccagaaac gctggtgaaa gtaaaagatg ctgaagatca gttgggacgc gtagtctaga   2160
ccagccagga cagaaatgcc tcgacttcgc tgctacccaa ggttgccggg tgacgcacac   2220
cgtggaaacg gatgaaggca cgaacccagt ggacataagc ctgttcggtt cgtaagctgt   2280
aatgcaagta gcgtatgcgc tcacgcaact ggtccagaac cttgaccgaa cgcagcggtg   2340
gtaacggcgc agtggcggtt ttcatggctt gttatgactg tttttttggg gtacagtcta   2400
tgcctcgggc atccaagcag caagcgcgtt acgccgtggg tcgatgtttg atgttatgga   2460
gcagcaacga tgttacgcag cagggcagtc gccctaaaac aaagttaaac attatgaggg   2520
aagcggtgat cgccgaagta tcgactcaac tatcagaggt agttggcgcc atcgagcgcc   2580
atctcgaacc gacgttgctg gccgtacatt tgtacggctc cgcagtggat ggcggcctga   2640
agccacacag tgatattgat ttgctggtta cggtgaccgt aaggcttgat gaaacaacgc   2700
ggcgagcttt gatcaacgac cttttggaaa cttcggcttc cctggagag agcgagattc   2760 tccgcgctgt agaagtcacc attgttgtgc acgacgacat cattccgtgg cgttatccag   2820
ctaagcgcga actgcaattt ggagaatggc agcgcaatga cattcttgca ggtatcttcg   2880
```

| | | | | | |
|---|---|---|---|---|---|
| agccagccac | gatcgacatt | gatctggcta | tcttgctgac | aaaagcaaga | gaacatagcg | 2940 |
| ttgccttggt | aggtccagcg | gcggaggaac | tctttgatcc | ggttcctgaa | caggatctat | 3000 |
| ttgaggcgct | aaatgaaacc | ttaacgctat | ggaactcgcc | gcccgactgg | gctggcgatg | 3060 |
| agcgaaatgt | agtgcttacg | ttgtcccgca | tttggtacag | cgcagtaacc | ggcaaaatcg | 3120 |
| cgccgaagga | tgtcgctgcc | ggctgggcaa | tggagcgcct | gccggcccag | tatcagcccg | 3180 |
| tcatacttga | agctagacag | gcttatcttg | acaagaaga | agatcgcttg | gcctcgcgcg | 3240 |
| cagatcagtt | ggaagaattt | gtccactacg | tgaaggcga | gatcaccaag | gtagtcggca | 3300 |
| aataaccctc | gagcattcaa | ggcgccttga | ttatttgacg | tggtttgatg | gcctccacgc | 3360 |
| acgttgtgat | atgtagatga | ttcagttcga | gtttatcatt | atcaatactg | ccatttcaaa | 3420 |
| gaatacgtaa | ataattaata | gtagtgattt | tcctaacttt | atttagtcaa | aaattagcc | 3480 |
| ttttaattct | gctgtaaccc | gtacatgccc | aaaatagggg | gcgggttaca | cagaatatat | 3540 |
| aacatcgtag | gtgtctgggt | gaacagttta | ttcctggcat | ccactaaata | taatggagcc | 3600 |
| cgcttttttaa | gctggcatcc | agaaaaaaaa | agaatcccag | caccaaaata | ttgttttctt | 3660 |
| caccaaccat | cagttcatag | gtccattctc | ttagcgcaac | tacagagaac | aggggcacaa | 3720 |
| acaggcaaaa | aacgggcaca | acctcaatgg | agtgatgcaa | cctgcctgga | gtaaatgatg | 3780 |
| acacaaggca | attgacccac | gcatgtatct | atctcatttt | cttacacctt | ctattacctt | 3840 |
| ctgctctctc | tgatttggaa | aaagctgaaa | aaaaggttg | aaaccagttc | cctgaaatta | 3900 |
| ttcccctact | tgactaataa | gtatataaag | acggtaggta | ttgattgtaa | ttctgtaaat | 3960 |
| ctatttctta | aacttcttaa | attctacttt | tatagttagt | ctttttttta | gttttaaaac | 4020 |
| accaagaact | tagtttcgaa | taaacacaca | taaacaaaca | aatggaact | tcagtacttc | 4080 |
| tcctattttc | aacccacttc | atctgtcgta | gccctactac | tagcactagt | gagtatttta | 4140 |
| tttagcgtag | ttgttttgag | gaagactttc | agtaacaatt | actccagccc | cgcgtcaagt | 4200 |
| acggaaaccg | ctgtgctgtg | tcatcagagg | caacagagtt | gcgccctacc | tatcagcggc | 4260 |
| cttcttcacg | tgttcatgaa | taagaacggc | ctgattcatg | tcaccttggg | aaatatggct | 4320 |
| gacaaatatg | gccctatctt | cagttttccg | acaggcagcc | accgtacttt | agtagtcagt | 4380 |
| tcctgggaaa | tggtgaaaga | gtgtttcacc | ggtaataacg | acacggcatt | ctccaacaga | 4440 |
| ccaatccctt | tggcttttca | aaccatattc | tacgcctgtg | gcggcattga | ttcttacggt | 4500 |
| ttaagtagtg | tcccgtatgg | taaatactgg | agggagttga | gaaaggtgtg | tgttcacaac | 4560 |
| ctgctgagta | atcagcaatt | gctgaagttc | agacatctta | taatctccca | agtggatacg | 4620 |
| tcttttaaca | agttgtatga | gctgtgtaag | aactctgaag | ataatcaagg | tatggtaagg | 4680 |
| atggatgatt | ggctagctca | actttccttt | aacgtcatcg | gtaggatcgt | ttgcggattc | 4740 |
| cagtctgacc | caaagacggg | tgcaccttca | agggtagaac | agtttaagga | agtcataaat | 4800 |
| gaggcgtcat | attttatgtc | aacagtcca | gtctccgata | acgtaccaat | gttgggatgg | 4860 |
| atcgaccaat | tgaccggtct | gacgaggaac | atgaagcatt | gtgggaagaa | gcttgactta | 4920 |
| gtagtggagt | caattatcaa | ggaccatagg | caaaagagac | gttttcacg | tacaaaaggt | 4980 |
| ggcgatgaga | aggatgacga | acaggacgac | tttattgata | tttgcttgag | catcatggag | 5040 |
| cagccacagt | tgcccgggaa | caattctccc | cctcaaattc | cgatcaaatc | tatcgtgcta | 5100 |
| gacatgattg | ggggtggtac | cgacactacg | aaacttacaa | ccatatggac | cctatcactt | 5160 |
| ttgttgaaca | atcctcacgt | gttagataaa | gctaaacaag | aggtcgacgc | tcactttcgt | 5220 |

| | |
|---|---|
| aaaaagagaa gatcaacaga tgacgcagca gcggcagtcg ttgattttga cgacataaga | 5280 |
| aatttagtat acatccaagc catcattaaa gaaagtatga ggctttatcc agccagcccg | 5340 |
| gtggttgagc gtcttccgg cgaggattgc gttgttggag gttttcacgt gcctgctggt | 5400 |
| acgagactat gggctaacgt ttggaagatg caaagagatc ccaaagtttg ggacgatcct | 5460 |
| ctagtattca gacctgaaag gttttgagc gacgagcaaa agatggtaga cgttcgtggc | 5520 |
| caaaactatg aacttctgcc attcggcgca ggaagaagaa tctgtccagg cgtttccttt | 5580 |
| agtcttgacc ttatgcaact tgtcctaacc aggttaatcc tagagttcga aatgaagtcc | 5640 |
| ccgtccggca aggtagatat gaccgcaact ccaggactaa tgtcttacaa ggtggttcca | 5700 |
| ttggacatat tgctgactca ccgtcgtatc aagtcatgcg ttcaattggc gtcttctgaa | 5760 |
| cgtgattaag cgaatttctt atgatttatg attttattta ttaaataagt tataaaaaaa | 5820 |
| ataagtgtat acaaatttta aagtgactct taggttttaa aacgaaaatt cttattcttg | 5880 |
| agtaactctt tcctgtaggt caggttgctt tctcaggtac atagcttcaa aatgtttcta | 5940 |
| ctcctttttt actcttccag attttctcgg actccgcgca tcgccgtacc acttcaaaac | 6000 |
| acccaagcac agcatactaa atttcccctc tttcttcctc tagggtgtcg ttaattaccc | 6060 |
| gtactaaagg tttggaaaag aaaaaagaga ccgcctcgtt tcttttcttt cgtcgaaaaa | 6120 |
| ggcaataaaa attttatca cgtttctttt tcttgaaaat tttttttttt gattttttc | 6180 |
| tctttcgatg acctcccatt gatatttaag ttaataaacg gtcttcaatt tctcaagttt | 6240 |
| cagtttcatt tttcttgttc tattacaact tttttactt cttgctcatt agaaagaaag | 6300 |
| catagcaatc taatctaagt tttaattaca aaatggaaag ttctggggtg cctgtgatca | 6360 |
| cattgtcctc aggtaaagta atgcccgtac tgggcatggg aaccttcgaa aaggtgggta | 6420 |
| aggggtctga acgtgagcgt ttagccattc ttaaagcgat cgaagttggt taccgttact | 6480 |
| ttgataccgc agcggcatat gaaacggaag aagttctagg ggaagccatt gctgaagctt | 6540 |
| tacaattggg tctgatagag agccgtgacg agctgttcat cagctcaatg ctttggtgca | 6600 |
| ccgacgcaca tccagaccgt gtgctacttg ctctgcaaaa cagtctgaga atctaaaac | 6660 |
| ttgaatatct agacctatat atgttgccgt ttcctgccag ccttaagccg ggcaaaatta | 6720 |
| cgatggatat tcctgaggag gatatttgcc gtatggatta tcgttcagtc tggagcgcca | 6780 |
| tggaagagtg tcaaaactta ggatttacta aaagtattgg tgtaagcaac ttttcttgca | 6840 |
| agaaattaca agaattaatg gccactgcaa atatcccgcc cgcggtaaat caagtagaga | 6900 |
| tgtcaccagc tttccaacag aaaaaactga gggaatattg taacgcaaac aacatattgg | 6960 |
| tatccgcagt aagcattctg ggatcaaacg ggacgccctg gggtagtaat gctgttcttg | 7020 |
| gaagcgaagt tttgaaacag atcgcgatgg cgaaaggcaa aagcgttgcg caagtcagta | 7080 |
| tgaggtgggt ctatgagcag ggcgcgtctt tagtagtcaa gagtttctct gaagaacgtt | 7140 |
| taagagaaaa cctgaatatt tttgactggg agcttacgaa agaagacaat gagaagatag | 7200 |
| gcgaaatccc gcaatgtaga atccttactg cgtacttcct tgtctccccg aacggcccgt | 7260 |
| ttaaatctca ggaagagctt tgggatgaca aggcataaac aggcccctttt tcctttgtcg | 7320 |
| atatcatgta attagttatg tcacgcttac attcacgccc tcctcccaca tccgctctaa | 7380 |
| ccgaaaagga aggagttaga caacctgaag tctaggtccc tatttatttt tttaatagt | 7440 |
| tatgttagta ttaagaacgt tatttatatt tcaattttt cttttttttc tgtacaaacg | 7500 |
| cgtgtacgca tgtaacatta tactgaaaac cttgcttgag aaggttttgg gacgctcgaa | 7560 |
| ggctttaatt tgtaatcatt atcactttac gggtcctttc cggtgatccg acaggttacg | 7620 |

```
gggcggcgac ctcgcgggtt ttcgctattt atgaaaattt tccggtttaa ggcgtttccg      7680
ttcttcttcg tcataactta atgttttat ttaaaatacc tcgcgagtgg caacactgaa       7740
aatacccatg gagcggcgta accgtcgcac aggatctagg tgaagatcct ttttgataat      7800
ctcatgacca aaatcccta acgtgagttt tcgttccact gagcgtcaga ccccgtagaa       7860
aagatcaaag gatcttcttg agatcctttt tttctgcgcg taatctgctg cttgcaaaca      7920
aaaaaaccac cgctaccagc ggtggtttgt ttgccggatc aagagctacc aactctttt      7980 ccgaaggtaa ctggcttcag cagagcgcag ataccaaata ctgtccttct agtgtagccg      8040
tagttaggcc accacttcaa gaactctgta gcaccgccta catcctcgc tctgctaatc      8100 ctgttaccag tggctgctgc cagtggcgat aagtcgtgtc ttaccgggtt ggactcaaga      8160
cgatagttac cggataaggc gcagcggtcg gctgaacgg ggggtcgtg cacacagccc       8220 agcttggagc gaacgaccta caccgaactg agatacctac agcgtgagct atgagaaagc      8280
gccacgcttc ccgaagggag aaaggcggac aggtatccgg taagcggcag gtcggaaca      8340 ggagagcgca cgagggagct ccaggggga aacgcctggt atctttatag tcctgtcggg      8400
tttcgccacc tctgacttga gcgtcgattt ttgtgatgct cgtcagggg gcggagccta       8460 tggaaaaacg ccagcaacgc ggcagtggaa cgtgcattat gaattagtta cgctagggat      8520
aacagggtaa tatagaaccc gaacgaccga gcgcagcggc ggccgcgctg ataccgccgc      8580
```

<210> SEQ ID NO 28
<211> LENGTH: 8456
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
cctcgccgca gttaattaaa gtcagtgagc gaggaagcgc gtaactataa cggtcctaag       60
gtagcgaatc ctgatgcggt attttctcct tacgcatctg tgcggtattt cacaccgcat      120
agatcggcaa gtgcacaaac aatacttaaa taaatactac tcagtaataa cctatttctt      180 agcattttg acgaaatttg ctattttgtt agagtctttt acaccatttg tctccacacc       240
tccgcttaca tcaacaccaa taacgccatt taatctaagc gcatcaccaa cattttctgg      300
cgtcagtcca ccagctaaca taaaatgtaa gctttcgggg ctctcttgcc ttccaaccca      360
gtcagaaatc gagttccaat ccaaaagttc acctgtccca cctgcttctg aatcaaacaa      420
gggaataaac gaatgaggtt tctgtgaagc tgcactgagt agtatgttgc agtcttttgg      480
aaatacgagt cttttaataa ctggcaaacc gaggaactct tggtattctt gccacgactc      540
atctccatgc agttggacga tatcaatgcc gtaatcattg accagagcca aacatcctc       600 cttaagttga ttacgaaaca cgccaaccaa gtatttcgga gtgcctgaac tatttttata      660
tgcttttaca agacttgaaa ttttccttgc aataaccggg tcaattgttc tctttctatt      720
gggcacacat ataatacccca gcaagtcagc atcggaatct agagcacatt ctgcggcctc      780
tgtgctctgc aagccgcaaa cttt caccaa tggaccagaa ctacctgtga attaataac       840 agacatactc caagctgcct ttgtgtgctt aatcacgtat actcacgtgc tcaatagtca      900
ccaatgccct ccctcttggc cctctccttt tctttttcg accgaattaa ttcttaatcg       960 gcaaaaaag aaaagctccg gatcaagatt gtacgtaagg tgacaagcta tttttcaata    1020
aagaatatct tccactactg ccatctggcg tcataactgc aaagtacaca tatattacga    1080
```

```
tgctgttcta ttaaatgctt cctatattat atatatagta atgtcgtgat ctatggtgca    1140
ctctcagtac aatctgctct gatgccgcat agttaagcca gccccgacac ccgccaacac    1200
ccgctgacgc gccctgacgg gcttgtctgc tcccggcatc cgcttacaga caagctgtga    1260
ccgtctccgg gagctgcatg tgtcagaggt tttcaccgtc atcaccgaaa cgcgcgagac    1320
gaaagggcct cgtgatacgc ctattttat aggttaatgt catgataata atggtttctt    1380
agacggatcg cttgcctgta acttacacgc gcctcgtatc ttttaatgat ggaataattt    1440
gggaatttac tctgtgttta tttatttta tgttttgtat ttggatttta gaaagtaaat    1500
aaagaaggta gaagagttac ggaatgaaga aaaaaaata aacaaaggtt taaaaaattt    1560
caacaaaaag cgtactttac atatatattt attagacaag aaaagcagat taaatagata    1620
tacattcgat taacgataag taaaatgtaa aatcacagga ttttcgtgtg tggtcttcta    1680
cacagacaag gtgaaacaat tcggcattaa tacctgagag caggaagagc aagataaaag    1740
gtagtatttg ttggcgatcc ccctagagtc ttttacatct tcggaaaaca aaaactatt     1800 tttcttaat ttcttttttt actttctatt tttaatttat atatttatat taaaaaattt     1860
aaattataat tattttata gcacgtgatg aaaaggaccc aggtggcact tttcggggaa    1920
atgtgcgcgg aaccctatt tgtttatttt tctaaataca ttcaaatatg tatccgctca     1980
tgagacaata accctgataa atgcttcaat aatattgaaa aaggaagagt atgagtattc    2040
aacatttccg tgtcgccctt attccttttt ttgcggcatt ttgccttcct gtttttgctc    2100
acccagaaac gctggtgaaa gtaaaagatg ctgaagatca gttgggacgc gtagtctaga    2160
ccagccagga cagaaatgcc tcgacttcgc tgctacccaa ggttgccggg tgacgcacac    2220
cgtggaaacg gatgaaggca cgaacccagt ggacataagc ctgttcggtt cgtaagctgt    2280
aatgcaagta gcgtatgcgc tcacgcaact ggtccagaac cttgaccgaa cgcagcggtg    2340
gtaacggcgc agtggcggtt ttcatggctt gttatgactg ttttttttggg gtacagtcta    2400 tgcctcgggc atccaagcag caagcgcgtt acgccgtggg tcgatgtttg atgttatgga    2460
gcagcaacga tgttacgcag cagggcagtc gccctaaaac aaagttaaac attatgaggg    2520
aagcggtgat cgccgaagta tcgactcaac tatcagaggt agttggcgcc atcgagcgcc    2580
atctcgaacc gacgttgctg gccgtacatt tgtacggctc cgcagtggat ggcggcctga    2640
agccacacag tgatattgat ttgctggtta cggtgaccgt aaggcttgat gaaacaacgc    2700
ggcgagcttt gatcaacgac cttttggaaa cttcggcttc ccctggagag agcgagattc    2760
tccgcgctgt agaagtcacc attgttgtgc acgacgacat cattccgtgg cgttatccag    2820
ctaagcgcga actgcaattt ggagaatggc agcgcaatga cattcttgca ggtatcttcg    2880
agccagccac gatcgacatt gatctggcta tcttgctgac aaaagcaaga gaacatagcg    2940
ttgccttggt aggtccagcg gcggaggaac tctttgatcc ggttcctgaa caggatctat    3000
ttgaggcgct aaatgaaacc ttaacgctat ggaactcgcc gcccgactgg gctggcgatg    3060
agcgaaatgt agtgcttacg ttgtcccgca tttggtacag cgcagtaacc ggcaaaatcg    3120
cgccgaagga tgtcgctgcc ggctgggcaa tggagcgcct gccggcccag tatcagcccg    3180
tcatacttga agctagacag gcttatcttg acaagaagaa agatcgcttg gcctcgcgcg    3240
cagatcagtt ggaagaattt gtccactacg tgaaaggcga gatcaccaag gtagtcggca    3300
aataaccctc gagcattcaa ggcgccttga ttatttgacg tggtttgatg gcctccacgc    3360
acgttgtgat atgtagatga gagcgttggt tggtggatca agcccacgcg taggcaatcc    3420
```

```
tcgagcagat ccgccaggcg tgtatatata gcgtggatgg ccaggcaact ttagtgctga   3480
cacatacagg catatatata tgtgtgcgac gacacatgat catatggcat gcatgtgctc   3540
tgtatgtata taaaactctt gttttcttct tttctctaaa tattctttcc ttatacatta   3600
ggacctttgc agcataaatt actatacttc tatagacaca caaacacaaa tacacacact   3660
aaattaataa tggaacttca gtacttctcc tattttcaac ccacttcatc tgtcgtagcc   3720
ctactactag cactagtgag tattttattt agcgtagttg ttttgaggaa gactttcagt   3780
aacaattact ccagccccgc gtcaagtacg gaaaccgctg tgctgtgtca tcagaggcaa   3840
cagagttgcg ccctacctat cagcggcctt cttcacgtgt tcatgaataa gaacggcctg   3900
attcatgtca ccttgggaaa tatggctgac aaatatggcc ctatcttcag ttttccgaca   3960
ggcagccacc gtactttagt agtcagttcc tgggaaatgg tgaaagagtg tttcaccggt   4020
aataacgaca cggcattctc caacagacca atccctttgg cttttcaaac catattctac   4080
gcctgtggcg gcattgattc ttacggttta agtagtgtcc cgtatggtaa atactggagg   4140
gagttgagaa aggtgtgtgt tcacaacctg ctgagtaatc agcaattgct gaagttcaga   4200
catcttataa tctcccaagt ggatacgtct tttaacaagt tgtatgagct gtgtaagaac   4260
tctgaagata atcaaggtat ggtaaggatg gatgattggc tagctcaact ttcctttaac   4320
gtcatcggta ggatcgtttg cggattccag tctgacccaa agacgggtgc accttcaagg   4380
gtagaacagt ttaaggaagt cataaatgag gcgtcatatt ttatgtcaac aagtccagtc   4440
tccgataacg taccaatgtt gggatggatc gaccaattga ccggtctgac gaggaacatg   4500
aagcattgtg gaagaagct tgacttagta gtggagtcaa ttatcaagga ccataggcaa   4560
aagagacgtt tttcacgtac aaaaggtggc gatgagaagg atgacgaaca ggacgacttt   4620
attgatattt gcttgagcat catggagcag ccacagttgc ccgggaacaa ttctcccccct   4680
caaattccga tcaaatctat cgtgctagac atgattgggg gtggtaccga cactacgaaa   4740
cttacaacca tatggaccct atcacttttg ttgaacaatc ctcacgtgtt agataaagct   4800
aaacaagagg tcgacgctca ctttcgtaaa aagagaagat caacagatga cgcagcagcg   4860
gcagtcgttg attttgacga cataagaaat ttagtataca tccaagccat cattaaagaa   4920
agtatgaggc tttatccagc cagcccggtg gttgagcgtc tttccggcga ggattgcgtt   4980
gttggaggtt ttcacgtgcc tgctggtacg agactatggg ctaacgtttg gaagatgcaa   5040
agagatccca aagtttggga cgatcctcta gtattcagac ctgaaaggtt tttgagcgac   5100
gagcaaaaga tggtagacgt tcgtggccaa aactatgaac ttctgccatt cggcgcagga   5160
agaagaatct gtccaggcgt ttcctttagt cttgaccttta tgcaacttgt cctaaccagg   5220
ttaatcctag agttcgaaat gaagtccccg tccggcaagg tagatatgac cgcaactcca   5280
ggactaatgt cttacaaggt ggttccattg gacatattgc tgactcaccg tcgtatcaag   5340
tcatgcgttc aattggcgtc ttctgaacgt gattaagcga atttcttatg atttatgatt   5400
tttattatta aataagttat aaaaaaaata agtgtataca aattttaaag tgactcttag   5460
gttttaaaac gaaaattctt attcttgagt aactctttcc tgtaggtcag gttgctttct   5520
caggtattca gttcgagttt atcattatca atactgccat ttcaaagaat acgtaaataa   5580
ttaatagtag tgattttcct aactttattt agtcaaaaaa ttagccttt aattctgctg   5640
taacccgtac atgcccaaaa taggggcgg gttacacaga atatataaca tcgtaggtgt   5700
ctgggtgaac agtttattcc tggcatccac taaaatataat ggagcccgct ttttaagctg   5760
gcatccagaa aaaaaaagaa tcccagcacc aaaatattgt tttcttcacc aaccatcagt   5820
```

```
tcataggtcc attctcttag cgcaactaca gagaacaggg gcacaaacag gcaaaaaacg   5880
ggcacaacct caatggagtg atgcaacctg cctggagtaa atgatgacac aaggcaattg   5940
acccacgcat gtatctatct cattttctta caccttctat taccttctgc tctctctgat   6000
ttggaaaaag ctgaaaaaaa aggttgaaac cagttccctg aaattattcc cctacttgac   6060
taataagtat ataaagacgg taggtattga ttgtaattct gtaaatctat ttcttaaact   6120
tcttaaattc tacttttata gttagtcttt tttttagttt taaaacacca agaacttagt   6180
ttcgaataaa cacacataaa caaacaaaat ggaaagttct ggggtgcctg tgatcacatt   6240
gtcctcaggt aaagtaatgc ccgtactggg catgggaacc ttcgaaaagg tgggtaaggg   6300
gtctgaacgt gagcgtttag ccattcttaa agcgatcgaa gttggttacc gttactttga   6360
taccgcagcg gcatatgaaa cggaagaagt tctaggggaa gccattgctg aagctttaca   6420
attgggtctg atagagagcc gtgacgagct gttcatcagc tcaatgcttt ggtgcaccga   6480
cgcacatcca gaccgtgtgc tacttgctct gcaaaacagt ctgagaaatc taaaacttga   6540
atatctagac ctatatatgt tgccgtttcc tgccagcctt aagccgggca aaattacgat   6600
ggatattcct gaggaggata tttgccgtat ggattatcgt tcagtctgga gcgccatgga   6660
agagtgtcaa aacttaggat ttactaaaag tattggtgta agcaactttt cttgcaagaa   6720
attacaagaa ttaatggcca ctgcaaatat cccgcccgcg gtaaatcaag tagagatgtc   6780
accagctttc caacagaaaa aactgaggga atattgtaac gcaaacaaca tattggtatc   6840
cgcagtaagc attctgggat caaacgggac gccctgggt agtaatgctg ttcttggaag   6900
cgaagttttg aaacagatcg cgatggcgaa aggcaaaagc gttgcgcaag tcagtatgag   6960
gtgggtctat gagcagggcg cgtctttagt agtcaagagt ttctctgaag aacgtttaag   7020
agaaaacctg aatattttg actgggagct tacgaaagaa gacaatgaga agataggcga   7080
aatcccgcaa tgtagaatcc ttactgcgta cttccttgtc tccccgaacg gcccgtttaa   7140
atctcaggaa gagctttggg atgacaaggc ataaacaggc ccctttcct ttgtcgatat   7200 catgtaatta gttatgtcac gcttacattc acgccctcct cccacatccg ctctaaccga   7260
aaaggaagga gttagacaac ctgaagtcta ggtcccatt tattttttt aatagttatg   7320 ttagtattaa gaacgttatt tatatttcaa attttctttt ttttctgta caaacgcgtg   7380 tacgcatgta acattatact gaaaaccttg cttgagaagg ttttgggacg ctcgaaggct   7440
ttaatttgta atcattatca ctttacgggt ccttttccggt gatccgacag gttacggggc   7500
ggcgacctcg cgggttttcg ctatttatga aaattttccg gtttaaggcg tttccgttct   7560
tcttcgtcat aacttaatgt ttttatttaa aatacctcgc gagtggcaac actgaaaata   7620
cccatggagc ggcgtaaccg tcgcacagga tctaggtgaa gatccttttt gataatctca   7680
tgaccaaaat cccttaacgt gagttttcgt tccactgagc gtcagacccc gtagaaaaga   7740
tcaaaggatc ttcttgagat cctttttttc tgcgcgtaat ctgctgcttg caaacaaaaa   7800
aaccaccgct accagcggtg gtttgtttgc cggatcaaga gctaccaact ctttttccga   7860
aggtaactgg cttcagcaga gcgcagatac caaatactgt ccttctagtg tagccgtagt   7920
taggccacca cttcaagaac tctgtagcac cgcctacata cctcgctctg ctaatcctgt   7980
taccagtggc tgctgccagt ggcgataagt cgtgtcttac cgggttggac tcaagacgat   8040
agttaccgga taaggcgcag cggtcgggct gaacggggg ttcgtgcaca cagcccagct   8100
tggagcgaac gacctacacc gaactgagat acctacagcg tgagctatga gaaagcgcca   8160
```

```
cgcttcccga agggagaaag gcggacaggt atccggtaag cggcagggtc ggaacaggag      8220
agcgcacgag ggagcttcca gggggaaacg cctggtatct ttatagtcct gtcgggtttc      8280
gccacctctg acttgagcgt cgattttttgt gatgctcgtc agggggggcgg agcctatgga    8340 aaaacgccag caacgcggca gtggaacgtg cattatgaat tagttacgct agggataaca      8400
gggtaatata gaacccgaac gaccgagcgc agcggcggcc gcgctgatac cgccgc          8456

<210> SEQ ID NO 29
<211> LENGTH: 8456
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
cctcgccgca gttaattaaa gtcagtgagc gaggaagcgc gtaactataa cggtcctaag        60
gtagcgaatc ctgatgcggt attttctcct tacgcatctg tgcggtattt cacaccgcat       120
agatcggcaa gtgcacaaac aatacttaaa taaatactac tcagtaataa cctatttctt       180 agcattttg acgaaatttg ctattttgtt agagtctttt acaccatttg tctccacacc        240
tccgcttaca tcaacaccaa taacgccatt taatctaagc gcatcaccaa catttctgg        300 cgtcagtcca ccagctaaca taaaatgtaa gctttcgggg ctctcttgcc ttccaaccca       360
gtcagaaatc gagttccaat ccaaaagttc acctgtccca cctgcttctg aatcaaacaa       420
gggaataaac gaatgaggtt tctgtgaagc tgcactgagt agtatgttgc agtcttttgg      480
aaatacgagt cttttaataa ctggcaaacc gaggaactct tggtattctt gccacgactc       540
atctccatgc agttggacga tatcaatgcc gtaatcattg accagagcca aaacatcctc      600
cttaagttga ttacgaaaca cgccaaccaa gtatttcgga gtgcctgaac tattttttata    660 tgcttttaca agacttgaaa ttttccttgc aataaccggg tcaattgttc tctttctatt      720
gggcacacat ataatacca gcaagtcagc atcggaatct agagcacatt ctgcggcctc        780
tgtgctctgc aagccgcaaa cttttcaccaa tggaccagaa ctacctgtga aattaataac      840
agacatactc caagctgcct ttgtgtgctt aatcacgtat actcacgtgc tcaatagtca      900
ccaatgccct ccctcttggc cctctccttt tcttttttcg accgaattaa ttccttaatcg     960 gcaaaaaaag aaaagctccg gatcaagatt gtacgtaagg tgacaagcta ttttcaata       1020 aagaatatct tccactactg ccatctggcg tcataactgc aaagtacaca tatattacga     1080
tgctgttcta ttaaatgctt cctatattat atatatagta atgtcgtgat ctatggtgca      1140
ctctcagtac aatctgctct gatgccgcat agttaagcca gccccgacac ccgccaacac     1200
ccgctgacgc gccctgacgg gcttgtctgc tcccggcatc cgcttacaga caagctgtga     1260
ccgtctccgg gagctgcatg tgtcagaggt tttcaccgtc atcaccgaaa cgcgcgagac     1320
gaaagggcct cgtgatacgc ctatttttat aggttaatgt catgataata atggtttctt     1380
agacggatcg cttgcctgta acttacacgc gcctcgtatc ttttaatgat ggaataattt     1440 gggaattttac tctgtgttta tttatttta tgttttgtat ttggatttta gaaagtaaat     1500
aaagaaggta gaagagttac ggaatgaaga aaaaaaaata aacaaggtt taaaaaattt      1560 caacaaaaag cgtactttac atatatattt attagacaag aaaagcagat taaatagata     1620
tacattcgat taacgataag taaaatgtaa aatcacagga ttttcgtgtg tggtcttcta     1680
cacagacaag gtgaaacaat tcggcattaa tacctgagag caggaagagc aagataaaag     1740
```

-continued

```
gtagtatttg ttggcgatcc ccctagagtc ttttacatct tcggaaaaca aaaactattt    1800
tttctttaat ttcttttttt actttctatt tttaatttat atatttatat taaaaaattt    1860
aaattataat tatttttata gcacgtgatg aaaaggaccc aggtggcact tttcggggaa    1920
atgtgcgcgg aaccccctatt tgtttatttt tctaaataca ttcaaatatg tatccgctca    1980
tgagacaata accctgataa atgcttcaat aatattgaaa aaggaagagt atgagtattc    2040
aacatttccg tgtcgccctt attccctttt ttgcggcatt ttgccttcct gttttttgctc   2100 acccagaaac gctggtgaaa gtaaaagatg ctgaagatca gttgggacgc gtagtctaga    2160
ccagccagga cagaaatgcc tcgacttcgc tgctacccaa ggttgccggg tgacgcacac    2220
cgtggaaacg gatgaaggca cgaacccagt ggacataagc ctgttcggtt cgtaagctgt    2280
aatgcaagta gcgtatgcgc tcacgcaact ggtccagaac cttgaccgaa cgcagcggtg    2340
gtaacggcgc agtggcggtt ttcatggctt gttatgactg tttttttggg gtacagtcta    2400
tgcctcgggc atccaagcag caagcgcgtt acgccgtggg tcgatgtttg atgttatgga    2460
gcagcaacga tgttacgcag cagggcagtc gccctaaaac aaagttaaac attatgaggg    2520
aagcggtgat cgccgaagta tcgactcaac tatcagaggt agttggcgcc atcgagcgcc    2580
atctcgaacc gacgttgctg gccgtacatt tgtacggctc cgcagtggat ggcggcctga    2640
agccacacag tgatattgat ttgctggtta cggtgaccgt aaggcttgat gaaacaacgc    2700
ggcgagcttt gatcaacgac cttttggaaa cttcggcttc cctggagag agcgagattc     2760 tccgcgctgt agaagtcacc attgttgtgc acgacgacat cattccgtgg cgttatccag    2820
ctaagcgcga actgcaattt ggagaatggc agcgcaatga cattcttgca ggtatcttcg    2880
agccagccac gatcgacatt gatctggcta tcttgctgac aaaagcaaga gaacatagcg    2940
ttgccttggt aggtccagcg gcggaggaac tctttgatcc ggttcctgaa caggatctat    3000
ttgaggcgct aaatgaaacc ttaacgctat ggaactcgcc gcccgactgg gctggcgatg    3060
agcgaaatgt agtgcttacg ttgtcccgca tttggtacag cgcagtaacc ggcaaaatcg    3120
cgccgaagga tgtcgctgcc ggctgggcaa tggagcgcct gccggcccag tatcagcccg    3180
tcatacttga agctagacag gcttatcttg acaagaagaa gatcgcttg gcctcgcgcg     3240 cagatcagtt ggaagaattt gtccactacg tgaaggcga gatcaccaag gtagtcggca     3300
aataaccctc gagcattcaa ggcgccttga ttatttgacg tggtttgatg gcctccacgc    3360
acgttgtgat atgtagatga ttcagttcga gtttatcatt atcaatactg ccatttcaaa    3420
gaatacgtaa ataattaata gtagtgattt tcctaacttt atttagtcaa aaaattagcc    3480
ttttaattct gctgtaaccc gtacatgccc aaaatagggg gcgggttaca cagaatatat    3540
aacatcgtag gtgtctgggt gaacagttta ttcctggcat ccactaaata taatggagcc    3600
cgctttttaa gctggcatcc agaaaaaaaa agaatcccag caccaaaata ttgttttctt    3660
caccaaccat cagttcatag gtccattctc ttagcgcaac tacagagaac aggggcacaa    3720
acaggcaaaa acgggcaca acctcaatgg agtgatgcaa cctgcctgga gtaaatgatg     3780
acacaaggca attgacccac gcatgtatct atctcatttt cttacacctt ctattacctt    3840
ctgctctctc tgatttggaa aaagctgaaa aaaaggttg aaaccagttc cctgaaatta     3900
ttcccctact tgactaataa gtatataaag acggtaggta ttgattgtaa ttctgtaaat    3960
ctatttctta aacttcttaa attctacttt tatagttagt cttttttta gttttaaaac     4020 accaagaact tagtttcgaa taaacacaca taaacaaaca aaatgaact tcagtacttc     4080 tcctattttc aacccacttc atctgtcgta gccctactac tagcactagt gagtatttta   4140
```

```
tttagcgtag ttgttttgag gaagactttc agtaacaatt actccagccc cgcgtcaagt    4200
acggaaaccg ctgtgctgtg tcatcagagg caacagagtt gcgccctacc tatcagcggc    4260
cttcttcacg tgttcatgaa taagaacggc ctgattcatg tcaccttggg aaatatggct    4320
gacaaatatg gccctatctt cagttttccg acaggcagcc accgtacttt agtagtcagt    4380
tcctgggaaa tggtgaaaga gtgtttcacc ggtaataacg acacggcatt ctccaacaga    4440
ccaatccctt tggcttttca aaccatattc tacgcctgtg gcggcattga ttcttacggt    4500
ttaagtagtg tcccgtatgg taaatactgg agggagttga gaaggtgtg tgttcacaac     4560 ctgctgagta atcagcaatt gctgaagttc agacatctta taatctccca gtggatacg     4620 tcttttaaca agttgtatga gctgtgtaag aactctgaag ataatcaagg tatggtaagg    4680
atggatgatt ggctagctca actttccttt aacgtcatcg gtaggatcgt ttgcggattc    4740
cagtctgacc caaagacggg tgcaccttca agggtagaac agtttaagga agtcataaat    4800
gaggcgtcat attttatgtc aacaagtcca gtctccgata acgtaccaat gttgggatgg    4860
atcgaccaat tgaccggtct gacgaggaac atgaagcatt gtgggaagaa gcttgactta    4920
gtagtggagt caattatcaa ggaccatagg caaaagagac gttttcacg tacaaaaggt     4980 ggcgatgaga aggatgacga acaggacgac tttattgata tttgcttgag catcatggag    5040
cagccacagt tgcccgggaa caattctccc cctcaaattc cgatcaaatc tatcgtgcta    5100
gacatgattg ggggtggtac cgacactacg aaacttacaa ccatatggac cctatcactt    5160
ttgttgaaca atcctcacgt gttagataaa gctaaacaag aggtcgacgc tcactttcgt    5220
aaaaagagaa gatcaacaga tgacgcagca gcggcagtcg ttgattttga cgacataaga    5280
aatttagtat acatccaagc catcattaaa gaaagtatga ggctttatcc agccagcccg    5340
gtggttgagc gtctttccgg cgaggattgc gttgttggag gttttcacgt gcctgctggt    5400
acgagactat gggctaacgt ttggaagatg caaagagatc ccaaagtttg gacgatcct    5460 ctagtattca gacctgaaag gttttttgagc gacgagcaaa agatggtaga cgttcgtggc    5520
caaaactatg aacttctgcc attcggcgca ggaagaagaa tctgtccagg cgtttccttt    5580
agtcttgacc ttatgcaact tgtcctaacc aggttaatcc tagagttcga aatgaagtcc    5640
ccgtccggca aggtagatat gaccgcaact ccaggactaa tgtcttacaa ggtggttcca    5700
ttggacatat tgctgactca ccgtcgtatc aagtcatgcg ttcaattggc gtcttctgaa    5760
cgtgattaag cgaatttctt atgatttatg attttattta ttaaataagt tataaaaaaa    5820
ataagtgtat acaaattta aagtgactct taggttttaa aacgaaaatt cttattcttg      5880
agtaactctt tcctgtaggt caggttgctt tctcaggtag agcgttggtt ggtggatcaa    5940
gcccacgcgt aggcaatcct cgagcagatc cgccaggcgt gtatatatag cgtggatggc    6000
caggcaactt tagtgctgac acatacaggc atatatatat gtgtgcgaca acacatgatc    6060
atatggcatg catgtgctct gtatgtatat aaaactcttg ttttcttctt ttctctaaat    6120
attctttcct tatacattag gacctttgca gcataaatta ctatacttct atagacacac    6180
aaacacaaat acacacacta aattaataat ggaaagttct ggggtgcctg tgatcacatt    6240
gtcctcaggt aaagtaatgc ccgtactggg catgggaacc ttcgaaaagg tgggtaaggg    6300
gtctgaacgt gagcgtttag ccattcttaa agcgatcgaa gttggttacc gttactttga    6360
taccgcagcg gcatatgaaa cggaagaagt tctaggggaa gccattgctg aagctttaca    6420
attgggtctg atagagagcc gtgacgagct gttcatcagc tcaatgcttt ggtgcaccga    6480
```

| | |
|---|---|
| cgcacatcca gaccgtgtgc tacttgctct gcaaaacagt ctgagaaatc taaaacttga | 6540 |
| atatctagac ctatatatgt tgccgtttcc tgccagcctt aagccgggca aaattacgat | 6600 |
| ggatattcct gaggaggata tttgccgtat ggattatcgt tcagtctgga gcgccatgga | 6660 |
| agagtgtcaa aacttaggat ttactaaaag tattggtgta agcaactttt cttgcaagaa | 6720 |
| attacaagaa ttaatggcca ctgcaaatat cccgcccgcg gtaaatcaag tagagatgtc | 6780 |
| accagctttc caacagaaaa aactgaggga atattgtaac gcaaacaaca tattggtatc | 6840 |
| cgcagtaagc attctgggat caaacgggac gccctggggt agtaatgctg ttcttggaag | 6900 |
| cgaagttttg aaacagatcg cgatggcgaa aggcaaaagc gttgcgcaag tcagtatgag | 6960 |
| gtgggtctat gagcagggcg cgtctttagt agtcaagagt ttctctgaag aacgtttaag | 7020 |
| agaaaacctg aatattttg actgggagct tacgaaagaa gacaatgaga agataggcga | 7080 |
| aatcccgcaa tgtagaatcc ttactgcgta cttccttgtc tccccgaacg gcccgtttaa | 7140 |
| atctcaggaa gagctttggg atgacaaggc ataaacaggc ccctttttcct ttgtcgatat | 7200 |
| catgtaatta gttatgtcac gcttacattc acgccctcct cccacatccg ctctaaccga | 7260 |
| aaaggaagga gttagacaac ctgaagtcta ggtccctatt tatttttttt aatagttatg | 7320 |
| ttagtattaa gaacgttatt tatatttcaa attttctttt ttttctgta caaacgcgtg | 7380 |
| tacgcatgta acattatact gaaaaccttg cttgagaagg ttttgggacg ctcgaaggct | 7440 |
| ttaatttgta atcattatca ctttacgggt cctttccggt gatccgacag gttacggggc | 7500 |
| ggcgacctcg cgggttttcg ctatttatga aaattttccg gtttaaggcg tttccgttct | 7560 |
| tcttcgtcat aacttaatgt ttttatttaa aatacctcgc gagtggcaac actgaaaata | 7620 |
| cccatggagc ggcgtaaccg tcgcacagga tctaggtgaa gatcctttt gataatctca | 7680 |
| tgaccaaaat cccttaacgt gagttttcgt tccactgagc gtcagacccc gtagaaaaga | 7740 |
| tcaaaggatc ttcttgagat cctttttttc tgcgcgtaat ctgctgcttg caaacaaaaa | 7800 |
| aaccaccgct accagcggtg gtttgtttgc cggatcaaga gctaccaact cttttttccga | 7860 |
| aggtaactgg cttcagcaga gcgcagatac caaatactgt ccttctagtg tagccgtagt | 7920 |
| taggccacca cttcaagaac tctgtagcac cgcctacata cctcgctctg ctaatcctgt | 7980 |
| taccagtggc tgctgccagt ggcgataagt cgtgtcttac cgggttggac tcaagacgat | 8040 |
| agttaccgga taaggcgcag cggtcgggct gaacgggggg ttcgtgcaca cagcccagct | 8100 |
| tggagcgaac gacctacacc gaactgagat acctacagcg tgagctatga gaaagcgcca | 8160 |
| cgcttcccga agggagaaag gcggacaggt atccggtaag cggcagggtc ggaacaggag | 8220 |
| agcgcacgag ggagcttcca gggggaaacg cctggtatct ttatagtcct gtcgggtttc | 8280 |
| gccacctctg acttgagcgt cgatttttgt gatgctcgtc aggggggcgg agcctatgga | 8340 |
| aaaacgccag caacgcggca gtggaacgtg cattatgaat tagttacgct agggataaca | 8400 |
| gggtaatata gaacccgaac gaccgagcgc agcggcggcc gcgctgatac cgccgc | 8456 |

```
<210> SEQ ID NO 30
<211> LENGTH: 153
<212> TYPE: PRT
<213> ORGANISM: Papaver bracteatum

<400> SEQUENCE: 30

Met Ala Pro Arg Gly Val Ser Gly Leu Val Gly Lys Leu Ser Thr Glu
1               5                   10                  15

Leu Asp Val Asn Cys Asp Ala Glu Lys Tyr Tyr Asn Met Tyr Lys Asn
            20                  25                  30
```

```
Gly Glu Asp Val Gln Lys Ala Val Pro His Leu Cys Met Asp Val Lys
            35                  40                  45

Val Ile Ser Gly Asp Ala Thr Arg Ser Gly Cys Ile Lys Glu Trp Asn
 50                  55                  60

Val Asn Ile Asp Gly Lys Thr Ile Arg Ser Val Glu Glu Thr Thr His
 65                  70                  75                  80

Asn Asp Glu Thr Lys Thr Leu Arg His Arg Val Phe Glu Gly Asp Met
                85                  90                  95

Met Lys Asp Tyr Lys Lys Phe Asp Thr Ile Met Glu Val Asn Pro Lys
               100                 105                 110

Pro Asp Gly Asn Gly Cys Val Val Thr Arg Ser Ile Glu Tyr Glu Lys
               115                 120                 125

Val Asn Glu Asn Ser Pro Thr Pro Phe Asp Tyr Leu Gln Phe Gly His
130                 135                 140

Gln Ala Met Glu Asp Met Asn Lys Tyr
145                 150
```

<210> SEQ ID NO 31
<211> LENGTH: 144
<212> TYPE: PRT
<213> ORGANISM: Papaver setigerum

<400> SEQUENCE: 31

```
Met Leu Val Gly Lys Leu Ser Thr Glu Leu Glu Val Asp Cys Asp Ala
  1               5                  10                  15

Glu Lys Tyr Tyr Asn Met Tyr Lys His Gly Asp Val Lys Lys Ala
                20                  25                  30

Leu Cys Val Asp Val Lys Val Ile Ser Gly Asp Pro Thr Arg Ser Gly
            35                  40                  45

Cys Ile Lys Glu Trp Asn Val Asn Ile Asp Gly Lys Thr Ile Arg Ser
 50                  55                  60

Val Glu Glu Thr Thr His Asn Asp Glu Thr Lys Thr Leu Arg His Arg
 65                  70                  75                  80

Val Phe Glu Gly Asp Met Met Lys Asp Phe Lys Lys Phe Asp Thr Ile
                85                  90                  95

Met Val Val Asn Pro Lys Pro Asp Gly Asn Gly Cys Val Val Thr Arg
               100                 105                 110

Ser Ile Glu Tyr Glu Lys Thr Asn Glu Asn Ser Pro Thr Pro Phe Asp
               115                 120                 125

Tyr Leu Gln Phe Gly His Gln Ala Ile Glu Asp Met Asn Lys Tyr Leu
130                 135                 140
```

<210> SEQ ID NO 32
<211> LENGTH: 141
<212> TYPE: PRT
<213> ORGANISM: Papaver setigerum

<400> SEQUENCE: 32

```
Met Leu Val Gly Lys Leu Ser Thr Glu Leu Glu Val Asp Cys Asp Ala
  1               5                  10                  15

Glu Lys Tyr Tyr Asn Met Tyr Lys His Gly Asp Lys Arg Gln Cys
                20                  25                  30

Val Asp Val Lys Val Ile Ser Gly Asp Pro Thr Arg Ser Gly Cys Ile
            35                  40                  45

Lys Glu Trp Asn Val Asn Ile Asp Gly Lys Thr Ile Arg Ser Val Glu
 50                  55                  60
```

Glu Thr Thr His Asn Asp Glu Thr Lys Thr Leu Arg His Arg Val Phe
65                  70                  75                  80

Glu Gly Asp Met Met Lys Asp Phe Lys Phe Asp Thr Ile Met Val
            85                  90                  95

Val Asn Pro Lys Pro Asp Gly Asn Gly Cys Val Val Thr Arg Ser Ile
            100                 105                 110

Glu Tyr Glu Lys Thr Asn Glu Asn Ser Pro Thr Pro Phe Asp Tyr Leu
        115                 120                 125

Gln Phe Gly His Gln Ala Ile Glu Asp Met Asn Lys Tyr
    130                 135                 140

<210> SEQ ID NO 33
<211> LENGTH: 147
<212> TYPE: PRT
<213> ORGANISM: Papaver setigerum

<400> SEQUENCE: 33

Met Leu Val Gly Lys Leu Ser Thr Glu Leu Glu Val Asp Cys Asp Ala
1               5                   10                  15

Glu Lys Tyr Tyr Asn Met Tyr Lys His Gly Glu Asp Val Lys Lys Ala
            20                  25                  30

Val Pro His Leu Cys Val Asp Val Lys Ile Ile Ser Gly Asp Pro Thr
        35                  40                  45

Ser Ser Gly Cys Ile Lys Glu Trp Asn Val Asn Ile Asp Gly Lys Thr
    50                  55                  60

Ile Arg Ser Val Glu Glu Thr Thr His Asp Asp Glu Thr Lys Thr Leu
65                  70                  75                  80

Arg His Arg Val Phe Glu Gly Asp Val Met Lys Asp Phe Lys Lys Phe
                85                  90                  95

Asp Thr Ile Met Val Val Asn Pro Lys Pro Asp Gly Asn Gly Cys Val
            100                 105                 110

Val Thr Arg Ser Ile Glu Tyr Glu Lys Thr Asn Glu Asn Ser Pro Thr
        115                 120                 125

Pro Phe Asp Tyr Leu Gln Phe Gly His Gln Ala Ile Glu Asp Met Asn
    130                 135                 140

Lys Tyr Leu
145

<210> SEQ ID NO 34
<211> LENGTH: 109
<212> TYPE: PRT
<213> ORGANISM: Papaver setigerum

<400> SEQUENCE: 34

Met Val Lys Ile Ile Ser Gly Asp Pro Thr Ser Ser Gly Cys Ile Lys
1               5                   10                  15

Glu Trp Asn Val Asn Ile Asp Gly Lys Thr Ile Arg Ser Val Glu Glu
            20                  25                  30

Thr Thr His Asp Asp Glu Thr Lys Thr Leu Arg His Arg Val Phe Glu
        35                  40                  45

Gly Asp Val Met Lys Asp Phe Lys Phe Asp Thr Ile Met Val Val
    50                  55                  60

Asn Pro Lys Pro Asp Gly Asn Gly Cys Val Val Thr Arg Ser Ile Glu
65                  70                  75                  80

Tyr Glu Lys Thr Asn Glu Asn Ser Pro Thr Pro Phe Asp Tyr Leu Gln
                85                  90                  95

```
Phe Gly His Gln Ala Ile Glu Asp Met Asn Lys Tyr Leu
            100                 105

<210> SEQ ID NO 35
<211> LENGTH: 180
<212> TYPE: PRT
<213> ORGANISM: Papaver somniferum

<400> SEQUENCE: 35

Met Asp Ser Ile Asn Ser Ser Ile Tyr Phe Cys Ala Tyr Phe Arg Glu
1               5                   10                  15

Leu Ile Ile Lys Leu Leu Met Ala Pro Pro Gly Val Ser Gly Leu Val
            20                  25                  30

Gly Lys Leu Ser Thr Glu Leu Glu Val Asn Cys Asp Ala Glu Lys Tyr
        35                  40                  45

Tyr Asn Met Tyr Lys His Gly Glu Asp Val Gln Lys Ala Val Pro His
    50                  55                  60

Leu Cys Val Asp Val Lys Val Ile Ser Gly Asp Pro Thr Arg Ser Gly
65                  70                  75                  80

Cys Ile Lys Glu Trp Asn Val Asn Ile Asp Gly Lys Thr Ile Arg Ser
                85                  90                  95

Val Glu Glu Thr Thr His Asn Asp Glu Thr Lys Thr Leu Arg His Arg
            100                 105                 110

Val Phe Glu Gly Asp Val Met Lys Asp Phe Lys Lys Phe Asp Thr Ile
        115                 120                 125

Met Val Val Asn Pro Lys Pro Asp Gly Asn Gly Cys Val Val Thr Arg
    130                 135                 140

Ser Ile Glu Tyr Glu Lys Thr Asn Asp Asn Ser Pro Thr Pro Phe Asp
145                 150                 155                 160

Tyr Leu Gln Phe Gly His Gln Ala Ile Glu Asp Met Asn Lys Tyr Leu
                165                 170                 175

Arg Asp Ser Glu
            180

<210> SEQ ID NO 36
<211> LENGTH: 164
<212> TYPE: PRT
<213> ORGANISM: Papaver somniferum

<400> SEQUENCE: 36

Met Asn Phe Phe Ile Lys Asp His Leu Tyr Ile Cys Leu Val Gly Lys
1               5                   10                  15

Leu Ser Thr Glu Leu Glu Val Asp Cys Asp Ala Glu Lys Tyr Tyr Asn
            20                  25                  30

Met Tyr Lys His Gly Glu Asp Val Lys Lys Ala Val Pro His Leu Cys
        35                  40                  45

Val Asp Val Lys Ile Ile Ser Gly Asp Pro Thr Ser Ser Gly Cys Ile
    50                  55                  60

Lys Glu Trp Asn Val Asn Ile Asp Gly Lys Thr Ile Arg Ser Val Glu
65                  70                  75                  80

Glu Thr Thr His Asp Asp Glu Thr Lys Thr Leu Arg His Arg Val Phe
                85                  90                  95

Glu Gly Asp Val Met Lys Asp Phe Lys Lys Phe Asp Thr Ile Met Val
            100                 105                 110

Val Asn Pro Lys Pro Asp Gly Asn Gly Cys Val Val Thr Arg Ser Ile
        115                 120                 125
```

Glu Tyr Glu Lys Thr Asn Glu Asn Ser Pro Thr Pro Phe Asp Tyr Leu
            130                 135                 140

Gln Phe Gly His Gln Ala Ile Glu Asp Met Asn Lys Tyr Leu Arg Asp
145                 150                 155                 160

Ser Glu Ser Asn

<210> SEQ ID NO 37
<211> LENGTH: 160
<212> TYPE: PRT
<213> ORGANISM: Papaver somniferum

<400> SEQUENCE: 37

Met Ala Pro Leu Gly Val Ser Gly Leu Val Gly Lys Leu Ser Thr Glu
1               5                   10                  15

Leu Glu Val Asp Cys Asp Ala Glu Lys Tyr Tyr Asn Met Tyr Lys His
                20                  25                  30

Gly Glu Asp Val Lys Lys Ala Val Pro His Leu Cys Val Asp Val Lys
            35                  40                  45

Ile Ile Ser Gly Asp Pro Thr Ser Ser Gly Cys Ile Lys Glu Trp Asn
50                  55                  60

Val Asn Ile Asp Gly Lys Thr Ile Arg Ser Val Glu Glu Thr Thr His
65                  70                  75                  80

Asp Asp Glu Thr Lys Thr Leu Arg His Arg Val Phe Glu Gly Asp Val
                85                  90                  95

Met Lys Asp Phe Lys Lys Phe Asp Thr Ile Met Val Val Asn Pro Lys
            100                 105                 110

Pro Asp Gly Asn Gly Cys Val Val Thr Arg Ser Ile Glu Tyr Glu Lys
        115                 120                 125

Thr Asn Glu Asn Ser Pro Thr Pro Phe Asp Tyr Leu Gln Phe Gly His
130                 135                 140

Gln Ala Ile Glu Asp Met Asn Lys Tyr Leu Arg Asp Ser Glu Ser Asn
145                 150                 155                 160

<210> SEQ ID NO 38
<211> LENGTH: 400
<212> TYPE: PRT
<213> ORGANISM: Papaver somniferum

<400> SEQUENCE: 38

Met Met Lys Val Cys Val Ser Ser Arg Glu Lys Ile Lys Pro Ser Arg
1               5                   10                  15

Pro Thr Pro Gly His Leu Lys Thr His Lys Leu Ser Phe Leu Asp Gln
                20                  25                  30

Val Ala Ala Arg Ile Tyr Val Pro Leu Leu Leu Tyr Tyr Ala Gly Asn
            35                  40                  45

Lys Glu Asn Val Asp Thr Asp Thr Arg Cys Asn Ile Ile Lys Lys Ser
50                  55                  60

Leu Ala Glu Thr Leu Thr Lys Phe Tyr Ile Leu Ala Gly Lys Ile Val
65                  70                  75                  80

Asn Asp Glu Ile Glu Arg Phe Val Asn Cys Asn Asp Asp Gly Val Asp
                85                  90                  95

Phe Cys Val Thr Lys Val Ser Asn Cys Gln Leu Phe Gln Val Ile Lys
            100                 105                 110

Arg Pro Asp Ile Phe Asp Gln Val Thr Leu Phe Leu Pro Phe Asp Pro
        115                 120                 125

Cys Asp Asn Glu Ile Thr Ala Ser Gly Asp Phe Leu Leu Ser Val Gln
            130                 135                 140

Val Asn Val Phe Glu Asp Cys Arg Gly Met Val Ile Gly Leu Cys Ile
145                 150                 155                 160

Asn His Lys Val Ala Asp Ala Ser Ser Ile Thr Thr Phe Val Asn Tyr
                165                 170                 175

Trp Ala Thr Ile Ala Arg Gly Leu Val Leu Asn Val Asp Asp Arg Gln
            180                 185                 190

Ile Gln Asp Pro Cys Phe Gln Val Gln Ser Ile Phe Pro Gln Lys Glu
        195                 200                 205

Lys Gly Ile Gly Phe Lys Ile Ser Ser Ser Ile Asp Gly Thr Leu
210                 215                 220

Val Thr Lys Lys Phe Gly Phe Glu Ala Ser Lys Leu Ala Glu Leu Lys
225                 230                 235                 240

Glu Arg Cys Lys Phe Ala Gly Ala Thr Glu Asp Ile Arg Gly Tyr
                245                 250                 255

Lys Pro Asn Arg Val Glu Ala Leu Ser Thr Phe Leu Trp Lys Cys Phe
                260                 265                 270

Ile Asp Ile Asp Gln Ala Lys Thr Lys Ala Ala Ala Pro Ala Arg Val
        275                 280                 285

Tyr Leu Ala Ser Asn Ala Val Asn Ile Arg Ser Arg Ile Val Pro Gln
290                 295                 300

Leu Pro Thr Ser Ser Phe Gly Asn Met Val Ala Ile Thr Asp Ala Ile
305                 310                 315                 320

Phe Thr Val Asn Ser Asn Glu Asn Asn Gly Ile Asn Asp Pro Tyr Tyr
                325                 330                 335

Pro Lys Leu Val Gln Lys Phe Arg Asp Ala Val Lys Arg Val Asp Gly
                340                 345                 350

Glu Tyr Ile Glu Ala Leu Gln Ser Thr Asp Leu Leu Leu Asn Asn Val
            355                 360                 365

Thr Lys Leu Phe Lys His Ile Leu Asn Gly Gln Thr Leu Ser Ile Ser
        370                 375                 380

Phe Thr Ser Trp Cys Arg Phe Pro Phe Tyr Asp Thr Asp Leu Leu Asp
385                 390                 395                 400

<210> SEQ ID NO 39
<211> LENGTH: 386
<212> TYPE: PRT
<213> ORGANISM: Papaver somniferum

<400> SEQUENCE: 39

Met Lys Val Gln Val Ile Ser Lys Glu Leu Ile Lys Pro Ser Thr Pro
1               5                   10                  15

Thr Pro Pro Arg Leu Arg Asn Phe Lys Leu Ser Leu Leu Asp Gln Leu
            20                  25                  30

Leu Pro Pro Phe Tyr Val Pro Ile Ile Phe Tyr Pro Ala Asn Asp
        35                  40                  45

Asp His Glu Ser Asn Asn Asn Asp Gln Cys Ile Lys Ala Asn Ile Leu
    50                  55                  60

Lys Lys Ser Leu Ser Glu Thr Leu Thr Arg Phe Tyr Pro Ile Ala Gly
65                  70                  75                  80

Arg Ile Arg Asp Lys Ile Leu Val Glu Cys Asn Asp Glu Gly Val His
                85                  90                  95

Tyr Ile Glu Ala Lys Val Asn Ala Val Met Ser Asp Phe Met Ser Leu
            100                 105                 110

-continued

Asp Val Ile His Gln Leu His Pro Ser Tyr Ile Thr Leu Asp Asp Leu
            115                 120                 125

Ala Glu Glu Ala Gln Leu Ala Val Gln Val Thr Met Phe Asp Cys Gly
        130                 135                 140

Gly Ile Ala Leu Ser Ile Cys Ser Ser His Lys Ile Ile Asp Gly Cys
145                 150                 155                 160

Thr Ser Thr Thr Phe Leu Asn Ser Trp Ala Thr Ala Arg Ala Pro
                165                 170                 175

Ser Asn Pro Glu Ile Val Tyr Pro Thr Phe Asp Ala Ala Ile Phe
            180                 185                 190

Pro Ala Gln Pro Ser Gly Val Gln Val Ser Thr Leu Glu Ser Asp Asp
        195                 200                 205

Arg Leu Gln Gly Glu Asn Val Val Thr Lys Arg Phe Leu Phe Ser Ala
    210                 215                 220

Ser Lys Ile Thr Ala Leu Arg Ala Arg Ile Ala Glu Ser Arg Ser Ser
225                 230                 235                 240

Asn Ile Leu Ser Lys Tyr Pro Ser Arg Ser Glu Ala Val Ser Ala Leu
                245                 250                 255

Val Trp Lys Ser Phe Met Glu Thr Ser Arg Val Lys Val Thr Arg Glu
        260                 265                 270

His Thr Phe Ser Ala Glu Ala Ser Thr Lys Pro Ile Val Arg Ser Ile
    275                 280                 285

Ala Asn Phe Val Val Asn Leu Arg Thr Arg Leu Asn Pro Pro Leu Pro
290                 295                 300

Asn Val Ser Phe Gly Asn Ile Ile Met Asp Ala Thr Ala Glu Ser Leu
305                 310                 315                 320

Ile Ile Asp Asn Gly Glu Asn Thr Leu Gly Phe Val Glu Thr Leu Asp
                325                 330                 335

Gly Leu Ile Ser Gln Leu Arg Leu Gly Val Thr Lys Met Asp Asp Glu
        340                 345                 350

Tyr Val Arg Lys Leu Arg Glu Asp Val Glu Phe Leu Lys Ser Leu
    355                 360                 365

Asp Glu Ala Ser His Pro Ser Asn Gly Glu Gly Asp Gly Asn Gly Glu
    370                 375                 380

Arg Val
385

<210> SEQ ID NO 40
<211> LENGTH: 525
<212> TYPE: PRT
<213> ORGANISM: Papaver setigerum

<400> SEQUENCE: 40

Met Asn Asp Thr Met Lys Ile Glu Val Val Ser Lys Glu Ser Ile Lys
1               5                   10                  15

Pro Ser Tyr Pro Thr Pro Asn Asn Leu Lys Ile His Asn Leu Ser Asn
            20                  25                  30

Leu Asp Gln Leu Ile Pro Ala Phe Tyr Met Asp His Ile Leu Tyr Tyr
        35                  40                  45

Pro Ser Leu Asp Ser Asn Asp Ser Ser Leu Gly Asp Asp Glu Glu Asp
    50                  55                  60

Lys Lys Met Ile Phe Ser Ala Ser Ser Arg His Arg Cys Asp Val Val
65                  70                  75                  80

Lys Lys Ser Leu Ala Glu Thr Leu Thr Arg Tyr Tyr Pro Leu Ala Gly

-continued

```
                85                  90                  95
Arg Ile Lys Asp Glu Lys Ser Val Glu Cys Asn Asp Glu Gly Val Asp
            100                 105                 110

Tyr Ile Glu Ala Arg Val Val Gly Ile Thr Val Ser Gln Val Ile Gln
            115                 120                 125

Leu Ala Ser Ser Asp Ile Glu Val Met Glu Pro Phe Leu Pro Tyr Glu
            130                 135                 140

Pro Tyr Gly Gly Thr Gly Ser Ala Phe Arg Arg Ala Gly Ile His Ser
145                 150                 155                 160

Asn Ser Lys Pro Leu Leu Lys Ile Gln Val Asn Val Phe Asp Cys Gly
                165                 170                 175

Gly Met Val Ile Cys Leu Ser Gly Ser His Lys Val Ile Asp Ala Thr
                180                 185                 190

Ser Ile Leu Asn Phe Val Asn Asp Trp Ala Ala Thr Ala Arg Gly Gly
                195                 200                 205

Phe Asp Thr His Asp Asp Glu Leu Lys Val Ala Val Asp Lys Pro
            210                 215                 220

Cys Tyr Ile Phe Ser Ser Met Phe Pro Pro Thr Ser Phe Gly Asn Gln
225                 230                 235                 240

Glu Glu Lys Asp Thr Ala Asp Gln Ala Gln Leu Val Pro Asp Arg Ile
                245                 250                 255

Glu Ile Val Thr Lys Arg Phe Val Phe Lys Asp Ser Ser Ile Ala Lys
                260                 265                 270

Leu Lys Lys Lys Cys Ile His Val Asn Thr Asn Asn Gly Ser Asp His
                275                 280                 285

Gln Val Asp Lys Gln Glu His Asn Met Gln Gln Met Pro Ser Arg Ile
            290                 295                 300

Glu Ala Leu Thr Ser Leu Ile Trp Met Cys Phe Met Asp Val Asp Arg
305                 310                 315                 320

Arg Phe Arg Val Lys Gln Ile Asp Asp Ala Val Ser Pro Val Asn Thr
                325                 330                 335

Val Asn Glu Val Ser Leu Pro Lys Gln Val Gln Tyr Val Ala Gly Phe
                340                 345                 350

Ala Ile Asn Leu Arg Thr Arg Thr Ile Gln Pro Leu Pro Thr Asn Ser
            355                 360                 365

Phe Gly Asn Met Thr Asp Thr Ala Ile Ala Glu Val Thr Leu Asn Leu
            370                 375                 380

Thr Gly Ser Asp His Phe Asn Asn Glu Lys Gly Ile Arg Asp Gln Ser
385                 390                 395                 400

Gln Asn Tyr Pro Glu Leu Val Ser Lys Ile Lys Asp Ser Ile Lys Leu
                405                 410                 415

Val Asp Asn Lys His Ile Glu Ala Met Lys Arg Asn Leu Ala Ile Ser
            420                 425                 430

Cys Asn Asn Ile Lys Met His Gln Met Met Lys Glu Ser Thr Phe Asp
            435                 440                 445

Gln Asn Thr Arg Glu Leu Leu Met Phe Ser Ser Trp Cys Arg Phe Pro
450                 455                 460

Ile Tyr Glu Ala Asp Phe Gly Trp Gly Lys Pro Ser Trp Ala Ser Ile
465                 470                 475                 480

Thr Lys Leu Leu Tyr Lys Asn Cys Val Met Phe Leu Asp Thr Ser Ser
                485                 490                 495

Gly Asp Gly Ile Glu Ala Trp Val Ser Leu Lys Glu Glu Asp Met Val
            500                 505                 510
```

```
Glu Phe Glu Arg His Glu Leu Val Ala Leu Ala Ser
        515                 520                 525

<210> SEQ ID NO 41
<211> LENGTH: 459
<212> TYPE: PRT
<213> ORGANISM: Papaver somniferum

<400> SEQUENCE: 41

Met Lys Val Gln Val Ile Ser Lys Glu Ile Ile Lys Pro Ser Ser Pro
1               5                   10                  15

Thr Pro Pro His Leu Arg Asn Phe Lys Leu Ser Leu Leu Asp Gln Ile
            20                  25                  30

Leu Pro Pro Phe Tyr Val Pro Ile Val Met Phe Tyr Pro Ala Gly Asp
        35                  40                  45

Asp Tyr Val Thr Asn Asn Ile His Asp Gln Ser Ser Lys Ser Glu
    50                  55                  60

Phe Leu Lys Lys Ser Leu Ser Glu Thr Leu Thr Arg Phe Tyr Pro Ile
65                  70                  75                  80

Ala Gly Arg Ile Lys Asp Asn Ile Leu Ile Asp Cys Asn Asn Glu Gly
                85                  90                  95

Val Asp Tyr Ile Glu Ala Lys Val Asn Gly Ile Met Ser Asp Phe Met
            100                 105                 110

Ser Val Asp Val His Gln Leu His Pro Ser His Ile Met Leu Asp
            115                 120                 125

Asp Val Ala Lys Glu Ala Gln Leu Ala Val Gln Val Asn Leu Phe Asp
130                 135                 140

Cys Gly Gly Ile Ala Ile Ser Ile Ser Met Ser His Lys Ile Val Asp
145                 150                 155                 160

Ala Cys Thr Ala Ile Thr Phe Ile Asn Gly Trp Ala Ala Thr Ala Arg
                165                 170                 175

Ala Ala Pro Lys Gln Glu Ile Val Cys Pro Thr Phe Asp Ser Ala Ala
            180                 185                 190

Ile Phe Pro Ala Leu Pro Pro Gly Val Gln Val Ser Ser Leu Glu Ser
        195                 200                 205

Asp Asp Ser Val Gln Gly Val Asn Val Val Thr Lys Met Phe Ala Phe
    210                 215                 220

Thr Ala Pro Lys Ile Ala Ser Leu Arg Ala Arg Ile Ala Glu Leu Arg
225                 230                 235                 240

Ser Ser Ser Asp Gly Leu Ser Lys Tyr Pro Thr Arg Thr Glu Ala Leu
                245                 250                 255

Ser Ala Leu Val Trp Lys Ser Phe Ile Arg Thr Ser Arg Val Lys Ala
            260                 265                 270

Ala Arg Lys Tyr Ser Leu Ser Pro Ala Ser Thr Lys Pro Val Ile Lys
        275                 280                 285

Ser Val Ala Asn Tyr Ala Val Asn Leu Arg Thr Arg Leu Asn Pro Pro
    290                 295                 300

Leu Pro Gln Val Ser Phe Gly Asn Ile Leu Met Asp Ala Thr Ala Glu
305                 310                 315                 320

Ser Thr Thr Thr Ile Asp Asp Asp Ser His Glu Phe Ala Asp Thr
                325                 330                 335

Leu Ala Gly Leu Ile Gly Gln Leu Arg Leu Gly Val Ser Arg Ile Asn
            340                 345                 350

Gly Asp Tyr Ile Arg Lys Leu Gln Glu Gly Asp Leu Ala Phe Leu Lys
```

-continued

```
                  355                 360                 365
Ser Leu Asp Glu Ala Ser His Asp Ser Asn Gly Glu Lys Val Gln Ile
    370                 375                 380

Cys Trp Ile Ser Ser Leu Cys Arg Phe Pro Phe Tyr Glu Ala Asp Phe
385                 390                 395                 400

Gly Trp Gly Lys Pro Ser Trp Val Ala Leu Asn Thr Asn Ala Glu Tyr
                405                 410                 415

Lys Asn Ser Leu Phe Leu Met Asp Thr Lys Cys Gly Thr Gly Ile Glu
            420                 425                 430

Ala Trp Val Ser Leu Glu Glu Asp Asp Met Ala Ile Phe Glu Glu Asp
        435                 440                 445

Gln Asp Leu Leu Gln Cys Val Lys Ser Ile Asn
    450                 455

<210> SEQ ID NO 42
<211> LENGTH: 477
<212> TYPE: PRT
<213> ORGANISM: Papaver setigerum

<400> SEQUENCE: 42

Met Glu Asn Met Lys Val Glu Val Leu Lys Gln Thr Ile Lys Pro
1               5                   10                  15

Ser Thr Gln Thr Pro Leu His Ser Lys Thr Phe Asn Leu Ser Phe Leu
            20                  25                  30

Asp Gln His Leu Gly Pro Pro Ile Tyr Ile Pro Phe Thr Leu Tyr Tyr
        35                  40                  45

Glu Ser Gly Asp Val Asn Lys Asn Asn His Cys Asp Gly Tyr Lys
    50                  55                  60

Asn Asn Leu Glu Glu Ala Cys Glu His Arg Val Ser Val Ile Lys Gln
65                  70                  75                  80

Ser Leu Ser Glu Thr Leu Ala Arg Tyr Tyr Pro Leu Ala Gly Arg Met
                85                  90                  95

Lys Glu Asp Asn Leu Ala Val Glu Cys Asn Asp Glu Gly Val Glu Tyr
            100                 105                 110

Phe Glu Thr Arg Val Ser Asp Val Arg Leu Ser Gln Val Ile Lys Arg
        115                 120                 125

Ser Pro Asn His Asn Ser Val Leu Arg Lys Phe Leu Pro Pro Cys Ile
    130                 135                 140

Ser Ser Cys Asp Asn Ser Met Ser Ile Pro Phe Asp Tyr Gly Phe Lys
145                 150                 155                 160

Ser Lys Thr Leu Leu Ala Ile Gln Val Asn Ile Phe Glu Cys Gly Gly
                165                 170                 175

Ile Val Ile Gly Met Cys Met Ala His Arg Leu Ala Asp Ala Ser Thr
            180                 185                 190

Met Phe Thr Phe Ile Thr Asp Trp Ala Ala Thr Ala Arg Gly Ala Ile
        195                 200                 205

Glu Asp Ile Lys Gly Pro Ser Phe Asp Phe Ser Tyr Thr Leu Phe Pro
    210                 215                 220

Gln Lys Asp Val Ile Asn Asn Phe Lys Pro Phe Asp Pro Met Leu Thr
225                 230                 235                 240

Arg Glu Glu Asp Leu Val Thr Lys Tyr Phe Val Phe Pro Ala Ser Lys
                245                 250                 255

Ile Val Glu Leu Lys Arg Arg Asn Val Asn Asn Ile Val Cys Gln Asp
            260                 265                 270
```

Thr Ser Gln Gln Asn Thr Ser Pro Cys Thr Arg Val Glu Ala Val Thr
            275                 280                 285

Ser Phe Met Trp Lys Arg Tyr Met Asp Ser Val Arg Ala Lys Asn Gln
    290                 295                 300

Thr Gln Ala Thr Ser Val Glu Lys Tyr Gly Ala Leu Tyr Thr Val Asn
305                 310                 315                 320

Leu Arg Ser Arg Ile Thr Pro Pro Leu Pro Ala Asn Ser Phe Gly Asn
                325                 330                 335

Ile Tyr Thr Phe Thr Ile Ala Leu Ser Thr Pro Ser Asp Glu Asn Asp
            340                 345                 350

Ile Asp Asp Gly Leu Arg Lys Asp Val Ser Ser Pro Asn Asp Leu Asn
        355                 360                 365

Leu Val Gly Lys Val Arg Asp Ala Ile Lys Lys Ile Asp Asp Lys Tyr
    370                 375                 380

Thr Arg Lys Leu Gln Ser Ser Glu Asp Glu Leu Val Asn Asp Val Lys
385                 390                 395                 400

Pro Leu Thr Ser Gly Glu Ala Ile Phe Leu Gly Phe Ser Ser Trp Cys
                405                 410                 415

Arg Phe Pro Ile Tyr Glu Ala Asp Phe Gly Trp Gly Lys Pro Thr Trp
            420                 425                 430

Val Ser Ile Gly Thr Met Ala Leu Arg Asn Thr Val Phe Leu Met Asp
        435                 440                 445

Thr Lys Ser Gly Asp Gly Ile Glu Ala Phe Val Asn Met Ala Lys Glu
    450                 455                 460

Asp Met Asp Asn Phe Glu Val Lys Leu Leu Ala Asp Gln
465                 470                 475

<210> SEQ ID NO 43
<211> LENGTH: 485
<212> TYPE: PRT
<213> ORGANISM: Papaver setigerum

<400> SEQUENCE: 43

Met Glu Asn Met Lys Val Glu Val Leu Glu Gln Thr Ile Lys Pro
1               5                   10                  15

Ser Thr Gln Thr Pro Leu His Ser Lys Thr Phe Asn Leu Ser Phe Leu
            20                  25                  30

Asp Gln His Leu Gly Pro Pro Ile Tyr Ile Pro Phe Thr Leu Tyr Tyr
        35                  40                  45

Glu Ser Gly Asp Val Asn Asn Lys Asn Asn His Cys Asp Gly Tyr Lys
    50                  55                  60

Asn Asn Leu Glu Glu Val Cys Glu His Arg Val Ser Val Ile Lys Gln
65                  70                  75                  80

Ser Leu Ser Glu Thr Leu Ala Arg Tyr Tyr Pro Leu Ala Gly Arg Met
                85                  90                  95

Lys Glu Asp Asn Leu Ala Val Glu Cys Asn Asp Glu Gly Val Glu Tyr
            100                 105                 110

Phe Glu Thr Arg Val Ser Asp Val Arg Leu Ser Gln Val Ile Lys Arg
        115                 120                 125

Ser Pro Asn His Asn Ser Val Leu Arg Lys Phe Leu Pro Pro Cys Ile
    130                 135                 140

Ser Ser Cys Asp Asn Ser Met Ser Ile Pro Phe Asp Tyr Gly Phe Lys
145                 150                 155                 160

Ser Lys Thr Leu Leu Ala Ile Gln Val Asn Ile Phe Glu Cys Gly Gly
                165                 170                 175

```
Ile Val Ile Gly Met Cys Met Ala His Arg Leu Ala Asp Ala Ser Thr
            180                 185                 190

Met Phe Thr Phe Ile Thr Asp Trp Ala Ala Thr Ala Arg Gly Ala Ile
            195                 200                 205

Glu Asp Ile Lys Gly Pro Ser Phe Asp Phe Ser Tyr Thr Leu Phe Pro
210                 215                 220

Gln Lys Asp Val Ile Asn Asn Phe Lys Pro Phe Asp Pro Met Leu Thr
225                 230                 235                 240

Arg Glu Glu Asp Leu Val Thr Lys Tyr Phe Val Phe Pro Ala Ser Lys
            245                 250                 255

Ile Val Glu Leu Lys Arg Arg Asn Val Asn Asn Ile Val Cys Gln Asp
            260                 265                 270

Thr Ser Gln Gln Asn Thr Ser Pro Cys Thr Arg Val Glu Ala Val Thr
            275                 280                 285

Ser Phe Met Trp Lys Arg Tyr Met Asp Ser Val Arg Ala Lys Asn Gln
            290                 295                 300

Thr Gln Ala Thr Ser Val Glu Lys Tyr Gly Ala Leu Tyr Thr Val Asn
305                 310                 315                 320

Leu Arg Ser Arg Ile Thr Pro Pro Leu Pro Ala Asn Ser Phe Gly Asn
            325                 330                 335

Ile Tyr Thr Phe Thr Ile Ala Leu Ser Thr Pro Ser Asp Glu Asn Asp
            340                 345                 350

Ile Asp Asp Gly Leu Arg Lys Asp Val Ser Ser Pro Asn Asp Leu Asn
            355                 360                 365

Leu Val Gly Lys Val Arg Asp Ala Ile Lys Lys Ile Asp Asp Lys Tyr
            370                 375                 380

Thr Arg Lys Leu Gln Ser Ser Glu Asp Glu Leu Val Asn Asp Val Lys
385                 390                 395                 400

Pro Leu Thr Ser Gly Glu Ala Ile Phe Leu Gly Phe Ser Ser Trp Cys
            405                 410                 415

Arg Phe Pro Ile Tyr Glu Ala Asp Phe Gly Trp Gly Lys Pro Thr Trp
            420                 425                 430

Val Ser Ile Gly Thr Met Ala Leu Arg Asn Thr Val Phe Leu Met Asp
            435                 440                 445

Thr Lys Ser Gly Asp Gly Ile Glu Ala Phe Val Asn Met Ala Lys Glu
            450                 455                 460

Asp Met Asp Asn Phe Glu Val Lys Leu Leu Ala Asp Gln Leu Leu His
465                 470                 475                 480

Val His Pro Thr Val
            485

<210> SEQ ID NO 44
<211> LENGTH: 452
<212> TYPE: PRT
<213> ORGANISM: Papaver setigerum

<400> SEQUENCE: 44

Met Ser Ser Thr Val Glu Val Ile Ser Lys Gln Thr Ile Lys Pro Ser
1               5                   10                  15

Thr Pro Thr Pro Ile Gln Arg Lys Asn His Ser Leu Ser Leu Ile Asp
            20                  25                  30

Gln His Phe Ala Pro Ile Tyr Ile Pro Ile Val Leu Phe Tyr Pro Ala
            35                  40                  45

Ala Ala Val Asn Asp Thr Gly Asn Val Gln His Gly Asp Asn Thr Cys
```

```
            50                  55                  60
Val Leu Lys Arg Ser Leu Ser Glu Thr Leu Val His Phe Tyr Pro Leu
 65                  70                  75                  80

Ala Gly Arg Met Lys Asp Asn Ile Val Val Asp Cys Asn Asp Gln Gly
                 85                  90                  95

Val Glu Phe Thr Glu Val Lys Val Ser Gly Thr Met Cys Asp Phe Leu
                100                 105                 110

Met Lys Pro Asp Glu Gln Leu Ser Gly Leu Leu Pro Ser Glu Ala Val
            115                 120                 125

Cys Met Asn Phe Val Arg Glu Ala Gln Val Met Ile Gln Val Asn Thr
        130                 135                 140

Phe Asp Cys Gly Ser Lys Ala Ile Ser Leu Cys Val Ser His Lys Ile
145                 150                 155                 160

Ala Asp Ala Ser Thr Ile Thr Thr Phe Ser Arg Cys Trp Ala Glu Thr
                165                 170                 175

Thr Ile Ala Val Ser Lys Ser Thr Ser Ala Val Thr Pro Ile Val Ser
                180                 185                 190

Ser Lys Phe His Pro Thr Phe Asp Ala Ala Ser Leu Phe Pro Pro Ile
            195                 200                 205

Lys Gln Leu Ile Ser Pro Ser Gly Val Thr Pro Ala Leu Pro Glu Leu
        210                 215                 220

Ile Pro Ser Glu Glu Ser Lys Phe Gly Lys Ile Ile Ser Lys Arg Phe
225                 230                 235                 240

Leu Phe Ser Ala Thr Thr Ile Asn Ser Val Arg Glu Lys Leu Ser Ala
                245                 250                 255

Leu Met Ala Asp Lys Leu Lys Tyr Arg Arg Leu Thr Arg Val Glu Val
                260                 265                 270

Val Ser Ala Leu Ile Trp Asn Ser Phe Asp Lys Leu Ala Thr Thr Gly
            275                 280                 285

Ser Val Ala Val Met Val Lys His Ala Val Asn Leu Arg Lys Arg Ile
        290                 295                 300

Asp Pro Pro Leu Pro Asp Val Ser Phe Gly Asn Ile Leu Glu Phe Thr
305                 310                 315                 320

Lys Ala Val Val Gly Glu Ala Ala Asn Thr Thr Gln Gly Thr
                325                 330                 335

Val Gly Ser Ser Ser Lys Leu Leu Glu Glu Leu Ser Glu Phe Ala Gly
            340                 345                 350

Gln Leu Arg Glu Pro Val Ser Lys Met Asn Lys Gly Asp His Asp Phe
        355                 360                 365

Asp Met Glu Asn Thr Asp Tyr Glu Glu Arg Asp Leu Trp Met Ser Ser
    370                 375                 380

Trp Cys Asn Tyr Gly Leu Tyr Asp Ile Asp Phe Gly Cys Gly Lys Pro
385                 390                 395                 400

Val Trp Val Thr Thr Val Ala Thr Met Tyr Pro Tyr Ser Asp Gly Phe
                405                 410                 415

Phe Met Asn Asp Thr Arg Cys Gly Gln Gly Ile Glu Val Trp Gly Asn
            420                 425                 430

Leu Val Glu Glu Asp Met Ala Asn Phe Gln Leu Asn Leu Ser Glu Leu
        435                 440                 445

Leu Asp Arg Ile
    450

<210> SEQ ID NO 45
```

```
<211> LENGTH: 451
<212> TYPE: PRT
<213> ORGANISM: Papaver somniferum

<400> SEQUENCE: 45

Met Met Lys Val Cys Val Ser Ser Arg Glu Lys Ile Lys Pro Ser Arg
1               5                   10                  15

Pro Thr Pro Gly His Leu Lys Thr His Lys Leu Ser Phe Leu Asp Gln
            20                  25                  30

Val Ala Ala Arg Ile Tyr Val Pro Leu Leu Leu Tyr Tyr Ala Gly Asn
        35                  40                  45

Lys Glu Asn Val Asp Thr Asp Thr Arg Cys Asn Ile Ile Lys Lys Ser
    50                  55                  60

Leu Ala Glu Thr Leu Thr Lys Phe Tyr Ile Leu Ala Gly Lys Ile Val
65                  70                  75                  80

Asn Asp Glu Ile Glu Arg Phe Val Asn Cys Asn Asp Asp Gly Val Asp
                85                  90                  95

Phe Cys Val Thr Lys Val Ser Asn Cys Gln Leu Phe Gln Val Ile Lys
            100                 105                 110

Arg Pro Asp Ile Phe Asp Gln Val Thr Leu Phe Leu Pro Phe Asp Pro
        115                 120                 125

Cys Asp Asn Glu Ile Thr Ala Ser Gly Asp Phe Leu Leu Ser Val Gln
    130                 135                 140

Val Asn Val Phe Glu Asp Cys Arg Gly Met Val Ile Gly Leu Cys Ile
145                 150                 155                 160

Asn His Lys Val Ala Asp Ala Ser Ser Ile Thr Thr Phe Val Asn Tyr
                165                 170                 175

Trp Ala Thr Ile Ala Arg Gly Leu Val Leu Asn Val Asp Asp Arg Gln
            180                 185                 190

Ile Gln Asp Pro Cys Phe Gln Val Gln Ser Ile Phe Pro Gln Lys Glu
        195                 200                 205

Lys Gly Ile Gly Phe Lys Ile Ser Ser Ser Ile Asp Gly Thr Leu
    210                 215                 220

Val Thr Lys Lys Phe Gly Phe Glu Ala Ser Lys Leu Ala Glu Leu Lys
225                 230                 235                 240

Glu Arg Cys Lys Phe Thr Thr Glu Pro Glu Asp Gly Tyr Lys Pro Thr
                245                 250                 255

Arg Val Glu Ala Leu Ser Ala Phe Leu Trp Lys Cys Phe Ile Asp Ile
            260                 265                 270

Asp Gln Ala Lys Leu Lys Gly Val Ala Arg Thr Lys Val Tyr Leu Ala
        275                 280                 285

Thr Asn Ala Val Asn Met Arg Ser Arg Met Val Pro Gln Leu Pro Thr
    290                 295                 300

Ser Ser Phe Gly Asn Ile Ile Ser Ile Thr Asp Ala Val Phe Ser Ile
305                 310                 315                 320

Asn Asn Asp Asp Ser Thr Gly Ile Asn Asp Pro Tyr Tyr Pro Lys Leu
                325                 330                 335

Val Arg Lys Phe Arg Asp Ala Ile Lys Lys Ile Asp Arg Asp Tyr Ile
            340                 345                 350

Glu Ala Leu Arg Ser Thr Asp Leu Leu Asn Asn Met Met Lys Leu
        355                 360                 365

Ile Glu His Val Leu Ser Gly His Thr Leu Ser Ile Tyr Phe Ser Ser
    370                 375                 380

Trp Cys Arg Phe Pro Leu Tyr Glu Thr Asp Phe Gly Trp Gly Lys Pro
```

```
                385                 390                 395                 400
Ile Trp Val Ser Thr Cys Thr Ile Pro Gln Lys Asn Val Ile Val Leu
                    405                 410                 415

Met Asp Ser Asn Ser Ala Asp Gly Ile Glu Ala Tyr Val Thr Leu
                420                 425                 430

Ala Lys Glu Asp Met Gly Glu Leu Glu His His Glu Glu Leu Leu Ala
            435                 440                 445

Leu Ile Ser
    450

<210> SEQ ID NO 46
<211> LENGTH: 232
<212> TYPE: PRT
<213> ORGANISM: Papaver somniferum

<400> SEQUENCE: 46

Met Gly Ala Met Lys Phe Phe Ser Phe Leu Ala Val Ala Met Val Leu
1               5                   10                  15

Ser Leu Ala His Ile Gln Ala Gln Gln Gly Asn Trp Gly Asp Glu Thr
            20                  25                  30

Val Pro Tyr Thr Met Gly Pro Glu Lys Ile Thr Lys Leu Arg Phe Tyr
        35                  40                  45

Phe His Asp Ile Val Thr Gly Asn Asn Pro Thr Ala Val Gln Ile Ala
    50                  55                  60

Gln Ala Thr Gly Thr Asn Ser Ser Thr Leu Phe Gly Ala Leu Phe
65                  70                  75                  80

Met Ile Asp Asp Pro Leu Thr Glu Gly Pro Asp Pro Asp Ser Arg Leu
                85                  90                  95

Val Gly Arg Ala Gln Gly Phe Tyr Gly Ser Ala Gly Gln Asn Glu Ala
            100                 105                 110

Ala Leu Ile Leu Gly Met Ser Leu Val Phe Thr Gly Asn Glu Lys Phe
        115                 120                 125

Asn Gly Ser Thr Ile Ser Val Leu Ser Arg Asn Pro Val Thr His Thr
    130                 135                 140

Glu Arg Glu Phe Ala Ile Val Gly Gly Thr Gly Tyr Phe Gln Phe Ala
145                 150                 155                 160

Arg Gly Phe Ile Ser Ala Lys Thr Tyr Ser Leu Val Gly Pro Asn Ala
                165                 170                 175

Val Val Glu Tyr Asn Cys Thr Ile Val His Pro Ser Val Ser Glu
            180                 185                 190

Ser Gly Lys Ser Asn Ser Ser Pro Gly Lys Ser Asp Ser Asn Ser Gly
        195                 200                 205

Ser Gln Ile Ser Leu Gly Ser Asn Leu Val Phe Val Ser Val Ile Ala
    210                 215                 220

Tyr Val Thr Ile Ile Leu Ser Leu
225                 230

<210> SEQ ID NO 47
<211> LENGTH: 224
<212> TYPE: PRT
<213> ORGANISM: Papaver setigerum

<400> SEQUENCE: 47

Met Val Leu Ser Met Ser His Ser Gln Ala Gln Glu Gly Asn Trp Gly
1               5                   10                  15

Asp Glu Ser Val Pro Tyr Thr Met Gly Pro Glu Lys Met Thr Lys Leu
```

```
                    20                  25                  30
Arg Phe Tyr Phe His Asp Ile Ile Thr Gly Asn Ser Pro Thr Ala Val
                35                  40                  45
Gln Ile Ala Gln Ala Thr Gly Thr Asn Thr Ser Ala Thr Met Phe Gly
 50                  55                  60
Ala Leu Met Met Ile Asp Asp Pro Leu Thr Glu Gly Pro Asp Pro Asn
 65                  70                  75                  80
Ser Arg Leu Val Gly Arg Ala Gln Gly Phe Tyr Gly Ser Ala Gly Gln
                 85                  90                  95
Asn Glu Leu Ala Leu Ile Leu Gly Met Ser Leu Val Phe Thr Gly Asn
                100                 105                 110
Glu Lys Phe Asn Gly Ser Thr Ile Ser Val Leu Ser Arg Asn Pro Val
                115                 120                 125
Met His Thr Glu Arg Glu Phe Ala Ile Val Gly Gly Thr Gly Tyr Phe
                130                 135                 140
Gln Phe Ala Arg Gly Phe Ile Ser Ala Lys Thr Tyr Ser Leu Val Gly
145                 150                 155                 160
Pro Asn Ala Val Val Glu Tyr Asn Cys Thr Ile Val His Pro Ser Ser
                165                 170                 175
Val Ser Glu Ser Gly Lys Ser Asp Ser Ser Gly Lys Ser Asp Ser
                180                 185                 190
Ser Ser Gly Ser Gln Ile Ser Leu Gly Thr Asn Leu Val Phe Leu Ser
                195                 200                 205
Val Ile Ala Phe Val Thr Ile Ile Val Ser Pro Gln His Phe Ser Trp
210                 215                 220

<210> SEQ ID NO 48
<211> LENGTH: 210
<212> TYPE: PRT
<213> ORGANISM: Papaver somniferum

<400> SEQUENCE: 48

Met Thr Lys Thr Val Leu Val Asp Asp Ile Pro Phe Pro Gln Asn Ile
 1                5                  10                  15
Thr Thr Val Thr Thr Glu Lys Gln Leu Pro Leu Leu Gly Gln Gly Ile
                 20                  25                  30
Thr Asp Met Glu Ile His Phe Leu Gln Ile Lys Phe Thr Ala Ile Gly
                 35                  40                  45
Thr Ala Ile Gly Val Tyr Leu Glu Pro Glu Ile Ala Ser His Leu Gln
 50                  55                  60
Gln Trp Lys Gly Lys Thr Gly Ala Glu Leu Ser Gln Asp Asp Glu Phe
 65                  70                  75                  80
Phe Ala Ala Val Val Ser Ala Ser Val Glu Lys Tyr Val Arg Val Val
                 85                  90                  95
Val Ile Lys Glu Ile Lys Gly Ser Gln Tyr Met Leu Gln Leu Glu Ser
                100                 105                 110
Trp Val Arg Asp Glu Leu Ala Ala Ala Asp Lys Tyr Glu Asp Glu Glu
                115                 120                 125
Glu Glu Ser Leu Asp Lys Val Ile Glu Phe Gln Ser Lys Tyr Leu
                130                 135                 140
Lys Gln Leu Ser Phe Ile Pro Ser His Phe Ser Ala Thr Thr Pro Ala
145                 150                 155                 160
Val Ala Glu Ile Gly Leu Glu Ile Glu Gly Gln Lys Asp Leu Lys Ile
                165                 170                 175
```

Lys Val Glu Asn Gly Asn Val Ile Glu Met Ile Gln Lys Trp Tyr Leu
            180                 185                 190

Gly Gly Thr Arg Gly Val Ser Pro Ser Thr Thr Gln Ser Leu Ala Thr
        195                 200                 205

Ser Leu
    210

<210> SEQ ID NO 49
<211> LENGTH: 210
<212> TYPE: PRT
<213> ORGANISM: Papaver somniferum

<400> SEQUENCE: 49

Met Pro Phe Leu Lys Ala Ile Glu Ile Glu Gly Cys Lys Phe Arg Pro
1               5                   10                  15

Phe Val Thr Pro Pro Gly Ser Thr Gln Ile Leu Phe Leu Ala Gly Ser
            20                  25                  30

Gly Val Lys Glu Glu Phe Gly Asp Ser Lys Ser Met Lys Tyr Ser Ser
        35                  40                  45

Cys Ala Ile Tyr Leu Gln Pro Thr Cys Ile Leu Tyr Leu Ala Lys Ala
    50                  55                  60

Trp Ala Gln Lys Ser Val Val Asp Ile Thr Gln Ser Leu Asn Phe Phe
65                  70                  75                  80

Met Asp Ile Ala Thr Gly Pro Phe Glu Lys Tyr Cys Arg Ile Thr Met
                85                  90                  95

Leu Glu Thr Ala Lys Gly Glu Asp Tyr Ala Ala Met Ile Thr Lys Asn
            100                 105                 110

Cys Glu Glu Met Leu Thr Asn Ser Lys Arg Tyr Ser Glu Thr Ala Lys
        115                 120                 125

Ala Ala Leu Thr Lys Phe Ser Glu Ala Phe Asn Gly Arg Thr Leu Ala
    130                 135                 140

Ser Gly Ser Ser Ile His Val Thr Val Ser Thr Ser Asn Ser Val Thr
145                 150                 155                 160

Leu Ala Phe Thr Glu Asp Gly Ser Thr Pro Lys Gln Gly Asp Val Thr
                165                 170                 175

Leu Asp Cys Lys Glu Val Gly Glu Ala Phe Leu Met Ser Thr Ile Ser
            180                 185                 190

Leu His Thr Thr Ile Arg Glu Ser Met Gly Ser Arg Ile Ser Gly Leu
        195                 200                 205

Tyr Lys
    210

<210> SEQ ID NO 50
<211> LENGTH: 166
<212> TYPE: PRT
<213> ORGANISM: Papaver setigerum

<400> SEQUENCE: 50

Met Ala Pro Met Ala Gln Leu Ser Glu Ile Gln Val Glu Gln Phe Val
1               5                   10                  15

Phe Pro Pro Thr Met Thr Pro Pro Ser Ser Thr Glu Ser Leu Phe Leu
            20                  25                  30

Gly Gly Ala Gly Val Arg Gly Leu Gln Ile Gln Asp Arg Phe Ile Lys
        35                  40                  45

Phe Thr Ala Ile Gly Val Tyr Leu Ala Glu Glu Ala Ile Pro Ser Leu
    50                  55                  60

-continued

```
Ser Pro Lys Trp Lys Ser Lys Ser Pro Glu Glu Leu Thr Asp Asp Val
 65                  70                  75                  80

Glu Phe Phe Met Asp Ile Val Thr Gly Pro Phe Glu Lys Phe Val Lys
                 85                  90                  95

Ile Thr Met Ile Leu Pro Leu Thr Gly Asp Gln Tyr Ala Glu Lys Val
            100                 105                 110

Thr Glu Asn Cys Ile Gln Tyr Leu Lys Ser Lys Asp Met Tyr Thr Asp
            115                 120                 125

Ala Glu Ala Lys Ala Val Glu Arg Phe Ile Glu Ile Phe Lys Asn Glu
        130                 135                 140

Met Phe Pro Pro Ala Ser Ser Ile Leu Phe Thr Ile Ser Pro Ala Gly
145                 150                 155                 160

Ser Leu Thr Val Gly Phe
                165

<210> SEQ ID NO 51
<211> LENGTH: 160
<212> TYPE: PRT
<213> ORGANISM: Papaver rhoeas

<400> SEQUENCE: 51

Met Val Tyr Leu Glu Pro Glu Ile Ala Thr His Leu Lys Gln Trp Lys
  1               5                  10                  15

Gly Lys Thr Gly Ala Glu Leu Ser Gln Asp Asp Phe Phe Ser Ala
                 20                  25                  30

Val Val Ser Ala Pro Val Glu Lys Tyr Val Arg Val Val Ile Lys
             35                  40                  45

Glu Ile Lys Gly Ser Gln Tyr Met Leu Gln Leu Glu Ser Trp Val Arg
         50                  55                  60

Asp Glu Leu Ala Ala Ala Asp Lys Tyr Glu Asp Glu Glu Glu Ser
 65                  70                  75                  80

Leu Asp Lys Val Ile Glu Phe Phe Gln Ser Lys Tyr Leu Lys Gln His
                 85                  90                  95

Ser Val Ile Ile Thr Phe His Phe Ser Ala Thr Thr Pro Ala Val Ala
            100                 105                 110

Glu Ile Gly Leu Glu Ile Glu Gly Gln Lys Asp Leu Lys Ile Lys Val
            115                 120                 125

Glu Asn Gly Asn Val Val Glu Met Ile Gln Lys Trp Tyr Leu Gly Gly
        130                 135                 140

Thr Arg Gly Val Ser Pro Ser Thr Thr Gln Ser Leu Ala Thr Ser Leu
145                 150                 155                 160

<210> SEQ ID NO 52
<211> LENGTH: 206
<212> TYPE: PRT
<213> ORGANISM: Papaver bracteatum

<400> SEQUENCE: 52

Met Thr Lys Met Val Leu Val Asp Asp Ile Pro Phe Pro Gln Asn Ile
  1               5                  10                  15

Thr Thr Ala Thr Thr Ala Lys Gln Leu Pro Leu Leu Gly Gln Gly Ile
                 20                  25                  30

Thr Asp Met Glu Ile His Phe Leu Gln Ile Lys Phe Thr Ala Ile Gly
             35                  40                  45

Val Tyr Leu Glu Pro Glu Ile Ala Ser His Leu Lys Gln Trp Lys Gly
         50                  55                  60
```

```
Lys Thr Gly Ala Glu Leu Ser Gln Asp Asp Glu Phe Phe Ser Ala Ile
 65                  70                  75                  80

Val Ser Ala Pro Val Glu Lys Tyr Val Arg Val Val Ile Lys Glu
                 85                  90                  95

Ile Lys Gly Ser Gln Tyr Met Leu Gln Leu Glu Ser Trp Val Arg Asp
                100                 105                 110

Glu Leu Ala Ala Asp Lys Tyr Glu Asp Glu Glu Glu Ser Leu
            115                 120                 125

Glu Lys Val Ile Glu Phe Phe Gln Ser Lys Tyr Leu Lys Gln His Ser
        130                 135                 140

Val Ile Pro Phe His Phe Ser Ala Thr Thr Pro Ala Val Ala Glu Ile
145                 150                 155                 160

Gly Leu Glu Ile Glu Gly His Lys Asp Leu Lys Met Lys Val Glu Asn
                165                 170                 175

Gly Asn Val Val Glu Met Ile Gln Lys Trp Tyr Leu Ala Gly Thr Arg
                180                 185                 190

Gly Val Ser Pro Ser Thr Thr Gln Ser Leu Ala Thr Ser Leu
                195                 200                 205

<210> SEQ ID NO 53
<211> LENGTH: 216
<212> TYPE: PRT
<213> ORGANISM: Papaver bracteatum

<400> SEQUENCE: 53

Met Ala Pro Met Ala Gln Leu Ser Glu Ile Gln Val Glu Gln Phe Val
  1               5                  10                  15

Phe Pro Pro Thr Met Thr Pro Ser Ser Thr Glu Ser Leu Phe Leu
                 20                  25                  30

Gly Gly Ala Gly Val Arg Gly Leu Gln Ile Gln Asp Arg Phe Ile Lys
             35                  40                  45

Phe Thr Ala Ile Gly Val Tyr Leu Ala Glu Ala Ile Pro Ser Leu
         50                  55                  60

Ser Pro Lys Trp Lys Ser Lys Thr Pro Glu Glu Leu Thr Asn Asp Val
 65                  70                  75                  80

Glu Phe Phe Met Asp Ile Val Thr Gly Pro Phe Glu Lys Phe Val Lys
                 85                  90                  95

Ile Thr Met Ile Leu Pro Leu Thr Gly Asp Gln Tyr Ala Glu Lys Val
                100                 105                 110

Thr Glu Asn Cys Val Glu Tyr Leu Lys Ser Lys Asp Leu Tyr Thr Asp
            115                 120                 125

Ala Glu Ala Lys Ala Val Glu Arg Phe Ile Glu Ile Phe Lys Asn Glu
        130                 135                 140

Met Phe Pro Pro Ala Ser Ser Ile Leu Phe Thr Ile Ser Pro Thr Gly
145                 150                 155                 160

Ser Leu Thr Val Gly Phe Ser Lys Asp Thr Ser Ile Pro Glu Ala Arg
                165                 170                 175

Asn Ala Val Ile Glu Asn Lys Ala Leu Ser Glu Ser Ile Leu Glu Ser
                180                 185                 190

Ile Ile Gly Lys Asn Gly Val Ser Pro Ala Ala Lys Gln Ser Leu Ala
            195                 200                 205

Glu Arg Ile Ser Glu Leu Leu Lys
        210                 215

<210> SEQ ID NO 54
```

```
<211> LENGTH: 151
<212> TYPE: PRT
<213> ORGANISM: Panax ginseng

<400> SEQUENCE: 54

Met Gly Leu Thr Gly Lys Leu Ile Cys Gln Thr Gly Ile Lys Ser Asp
1               5                   10                  15

Gly Asp Val Phe His Glu Leu Phe Gly Thr Arg Pro His His Val Pro
            20                  25                  30

Asn Ile Thr Pro Ala Asn Ile Gln Gly Cys Asp Leu His Glu Gly Glu
        35                  40                  45

Phe Gly Lys Val Gly Ser Val Val Ile Trp Asn Tyr Ser Ile Asp Gly
    50                  55                  60

Asn Ala Met Ile Ala Lys Glu Glu Ile Val Ala Ile Asp Glu Glu Asp
65                  70                  75                  80

Lys Ser Val Thr Phe Lys Val Val Glu Gly His Leu Phe Glu Glu Phe
                85                  90                  95

Lys Ser Ile Val Phe Ser Val His Val Asp Thr Lys Gly Glu Asp Asn
            100                 105                 110

Leu Val Thr Trp Ser Ile Asp Tyr Glu Lys Leu Asn Glu Ser Val Lys
        115                 120                 125

Asp Pro Thr Ser Tyr Leu Asp Phe Leu Leu Ser Val Thr Arg Asp Ile
    130                 135                 140

Glu Ala His His Leu Pro Lys
145                 150

<210> SEQ ID NO 55
<211> LENGTH: 157
<212> TYPE: PRT
<213> ORGANISM: Arachis hypogaea

<400> SEQUENCE: 55

Met Gly Val Phe Thr Phe Glu Asp Glu Ile Thr Ser Thr Val Pro Pro
1               5                   10                  15

Ala Lys Leu Tyr Asn Ala Met Lys Asp Ala Asp Ser Ile Thr Pro Lys
            20                  25                  30

Ile Ile Asp Asp Val Lys Ser Val Glu Ile Val Glu Gly Asn Gly Gly
        35                  40                  45

Pro Gly Thr Ile Lys Lys Leu Thr Ile Val Glu Asp Gly Glu Thr Lys
    50                  55                  60

Phe Ile Leu His Lys Val Glu Ser Ile Asp Glu Ala Asn Tyr Ala Tyr
65                  70                  75                  80

Asn Tyr Ser Val Val Gly Gly Val Ala Leu Pro Pro Thr Ala Glu Lys
                85                  90                  95

Ile Thr Phe Glu Thr Lys Leu Val Gly Pro Asn Gly Gly Ser Ile
            100                 105                 110

Gly Lys Leu Thr Leu Lys Tyr His Thr Lys Gly Asp Ala Lys Pro Asp
        115                 120                 125

Glu Glu Glu Leu Lys Lys Gly Lys Ala Lys Gly Glu Gly Leu Phe Arg
    130                 135                 140

Ala Ile Glu Gly Tyr Val Leu Ala Asn Pro Thr Gln Tyr
145                 150                 155

<210> SEQ ID NO 56
<211> LENGTH: 166
<212> TYPE: PRT
<213> ORGANISM: Hypericum perforatum
```

<400> SEQUENCE: 56

Met Gly Ile Asp Pro Phe Thr Met Ala Ala Tyr Thr Ile Val Lys Glu
1               5                   10                  15

Glu Glu Ser Pro Ile Ala Pro His Arg Leu Phe Lys Ala Leu Val Leu
            20                  25                  30

Glu Arg His Gln Val Leu Val Lys Ala Gln Pro His Val Phe Lys Ser
        35                  40                  45

Gly Glu Ile Ile Glu Gly Asp Gly Gly Val Gly Thr Val Thr Lys Ile
    50                  55                  60

Thr Phe Val Asp Gly His Pro Leu Thr Tyr Met Leu His Lys Phe Asp
65                  70                  75                  80

Glu Ile Asp Ala Ala Asn Phe Tyr Cys Lys Tyr Thr Leu Phe Glu Gly
                85                  90                  95

Asp Val Leu Arg Asp Asn Ile Glu Lys Val Val Tyr Glu Val Lys Leu
            100                 105                 110

Glu Ala Val Gly Gly Gly Ser Lys Gly Lys Ile Thr Val Thr Tyr His
        115                 120                 125

Pro Lys Pro Gly Cys Thr Val Asn Glu Glu Val Lys Ile Gly Glu
130                 135                 140

Lys Lys Ala Tyr Glu Phe Tyr Lys Gln Val Glu Glu Tyr Leu Ala Ala
145                 150                 155                 160

Asn Pro Glu Val Phe Ala
                165

<210> SEQ ID NO 57
<211> LENGTH: 158
<212> TYPE: PRT
<213> ORGANISM: Lupinus luteus

<400> SEQUENCE: 57

Met Gly Val Phe Thr Phe Gln Asp Glu Tyr Thr Ser Thr Ile Ala Pro
1               5                   10                  15

Ala Lys Leu Tyr Lys Ala Leu Val Thr Asp Ala Asp Ile Ile Ile Pro
            20                  25                  30

Lys Ala Val Glu Thr Ile Gln Ser Val Glu Ile Val Glu Gly Asn Gly
        35                  40                  45

Gly Pro Gly Thr Ile Lys Lys Leu Thr Phe Ile Glu Gly Gly Glu Ser
    50                  55                  60

Lys Tyr Val Leu His Lys Ile Glu Ala Ile Asp Glu Ala Asn Leu Gly
65                  70                  75                  80

Tyr Asn Tyr Ser Ile Val Gly Gly Val Gly Leu Pro Asp Thr Ile Glu
                85                  90                  95

Lys Ile Ser Phe Glu Thr Lys Leu Val Glu Gly Ala Asn Gly Gly Ser
            100                 105                 110

Ile Gly Lys Val Thr Ile Lys Ile Glu Thr Lys Gly Asp Ala Gln Pro
        115                 120                 125

Asn Glu Glu Glu Gly Lys Ala Ala Lys Ala Arg Gly Asp Ala Phe Phe
    130                 135                 140

Lys Ala Ile Glu Ser Tyr Leu Ser Ala His Pro Asp Tyr Asn
145                 150                 155

<210> SEQ ID NO 58
<211> LENGTH: 161
<212> TYPE: PRT
<213> ORGANISM: Fragaria x ananassa

<400> SEQUENCE: 58

```
Met Ala Gly Val Phe Thr Tyr Glu Thr Glu Phe Thr Ser Val Ile Pro
1               5                   10                  15

Pro Pro Arg Leu Phe Lys Ala Phe Ile Leu Asp Ala Asp Asn Leu Ile
            20                  25                  30

Pro Lys Ile Ala Pro Gln Ala Val Lys Cys Ala Glu Ile Ile Glu Gly
        35                  40                  45

Asp Gly Val Gly Thr Ile Lys Lys Ile Thr Phe Gly Glu Gly Ser
    50                  55                  60

Gln Phe Gly Ser Val Thr His Lys Ile Asp Gly Ile Asp Lys Glu Asn
65                  70                  75                  80

Phe Val Tyr Ser Tyr Ser Leu Ile Glu Gly Asp Ala Leu Ser Asp Lys
                85                  90                  95

Ile Glu Lys Ile Ser Tyr Glu Thr Lys Leu Val Ser Ser Asp Gly
            100                 105                 110

Gly Ser Ile Ile Lys Ser Thr Ser Asn Tyr His Thr Lys Gly Asp Val
        115                 120                 125

Glu Ile Lys Glu Glu His Val Lys Ala Gly Lys Glu Lys Phe Ser His
130                 135                 140

Leu Phe Lys Leu Val Glu Gly Tyr Leu Leu Ala Asn Pro Asn Glu Tyr
145                 150                 155                 160

Cys
```

<210> SEQ ID NO 59
<211> LENGTH: 150
<212> TYPE: PRT
<213> ORGANISM: Actinidia deliciosa

<400> SEQUENCE: 59

```
Met Asp Leu Ser Gly Lys Met Val Lys Gln Val Glu Ile Leu Ser Asp
1               5                   10                  15

Gly Ile Val Phe Tyr Glu Ile Phe Arg Tyr Arg Leu Tyr Leu Ile Ser
            20                  25                  30

Glu Met Ser Pro Val Asn Ile Gln Gly Val Asp Leu Leu Glu Gly Asn
        35                  40                  45

Trp Gly Thr Val Gly Ser Val Ile Phe Phe Lys Tyr Thr Ile Asp Gly
    50                  55                  60

Lys Glu Lys Thr Ala Lys Asp Ile Val Glu Ala Ile Asp Glu Thr
65                  70                  75                  80

Lys Ser Val Thr Phe Lys Ile Val Glu Gly Asp Leu Met Glu Leu Tyr
                85                  90                  95

Lys Thr Phe Ile Ile Ile Val Gln Val Asp Thr Lys Gly Glu His Asn
            100                 105                 110

Ser Val Thr Trp Thr Phe His Tyr Glu Lys Leu Lys Glu Asp Val Glu
        115                 120                 125

Glu Pro Asn Thr Leu Met Asn Phe Cys Ile Glu Ile Thr Lys Asp Ile
130                 135                 140

Glu Thr Tyr His Leu Lys
145                 150
```

<210> SEQ ID NO 60
<211> LENGTH: 164
<212> TYPE: PRT
<213> ORGANISM: Thalictrum flavum

```
<400> SEQUENCE: 60

Met Gly Ile Ile Asn Gln Val Ser Thr Val Thr Lys Val Ile His His
1               5                   10                  15

Glu Leu Glu Val Ala Ala Ser Ala Asp Asp Ile Trp Thr Val Tyr Ser
                20                  25                  30

Trp Pro Gly Leu Ala Lys His Leu Pro Asp Leu Leu Pro Gly Ala Phe
                35                  40                  45

Glu Lys Leu Glu Ile Ile Gly Asp Gly Val Gly Thr Ile Leu Asp
    50                  55                  60

Met Thr Phe Val Pro Gly Glu Phe Pro His Glu Tyr Lys Glu Lys Phe
65                  70                  75                  80

Ile Leu Val Asp Asn Glu His Arg Leu Lys Lys Val Gln Met Ile Glu
                85                  90                  95

Gly Gly Tyr Leu Asp Leu Gly Val Thr Tyr Tyr Met Asp Thr Ile His
                100                 105                 110

Val Val Pro Thr Gly Lys Asp Ser Cys Val Ile Lys Ser Ser Thr Glu
                115                 120                 125

Tyr His Val Lys Pro Glu Phe Val Lys Ile Val Glu Pro Leu Ile Thr
                130                 135                 140

Thr Gly Pro Leu Ala Ala Met Ala Asp Ala Ile Ser Lys Leu Val Leu
145                 150                 155                 160

Glu His Lys Ser

<210> SEQ ID NO 61
<211> LENGTH: 155
<212> TYPE: PRT
<213> ORGANISM: Vigna radiata

<400> SEQUENCE: 61

Met Val Lys Glu Phe Asn Thr Gln Thr Glu Leu Ser Val Arg Leu Glu
1               5                   10                  15

Ala Leu Trp Ala Val Leu Ser Lys Asp Phe Ile Thr Val Pro Lys
                20                  25                  30

Val Leu Pro His Ile Val Lys Asp Val Gln Leu Ile Glu Gly Asp Gly
                35                  40                  45

Gly Val Gly Thr Ile Leu Ile Phe Asn Phe Leu Pro Glu Val Ser Pro
    50                  55                  60

Ser Tyr Gln Arg Glu Glu Ile Thr Glu Phe Asp Glu Ser Ser His Glu
65                  70                  75                  80

Ile Gly Leu Gln Val Ile Glu Gly Gly Tyr Leu Ser Gln Gly Leu Ser
                85                  90                  95

Tyr Tyr Lys Thr Thr Phe Lys Leu Ser Glu Ile Glu Glu Asp Lys Thr
                100                 105                 110

Leu Val Asn Val Lys Ile Ser Tyr Asp His Asp Ser Asp Ile Glu Glu
                115                 120                 125

Lys Val Thr Pro Thr Lys Thr Ser Gln Ser Thr Leu Met Tyr Leu Arg
                130                 135                 140

Arg Leu Glu Arg Tyr Leu Ser Asn Gly Ser Ala
145                 150                 155

<210> SEQ ID NO 62
<211> LENGTH: 364
<212> TYPE: PRT
<213> ORGANISM: Papaver sp.

<400> SEQUENCE: 62
```

Met Glu Lys Ala Lys Leu Met Lys Leu Gly Asn Gly Met Glu Ile Pro
1               5                   10                  15

Ser Val Gln Glu Leu Ala Lys Leu Thr Leu Ala Glu Ile Pro Ser Arg
            20                  25                  30

Tyr Val Cys Ala Asn Glu Asn Leu Leu Pro Met Gly Ala Ser Val
        35                  40                  45

Ile Asn Asp His Glu Thr Ile Pro Val Ile Asp Ile Glu Asn Leu Leu
    50                  55                  60

Ser Pro Glu Pro Ile Ile Gly Lys Leu Glu Leu Asp Arg Leu His Phe
65                  70                  75                  80

Ala Cys Lys Glu Trp Gly Phe Phe Gln Val Val Asn His Gly Val Asp
                85                  90                  95

Ala Ser Leu Val Asp Ser Val Lys Ser Glu Ile Gln Gly Phe Phe Asn
            100                 105                 110

Leu Ser Met Asp Glu Lys Thr Lys Tyr Glu Gln Glu Asp Gly Asp Val
        115                 120                 125

Glu Gly Phe Gly Gln Gly Phe Ile Glu Ser Glu Asp Gln Thr Leu Asp
130                 135                 140

Trp Ala Asp Ile Phe Met Met Phe Thr Leu Pro Leu His Leu Arg Lys
145                 150                 155                 160

Pro His Leu Phe Ser Lys Leu Pro Val Pro Leu Arg Glu Thr Ile Glu
                165                 170                 175

Ser Tyr Ser Ser Glu Met Lys Lys Leu Ser Met Val Leu Phe Asn Lys
            180                 185                 190

Met Glu Lys Ala Leu Gln Val Gln Ala Ala Glu Ile Lys Gly Met Ser
        195                 200                 205

Glu Val Phe Ile Asp Gly Thr Gln Ala Met Arg Met Asn Tyr Tyr Pro
210                 215                 220

Pro Cys Pro Gln Pro Asn Leu Ala Ile Gly Leu Thr Ser His Ser Asp
225                 230                 235                 240

Phe Gly Gly Leu Thr Ile Leu Leu Gln Ile Asn Glu Val Glu Gly Leu
                245                 250                 255

Gln Ile Lys Arg Glu Gly Thr Trp Ile Ser Val Lys Pro Leu Pro Asn
            260                 265                 270

Ala Phe Val Val Asn Val Gly Asp Ile Leu Glu Ile Met Thr Asn Gly
        275                 280                 285

Ile Tyr His Ser Val Asp His Arg Ala Val Val Asn Ser Thr Asn Glu
290                 295                 300

Arg Leu Ser Ile Ala Thr Phe His Asp Pro Ser Leu Glu Ser Val Ile
305                 310                 315                 320

Gly Pro Ile Ser Ser Leu Ile Thr Pro Glu Thr Pro Ala Leu Phe Lys
                325                 330                 335

Ser Gly Ser Thr Tyr Gly Asp Leu Val Glu Glu Cys Lys Thr Arg Lys
            340                 345                 350

Leu Asp Gly Lys Ser Phe Leu Asp Ser Met Arg Ile
        355                 360

<210> SEQ ID NO 63
<211> LENGTH: 360
<212> TYPE: PRT
<213> ORGANISM: Papaver sp.

<400> SEQUENCE: 63

Met Glu Thr Pro Ile Leu Ile Lys Leu Gly Asn Gly Leu Ser Ile Pro

```
             1               5                  10                 15
            Ser Val Gln Glu Leu Ala Lys Leu Thr Leu Ala Glu Ile Pro Ser Arg
                           20                  25                 30
            Tyr Thr Cys Thr Gly Glu Ser Pro Leu Asn Asn Ile Gly Ala Ser Val
                           35                  40                 45
            Thr Asp Asp Glu Thr Val Pro Val Ile Asp Leu Gln Asn Leu Leu Ser
             50                  55                 60
            Pro Glu Pro Val Val Gly Lys Leu Glu Leu Asp Lys Leu His Ser Ala
             65                  70                 75                 80
            Cys Lys Glu Trp Gly Phe Phe Gln Leu Val Asn His Gly Val Asp Ala
                           85                  90                 95
            Leu Leu Met Asp Asn Ile Lys Ser Glu Ile Lys Gly Phe Phe Asn Leu
                           100                 105                110
            Pro Met Asn Glu Lys Thr Lys Tyr Gly Gln Gln Asp Gly Asp Phe Glu
                           115                 120                125
            Gly Phe Gly Gln Pro Tyr Ile Glu Ser Glu Asp Gln Arg Leu Asp Trp
                           130                 135                140
            Thr Glu Val Phe Ser Met Leu Ser Leu Pro Leu His Leu Arg Lys Pro
             145                 150                155                160
            His Leu Phe Pro Glu Leu Pro Leu Pro Phe Arg Glu Thr Leu Glu Ser
                           165                 170                175
            Tyr Leu Ser Lys Met Lys Lys Leu Ser Thr Val Val Phe Glu Met Leu
                           180                 185                190
            Glu Lys Ser Leu Gln Leu Val Glu Ile Lys Gly Met Thr Asp Leu Phe
                           195                 200                205
            Glu Asp Gly Leu Gln Thr Met Arg Met Asn Tyr Tyr Pro Pro Cys Pro
                           210                 215                220
            Arg Pro Glu Leu Val Leu Gly Leu Thr Ser His Ser Asp Phe Ser Gly
             225                 230                235                240
            Leu Thr Ile Leu Leu Gln Leu Asn Glu Val Glu Gly Leu Gln Ile Arg
                           245                 250                255
            Lys Glu Glu Arg Trp Ile Ser Ile Lys Pro Leu Pro Asp Ala Phe Ile
                           260                 265                270
            Val Asn Val Gly Asp Ile Leu Glu Ile Met Thr Asn Gly Ile Tyr Arg
                           275                 280                285
            Ser Val Glu His Arg Ala Val Val Asn Ser Thr Lys Glu Arg Leu Ser
                           290                 295                300
            Ile Ala Thr Phe His Asp Ser Lys Leu Glu Ser Glu Ile Gly Pro Ile
             305                 310                315                320
            Ser Ser Leu Val Thr Pro Glu Thr Pro Ala Leu Phe Lys Arg Gly Arg
                           325                 330                335
            Tyr Glu Asp Ile Leu Lys Glu Asn Leu Ser Arg Lys Leu Asp Gly Lys
                           340                 345                350
            Ser Phe Leu Asp Tyr Met Arg Met
                           355                 360

<210> SEQ ID NO 64
<211> LENGTH: 364
<212> TYPE: PRT
<213> ORGANISM: Papaver somniferum

<400> SEQUENCE: 64

Met Glu Lys Ala Lys Leu Met Lys Leu Gly Asn Gly Leu Ser Ile Pro
             1               5                  10                 15
```

Ser Val Gln Glu Leu Ala Glu Leu Thr Phe Ala Glu Val Pro Ser Arg
            20                  25                  30

Tyr Val Cys Thr Asn Asp Glu Asn Leu Leu Met Thr Met Gly Ala
            35                  40                  45

Ser Glu Ile Asp Asp Glu Thr Val Pro Val Ile Asp Leu Gln Asn Leu
50                      55                  60

Leu Ser Pro Glu Pro Ala Ile Gly Lys Ser Glu Leu Asp Trp Leu His
65                  70                  75                  80

Tyr Ser Cys Lys Glu Trp Gly Phe Phe Gln Leu Val Asn His Gly Val
                85                  90                  95

Asp Ala Leu Leu Val Asp His Val Lys Ser Glu Ile His Ser Phe Phe
            100                 105                 110

Asn Leu Pro Leu Asn Glu Lys Thr Lys Tyr Gly Gln Arg Asp Gly Asp
            115                 120                 125

Val Glu Gly Phe Gly Gln Ala Phe Leu Val Ser Glu Asn Gln Lys Leu
            130                 135                 140

Asp Trp Ala Asp Met Phe Phe Ile Asn Thr Leu Pro Leu His Leu Arg
145                 150                 155                 160

Lys Pro His Leu Phe Pro Asn Leu Pro Leu Pro Leu Arg Glu Thr Ile
                165                 170                 175

Glu Ser Tyr Ser Ser Glu Met Lys Lys Leu Ser Met Val Leu Phe Glu
            180                 185                 190

Met Met Gly Lys Ala Ile Glu Val Ile Asp Ile Lys Glu Ala Ile Thr
            195                 200                 205

Glu Met Phe Glu Asp Gly Met Gln Ser Met Arg Met Asn Tyr Tyr Pro
            210                 215                 220

Pro Cys Pro Gln Pro Glu Arg Val Ile Gly Ile Thr Pro His Ser Asp
225                 230                 235                 240

Phe Asp Gly Leu Thr Ile Leu Leu Gln Leu Asn Glu Val Glu Gly Leu
                245                 250                 255

Gln Ile Arg Lys Glu Asp Lys Trp Ile Ser Ile Lys Pro Leu Pro Asp
            260                 265                 270

Ala Phe Ile Val Asn Val Gly Asp Ile Trp Glu Ile Met Thr Asn Gly
            275                 280                 285

Val His Arg Ser Val Asp His Arg Gly Val Ile Asn Ser Thr Lys Glu
            290                 295                 300

Arg Leu Ser Ile Ala Thr Phe His Ser Pro Lys Leu Glu Leu Glu Ile
305                 310                 315                 320

Gly Pro Ile Ser Ser Leu Ile Arg Pro Glu Thr Pro Ala Val Phe Lys
            325                 330                 335

Ser Ala Gly Arg Phe Glu Asp Leu Leu Lys Glu Gly Leu Ser Arg Lys
            340                 345                 350

Leu Asp Gly Lys Ser Phe Leu Asp Cys Met Arg Met
            355                 360

<210> SEQ ID NO 65
<211> LENGTH: 294
<212> TYPE: PRT
<213> ORGANISM: Papaver somniferum

<400> SEQUENCE: 65

Met Glu Lys Ala Lys Leu Met Lys Leu Gly Asn Gly Met Glu Ile Pro
1               5                   10                  15

Ser Val Gln Glu Leu Ala Lys Leu Thr Leu Ala Glu Ile Pro Ser Arg
            20                  25                  30

```
Tyr Val Cys Ala Asn Glu Asn Leu Leu Pro Met Gly Ala Ser Val
            35                  40                  45

Ile Asn Asp His Glu Thr Ile Pro Val Ile Asp Ile Glu Asn Leu Leu
 50                  55                  60

Ser Pro Glu Pro Ile Ile Gly Lys Leu Glu Leu Asp Arg Leu His Phe
 65                  70                  75                  80

Ala Cys Lys Glu Trp Gly Phe Phe Gln Val Val Asn His Gly Val Asp
                85                  90                  95

Ala Ser Leu Val Asp Ser Val Lys Ser Glu Ile Gln Gly Phe Phe Asn
            100                 105                 110

Leu Ser Met Asp Glu Lys Thr Lys Tyr Glu Gln Glu Asp Gly Asp Val
            115                 120                 125

Glu Gly Phe Gly Gln Gly Phe Ile Glu Ser Gly Asp Gln Thr Leu Asp
            130                 135                 140

Trp Ala Asp Ile Phe Met Met Phe Thr Leu Pro Leu His Leu Arg Lys
145                 150                 155                 160

Pro His Leu Phe Ser Lys Leu Pro Val Pro Leu Arg Glu Thr Ile Glu
                165                 170                 175

Ser Tyr Ser Ser Glu Met Lys Lys Leu Ser Met Val Leu Phe Asn Lys
            180                 185                 190

Met Glu Lys Ala Leu Gln Val Gln Ala Ala Glu Ile Lys Gly Met Ser
            195                 200                 205

Glu Val Phe Ile Asp Gly Thr Gln Ala Met Arg Met Asn Tyr Tyr Pro
210                 215                 220

Pro Cys Pro Gln Pro Asn Leu Ala Ile Gly Leu Thr Ser His Ser Asp
225                 230                 235                 240

Phe Gly Gly Leu Thr Ile Leu Leu Gln Ile Asn Glu Val Glu Gly Leu
                245                 250                 255

Gln Ile Lys Arg Glu Gly Thr Trp Ile Ser Val Lys Pro Leu Pro Asn
            260                 265                 270

Ala Phe Val Val Asn Val Gly Asp Ile Leu Glu Ile Met Thr Asn Gly
            275                 280                 285

Ile Tyr His Ser Val Asp
            290

<210> SEQ ID NO 66
<211> LENGTH: 364
<212> TYPE: PRT
<213> ORGANISM: Papaver somniferum

<400> SEQUENCE: 66

Met Glu Thr Ala Lys Leu Met Lys Leu Gly Asn Gly Met Ser Ile Pro
 1               5                  10                  15

Ser Val Gln Glu Leu Ala Lys Leu Thr Leu Ala Glu Ile Pro Ser Arg
            20                  25                  30

Tyr Ile Cys Thr Val Glu Asn Leu Gln Leu Pro Val Gly Ala Ser Val
            35                  40                  45

Ile Asp Asp His Glu Thr Val Pro Val Ile Asp Ile Glu Asn Leu Ile
 50                  55                  60

Ser Ser Glu Pro Val Thr Glu Lys Leu Glu Leu Asp Arg Leu His Ser
 65                  70                  75                  80

Ala Cys Lys Glu Trp Gly Phe Phe Gln Val Val Asn His Gly Val Asp
                85                  90                  95

Thr Ser Leu Val Asp Asn Val Lys Ser Asp Ile Gln Gly Phe Phe Asn
```

```
            100                 105                 110

Leu Ser Met Asn Glu Lys Ile Lys Tyr Gly Gln Lys Asp Gly Asp Val
            115                 120                 125

Glu Gly Phe Gly Gln Ala Phe Val Ala Ser Glu Asp Gln Thr Leu Asp
        130                 135                 140

Trp Ala Asp Ile Phe Met Ile Leu Thr Leu Pro Leu His Leu Arg Lys
145                 150                 155                 160

Pro His Leu Phe Ser Lys Leu Pro Leu Pro Leu Arg Glu Thr Ile Glu
                165                 170                 175

Ser Tyr Ser Ser Glu Met Lys Lys Leu Ser Met Val Leu Phe Glu Lys
                180                 185                 190

Met Glu Lys Ala Leu Gln Val Gln Ala Val Glu Ile Lys Glu Ile Ser
            195                 200                 205

Glu Val Phe Lys Asp Met Thr Gln Val Met Arg Met Asn Tyr Tyr Pro
        210                 215                 220

Pro Cys Pro Gln Pro Glu Leu Ala Ile Gly Leu Thr Pro His Ser Asp
225                 230                 235                 240

Phe Gly Gly Leu Thr Ile Leu Leu Gln Leu Asn Glu Val Glu Gly Leu
                245                 250                 255

Gln Ile Lys Asn Glu Gly Arg Trp Ile Ser Val Lys Pro Leu Pro Asn
                260                 265                 270

Ala Phe Val Val Asn Val Gly Asp Val Leu Glu Ile Met Thr Asn Gly
            275                 280                 285

Met Tyr Arg Ser Val Asp His Arg Ala Val Val Asn Ser Thr Lys Glu
        290                 295                 300

Arg Leu Ser Ile Ala Thr Phe His Asp Pro Asn Leu Glu Ser Glu Ile
305                 310                 315                 320

Gly Pro Ile Ser Ser Leu Ile Thr Pro Asn Thr Pro Ala Leu Phe Arg
                325                 330                 335

Ser Gly Ser Thr Tyr Gly Glu Leu Val Glu Glu Phe His Ser Arg Lys
                340                 345                 350

Leu Asp Gly Lys Ser Phe Leu Asp Ser Met Arg Met
            355                 360

<210> SEQ ID NO 67
<211> LENGTH: 369
<212> TYPE: PRT
<213> ORGANISM: Papaver bracteatum

<400> SEQUENCE: 67

Met Glu Thr Pro Lys Ser Ile Lys Leu Gly Gly Ser Leu Leu Val Pro
1               5                   10                  15

Ser Val Gln Glu Leu Ala Gln Gln Ser Phe Ala Glu Val Pro Ala Arg
            20                  25                  30

Tyr Val Arg Asp Asp Leu Glu Pro Leu Thr Asp Leu Ser Gly Val Ser
        35                  40                  45

Met Ile Asp Gln Thr Ile Pro Val Ile Asp Leu Gln Lys Leu Gln Ser
    50                  55                  60

Pro Val Pro Ile Ile Arg Glu Leu Glu Ser Glu Lys Leu His Ser Ala
65                  70                  75                  80

Cys Lys Glu Trp Gly Phe Phe Gln Val Val Asn His Gly Val Asp Ile
                85                  90                  95

Leu Leu Val Glu Lys Thr Lys Ser Glu Ile Lys Asp Phe Phe Asn Leu
            100                 105                 110
```

```
Pro Met Asp Glu Lys Lys Phe Trp Gln Glu Gly Asp Ile Gln
        115                 120                 125

Gly Phe Gly Gln Ala Phe Val Gln Ser Glu Asp Gln Lys Leu Asp Trp
130                 135                 140

Ala Asp Ile Phe Leu Met Val Thr Leu Pro Arg His Thr Arg Asn Pro
145                 150                 155                 160

Arg Leu Phe Pro Lys Leu Pro Leu Pro Leu Arg Asn Thr Met Asp Ser
                165                 170                 175

Tyr Ser Ser Lys Leu Ser Lys Leu Ala Ser Thr Leu Ile Glu Met Met
            180                 185                 190

Gly Lys Ala Leu His Met Glu Thr Ser Val Leu Ala Glu Leu Phe Glu
        195                 200                 205

Asp Gly Arg Gln Thr Met Arg Ile Asn Tyr Tyr Pro Pro Cys Pro Gln
210                 215                 220

Pro Lys Asp Val Ile Gly Leu Thr Pro His Ser Asp Gly Gly Gly Leu
225                 230                 235                 240

Thr Ile Leu Leu Gln Leu Asn Glu Val Asp Gly Leu Gln Ile Arg Lys
                245                 250                 255

Glu Lys Ile Trp Ile Pro Ile Lys Pro Leu Pro Asn Ala Phe Val Val
            260                 265                 270

Asn Ile Gly Asn Ile Leu Glu Ile Met Thr Asn Gly Ile Tyr Arg Ser
        275                 280                 285

Val Glu His Arg Ala Thr Ile His Ser Thr Lys Glu Arg Leu Ser Val
        290                 295                 300

Ala Ala Phe His Asn Pro Lys Val Gly Val Glu Ile Gly Pro Ile Val
305                 310                 315                 320

Ser Met Ile Thr Pro Glu Ser Pro Ala Leu Phe Arg Thr Ile Glu Tyr
                325                 330                 335

Asp Asp Tyr Gly Lys Lys Tyr Phe Ser Arg Lys Leu Asp Gly Lys Ser
            340                 345                 350

Ser Leu Asp Phe Met Arg Ile Gly Glu Gly Asp Glu Glu Asn Lys Ala
        355                 360                 365

Thr
```

<210> SEQ ID NO 68
<211> LENGTH: 366
<212> TYPE: PRT
<213> ORGANISM: Papaver bracteatum

<400> SEQUENCE: 68

```
Met Glu Thr Pro Lys Leu Ile Lys Leu Gly Gly Ser Leu Leu Val Pro
1               5                   10                  15

Ser Val Leu Glu Leu Thr Lys Gln Ser Pro Ala Glu Val Pro Ala Arg
                20                  25                  30

Tyr Ile Arg Asn Asp Leu Glu Pro Met Thr Asp Leu Ser Ser Ala Ser
            35                  40                  45

Leu Thr Asp Gln Thr Ile Pro Val Ile Asp Leu Gln Asn Leu Leu Ser
        50                  55                  60

Pro Glu Pro Glu Leu Glu Leu Glu Lys Leu His Ser Gly Cys Lys Glu
65                  70                  75                  80

Trp Gly Phe Phe Gln Val Met Asn His Gly Val Asp Ile Leu Leu Val
                85                  90                  95

Glu Lys Val Lys Ser Glu Ile Gln Gly Phe Phe Asn Leu Pro Ile Asp
            100                 105                 110
```

```
Glu Lys Asn Lys Phe Trp Gln Glu Glu Gly Asp Leu Glu Gly Tyr Gly
            115                 120                 125

Lys Ala Phe Val His Ser Glu Asp Lys Leu Asp Trp Ala Asp Met
        130                 135                 140

Phe Phe Ile Leu Thr Gln Pro Gln Tyr Met Arg Lys Pro Arg Val Phe
145                 150                 155                 160

Pro Lys Leu Pro Leu Arg Leu Arg Glu Thr Ile Glu Ser Tyr Ser Leu
                165                 170                 175

Glu Leu Ser Lys Leu Gly Leu Thr Leu Leu Asp Leu Met Gly Lys Ala
                180                 185                 190

Leu Gln Ile Glu Thr Gly Val Met Ser Glu Leu Phe Glu Asp Gly Arg
            195                 200                 205

Gln Thr Met Arg Met Asn Tyr Tyr Pro Pro Cys Pro Gln Pro Glu His
            210                 215                 220

Val Ile Gly Leu Thr Pro His Ser Asp Gly Gly Ala Leu Thr Ile Leu
225                 230                 235                 240

Leu Gln Leu Asn Gln Val Asp Gly Leu Gln Ile Arg Lys Glu Glu Ile
                245                 250                 255

Trp Val Pro Ile Lys Pro Leu Pro Asn Ala Phe Val Val Asn Ile Gly
            260                 265                 270

Asp Ile Leu Glu Ile Met Ser Asn Gly Val Tyr Arg Ser Val Glu His
            275                 280                 285

Arg Ala Thr Ile Asn Ser Ser Lys Glu Arg Leu Ser Val Ala Ile Phe
            290                 295                 300

Gln Ser Pro Lys His Gly Thr Glu Ile Gly Pro Ile Leu Ser Met Ile
305                 310                 315                 320

Thr Pro Glu Ala Pro Ala Leu Phe Lys Thr Ile Pro Tyr Glu Asp Tyr
                325                 330                 335

Leu Arg Lys Phe Phe Ser Arg Lys Leu Gly Lys Ser Phe Val Asp
                340                 345                 350

Ser Met Arg Ile Gly Glu Ser Asp Glu Asp Asn Thr Ala
                355                 360                 365

<210> SEQ ID NO 69
<211> LENGTH: 366
<212> TYPE: PRT
<213> ORGANISM: Papaver bracteatum

<400> SEQUENCE: 69

Met Glu Thr Gln Lys Gln Glu Asn Phe Gly Ala Ser Leu Ser Val Pro
1               5                   10                  15

Asn Val Gln Glu Leu Ala Lys Gln Ser Pro Glu Gln Val Pro Asp Arg
            20                  25                  30

Tyr Ile Arg Ser Asp Gln Asp Ser Thr Asn Ile Ser Cys Pro Ser
        35                  40                  45

Met Thr Asp Gln Ile Pro Val Ile Asp Leu Gln Ser Leu Leu Ser Pro
    50                  55                  60

Asp Pro Ile Ile Gly Glu Leu Glu Leu Glu Arg Leu His Ser Ala Cys
65                  70                  75                  80

Lys Glu Trp Gly Phe Phe Gln Val Val Asn His Gly Val Asp Asn Leu
                85                  90                  95

Leu Val Glu Lys Val Lys Ser Glu Ile Gln Gly Phe Phe Asn Leu Pro
            100                 105                 110

Met Asp Glu Lys Lys Phe Trp Gln Glu Glu Gly Asp Phe Glu Gly
            115                 120                 125
```

```
Phe Gly Gln Ala Phe Val Phe Ser Glu Asp Gln Lys Leu Asp Trp Gly
    130                 135                 140

Asp Val Phe Phe Ile Leu Thr Gln Pro Gln His Met Arg Lys Pro Arg
145                 150                 155                 160

Leu Phe Pro Lys Leu Pro Leu Pro Phe Arg Lys Thr Ile Glu Ser Tyr
                165                 170                 175

Ser Leu Glu Thr Asn Lys Leu Ser Met Thr Leu Leu Glu Leu Met Glu
            180                 185                 190

Lys Ala Leu Lys Ile Glu Thr Gly Val Met Thr Gly Leu Phe Glu Gly
        195                 200                 205

Gly Ile Gln Arg Met Arg Met Thr Tyr Tyr Pro Pro Cys Pro Gln Pro
    210                 215                 220

Lys His Val Ile Gly Leu Thr Pro His Ser Asp Pro Asp Ala Leu Thr
225                 230                 235                 240

Ile Leu Leu Gln Leu Asn Glu Val Asp Gly Leu Gln Ile Arg Lys Glu
                245                 250                 255

Lys Ile Trp Val Pro Ile Lys Pro Leu Ser Asn Ala Phe Val Val Asn
            260                 265                 270

Ile Gly Asp Ile Leu Glu Ile Met Ser Asn Gly Ile Tyr Arg Ser Val
        275                 280                 285

Glu His Arg Ala Thr Val Asn Ser Thr Lys Glu Arg Leu Ser Val Ala
    290                 295                 300

Thr Phe His Ser Pro Arg Lys Asp Thr Glu Ile Gly Pro Ile Leu Ile
305                 310                 315                 320

Thr Pro Glu Thr Pro Ala Leu Phe Arg Thr Ser Gly Phe Glu Asp Tyr
                325                 330                 335

Phe Arg Lys Phe Phe Ala His Lys Leu Asn Gly Lys Ser Phe Leu Ser
            340                 345                 350

Ser Ile Arg Ile Gly Glu Thr Asp Glu Gly Asn Asn Ala Thr
        355                 360                 365

<210> SEQ ID NO 70
<211> LENGTH: 379
<212> TYPE: PRT
<213> ORGANISM: Papaver bracteatum

<400> SEQUENCE: 70

Met Glu Ala Pro Lys Leu Ile Met Leu Gly Gly Ser Leu Phe Val Pro
1               5                   10                  15

Ser Val Gln Glu Leu Ala Lys Gln Ser Leu Ala Glu Val Pro Val Arg
            20                  25                  30

Tyr Val Arg Asp Asp Gln Asp Thr Leu Gly Asn Asn Ile Asn Ile Thr
        35                  40                  45

Pro Met Ser Met Ile Asp Gln Ser Ile Pro Val Ile Asp Leu Glu Lys
    50                  55                  60

Leu Leu Ser Pro Glu Pro Ile Val Gly Glu Leu Glu Arg Leu
65                  70                  75                  80

His Ser Ala Cys Lys Glu Trp Gly Phe Phe Gln Val Val Asn His Gly
                85                  90                  95

Val Asp Ser Leu Leu Val Glu Lys Val Lys Ser Glu Ile Glu Gly Phe
            100                 105                 110

Phe Lys Leu Pro Met Asp Glu Lys Thr Lys Phe Trp Gln Glu Glu Gly
        115                 120                 125

Asp Ile Glu Gly Phe Gly Gln Val Phe Val His Ser Gln Asp Gln Lys
```

```
                130                 135                 140
Leu Asp Trp Gly Asp Met Phe Leu Met Gln Thr Leu Pro Arg His Thr
145                 150                 155                 160

Arg Lys Pro Arg Leu Phe Pro Asn Leu Pro Leu Pro Leu Arg Gln Thr
                165                 170                 175

Ile Glu Ser Tyr Ser Ser Glu Leu Ser Lys Leu Val Leu Thr Leu Val
                180                 185                 190

Asp Leu Met Gly Lys Ala Leu Gln Met Glu Ser Gly Val Leu Thr Glu
                195                 200                 205

Leu Phe Glu Asn Gly Ile Gln Arg Met Arg Met Asn Tyr Tyr Pro Pro
                210                 215                 220

Cys Pro Gln Pro Glu Gln Val Ile Gly Leu Thr Pro His Ser Asp Val
225                 230                 235                 240

Gly Gly Leu Thr Ile Leu Leu Gln Leu Asn Glu Val Asp Gly Leu Gln
                245                 250                 255

Ile Lys Lys Asp Lys Val Trp Val Pro Ile Lys Pro Leu Ala Asn Ala
                260                 265                 270

Phe Val Val Asn Val Gly Asp Ala Leu Glu Ile Met Ser Asn Gly Ile
                275                 280                 285

Tyr Arg Ser Val Glu His Arg Ala Thr Ile Asn Ser Thr Lys Glu Arg
                290                 295                 300

Leu Ser Ile Ala Thr Phe His Asn Pro Arg Ala Asp Arg Glu Ile Gly
305                 310                 315                 320

Pro Ile Pro Ser Met Ile Ser Pro Glu Thr Pro Ala Leu Phe Lys Thr
                325                 330                 335

Thr Gly Tyr Glu Glu Tyr Phe Lys Lys Phe Phe Ser Arg Lys Leu Glu
                340                 345                 350

Gly Lys Ser Phe Leu Asp Ser Leu Arg Ile Arg Glu Gly Asp Glu His
                355                 360                 365

Cys Gly Arg Leu Asp Val Lys Gly Pro Cys Asn
                370                 375

<210> SEQ ID NO 71
<211> LENGTH: 365
<212> TYPE: PRT
<213> ORGANISM: Papaver bracteatum

<400> SEQUENCE: 71

Met Glu Ile Pro Asn Pro Ile Lys Ile Gly Ser Ser Leu Leu Val Pro
1               5                   10                  15

Ser Val Gln Glu Leu Ala Lys Gln Ser Phe Ala Glu Val Pro Ala Arg
                20                  25                  30

Tyr Ile Arg Asn Asp Val Asp Pro Leu Ile Thr Lys Leu Ser Asp Val
                35                  40                  45

Ser Leu Ile Asp Gln Thr Val Pro Val Ile Asp Leu Gln Lys Leu Leu
                50                  55                  60

Ser Pro Glu Pro Ile Val Gly Glu Leu Glu Leu Glu Arg Leu His Ser
65                  70                  75                  80

Ala Cys Lys Glu Trp Gly Phe Phe Gln Val Val Asn His Gly Val Asp
                85                  90                  95

Asn Leu Leu Val Glu Lys Val Lys Ser Glu Ile Gln Gly Phe Phe Asn
                100                 105                 110

Leu Pro Met Glu Glu Lys Lys Lys Phe Trp Gln Glu Glu Gly Asp Phe
                115                 120                 125
```

```
Glu Gly Phe Gly Gln Met Phe Val Gln Ser Glu Glu Gln Lys Leu Asp
            130                 135                 140

Trp Gly Asp Met Phe Phe Ile Leu Thr Gln Pro Gln His Met Arg Lys
145                 150                 155                 160

Pro Arg Leu Phe Ser Lys Leu Pro Leu Pro Leu Arg Glu Thr Ile Glu
                165                 170                 175

Ser Tyr Ser Leu Glu Leu Ile Lys Leu Gly Leu Thr Ile Ile Lys Leu
                180                 185                 190

Met Glu Lys Ala Leu Gln Ile Asp Ala Gly Val Met Ala Glu Leu Phe
            195                 200                 205

Glu Asp Gly Ile His Thr Met Arg Met Asn Tyr Tyr Pro Pro Cys Pro
210                 215                 220

Gln Pro Glu His Val Ile Gly Leu Thr Pro His Ser Asp Gly Gly Gly
225                 230                 235                 240

Leu Thr Ile Leu Leu Gln Leu Asn Glu Val Asp Gly Leu Gln Ile Arg
                245                 250                 255

Arg Glu Asn Ile Trp Val Pro Ile Lys Pro Leu Pro Asn Ala Phe Val
                260                 265                 270

Val Asn Ile Gly Asp Ile Leu Glu Ile Leu Ser Asn Gly Ile Tyr Arg
            275                 280                 285

Ser Val Glu His Arg Ser Thr Val Asn Ala Thr Lys Glu Arg Leu Ser
            290                 295                 300

Val Ala Thr Phe Gln Asn Pro Lys Gln Glu Ser Val Ile Gly Pro Asn
305                 310                 315                 320

Met Ile Thr Pro Glu Arg Pro Ala Leu Phe Arg Lys Ile Val Tyr Lys
                325                 330                 335

Asp Tyr Met Lys Lys Leu Phe Ser Arg Lys Leu Asp Gly Lys Ser Phe
            340                 345                 350

Leu Asp Ser Leu Arg Ile Gly Glu Gly Asp Glu Arg Pro
                355                 360                 365

<210> SEQ ID NO 72
<211> LENGTH: 349
<212> TYPE: PRT
<213> ORGANISM: Papaver bracteatum

<400> SEQUENCE: 72

Met Glu Thr Leu Lys Thr Val Lys Pro Gly Gly Ser Leu Phe Ile Pro
1               5                   10                  15

Asn Gly Gln Glu Leu Ala Lys Gln Ser Leu Glu Glu Val Tyr Val Gly
            20                  25                  30

Asn Asp Gln Asp Thr Met Leu Leu Ile Gly Gln Thr Ile Pro Val Ile
        35                  40                  45

Asp Leu Gln Lys Leu Leu Ser Pro Glu Pro Ile Thr Gly Asp Met Glu
    50                  55                  60

Leu Asp Lys Leu His Ser Ala Cys Lys Glu Trp Gly Phe Phe Gln Val
65                  70                  75                  80

Val Asn His Gly Val Asp Ile Leu Leu Val Glu Lys Val Lys Ser Glu
                85                  90                  95

Val His Asp Phe Phe Asn Ile Pro Met Asp Glu Lys Lys Pro Phe Trp
            100                 105                 110

Gln Glu Glu Gly Asp Leu Glu Gly Phe Gly Gln Val Phe Ile Thr Ser
        115                 120                 125

Glu Asp Gln Gln Leu Asp Trp Gly Asp Met Phe Phe Met Val Thr Leu
    130                 135                 140
```

```
Pro Lys His Met Arg Lys Pro Arg Leu Phe Leu Lys Leu Pro Leu Pro
145                 150                 155                 160

Leu Arg Glu Thr Ile Glu Ser Tyr Ser Leu Lys Leu Ser Lys Leu Gly
                165                 170                 175

Val Thr Leu Val Glu Leu Met Gly Lys Ala Leu Gln Met Glu Asp Arg
            180                 185                 190

Ile Met Ser Glu Leu Phe Asp Asp Gly Arg Gln Thr Met Arg Met Asn
        195                 200                 205

Tyr Tyr Pro Pro Cys Pro Gln Pro Glu Gln Val Ile Gly Leu Thr Pro
    210                 215                 220

His Ser Asp Pro Gly Gly Leu Thr Ile Leu Glu Leu Asn Glu Val
225                 230                 235                 240

Asn Gly Leu Ile Arg Lys Glu Asn Ile Trp Val Pro Ile Pro Leu
                245                 250                 255

Pro Asn Ala Phe Ile Val Asn Ile Gly Asp Ile Leu Glu Ile Met Ser
            260                 265                 270

Asn Gly Ile Tyr His Ser Val Glu His Arg Ala Thr Ile Asn Ser Thr
        275                 280                 285

Lys Glu Arg Leu Ser Val Ala Met Phe Asn Ser Pro Lys Val Asp Thr
    290                 295                 300

Glu Ile Gly Pro Ile His Ser Met Ile Thr Pro Glu Thr Pro Ala Leu
305                 310                 315                 320

Phe Arg Thr Ile Gly Tyr Asp Glu Tyr Leu Lys Ile Phe Ser Arg
                325                 330                 335

Lys Leu Asp Gly Lys Ser Leu Leu Glu Ser Met Lys Ile
            340                 345
```

<210> SEQ ID NO 73
<211> LENGTH: 379
<212> TYPE: PRT
<213> ORGANISM: Papaver bracteatum
<220> FEATURE:
<221> NAME/KEY: MOD_RES
<222> LOCATION: (373)..(373)
<223> OTHER INFORMATION: Any amino acid
<220> FEATURE:
<221> NAME/KEY: MOD_RES
<222> LOCATION: (377)..(377)
<223> OTHER INFORMATION: Any amino acid

<400> SEQUENCE: 73

```
Met Glu Ala Pro Lys Leu Ile Met Leu Gly Gly Ser Leu Phe Val Pro
1               5                   10                  15

Ser Val Gln Glu Leu Ala Lys Gln Ser Leu Ala Glu Val Pro Val Arg
                20                  25                  30

Tyr Val Arg Asp Asp Gln Asp Thr Leu Gly Asn Asn Ile Asn Ile Thr
            35                  40                  45

Pro Met Ser Met Ile Asp Gln Ser Ile Pro Val Ile Asp Leu Glu Lys
        50                  55                  60

Leu Leu Ser Pro Glu Pro Ile Val Gly Glu Leu Glu Leu Glu Arg Leu
65                  70                  75                  80

His Ser Ala Cys Lys Glu Trp Gly Phe Phe Gln Val Val Asn His Gly
                85                  90                  95

Val Asp Ser Leu Leu Val Glu Lys Val Lys Ser Glu Ile Glu Gly Phe
            100                 105                 110

Phe Glu Leu Pro Val Asp Glu Lys Lys Lys Phe Trp Gln Glu Glu Gly
        115                 120                 125
```

```
Asp Ile Glu Gly Phe Gly Gln Ile Phe Val His Ser Glu Asp Gln Lys
            130                 135                 140

Leu Asp Trp Ala Asp Met Phe Tyr Met Leu Thr Leu Pro Pro Asn Met
145                 150                 155                 160

Arg Lys Pro Arg Leu Phe Pro Asn Leu Pro Leu Pro Leu Arg Gln Thr
                165                 170                 175

Ile Asp Ser Tyr Ser Ser Glu Leu Ser Lys Leu Val Leu Thr Leu Val
            180                 185                 190

Asp Leu Met Gly Lys Ala Leu Gln Met Glu Ser Gly Val Leu Thr Glu
        195                 200                 205

Leu Phe Glu Asn Gly Ile Gln Arg Met Arg Met Asn Tyr Tyr Pro Pro
210                 215                 220

Cys Pro Gln Pro Glu Gln Val Ile Gly Leu Thr Pro His Ser Asp Val
225                 230                 235                 240

Gly Gly Leu Thr Ile Leu Leu Gln Leu Asn Glu Val Asp Gly Leu Gln
                245                 250                 255

Ile Lys Lys Asp Lys Ile Trp Val Pro Ile Lys Pro Leu Arg Asn Ala
            260                 265                 270

Phe Val Val Asn Val Gly Asp Ala Leu Glu Ile Met Ser Asn Gly Ile
        275                 280                 285

Tyr Arg Ser Val Glu His Arg Ala Thr Ile Asn Ser Thr Lys Glu Arg
290                 295                 300

Leu Ser Ile Ala Thr Phe His Asn Pro Arg Ala Asp Arg Glu Ile Gly
305                 310                 315                 320

Pro Ile Pro Ser Met Ile Ser Pro Glu Thr Pro Ala Leu Phe Lys Thr
                325                 330                 335

Thr Gly Tyr Glu Glu Tyr Phe Lys Lys Phe Ser Arg Lys Leu Glu
            340                 345                 350

Gly Lys Ser Phe Leu Asp Ser Leu Arg Ile Gly Glu Gly Asp Glu His
        355                 360                 365

Cys Gly Arg Leu Xaa Val Lys Gly Xaa Cys Asn
370                 375
```

<210> SEQ ID NO 74
<211> LENGTH: 362
<212> TYPE: PRT
<213> ORGANISM: Papaver bracteatum

<400> SEQUENCE: 74

```
Met Glu Thr Pro Lys Leu Met Lys Leu Gly Gly Ser Leu Phe Val Pro
1               5                   10                  15

Ser Val Gln Glu Leu Ala Lys Gln Ser Leu Ala Glu Val Pro Ala Arg
            20                  25                  30

Tyr Val Arg Asp Asp Arg Asp Met Val Gly Asn Ile Ile Asn Val Thr
        35                  40                  45

Pro Met Ser Met Ile Asp Gln Ser Ile Pro Val Ile Asp Leu Glu Lys
    50                  55                  60

Leu Leu Ser Pro Asp Leu Ile Val Gly Glu Leu Glu Leu Glu Arg Leu
65                  70                  75                  80

His Ser Ala Cys Lys Glu Trp Gly Phe Phe Gln Val Val Asn His Gly
                85                  90                  95

Val Asp Ser Leu Leu Val Glu Lys Val Lys Ser Glu Ile Glu Gly Phe
            100                 105                 110

Phe Glu Leu Pro Met Asp Glu Lys Lys Lys Phe Trp Gln Glu Glu Gly
```

```
            115                 120                 125
Asp Ala Glu Gly Phe Ala Gln Phe Val Gln Ser Glu Asp Gln Lys
    130                 135                 140

Leu Asp Tyr Ser Gly Asp Met Phe Phe Met Leu Asn Leu Pro Gln His
145                 150                 155                 160

Met Arg Lys Pro Arg Leu Phe Leu Lys Leu Pro Leu Pro Leu Arg Glu
                165                 170                 175

Thr Ile Glu Ser Tyr Ser Leu Lys Leu Ser Lys Leu Gly Val Thr Leu
                180                 185                 190

Val Glu Leu Met Gly Lys Ala Leu Gln Met Glu Asp Arg Ile Met Ser
                195                 200                 205

Glu Leu Phe Asp Asp Gly Arg Gln Thr Met Arg Met Asn Tyr Tyr Pro
    210                 215                 220

Pro Cys Pro Gln Pro Glu Gln Val Ile Gly Leu Thr Pro His Ser Asp
225                 230                 235                 240

Pro Gly Gly Leu Thr Ile Leu Leu Glu Leu Asn Glu Val Asn Gly Leu
                245                 250                 255

Ile Arg Lys Glu Asn Ile Trp Val Pro Ile Ile Pro Leu Pro Asn Ala
                260                 265                 270

Phe Ile Val Asn Ile Gly Asp Ile Leu Glu Ile Met Ser Asn Gly Ile
            275                 280                 285

Tyr His Ser Val Glu His Arg Ala Thr Ile Asn Ser Thr Lys Glu Arg
    290                 295                 300

Leu Ser Val Ala Met Phe Asn Ser Pro Lys Val Asp Thr Glu Ile Gly
305                 310                 315                 320

Pro Ile His Ser Met Ile Thr Pro Glu Thr Pro Ala Leu Phe Arg Thr
                325                 330                 335

Ile Gly Tyr Asp Glu Tyr Leu Lys Ile Phe Phe Ser Arg Lys Leu Asp
                340                 345                 350

Gly Lys Ser Leu Leu Glu Ser Met Lys Ile
            355                 360

<210> SEQ ID NO 75
<211> LENGTH: 365
<212> TYPE: PRT
<213> ORGANISM: Papaver bracteatum

<400> SEQUENCE: 75

Met Glu Thr Pro Lys Leu Arg Asp Phe Gly Ser Phe Leu Pro Val Pro
1               5                   10                  15

Ser Val Gln Glu Leu Ala Lys Gln Val Leu Thr Glu Ile Pro Pro Arg
                20                  25                  30

Tyr Ile Arg Thr Asp Leu Glu Ala Leu Asn Lys Leu Ser Cys Ala Ser
            35                  40                  45

Asn Thr Asp Gln Thr Val Pro Ile Ile Asp Met Gln Cys Leu Leu Ser
    50                  55                  60

Ala Glu Pro Glu Met Glu Leu Glu Lys Leu His Ser Ala Cys Lys Glu
65                  70                  75                  80

Trp Gly Phe Phe Arg Val Val Asn His Gly Val Asp Asn Leu Glu Ser
                85                  90                  95

Val Lys Ser Glu Ile Glu Ser Phe Leu Asn Leu Pro Val Asn Ala Lys
                100                 105                 110

Asn Lys Tyr Gly Gln Lys Gln Gly Asp Asp Gln Gly Phe Gly Ser Arg
            115                 120                 125
```

```
Phe Val Leu Ser Glu Glu Gln Lys Leu Asp Trp Gly Asp Phe Tyr
    130                 135                 140

Met Val Thr Arg Pro Leu Tyr Leu Arg Lys Pro His Leu Phe Pro Glu
145                 150                 155                 160

Leu Pro Leu Pro Leu Arg Glu Thr Ile Glu Ser Tyr Ser Ser Glu Val
                165                 170                 175

Ser Lys Leu Ala Met Ala Leu Phe Glu Met Met Gly Lys Ala Leu Lys
            180                 185                 190

Ile Glu Thr Gly Val Met Thr Glu Ile Phe Glu Gly Gly Met Gln Ala
                195                 200                 205

Met Arg Met Asn Tyr Tyr Pro Pro Cys Pro Arg Pro Asp Leu Val Ile
210                 215                 220

Gly Leu Asn Ala His Ser Asp Phe Gly Gly Leu Thr Ile Leu Leu Gln
225                 230                 235                 240

Leu Asn Glu Val Glu Gly Leu Glu Ile Arg Asn Lys Gly Glu Trp Val
                245                 250                 255

Ser Val Lys Pro Leu Ala Asn Ala Phe Val Val Asn Val Gly Asp Val
                260                 265                 270

Met Glu Ile Leu Thr Asn Gly Ile Tyr His Ser Val Glu His Arg Ala
                275                 280                 285

Thr Ile Asn Ser Ser Lys Glu Arg Leu Ser Val Ala Thr Phe His Tyr
    290                 295                 300

Pro Lys Leu Glu Thr Gly Ile Gly Pro Leu Pro Cys Met Ile Thr Pro
305                 310                 315                 320

Lys Thr Pro Ala Leu Phe Gly Arg Ile Glu Arg Tyr Glu Leu Leu Leu
                325                 330                 335

Arg Lys Tyr Tyr Ala Arg Lys Leu Asn Gly Lys Ser Thr Leu Asp Cys
            340                 345                 350

Met Arg Ile Gly Asn Gly Phe Glu Asp Asp Asn Thr Ala
            355                 360                 365

<210> SEQ ID NO 76
<211> LENGTH: 370
<212> TYPE: PRT
<213> ORGANISM: Papaver bracteatum

<400> SEQUENCE: 76

Met Glu Ala Pro Lys Leu Ile Met Leu Gly Gly Ser Leu Phe Val Pro
1               5                   10                  15

Ser Val Gln Glu Leu Ala Lys Gln Ser Leu Ala Glu Val Pro Ala Arg
                20                  25                  30

Tyr Val Arg Asp Asp Gln Asp Thr Leu Gly Asn Asn Ile Asn Ile Thr
            35                  40                  45

Pro Met Ser Met Ile Asp Gln Ser Ile Pro Val Ile Asp Leu Glu Lys
    50                  55                  60

Leu Leu Ser Pro Glu Pro Ile Val Gly Glu Leu Glu Leu Glu Arg Leu
65                  70                  75                  80

His Ser Ala Cys Lys Glu Trp Gly Phe Phe Gln Val Val Asn His Gly
                85                  90                  95

Val Asp Ser Leu Leu Val Glu Lys Val Lys Ser Glu Ile Glu Gly Phe
                100                 105                 110

Phe Glu Leu Pro Val Asp Glu Lys Lys Phe Trp Gln Glu Glu Gly
            115                 120                 125

Asp Ile Glu Gly Phe Gly Gln Ile Phe Val His Ser Glu Asp Gln Lys
            130                 135                 140
```

-continued

```
Leu Asp Trp Ala Asp Met Phe Tyr Met Leu Thr Leu Pro Pro Asn Met
145                 150                 155                 160

Arg Lys Pro Arg Leu Phe Pro Asn Leu Pro Leu Pro Leu Arg Gln Thr
                165                 170                 175

Ile Asp Ser Tyr Ser Ser Glu Leu Ser Lys Leu Val Leu Thr Leu Val
            180                 185                 190

Asp Leu Met Gly Lys Ala Leu Gln Met Glu Ser Gly Val Leu Thr Glu
        195                 200                 205

Leu Phe Glu Asn Gly Ile Gln Arg Met Arg Met Asn Tyr Tyr Pro Pro
    210                 215                 220

Cys Pro Gln Pro Glu Gln Val Ile Gly Leu Thr Pro His Ser Glu Val
225                 230                 235                 240

Gly Gly Leu Thr Ile Leu Leu Gln Leu Asn Glu Val Asp Gly Leu Gln
                245                 250                 255

Ile Arg Lys Glu Lys Ile Trp Val Pro Ile Lys Pro Leu Ser Asn Ala
            260                 265                 270

Phe Ile Val Asn Ile Gly Asp Ile Leu Glu Ile Met Ser Asn Gly Ile
        275                 280                 285

Tyr Arg Ser Val Glu His Arg Ala Thr Val Asn Ser Thr Lys Glu Arg
    290                 295                 300

Leu Ser Val Ala Thr Phe His Ser Pro Arg Lys Asp Thr Glu Ile Gly
305                 310                 315                 320

Pro Ile Leu Ile Thr Pro Glu Thr Pro Ala Leu Phe Arg Thr Ser Gly
                325                 330                 335

Phe Glu Asp Tyr Phe Arg Lys Phe Ala His Lys Leu Asn Gly Lys
            340                 345                 350

Ser Phe Leu Ser Ser Ile Arg Ile Gly Glu Thr Asp Glu Gly Asn Asn
        355                 360                 365

Ala Thr
    370

<210> SEQ ID NO 77
<211> LENGTH: 313
<212> TYPE: PRT
<213> ORGANISM: Papaver bracteatum

<400> SEQUENCE: 77

Met Ser Met Ile Asp Gln Ser Ile Pro Val Ile Asp Leu Glu Lys Leu
1               5                   10                  15

Leu Ser Pro Glu Pro Ile Val Gly Glu Leu Glu Leu Glu Arg Leu His
            20                  25                  30

Ser Ala Cys Lys Glu Trp Gly Phe Phe Gln Val Val Asn His Gly Val
        35                  40                  45

Asp Ser Leu Leu Val Glu Lys Val Lys Ser Glu Ile Glu Gly Phe Phe
    50                  55                  60

Glu Leu Pro Val Asp Glu Lys Lys Phe Trp Gln Glu Glu Gly Asp
65                  70                  75                  80

Ile Glu Gly Phe Gly Gln Ile Phe Val His Ser Glu Asp Gln Lys Leu
                85                  90                  95

Asp Trp Ala Asp Met Phe Tyr Met Leu Thr Leu Pro Asn Met Arg
            100                 105                 110

Lys Pro Arg Leu Phe Pro Asn Leu Pro Leu Pro Leu Arg Gln Thr Ile
        115                 120                 125

Asp Ser Tyr Ser Ser Glu Leu Ser Lys Leu Val Leu Thr Leu Val Asp
```

```
                130                 135                 140
Leu Met Gly Lys Ala Leu Gln Met Glu Ser Gly Val Leu Thr Glu Leu
145                 150                 155                 160

Phe Glu Asn Gly Ile Gln Arg Met Arg Met Asn Tyr Tyr Pro Pro Cys
                165                 170                 175

Pro Gln Pro Glu Gln Val Ile Gly Leu Thr Pro His Ser Asp Val Gly
                180                 185                 190

Gly Leu Thr Ile Leu Leu Gln Leu Asn Glu Val Asp Gly Leu Gln Ile
                195                 200                 205

Arg Lys Glu Lys Ile Trp Val Pro Ile Lys Pro Leu Ser Asn Ala Phe
                210                 215                 220

Ile Val Asn Ile Gly Asp Ile Leu Glu Ile Met Ser Asn Gly Ile Tyr
225                 230                 235                 240

His Ser Val Glu His Arg Ala Thr Ile Asn Ser Thr Lys Glu Arg Leu
                245                 250                 255

Ser Val Ala Met Phe Asn Ser Pro Lys Val Asp Thr Glu Ile Gly Pro
                260                 265                 270

Ile His Ser Met Ile Thr Pro Glu Thr Pro Ala Leu Phe Arg Thr Ile
                275                 280                 285

Gly Tyr Asp Glu Tyr Leu Lys Ile Phe Phe Ser Arg Lys Leu Asp Gly
                290                 295                 300

Lys Ser Leu Leu Glu Ser Met Lys Ile
305                 310

<210> SEQ ID NO 78
<211> LENGTH: 365
<212> TYPE: PRT
<213> ORGANISM: Papaver bracteatum

<400> SEQUENCE: 78

Met Glu Thr Pro Lys Leu Val Lys Ser Ser Gly Ser Ser Leu Phe Leu
1               5                   10                  15

Ser Thr Ser Val Gln Glu Leu Ala Lys Gln Ser Leu Pro Glu Val Pro
                20                  25                  30

Ala Arg Tyr Ile Arg Thr Asn Leu Glu Pro Leu Ser Asn Val Ser Gly
                35                  40                  45

Asp Ser Gln Ser Val Pro Val Ile Asp Leu Gln Lys Leu Leu Ser Ser
                50                  55                  60

Glu Pro Ile Ile Gly Glu Leu Glu Leu Asp Lys Leu His Ser Ala Cys
65                  70                  75                  80

Lys Glu Trp Gly Phe Phe Gln Val Val Asn His Gly Val Asp Asn Leu
                85                  90                  95

Val Met Glu Lys Ile Lys Thr Glu Ile Gln Gly Phe Phe Asn Leu Ser
                100                 105                 110

Leu Asp Glu Lys Gln Lys Phe Trp Lys Lys Glu Gly Asp Ala Glu Gly
                115                 120                 125

Phe Gly Gln Asn Phe Ile Glu Ser Asp Gln Lys Leu Asp Trp Gly
                130                 135                 140

Asp Thr Phe Gly Met Phe Thr Leu Pro Ile His Met Arg Asn Pro Arg
145                 150                 155                 160

Leu Phe Pro Glu Leu Pro Leu Pro Leu Arg Glu Thr Ile Glu Ser Tyr
                165                 170                 175

Ser Leu Asp Val Arg Lys Leu Ala Leu Ala Leu Ile Gly Leu Met Glu
                180                 185                 190
```

```
Lys Ala Leu Lys Ile Lys Thr Ser Ala Met Ser Glu Leu Phe Glu Asp
            195                 200                 205

Gly Gly Gln Ala Met Arg Met Asn Tyr Tyr Pro Pro Cys Pro Gln Pro
    210                 215                 220

Glu His Val Ile Gly Leu Thr Pro His Ser Asp Ala Gly Gly Leu Thr
225                 230                 235                 240

Ile Leu Leu Gln Leu Asn Glu Val Asp Gly Leu Gln Ile Lys Lys Asp
                245                 250                 255

Lys Ile Trp Val Pro Ile Lys Pro Leu Pro Asn Ala Phe Val Val Asn
            260                 265                 270

Ile Gly Asp Ile Leu Glu Ile Met Thr Asn Gly Ile Tyr Arg Ser Val
        275                 280                 285

Glu His Arg Ala Thr Ile Asn Ser Ser Lys Glu Arg Leu Ser Val Ala
    290                 295                 300

Ala Phe His Ser Pro Lys Gly Asp Thr Leu Ile Gly Pro Met Val Ser
305                 310                 315                 320

Leu Ile Thr Pro Glu Thr Pro Ala Leu Phe Arg Thr Ile Gly Tyr Gln
                325                 330                 335

Asp Tyr Met Lys Lys Phe Met Ser Arg Lys Leu Asp Gly Lys Ser Leu
            340                 345                 350

Val Asn Ser Met Arg Ile Gly Glu Gly Asp Glu Asp Lys
        355                 360                 365

<210> SEQ ID NO 79
<211> LENGTH: 356
<212> TYPE: PRT
<213> ORGANISM: Papaver bracteatum

<400> SEQUENCE: 79

Met Glu Thr Pro Thr Leu Met Lys Leu Gly Asn Gly Leu Ser Val Pro
1               5                   10                  15

Ser Val Gln Glu Leu Ala Lys Ala Thr Leu Ala Glu Ile Pro Ser Arg
            20                  25                  30

Tyr Ile Cys Thr Asp Glu Asn Leu Leu Thr Met Gly Ala Ser Thr Thr
        35                  40                  45

Asp Asn Glu Thr Val Pro Val Ile Asp Leu Gln Asn Leu Leu Ser Pro
50                  55                  60

Glu Pro Val Ile Gly Met Leu Glu Leu Asp Arg Leu His Ser Ala Cys
65                  70                  75                  80

Lys Glu Trp Gly Phe Phe Gln Leu Val Asn His Gly Val Asp Ala Leu
                85                  90                  95

Leu Val Asp Asn Glu Val Gln Gly Phe Phe Asn Leu Pro Met Asp Glu
            100                 105                 110

Lys Thr Lys Tyr Gly Gln Lys Asp Gly Asp Glu Gly Phe Gly Gln
        115                 120                 125

Phe Phe Val Ile Ser Glu Asp Gln Lys Leu Asp Trp Ala Asp Val Phe
130                 135                 140

Tyr Met Ser Thr Leu Pro Leu His Ser Arg Lys Pro His Leu Phe Pro
145                 150                 155                 160

Glu Leu Pro Leu Pro Leu Arg Gly Thr Met Glu Ser Tyr Ser Ser Glu
                165                 170                 175

Met Lys Lys Leu Ser Met Val Leu Phe Asp Met Met Gly Lys Ala Leu
            180                 185                 190

Gln Val Val Glu Ile Lys Gly Ile Thr Glu Leu Phe Glu Asp Gly Ala
        195                 200                 205
```

```
Gln Gln Ile Arg Met Asn Tyr Tyr Pro Pro Cys Pro Gln Pro Glu Leu
        210                 215                 220

Val Phe Gly Leu Thr Ser His Ser Asp Phe Asp Gly Leu Thr Ile Leu
225                 230                 235                 240

Leu Gln Leu Gly Glu Val Glu Gly Leu Gln Ile Lys Lys Glu Glu Arg
                245                 250                 255

Trp Ile Ser Ile Lys Pro Leu Pro Asp Ala Phe Ile Val Asn Val Gly
                260                 265                 270

Asp Ile Leu Glu Ile Met Thr Asn Gly Ile Tyr Arg Ser Val Asp His
            275                 280                 285

Arg Ala Val Val Asn Ser Ile Lys Glu Arg Leu Thr Ile Ala Thr Phe
290                 295                 300

His Asp Pro Arg Leu Glu Ala Glu Ile Gly Pro Ile Ser Ser Leu Ile
305                 310                 315                 320

Thr Pro Glu Thr Pro Ala Leu Phe Lys Arg Gly Val Phe Glu Asp Leu
                325                 330                 335

Leu Lys Glu Met Phe Leu Arg Lys Leu Asp Gly Lys Ser Phe Leu Asp
                340                 345                 350

Cys Met Arg Met
            355

<210> SEQ ID NO 80
<211> LENGTH: 350
<212> TYPE: PRT
<213> ORGANISM: Papaver rhoeas

<400> SEQUENCE: 80

Gly Asn Gly Leu Ser Val Pro Ser Val Gln Glu Leu Ala Lys Gln Thr
1               5                   10                  15

Leu Ala Glu Ile Pro Ser Arg Tyr Ile Cys Thr Asp Glu Asn Pro Leu
                20                  25                  30

Ile Thr Gly Ala Ser Val Val Asp Asp Glu Thr Val Pro Val Ile Asn
            35                  40                  45

Leu Gln Asn Leu Leu Ser Pro Glu Pro Val Ile Gly Lys Leu Glu Leu
50                  55                  60

Asp Lys Leu His Ser Ala Cys Lys Glu Trp Gly Phe Phe Gln Val Val
65                  70                  75                  80

Asn His Gly Val Asn Asp Ser Leu Val Asp Ser Val Lys Ser Glu Ile
                85                  90                  95

Glu Gly Phe Phe Asn Leu Pro Ala Asn Glu Lys Leu Leu Tyr Gly Gln
                100                 105                 110

Lys Asp Gly Asp Val Glu Gly Phe Gly Gln His Phe Val Val Ser Glu
            115                 120                 125

Asp Gln Lys Leu Asp Trp Ala Asp Val Phe Tyr Met Val Thr Leu Pro
130                 135                 140

Val Arg Leu Arg Lys Pro His Leu Phe Pro Glu Leu Pro Leu Pro Leu
145                 150                 155                 160

Arg Asp Thr Leu Asp Ser Tyr Ser Ser Glu Leu Asn Lys Leu Ser Met
                165                 170                 175

Val Leu Leu Glu Met Met Glu Lys Ala Leu Lys Leu Val Glu Cys Lys
                180                 185                 190

Gly Ile Thr Asp Phe Phe Glu Asp Gly Phe Gln Gln Met Arg Met Asn
            195                 200                 205

Tyr Tyr Pro Pro Cys Pro Arg Pro Glu Leu Val Thr Gly Leu Thr Ser
```

```
                210                 215                 220
His Ser Asp Phe Gly Gly Leu Thr Ile Leu Leu Gln Leu Asn Asp Val
225                 230                 235                 240

Glu Gly Leu Gln Ile Lys Lys Glu Arg Trp Ile Ser Ile Lys Pro
            245                 250                 255

Leu Pro Asn Ala Phe Ile Val Asn Ile Gly Asp Val Leu Glu Ile Met
            260                 265                 270

Ser Asn Gly Ile Tyr Arg Ser Val Asp His Arg Ala Val Ile Asn Ser
            275                 280                 285

Thr Lys Val Arg Met Ser Val Ala Thr Phe His Asp Pro Arg Leu Glu
290                 295                 300

Ala Val Ile Gly Pro Ile Ser Ser Leu Ile Thr Pro Glu Thr Pro Ala
305                 310                 315                 320

Leu Phe Lys Arg Gly Val Phe Glu Asp Leu Leu Lys Glu Met Phe Leu
            325                 330                 335

Arg Lys Leu Asp Gly Lys Ser Phe Leu Asp Cys Met Arg Ile
            340                 345                 350
```

<210> SEQ ID NO 81
<211> LENGTH: 351
<212> TYPE: PRT
<213> ORGANISM: Papaver setigerum

<400> SEQUENCE: 81

```
Leu Met Lys Leu Ala Asn Gly Met Ser Val Pro Ile Val Gln Glu Leu
1               5                   10                  15

Ala Lys Leu Thr Val Gly Glu Ile Pro Ser Arg Tyr Ile Cys Thr Asp
            20                  25                  30

Gly Asn Leu Leu Thr Met Gly Ala Ser Val Ile Asp Tyr Glu Thr Val
            35                  40                  45

Pro Val Ile Asp Leu Gln Asn Leu Gln Ser Arg Glu Pro Val Ile Glu
            50                  55                  60

Lys Leu Glu Leu Asp Arg Leu His Ser Ala Cys Lys Glu Trp Gly Phe
65                  70                  75                  80

Phe Gln Leu Leu Asn His Gly Val Asp Ala Ser Leu Met Asp Asn Val
                85                  90                  95

Arg Ser Glu Ile Arg Gly Phe Phe Asn Leu Pro Ile Ser Asp Lys Met
            100                 105                 110

Lys Tyr Gly Gln Lys Asp Gly Asp Glu Glu Gly Phe Gly Gln His Phe
            115                 120                 125

Ile Val Ser Glu Asp Gln Lys Leu Asp Trp Val Asp Ala Phe Met Met
            130                 135                 140

Phe Thr Leu Pro Leu His Ser Arg Asn Pro Arg Leu Thr Pro Glu Phe
145                 150                 155                 160

Pro Gln Pro Leu Arg Glu Thr Val Glu Ser Tyr Ser Ser Glu Met Lys
            165                 170                 175

Lys Leu Ser Val Leu Leu Phe Glu Leu Met Glu Lys Ala Leu Gln Val
            180                 185                 190

Lys Gly Ile Thr Glu Met Phe Glu Asp Gly Leu Gln Ser Ile Arg Met
            195                 200                 205

Asn Tyr Tyr Pro Pro Cys Pro Arg Pro Glu Leu Ala Ile Gly Leu Thr
            210                 215                 220

Ser His Ser Asp Phe Asp Gly Leu Thr Ile Leu Leu Gln Leu Asn Glu
225                 230                 235                 240
```

Val Glu Gly Leu Gln Ile Lys Lys Glu Glu Arg Trp Ile Ser Ile Lys
            245                 250                 255

Pro Leu Pro Asn Ala Phe Ile Val Asn Val Gly Asp Val Leu Glu Val
            260                 265                 270

Met Thr Asn Gly Ile Tyr Arg Ser Val Asp His Arg Ala Val Val Asn
            275                 280                 285

Ser Thr Lys Glu Arg Leu Ser Ile Ala Thr Phe His Asp Pro Glu Leu
            290                 295                 300

Glu Ser Glu Ile Gly Pro Ile Ala Ser Leu Ile Thr Pro Glu Thr Pro
305                 310                 315                 320

Ala Leu Phe Lys Arg Gly Arg Phe Lys Asp Leu Leu Lys Glu Asn Leu
            325                 330                 335

Ser Thr Lys Leu Asp Gly Lys Ser Phe Leu Asp Cys Ile Arg Met
            340                 345                 350

<210> SEQ ID NO 82
<211> LENGTH: 497
<212> TYPE: PRT
<213> ORGANISM: Homo sapiens

<400> SEQUENCE: 82

Met Gly Leu Glu Ala Leu Val Pro Leu Ala Val Ile Val Ala Ile Phe
1               5                   10                  15

Leu Leu Leu Val Asp Leu Met His Arg Arg Gln Arg Trp Ala Ala Arg
            20                  25                  30

Tyr Ser Pro Gly Pro Leu Pro Leu Pro Gly Leu Gly Asn Leu Leu His
            35                  40                  45

Val Asp Phe Gln Asn Thr Pro Tyr Cys Phe Asp Gln Leu Arg Arg Arg
50                  55                  60

Phe Gly Asp Val Phe Ser Leu Gln Leu Ala Trp Thr Pro Val Val Val
65                  70                  75                  80

Leu Asn Gly Leu Ala Ala Val Arg Glu Ala Leu Val Thr His Gly Glu
            85                  90                  95

Asp Thr Ala Asp Arg Pro Pro Val Pro Ile Thr Gln Ile Leu Gly Phe
            100                 105                 110

Gly Pro Arg Ser Gln Gly Val Phe Leu Ala Arg Tyr Gly Pro Ala Trp
            115                 120                 125

Arg Glu Gln Arg Arg Phe Ser Val Ser Thr Leu Arg Asn Leu Gly Leu
            130                 135                 140

Gly Lys Lys Ser Leu Glu Gln Trp Val Thr Glu Glu Ala Ala Cys Leu
145                 150                 155                 160

Cys Ala Ala Phe Ala Asn His Ser Gly Arg Pro Phe Arg Pro Asn Gly
            165                 170                 175

Leu Leu Asp Lys Ala Val Ser Asn Val Ile Ala Ser Leu Thr Cys Gly
            180                 185                 190

Arg Arg Phe Glu Tyr Asp Asp Pro Arg Phe Leu Arg Leu Leu Asp Leu
            195                 200                 205

Ala Gln Glu Gly Leu Lys Glu Glu Ser Gly Phe Leu Arg Glu Val Leu
            210                 215                 220

Asn Ala Val Pro Val Leu Leu His Ile Pro Ala Leu Ala Gly Lys Val
225                 230                 235                 240

Leu Arg Phe Gln Lys Ala Phe Leu Thr Gln Leu Asp Glu Leu Leu Thr
            245                 250                 255

Glu His Arg Met Thr Trp Asp Pro Ala Gln Pro Pro Arg Asp Leu Thr
            260                 265                 270

```
Glu Ala Phe Leu Ala Glu Met Glu Lys Ala Lys Gly Asn Pro Glu Ser
            275                 280                 285

Ser Phe Asn Asp Glu Asn Leu Arg Ile Val Val Ala Asp Leu Phe Ser
    290                 295                 300

Ala Gly Met Val Thr Thr Ser Thr Thr Leu Ala Trp Gly Leu Leu Leu
305                 310                 315                 320

Met Ile Leu His Pro Asp Val Gln Arg Val Gln Gln Glu Ile Asp
                325                 330                 335

Asp Val Ile Gly Gln Val Arg Arg Pro Glu Met Gly Asp Gln Ala His
            340                 345                 350

Met Pro Tyr Thr Thr Ala Val Ile His Glu Val Gln Arg Phe Gly Asp
            355                 360                 365

Ile Val Pro Leu Gly Val Thr His Met Thr Ser Arg Asp Ile Glu Val
            370                 375                 380

Gln Gly Phe Arg Ile Pro Lys Gly Thr Thr Leu Ile Thr Asn Leu Ser
385                 390                 395                 400

Ser Val Leu Lys Asp Glu Ala Val Trp Glu Lys Pro Phe Arg Phe His
                405                 410                 415

Pro Glu His Phe Leu Asp Ala Gln Gly His Phe Val Lys Pro Glu Ala
                420                 425                 430

Phe Leu Pro Phe Ser Ala Gly Arg Arg Ala Cys Leu Gly Glu Pro Leu
            435                 440                 445

Ala Arg Met Glu Leu Phe Leu Phe Phe Thr Ser Leu Leu Gln His Phe
            450                 455                 460

Ser Phe Ser Val Pro Thr Gly Gln Pro Arg Pro Ser His His Gly Val
465                 470                 475                 480

Phe Ala Phe Leu Val Thr Pro Ser Pro Tyr Glu Leu Cys Ala Val Pro
                485                 490                 495

Arg

<210> SEQ ID NO 83
<211> LENGTH: 1049
<212> TYPE: PRT
<213> ORGANISM: Bacillus megaterium

<400> SEQUENCE: 83

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Ala Lys Phe Ala Arg
65                  70                  75                  80

Asp Phe Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140
```

```
Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Ala Asp Glu Val Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Ala Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Val Met Val Leu Ile Pro Gln Leu His Arg Asp Lys Thr Val Trp
        355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Lys Gly Phe Val Val Lys
        435                 440                 445

Ala Lys Ser Lys Lys Ile Pro Leu Gly Gly Ile Pro Ser Pro Ser Thr
        450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560
```

```
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
            580                 585                 590
Lys Gly Ala Glu Asn Ile Ala Asp Arg Gly Glu Ala Asp Ala Ser Asp
        595                 600                 605
Asp Phe Glu Gly Thr Tyr Glu Glu Trp Arg Glu His Met Trp Ser Asp
    610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
            660                 665                 670
Leu Gln Gln Pro Gly Ser Ala Arg Ser Thr Arg His Leu Glu Ile Glu
        675                 680                 685
Leu Pro Lys Glu Ala Ser Tyr Gln Glu Gly Asp His Leu Gly Val Ile
    690                 695                 700
Pro Arg Asn Tyr Glu Gly Ile Val Asn Arg Val Thr Ala Arg Phe Gly
705                 710                 715                 720
Leu Asp Ala Ser Gln Gln Ile Arg Leu Glu Ala Glu Glu Lys Leu
                725                 730                 735
Ala His Leu Pro Leu Ala Lys Thr Val Ser Val Glu Leu Leu Gln
            740                 745                 750
Tyr Val Glu Leu Gln Asp Pro Val Thr Arg Thr Gln Leu Arg Ala Met
        755                 760                 765
Ala Ala Lys Thr Val Cys Pro Pro His Lys Val Glu Leu Glu Ala Leu
    770                 775                 780
Leu Glu Lys Gln Ala Tyr Lys Glu Gln Val Leu Ala Lys Arg Leu Thr
785                 790                 795                 800
Met Leu Glu Leu Leu Glu Lys Tyr Pro Ala Cys Glu Met Lys Phe Ser
                805                 810                 815
Glu Phe Ile Ala Leu Leu Pro Ser Ile Arg Pro Arg Tyr Tyr Ser Ile
            820                 825                 830
Ser Ser Ser Pro Arg Val Asp Glu Lys Gln Ala Ser Ile Thr Val Ser
        835                 840                 845
Val Val Ser Gly Glu Ala Trp Ser Gly Tyr Gly Glu Tyr Lys Gly Ile
    850                 855                 860
Ala Ser Asn Tyr Leu Ala Glu Leu Gln Glu Gly Asp Thr Ile Thr Cys
865                 870                 875                 880
Phe Ile Ser Thr Pro Gln Ser Glu Phe Thr Leu Pro Lys Asp Pro Glu
                885                 890                 895
Thr Pro Leu Ile Met Val Gly Pro Gly Thr Gly Val Ala Pro Phe Arg
            900                 905                 910
Gly Phe Val Gln Ala Arg Lys Gln Leu Lys Glu Gln Gly Gln Ser Leu
        915                 920                 925
Gly Glu Ala His Leu Tyr Phe Gly Cys Arg Ser Pro His Glu Asp Tyr
    930                 935                 940
Leu Tyr Gln Glu Glu Leu Glu Asn Ala Gln Ser Glu Gly Ile Ile Thr
945                 950                 955                 960
Leu His Thr Ala Phe Ser Arg Met Pro Asn Gln Pro Lys Thr Tyr Val
                965                 970                 975
Gln His Val Met Glu Gln Asp Gly Lys Lys Leu Ile Glu Leu Leu Asp
```

```
                    980                 985                 990
Gln Gly Ala His Phe Tyr Ile Cys Gly Asp Gly Ser Gln Met Ala Pro
        995                1000                1005

Ala Val Glu Ala Thr Leu Met Lys Ser Tyr Ala Asp Val His Gln
       1010                1015                1020

Val Ser Glu Ala Asp Ala Arg Leu Trp Leu Gln Gln Leu Glu Glu
       1025                1030                1035

Lys Gly Arg Tyr Ala Lys Asp Val Trp Ala Gly
       1040                1045

<210> SEQ ID NO 84
<211> LENGTH: 503
<212> TYPE: PRT
<213> ORGANISM: Homo sapiens

<400> SEQUENCE: 84

Met Ala Leu Ile Pro Asp Leu Ala Met Glu Thr Trp Leu Leu Leu Ala
1               5                   10                  15

Val Ser Leu Val Leu Leu Tyr Leu Tyr Gly Thr His Ser His Gly Leu
                20                  25                  30

Phe Lys Lys Leu Gly Ile Pro Gly Pro Thr Pro Leu Pro Phe Leu Gly
            35                  40                  45

Asn Ile Leu Ser Tyr His Lys Gly Phe Cys Met Phe Asp Met Glu Cys
        50                  55                  60

His Lys Lys Tyr Gly Lys Val Trp Gly Phe Tyr Asp Gly Gln Gln Pro
65                  70                  75                  80

Val Leu Ala Ile Thr Asp Pro Asp Met Ile Lys Thr Val Leu Val Lys
                85                  90                  95

Glu Cys Tyr Ser Val Phe Thr Asn Arg Arg Pro Phe Gly Pro Val Gly
            100                 105                 110

Phe Met Lys Ser Ala Ile Ser Ile Ala Glu Asp Glu Glu Trp Lys Arg
        115                 120                 125

Leu Arg Ser Leu Leu Ser Pro Thr Phe Thr Ser Gly Lys Leu Lys Glu
    130                 135                 140

Met Val Pro Ile Ile Ala Gln Tyr Gly Asp Val Leu Val Arg Asn Leu
145                 150                 155                 160

Arg Arg Glu Ala Glu Thr Gly Lys Pro Val Thr Leu Lys Asp Val Phe
                165                 170                 175

Gly Ala Tyr Ser Met Asp Val Ile Thr Ser Thr Ser Phe Gly Val Asn
            180                 185                 190

Ile Asp Ser Leu Asn Asn Pro Gln Asp Pro Phe Val Glu Asn Thr Lys
        195                 200                 205

Lys Leu Leu Arg Phe Asp Phe Leu Asp Pro Phe Phe Leu Ser Ile Thr
    210                 215                 220

Val Phe Pro Phe Leu Ile Pro Ile Leu Glu Val Leu Asn Ile Cys Val
225                 230                 235                 240

Phe Pro Arg Glu Val Thr Asn Phe Leu Arg Lys Ser Val Lys Arg Met
                245                 250                 255

Lys Glu Ser Arg Leu Glu Asp Thr Gln Lys His Arg Val Asp Phe Leu
            260                 265                 270

Gln Leu Met Ile Asp Ser Gln Asn Ser Lys Glu Thr Glu Ser His Lys
        275                 280                 285

Ala Leu Ser Asp Leu Glu Leu Val Ala Gln Ser Ile Ile Phe Ile Phe
    290                 295                 300
```

```
Ala Gly Tyr Glu Thr Thr Ser Ser Val Leu Ser Phe Ile Met Tyr Glu
305                 310                 315                 320

Leu Ala Thr His Pro Asp Val Gln Gln Lys Leu Gln Glu Glu Ile Asp
            325                 330                 335

Ala Val Leu Pro Asn Lys Ala Pro Pro Thr Tyr Asp Thr Val Leu Gln
        340                 345                 350

Met Glu Tyr Leu Asp Met Val Val Asn Glu Thr Leu Arg Leu Phe Pro
    355                 360                 365

Ile Ala Met Arg Leu Glu Arg Val Cys Lys Lys Asp Val Glu Ile Asn
370                 375                 380

Gly Met Phe Ile Pro Lys Gly Val Val Met Ile Pro Ser Tyr Ala
385                 390                 395                 400

Leu His Arg Asp Pro Lys Tyr Trp Thr Glu Pro Glu Lys Phe Leu Pro
                405                 410                 415

Glu Arg Phe Ser Lys Lys Asn Lys Asp Asn Ile Asp Pro Tyr Ile Tyr
                420                 425                 430

Thr Pro Phe Gly Ser Gly Pro Arg Asn Cys Ile Gly Met Arg Phe Ala
            435                 440                 445

Leu Met Asn Met Lys Leu Ala Leu Ile Arg Val Leu Gln Asn Phe Ser
450                 455                 460

Phe Lys Pro Cys Lys Glu Thr Gln Ile Pro Leu Lys Leu Ser Leu Gly
465                 470                 475                 480

Gly Leu Leu Gln Pro Glu Lys Pro Val Val Leu Lys Val Glu Ser Arg
                485                 490                 495

Asp Gly Thr Val Ser Gly Ala
            500

<210> SEQ ID NO 85
<211> LENGTH: 502
<212> TYPE: PRT
<213> ORGANISM: Homo sapiens

<400> SEQUENCE: 85

Met Ala Leu Ile Pro Asp Leu Ala Met Glu Thr Trp Leu Leu Leu Ala
1               5                   10                  15

Val Ser Leu Val Leu Leu Tyr Leu Tyr Gly Thr His Ser His Gly Leu
                20                  25                  30

Phe Lys Lys Leu Gly Ile Pro Gly Pro Thr Pro Leu Pro Phe Leu Gly
            35                  40                  45

Asn Ile Leu Ser Tyr His Lys Gly Phe Cys Met Phe Asp Met Glu Cys
        50                  55                  60

His Lys Lys Tyr Gly Lys Val Trp Gly Phe Tyr Asp Gly Gln Gln Pro
65                  70                  75                  80

Val Leu Ala Ile Thr Asp Pro Asp Met Ile Lys Thr Val Leu Val Lys
                85                  90                  95

Glu Cys Tyr Ser Val Phe Thr Asn Arg Arg Pro Phe Gly Pro Val Gly
                100                 105                 110

Phe Met Lys Ser Ala Ile Ser Ile Ala Glu Asp Glu Glu Trp Lys Arg
            115                 120                 125

Leu Arg Ser Leu Leu Ser Pro Thr Phe Thr Ser Gly Lys Leu Lys Glu
        130                 135                 140

Met Val Pro Ile Ile Ala Gln Tyr Gly Asp Val Leu Val Arg Asn Leu
145                 150                 155                 160

Arg Arg Glu Ala Glu Thr Gly Lys Pro Val Thr Leu Lys Asp Val Phe
                165                 170                 175
```

Gly Ala Tyr Ser Met Asp Val Ile Thr Ser Thr Ser Phe Gly Val Asn
            180                 185                 190

Ile Asp Ser Leu Asn Asn Pro Gln Asp Pro Phe Val Glu Asn Thr Lys
        195                 200                 205

Lys Leu Leu Arg Phe Asp Phe Leu Asp Pro Phe Leu Ser Ile Ile
210                 215                 220

Phe Pro Phe Leu Ile Pro Ile Leu Glu Val Leu Asn Ile Cys Val Phe
225                 230                 235                 240

Pro Arg Glu Val Thr Asn Phe Leu Arg Lys Ser Val Lys Arg Met Lys
                245                 250                 255

Glu Ser Arg Leu Glu Asp Thr Gln Lys His Arg Val Asp Phe Leu Gln
            260                 265                 270

Leu Met Ile Asp Ser Gln Asn Ser Lys Glu Thr Glu Ser His Lys Ala
        275                 280                 285

Leu Ser Asp Leu Glu Leu Val Ala Gln Ser Ile Ile Phe Ile Phe Ala
    290                 295                 300

Gly Tyr Glu Thr Thr Ser Ser Val Leu Ser Phe Ile Met Tyr Glu Leu
305                 310                 315                 320

Ala Thr His Pro Asp Val Gln Gln Lys Leu Gln Glu Glu Ile Asp Ala
                325                 330                 335

Val Leu Pro Asn Lys Ala Pro Pro Thr Tyr Asp Thr Val Leu Gln Met
            340                 345                 350

Glu Tyr Leu Asp Met Val Val Asn Glu Thr Leu Arg Leu Phe Pro Ile
        355                 360                 365

Ala Met Arg Leu Glu Arg Val Cys Lys Lys Asp Val Glu Ile Asn Gly
    370                 375                 380

Met Phe Ile Pro Lys Gly Val Val Met Ile Pro Ser Tyr Ala Leu
385                 390                 395                 400

His Arg Asp Pro Lys Tyr Trp Thr Gly Pro Glu Lys Phe Leu Pro Glu
                405                 410                 415

Arg Phe Ser Lys Lys Asn Lys Asp Asn Ile Asp Pro Tyr Ile Tyr Thr
            420                 425                 430

Pro Phe Gly Ser Gly Pro Arg Asn Cys Ile Gly Met Arg Phe Ala Leu
        435                 440                 445

Met Asn Met Lys Leu Ala Leu Ile Arg Val Leu Gln Asn Phe Ser Phe
    450                 455                 460

Lys Pro Cys Lys Glu Thr Gln Ile Pro Leu Lys Leu Ser Leu Gly Gly
465                 470                 475                 480

Leu Leu Gln Pro Glu Lys Pro Val Val Leu Lys Val Glu Ser Arg Asp
                485                 490                 495

Gly Thr Val Ser Gly Ala
            500

<210> SEQ ID NO 86
<211> LENGTH: 534
<212> TYPE: PRT
<213> ORGANISM: Menispermum canadense

<400> SEQUENCE: 86

Met Ile Met Met Phe Ile Asp Tyr Tyr Ser Ser Trp Leu Pro Gln Thr
1               5                   10                  15

Leu Leu Leu Gln Ser Ile Leu Leu Ala Val Ser Leu Val Ile Phe Ile
            20                  25                  30

Asn Leu Phe Leu Thr Arg Arg Arg Ser Tyr Ser Ser Lys Ser His Thr

```
            35                  40                  45
Asn Ile Ile His Pro Lys Ala Gly Ala Leu Pro Val Ile Gly
 50                  55                  60

His Leu Tyr Thr Leu Phe Arg Gly Leu Ser Ala Gly Val Pro Leu Tyr
 65                  70                  75                  80

Arg Gln Leu Asp Ala Met Ala Asp Arg Tyr Gly Pro Ala Phe Ile Ile
                 85                  90                  95

His Leu Gly Val Tyr Pro Thr Leu Val Val Thr Cys Arg Glu Leu Ala
                100                 105                 110

Lys Glu Cys Phe Thr Thr Asn Asp Gln Thr Phe Ala Thr Arg Pro Ser
                115                 120                 125

Thr Cys Ala Gly Lys Tyr Ile Gly Tyr Asn Tyr Ala Phe Phe Gly Phe
130                 135                 140

Ala Pro Tyr Gly Pro Tyr Trp Arg Glu Ala Arg Lys Ile Ala Thr Val
145                 150                 155                 160

Glu Leu Leu Ser Asn Tyr Arg Leu Asp Ser Leu Arg His Val Arg Glu
                165                 170                 175

Ala Glu Val Gly Arg Asn Val Asp Glu Leu Tyr Ala Leu His Ala Ser
                180                 185                 190

Ser Ser Thr Asn Lys Gln Asn Met Met Lys Ile Asp Met Lys Gln Trp
                195                 200                 205

Phe Asp Gln Val Thr Leu Asn Val Ile Leu Met Met Val Val Gly Lys
210                 215                 220

Arg Cys Val Thr Thr Gly Gly Asn Glu Glu Val Arg Val Val Lys
225                 230                 235                 240

Val Leu His Glu Phe Phe Lys His Leu Gly Thr Leu Ser Val Ser Asp
                245                 250                 255

Val Val Pro Tyr Val Glu Trp Met Asp Leu Asp Gly Asn Ile Gly Arg
                260                 265                 270

Met Lys Ser Thr Ala Lys Glu Leu Asp Cys Ile Leu Gly Arg Trp Leu
                275                 280                 285

Glu Glu His Arg Arg Glu Arg Arg Ser Asp Phe Met Asp Ala Met Leu
290                 295                 300

Ala Met Val Glu Gly Ile Lys Ile Pro Tyr Tyr Asp Ser Asp Thr Val
305                 310                 315                 320

Ile Lys Ala Ile Cys Leu Asn Leu Leu Asn Ala Gly Ser Asp Thr Leu
                325                 330                 335

Gly Ile Thr Met Thr Trp Ala Leu Ser Leu Leu Asn Asn Arg His
                340                 345                 350

Val Leu Lys Lys Val Lys Asp Glu Leu Asp Val His Val Gly Lys Asn
                355                 360                 365

Arg Gln Val Glu Glu Leu Asp Val Lys Asn Leu Val Tyr Leu His Ala
                370                 375                 380

Val Val Lys Glu Thr Leu Arg Leu Phe Pro Pro Ala Pro Leu Gly Val
385                 390                 395                 400

Pro His Glu Ala Met Glu Asp Cys Val Val Gly Gly Phe His Val Ala
                405                 410                 415

Lys Gly Thr Arg Leu Val Asn Val Trp Lys Leu His Arg Asp Pro
                420                 425                 430

Ser Val Trp Ser Asp Pro Leu Ala Phe Lys Pro Glu Arg Phe Leu Asp
                435                 440                 445

Asn Asn Thr Val Asp Val Arg Gly Gln His Phe Gln Leu Leu Pro Phe
                450                 455                 460
```

```
Gly Ser Gly Arg Arg Gly Cys Pro Gly Ile Thr Phe Ala Leu Gln Val
465                 470                 475                 480

Ala His Leu Thr Leu Ala Arg Leu Leu His Gly Phe Glu Trp Asp Thr
                485                 490                 495

Pro Asp Gly Ala Pro Val Asp Met Ser Glu Val Ser Val Leu Thr Thr
            500                 505                 510

Ala Lys Lys Asn Pro Val Glu Val Leu Phe Thr Pro Arg Leu Pro Ala
            515                 520                 525

Glu Val Tyr Thr Gln Asn
            530

<210> SEQ ID NO 87
<211> LENGTH: 527
<212> TYPE: PRT
<213> ORGANISM: Nigella sativa

<400> SEQUENCE: 87

Met Leu Ser Ile His Asp Ser Thr Met Val Phe Leu Gln Leu Gln Ala
1               5                   10                  15

Ile Cys Gly Ile Phe Gly Phe Ile Phe Ile Ile Thr Trp Trp Thr Arg
            20                  25                  30

Trp Lys Ser Ser Asn Lys Met Lys Ala Pro Glu Val Ala Gly Ala Trp
        35                  40                  45

Pro Val Ile Gly His Leu His Leu Leu Gly Gly Arg Pro Leu Tyr
    50                  55                  60

Gln Leu Leu Gly Asp Met Ser Asp Lys Tyr Gly Pro Ala Phe Thr Leu
65                  70                  75                  80

Arg Met Gly Ile Gln Lys Ala Leu Val Val Ser Ser Trp Glu Val Ala
                85                  90                  95

Lys Glu Cys Leu Thr Thr Asn Asp Arg Ala Leu Ala Thr Arg Pro Ser
            100                 105                 110

Ser Ala Gly Gly Lys Tyr Met Gly Tyr Asn Asn Ala Leu Ile Pro Phe
        115                 120                 125

Ser Pro Tyr Gly Pro Tyr Trp Arg Asp Met Arg Lys Ile Ala Thr Leu
    130                 135                 140

Glu Leu Leu Ser Asn His Arg Leu Glu Glu Leu Lys His Val Arg Glu
145                 150                 155                 160

Met Glu Ile Asn Thr Cys Ile Ser Asp Met Tyr Lys Leu Cys Gln Val
                165                 170                 175

Glu Asp Gly Val Glu Ile Lys Pro Ile Ser Val Asp Leu Ser Gln Trp
            180                 185                 190

Phe Ala Asp Leu Thr Phe Asn Val Val Met Met Ile Thr Gly Lys
        195                 200                 205

Arg Tyr Ile Gly Ser Thr Asp Ala Gly Asp Met Asn Glu Ile Arg His
    210                 215                 220

Phe Gln Ala Ala Leu Val Lys Phe Met Arg Leu Leu Arg Ile Ser Leu
225                 230                 235                 240

Leu Val Asp Val Phe Pro Val Leu Gln Trp Ile Asn Tyr Gly Gly Phe
                245                 250                 255

Lys Gly Val Met Lys Ser Thr Ala Arg Asp Ile Asp Ser Val Leu Glu
            260                 265                 270

Asn Trp Leu Gln Glu His Gln Arg Lys Arg Leu Ser Pro Asp Phe Asn
        275                 280                 285

Gly Asn His Asp Phe Ile Asp Val Met Ile Ser Thr Leu Glu Gly Thr
```

```
            290                 295                 300
Glu Phe Ser Asp Tyr Asp His Asn Thr Ile Ile Lys Ala Ile Ser Met
305                 310                 315                 320

Ala Met Val Val Gly Gly Thr Asp Thr Thr Thr Thr Thr Leu Ile Trp
                325                 330                 335

Ala Ile Ser Leu Leu Asn Asn Pro Asn Ala Met Lys Lys Val Gln
            340                 345                 350

Glu Glu Leu Glu Ile His Val Gly Lys Glu Arg Asn Val Asp Gly Ser
            355                 360                 365

Asp Ile Gln His Leu Val Tyr Leu Gln Ala Val Val Lys Glu Thr Leu
            370                 375                 380

Arg Leu Tyr Pro Pro Val Pro Leu Ser Val Met His Gln Ala Met Glu
385                 390                 395                 400

Asp Cys Val Ile Gly Ser Tyr Asn Ile Gln Ala Gly Thr Arg Val Leu
                405                 410                 415

Phe Asn Leu Trp Lys Leu His Arg Asp Ser Ser Val Trp Ser Asp Pro
                420                 425                 430

Leu Glu Phe Arg Pro Glu Arg Phe Leu Thr Ser His Val Asp Val Asp
            435                 440                 445

Val Arg Gly Gln His Phe Glu Leu Ile Pro Phe Gly Ser Gly Arg Arg
450                 455                 460

Ser Cys Pro Gly Ile Ser Phe Ala Leu Gln Val Ile His Leu Thr Ile
465                 470                 475                 480

Ala Arg Leu Phe His Gly Phe Asn Leu Thr Thr Pro Gly Asn Ser Ser
                485                 490                 495

Val Asp Met Ser Glu Ile Ser Gly Ala Thr Leu Ser Lys Val Thr Pro
            500                 505                 510

Leu Glu Val Leu Val Thr Pro Arg Leu Ser Ser Lys Leu Tyr Asn
            515                 520                 525

<210> SEQ ID NO 88
<211> LENGTH: 525
<212> TYPE: PRT
<213> ORGANISM: Hydrastis canadensis

<400> SEQUENCE: 88

Met Asp Ser Leu Leu Gln Leu Gln Ile Ile Gly Ala Leu Ala Ala Leu
1               5                   10                  15

Ile Phe Thr Tyr Lys Leu Leu Lys Val Ile Cys Arg Ser Pro Met Thr
                20                  25                  30

Asp Gly Met Glu Ala Pro Glu Pro Pro Gly Ala Trp Pro Ile Ile Gly
            35                  40                  45

His Leu His Leu Leu Gly Gly Gln Asp Pro Ile Ala Arg Thr Leu Gly
        50                  55                  60

Val Met Thr Asp Lys Tyr Gly Pro Ile Leu Lys Leu Arg Leu Gly Val
65                  70                  75                  80

His Thr Gly Leu Val Val Ser Asn Trp Glu Leu Ala Lys Glu Cys Phe
                85                  90                  95

Thr Thr Asn Asp Arg Val Leu Ala Ser Arg Pro Met Gly Ala Ala Gly
            100                 105                 110

Lys Tyr Leu Gly Tyr Asn Tyr Ala Ile Phe Gly Leu Ala Pro His Gly
        115                 120                 125

Pro Tyr Trp Ser Glu Val Arg Lys Ile Val Leu Arg Glu Leu Leu Ser
    130                 135                 140
```

```
Asn Gln Ser Leu Glu Lys Leu Lys His Val Arg Ile Ser Glu Ile Asn
145                 150                 155                 160

Thr Cys Leu Lys Asn Leu Phe Ser Leu Asn Asn Gly Asn Thr Pro Ile
            165                 170                 175

Lys Val Asp Met Lys Gln Trp Phe Glu Arg Pro Met Phe Asn Val Val
        180                 185                 190

Thr Met Met Ile Ala Gly Lys Arg Tyr Phe Ser Met Glu Asn Asp Asn
    195                 200                 205

Glu Ala Met Asn Phe Arg Lys Val Ala Thr Glu Phe Met Tyr Leu Thr
210                 215                 220

Gly Val Phe Val Val Ser Asp Ala Leu Pro Tyr Leu Glu Trp Leu Asp
225                 230                 235                 240

Leu Gln Gly His Val Ser Ala Met Lys Arg Thr Ala Lys Glu Leu Asp
                245                 250                 255

Ile His Val Gly Lys Trp Leu Glu Glu His Arg Arg Ala Lys Leu Leu
            260                 265                 270

Gly Glu Thr Lys Asn Glu Asp Asp Phe Val Asp Val Leu Leu Thr Ile
        275                 280                 285

Leu Pro Glu Asp Leu Lys Asp Asn Gln Thr Tyr Ile His Asp Arg Asp
    290                 295                 300

Thr Ile Ile Lys Ala Thr Ala Leu Ala Leu Phe Leu Ala Ala Ser Asp
305                 310                 315                 320

Thr Thr Ala Ile Thr Leu Thr Trp Ala Leu Ser Leu Ile Leu Asn Asn
                325                 330                 335

Pro Asp Val Leu Lys Arg Ala Gln Asp Glu Leu Asp Lys His Val Gly
            340                 345                 350

Lys Glu Lys Leu Val Lys Glu Ser Asp Ile Ile Asn Leu Val Tyr Leu
        355                 360                 365

Gln Ala Ile Ile Lys Glu Thr Leu Arg Leu Tyr Pro Ala Ala Pro Leu
    370                 375                 380

Leu Leu Pro His Glu Ala Met Glu Asp Cys Thr Val Gly Gly Tyr His
385                 390                 395                 400

Val Pro Lys Gly Thr Arg Ile Phe Val Asn Ile Trp Lys Leu Gln Arg
                405                 410                 415

Asp Pro Arg Val Trp Phe Asp Pro Asn Glu Phe Arg Pro Glu Arg Phe
            420                 425                 430

Leu Thr Thr His Ala Asn Val Asp Phe Lys Gly Gln His Phe Glu Tyr
        435                 440                 445

Ile Pro Phe Ser Ser Gly Arg Arg Val Cys Pro Gly Ile Thr Phe Ser
    450                 455                 460

Thr Gln Ile Met His Leu Thr Leu Ala His Leu Leu His Glu Phe Asn
465                 470                 475                 480

Ile Val Thr Pro Thr Lys Ser Asn Ala Gly Val Asp Met Thr Glu Ser
                485                 490                 495

Leu Gly Ile Thr Met Pro Lys Ala Thr Pro Leu Glu Val Leu Leu Thr
            500                 505                 510

Pro Arg Leu Pro Ser Asn Leu Tyr Asn Gln Tyr Arg Asp
        515                 520                 525
```

<210> SEQ ID NO 89
<211> LENGTH: 550
<212> TYPE: PRT
<213> ORGANISM: Eschscholzia californica

<400> SEQUENCE: 89

```
Met Asn Leu Leu Ile Phe Phe Gln Phe Leu Leu Gln Phe Gln Val Leu
1               5                   10                  15

Val Gly Leu Ser Val Leu Leu Ala Phe Ser Tyr Tyr Leu Trp Val Ser
            20                  25                  30

Lys Asn Pro Lys Ile Asn Lys Phe Lys Gly Gly Ala Leu Leu Ala
            35                  40                  45

Pro Gln Ala Ala Gly Ala Trp Pro Ile Val Gly His Leu Pro Gln Leu
        50                  55                  60

Val Gly Pro Lys Pro Leu Phe Arg Ile Leu Gly Ala Met Ala Asp Asn
65                  70                  75                  80

Tyr Gly Pro Ile Phe Met Leu Arg Phe Gly Val His Pro Thr Val Val
                85                  90                  95

Val Ser Ser Trp Glu Met Thr Lys Glu Cys Phe Thr Thr Asn Asp Arg
            100                 105                 110

His Leu Ala Ser Arg Pro Ser Asn Ala Ala Ser Gln Tyr Leu Ile Tyr
        115                 120                 125

Glu Val Tyr Ala Leu Phe Gly Phe Ser Leu Tyr Gly Ser Ser Tyr Trp
        130                 135                 140

Arg Asp Ala Arg Lys Ile Ala Thr Leu Glu Leu Leu Ser His Arg Arg
145                 150                 155                 160

Leu Glu Leu Leu Lys His Val Pro Tyr Thr Glu Ile Asp Thr Cys Ile
                165                 170                 175

Lys Gln Leu His Arg Leu Trp Thr Lys Asn Asn Lys Asn Gln Asn Asn
            180                 185                 190

Pro Glu Leu Lys Val Glu Met Asn Gln Phe Phe Thr Asp Leu Thr Met
        195                 200                 205

Asn Val Ile Leu Lys Leu Val Val Gly Lys Arg Phe Phe Asn Val Asp
210                 215                 220

Asp Ala Ala Asp His Glu Lys Glu Ala Arg Lys Ile Gln Gly Thr
225                 230                 235                 240

Ile Phe Glu Phe Phe Lys Leu Thr Glu Gly Ser Val Ser Ala Gly Ala
                245                 250                 255

Leu Pro Leu Leu Asn Trp Leu Asp Leu Asn Gly Gln Lys Arg Ala Met
            260                 265                 270

Lys Arg Thr Ala Lys Lys Met Asp Ser Ile Ala Glu Lys Leu Leu Asp
            275                 280                 285

Glu His Arg Gln Lys Arg Leu Ser Lys Glu Gly Val Lys Gly Thr His
        290                 295                 300

Asp His Asn Asp Phe Met Asp Val Leu Leu Ser Ile Leu Asp Ala Asp
305                 310                 315                 320

Gln Gly Asp Tyr Ser His His Pro Phe Asn Tyr Ser Arg Asp His Val
                325                 330                 335

Ile Lys Ala Thr Thr Leu Ser Met Ile Leu Ser Ser Met Ser Ile Ser
            340                 345                 350

Val Ser Leu Ser Trp Ala Leu Ser Leu Leu Asn Asn Arg His Val
            355                 360                 365

Leu Lys Lys Ala Gln Asp Glu Leu Asp Met Asn Val Gly Lys Asp Arg
        370                 375                 380

Gln Val Glu Glu Gly Asp Ile Lys Asn Leu Val Tyr Leu Gln Ala Ile
385                 390                 395                 400

Val Lys Glu Thr Phe Arg Met Tyr Pro Ala Asn Pro Leu Leu Leu Pro
                405                 410                 415
```

His Glu Ala Ile Glu Asp Cys Lys Ile Gly Phe Asn Val Pro Ala
            420                 425                 430

Gly Thr Arg Val Val Asn Ala Trp Lys Leu Gln His Asp Pro Arg
            435                 440                 445

Val Trp Ser Asn Pro Ser Glu Phe Lys Pro Glu Arg Phe Leu Asn Asp
            450                 455                 460

Gln Ala Ala Lys Val Val Asp Val Arg Gly Gln Asn Phe Glu Tyr Leu
465                 470                 475                 480

Pro Phe Gly Ser Gly Arg Arg Val Cys Pro Gly Ile Ser Phe Ser Leu
                485                 490                 495

Gln Thr Ile His Met Ser Leu Ala Arg Leu Val Gln Ala Phe Glu Leu
            500                 505                 510

Gly Thr Pro Ser Asn Glu Arg Ile Asp Met Thr Glu Gly Ser Gly Leu
            515                 520                 525

Thr Met Pro Lys Thr Thr Pro Leu His Val Leu Leu Asn Pro Arg Leu
            530                 535                 540

Pro Leu Pro Leu Tyr Glu
545                 550

<210> SEQ ID NO 90
<211> LENGTH: 537
<212> TYPE: PRT
<213> ORGANISM: Glaucium flavum

<400> SEQUENCE: 90

Met Glu Leu Ile Asn Ser Leu Glu Ile Gln Pro Ile Thr Ile Ser Ile
1               5                   10                  15

Leu Ala Leu Leu Thr Val Ser Ile Leu Leu Tyr Lys Ile Ile Trp Asn
            20                  25                  30

His Gly Ser Arg Lys Asn Lys Ser Asn Lys Asn Arg Lys Thr
            35                  40                  45

Ser Ser Ser Ala Gly Val Val Glu Ile Pro Gly Ala Trp Pro Ile Ile
50                  55                  60

Gly His Leu His Leu Phe Asn Gly Ser Glu Gln Met Phe His Lys Leu
65                  70                  75                  80

Gly Ser Leu Ala Asp Gln Tyr Gly Pro Ala Pro Phe Phe Ile Arg Phe
            85                  90                  95

Gly Ser Arg Lys Tyr Val Val Ser Asn Trp Glu Leu Val Lys Thr
            100                 105                 110

Cys Phe Thr Ala Gln Ser Gln Ile Phe Val Ser Arg Pro Pro Met Leu
            115                 120                 125

Ala Met Asn Ile Leu Phe Phe Pro Lys Asp Ser Leu Ser Tyr Ile Gln
130                 135                 140

His Gly Asp His Trp Arg Glu Leu Arg Lys Ile Ser Ser Thr Lys Leu
145                 150                 155                 160

Leu Ser Ser His Arg Val Glu Thr Gln Lys His Leu Ile Ala Ser Glu
            165                 170                 175

Val Asp Tyr Cys Phe Lys Gln Leu Tyr Lys Leu Ser Asn Asn Gly Glu
            180                 185                 190

Phe Thr Leu Val Arg Leu Asn Thr Trp Cys Glu Asp Met Ala Leu Asn
            195                 200                 205

Val His Val Arg Met Ile Ala Gly Met Lys Asn Tyr Val Ala Ala Pro
210                 215                 220

Gly Ser Gly Glu Tyr Gly Gly Gln Ala Arg Arg Tyr Arg Lys Ala Leu
225                 230                 235                 240

```
Glu Glu Ala Leu Asp Leu Leu Asn Gln Phe Thr Ile Thr Asp Val Val
                245                 250                 255

Pro Trp Leu Gly Trp Leu Asp His Phe Arg Asp Val Val Gly Arg Met
            260                 265                 270

Lys Arg Cys Gly Ala Glu Leu Asp Ser Ile Phe Ala Thr Trp Val Glu
        275                 280                 285

Glu His Arg Val Lys Arg Ala Ser Gly Lys Gly Asp Val Glu Pro
    290                 295                 300

Asp Phe Ile Asp Leu Cys Trp Glu Ser Met Glu Gln Leu Pro Gly Asn
305                 310                 315                 320

Asp Pro Ala Thr Val Ile Lys Leu Met Cys Lys Glu His Ile Phe Asn
                325                 330                 335

Gly Ser Gly Thr Ser Ser Leu Thr Leu Ala Trp Ile Leu Ser Leu Ile
            340                 345                 350

Met Asn Asn Pro Tyr Val Ile Lys Lys Ala Arg Glu Glu Leu Glu Lys
        355                 360                 365

His Val Gly Asn His Arg Gln Val Glu Glu Ser Asp Leu Pro Asn Leu
    370                 375                 380

Leu Tyr Ile Gln Ala Ile Ile Lys Glu Gly Met Arg Leu Tyr Thr Pro
385                 390                 395                 400

Gly Pro Phe Ile Asp Arg Asn Thr Thr Glu Asp Tyr Glu Ile Asn Gly
                405                 410                 415

Val His Ile Pro Ala Gly Thr Cys Leu Tyr Val Asn Leu Trp Lys Ile
            420                 425                 430

His Arg Asp Pro Asn Val Tyr Glu Asp Pro Leu Glu Phe Lys Pro Glu
        435                 440                 445

Arg Phe Leu Lys Asn Asn Ser Asp Leu Asp Leu Lys Gly Gln Asn Tyr
    450                 455                 460

Gln Leu Leu Pro Phe Gly Ala Gly Arg Arg Ile Cys Pro Gly Val Ser
465                 470                 475                 480

Leu Ala Leu Pro Leu Met Tyr Leu Thr Val Ser Arg Leu Ile His Gly
                485                 490                 495

Phe Asp Met Lys Leu Pro Lys Gly Val Glu Lys Ala Asp Met Thr Ala
            500                 505                 510

His Gly Gly Val Ile Asn Gln Arg Ala Tyr Pro Leu Glu Val Leu Leu
        515                 520                 525

Lys Pro Arg Leu Thr Phe Gln Gln Ala
    530                 535

<210> SEQ ID NO 91
<211> LENGTH: 568
<212> TYPE: PRT
<213> ORGANISM: Stylophorum diphyllum

<400> SEQUENCE: 91

Met Thr Ile Gly Ala Leu Ala Leu Leu Ser Phe Ile Tyr Phe Leu Arg
1               5                   10                  15

Val Ser Val Ile Lys Arg Thr Lys Tyr Thr Asn Thr Ala Val Thr Ala
            20                  25                  30

Thr Asn Lys Leu Glu Asn Asp Glu Asp Glu Ala Asn His Ser Lys Arg
        35                  40                  45

Val Val Ala Pro Pro Glu Val Ala Gly Ala Trp Pro Ile Leu Gly His
    50                  55                  60

Leu Pro Gln Leu Val Gly Leu Lys Gln Pro Leu Phe Arg Val Leu Gly
```

-continued

```
                65                  70                  75                  80
Asp Met Ala Asp Lys Tyr Gly Pro Ile Phe Ile Val Arg Phe Gly Met
                        85                  90                  95
Tyr Pro Thr Leu Val Val Ser Ser Trp Glu Met Ala Lys Glu Cys Phe
                100                 105                 110
Thr Thr Asn Asp Arg Val Leu Ala Ser Arg Pro Ala Ser Ala Ser Gly
                115                 120                 125
Lys Tyr Leu Thr Tyr Asn Tyr Ala Met Phe Gly Phe Thr Asn Gly Pro
                130                 135                 140
Tyr Trp Arg Glu Ile Arg Lys Ile Ser Met Leu Glu Leu Leu Ser His
145                 150                 155                 160
Arg Arg Val Glu Leu Leu Lys His Val Pro Ser Thr Glu Ile Asp Ser
                165                 170                 175
Ser Ile Lys Gln Leu Tyr His Leu Trp Val Glu Asn Gln Asn Gln Asn
                180                 185                 190
Lys Gln Gly Asp His Gln Val Lys Val Asp Met Ser Gln Leu Leu Arg
                195                 200                 205
Asp Leu Thr Leu Asn Ile Val Leu Lys Leu Val Val Gly Lys Arg Leu
                210                 215                 220
Phe Asn Asn Asn Asp Met Asp His Glu Gln Asp Glu Ala Ala Arg Lys
225                 230                 235                 240
Leu Gln Lys Thr Met Val Glu Leu Ile Lys Val Ala Gly Ala Ser Val
                245                 250                 255
Ala Ser Asp Ala Leu Pro Phe Leu Gly Trp Leu Asp Val Asp Gly Leu
                260                 265                 270
Lys Arg Thr Met Lys Arg Ile Ala Lys Glu Ile Asp Val Ile Ala Glu
                275                 280                 285
Arg Trp Leu Gln Glu His Arg Gln Lys Lys Leu Thr Ser Asn Asp Lys
                290                 295                 300
Gly Gly Ser Asn Asn Ile Gln Gly Gly Gly Asp Asn Asp Phe Met
305                 310                 315                 320
Asp Val Met Leu Ser Ile Leu Asp Asp Ser Asn Phe Phe Ile Asn
                325                 330                 335
Tyr Asn Arg Asp Thr Val Ile Lys Ala Thr Ser Leu Thr Met Ile Leu
                340                 345                 350
Ala Gly Ser Asp Thr Thr Thr Leu Ser Leu Thr Trp Ala Leu Thr Leu
                355                 360                 365
Leu Ala Thr Asn Pro Gly Ala Leu Arg Lys Ala Gln Asp Glu Leu Asp
                370                 375                 380
Thr Lys Val Gly Arg Asp Arg Gln Val Asp Glu Arg Asp Ile Lys Asn
385                 390                 395                 400
Leu Val Tyr Leu Gln Ala Ile Val Lys Glu Thr Leu Arg Met Tyr Pro
                405                 410                 415
Ala Ala Pro Leu Ala Ile Pro His Glu Ala Thr Gln Asp Cys Ile Val
                420                 425                 430
Gly Gly Tyr His Val Thr Ala Gly Thr Arg Val Trp Val Asn Leu Trp
                435                 440                 445
Lys Leu Gln Arg Asp Pro His Ala Trp Pro Asn Pro Ser Glu Phe Arg
                450                 455                 460
Pro Glu Arg Phe Leu Ala Val Glu Asn Asp Cys Lys Gln Gln Gly Thr
465                 470                 475                 480
Cys Asp Gly Glu Ala Ala Asn Met Asp Phe Arg Gly Gln His Phe Glu
                485                 490                 495
```

-continued

```
Tyr Met Pro Phe Gly Ser Gly Arg Arg Met Cys Pro Gly Ile Asn Phe
            500                 505                 510

Ala Ile Gln Ile Ile His Met Thr Leu Ala Arg Leu Leu His Ser Phe
        515                 520                 525

Glu Leu Arg Val Pro Glu Glu Val Ile Asp Met Ala Glu Asp Ser
    530                 535                 540

Gly Leu Thr Ile Ser Lys Val Thr Pro Leu Glu Leu Leu Thr Pro
545                 550                 555                 560

Arg Leu Pro Leu Pro Leu Tyr Ile
                565

<210> SEQ ID NO 92
<211> LENGTH: 561
<212> TYPE: PRT
<213> ORGANISM: Stylophorum diphyllum

<400> SEQUENCE: 92

Phe Cys Gln Phe Gln Gly Ile Val Gly Ile Leu Leu Ala Phe Leu Thr
1               5                   10                  15

Phe Leu Tyr Tyr Leu Trp Arg Ala Ser Ile Thr Gly Leu Arg Thr Lys
            20                  25                  30

Pro Lys His Asn Asp Phe Lys Val Thr Lys Ala Ala Pro Glu Ala Asp
        35                  40                  45

Gly Ala Trp Pro Ile Val Gly His Phe Ala Gln Phe Ile Gly Pro Arg
    50                  55                  60

Pro Leu Phe Arg Ile Leu Gly Asp Met Ala Asp Lys Tyr Gly Ser Ile
65                  70                  75                  80

Phe Met Val Arg Phe Gly Met Tyr Pro Thr Leu Val Val Ser Ser Trp
                85                  90                  95

Glu Met Ala Lys Glu Cys Phe Thr Thr Asn Asp Arg Phe Leu Ala Ser
            100                 105                 110

Arg Pro Ala Ser Ala Ala Gly Lys Tyr Leu Thr Tyr Asp Phe Ala Met
        115                 120                 125

Leu Ser Phe Ser Phe Tyr Gly Pro Tyr Trp Arg Glu Ile Arg Lys Ile
130                 135                 140

Ser Met Leu Glu Leu Leu Ser His Arg Arg Val Glu Leu Leu Lys His
145                 150                 155                 160

Val Pro Ser Thr Glu Ile Asp Ser Ser Ile Lys Gln Leu Tyr His Leu
                165                 170                 175

Trp Val Glu Asn Gln Asn Gln Asn Lys Gln Gly Asp His Gln Val Lys
            180                 185                 190

Val Asp Met Ser Gln Leu Leu Arg Asp Leu Thr Leu Asn Ile Val Leu
        195                 200                 205

Lys Leu Val Val Gly Lys Arg Leu Phe Asn Asn Asn Asp Met Asp His
210                 215                 220

Glu Gln Asp Glu Ala Ala Arg Lys Leu Gln Lys Thr Met Val Glu Leu
225                 230                 235                 240

Ile Lys Val Ala Gly Ala Ser Val Ala Ser Asp Ala Leu Pro Phe Leu
                245                 250                 255

Gly Trp Leu Asp Val Asp Gly Leu Lys Arg Thr Met Lys Arg Ile Ala
            260                 265                 270

Lys Glu Ile Asp Val Ile Ala Glu Arg Trp Leu Gln Glu His Arg Gln
        275                 280                 285

Lys Lys Leu Thr Ser Asn Asp Lys Gly Gly Ser Asn Asn Ile Gln Gly
```

```
                290                 295                 300
    Gly Gly Gly Asp Asn Asp Phe Met Asp Val Met Leu Ser Ile Leu Asp
    305                 310                 315                 320

Asp Asp Ser Asn Phe Phe Ile Asn Tyr Asn Arg Asp Thr Val Ile Lys
                    325                 330                 335

Ala Thr Ser Leu Thr Met Ile Leu Ala Gly Ser Asp Thr Thr Thr Leu
                340                 345                 350

Ser Leu Thr Trp Ala Leu Thr Leu Leu Ala Thr Tyr Pro Leu Cys Ala
                355                 360                 365

Leu Arg Lys Ala Gln Asp Glu Leu Asp Thr Lys Val Gly Arg Asp Arg
                370                 375                 380

Gln Val Asp Glu Arg Asp Ile Lys Asn Leu Val Tyr Leu Gln Ala Ile
    385                 390                 395                 400

Val Lys Glu Thr Leu Arg Met Tyr Pro Ala Ala Pro Leu Ala Ile Pro
                    405                 410                 415

His Glu Ala Thr Gln Asp Cys Ile Val Gly Gly Tyr His Val Thr Ala
                420                 425                 430

Gly Thr Arg Val Trp Val Asn Leu Trp Lys Leu Gln Arg Asp Pro His
                435                 440                 445

Ala Trp Pro Asn Pro Ser Glu Phe Arg Pro Glu Arg Phe Leu Ala Val
                450                 455                 460

Glu Asn Asp Cys Lys Gln Gln Gly Thr Cys Asp Gly Glu Ala Ala Asn
    465                 470                 475                 480

Met Asp Phe Arg Gly Gln His Phe Glu Tyr Met Pro Phe Gly Ser Gly
                    485                 490                 495

Arg Arg Met Cys Pro Gly Ile Asn Phe Ala Ile Gln Ile Ile His Met
                500                 505                 510

Thr Leu Ala Arg Leu Leu His Ser Phe Glu Leu Arg Val Pro Glu Glu
                515                 520                 525

Glu Val Ile Asp Met Ala Glu Asp Ser Gly Leu Thr Ile Ser Lys Val
                530                 535                 540

Thr Pro Leu Glu Leu Leu Leu Thr Pro Arg Leu Pro Leu Pro Leu Tyr
    545                 550                 555                 560

Ile

<210> SEQ ID NO 93
<211> LENGTH: 561
<212> TYPE: PRT
<213> ORGANISM: Chelidonium majus

<400> SEQUENCE: 93

Met Asp Leu Phe Ile Phe Phe Ser Arg Phe Gln Tyr Ile Val Gly Leu
    1               5                   10                  15

Leu Ala Phe Leu Thr Phe Phe Tyr Tyr Leu Trp Arg Val Ser Ile Thr
                    20                  25                  30

Gly Thr Arg Ile Lys Thr Asn Gln Asn Ile Met Asn Gly Thr Asn Met
                35                  40                  45

Met Ala Pro Glu Ala Ala Gly Ala Trp Pro Ile Val Gly His Leu Pro
        50                  55                  60

Gln Leu Val Gly Pro Gln Pro Leu Phe Lys Ile Leu Gly Asp Met Ala
    65                  70                  75                  80

Asp Lys Tyr Gly Ser Ile Phe Met Val Arg Phe Gly Met His Pro Thr
                    85                  90                  95

Leu Val Val Ser Ser Trp Glu Met Ala Lys Glu Cys Phe Thr Thr Asn
```

-continued

```
                100                 105                 110
Asp Lys Phe Leu Ala Ser Arg Pro Thr Ser Ala Gly Gly Lys Tyr Leu
                115                 120                 125

Thr Tyr Asp Phe Ala Met Phe Gly Phe Ser Phe Tyr Gly Pro Tyr Trp
                130                 135                 140

Arg Glu Ile Arg Lys Ile Ser Thr Leu Glu Leu Leu Ser His Arg Arg
145                 150                 155                 160

Val Glu Leu Leu Lys His Val Pro Tyr Thr Glu Ile Gly Gly Ser Ile
                165                 170                 175

Lys Gln Leu Tyr Lys Leu Trp Met Glu Thr Gln Asn Gln Asn Lys Gln
                180                 185                 190

Arg Asp Asp His Gln Val Lys Val Asp Met Ser Gln Val Phe Gly Tyr
                195                 200                 205

Leu Thr Leu Asn Thr Val Leu Lys Leu Val Gly Lys Gly Leu Phe
                210                 215                 220

Asn Asn Asn Asp Met Asn His Glu Gln Glu Glu Gly Arg Lys Leu His
225                 230                 235                 240

Glu Thr Val Leu Glu Phe Phe Lys Leu Ala Gly Val Ser Val Ala Ser
                245                 250                 255

Asp Ala Leu Pro Phe Leu Gly Trp Leu Asp Val Asp Gly Gln Lys Arg
                260                 265                 270

Ser Met Lys Arg Ile Ala Lys Glu Met Asp Leu Ile Ala Glu Arg Trp
                275                 280                 285

Leu Gln Glu His Arg Gln Lys Arg Leu Thr Ser Asn Asn Lys Ala Ser
                290                 295                 300

Ser Gly His Asp Asp Phe Met Ser Val Leu Leu Ser Ile Leu Asp Asp
305                 310                 315                 320

Asp Ser Asn Phe Phe Asn Tyr Asn Arg Asp Thr Val Ile Lys Ala Thr
                325                 330                 335

Ser Leu Asn Leu Ile Leu Ala Ala Ser Asp Thr Thr Ser Val Ser Leu
                340                 345                 350

Thr Trp Val Leu Ser Leu Leu Val Thr Asn Pro Gly Ala Leu Lys Lys
                355                 360                 365

Val Gln Asp Glu Leu Asp Thr Lys Val Gly Arg Asn Arg His Val Glu
                370                 375                 380

Glu Arg Asp Ile Glu Lys Leu Val Tyr Leu Gln Ala Thr Val Lys Glu
385                 390                 395                 400

Thr Leu Arg Met Tyr Pro Ala Gly Pro Leu Ser Val Pro His Glu Ala
                405                 410                 415

Thr Gln Asp Cys Thr Val Gly Gly Tyr Gln Val Thr Ala Gly Thr Arg
                420                 425                 430

Leu Val Val Asn Val Trp Lys Leu Gln Arg Asp Pro Arg Val Trp Pro
                435                 440                 445

Asn Pro Ser Glu Phe Lys Pro Glu Arg Phe Leu Pro Asp Gly Cys Glu
                450                 455                 460

Val Gly Cys Gly Glu Ala Ala Asn Met Asp Phe Arg Gly Gln His Phe
465                 470                 475                 480

Glu Tyr Ile Pro Phe Gly Ser Gly Arg Arg Met Cys Pro Gly Ile Asp
                485                 490                 495

Phe Ala Ile Gln Ile Ile His Met Thr Leu Ala Cys Leu Leu His Ala
                500                 505                 510

Phe Glu Phe Gln Val Pro Ser Ser Leu Asp Lys His Leu Val Pro Ala
                515                 520                 525
```

```
Val Ile Asp Met Ser Glu Gly Ser Gly Leu Thr Met Pro Lys Val Thr
            530                 535                 540

Pro Leu Glu Val Leu Leu Asn Pro Arg Leu Pro Leu Pro Leu Tyr Glu
545                 550                 555                 560

Leu

<210> SEQ ID NO 94
<211> LENGTH: 561
<212> TYPE: PRT
<213> ORGANISM: Eschscholzia californica

<400> SEQUENCE: 94

Met Glu Lys Pro Ile Leu Leu Gln Leu Gln Pro Gly Ile Leu Gly Leu
1               5                   10                  15

Leu Ala Leu Met Cys Phe Leu Tyr Tyr Val Ile Lys Val Ser Leu Ser
            20                  25                  30

Thr Arg Asn Cys Asn Gln Leu Val Arg His Pro Pro Glu Ala Ala Gly
        35                  40                  45

Ser Trp Pro Ile Val Gly His Leu Pro Gln Leu Val Gly Ser Gly Lys
    50                  55                  60

Pro Leu Phe Arg Val Leu Gly Asp Met Ala Asp Lys Phe Gly Pro Ile
65                  70                  75                  80

Phe Met Val Arg Phe Gly Val His Pro Thr Leu Val Val Ser Ser Trp
                85                  90                  95

Glu Met Ala Lys Glu Cys Phe Thr Ser Asn Asp Lys Phe Leu Ala Ser
            100                 105                 110

Arg Pro Pro Ser Ala Ala Ser Ile Tyr Met Ala Tyr Asp His Ala Met
        115                 120                 125

Leu Gly Phe Ser Ser Tyr Gly Pro Tyr Trp Arg Glu Ile Arg Lys Ile
    130                 135                 140

Ser Thr Leu His Leu Leu Ser His Arg Arg Leu Glu Leu Leu Lys His
145                 150                 155                 160

Val Pro His Leu Glu Ile His Asn Phe Ile Lys Gly Leu Tyr Gly Ile
                165                 170                 175

Trp Lys Asp His Gln Lys Gln Gln Gln Pro Thr Ala Arg Asp Asp
            180                 185                 190

Gln Asp Ser Val Met Leu Glu Met Ser Gln Leu Phe Gly Tyr Leu Thr
        195                 200                 205

Leu Asn Ile Val Leu Ser Leu Val Val Gly Lys Arg Val Cys Asn Tyr
    210                 215                 220

His Ala Asp Gly His Leu Asp Asp Gly Glu Glu Ala Gly Gln Gly Gln
225                 230                 235                 240

Lys Leu His Gln Thr Ile Thr Asp Phe Phe Lys Leu Ser Gly Val Ser
                245                 250                 255

Val Ala Ser Asp Ala Leu Pro Phe Leu Gly Leu Phe Asp Leu Asp Gly
            260                 265                 270

Gln Lys Lys Ile Met Lys Arg Val Ala Lys Glu Met Asp Phe Val Ala
        275                 280                 285

Glu Arg Trp Leu Gln Asp Lys Lys Ser Ser Leu Leu Ser Ser Lys
    290                 295                 300

Ser Asn Asn Lys Gln Asn Glu Ala Gly Glu Gly Asp Val Asp Asp Phe
305                 310                 315                 320

Met Asp Val Leu Met Ser Thr Leu Pro Asp Asp Asp Ser Phe Phe
                325                 330                 335
```

```
Thr Lys Tyr Ser Arg Asp Thr Val Ile Lys Ala Asn Ser Leu Ser Met
            340                 345                 350

Val Val Ala Gly Ser Asp Thr Thr Ser Val Ser Leu Thr Trp Ala Leu
            355                 360                 365

Ser Leu Leu Leu Asn Asn Ile Gln Val Leu Arg Lys Ala Gln Asp Glu
    370                 375                 380

Leu Asp Thr Lys Val Gly Arg Asp Arg His Val Glu Glu Lys Asp Ile
385                 390                 395                 400

Asp Asn Leu Val Tyr Leu Gln Ala Ile Val Lys Glu Thr Leu Arg Met
                405                 410                 415

Tyr Pro Ala Gly Pro Leu Ser Val Pro His Glu Ala Ile Glu Asp Cys
            420                 425                 430

Asn Val Gly Gly Tyr His Ile Lys Thr Gly Thr Arg Leu Leu Val Asn
            435                 440                 445

Ile Trp Lys Leu Gln Arg Asp Pro Arg Val Trp Ser Asn Pro Ser Glu
    450                 455                 460

Phe Arg Pro Glu Arg Phe Leu Asp Asn Gln Ser Asn Gly Thr Leu Leu
465                 470                 475                 480

Asp Phe Arg Gly Gln His Phe Glu Tyr Ile Pro Phe Gly Ser Gly Arg
                485                 490                 495

Arg Met Cys Pro Gly Val Asn Leu Ala Thr Pro Ile Leu His Met Thr
            500                 505                 510

Leu Ala Arg Leu Leu Gln Ser Phe Asp Leu Thr Thr Pro Ser Ser Ser
            515                 520                 525

Pro Val Asp Met Thr Glu Gly Ser Gly Leu Thr Met Pro Lys Val Thr
            530                 535                 540

Pro Leu Lys Val Leu Leu Thr Pro Arg Leu Pro Leu Pro Leu Tyr Asp
545                 550                 555                 560

Tyr

<210> SEQ ID NO 95
<211> LENGTH: 567
<212> TYPE: PRT
<213> ORGANISM: Papaver bracteatum

<400> SEQUENCE: 95

Met Asp Val Ala Ile Ile Val Asp His His Tyr Leu Gln Pro Phe Val
1               5                   10                  15

Ser Ile Ala Gly Leu Leu Ala Leu Leu Ser Phe Phe Tyr Cys Ile Trp
            20                  25                  30

Val Phe Ile Ile Arg Pro Arg Ile Ile Lys Ser Asn Leu Asp Glu Arg
            35                  40                  45

Lys Leu Ser Pro Ser Ser Pro Pro Glu Val Ala Gly Ala Trp Pro Ile
50                  55                  60

Val Gly His Leu Pro Gln Leu Ile Gly Ser Thr Pro Leu Phe Lys Ile
65                  70                  75                  80

Leu Ala Asp Met Ser Asn Lys Tyr Gly Pro Ile Phe Met Val Arg Phe
                85                  90                  95

Gly Met Tyr Pro Thr Leu Val Val Ser Ser Trp Glu Met Ser Lys Glu
            100                 105                 110

Cys Phe Thr Thr Asn Asp Arg Leu Phe Ala Thr Arg Pro Pro Ser Ala
            115                 120                 125

Ala Gly Lys Tyr Leu Thr Lys Ala Leu Phe Ala Phe Ser Val Tyr Gly
130                 135                 140
```

```
Pro Tyr Trp Arg Glu Ile Arg Lys Ile Ser Thr Ile His Leu Leu Ser
145                 150                 155                 160

Leu Arg Arg Leu Glu Leu Leu Lys His Gly Arg Tyr Leu Glu Ile Asp
            165                 170                 175

Lys Cys Met Lys Arg Leu Phe Glu Tyr Trp Met Glu His His Lys Asn
            180                 185                 190

Ile Ile Ser Thr Thr Ser Ser Val Lys Val Asn Met Ser Gln Val Phe
            195                 200                 205

Ala Glu Leu Ser Leu Asn Val Val Leu Lys Ile Ile Val Gly Lys Thr
        210                 215                 220

Leu Phe Ile Lys Asn Gly Asn Glu Asp Tyr Thr Lys Glu Glu Glu
225                 230                 235                 240

Gly Gln Lys Leu His Lys Thr Ile Leu Lys Phe Met Glu Leu Ala Gly
                245                 250                 255

Val Ser Val Ala Ser Asp Val Leu Pro Phe Leu Gly Trp Leu Asp Val
            260                 265                 270

Asp Gly Gln Lys Lys Gln Met Lys Arg Val Tyr Lys Glu Met Asn Leu
        275                 280                 285

Ile Ala Ser Lys Trp Leu Gly Glu His Arg Glu Arg Lys Arg Leu Gln
290                 295                 300

Ile Ile Gln Lys Arg Gly Ala Ala Arg Gly Ser Asn Tyr Asp Asp Gly
305                 310                 315                 320

Asn Asp Phe Met Asp Val Leu Met Ser Ile Leu Asp Glu Glu Asn Asp
                325                 330                 335

Asp Leu Phe Phe Gly Tyr Ser Arg Asp Thr Val Ile Lys Ser Thr Cys
            340                 345                 350

Leu Gln Leu Ile Val Ala Ala Ser Asp Thr Thr Ser Leu Ala Met Thr
        355                 360                 365

Trp Ala Leu Ser Leu Leu Leu Thr Asn Pro Asn Val Leu Gln Lys Ala
370                 375                 380

Gln Asp Glu Leu Asp Thr Lys Val Gly Arg Asp Arg Ile Ile Glu Glu
385                 390                 395                 400

His Asp Ile Glu Cys Leu Val Tyr Leu Gln Ala Ile Val Lys Glu Thr
                405                 410                 415

Leu Arg Leu Tyr Pro Pro Ala Pro Leu Ser Leu Pro His Glu Ala Met
            420                 425                 430

Glu Asp Cys Thr Val Gly Gly Tyr Gln Val Lys Ala Gly Thr Arg Leu
        435                 440                 445

Val Val Asn Leu Trp Lys Leu Gln Arg Asp Pro Arg Val Trp Ser Asn
450                 455                 460

Pro Leu Glu Phe Lys Pro Glu Arg Phe Leu Pro Gln Ser Asp Gly Gly
465                 470                 475                 480

Phe Gly Gly Glu Glu Ala Arg Met Asp Phe Arg Gly Gln His Phe Glu
                485                 490                 495

Tyr Thr Pro Phe Gly Ser Gly Arg Arg Ile Cys Pro Gly Ile Asp Phe
            500                 505                 510

Phe Leu Gln Thr Val His Met Ala Leu Ala Arg Leu Leu Gln Ala Phe
        515                 520                 525

Asp Phe Asn Thr Ala Gly Gly Leu Val Ile Asp Met Val Glu Gly Pro
530                 535                 540

Gly Leu Thr Met Pro Lys Val Thr Pro Leu Glu Val His Leu Asn Pro
545                 550                 555                 560
```

```
                            Arg Leu Pro Val Thr Leu Tyr
                                            565

<210> SEQ ID NO 96
<211> LENGTH: 558
<212> TYPE: PRT
<213> ORGANISM: Papaver bracteatum

<400> SEQUENCE: 96

Met Gln Val Asp Trp Pro Asn Ile Leu Gln Lys Tyr Tyr Pro Ile Ile
1               5                   10                  15

Thr Cys Ser Leu Leu Thr Leu Leu Ser Phe Tyr Tyr Ile Trp Val Ser
            20                  25                  30

Ile Thr Lys Pro Ser Arg Asn Ser Lys Thr Lys Leu Pro Pro Pro Glu
        35                  40                  45

Val Ala Gly Ser Trp Pro Ile Val Gly His Leu Pro Gln Leu Val Gly
    50                  55                  60

Ser Thr Pro Leu Phe Lys Ile Leu Ala Asn Met Ser Asp Lys Tyr Gly
65                  70                  75                  80

Pro Ile Phe Met Val Arg Phe Gly Met His Pro Thr Leu Val Val Ser
                85                  90                  95

Ser Trp Glu Met Ser Lys Glu Cys Phe Thr Thr Asn Asp Lys Phe Leu
            100                 105                 110

Ala Ser Arg Pro Pro Ser Ala Ser Ala Lys Tyr Leu Gly Tyr Asp Asn
        115                 120                 125

Ala Met Phe Val Phe Ser Asp Tyr Gly Pro Tyr Trp Arg Glu Ile Arg
    130                 135                 140

Lys Ile Ser Thr Leu Gln Leu Leu Thr His Lys Arg Leu Asp Ser Leu
145                 150                 155                 160

Lys Asn Ile Pro Tyr Leu Glu Ile Asn Ser Cys Val Lys Thr Leu Tyr
                165                 170                 175

Thr Arg Trp Ala Lys Thr Gln Ser Gln Ile Lys Gln Asn Val Gly Gly
            180                 185                 190

Ala Ala Asp Asp Phe Val Lys Val Asp Met Thr Glu Met Phe Gly His
        195                 200                 205

Leu Asn Leu Asn Val Val Leu Arg Leu Val Val Gly Lys Pro Ile Phe
    210                 215                 220

Ile Gln Lys Asp Asn Ala Asp Glu Asp Tyr Thr Lys Asp Gly His Asn
225                 230                 235                 240

Lys Glu Glu Leu Gly Gln Lys Leu His Lys Thr Ile Ile Glu Phe Phe
                245                 250                 255

Glu Leu Ala Gly Ala Ser Val Ala Ser Asp Val Leu Pro Tyr Leu Gly
            260                 265                 270

Trp Leu Asp Val Asp Gly Gln Lys Lys Arg Met Lys Lys Ile Ala Met
        275                 280                 285

Glu Met Asp Leu Phe Ala Gln Lys Trp Leu Glu His Arg Gln Lys
    290                 295                 300

Gly Ile Asn His Asp Asn Glu Asn Asp Phe Met Ala Val Leu Ile Ser
305                 310                 315                 320

Val Leu Gly Glu Gly Lys Asp Asp His Ile Phe Gly Tyr Ser Arg Asp
                325                 330                 335

Thr Val Ile Lys Ala Thr Cys Leu Thr Leu Ile Val Ala Ala Thr Asp
            340                 345                 350

Thr Thr Leu Val Ser Leu Thr Trp Ala Leu Ser Leu Leu Leu Thr Asn
        355                 360                 365
```

```
Pro Arg Val Leu Ser Lys Ala Gln Asp Glu Leu Asp Thr Val Val Gly
    370                 375                 380

Lys Glu Arg Asn Val Glu Asp Arg Asp Val Asn His Leu Val Tyr Leu
385                 390                 395                 400

Gln Ala Val Ile Lys Glu Thr Leu Arg Leu Tyr Pro Pro Ser Pro Leu
            405                 410                 415

Ala Val Pro His Glu Ala Ile Glu Asn Cys Asn Val Gly Gly Tyr Glu
            420                 425                 430

Val Lys Ala Arg Thr Arg Leu Leu Val Asn Leu Trp Lys Ile His Arg
        435                 440                 445

Asp Pro Arg Val Trp Ser Asn Pro Leu Glu Phe Lys Pro Glu Arg Phe
    450                 455                 460

Leu Pro Lys Leu Asp Gly Gly Thr Gly Glu Ala Ser Lys Leu Asp Phe
465                 470                 475                 480

Lys Gly Gln Asp Phe Val Tyr Thr Pro Phe Gly Ser Gly Arg Arg Met
                485                 490                 495

Cys Pro Gly Ile Asn Phe Ala Ser Gln Thr Leu His Met Thr Leu Ala
            500                 505                 510

Arg Leu Leu His Ala Phe Asp Phe Asp Ile Glu Ser Asn Gly Leu Val
        515                 520                 525

Ile Asp Met Thr Glu Gly Ser Gly Leu Thr Met Pro Lys Val Thr Pro
    530                 535                 540

Leu Gln Val His Leu Arg Pro Arg Leu Pro Ala Thr Leu Tyr
545                 550                 555
```

<210> SEQ ID NO 97
<211> LENGTH: 571
<212> TYPE: PRT
<213> ORGANISM: Papaver bracteatum

<400> SEQUENCE: 97

```
Met Met Asp Leu Ala Met Phe Ile Asp Gln Tyr Phe Ser Leu Ala Lys
1               5                   10                  15

Ile Ala Gly Leu Leu Ala Leu Leu Ser Phe Phe Tyr Tyr Leu Trp Ile
            20                  25                  30

Ser Thr Leu Trp Ser Pro Arg Asn Pro Lys Leu Ser Ser Val Ser Pro
        35                  40                  45

Pro Glu Val Ala Gly Ala Trp Pro Ile Leu Gly His Leu Pro Gln Leu
    50                  55                  60

Leu Gly Ser Arg Pro Leu Phe Lys Ile Leu Ala Asp Met Ser Asp Asn
65                  70                  75                  80

Tyr Gly Pro Ile Phe Met Val Arg Phe Gly Met His Pro Thr Leu Val
                85                  90                  95

Val Ser Ser Trp Glu Met Ala Lys Glu Cys Phe Thr Thr Asn Asp Arg
            100                 105                 110

Phe Leu Ala Gly Arg Pro Ser Gly Ala Ala Asn Lys Tyr Leu Thr Phe
        115                 120                 125

Ala Leu Phe Gly Phe Ser Thr Tyr Gly Pro Tyr Trp Arg Glu Ile Arg
    130                 135                 140

Lys Ile Ala Thr Leu His Leu Leu Ser His Arg Arg Leu Glu Leu Leu
145                 150                 155                 160

Lys His Val Pro Asp Leu Glu Val Thr Asn Cys Met Lys His Leu His
                165                 170                 175

Arg Arg Trp Ile Asp Ser Gln Asn Gln Ile Lys Gln Asn Asp Ala Ala
```

```
                180             185             190
Ala Gly Ser Val Lys Val Asp Met Gly Arg Val Phe Gly Glu Leu Thr
            195                 200                 205
Leu Asn Val Val Leu Lys Leu Val Ala Gly Lys Ser Ile Phe Phe Lys
            210                 215                 220
Asn Asp Asn Thr Arg Gln Tyr Asp Ser Lys Asp Gly His Asn Lys Glu
225                 230                 235                 240
Glu Glu Glu Gly Lys Lys Leu His Lys Thr Ile Ile Asp Phe Tyr Ser
                245                 250                 255
Leu Ala Gly Ala Ser Val Ala Ser Asp Val Leu Pro Phe Leu Gly Trp
            260                 265                 270
Leu Asp Val Asp Gly Gln Lys Lys Arg Met Lys Arg Val Ala Lys Asp
            275                 280                 285
Met Asp Phe Ile Ala Ala Lys Trp Leu Glu Glu His Arg His Gln Lys
290                 295                 300
Arg Gln Thr Val Leu Ser Ser Ser Ala Thr Leu Gly Ser Ser Asn His
305                 310                 315                 320
Asp Asp Ala Lys Asp Phe Met Asp Val Leu Met Ser Ile Leu Asp Gly
                325                 330                 335
Glu Asn Asp Asp Leu Phe Phe Gly Tyr Ser Arg Asp Thr Val Ile Lys
                340                 345                 350
Thr Thr Cys Leu Gln Leu Ile Ala Ala Ala Asp Thr Thr Ser Val
                355                 360                 365
Thr Met Thr Trp Ala Leu Ala Leu Leu Ile Thr Asn Pro Thr Ile Leu
        370                 375                 380
Arg Lys Ala Gln Asp Glu Leu Asp Thr Lys Val Gly Lys Asp Arg Asn
385                 390                 395                 400
Ile Glu Glu Arg Asp Ile Asn Asp Leu Val Tyr Leu Gln Ala Ile Val
                405                 410                 415
Lys Glu Thr Leu Arg Met Tyr Pro Ala Gly Pro Leu Asn Val Pro His
                420                 425                 430
Glu Ala Ile Ala Asp Cys Asn Ile Gly Gly Tyr Glu Val Arg Ala Gly
                435                 440                 445
Thr Arg Leu Leu Val Asn Leu Trp Lys Met His Arg Asp Pro Arg Val
        450                 455                 460
Trp Ser Asn Pro Ser Glu Phe Lys Pro Glu Arg Phe Leu Pro Gln Leu
465                 470                 475                 480
Asp Gly Gly Ser Gly Gly Glu Ala Ala Asn Leu Asp Phe Arg Gly Gln
                485                 490                 495
Asp Phe Glu Tyr Leu Pro Phe Ser Ala Gly Arg Arg Met Cys Pro Gly
                500                 505                 510
Ile Asp Phe Ser Leu Gln Thr His Met Thr Leu Ala Arg Leu Leu
                515                 520                 525
His Gly Phe Asp Phe Asn Asn Asp Ser Ala Gly Ile Ile Ile Asp Met
        530                 535                 540
Glu Gly Ser Gly Leu Thr Met Pro Lys Leu Thr Pro Leu Glu Ile
545                 550                 555                 560
Tyr Leu Cys Pro Arg Leu Pro Ala Lys Leu Tyr
                565                 570

<210> SEQ ID NO 98
<211> LENGTH: 361
<212> TYPE: PRT
<213> ORGANISM: Thalictrum flavum
```

<400> SEQUENCE: 98

```
Met Ala Val Glu Gly Lys Gln Val Ala Pro Lys Ala Ile Ile Val
1               5                   10                  15

Glu Leu Leu Lys Lys Leu Glu Leu Gly Leu Val Pro Asp Asp Glu Ile
                20                  25                  30

Lys Lys Leu Ile Arg Ile Gln Leu Gly Arg Arg Leu Gln Trp Gly Cys
                35                  40                  45

Lys Ser Thr Tyr Glu Glu Gln Ile Ala Gln Leu Val Asn Leu Thr His
            50                  55                  60

Ser Leu Arg Gln Met Lys Ile Ala Thr Glu Val Glu Thr Leu Asp Asp
65                  70                  75                  80

Gln Met Tyr Glu Val Pro Ile Asp Phe Leu Lys Ile Met Asn Gly Ser
                85                  90                  95

Asn Leu Lys Gly Ser Cys Cys Tyr Phe Lys Asn Asp Ser Thr Thr Leu
                100                 105                 110

Asp Glu Ala Glu Ile Ala Met Leu Glu Leu Tyr Cys Glu Arg Ala Gln
            115                 120                 125

Ile Lys Asp Gly His Ser Val Leu Asp Leu Gly Cys Gly Gln Gly Ala
        130                 135                 140

Leu Thr Leu Tyr Val Ala Gln Lys Tyr Lys Asn Ser Arg Val Thr Ala
145                 150                 155                 160

Val Thr Asn Ser Val Ser Gln Lys Glu Phe Ile Glu Glu Ser Arg
                165                 170                 175

Lys Arg Asn Leu Ser Asn Val Glu Val Leu Leu Ala Asp Ile Thr Thr
                180                 185                 190

His Lys Met Pro Asp Thr Tyr Asp Arg Ile Leu Val Val Glu Leu Phe
            195                 200                 205

Glu His Met Lys Asn Tyr Glu Leu Leu Leu Arg Lys Ile Lys Glu Trp
        210                 215                 220

Met Ala Lys Asp Gly Leu Leu Phe Val Glu His Ile Cys His Lys Thr
225                 230                 235                 240

Phe Ala Tyr His Tyr Glu Pro Ile Asp Glu Asp Asp Trp Phe Thr Glu
                245                 250                 255

Tyr Val Phe Pro Ala Gly Thr Met Ile Ile Pro Ser Ala Ser Phe Phe
                260                 265                 270

Leu Tyr Phe Gln Asp Asp Val Ser Val Val Asn His Trp Thr Leu Ser
            275                 280                 285

Gly Lys His Phe Ser Arg Thr Asn Glu Glu Trp Leu Lys Arg Leu Asp
        290                 295                 300

Ala Asn Val Glu Leu Ile Lys Pro Met Phe Val Thr Ile Thr Gly Gln
305                 310                 315                 320

Cys Arg Gln Glu Ala Met Lys Leu Ile Asn Tyr Trp Arg Gly Phe Cys
                325                 330                 335

Leu Ser Gly Met Glu Met Phe Gly Tyr Asn Asn Gly Glu Glu Trp Met
            340                 345                 350

Ala Ser His Val Leu Phe Lys Lys Lys
        355                 360
```

<210> SEQ ID NO 99
<211> LENGTH: 358
<212> TYPE: PRT
<213> ORGANISM: Coptis japonica

<400> SEQUENCE: 99

Met Ala Val Glu Ala Lys Gln Thr Lys Lys Ala Ala Ile Val Glu Leu
1               5                   10                  15

Leu Lys Gln Leu Glu Leu Gly Leu Val Pro Tyr Asp Asp Ile Lys Gln
            20                  25                  30

Leu Ile Arg Arg Glu Leu Ala Arg Arg Leu Gln Trp Gly Tyr Lys Pro
        35                  40                  45

Thr Tyr Glu Glu Gln Ile Ala Glu Ile Gln Asn Leu Thr His Ser Leu
    50                  55                  60

Arg Gln Met Lys Ile Ala Thr Glu Val Glu Thr Leu Asp Ser Gln Leu
65              70                  75                  80

Tyr Glu Ile Pro Ile Glu Phe Leu Lys Ile Met Asn Gly Ser Asn Leu
                85                  90                  95

Lys Gly Ser Cys Cys Tyr Phe Lys Glu Asp Ser Thr Thr Leu Asp Glu
                100                 105                 110

Ala Glu Ile Ala Met Leu Asp Leu Tyr Cys Glu Arg Ala Gln Ile Gln
            115                 120                 125

Asp Gly Gln Ser Val Leu Asp Leu Gly Cys Gly Gln Gly Ala Leu Thr
        130                 135                 140

Leu His Val Ala Gln Lys Tyr Lys Asn Cys Arg Val Thr Ala Val Thr
145                 150                 155                 160

Asn Ser Val Ser Gln Lys Glu Tyr Ile Glu Glu Ser Arg Arg Arg
                165                 170                 175

Asn Leu Leu Asn Val Glu Val Lys Leu Ala Asp Ile Thr Thr His Glu
                180                 185                 190

Met Ala Glu Thr Tyr Asp Arg Ile Leu Val Ile Glu Leu Phe Glu His
            195                 200                 205

Met Lys Asn Tyr Glu Leu Leu Leu Arg Lys Ile Ser Glu Trp Ile Ser
210                 215                 220

Lys Asp Gly Leu Leu Phe Leu Glu His Ile Cys His Lys Thr Phe Ala
225                 230                 235                 240

Tyr His Tyr Glu Pro Leu Asp Asp Asp Trp Phe Thr Glu Tyr Val
            245                 250                 255

Phe Pro Ala Gly Thr Met Ile Ile Pro Ser Ala Ser Phe Phe Leu Tyr
            260                 265                 270

Phe Gln Asp Asp Val Ser Val Val Asn His Trp Thr Leu Ser Gly Lys
        275                 280                 285

His Phe Ser Arg Thr Asn Glu Glu Trp Leu Lys Arg Leu Asp Ala Asn
        290                 295                 300

Leu Asp Val Ile Lys Pro Met Phe Glu Thr Leu Met Gly Asn Glu Glu
305                 310                 315                 320

Glu Ala Val Lys Leu Ile Asn Tyr Trp Arg Gly Phe Cys Leu Ser Gly
            325                 330                 335

Met Glu Met Phe Gly Tyr Asn Asn Gly Glu Glu Trp Met Ala Ser His
            340                 345                 350

Val Leu Phe Lys Lys Lys
            355

<210> SEQ ID NO 100
<211> LENGTH: 351
<212> TYPE: PRT
<213> ORGANISM: Papaver somniferum

<400> SEQUENCE: 100

Met Gln Leu Lys Ala Lys Glu Glu Leu Leu Arg Asn Met Glu Leu Gly

```
 1               5                   10                  15
Leu Ile Pro Asp Gln Glu Ile Arg Gln Leu Ile Arg Val Glu Leu Glu
                20                  25                  30

Lys Arg Leu Gln Trp Gly Tyr Lys Glu Thr His Glu Glu Gln Leu Ser
                35                  40                  45

Gln Leu Leu Asp Leu Val His Ser Leu Lys Gly Met Lys Met Ala Thr
    50                  55                  60

Glu Met Glu Asn Leu Asp Leu Lys Leu Tyr Glu Ala Pro Met Glu Phe
65                  70                  75                  80

Leu Lys Ile Gln His Gly Ser Asn Met Lys Gln Ser Ala Gly Tyr Tyr
                85                  90                  95

Thr Asp Glu Ser Thr Thr Leu Asp Glu Ala Glu Ile Ala Met Leu Asp
                100                 105                 110

Leu Tyr Met Glu Arg Ala Gln Ile Lys Asp Gly Gln Ser Val Leu Asp
                115                 120                 125

Leu Gly Cys Gly Leu Gly Ala Val Ala Leu Phe Gly Ala Asn Lys Phe
130                 135                 140

Lys Lys Cys Gln Phe Thr Gly Val Thr Ser Ser Val Glu Gln Lys Asp
145                 150                 155                 160

Tyr Ile Glu Gly Lys Cys Lys Glu Leu Lys Leu Thr Asn Val Lys Val
                165                 170                 175

Leu Leu Ala Asp Ile Thr Thr Tyr Glu Thr Glu Glu Arg Phe Asp Arg
                180                 185                 190

Ile Phe Ala Val Glu Leu Ile Glu His Met Lys Asn Tyr Gln Leu Leu
                195                 200                 205

Leu Lys Lys Ile Ser Glu Trp Met Lys Asp Asp Gly Leu Leu Phe Val
                210                 215                 220

Glu His Val Cys His Lys Thr Leu Ala Tyr His Tyr Glu Pro Val Asp
225                 230                 235                 240

Ala Glu Asp Trp Tyr Thr Asn Tyr Ile Phe Pro Ala Gly Thr Leu Thr
                245                 250                 255

Leu Ser Ser Ala Ser Met Leu Leu Tyr Phe Gln Asp Asp Val Ser Val
                260                 265                 270

Val Asn Gln Trp Thr Leu Ser Gly Lys His Tyr Ser Arg Ser His Glu
                275                 280                 285

Glu Trp Leu Lys Asn Met Asp Lys Asn Ile Val Glu Phe Lys Glu Ile
                290                 295                 300

Met Arg Ser Ile Thr Lys Thr Glu Lys Glu Ala Ile Lys Leu Leu Asn
305                 310                 315                 320

Phe Trp Arg Ile Phe Cys Met Cys Gly Ala Glu Leu Phe Gly Tyr Lys
                325                 330                 335

Asn Gly Glu Glu Trp Met Leu Thr His Leu Leu Phe Lys Lys Lys
                340                 345                 350

<210> SEQ ID NO 101
<211> LENGTH: 358
<212> TYPE: PRT
<213> ORGANISM: Papaver somniferum

<400> SEQUENCE: 101

Met Gly Ser Ile Asp Glu Val Lys Lys Glu Ser Ala Gly Glu Thr Leu
1               5                   10                  15

Gly Arg Leu Leu Lys Gly Glu Ile Lys Asp Glu Glu Leu Lys Lys Leu
                20                  25                  30
```

```
Ile Lys Phe Gln Phe Glu Lys Arg Leu Gln Trp Gly Tyr Lys Ser Ser
            35                  40                  45

His Gln Glu Gln Leu Ser Phe Asn Leu Asp Phe Ile Lys Ser Leu Lys
 50                  55                  60

Lys Met Glu Met Ser Gly Glu Ile Glu Thr Met Asn Lys Glu Thr Tyr
 65                  70                  75                  80

Glu Leu Pro Ser Glu Phe Leu Glu Ala Val Phe Gly Lys Thr Val Lys
                 85                  90                  95

Gln Ser Met Cys Tyr Phe Thr His Glu Ser Ala Thr Ile Asp Glu Ala
                100                 105                 110

Glu Glu Ala Ala His Glu Leu Tyr Cys Glu Arg Ala Gln Ile Lys Asp
            115                 120                 125

Gly Gln Thr Val Leu Asp Ile Gly Cys Gly Gln Gly Leu Val Leu
        130                 135                 140

Tyr Ile Ala Gln Lys Tyr Lys Asn Cys His Val Thr Gly Leu Thr Asn
145                 150                 155                 160

Ser Lys Ala Gln Val Asn Tyr Leu Leu Lys Gln Ala Glu Lys Leu Gly
                165                 170                 175

Leu Thr Asn Val Asp Ala Ile Leu Ala Asp Val Thr Gln Tyr Glu Ser
            180                 185                 190

Asp Lys Thr Tyr Asp Arg Leu Leu Met Ile Glu Ala Ile Glu His Met
        195                 200                 205

Lys Asn Leu Gln Leu Phe Met Lys Lys Leu Ser Thr Trp Met Thr Lys
210                 215                 220

Glu Ser Leu Leu Phe Val Asp His Val Cys His Lys Thr Phe Ala His
225                 230                 235                 240

Phe Phe Glu Ala Val Asp Glu Asp Trp Tyr Ser Gly Phe Ile Phe
                245                 250                 255

Pro Pro Gly Cys Ala Thr Ile Leu Ala Ala Asn Ser Leu Leu Tyr Phe
                260                 265                 270

Gln Asp Asp Val Ser Val Val Asp His Trp Val Asn Gly Met His
            275                 280                 285

Met Ala Arg Ser Val Asp Ile Trp Arg Lys Ala Leu Asp Lys Asn Met
290                 295                 300

Glu Ala Ala Lys Glu Ile Leu Leu Pro Gly Leu Gly Ser His Glu
305                 310                 315                 320

Thr Val Asn Gly Val Val Thr His Ile Arg Thr Phe Cys Met Gly Gly
                325                 330                 335

Tyr Glu Gln Phe Ser Met Asn Asn Gly Asp Glu Trp Met Val Ala Gln
            340                 345                 350

Leu Leu Phe Lys Lys Lys
        355

<210> SEQ ID NO 102
<211> LENGTH: 350
<212> TYPE: PRT
<213> ORGANISM: Eschscholzia californica

<400> SEQUENCE: 102

Met Gly Ser Ser Ala Gly Glu Ile Met Gly Arg Leu Met Lys Gly Glu
 1               5                  10                  15

Ile Glu Asp Glu Glu Leu Lys Lys Leu Ile Arg His Gln Trp Asp Arg
            20                  25                  30

Arg Ile Glu Trp Gly Tyr Lys Pro Thr His Glu Lys Gln Leu Ala Phe
        35                  40                  45
```

```
Asn Leu Asp Phe Ile Lys Gly Leu Lys Glu Met Val Met Ser Gly Glu
        50                  55                  60

Ile Asp Thr Met Asn Lys Glu Thr Tyr Glu Leu Pro Thr Ala Phe Leu
 65                  70                  75                  80

Glu Ala Val Phe Gly Lys Thr Val Lys Gln Ser Cys Cys Tyr Phe Lys
                85                  90                  95

Asp Glu Asn Ser Thr Ile Asp Glu Ala Glu Ala Ala His Glu Leu
                100                 105                 110

Tyr Cys Glu Arg Ala Gln Ile Lys Asp Gly Gln Thr Val Leu Asp Ile
            115                 120                 125

Gly Cys Gly Gln Gly Gly Leu Val Leu Tyr Ile Ala Glu Lys Tyr Lys
    130                 135                 140

Asn Cys His Val Thr Gly Leu Thr Asn Ser Lys Ala Gln Ala Asn Tyr
145                 150                 155                 160

Ile Glu Gln Gln Ala Glu Lys Leu Glu Leu Thr Asn Val Asp Val Ile
                165                 170                 175

Phe Ala Asp Val Thr Lys Phe Asp Thr Asp Lys Thr Tyr Asp Arg Ile
                180                 185                 190

Leu Val Val Glu Thr Ile Glu His Met Lys Asn Ile Gln Leu Phe Met
            195                 200                 205

Lys Lys Leu Ser Thr Trp Met Thr Glu Asp Ser Leu Leu Phe Val Asp
    210                 215                 220

His Ile Ser His Lys Thr Phe Asn His Asn Phe Glu Ala Leu Asp Glu
225                 230                 235                 240

Asp Asp Trp Tyr Ser Gly Phe Ile Phe Pro Lys Gly Cys Val Thr Ile
                245                 250                 255

Leu Ser Ser Ser Thr Leu Leu Tyr Phe Gln Asp Asp Val Ser Ala Leu
                260                 265                 270

Asp His Trp Val Val Asn Gly Met His Met Ala Arg Ser Val Glu Ala
            275                 280                 285

Trp Arg Lys Lys Leu Asp Glu Thr Ile Glu Ala Ala Arg Glu Ile Leu
    290                 295                 300

Glu Pro Gly Leu Gly Ser Lys Glu Ala Val Asn Gln Val Ile Thr His
305                 310                 315                 320

Ile Arg Thr Phe Cys Ile Gly Gly Tyr Glu Gln Phe Ser Tyr Asn Asn
                325                 330                 335

Gly Glu Glu Trp Met Ile Thr Gln Ile Leu Phe Lys Lys Lys
                340                 345                 350

<210> SEQ ID NO 103
<211> LENGTH: 363
<212> TYPE: PRT
<213> ORGANISM: Papaver somniferum

<400> SEQUENCE: 103

Met Ser Thr Thr Met Glu Thr Thr Lys Ile Ser Gln Gln Asp Asp Leu
 1               5                  10                  15

Trp Lys Asn Met Glu Leu Gly Gln Ile Ser Asp Glu Val Arg Arg
                20                  25                  30

Leu Met Lys Ile Gly Ile Glu Lys Arg Ile Lys Trp Gly Thr Lys Pro
            35                  40                  45

Thr Gln Gln Glu Gln Leu Ala Gln Leu Leu Asp Phe Asn Lys Ser Leu
        50                  55                  60

Arg Gly Met Lys Met Ala Thr Glu Ile Asp Thr Leu Glu Asn His Lys
```

```
            65                  70                  75                  80
Ile Tyr Glu Thr Pro Glu Ser Phe Asn Gln Ile Ile Gly Gly Lys Glu
                85                  90                  95

Ser Ala Gly Leu Phe Thr Asp Glu Thr Thr Thr Met Glu Glu Ala
            100                 105                 110

Asn Thr Lys Met Met Asp Leu Tyr Cys Glu Arg Ala Gly Leu Lys Asp
            115                 120                 125

Gly His Thr Ile Leu Asp Leu Gly Cys Gly Ala Gly Leu Leu Val Leu
        130                 135                 140

His Leu Ala Lys Lys Tyr Lys Ser Lys Ile Thr Gly Ile Thr Asn
145                 150                 155                 160

Thr Ser Ser His Lys Glu Tyr Ile Leu Lys Gln Cys Lys Asn Leu Asn
                165                 170                 175

Leu Ser Asn Val Glu Ile Ile Leu Ala Asp Val Thr Lys Val Asp Ile
            180                 185                 190

Glu Ser Thr Phe Asp Arg Val Phe Val Ile Gly Leu Ile Glu His Met
            195                 200                 205

Lys Asn Phe Glu Leu Phe Leu Arg Lys Ile Ser Lys Trp Met Lys Asp
210                 215                 220

Asp Gly Leu Leu Leu Glu His Leu Cys His Lys Ser Phe Ser Asp
225                 230                 235                 240

His Trp Glu Pro Leu Ser Glu Asp Asp Trp Tyr Ala Lys Asn Phe Phe
                245                 250                 255

Pro Ser Gly Thr Leu Val Ile Pro Ser Ala Thr Cys Leu Leu Tyr Phe
            260                 265                 270

Gln Glu Asp Val Thr Val Ile Asp His Trp Ile Leu Ser Gly Asn Asn
            275                 280                 285

Phe Ala Arg Ser Asn Glu Val Ile Leu Lys Arg Ile Asp Gly Lys Ile
        290                 295                 300

Glu Glu Val Lys Asp Ile Phe Met Ser Phe Tyr Gly Ile Gly Arg Glu
305                 310                 315                 320

Glu Ala Val Lys Leu Ile Asn Trp Trp Arg Leu Leu Cys Ile Thr Ala
                325                 330                 335

Asn Glu Leu Phe Lys Tyr Asn Asn Gly Glu Trp Leu Ile Ser Gln
            340                 345                 350

Leu Leu Phe Lys Lys Leu Met Thr Cys Ile
            355                 360

<210> SEQ ID NO 104
<211> LENGTH: 356
<212> TYPE: PRT
<213> ORGANISM: Thalictrum flavum

<400> SEQUENCE: 104

Met Glu Thr Lys Gln Thr Lys Lys Glu Ala Val Ala Asn Leu Ile Lys
1               5                   10                  15

Arg Ile Glu His Gly Glu Val Ser Asp Glu Ile Arg Gly Met Met
            20                  25                  30

Lys Ile Gln Val Gln Lys Arg Leu Lys Trp Gly Tyr Lys Pro Thr His
        35                  40                  45

Glu Gln Gln Leu Ala Gln Leu Val Thr Phe Ala Gln Ser Leu Lys Gly
    50                  55                  60

Met Glu Met Ala Glu Glu Val Asp Thr Leu Asp Ala Glu Leu Tyr Glu
65                  70                  75                  80
```

```
Ile Pro Leu Pro Phe Leu His Ile Met Cys Gly Lys Thr Leu Lys Phe
                85                  90                  95

Ser Pro Gly Tyr Phe Lys Asp Glu Ser Thr Thr Leu Asp Glu Ser Glu
            100                 105                 110

Val Tyr Met Met Asp Leu Tyr Cys Glu Arg Ala Gln Ile Lys Asp Gly
            115                 120                 125

Gln Ser Ile Leu Asp Leu Gly Cys Gly His Gly Ser Leu Thr Leu His
130             135                 140

Val Ala Gln Lys Tyr Arg Gly Cys Lys Val Thr Gly Ile Thr Asn Ser
145                 150                 155                 160

Val Ser Gln Lys Glu Phe Ile Met Asp Gln Cys Lys Lys Leu Asp Leu
                165                 170                 175

Ser Asn Val Glu Ile Ile Leu Glu Asp Val Thr Lys Phe Glu Thr Glu
            180                 185                 190

Ile Thr Tyr Asp Arg Ile Phe Ala Val Ala Leu Ile Glu His Met Lys
            195                 200                 205

Asn Tyr Glu Leu Phe Leu Lys Lys Val Ser Thr Trp Ile Ala Gln Tyr
    210                 215                 220

Gly Leu Leu Phe Val Glu His His Cys His Lys Val Phe Ala Tyr Gln
225                 230                 235                 240

Tyr Glu Pro Leu Asp Glu Asp Trp Tyr Thr Glu Tyr Ile Phe Pro
                245                 250                 255

Ser Gly Thr Leu Val Met Ser Ser Ser Ile Leu Leu Tyr Phe Gln
            260                 265                 270

Glu Asp Val Ser Val Val Asn His Trp Thr Leu Ser Gly Lys His Pro
            275                 280                 285

Ser Leu Gly Phe Lys Gln Trp Leu Lys Arg Leu Asp Asp Asn Ile Asp
    290                 295                 300

Glu Val Lys Glu Ile Phe Glu Ser Phe Tyr Gly Ser Lys Glu Lys Ala
305                 310                 315                 320

Met Lys Phe Ile Thr Tyr Trp Arg Val Phe Cys Ile Ala His Ser Gln
                325                 330                 335

Met Tyr Ser Thr Asn Asn Gly Glu Glu Trp Met Leu Ser Gln Val Leu
            340                 345                 350

Phe Lys Lys Lys
            355

<210> SEQ ID NO 105
<211> LENGTH: 358
<212> TYPE: PRT
<213> ORGANISM: Papaver bracteatum

<400> SEQUENCE: 105

Met Gly Ser Ile Asp Glu Val Lys Lys Glu Ser Ala Gly Glu Thr Leu
1               5                   10                  15

Gly Arg Leu Leu Lys Gly Glu Ile Lys Asp Glu Glu Leu Lys Lys Leu
            20                  25                  30

Ile Lys Phe Gln Phe Glu Lys Arg Leu Gln Trp Gly Tyr Lys Ser Ser
            35                  40                  45

His Gln Glu Gln Leu Ser Phe Asn Leu Asp Phe Ile Lys Ser Leu Lys
    50                  55                  60

Lys Met Glu Met Ser Gly Glu Ile Glu Thr Met Asn Lys Glu Thr Tyr
65                  70                  75                  80

Glu Leu Pro Ser Glu Phe Leu Glu Ala Val Phe Gly Lys Thr Val Lys
                85                  90                  95
```

```
Gln Ser Met Cys Tyr Phe Lys His Glu Ser Ala Thr Ile Asp Glu Ala
            100                 105                 110

Glu Glu Ala Ala His Glu Leu Tyr Cys Glu Arg Ala Gln Ile Lys Asp
        115                 120                 125

Gly Gln Thr Val Leu Asp Ile Gly Cys Gly Gln Gly Gly Leu Val Leu
    130                 135                 140

Tyr Ile Ala Arg Lys Tyr Lys Lys Cys His Val Thr Gly Leu Thr Asn
145                 150                 155                 160

Ser Lys Ala Gln Val Asn Tyr Leu Leu Lys Gln Ala Glu Lys Leu Gly
                165                 170                 175

Leu Thr Asn Val Asp Ala Ile Leu Ala Asp Val Thr Gln Tyr Glu Ser
            180                 185                 190

Asp Lys Thr Tyr Asp Arg Leu Leu Met Ile Glu Ala Ile Glu His Met
        195                 200                 205

Lys Asn Leu Gln Leu Phe Met Lys Lys Leu Ser Thr Trp Met Thr Glu
    210                 215                 220

Glu Ser Leu Leu Phe Val Asp His Val Cys His Lys Thr Phe Ala His
225                 230                 235                 240

Phe Phe Glu Ala Val Asp Glu Asp Trp Tyr Ser Gly Phe Ile Phe
                245                 250                 255

Pro Pro Gly Cys Ala Thr Ile Leu Ala Ala Asn Ser Leu Leu Tyr Phe
            260                 265                 270

Gln Asp Asp Val Ser Val Val Asp His Trp Val Val Asn Gly Met His
        275                 280                 285

Met Ala Arg Ser Val Asp Ile Trp Arg Lys Ala Leu Asp Lys Asn Met
    290                 295                 300

Glu Ala Ala Lys Glu Ile Leu Leu Pro Gly Leu Gly Gly Ser His Glu
305                 310                 315                 320

Ala Val Asn Gly Val Val Thr His Ile Arg Thr Phe Cys Met Gly Gly
                325                 330                 335

Tyr Glu Gln Phe Ser Met Asn Asp Gly Asp Glu Trp Met Val Ala Gln
            340                 345                 350

Leu Leu Phe Lys Lys Lys
        355

<210> SEQ ID NO 106
<211> LENGTH: 358
<212> TYPE: PRT
<213> ORGANISM: Papaver bracteatum

<400> SEQUENCE: 106

Met Gly Ser Ile Glu Glu Val Lys Lys Glu Ser Ala Glu Glu Thr Leu
1               5                   10                  15

Gly Arg Leu Leu Arg Gly Glu Ile Asn Asp Glu Glu Leu Lys Lys Leu
            20                  25                  30

Ile Lys Tyr Gln Leu Glu Lys Arg Leu Gln Trp Gly Tyr Lys Ser Ser
        35                  40                  45

His Gln Glu Gln Leu Ser Phe Asn Leu Asp Phe Ile Asn Ser Leu Lys
    50                  55                  60

Lys Met Gly Met Ser Gly Gln Val Glu Ala Phe Thr Asn Glu Val Tyr
65                  70                  75                  80

Glu Leu Pro Thr Glu Cys Phe Glu Ala Ala Tyr Gly Lys Ser Met Lys
                85                  90                  95

Leu Ser Gly Cys Tyr Phe Lys His Glu Ser Ser Thr Ile Asp Glu Ala
```

```
            100                 105                 110
Glu Glu Ala Ser His Glu Leu Tyr Cys Glu Arg Ala Gln Ile Lys Asp
        115                 120                 125

Gly Gln Thr Val Leu Asp Ile Gly Cys Gly Gln Gly Leu Val Leu
130                 135                 140

Tyr Val Ala Gln Lys Tyr Lys Asn Cys His Val Thr Gly Leu Thr Asn
145                 150                 155                 160

Ser Lys Glu Gln Val Asn Tyr Ile Leu Lys Gln Ala Glu Lys Leu Gly
                165                 170                 175

Leu Arg Asn Val Asp Val Ile Leu Ala Asp Val Thr Gln Tyr Glu Ser
            180                 185                 190

Asp Lys Thr Tyr Asp Arg Ile Leu Val Ile Gly Val Glu His Met
        195                 200                 205

Lys Asn Met Gln Leu Phe Ile Lys Lys Leu Ser Thr Trp Met Ala Glu
210                 215                 220

Asp Ser Leu Leu Phe Val Asp His Ser Cys His Lys Thr Phe Asn His
225                 230                 235                 240

Phe Phe Glu Ala Leu Asp Glu Asp Trp Tyr Ser Gly Tyr Ile Phe
                245                 250                 255

Pro Pro Gly Cys Ala Thr Phe Leu Ser Ala Asp Ser Leu Leu Tyr Phe
            260                 265                 270

Gln Asp Asp Val Ser Val Asp His Trp Val Val Asn Gly Met His
        275                 280                 285

Phe Ala Arg Thr Val Asp Ala Trp Arg Lys Lys Leu Asp Lys Asn Met
290                 295                 300

Glu Ala Val Lys Glu Ile Leu Leu Pro Gly Leu Gly Gly Asn His Glu
305                 310                 315                 320

Ala Val Asn Gly Val Ile Thr His Ile Arg Thr Cys Cys Val Gly Gly
                325                 330                 335

Tyr Val Gln Phe Ser Leu Asn Asp Gly Asp Glu Trp Met Asn Ala Gln
            340                 345                 350

Leu Leu Phe Lys Lys Lys
            355

<210> SEQ ID NO 107
<211> LENGTH: 368
<212> TYPE: PRT
<213> ORGANISM: Argemone mexicana

<400> SEQUENCE: 107

Met Cys Leu Phe Phe Ala Glu Lys Met Gly Leu Met Ala Glu Ala Asn
1               5                   10                  15

Asn Gln Gln Gln Leu Lys Lys Glu Asp Leu Leu Lys Asn Met Glu Leu
                20                  25                  30

Gly Leu Ile Pro Asp Glu Glu Ile Arg Lys Leu Ile Arg Val Gln Leu
            35                  40                  45

Glu Lys Arg Leu Asn Trp Gly Tyr Lys Ser Thr His Glu Gln Gln Leu
        50                  55                  60

Ser Gln Leu Leu His Leu Val His Ser Leu Lys Lys Met Lys Ile Ala
65                  70                  75                  80

Thr Glu Met Glu Asn Leu Asp Leu Lys Leu Tyr Glu Ala Pro Phe Ser
                85                  90                  95

Phe Val Gln Ile Gln His Gly Ser Thr Ile Lys Glu Ser Ser Gly Leu
            100                 105                 110
```

Phe Lys Asp Glu Ser Thr Thr Leu Asp Glu Ala Glu Ile Ala Met Leu
            115                 120                 125

Asp Leu Tyr Thr Lys Arg Ala Lys Ile Glu Asp Gly Gln Ser Val Leu
            130                 135                 140

Asp Leu Gly Cys Gly Leu Gly Ala Val Thr Leu Tyr Val Ala Gln Lys
145                 150                 155                 160

Phe Lys Asn Cys Tyr Val Thr Gly Ile Thr Ser Ser Val Glu Gln Lys
                165                 170                 175

Asp Phe Ile Glu Gly Arg Cys Lys Glu Leu Lys Leu Ser Asn Val Lys
            180                 185                 190

Val Ile Leu Ala Asp Ile Thr Thr Tyr Glu Thr Glu Glu Lys Tyr Asn
195                 200                 205

Arg Ile Phe Ala Val Glu Leu Ile Glu His Met Lys Asn Tyr Glu Leu
            210                 215                 220

Leu Leu Arg Lys Ile Ser Glu Trp Met Lys Gln Asp Gly Leu Leu Phe
225                 230                 235                 240

Ile Glu His Val Cys His Lys Thr Leu Ala Tyr His Tyr Glu Pro Leu
                245                 250                 255

Asp Glu Glu Asp Trp Tyr Thr Asn Tyr Ile Phe Pro Ala Gly Thr Leu
            260                 265                 270

Thr Leu Ser Ser Ala Thr Leu Leu Tyr Phe Gln Asp Asp Val Ala
275                 280                 285

Val Val Asp Gln Trp Thr Leu Ser Gly Lys His Tyr Ser Arg Ser His
            290                 295                 300

Glu Glu Trp Leu Lys Arg Ile Asp Gly Asn Ile Glu Glu Val Lys Glu
305                 310                 315                 320

Ile Met Lys Ser Ile Thr Lys Ser Glu Glu Ala Lys Lys Leu Leu
                325                 330                 335

Asn Phe Trp Arg Ile Phe Cys Met Cys Gly Ala Glu Leu Phe Gly Tyr
            340                 345                 350

Lys Asn Gly Glu Glu Trp Met Met Thr His Ile Leu Phe Lys Lys Lys
            355                 360                 365

<210> SEQ ID NO 108
<211> LENGTH: 364
<212> TYPE: PRT
<213> ORGANISM: Glaucium flavum

<400> SEQUENCE: 108

Met Asp Leu Met Ala Thr Ser Lys Gln Val Lys Lys Glu Glu Leu
1               5                   10                  15

Leu Lys Asn Met Glu Leu Gly Leu Val Pro Asp Glu Glu Ile Arg Arg
            20                  25                  30

Leu Ile Arg Ile Glu Leu Glu Lys Arg Leu Lys Trp Gly Tyr Lys Pro
        35                  40                  45

Thr His Gln Gln Leu Ala Gln Leu Leu Asp Leu Val His Ser Leu
            50                  55                  60

Lys Lys Met Lys Ile Ala Thr Glu Met Glu Ser Leu Asp Leu Lys Leu
65                  70                  75                  80

Tyr Glu Ala Pro Phe Ser Phe Val Gln Ile Lys His Gly Ser Thr Ile
                85                  90                  95

Lys Glu Ser Ser Ser Tyr Phe Lys Asp Glu Ser Met Thr Leu Asp Glu
            100                 105                 110

Ala Glu Ile Ala Met Leu Asp Leu Tyr Val Glu Arg Ala Gln Ile Glu
            115                 120                 125

Asp Gly Gln Ser Val Leu Asp Leu Gly Cys Gly Leu Gly Ala Val Thr
        130                 135                 140

Leu His Val Ala Lys Lys Tyr Lys Asn Cys His Val Thr Gly Leu Thr
145                 150                 155                 160

Asn Ser Val Glu Gln Lys Asp Phe Ile Glu Gly Lys Cys Lys Glu Leu
                165                 170                 175

Asn Leu Ser Asn Val Lys Val Ile Leu Ala Asp Val Thr Ser His Glu
            180                 185                 190

Met Glu Asp Lys Phe Asp Arg Ile Phe Ala Val Glu Leu Ile Glu His
        195                 200                 205

Met Lys Asn Tyr Glu Leu Leu Leu Arg Arg Ile Ser Lys Trp Met Lys
210                 215                 220

Asp Asp Gly Leu Leu Phe Ile Glu His Val Cys His Lys Thr Phe Ala
225                 230                 235                 240

Tyr His Tyr Glu Pro Ile Asp Glu Asp Trp Tyr Thr Glu Tyr Ile
                245                 250                 255

Phe Pro Ala Gly Thr Leu Thr Leu Ser Ser Ala Ser Leu Leu Leu Tyr
                260                 265                 270

Phe Gln Asp Asp Val Ser Val Val Asn His Trp Thr Leu Ser Gly Lys
            275                 280                 285

His Tyr Ser Arg Ser His Glu Glu Trp Leu Lys Arg Ile Asp Gly Asn
290                 295                 300

Met Asp Ala Val Lys Glu Ile Met Lys Ser Ile Thr Lys Thr Glu Glu
305                 310                 315                 320

Glu Ala Val Lys Leu Ile Asn Phe Trp Arg Ile Phe Cys Met Cys Gly
                325                 330                 335

Ala Glu Leu Phe Gly Tyr Lys Asp Gly Glu Glu Trp Met Met Ser His
            340                 345                 350

Val Leu Phe Lys Lys Lys Gln Leu Leu Gln Gln Cys
                355                 360

<210> SEQ ID NO 109
<211> LENGTH: 353
<212> TYPE: PRT
<213> ORGANISM: Eschscholzia californica

<400> SEQUENCE: 109

Met Val Asp Leu Lys Val Glu Lys Glu Glu Leu Leu Lys Ser Met Glu
1               5                   10                  15

Leu Gly Leu Val Pro Asp Glu Asp Ile Arg Lys His Ile Arg Ser Gln
                20                  25                  30

Leu Glu Lys Arg Leu Lys Trp Gly Tyr Lys Pro Asn His Glu Gln Gln
            35                  40                  45

Leu Ala Gln Leu Leu Asp Val Ile His Ser Leu Lys Lys Met Lys Ile
        50                  55                  60

Ser Lys Glu Tyr Glu Ser Phe Asp Leu Arg Leu Tyr Glu Ala Pro Phe
65                  70                  75                  80

Asp Phe His Lys Ile Gln Leu Gly Thr His Leu Lys Glu Ser Cys Ser
                85                  90                  95

Tyr Tyr Lys Asp Glu Ser Thr Thr Leu Asp Glu Ala Glu Gly Ala Met
                100                 105                 110

Leu Asp Leu Tyr Thr Gln Lys Ala Lys Ile Glu Asp Gly Gln Ser Ile
            115                 120                 125

Leu Asp Leu Gly Cys Gly Val Gly Ala Val Thr Leu Phe Val Ala Asn

```
            130                 135                 140
Lys Tyr Lys Asn Cys Lys Val Thr Gly Ile Thr Ser Cys Gln Trp Gln
145                 150                 155                 160

Lys Asp Phe Ile Glu Asn Lys Cys Lys Glu Leu Asn Leu Thr Asn Val
                165                 170                 175

Arg Val Ile Ile Gly Asp Val Thr Ala Tyr Glu Met Glu Thr Phe
                    180                 185                 190

Asp Arg Ile Phe Ala Ile Glu Leu Ile Glu His Met Lys Asn Tyr Glu
                    195                 200                 205

Leu Leu Leu Arg Lys Ile Ser Lys Trp Met Lys Asp Asp Gly Leu Leu
210                 215                 220

Phe Ile Glu His Val Cys His Lys Ile Leu Ala Tyr Pro Tyr Glu Pro
225                 230                 235                 240

Ile Asp Glu Glu Asp Trp Phe Thr Glu Tyr Ile Phe Pro Gly Gly Thr
                    245                 250                 255

Leu Thr Leu Ser Ser Ala Ser Leu Leu Leu Tyr Phe Gln Asp Asp Val
                    260                 265                 270

Ser Val Val Glu His Ser Ser Leu Asn Gly Lys His Tyr Ser Arg Ser
                    275                 280                 285

His Gly Glu Trp Leu Lys Asn Ile Asp Ala Asn Ile Asp Glu Val Lys
        290                 295                 300

Gly Ile Met Arg Ser Ile Thr Lys Thr Glu Glu Ala Val Arg Leu
305                 310                 315                 320

Val Asn Phe Trp Arg Ile Phe Cys Met Cys Gly Ile Glu Leu Phe Gly
                    325                 330                 335

Tyr Asn Asn Gly Glu Glu Trp Met Val Ser His Ile Leu Leu Lys Lys
                340                 345                 350

Lys

<210> SEQ ID NO 110
<211> LENGTH: 359
<212> TYPE: PRT
<213> ORGANISM: Eschscholzia californica

<400> SEQUENCE: 110

Met Ala Ala Asp Leu Val Val Lys Lys Trp Asn Asn Lys Lys Glu Leu
1               5                   10                  15

Ile Asp Glu Met Glu Leu Gly Leu Val Gly Asp Glu Ile Arg Glu
                    20                  25                  30

Leu Ile Arg Asn Asp Leu Glu Lys Arg Leu Lys Trp Gly Tyr Lys Ser
                35                  40                  45

Asn His Glu Gln Gln Leu Ala Gln Leu Leu His Phe Val His Ser Leu
            50                  55                  60

Arg Gly Met Lys Ile Ala Ala Asp Glu Val Glu Ser Phe Asn Ile Lys
65                  70                  75                  80

Val Tyr Glu Ala Pro Phe Ser Phe Asn Lys Ile Gln Leu Gly Ser Ser
                    85                  90                  95

Leu Lys Glu Ser Ser Cys Tyr Tyr Lys His Asp Glu Thr Thr Leu Asp
                100                 105                 110

Glu Gly Glu Ile Ala Met Met Glu Leu Tyr Thr Glu Lys Ala Gln Ile
            115                 120                 125

Lys Asp Gly Gln Ser Val Leu Asp Leu Gly Cys Gly Leu Gly Ser Leu
        130                 135                 140

Thr Leu Tyr Val Ala Asn Lys Tyr Pro Asn Cys Lys Val Thr Gly Thr
```

```
                145                 150                 155                 160
Thr Ala Ser Leu Trp His Lys Asp Phe Ile Glu Ser Lys Cys Lys Glu
            165                 170                 175

Gln Glu Leu Thr Asn Val Lys Ile Val Leu Gly Asp Ala Thr Thr His
        180                 185                 190

Glu Met Glu Glu Arg Phe Asp Arg Ile Leu Ala Ile Gly Leu Ile Glu
    195                 200                 205

His Leu Lys Asn Tyr Gly Leu Leu Gly Arg Ile Ser Lys Trp Leu
        210                 215                 220

Lys Asp Asp Gly Phe Leu Phe Ile Gln His Val Cys His Lys Thr Leu
225                 230                 235                 240

Ala Tyr Pro Leu Val Pro Val Asp Glu Glu Asp Trp Ile Gly Glu Tyr
                245                 250                 255

Ile Phe Pro Gly Gly Thr Leu Thr Met Pro Ser Ala Ser Leu Leu Leu
            260                 265                 270

Tyr Phe Gln Asp Glu Leu Ser Val Val Asp His Ser Thr Leu Asn Gly
        275                 280                 285

Lys His Phe Ser Arg Thr His Glu Glu Trp Leu Lys Asn Ile Asp Ala
    290                 295                 300

Lys Ile Asp Glu Val Lys Glu Ile Leu Lys Ser Val Thr Lys Thr Glu
305                 310                 315                 320

Glu Glu Val Val Arg Leu Thr Asn Phe Trp Arg Ile Phe Cys Met Phe
                325                 330                 335

Gly Val Glu Met Phe Gly Tyr Asn Glu Gly Glu Glu Trp Met Leu Ser
            340                 345                 350

Gln Ile Leu Phe Lys Lys Lys
        355

<210> SEQ ID NO 111
<211> LENGTH: 353
<212> TYPE: PRT
<213> ORGANISM: Chelidonium majus

<400> SEQUENCE: 111

Met Ala Ser Gly Lys Val Val Asp Leu Leu Lys Arg Leu Asp Ser Gly
1               5                   10                  15

Leu Val Ser Asp Glu Glu Leu Arg Arg Val Ile Arg Phe Glu Leu Glu
            20                  25                  30

Arg Arg Leu Lys Trp Gly Tyr Lys Pro Thr His Glu Gln Gln Leu Ala
        35                  40                  45

Glu Leu Leu Asn Leu Ala His Ala Thr Lys Gln Met Glu Ile Ala Thr
    50                  55                  60

Lys Ile Asp Thr Leu Asn Ser Thr Met Tyr Glu Val Pro Asn Ser Phe
65                  70                  75                  80

Leu Glu Ile Gln Leu Gly Ser Thr Leu Lys Glu Ser Cys Leu Tyr Phe
                85                  90                  95

Lys Asp Glu Ser Thr Thr Val Asp Glu Ala Glu Ile Ala Met Met Asp
            100                 105                 110

Leu Tyr Leu Glu Arg Ala Gln Ile Lys Asp Gly Gln Ile Ile Leu Asp
        115                 120                 125

Leu Gly Cys Gly Leu Gly Ala Leu Ala Phe His Ile Ala Gln Lys Tyr
    130                 135                 140

Thr Asn Cys Asn Val Thr Ser Val Thr Asn Ser Val Lys Gln Lys Glu
145                 150                 155                 160
```

-continued

```
Phe Ile Glu Glu Lys Cys Lys Ile Leu Asn Val Ser Asn Val Lys Val
                165                 170                 175

Ile Leu Thr Asp Ile Cys Thr Leu Glu Met Glu Ala Thr Phe Asp Arg
            180                 185                 190

Ile Phe Ala Ile Gly Leu Ile Glu His Met Lys Asn Tyr Glu Leu Leu
        195                 200                 205

Leu Arg Lys Phe Ser Ala Trp Met Lys Gln Asp Gly Leu Leu Phe Ile
    210                 215                 220

Glu His Leu Cys His Lys Thr Leu Gly Tyr His Asn Glu Pro Ile Asp
225                 230                 235                 240

Glu Asp Asp Trp Tyr Thr Ala Tyr Phe Phe Pro Ala Gly Thr Leu Thr
                245                 250                 255

Phe Ile Pro Ser Ser Phe Leu Leu Tyr Phe Gln Asp Asp Val Ser Val
            260                 265                 270

Val Asn His Trp Thr Leu Ser Gly Lys His Phe Ser Arg Ser Asn Glu
        275                 280                 285

Glu Trp Leu Lys Arg Met Asp Asn Lys Ile Asp Glu Val Lys Glu Ile
    290                 295                 300

Tyr Lys Ala Ala Ala Ser Glu Thr Lys Asp Asp Asp Ile Met Lys Leu
305                 310                 315                 320

Ile Arg Leu Trp Arg Phe Leu Ser Ile Ser Ala Ala Glu Met Phe Gly
                325                 330                 335

Tyr Lys Asp Gly Glu Glu Trp Met Ile Ser Gln Val Leu Phe Lys Lys
            340                 345                 350

Lys
```

<210> SEQ ID NO 112
<211> LENGTH: 366
<212> TYPE: PRT
<213> ORGANISM: Eschscholzia californica

<400> SEQUENCE: 112

```
Met Ala Ser Leu Val Glu Glu Gly Ser Phe Val Asn Asn Lys Glu Ser
1               5                   10                  15

Val Lys Glu Arg Val Ser Glu Leu Val Lys Arg Leu Lys Asn Gly Leu
                20                  25                  30

Val Ser Asp Glu Glu Leu Arg Lys Leu Met Arg Val Glu Leu Glu Lys
            35                  40                  45

Arg Leu Glu Trp Gly Tyr Lys Ser Thr His Glu Gln Gln Leu Ser Gln
    50                  55                  60

Leu Ile Asp Leu Ala His Ser Met Lys Lys Met Glu Ile Ala Met Glu
65                  70                  75                  80

Ile Asp Ala Leu Asn Ser Thr Val Tyr Glu Val Pro Leu Ser Phe Leu
                85                  90                  95

Gln Ile Ile His Gly Thr Thr Ile Lys Glu Ser Cys Leu Tyr Phe Lys
            100                 105                 110

Asp Glu Ser Thr Thr Val Asp Glu Ala Glu Ile Ala Met Met Asp Leu
        115                 120                 125

Tyr Leu Glu Arg Ala Gln Ile Lys Asp Gly Gln Ser Ile Leu Asp Leu
    130                 135                 140

Gly Cys Gly Leu Gly Gly Phe Ser Phe His Ile Ala Ser Lys Phe Thr
145                 150                 155                 160

Gly Cys Asn Ile Thr Ala Val Thr Asn Ser Val Lys Gln Lys Glu Phe
                165                 170                 175
```

```
Ile Glu Glu Lys Cys Lys Thr Leu Asn Val Pro Asn Ile Lys Val Ile
            180                 185                 190

Leu Ala Asp Ile Cys Thr Thr Glu Ile Glu Asn Val Phe Asp Arg Ile
            195                 200                 205

Ile Ala Ile Gly Leu Ile Glu His Met Lys Asn Tyr Glu Leu Leu Leu
            210                 215                 220

Lys Lys Phe Ser Lys Trp Met Thr Gln Asp Gly Leu Leu Phe Ile Glu
225                 230                 235                 240

His Leu Cys His Lys Thr Phe Gly Tyr His Asn Glu Pro Leu Asp Glu
            245                 250                 255

Asp Asp Trp Tyr Thr Thr Tyr Phe Phe Pro Ala Gly Thr Leu Thr Phe
            260                 265                 270

Ile Pro Ser Ser Phe Leu Leu Tyr Phe Gln Asp Asp Val Ser Val Val
            275                 280                 285

Asp His Trp Thr Leu Asn Gly Lys His Phe Ala Arg Ser Asn Glu Glu
            290                 295                 300

Trp Leu Lys Arg Met Asp Glu Lys Met Asp Glu Val Lys Gln Ile Phe
305                 310                 315                 320

Arg Ser Asn Leu Lys Ser Glu Asn Glu Val Thr Lys Thr Ile Gly Glu
            325                 330                 335

Trp Arg Phe Leu Ser Met Ser Ala Ala Glu Met Phe Gly Tyr Asn Asn
            340                 345                 350

Gly Glu Glu Trp Met Val Ser Gln Leu Leu Phe Lys Lys Lys
            355                 360                 365

<210> SEQ ID NO 113
<211> LENGTH: 362
<212> TYPE: PRT
<213> ORGANISM: Glaucium flavum

<400> SEQUENCE: 113

Met Gly Ser Asn Glu Thr Asn Gly Glu Leu Lys Thr Lys Glu Met Val
1               5                   10                  15

Pro Asp Leu Leu Lys Arg Leu Glu Ser Gly Leu Val Ala Asp Glu Glu
            20                  25                  30

Leu Arg Lys Leu Ile Arg Phe Glu Leu Glu Arg Arg Leu Lys Trp Gly
            35                  40                  45

Tyr Lys Pro Thr His Glu Gln Gln Leu Ala Glu Leu Leu Lys Leu Ala
            50                  55                  60

His Ser Thr Lys Gln Met Lys Ile Ala Thr Glu Thr Asp Ser Leu Asn
65                  70                  75                  80

Ser Thr Met Tyr Glu Val Pro Ile Pro Phe Leu Gln Leu Gln Phe Gly
            85                  90                  95

Ser Ala Ile Lys Glu Ser Cys Cys Tyr Phe Lys Asp Glu Ser Thr Thr
            100                 105                 110

Leu Asp Glu Ala Glu Val Ala Met Met Asp Leu Tyr Leu Glu Arg Thr
            115                 120                 125

Gln Ile Lys Asp Gly Gln Ser Ile Leu Asp Leu Gly Cys Gly Leu Gly
            130                 135                 140

Ala Leu Ala Phe His Ile Val Gln Lys Tyr Pro Asn Cys Asn Val Leu
145                 150                 155                 160

Ala Ile Thr Asn Ser Val Glu Gln Lys Glu Phe Ile Glu Glu Lys Cys
            165                 170                 175

Lys Ile Arg Lys Val Glu Asn Val Lys Val Ser Leu Ala Asp Ile Cys
            180                 185                 190
```

```
Thr Leu Glu Met Lys Thr Thr Phe Asp Arg Ile Phe Ala Ile Gly Leu
            195                 200                 205

Leu Glu His Met Lys Asn Tyr Gln Leu Leu Leu Lys Lys Phe Ser Asn
            210                 215                 220

Trp Met Lys Gln Asp Gly Leu Leu Phe Ile Glu His Leu Cys His Lys
225                 230                 235                 240

Thr Leu Ala Tyr His Tyr Glu Pro Leu Asp Glu Asp Trp Tyr Thr
            245                 250                 255

Glu Tyr Phe Phe Pro Ala Gly Thr Leu Thr Ile Ile Ser Ser Ser Phe
            260                 265                 270

Leu Leu Tyr Phe Gln Asp Asp Val Ser Ile Val Asn His Trp Ser Leu
            275                 280                 285

Ser Gly Lys His Phe Ser Arg Ser Asn Glu Gly Trp Leu Lys Arg Met
            290                 295                 300

Asp Met Lys Ile Asp Glu Val Lys Glu Ile Leu Glu Ala Ala Phe Glu
305                 310                 315                 320

Asn Lys Asp His Asp Ile Thr Lys Leu Ile Asn His Trp Arg Phe Leu
            325                 330                 335

Ala Ile Asn Ala Thr Glu Met Phe Gly Tyr Asn Asn Gly Glu Glu Trp
            340                 345                 350

Met Val Ser Gln Val Leu Phe Lys Lys Lys
            355                 360

<210> SEQ ID NO 114
<211> LENGTH: 365
<212> TYPE: PRT
<213> ORGANISM: Sanguinaria canadensis

<400> SEQUENCE: 114

Met Ala Ser Asp His Glu Val Ser Asn Lys Glu Leu Lys Lys Lys
1               5                   10                  15

Glu Val Ile Thr Glu Leu Leu Lys Arg Leu Glu Ser Gly Leu Val Ser
            20                  25                  30

Asp Glu Glu Leu Arg Gly Leu Ile Arg Phe Glu Leu Glu Arg Arg Leu
            35                  40                  45

Arg Trp Gly Tyr Lys Pro Thr His Glu Gln Gln Leu Ala Gln Leu Leu
50                  55                  60

Asn Leu Ala His Ser Met Lys Gln Met Lys Ile Ala Thr Glu Ile Asp
65                  70                  75                  80

Ala Leu Asn Ser Thr Met Tyr Glu Val Pro Ile Pro Phe Leu Gln Ile
            85                  90                  95

Gln Leu Gly Ser Thr Leu Lys Glu Ser Cys Cys Tyr Phe Lys Asp Glu
            100                 105                 110

Ser Thr Thr Val Asp Glu Ala Glu Ile Ala Met Met Asp Leu Tyr Leu
            115                 120                 125

Glu Arg Ala Gln Ile Lys Asp Gly Gln Ser Ile Leu Asp Leu Gly Cys
            130                 135                 140

Gly Leu Gly Ala Leu Ala Phe His Ile Ala Gln Lys Tyr Thr Asn Cys
145                 150                 155                 160

Asn Ile Thr Ala Ile Thr Asn Ser Val Arg Gln Lys Glu Phe Ile Glu
            165                 170                 175

Glu Lys Cys Lys Ile Leu Asn Val Ser Asn Val Lys Val Ser Leu Ala
            180                 185                 190

Asp Ile Cys Thr Leu Glu Met Glu Ala Thr Phe Asp Arg Ile Phe Ala
```

-continued

```
            195                 200                 205
Ile Gly Leu Ile Glu His Met Lys Asn Tyr Glu Leu Leu Lys Lys
    210                 215                 220

Phe Ser Glu Trp Met Lys Gln Asp Gly Leu Ile Phe Ile Glu His Leu
225                 230                 235                 240

Cys His Lys Thr Leu Ala Tyr His Tyr Glu Pro Leu Asp Glu Asp
                245                 250                 255

Trp Tyr Thr Glu Tyr Phe Phe Pro Ala Gly Thr Leu Thr Leu Ile Ser
                260                 265                 270

Ser Ser Phe Leu Leu Tyr Phe Gln Asp Asp Val Ser Val Asp His
        275                 280                 285

Trp Thr Leu Ser Gly Lys His Phe Ser Arg Ser Asn Glu Glu Trp Leu
290                 295                 300

Lys Arg Met Asp Glu Lys Ile Asp Glu Val Lys Glu Ile Phe Glu Ser
305                 310                 315                 320

Val Ser Asp Ser Lys Asp Asp Val Thr Lys Leu Ile Asn His Trp
                325                 330                 335

Arg Phe Phe Cys Ile Ser Ser Ala Glu Met Phe Gly Tyr Asn Asn Gly
                340                 345                 350

Glu Glu Trp Met Ile Ser Gln Val Leu Phe Lys Lys Lys
                355                 360                 365
```

<210> SEQ ID NO 115
<211> LENGTH: 371
<212> TYPE: PRT
<213> ORGANISM: Corydalis chelanthifolia

<400> SEQUENCE: 115

```
Met Ile Lys Lys Ser Lys Ile Met Ala Phe Ser Asp His His Glu
1               5                   10                  15

Val Val Lys Asn His Ser Lys Lys Glu Met Ile Ala Asp Leu Leu Lys
                20                  25                  30

Arg Leu Glu Ala Gly Leu Val Pro Asp Glu Glu Met Arg Asn Leu Phe
            35                  40                  45

Arg Phe Glu Leu Glu Arg Arg Leu Gln Trp Gly Tyr Lys Ser Ile His
        50                  55                  60

Gln Glu Gln Leu Ser Gln Leu Leu Lys Leu Ala His Ser Thr Lys Glu
65                  70                  75                  80

Met Thr Ile Val Ala Glu Met Asp Ala Leu Asn Ser Ser Met Tyr Glu
                85                  90                  95

Leu Pro Ile Ser Phe Leu Gln Ile Gln Leu Gly Ser Asn Leu Lys Gln
                100                 105                 110

Ser Ser Leu Tyr Phe Lys Asp Glu Leu Thr Thr Val Asp Glu Ala Glu
        115                 120                 125

Val Ala Ile Met Asp Leu Tyr Leu Glu Arg Ala Gln Ile Glu Asp Gly
130                 135                 140

Gln Ser Ile Leu Asp Leu Gly Cys Gly Leu Gly Ala Phe Ser Phe His
145                 150                 155                 160

Val Ala Arg Lys Tyr Thr Asn Cys Asn Ile Thr Ala Val Thr Asn Ser
                165                 170                 175

Leu Thr Gln Lys Glu Phe Ile Glu Lys Lys Ser Lys Ile Leu Asn Ile
                180                 185                 190

Gln Asn Val Lys Val Ile Phe Ala Asp Val Thr Thr Val Glu Met Glu
        195                 200                 205
```

```
Thr Thr Phe Asp Arg Val Phe Ala Ile Gly Leu Ile Glu His Met Gln
    210                 215                 220

Asn Tyr Glu Leu Phe Leu Lys Lys Leu Ser Lys Trp Met Lys Gln Asp
225                 230                 235                 240

Gly Leu Leu Phe Ile Glu His Phe Cys His Lys Thr Leu Ala Tyr His
                245                 250                 255

Tyr Lys Pro Ile Asp Glu Asp Trp Phe Thr Asn Leu Leu Tyr Pro
            260                 265                 270

Asn Gly Thr Val Ile Ser Ser Leu Leu Leu Tyr Phe Gln Asp Asp
                275                 280                 285

Val Ser Val Asp His Trp Ser Leu Ser Gly Lys His Phe Ser Arg
290                 295                 300

Ala Ser Glu Glu Ser Leu Lys Arg Met Asp Ala Lys Met Asp Glu Met
305                 310                 315                 320

Lys Glu Ile Phe Glu Ser Ile Thr Asp Ser Lys Glu Ala Met Lys
                325                 330                 335

Leu Ile Asn Gln Trp Arg Ile Phe Cys Ile Ser Cys Ala Glu Met Phe
                340                 345                 350

Gly Tyr Asn Asn Gly Glu Glu Trp Met Thr Ser His Phe Leu Phe Lys
                355                 360                 365

Lys Lys Leu
    370

<210> SEQ ID NO 116
<211> LENGTH: 373
<212> TYPE: PRT
<213> ORGANISM: Corydalis chelanthifolia

<400> SEQUENCE: 116

Met Gly Ser Ser Thr Ala Ser Asp His Glu Met Val Ile Met Glu Asn
1               5                   10                  15

Asp Ser Lys Asn Lys Gln Val Val Ile Ala Asp Leu Leu Lys Arg Leu
            20                  25                  30

Val Gly Gly Leu Val Pro Asp Glu Glu Met Arg Asn Met Phe Arg Phe
        35                  40                  45

Glu Leu Glu Lys Arg Leu Lys Trp Gly Tyr Lys Ser Thr His Gln Gln
50                  55                  60

Gln Leu Ser Gln Leu Leu Asn Leu Val Glu Leu Asn Lys Gly Ile Ala
65                  70                  75                  80

Lys Ile Ala Pro Glu Met Asp Ala Leu Asn Ser Ala Met Tyr Glu Val
                85                  90                  95

Pro Ile Pro Tyr Leu Lys Leu Met Leu Gly Ser Thr Leu Lys Gln Ser
            100                 105                 110

Cys Leu Tyr Phe Lys Asp Glu Ser Thr Thr Leu Asp Glu Ala Glu Ile
        115                 120                 125

Glu Met Met Asp Leu Tyr Leu Glu Arg Ala Asp Ile Gln Asp Gly Gln
130                 135                 140

Ser Ile Leu Asp Leu Gly Cys Gly Leu Gly Gly Leu Gly Phe His Ile
145                 150                 155                 160

Ala Gln Lys Tyr Ile Ser Cys Asn Ile Thr Ala Leu Thr Asn Ser Leu
                165                 170                 175

Thr Gln Lys Glu Phe Ile Glu Glu Lys Cys Lys Thr Leu Asn Ile Pro
            180                 185                 190

Asn Val Lys Val Ile Leu Ala Asp Val Thr Thr Val Glu Ile Glu Thr
        195                 200                 205
```

```
Thr Phe Asp Arg Leu Phe Ala Ile Gly Leu Val Glu His Met Glu Asn
    210                 215                 220

Tyr Glu Leu Phe Leu Arg Lys Leu Ser Lys Trp Met Lys Gln Asp Gly
225                 230                 235                 240

Leu Leu Phe Ile Glu His Leu Cys His Lys Thr Leu Ala Tyr His Tyr
                245                 250                 255

Lys Pro Ile Asp Glu Asp Asp Trp Tyr Ser Asn Leu Leu Tyr Pro Thr
            260                 265                 270

Gly Thr Leu Thr Ser Ala Ser Phe Leu Leu Tyr Phe Gln Asp Asp Leu
        275                 280                 285

Ser Val Val Asp His Trp Ser Leu Ser Gly Lys His Phe Ser Arg Ala
290                 295                 300

Thr Glu Glu Trp Leu Lys Met Ile Asp Ala Asn Met Asp Lys Ile Arg
305                 310                 315                 320

Glu Ile Tyr Glu Ser Val Thr Glu Ser Lys Glu Ala Thr Arg Ser
                325                 330                 335

Ile Asn Gln Trp Arg Ile Phe Cys Ile Ser Cys Ala Glu Met Phe Gly
                340                 345                 350

Tyr Asn Asp Gly Glu Glu Trp Met Ile Ser His Phe Leu Phe Lys Asn
            355                 360                 365

Lys Lys Gln Ile Glu
        370

<210> SEQ ID NO 117
<211> LENGTH: 366
<212> TYPE: PRT
<213> ORGANISM: Corydalis chelanthifolia

<400> SEQUENCE: 117

Met Ala Thr Ser Asp Gln Glu Val Lys Thr Ser Lys Met Glu Met Ile
1               5                   10                  15

Ala Asp Leu Leu Lys Arg Leu Glu Ala Gly Leu Val Pro Asp Asp Glu
            20                  25                  30

Ile Arg Ser Leu Ile Arg Val Glu Leu Glu Arg Arg Leu Lys Trp Gly
        35                  40                  45

Tyr Lys Ser Thr His Gln Glu Gln Leu Asp Gln Leu Leu Asn Leu Ala
    50                  55                  60

His Ser Ile Lys Lys Met Lys Ile Ala Ser Thr Glu Met Asp Gly Leu
65                  70                  75                  80

Thr Ser Thr Met Tyr Glu Val Pro Ile Ser Leu Val Gln Ile Gln Leu
                85                  90                  95

Gly Ser His Leu Lys Glu Ser Cys Leu Tyr Phe Lys Asp Glu Thr Thr
            100                 105                 110

Thr Val Asp Glu Ala Glu Ile Ala Met Met Asp Leu Tyr Leu Glu Arg
        115                 120                 125

Ala Gln Ile Lys Asp Gly Gln Ser Ile Leu Asp Leu Gly Cys Gly Leu
    130                 135                 140

Gly Ala Val Ser Phe His Ile Ala Gln Lys Tyr Thr Ser Cys Asn Ile
145                 150                 155                 160

Thr Ala Val Thr Asn Ser Val Arg Gln Lys Glu Phe Ile Glu Glu Lys
                165                 170                 175

Ser Lys Thr Leu Asn Val Pro Asn Val Lys Val Leu Leu Ala Asp Ile
            180                 185                 190

Thr Thr Leu Glu Met Glu His Thr Phe Asp Arg Leu Phe Ala Ile Ser
```

```
                195                 200                 205
Leu Ile Glu His Met Glu Asn Tyr Glu Leu Leu Arg Lys Leu Ser
210                 215                 220

Glu Trp Met Lys Gln Asp Gly Leu Leu Phe Ile Glu His Leu Cys His
225                 230                 235                 240

Lys Thr Leu Ser Tyr His Phe Glu Pro Met Asp Glu Asp Trp Tyr
                245                 250                 255

Thr Asn Leu Leu Phe Pro Ala Gly Thr Leu Thr Leu Val Ser Ala Ser
            260                 265                 270

Phe Leu Leu Tyr Phe Gln Asp Asp Leu Ser Val Val Asn Gln Trp Val
        275                 280                 285

Met Ser Gly Lys His Phe Ser Arg Ala Asn Glu Glu Trp Leu Lys Asn
    290                 295                 300

Met Asp Ala Lys Met Asp Glu Met Arg Glu Ile Phe Glu Ser Ile Thr
305                 310                 315                 320

Asp Ser Glu Glu Glu Val Val Lys Leu Ile Asn His Trp Arg Ile Phe
                325                 330                 335

Cys Ile Ser Ser Ala Glu Met Phe Ala Tyr Asn Asp Gly Glu Glu Trp
            340                 345                 350

Met Asn Ser His Val Leu Phe Lys Lys Lys Gln Ile Gln
        355                 360                 365

<210> SEQ ID NO 118
<211> LENGTH: 359
<212> TYPE: PRT
<213> ORGANISM: Corydalis chelanthifolia

<400> SEQUENCE: 118

Met Ala Gly Ser Gly Ala Asn Lys Glu Met Ile Ala Asp Leu Leu Lys
1               5                   10                  15

Arg Leu Glu Val Gly Leu Val Pro Asp Glu Glu Ile Arg Ser Leu Ile
                20                  25                  30

Arg Phe Gln Leu Lys Arg Arg Leu Lys Trp Gly Tyr Lys Thr Thr His
            35                  40                  45

Gln Glu Gln Leu Glu Gln Leu Leu Ser Leu Ala His Ser Ile Arg Lys
        50                  55                  60

Met Lys Ile Ala Thr Glu Met Asp Ala Leu Asn Ser Thr Met Tyr Glu
65                  70                  75                  80

Val Pro Ile Ser Phe Met Gln Ile Val Phe Gly Ser Thr Leu Lys Glu
                85                  90                  95

Ser Cys Leu Tyr Phe Lys Asp Glu Ala Thr Thr Val Asn Glu Ala Glu
            100                 105                 110

Ile Ala Met Met Asp Leu Tyr Leu Glu Arg Ala Gln Ile Lys Asp Gly
        115                 120                 125

Gln Ser Ile Leu Asp Leu Gly Cys Gly Met Gly Ser Leu Cys Phe His
    130                 135                 140

Ile Ala Arg Lys Tyr Thr Asn Cys Asn Ile Thr Ala Val Thr Asn Ser
145                 150                 155                 160

Val Ser Gln Lys Glu Phe Ile Glu Glu Lys Ser Lys Thr Leu Asn Leu
                165                 170                 175

Pro Asn Val Lys Val Ile Leu Ala Asp Ile Thr Thr Leu Glu Met Asp
            180                 185                 190

Asp Thr Tyr Asp Cys Leu Phe Ala Ile Gly Leu Ile Glu His Met Lys
        195                 200                 205
```

```
Asn Tyr Glu Leu Leu Leu Arg Lys Leu Ser Asn Trp Met Lys Gln Asp
    210                 215                 220

Ser Leu Leu Phe Ile Asp His Val Cys His Lys Thr Leu Ala Tyr His
225                 230                 235                 240

Tyr Glu Pro Ile Asp Glu Asp Trp Tyr Thr Asn Leu Leu Phe Pro
                245                 250                 255

Ala Gly Thr Leu Thr Leu Val Ser Ala Ser Phe Leu Leu Tyr Phe Gln
                260                 265                 270

Asp Asp Leu Ser Leu Val Asp His Trp Ser Met Ser Gly Lys His Phe
                275                 280                 285

Ser Arg Thr Asn Lys Glu Trp Leu Lys Asn Ile Asp Gly Lys Met Asp
290                 295                 300

Lys Ile Arg Glu Ile Val Lys Ser Ile Thr Asp Ser Glu Glu Glu Val
305                 310                 315                 320

Val Lys Leu Ile Asn His Trp Arg Met Leu Cys Ile Asn Ser Ser Glu
                325                 330                 335

Met Phe Gly Phe Asn Asp Gly Glu Glu Trp Met Asn Ser His Val Leu
                340                 345                 350

Phe Lys Lys Lys Lys Gln Ile
            355

<210> SEQ ID NO 119
<211> LENGTH: 353
<212> TYPE: PRT
<213> ORGANISM: Sanguinaria canadensis

<400> SEQUENCE: 119

Met Glu Met Ile Ala Asp Leu Leu Lys Arg Leu Glu Ala Gly Leu Val
1               5                   10                  15

Pro Asp Asp Glu Ile Arg Ser Leu Ile Arg Val Glu Leu Glu Arg Arg
                20                  25                  30

Leu Lys Trp Gly Tyr Lys Ser Thr His Gln Glu Gln Leu Asp Gln Leu
            35                  40                  45

Leu Asn Leu Ala His Ser Ile Lys Lys Met Lys Ile Ala Ser Thr Glu
50                  55                  60

Met Asp Gly Leu Thr Ser Thr Met Tyr Glu Val Pro Ile Ser Leu Val
65                  70                  75                  80

Gln Ile Gln Leu Gly Ser His Leu Lys Glu Ser Cys Leu Tyr Phe Lys
                85                  90                  95

Asp Glu Thr Thr Thr Val Asp Glu Ala Glu Ile Ala Met Met Asp Leu
                100                 105                 110

Tyr Leu Glu Arg Ala Gln Ile Lys Asp Gly Gln Ser Ile Leu Asp Leu
            115                 120                 125

Gly Cys Gly Leu Gly Ser Val Cys Phe His Ile Ala Arg Lys Tyr Thr
130                 135                 140

Ser Cys Asn Ile Thr Ala Val Thr Asn Ser Val Ser Gln Lys Glu Phe
145                 150                 155                 160

Ile Glu Glu Lys Ser Lys Thr Leu Asn Val Pro Asn Val Lys Val Leu
                165                 170                 175

Leu Ala Asp Ile Thr Thr Leu Glu Met Asp Asp Thr Phe Asp Cys Leu
            180                 185                 190

Phe Ala Ile Gly Leu Ile Glu His Met Glu Asn Tyr Glu Leu Leu Leu
        195                 200                 205

Arg Lys Leu Ser Asp Trp Met Lys Gln Asp Gly Leu Leu Phe Ile Asp
    210                 215                 220
```

His Val Cys His Lys Thr Leu Ser Tyr His Phe Glu Pro Met Asp Glu
225                 230                 235                 240

Asp Asp Trp Tyr Thr Asn Leu Leu Phe Pro Ala Gly Thr Leu Thr Leu
            245                 250                 255

Val Ser Ala Ser Phe Leu Leu Tyr Phe Gln Asp Asp Leu Ser Leu Val
        260                 265                 270

Asp His Trp Ser Met Ser Gly Lys His Phe Ser Arg Thr Asn Lys Glu
    275                 280                 285

Trp Leu Lys Asn Ile Asp Gly Lys Met Asp Lys Ile Arg Glu Ile Val
290                 295                 300

Lys Ser Ile Thr Asp Ser Glu Glu Val Val Lys Leu Ile Asn His
305                 310                 315                 320

Trp Arg Met Leu Cys Ile Asn Ser Ser Glu Met Phe Gly Phe Asn Asp
                325                 330                 335

Gly Glu Glu Trp Met Asn Ser His Val Leu Phe Lys Lys Lys Gln
            340                 345                 350

Ile

<210> SEQ ID NO 120
<211> LENGTH: 363
<212> TYPE: PRT
<213> ORGANISM: Papaver bracteatum

<400> SEQUENCE: 120

Met Cys Thr Thr Met Asp Thr Thr Lys Ile Ser Gln Gln Asp Asp Leu
1               5                   10                  15

Trp Lys Asn Met Glu Leu Gly Leu Ile Ser Asp Glu Val Arg Arg
            20                  25                  30

Leu Met Lys Ile Glu Thr Glu Lys Arg Ile Lys Trp Gly Thr Lys Pro
        35                  40                  45

Thr Gln Gln Glu Gln Leu Ala Gln Leu Leu Asp Phe Asn Lys Ser Leu
    50                  55                  60

Arg Gly Met Lys Met Ala Thr Glu Val His Ala Leu Glu Asn His Lys
65                  70                  75                  80

Ile Tyr Glu Ile Pro Asp Ser Phe Asn Gln Ile Ile Gly Gly Lys Glu
                85                  90                  95

Ser Ala Gly Leu Phe Thr Asp Glu Ala Thr Thr Thr Ile Glu Glu Ala
            100                 105                 110

Asn Thr Lys Met Met Asp Leu Tyr Cys Glu Arg Ala Gly Leu Lys Asp
        115                 120                 125

Gly Gln Thr Ile Leu Asp Ile Gly Cys Gly Ala Gly Leu Leu Val Leu
    130                 135                 140

His Leu Ala Lys Lys Tyr Lys Asn Cys Lys Ile Thr Gly Val Thr Asn
145                 150                 155                 160

Thr Ser Trp His Lys Glu His Ile Leu Glu Gln Cys Lys Asn Leu Asn
                165                 170                 175

Leu Ser Asn Val Glu Val Ile Leu Ala Asp Val Thr Val Asp Ile
            180                 185                 190

Glu Arg Thr Phe Asp Arg Val Phe Val Ile Gly Leu Ile Glu His Met
        195                 200                 205

Lys Asn Phe Glu Leu Phe Leu Arg Lys Ile Ser Lys Trp Met Lys Asp
    210                 215                 220

Asp Gly Leu Leu Phe Leu Glu His Leu Cys His Lys Ser Phe Ser Asp
225                 230                 235                 240

His Trp Glu Pro Leu Ser Glu Asp Trp Tyr Ala Lys Asn Phe Phe
            245                 250                 255

Pro Ser Gly Thr Leu Val Ile Pro Ser Ala Thr Cys Leu Leu Tyr Phe
            260                 265                 270

Gln Glu Asp Val Thr Val Lys Asp His Trp Leu Leu Ser Gly Asn Asn
            275                 280                 285

Phe Ala Arg Ser Asn Glu Ala Ile Leu Lys Arg Ile Asp Ser Lys Ile
290                 295                 300

Glu Glu Val Lys Asp Ile Phe Met Ser Phe Tyr Gly Ile Gly Glu Glu
305                 310                 315                 320

Glu Ala Val Lys Leu Ile Asn Trp Trp Arg Leu Leu Cys Ile Thr Ala
            325                 330                 335

Asn Glu Leu Phe Lys Tyr Asn Asn Gly Glu Glu Trp Leu Ile Ser Gln
            340                 345                 350

Leu Leu Phe Lys Lys Lys Leu Met Thr Cys Ile
            355                 360

<210> SEQ ID NO 121
<211> LENGTH: 366
<212> TYPE: PRT
<213> ORGANISM: Papaver bracteatum

<400> SEQUENCE: 121

Met Val Lys Gly Asp Gln Phe Gln Thr Thr Met Glu Glu Thr Lys
1               5                   10                  15

Ile Ser Gln Glu Asn Asp Leu Trp Thr Asn Met Glu Leu Gly Leu Ile
            20                  25                  30

Pro Asp Glu Glu Val Arg Arg Leu Met Lys Ile Glu Ile Glu Lys Arg
            35                  40                  45

Ile Glu Trp Gly Met Lys Pro Thr Gln His Gln Leu Ala Gln Leu
50                  55                  60

Leu Asp Phe Thr Lys Ser Leu Arg Gly Met Lys Met Ala Thr Glu Leu
65                  70                  75                  80

Asp Lys Leu Asp Ser Lys Leu Tyr Glu Thr Pro His Ser Phe Asn Gln
            85                  90                  95

Ile Val Asn Gly Ser Thr Leu Lys Glu Ser Ser Gly Leu Tyr Thr Asp
            100                 105                 110

Val Thr Thr Thr Met Asp Glu Ala Ser Ile Lys Met Met Asp Leu Tyr
            115                 120                 125

Cys Glu Arg Ala Asn Ile Lys Asp Gly Gln Thr Ile Leu Asp Leu Gly
130                 135                 140

Cys Gly Pro Gly Pro Leu Val Leu His Ile Ala Lys Lys Tyr Ser Asn
145                 150                 155                 160

Cys Lys Ile Thr Gly Val Thr Asn Ala Phe Ser Gln Arg Glu Tyr Ile
            165                 170                 175

Leu Glu Glu Cys Lys Lys Leu Ser Leu Ser Asn Val Glu Ile Ile Leu
            180                 185                 190

Ala Asp Val Thr Ser Leu Asp Leu Glu Thr Thr Phe Asp Arg Val Phe
            195                 200                 205

Val Ile Gly Phe Ile Glu His Met Lys Asn Phe Glu Leu Phe Leu Arg
            210                 215                 220

Lys Ile Ser Lys Trp Met Lys Asp Asp Ala Val Leu Phe Leu Glu His
225                 230                 235                 240

Phe Cys His Lys Ser Phe Ser Tyr His Gly Glu Pro Leu Ser Glu Asp

```
                    245                 250                 255
Asp Trp Tyr Ala Lys Asn Phe Phe Ala Pro Gly Thr Leu Val Ile Pro
            260                 265                 270

Ser Ala Thr Cys Leu Leu Tyr Phe Gln Glu Asp Leu Ala Val Ile Asp
        275                 280                 285

His Trp Phe Leu Ser Gly Asn His Phe Ala Arg Thr Asn Glu Glu Met
    290                 295                 300

Leu Lys Gly Ile Asp Gly Lys Ile Glu Ile Lys Asp Ile Phe Met
305                 310                 315                 320

Ser Phe Tyr Gly Ile Asn Glu Ala Glu Ala Val Lys Leu Ile Asn Trp
                325                 330                 335

Trp Arg Leu Phe Cys Ile Thr Gly Ala Glu Met Phe Ser Tyr Asn Asn
            340                 345                 350

Gly Glu Glu Trp Phe Ile Ser Gln Leu Leu Phe Lys Lys Lys
        355                 360                 365

<210> SEQ ID NO 122
<211> LENGTH: 364
<212> TYPE: PRT
<213> ORGANISM: Eschscholzia californica

<400> SEQUENCE: 122

Met Ala Leu Glu Gln Glu Asp Ser Met Ser Val Pro Glu Arg Asn Glu
1               5                   10                  15

Gly Val Ala Asp Leu Ile Lys Arg Met Glu Leu Gly Leu Val Asn Asp
            20                  25                  30

Glu Glu Ile Arg Arg Leu Met Arg Ile Gln Ile Glu Asn Arg Leu Lys
        35                  40                  45

Trp Gly Tyr Lys Pro Thr His Asp Gln Gln Leu Ala Gln His Leu His
    50                  55                  60

Phe Ile Asn Ser Leu Lys Glu Met Lys Met Ala Thr Glu Met Asp Ser
65                  70                  75                  80

Leu Asp Ser Gln Val Tyr Glu Ser Pro Asn Ser Phe Gln Gln Ile Met
                85                  90                  95

Cys Gly Arg Ser Met Lys Glu Ser Ala Gly Leu Phe Met Asp Asp Val
            100                 105                 110

Thr Thr Val Glu Glu Ala His Ile Arg Met Met Asp Leu Tyr Cys Asp
        115                 120                 125

Lys Ala Thr Phe Glu Asp Gly Gln Lys Ile Leu Asp Leu Gly Cys Gly
    130                 135                 140

His Gly Ser Val Val Leu His Val Ala Gln Lys Tyr Lys Gly Cys Gln
145                 150                 155                 160

Val Thr Gly Val Thr Asn Ser Ser Ala Gln Lys Gln Tyr Ile Leu Glu
                165                 170                 175

Gln Cys Lys Lys Leu Asp Leu Ser Asn Val Glu Ile Ile Leu Ala Asp
            180                 185                 190

Val Thr Thr Leu Glu Met Glu Glu Lys Phe Asp Arg Val Ile Ile Ile
        195                 200                 205

Gly Leu Ile Glu His Met Lys Asn Phe Lys Leu Phe Phe Gln Lys Val
    210                 215                 220

Ser Lys Trp Met Lys Glu Gly Gly Leu Leu Phe Leu Glu Asn Tyr Phe
225                 230                 235                 240

His Lys Asp Phe Ala Tyr His Cys Glu Lys Ile Asp Glu Asp Trp
                245                 250                 255
```

```
Tyr Asp Gly Tyr Ile Phe Pro Pro Gly Ser Leu Leu Met Pro Ser Ala
            260                 265                 270

Ser Thr Leu Leu Tyr Phe Gln Glu Asp Leu Thr Val Ala Asp His Trp
        275                 280                 285

Val Leu Pro Gly Thr His Phe Ala Lys Thr Phe Glu Glu Phe Leu Lys
    290                 295                 300

Lys Ile Asp Leu Arg Ile Glu Glu Val Arg Glu Ile Phe Glu Ala Phe
305                 310                 315                 320

Tyr Gly Ile Ser Lys Glu Glu Ala Met Lys Leu Ser Asn Tyr Trp Arg
                325                 330                 335

Asn Phe Cys Ile Ser Ala Met Glu Ile Phe Asn Tyr Asn Asn Gly Gln
                340                 345                 350

Glu Trp Met Ile Ser His Leu Leu Tyr Thr Lys Lys
                355                 360

<210> SEQ ID NO 123
<211> LENGTH: 368
<212> TYPE: PRT
<213> ORGANISM: Chelidonium majus

<400> SEQUENCE: 123

Met Glu Thr Gly Lys Asn Asn Gln Asn Met Lys Thr Thr Ile Asp Asp
1               5                   10                  15

Leu Trp Asn Gln Met Met Leu Gly Ile Val Pro Asp Lys Glu Ile Arg
            20                  25                  30

Arg Leu Met Lys Ile Glu Leu Lys Lys Arg Leu Asp Trp Gly Tyr Arg
        35                  40                  45

Pro Thr His Gln Gln Gln Leu Ser Gln Leu Leu Asp Phe Ala Lys Gly
    50                  55                  60

Leu Cys Asn Tyr Cys Trp Thr Ala Leu Arg Cys Met Lys Met Ser Ala
65                  70                  75                  80

Glu Phe Asp Thr Leu Asp Ser Lys Val Tyr Glu Thr Pro Lys Ser Phe
                85                  90                  95

Gln Gln Ile Met Cys Gly Thr Thr Ile Lys Glu Ser Ser Gly Leu Phe
            100                 105                 110

Met Asn Glu Ser Thr Thr Leu Asp Gln Ala Gln Ile Ser Met Leu Asp
        115                 120                 125

Leu Tyr Phe Asp Lys Ala Lys Ile Lys Asp Gly Gln Ser Ile Leu Asp
    130                 135                 140

Leu Gly Cys Gly His Gly Ala Leu Ile Leu Tyr Leu Ala Gln Lys Tyr
145                 150                 155                 160

Gln Asn Cys Asn Ile Thr Gly Val Thr Asn Ser Leu Ser Gln Lys Glu
                165                 170                 175

Phe Ile Val Glu Lys Cys Lys Lys Leu Gly Leu Ser Asn Val Glu Ile
            180                 185                 190

Leu Leu Ala Asp Val Thr Lys Leu Glu Met Glu Asp Met Phe Asp Arg
        195                 200                 205

Val Phe Val Ile Gly Leu Ile Glu His Met Lys Asn Phe Glu Leu Phe
    210                 215                 220

Leu Arg Lys Ile Ser Glu Trp Met Lys Pro Asp Gly Leu Leu Phe Leu
225                 230                 235                 240

Glu His Tyr Cys His Lys Ser Phe Ala His Gln Trp Glu Pro Ile Asp
                245                 250                 255

Glu Glu Asp Trp Phe Ser Lys Tyr Ile Phe Pro Pro Gly Thr Val Ile
            260                 265                 270
```

```
Ile Pro Ser Ala Ser Phe Leu Leu Tyr Phe Gln Glu Asp Val Lys Val
            275                 280                 285

Ile Asp His Trp Thr Leu Ser Gly Asn His Phe Ala Arg Thr Gln Glu
    290                 295                 300

Glu Trp Leu Lys Gly Ile Asp Gly His Ile Asp Glu Val Glu Lys Thr
305                 310                 315                 320

Phe Glu Ser Phe Tyr Gly Ile Ser Lys Glu Glu Ala Val Lys Leu Ile
                325                 330                 335

Asn Phe Trp Arg Val Phe Cys Leu Ser Gly Val Glu Met Phe Gly Tyr
                340                 345                 350

Asn Asn Gly Glu Glu Trp Met Ile Ser His Leu Leu Phe Lys Lys Lys
            355                 360                 365

<210> SEQ ID NO 124
<211> LENGTH: 361
<212> TYPE: PRT
<213> ORGANISM: Glaucium flavum

<400> SEQUENCE: 124

Met Thr Met Glu Ala Asn Asn Ala Lys Lys Glu Ala Ile Glu Asn Leu
1               5                   10                  15

Trp Glu Gln Met Met Gly Leu Val Pro Asp His Glu Ile Thr Arg
            20                  25                  30

Leu Met Lys Ser Glu Leu Gln Lys Arg Leu Asn Trp Gly Tyr Lys Pro
            35                  40                  45

Thr His Gln Gln Gln Ile Ser Gln Leu Leu Asp Phe Ala Lys Ser Leu
    50                  55                  60

Arg Arg Met Glu Met Ser Leu Asp Phe Asp Asn Leu Glu Leu Asp Thr
65                  70                  75                  80

Lys Met Tyr Glu Thr Pro Glu Ser Phe Gln Leu Ile Met Ser Gly Thr
                85                  90                  95

Thr Leu Lys Glu Ser Ser Gly Leu Phe Thr Asp Glu Thr Ala Thr Leu
            100                 105                 110

Asp Gln Thr Gln Ile Arg Met Met Asp Leu Tyr Leu Glu Lys Ala Lys
            115                 120                 125

Ile Lys Asp Gly Gln Ser Ile Leu Asp Leu Gly Cys Gly His Gly Ala
    130                 135                 140

Leu Ile Leu His Val Ala Gln Lys Tyr Arg Asn Cys Asn Val Thr Gly
145                 150                 155                 160

Val Thr Asn Ser Ile Ala Gln Lys Glu Phe Ile Phe Lys Gln Cys Lys
                165                 170                 175

Lys Leu Gly Leu Ser Asn Val Glu Met Val Leu Ala Asp Val Thr Lys
            180                 185                 190

Cys Glu Met Lys Ala Thr Phe Asp His Ile Phe Val Ile Gly Leu Ile
            195                 200                 205

Glu His Met Lys Asn Phe Glu Leu Phe Leu Arg Lys Val Ser Glu Trp
    210                 215                 220

Met Lys Ser Asp Gly Leu Leu Phe Met Glu His Tyr Cys His Lys Ser
225                 230                 235                 240

Phe Ala Tyr Gln Trp Glu Pro Met Asp Asp Asp Leu Phe Ser Lys
                245                 250                 255

Tyr Val Phe Pro Pro Gly Ser Ala Ile Ile Pro Ser Ala Ser Phe Leu
            260                 265                 270

Leu Tyr Phe Gln Asp Asp Leu Thr Val Val Asp His Trp Thr Leu Ser
```

```
                275                 280                 285
Gly Asn His Phe Ala Arg Thr His Gln Glu Trp Leu Lys Arg Ile Asp
    290                 295                 300

Ser Gln Ser Asp Glu Ile Lys Gly Ile Phe Glu Ser Phe Tyr Gly Ile
305                 310                 315                 320

Ser Lys Glu Glu Ala Val Lys Leu Ile Asn Tyr Trp Arg Val Phe Cys
                325                 330                 335

Leu Phe Gly Val Glu Met Phe Gly Tyr Asn Asn Gly Glu Glu Trp Met
            340                 345                 350

Ile Ser His Leu Leu Phe Lys Lys Lys
        355                 360

<210> SEQ ID NO 125
<211> LENGTH: 363
<212> TYPE: PRT
<213> ORGANISM: Corydalis chelanthifolia

<400> SEQUENCE: 125

Met Glu Val Val Ala Thr Ser Ser Ala Arg Asn Pro Lys Lys Glu Ile
1               5                   10                  15

Val Asp Leu Trp Lys Arg Met Glu Leu Gly Leu Ile Pro Asp Glu Glu
            20                  25                  30

Ile Arg Asp Leu Met Lys Ile Gly Leu Glu Lys Arg Leu Lys Trp Gly
        35                  40                  45

Tyr Lys Pro Thr His Glu Gln Gln Leu Ser Gln Leu Leu His Phe Ala
    50                  55                  60

Lys Ser Leu Arg Ser Met Lys Met Ala Ser Glu Met Glu Thr Leu Asp
65                  70                  75                  80

Asp Gln Met Tyr Glu Thr Pro Thr Ala Phe Gln Gln Leu Met Cys Gly
                85                  90                  95

Ser Thr Ile Lys Glu Ser Ala Gly Phe Phe Lys Asp Glu Ser Thr Thr
            100                 105                 110

Leu Asp Glu Ala Glu Ile Lys Met Leu Asp Leu Tyr Cys Glu Lys Ala
        115                 120                 125

Arg Ile Glu Asp Gly Gln Lys Ile Leu Asp Leu Gly Cys Gly His Gly
    130                 135                 140

Ala Val Met Leu His Ile Ala Gln Lys Tyr Lys Asn Cys Asn Val Thr
145                 150                 155                 160

Gly Val Thr Asn Ser Ile Ser Gln Gln Gln Phe Ile Val Gln Arg Ser
                165                 170                 175

Lys Glu Leu Asn Leu Ser Asn Val Asn Met Ile Leu Ala Asp Val Thr
            180                 185                 190

Met Leu Glu Met Asp Ala Thr Tyr Asp Arg Ile Phe Ile Ile Gly Leu
        195                 200                 205

Ile Glu His Met Lys Asn Phe Glu Leu Phe Leu Arg Lys Ile Ser Lys
    210                 215                 220

Trp Ile Thr Lys Glu Gly Leu Leu Phe Leu Glu His Tyr Cys His Lys
225                 230                 235                 240

Thr Phe Ala Tyr Gln Cys Glu Pro Val Asp Glu Asp Trp Tyr Asn
                245                 250                 255

Met Phe Ile Phe Pro Pro Gly Thr Leu Ile Leu Pro Ser Ala Ser Phe
            260                 265                 270

Leu Leu Tyr Phe Gln Asp Asp Leu Ile Val Val Asp Arg Trp Thr Leu
        275                 280                 285
```

```
Asn Gly Asn His Tyr Ala Arg Thr Gln Glu Glu Trp Leu Lys Arg Ile
        290                 295                 300

Asp Ala Asn Val Asp Gly Val Lys Gln Met Phe Glu Ser Val Cys Asp
305                 310                 315                 320

Gly Asn Lys Glu Glu Ala Val Lys Leu Met Asn Phe Trp Arg Ile Phe
                325                 330                 335

Cys Ile Ser Gly Ala Glu Met Leu Ala Tyr Asn Asn Gly Glu Glu Trp
                340                 345                 350

Met Ile Ser His Tyr Leu Phe Lys Lys Arg Asn
                355                 360

<210> SEQ ID NO 126
<211> LENGTH: 357
<212> TYPE: PRT
<213> ORGANISM: Nigella sativa

<400> SEQUENCE: 126

Met Glu Ala Thr Gln Ile Thr Lys Lys Gln Gly Val Ala Glu Leu Ile
1               5                   10                  15

Lys Arg Ile Glu Asn Gly Gln Val Pro Asp Glu Glu Ile Thr Arg Met
            20                  25                  30

Met Lys Ile Gln Ile Gln Lys Arg Leu Lys Leu Gly Tyr Lys Ser Thr
        35                  40                  45

His Glu Gln Gln Leu Ala Gln Leu Leu His Phe Val His Ser Leu Gln
    50                  55                  60

Lys Met Glu Met Ala Glu Val Asp Thr Leu Asp Ser Glu Leu Tyr
65                  70                  75                  80

Glu Ile Pro Leu Pro Phe Leu His Ile Met Cys Gly Lys Ala Leu Lys
                85                  90                  95

Phe Ser Pro Gly Tyr Phe Lys Asp Glu Ser Thr Thr Leu Asp Glu Ser
            100                 105                 110

Glu Val Asn Met Leu Asp Leu Tyr Cys Glu Arg Ala Gln Ile Glu Asp
        115                 120                 125

Gly Gln Thr Ile Leu Asp Leu Gly Cys Gly His Gly Ser Leu Thr Leu
130                 135                 140

His Val Ala Lys Lys Tyr Arg Gly Cys Lys Val Thr Gly Ile Thr Asn
145                 150                 155                 160

Ser Val Ser Gln Lys Asp Phe Ile Met Glu Glu Cys Lys Lys Leu Asn
                165                 170                 175

Leu Ser Asn Val Glu Ile Ile Leu Glu Asp Val Thr Lys Phe Glu Thr
            180                 185                 190

Gly Thr Thr Tyr Asp Arg Ile Phe Ala Val Ala Leu Ile Glu His Met
        195                 200                 205

Lys Asn Tyr Glu Leu Phe Leu Lys Lys Val Ser Ala Trp Met Ala Gln
    210                 215                 220

Asp Gly Leu Leu Phe Val Glu His His Cys His Lys Val Phe Ala Tyr
225                 230                 235                 240

Lys Tyr Glu Pro Ile Asp Asp Asp Trp Tyr Thr Glu Tyr Ile Phe
                245                 250                 255

Pro Thr Gly Thr Leu Val Met Ser Ser Ser Ile Leu Tyr Phe
            260                 265                 270

Gln Glu Asp Val Ser Val Val Asn His Trp Thr Leu Ser Gly Lys His
        275                 280                 285

Pro Ser Leu Gly Phe Lys Gln Trp Leu Lys Arg Ile Asp Asp Asn Ile
    290                 295                 300
```

```
Asp Glu Ile Lys Glu Ile Phe Glu Ser Phe Tyr Gly Ser Lys Glu Lys
305                 310                 315                 320

Ala Thr Lys Phe Ile Thr Tyr Trp Arg Val Phe Cys Ile Ala His Ser
            325                 330                 335

Glu Met Tyr Ala Thr Asn Gly Gly Glu Glu Trp Met Leu Ser Gln Val
        340                 345                 350

Leu Phe Lys Arg Lys
        355

<210> SEQ ID NO 127
<211> LENGTH: 349
<212> TYPE: PRT
<213> ORGANISM: Sanguinaria canadensis

<400> SEQUENCE: 127

Met Gly Gly Val Ala Asp Leu Leu Lys Lys Met Glu Leu Gly Leu Val
1               5                   10                  15

Pro Glu Glu Glu Ile Arg Arg Leu Met Arg Ile Ile Glu Lys Arg
            20                  25                  30

Leu Glu Trp Gly Tyr Lys Pro Thr His Ala Glu Gln Leu Asp His Leu
        35                  40                  45

Thr Asn Phe Ile Gln Cys Leu Arg Gly Met Lys Met Ala Asp Glu Ile
    50                  55                  60

Asp Ala Leu Asp Ala Lys Met Tyr Glu Ile Pro Leu Pro Phe Met Gln
65                  70                  75                  80

Thr Ile Cys Gly Ser Thr Leu Lys Phe Ser Pro Gly Tyr Phe Lys Asp
                85                  90                  95

Glu Ser Thr Thr Leu Asp Glu Ser Glu Ile His Met Met Asp Leu Tyr
            100                 105                 110

Cys Glu Arg Ala Glu Val Lys Asp Gly His Ser Ile Leu Asp Leu Gly
        115                 120                 125

Cys Gly His Gly Gly Phe Val Leu His Val Ala Gln Lys Tyr Lys Asn
    130                 135                 140

Ser Ile Val Thr Gly Val Thr Asn Ser Val Ala Glu Lys Glu Phe Ile
145                 150                 155                 160

Met Thr Gln Cys Lys Lys Leu Cys Leu Ser Asn Val Glu Ile Ile Leu
                165                 170                 175

Ala Asp Val Thr Lys Phe Glu Pro Glu Thr Thr Tyr Asp Arg Val Phe
            180                 185                 190

Ala Ile Ala Leu Ile Glu His Met Lys Asn Tyr Glu Leu Val Leu Glu
        195                 200                 205

Lys Leu Ser Lys Trp Val Ala Gln Asp Gly Phe Leu Phe Val Glu His
    210                 215                 220

His Cys His Lys Val Phe Pro Tyr Lys Tyr Glu Pro Leu Asp Glu Asp
225                 230                 235                 240

Asp Trp Tyr Thr Glu Tyr Ile Phe Pro Gly Gly Thr Ile Val Leu Pro
                245                 250                 255

Ser Ala Ser Ile Leu Leu Tyr Phe Gln Lys Asp Val Ser Val Val Asn
            260                 265                 270

His Trp Ser Leu Asn Gly Lys His Pro Ala Arg Gly Phe Lys Glu Trp
        275                 280                 285

Leu Lys Arg Leu Asp Glu Asn Met Asp Ala Val Lys Ala Ile Phe Glu
    290                 295                 300

Pro Phe Tyr Gly Ser Lys Glu Glu Ala Met Lys Trp Ile Thr Tyr Trp
```

```
305                 310                 315                 320
Arg Val Phe Cys Ile Thr His Ser Glu Met Tyr Ala Tyr Asn Asn Gly
                325                 330                 335

Glu Glu Trp Met Leu Ser Gln Val Leu Phe Lys Arg Lys
            340                 345
```

<210> SEQ ID NO 128
<211> LENGTH: 350
<212> TYPE: PRT
<213> ORGANISM: Jeffersonia diphylla

<400> SEQUENCE: 128

```
Met Ser Lys Gly Val Ala Lys Leu Val Glu Arg Met Glu Leu Gly Leu
1               5                   10                  15

Val Ser Asp Asp Glu Val Arg Arg Leu Met Arg Ile Leu Ile Glu Lys
                20                  25                  30

Arg Leu Lys Trp Gly Tyr Lys Pro Thr His Glu Glu Gln Leu Thr Tyr
            35                  40                  45

Leu Thr Asn Phe Ile Gln Gly Leu Lys Gly Met Lys Ile Ala Glu Glu
        50                  55                  60

Ile Asp Ala Leu Asp Ala Lys Met Tyr Glu Ile Pro Ile Ala Phe Met
65                  70                  75                  80

Gln Ile Leu Cys Gly Tyr Ser Leu Lys Phe Ser Pro Gly Phe Phe Glu
                85                  90                  95

Asp Glu Ser Thr Thr Leu Asp Glu Ser Glu Thr Ile Met Met Asp Leu
                100                 105                 110

Tyr Cys Glu Arg Ala Gln Val Gln Asp Gly Gln Ser Ile Leu Asp Leu
            115                 120                 125

Gly Cys Gly His Gly Gly Phe Val Leu His Val Ala Gln Lys Tyr Lys
        130                 135                 140

Asn Cys Lys Val Thr Gly Val Thr Asn Ser Val Ser Glu Thr Glu Tyr
145                 150                 155                 160

Ile Met Glu Gln Cys Lys Lys Leu Gly Leu Ser Asn Val Glu Ile Ile
                165                 170                 175

Ile Ala Asp Val Thr Lys Phe Glu Pro Glu Val Thr Tyr Asp Arg Val
                180                 185                 190

Phe Ala Ile Ala Leu Ile Glu His Met Lys Asn Tyr Glu Leu Val Leu
            195                 200                 205

Gln Lys Leu Ser Lys Trp Val Ala Gln Asp Gly Phe Leu Phe Val Asp
        210                 215                 220

His His Cys His Lys Val Phe Pro Tyr Lys Tyr Glu Pro Ile Asp Glu
225                 230                 235                 240

Asp Asp Trp Tyr Thr Gln Tyr Ile Phe Pro Gly Gly Thr Leu Val Leu
                245                 250                 255

Pro Ser Ala Ser Ile Leu Leu Tyr Phe Gln Glu Asp Val Ser Ile Val
                260                 265                 270

Asn His Trp Thr Leu Ser Gly Asn His Pro Ala Arg Gly Phe Lys Glu
            275                 280                 285

Trp Leu Lys Arg Leu Asp Asp Asn Met Asp Glu Ile Lys Ala Ile Phe
        290                 295                 300

Glu Pro Phe Tyr Gly Ser Lys Glu Glu Ala Met Lys Trp Ile Thr Tyr
305                 310                 315                 320

Trp Arg Val Phe Cys Ile Thr His Ser Glu Met Tyr Ala Tyr Asn Gly
                325                 330                 335
```

-continued

Gly Glu Glu Trp Met Ile Ser Gln Val Leu Phe Lys Arg Lys
                340                 345                 350

<210> SEQ ID NO 129
<211> LENGTH: 357
<212> TYPE: PRT
<213> ORGANISM: Berberis thunbergii

<400> SEQUENCE: 129

Met Glu Val Lys Gln Ala Gly Lys Glu Gly Val Thr Glu Leu Leu Val
1               5                   10                  15

Lys Arg Met Glu Leu Gly Leu Val Pro Glu Glu Ile Arg Arg Leu
            20                  25                  30

Met Arg Ile Gln Ile Gln Lys Arg Leu Asp Trp Gly Tyr Lys Pro Thr
            35                  40                  45

His Glu Glu Gln Leu Ala His Leu Thr Lys Phe Ile Gln Asn Ile Arg
    50                  55                  60

Gly Met Lys Met Ala Asp Glu Ile Asp Ala Leu Asp Ala Lys Met Tyr
65              70                  75                  80

Glu Ile Pro Leu Pro Phe Leu Gln Thr Ile Cys Gly Lys Thr Leu Lys
                85                  90                  95

Phe Ser Pro Gly Tyr Phe Lys Asp Glu Ser Thr Thr Leu Asp Glu Ser
            100                 105                 110

Glu Thr Leu Met Met Asp Leu Tyr Cys Glu Arg Ala Gln Val Lys Asp
            115                 120                 125

Gly Gln Ser Ile Leu Asp Leu Gly Cys Gly His Gly Gly Phe Val Leu
    130                 135                 140

His Leu Ala Gln Lys Tyr Arg Asn Ser Val Val Thr Gly Val Thr Asn
145             150                 155                 160

Ser Val Ser Glu Thr Glu Tyr Ile Lys Glu Gln Cys Lys Lys Leu Gly
                165                 170                 175

Leu Ser Asn Val Glu Ile Ile Ile Ala Asp Val Thr Lys Phe Glu Pro
            180                 185                 190

Glu Val Thr Tyr Asp Arg Val Phe Ala Ile Ala Leu Ile Glu His Met
            195                 200                 205

Lys Asn Tyr Ala Leu Val Leu Asn Lys Ile Ser Lys Trp Val Ala Gln
    210                 215                 220

Asp Gly Tyr Leu Phe Val Glu His His Cys His Lys Val Phe Pro Tyr
225             230                 235                 240

Lys Tyr Glu Pro Leu Asp Glu Asp Trp Tyr Thr Asn Tyr Ile Phe
                245                 250                 255

Pro Gly Gly Thr Leu Ile Leu Pro Ser Ala Ser Ile Leu Leu Tyr Phe
            260                 265                 270

Gln Glu Asp Val Thr Val Leu Asn His Trp Ser Leu Ser Gly Lys His
            275                 280                 285

Pro Ser Arg Gly Phe Ile Glu Trp Leu Lys Arg Leu Asp Glu Asn Ile
    290                 295                 300

Asp Val Ile Met Gly Ile Phe Glu Pro Phe Tyr Gly Ser Lys Glu Glu
305             310                 315                 320

Ala Thr Lys Trp Ile Asn Tyr Trp Arg Val Phe Cys Met Thr His Ser
                325                 330                 335

Glu Met Tyr Ala Tyr Gly Asn Gly Glu Glu Trp Met Leu Ser Gln Val
            340                 345                 350

Leu Leu Lys Arg Lys
            355

<210> SEQ ID NO 130
<211> LENGTH: 339
<212> TYPE: PRT
<213> ORGANISM: Mahonia aquifolium

<400> SEQUENCE: 130

Met Glu Leu Gly Leu Val Pro Glu Lys Glu Ile Arg Arg Leu Met Arg
1               5                   10                  15

Ile Gln Ile Gln Lys Arg Leu Glu Trp Gly Tyr Lys Pro Thr His Glu
            20                  25                  30

Glu Gln Leu Ala His Leu Thr Lys Phe Ile Gln Asn Ile Arg Gly Met
        35                  40                  45

Lys Met Ala Asp Glu Ile Asp Ala Leu Asp Ala Lys Met Tyr Glu Ile
50                  55                  60

Pro Leu Pro Phe Leu Gln Thr Ile Cys Gly Lys Thr Leu Lys Phe Ser
65                  70                  75                  80

Pro Gly Tyr Phe Lys Asp Glu Ser Thr Thr Leu Asp Glu Ser Glu Thr
                85                  90                  95

Leu Met Met Asp Leu Tyr Cys Glu Arg Ala Gln Val Lys Asp Gly Gln
            100                 105                 110

Ser Ile Leu Asp Leu Gly Cys Gly His Gly Phe Val Leu His Leu
        115                 120                 125

Ala Gln Lys Tyr Arg Asn Ser Ile Val Thr Gly Val Thr Asn Ser Val
130                 135                 140

Ser Glu Thr Glu Tyr Ile Lys Glu Gln Cys Lys Lys Leu Gly Leu Ser
145                 150                 155                 160

Asn Val Glu Ile Ile Ile Ala Asp Val Thr Lys Phe Glu Pro Glu Val
                165                 170                 175

Thr Tyr Asp Arg Val Phe Ala Ile Ala Leu Ile Glu His Met Lys Asn
            180                 185                 190

Tyr Ala Leu Val Leu Asn Lys Ile Ser Lys Trp Val Ala Gln Asp Gly
        195                 200                 205

Tyr Leu Phe Val Glu His His Cys His Lys Val Phe Pro Tyr Lys Tyr
210                 215                 220

Glu Pro Leu Asp Glu Asp Asp Trp Tyr Thr Asn Tyr Ile Phe Pro Gly
225                 230                 235                 240

Gly Thr Leu Ile Leu Pro Ser Ala Ser Ile Leu Leu Tyr Phe Gln Glu
                245                 250                 255

Asp Val Thr Val Leu Asn His Trp Ser Leu Ser Gly Lys His Pro Ser
            260                 265                 270

Arg Gly Phe Ile Glu Trp Leu Lys Arg Leu Asp Glu Asn Ile Asp Val
        275                 280                 285

Ile Met Gly Ile Phe Glu Pro Phe Tyr Gly Ser Lys Glu Glu Ala Thr
290                 295                 300

Lys Trp Ile Asn Tyr Trp Arg Val Phe Cys Ile Thr His Ser Glu Met
305                 310                 315                 320

Tyr Ala Tyr Gly Asn Gly Glu Glu Trp Met Leu Ser Gln Val Leu Leu
                325                 330                 335

Lys Arg Lys

<210> SEQ ID NO 131
<211> LENGTH: 355
<212> TYPE: PRT
<213> ORGANISM: Menispermum canadense -continued

```
<220> FEATURE:
<221> NAME/KEY: MOD_RES
<222> LOCATION: (86)..(86)
<223> OTHER INFORMATION: Any amino acid
<220> FEATURE:
<221> NAME/KEY: MOD_RES
<222> LOCATION: (96)..(96)
<223> OTHER INFORMATION: Any amino acid
<220> FEATURE:
<221> NAME/KEY: MOD_RES
<222> LOCATION: (127)..(127)
<223> OTHER INFORMATION: Any amino acid
<220> FEATURE:
<221> NAME/KEY: MOD_RES
<222> LOCATION: (138)..(138)
<223> OTHER INFORMATION: Any amino acid
<220> FEATURE:
<221> NAME/KEY: MOD_RES
<222> LOCATION: (153)..(153)
<223> OTHER INFORMATION: Any amino acid
<220> FEATURE:
<221> NAME/KEY: MOD_RES
<222> LOCATION: (292)..(292)
<223> OTHER INFORMATION: Any amino acid

<400> SEQUENCE: 131

Met Asp Lys Ala Asn Glu Arg Glu Leu Lys Arg Ala Glu Leu Phe Lys
 1               5                  10                  15

Lys Leu Glu Asp Asp Leu Val Thr Tyr Asp Glu Ile Lys Gln Val Met
            20                  25                  30

Arg Thr Glu Leu Ala Lys Arg Leu Glu Trp Gly Tyr Lys Pro Thr His
        35                  40                  45

Gln Gln Gln Leu Ala His Leu Leu Asp Phe Ala His Ala Leu Glu Gly
    50                  55                  60

Met Lys Ile Ala Asn Glu Val Glu Thr Leu Ala Ser Glu Val Tyr Glu
65                  70                  75                  80

Thr Pro Leu Pro Phe Xaa Glu Ile Val Leu Gly Pro Ala Lys Lys Xaa
                85                  90                  95

Ser Ser Cys Leu Phe Glu Asp Glu Ser Thr Thr Leu Glu Gln Ala Glu
            100                 105                 110

Ile Ala Met Leu Asp Leu Tyr Phe Glu Arg Ala Gln Ile Arg Xaa Gly
        115                 120                 125

Met Ser Val Leu Asp Leu Gly Cys Gly Xaa Gly Ser Val Gly Leu His
    130                 135                 140

Ile Ala Arg Lys Tyr Lys Asn Cys Xaa Val Thr Cys Ile Thr Asn Ser
145                 150                 155                 160

Ile Ser Gln Lys Gln Tyr Ile Glu Asn Gln Cys Lys Leu Tyr Asn Leu
                165                 170                 175

Ser Asn Val Lys Ile Ile Leu Ala Asp Ile Val Ala His Asp Thr Asp
            180                 185                 190

Asp Thr Phe Asp Val Val Leu Val Ile Gly Val Ile Glu His Met Lys
        195                 200                 205

Asn Tyr Ala Leu Leu Leu Asn Lys Ile Ser Lys Trp Met Ala Lys Asp
    210                 215                 220

Gly Leu Leu Phe Val Glu His Leu Cys His Lys Thr Phe Pro Tyr His
225                 230                 235                 240

Phe Glu Pro Leu Asp Glu Asp Trp Tyr Ser Asn Phe Val Phe Pro
                245                 250                 255

Thr Gly Thr Leu Thr Met Pro Ser Val Ser Phe Leu Tyr Phe Gln
            260                 265                 270

Ala Asp Val Ser Ile Leu Asn His Trp Ile Leu Ser Gly Lys Asn Phe
```

```
            275                 280                 285
Ser Arg Thr Xaa Glu Glu Phe Leu Lys Arg Ile Asp Ala Asn Val Asp
        290                 295                 300
Ala Ile Lys Asp Gly Leu Lys Pro Ser Leu Gly Ser Glu Gly Val Ala
305                 310                 315                 320
Lys Leu Ile Ser Tyr Trp Arg Gly Phe Cys Leu Thr Gly Met Glu Met
            325                 330                 335
Phe Gly Tyr Asn Asn Gly Glu Glu Trp Met Val Ser Gln Val Leu Phe
            340                 345                 350
Lys Asn Lys
        355

<210> SEQ ID NO 132
<211> LENGTH: 366
<212> TYPE: PRT
<213> ORGANISM: Tinospora cordifolia

<400> SEQUENCE: 132

Met Glu Asp Asn Asn Asn Leu Leu Gln Glu Glu Met Asn Val Val Glu
1               5                   10                  15
Leu Leu Gln Arg Pro Glu Leu Gly Leu Val Pro Asp Glu Lys Ile Arg
            20                  25                  30
Lys Leu Thr Arg Leu Gln Leu Gln Lys Arg Leu Lys Trp Gly Tyr Lys
        35                  40                  45
Pro Thr His Glu Ala Gln Leu Ser His Leu Phe Gln Phe Ile His Ser
    50                  55                  60
Leu Pro Ser Leu Asn Met Glu Ser Glu Asp Glu Asn Pro Lys Ser Trp
65                  70                  75                  80
Leu Tyr Glu Thr Pro Thr Ser Phe Leu Gln Leu Leu Tyr Gly Asp Cys
                85                  90                  95
Ile Lys Glu Ser Asp Thr Tyr Tyr Lys Glu Asp Thr Ala Thr Leu Glu
            100                 105                 110
Glu Ala Val Ile Asn Met Leu Glu Leu Tyr Cys Glu Arg Ala Arg Ile
        115                 120                 125
Thr Glu Gly Leu Ser Val Leu Asp Leu Gly Cys Gly Tyr Gly Ala Leu
    130                 135                 140
Thr Leu His Val Ala Gln Lys Tyr Lys Ser Cys Lys Val Thr Gly Val
145                 150                 155                 160
Thr Ser Ser Ile Ser Gln Lys Gln Tyr Ile Met Glu Lys Cys Lys Lys
                165                 170                 175
Leu Asn Leu Thr Asn Val Glu Ile Ile Leu Ala Asp Val Ala Thr Ile
            180                 185                 190
Glu Ile Glu Ala Ala Ser Tyr Asp Arg Ile Phe Ala Leu Gly Ile Phe
        195                 200                 205
Glu His Val Asn Asp Tyr Lys Leu Phe Leu Gly Lys Leu Ser Lys Trp
    210                 215                 220
Met Lys Gln Asp Gly Leu Leu Phe Val Glu Tyr Leu Cys His Lys Thr
225                 230                 235                 240
Phe Pro Tyr Gln Asn Lys Pro Leu Asp Lys Gly Asp Lys Trp Tyr Asn
                245                 250                 255
Glu Tyr Val Phe Pro Ser Gly Gly Leu Ile Ile Pro Ser Ala Ser Phe
            260                 265                 270
Ile Leu Tyr Phe Gln Asn Asp Val Ser Val Val Arg Gln Trp Thr Gln
        275                 280                 285
```

```
Gly Gly Gln His Ser Ala Arg Thr Phe Glu Glu Leu Leu Lys Arg Ile
    290                 295                 300

Asp Gly Asn Ile Asp Lys Ile Lys Glu Ile Phe Ile Glu Ser Tyr Gly
305                 310                 315                 320

Ser Lys Glu Asp Ala Val Arg Phe Ile Asn Tyr Trp Arg Val Phe Leu
                325                 330                 335

Ile Thr Gly Val Glu Met Phe Ser Tyr Asn Asp Gly Glu Glu Trp Met
            340                 345                 350

Gly Ala His Phe Leu Phe Lys Lys Lys Phe Ile Met Gln Glu
        355                 360                 365

<210> SEQ ID NO 133
<211> LENGTH: 359
<212> TYPE: PRT
<213> ORGANISM: Cissampelos mucronata

<400> SEQUENCE: 133

Met Glu Val Lys Gln Ser Lys Gly Asp Glu Leu Arg Ser Arg Val Ala
1               5                   10                  15

Glu Leu Leu Glu Arg Pro Glu Leu Gly Leu Val Pro Asp Glu Glu Ile
            20                  25                  30

Arg Arg Leu Ala Lys Ala Arg Leu Glu Lys Arg Leu Lys Trp Gly Tyr
        35                  40                  45

Lys Ala Thr His Gly Glu Gln Leu Ser Ser Leu Leu Gln Phe Val Glu
    50                  55                  60

Ser Leu Pro Ser Leu Asn Met Ala Ser Glu Asp Asp Ser Pro Lys Ala
65                  70                  75                  80

Trp Leu Tyr Glu Thr Pro Thr Ser Phe Leu Gln Leu Ile Tyr Gly Asp
                85                  90                  95

Ile Ile Lys Glu Ser Gly Ser Tyr Tyr Lys Asp Glu Ser Thr Thr Leu
            100                 105                 110

Glu Glu Ala Met Ile His Asn Met Asn Leu Cys Cys Glu Arg Ala Asn
        115                 120                 125

Ile Lys Glu Gly Gln Ser Val Val Asp Leu Gly Cys Gly Tyr Gly Ala
    130                 135                 140

Phe Ile Leu His Val Ala Gln Lys Tyr Lys Thr Cys Arg Val Thr Gly
145                 150                 155                 160

Ile Thr Ser Ser Ile Ser Gln Lys His Tyr Ile Met Glu Gln Cys Lys
                165                 170                 175

Lys Leu Asn Leu Ser Asn Val Glu Val Ile Leu Ala Asp Val Ala Thr
            180                 185                 190

Ile Lys Leu Asp Ala Thr Phe Asp Arg Val Phe Ala Ala Gly Met Phe
        195                 200                 205

Glu His Val Asn Asp Tyr Lys Ser Phe Leu Arg Lys Ile Thr Asn Trp
    210                 215                 220

Met Lys Pro Asp Gly Arg Leu Phe Val Glu His Leu Cys Asn Lys Thr
225                 230                 235                 240

Phe Pro Tyr Gln Asn Lys Pro Leu Asp Asp Gly Asp Asn Trp Gly Glu
                245                 250                 255

Tyr Val Phe Pro Ser Gly Gly Leu Ile Ile Pro Ser Ala Ser Leu Leu
            260                 265                 270

Leu Tyr Phe Gln Glu Asp Val Ser Ile Val Asn His Trp Thr Phe Ser
        275                 280                 285

Gly Lys His Ala Ala Asn Lys Phe Glu Glu Leu Leu Lys Arg Ile Asp
    290                 295                 300
```

```
Ala Lys Ile Asp Ala Ile Lys Arg Ile Phe Asn Glu Cys Tyr Gly Ser
305                 310                 315                 320

Lys Asp Ser Ile Arg Phe Ile Asn Tyr Trp Arg Val Phe Leu Ile Thr
                325                 330                 335

Ala Ala Glu Met Phe Gly Tyr Asn Asn Gly Glu Glu Trp Met Gly Val
            340                 345                 350

His Leu Leu Phe Lys Lys Lys
        355

<210> SEQ ID NO 134
<211> LENGTH: 352
<212> TYPE: PRT
<213> ORGANISM: Cocculus trilobus

<400> SEQUENCE: 134

Gly Leu Lys Ser Ser Val Ala Glu Leu Leu Glu Arg Pro Glu Leu Gly
1               5                   10                  15

Leu Val Pro Asp Gly Glu Ile Arg Lys Leu Thr Lys Thr Arg Leu Ala
            20                  25                  30

Lys Arg Leu Glu Trp Gly Tyr Lys Ala Thr His Glu Asp Gln Leu Ser
        35                  40                  45

His Leu Leu Arg Phe Ile His Ser Leu Pro Ser Leu Asn Met Ala Ser
    50                  55                  60

Glu Asp Asp Ser Pro Lys Ala Trp Leu Tyr Glu Thr Pro Thr Ser Phe
65                  70                  75                  80

Leu Gln Leu Ile Tyr Gly Asp Ile Ile Lys Glu Ser Gly Thr Tyr Tyr
                85                  90                  95

Lys Asp Glu Ser Ser Thr Leu Glu Glu Ala Ile Ile His Asn Met Asp
            100                 105                 110

Leu Cys Cys Glu Arg Ala Arg Ile Lys Glu Gly Gln Ser Val Leu Asp
        115                 120                 125

Leu Gly Cys Gly Tyr Gly Ala Phe Thr Leu His Val Ala Gln Lys Tyr
    130                 135                 140

Lys Ser Cys Ser Val Thr Gly Ile Thr Ser Ile Ser Gln Lys Asp
145                 150                 155                 160

Tyr Ile Met Glu Gln Cys Lys Lys Leu Asn Leu Ser Asn Val Glu Val
                165                 170                 175

Ile Leu Ala Asp Val Ala Thr Ile Lys Met Asn Thr Thr Phe Asp Arg
            180                 185                 190

Val Phe Ala Leu Gly Met Phe Glu His Ile Asn Asp Tyr Lys Leu Phe
        195                 200                 205

Leu Arg Arg Ile Ser Asn Trp Met Lys His Asp Gly Leu Leu Phe Val
    210                 215                 220

Glu His Leu Cys Asn Lys Thr Phe Ala Tyr Gln Asn Lys Pro Leu Asp
225                 230                 235                 240

Asp Gly Asp Asp Trp Phe Asn Glu Tyr Val Phe Pro Ser Ala Gly Leu
                245                 250                 255

Ile Ile Pro Ser Ala Ser Leu Leu Tyr Phe Gln Glu Asp Val Ser
            260                 265                 270

Ile Val His His Trp Thr Phe Ser Gly Lys His Ala Ala Tyr Lys Phe
        275                 280                 285

Glu Glu Leu Leu Glu Arg Ile Asp Ala Lys Ile Glu Ala Ile Lys Glu
    290                 295                 300

Ile Phe Ile Glu Cys Tyr Gly Ser Lys Glu Asp Ala Ile Arg Phe Ile
```

```
                305                 310                 315                 320
Asn Tyr Trp Arg Val Phe Leu Ile Thr Ala Ala Glu Met Phe Ala Tyr
                        325                 330                 335

Arg Asp Gly Glu Glu Trp Met Gly Ser His Val Leu Phe Lys Lys Lys
                340                 345                 350
```

<210> SEQ ID NO 135
<211> LENGTH: 364
<212> TYPE: PRT
<213> ORGANISM: Cissampelos mucronata

<400> SEQUENCE: 135

```
Met Glu Ala Lys Gln His Glu Ser Asn Asn Asn Ile Asp Glu Glu Leu
1               5                   10                  15

Lys Asn Arg Val Asn Ile Gly Glu Gln Glu Glu Arg Pro Gly Phe Glu
                20                  25                  30

Asp Glu Glu Ile Arg Arg Leu Ala Lys Ala Gln Leu Ala Lys Arg Leu
            35                  40                  45

Lys Trp Gly Tyr Lys Pro Thr His Glu Gln Gln Leu Ser His Leu Leu
    50                  55                  60

Gln Phe Leu Gln Ser Leu Pro Ser Leu Asn Met Ala Ser Glu Asp Glu
65                  70                  75                  80

Ser Ser Lys Ala Trp Leu Tyr Glu Thr Pro Thr Ser Phe Leu Gln Leu
                85                  90                  95

Leu Phe Gly Asn Val Ile Lys Phe Ser Gly Tyr Tyr Lys His Glu
            100                 105                 110

Ser Ser Thr Phe Glu Glu Ser Met Ile His Asn Met Asp Leu Cys Cys
        115                 120                 125

Glu Arg Ala Asn Ile Lys Glu Gly Gln Asn Val Ile Asp Leu Gly Cys
    130                 135                 140

Gly Tyr Gly Ala Phe Val Leu His Val Ala Gln Lys Tyr Lys Ser Cys
145                 150                 155                 160

Ser Val Thr Gly Ile Thr Cys Ser Ile Thr Gln Lys His His Ile Met
                165                 170                 175

Glu Glu Cys Lys Lys Leu Asn Leu Cys Asn Val Lys Val Ile Leu Ala
            180                 185                 190

Asp Val Ala Thr Ile Glu Leu Gly Thr Ala Phe Asp Arg Val Phe Ala
        195                 200                 205

Phe Gly Met Phe Glu Glu Ile Asn Asp Tyr Lys Leu Ile Leu Arg Lys
    210                 215                 220

Ile Ser Asn Trp Met Lys Pro Asp Gly Leu Phe Val Glu His Leu
225                 230                 235                 240

Cys His Lys Thr Leu Ala Tyr Gln Asn Lys Leu Ile Asp Asp Gln Asp
                245                 250                 255

Trp Tyr Glu Glu Tyr Ile Phe Pro Ser Gly Gly Leu Ile Val Pro Ser
            260                 265                 270

Ala Ser Leu Leu Leu Tyr Phe Gln Asp Asp Leu Ser Val Val Tyr His
        275                 280                 285

Trp Thr Tyr Asn Gly Lys His Gly Ala Arg Ser Phe Glu Lys Met Leu
    290                 295                 300

Glu Arg Thr Asp Ala Asn Ile Asp Thr Ile Lys Asp Met Phe Thr Glu
305                 310                 315                 320

Phe Tyr Gly Ser Lys Glu Lys Ala Ile Lys Phe Ile Asn Tyr Trp Arg
                325                 330                 335
```

Val Phe Phe Ile Thr Ala Ala Glu Met Phe Ala Tyr Asn Asp Gly Glu
                340                 345                 350

Glu Trp Met Cys Ser Gln Leu Leu Phe Lys Lys Lys
        355                 360

<210> SEQ ID NO 136
<211> LENGTH: 364
<212> TYPE: PRT
<213> ORGANISM: Cissampelos mucronata

<400> SEQUENCE: 136

Met Glu His Lys Ile Glu Asp Ile Arg Lys Leu Lys Ser Arg Val Glu
1               5                   10                  15

Glu Gln Leu Glu Arg Pro Glu Leu Gly Leu Val Lys Asp Glu Asp Ile
            20                  25                  30

Lys Thr Leu Ala Lys Ala Lys Leu Glu Lys Arg Leu Lys Trp Gly Tyr
        35                  40                  45

Lys Pro Thr Tyr Ala Glu Gln Leu Ser Asn Leu Leu Gln Phe Ala Gln
50                  55                  60

Ser Leu Pro Ser Leu Lys Met Glu Asn Val Asp Asp Gln Gly Ser Ser
65                  70                  75                  80

Lys Gln Trp Leu Tyr Gly Val Pro Ser Glu Phe Leu Gln Ile Ile Tyr
                85                  90                  95

Gly Gly Ile Ile Lys Met Ser Gly Ser Tyr Tyr Glu Asp Glu Ser Thr
            100                 105                 110

Thr Leu Glu Glu Ser Met Ile Lys Asp Met Asp Ser Cys Cys Glu Lys
        115                 120                 125

Ala Asn Val Lys Glu Gly His Ser Val Leu Asp Ile Gly Cys Gly Tyr
130                 135                 140

Gly Ser Leu Ile Ile His Ile Ala Lys Lys Tyr Arg Thr Cys Asn Val
145                 150                 155                 160

Thr Gly Ile Thr Asn Phe Val Glu Gln Lys Gln Tyr Ile Met Glu Glu
                165                 170                 175

Cys Lys Lys Leu Asn Leu Ser Asn Val Glu Val Ile Val Gly Asp Gly
            180                 185                 190

Thr Thr Ile Asn Leu Asn Thr Thr Thr Phe Asp Arg Val Phe Val Thr
        195                 200                 205

Gly Met Leu Glu Glu Ile Asn Asp Tyr Lys Leu Phe Leu Lys Ser Val
210                 215                 220

Ser Asp Trp Met Lys Pro Asp Gly Leu Leu Leu Val Thr His Phe Cys
225                 230                 235                 240

His Lys Thr Phe Ala Tyr Gln Asn Asn Lys Ala Leu Asp Asp Glu Asp
                245                 250                 255

Trp His Asn Glu Tyr Ile Phe Pro Gly Asn Leu Ile Val Pro Ser
            260                 265                 270

Ala Ser Leu Leu Leu Tyr Phe Gln Glu Asp Leu Ser Val Val Ser His
        275                 280                 285

Trp Ala Thr Asn Gly Thr His Thr Gly Arg Thr Cys Lys Lys Leu Val
290                 295                 300

Glu Arg Ile Asp Ala Asn Ile Glu Lys Ile Lys Glu Ile Phe Ser Glu
305                 310                 315                 320

Phe Tyr Gly Ser Lys Glu Asp Ala Ile Arg Met Ile Asn Tyr Trp Arg
                325                 330                 335

Val Leu Cys Ile Thr Gly Ala Glu Met Tyr Thr Cys Lys Asp Gly Glu
            340                 345                 350

```
Glu Trp Met Asp Val Tyr Tyr Leu Phe Lys Lys Lys
        355                 360
```

<210> SEQ ID NO 137
<211> LENGTH: 1049
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 137

```
Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Ala Arg
65                  70                  75                  80

Asp Phe Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Leu Asp Glu Val Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Val Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
```

```
              340            345            350
Glu Val Met Val Leu Ile Pro Gln Leu His Arg Asp Lys Thr Val Trp
            355                360                365
Gly Asp Asp Val Glu Glu Phe Arg Pro Glu Arg Phe Glu Asn Pro Ser
        370                375                380
Ala Ile Pro Gln His Ala Phe Lys Pro Phe Gly Asn Gly Gln Arg Ala
385                390                395                400
Cys Ile Gly Gln Gln Phe Ala Leu His Glu Ala Thr Leu Val Leu Gly
                405                410                415
Met Met Leu Lys His Phe Asp Phe Glu Asp His Thr Asn Tyr Glu Leu
            420                425                430
Asp Ile Lys Glu Thr Ala Thr Leu Lys Pro Lys Gly Phe Val Val Lys
        435                440                445
Ala Lys Ser Lys Lys Ile Pro Leu Gly Gly Ile Pro Ser Pro Ser Thr
450                455                460
Glu Gln Ser Ala Lys Lys Val Arg Lys Lys Ala Glu Asn Ala His Asn
465                470                475                480
Thr Pro Leu Leu Val Leu Tyr Gly Ser Asn Met Gly Thr Ala Glu Gly
                485                490                495
Thr Ala Arg Asp Leu Ala Asp Ile Ala Met Ser Lys Gly Phe Ala Pro
            500                505                510
Gln Val Ala Thr Leu Asp Ser His Ala Gly Asn Leu Pro Arg Glu Gly
        515                520                525
Ala Val Leu Ile Val Thr Ala Ser Tyr Asn Gly His Pro Pro Asp Asn
530                535                540
Ala Lys Gln Phe Val Asp Trp Leu Asp Gln Ala Ser Ala Asp Glu Val
545                550                555                560
Lys Gly Val Arg Tyr Ser Val Phe Gly Cys Gly Asp Lys Asn Trp Ala
                565                570                575
Thr Thr Tyr Gln Lys Val Pro Ala Phe Ile Asp Glu Thr Leu Ala Ala
            580                585                590
Lys Gly Ala Glu Asn Ile Ala Asp Arg Gly Glu Ala Asp Ala Ser Asp
        595                600                605
Asp Phe Glu Gly Thr Tyr Glu Glu Trp Arg Glu His Met Trp Ser Asp
        610                615                620
Val Ala Ala Tyr Phe Asn Leu Asp Ile Glu Asn Ser Glu Asp Asn Lys
625                630                635                640
Ser Thr Leu Ser Leu Gln Phe Val Asp Ser Ala Ala Asp Met Pro Leu
                645                650                655
Ala Lys Met His Gly Ala Phe Ser Thr Asn Val Val Ala Ser Lys Glu
            660                665                670
Leu Gln Gln Pro Gly Ser Ala Arg Ser Thr Arg His Leu Glu Ile Glu
        675                680                685
Leu Pro Lys Glu Ala Ser Tyr Gln Glu Gly Asp His Leu Gly Val Ile
        690                695                700
Pro Arg Asn Tyr Glu Gly Ile Val Asn Arg Val Thr Ala Arg Phe Gly
705                710                715                720
Leu Asp Ala Ser Gln Gln Ile Arg Leu Glu Ala Glu Glu Lys Leu
                725                730                735
Ala His Leu Pro Leu Ala Lys Thr Val Ser Val Glu Glu Leu Leu Gln
            740                745                750
Tyr Val Glu Leu Gln Asp Pro Val Thr Arg Thr Gln Leu Arg Ala Met
        755                760                765
```

-continued

```
Ala Ala Lys Thr Val Cys Pro Pro His Lys Val Glu Leu Glu Ala Leu
        770                 775                 780
Leu Glu Lys Gln Ala Tyr Lys Glu Gln Val Leu Ala Lys Arg Leu Thr
785                 790                 795                 800
Met Leu Glu Leu Leu Glu Lys Tyr Pro Ala Cys Glu Met Lys Phe Ser
                805                 810                 815
Glu Phe Ile Ala Leu Leu Pro Ser Ile Arg Pro Arg Tyr Tyr Ser Ile
                820                 825                 830
Ser Ser Ser Pro Arg Val Asp Glu Lys Gln Ala Ser Ile Thr Val Ser
                835                 840                 845
Val Val Ser Gly Glu Ala Trp Ser Gly Tyr Gly Glu Tyr Lys Gly Ile
850                 855                 860
Ala Ser Asn Tyr Leu Ala Glu Leu Gln Glu Gly Asp Thr Ile Thr Cys
865                 870                 875                 880
Phe Ile Ser Thr Pro Gln Ser Glu Phe Thr Leu Pro Lys Asp Pro Glu
                885                 890                 895
Thr Pro Leu Ile Met Val Gly Pro Gly Thr Gly Val Ala Pro Phe Arg
                900                 905                 910
Gly Phe Val Gln Ala Arg Lys Gln Leu Lys Glu Gln Gly Gln Ser Leu
                915                 920                 925
Gly Glu Ala His Leu Tyr Phe Gly Cys Arg Ser Pro His Glu Asp Tyr
930                 935                 940
Leu Tyr Gln Glu Glu Leu Glu Asn Ala Gln Ser Glu Gly Ile Ile Thr
945                 950                 955                 960
Leu His Thr Ala Phe Ser Arg Met Pro Asn Gln Pro Lys Thr Tyr Val
                965                 970                 975
Gln His Val Met Glu Gln Asp Gly Lys Lys Leu Ile Glu Leu Leu Asp
                980                 985                 990
Gln Gly Ala His Phe Tyr Ile Cys Gly Asp Gly Ser Gln Met Ala Pro
                995                 1000                1005
Ala Val Glu Ala Thr Leu Met Lys Ser Tyr Ala Asp Val His Gln
    1010                1015                1020
Val Ser Glu Ala Asp Ala Arg Leu Trp Leu Gln Gln Leu Glu Glu
    1025                1030                1035
Lys Gly Arg Tyr Ala Lys Asp Val Trp Ala Gly
    1040                1045
```

<210> SEQ ID NO 138
<211> LENGTH: 1049
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

```
Met Thr Ile Lys Glu Met Pro Gln Pro Lys Thr Phe Gly Glu Leu Lys
1               5                   10                  15
Asn Leu Pro Leu Leu Asn Thr Asp Lys Pro Val Gln Ala Leu Met Lys
                20                  25                  30
Ile Ala Asp Glu Leu Gly Glu Ile Phe Lys Phe Glu Ala Pro Gly Arg
            35                  40                  45
Val Thr Arg Tyr Leu Ser Ser Gln Arg Leu Ile Lys Glu Ala Cys Asp
        50                  55                  60
Glu Ser Arg Phe Asp Lys Asn Leu Ser Gln Ala Leu Lys Phe Ala Arg
```

```
              65                  70                  75                  80
Asp Phe Ala Gly Asp Gly Leu Val Thr Ser Trp Thr His Glu Lys Asn
                    85                  90                  95

Trp Lys Lys Ala His Asn Ile Leu Leu Pro Ser Phe Ser Gln Gln Ala
            100                 105                 110

Met Lys Gly Tyr His Ala Met Val Asp Ile Ala Val Gln Leu Val
            115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Ala Asp Glu Val Met Asn Lys Leu Gln Arg Ala
            180                 185                 190

Asn Pro Asp Asp Pro Ala Tyr Asp Glu Asn Lys Arg Gln Phe Gln Glu
            195                 200                 205

Asp Ile Lys Val Met Asn Asp Leu Val Asp Lys Ile Ile Ala Asp Arg
    210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Arg
                245                 250                 255

Tyr Gln Ile Ile Ala Phe Leu Ile Ala Gly His Glu Thr Thr Ser Gly
            260                 265                 270

Leu Leu Ser Phe Ala Leu Tyr Phe Leu Val Lys Asn Pro His Val Leu
            275                 280                 285

Gln Lys Val Ala Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Val Met Val Leu Ile Pro Gln Leu His Arg Asp Lys Thr Val Trp
            355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Ala Thr Leu Lys Pro Lys Gly Phe Val Val Lys
            435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Ala Glu Asn Ala His Asn
465                 470                 475                 480

Thr Pro Leu Leu Val Leu Tyr Gly Ser Asn Met Gly Thr Ala Glu Gly
                485                 490                 495
```

```
Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895

Thr Pro Leu Ile Met Val Gly Pro Gly Thr Gly Val Ala Pro Phe Arg
            900                 905                 910
```

Gly Phe Val Gln Ala Arg Lys Gln Leu Lys Glu Gln Gly Gln Ser Leu
            915                 920                 925

Gly Glu Ala His Leu Tyr Phe Gly Cys Arg Ser Pro His Glu Asp Tyr
        930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys Gly Asp Gly Ser Gln Met Ala Pro
        995                 1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 139
<211> LENGTH: 1049
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
50                  55                  60

Glu Ser Arg Phe Asp Lys Asn Leu Ser Gln Ala Ala Lys Phe Ala Arg
65                  70                  75                  80

Asp Phe Ala Gly Asp Gly Leu Val Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Ser Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Met Val Arg Ala Ala Asp Glu Val Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

```
Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Arg
            245                 250                 255

Tyr Gln Ile Ile Thr Phe Leu Ile Ala Gly His Glu Thr Thr Ser Gly
        260                 265                 270

Leu Leu Ser Phe Ala Leu Tyr Phe Leu Val Lys Asn Pro His Val Leu
    275                 280                 285

Gln Lys Val Ala Glu Ala Ala Arg Val Leu Val Asp Pro Val Pro
290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
            325                 330                 335

Lys Glu Asp Thr Val Leu Gly Gly Tyr Pro Leu Glu Lys Gly Asp
        340                 345                 350

Glu Val Met Val Leu Ile Pro Gln Leu His Arg Asp Lys Thr Val Trp
    355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
            405                 410                 415

Met Met Leu Lys His Phe Asp Phe Glu Asp His Thr Asn Tyr Glu Leu
        420                 425                 430

Asp Ile Lys Glu Thr Leu Thr Leu Lys Pro Lys Gly Phe Val Val Lys
    435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
            485                 490                 495

Thr Ala Arg Asp Leu Ala Asp Ile Ala Met Ser Lys Gly Phe Ala Pro
        500                 505                 510

Gln Val Ala Thr Leu Asp Ser His Ala Gly Asn Leu Pro Arg Glu Gly
    515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
            565                 570                 575

Thr Thr Tyr Gln Lys Val Pro Ala Phe Ile Asp Glu Thr Leu Ala Ala
        580                 585                 590

Lys Gly Ala Glu Asn Ile Ala Asp Arg Gly Glu Ala Asp Ala Ser Asp
    595                 600                 605

Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640
```

-continued

```
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
            660                 665                 670
Leu Gln Gln Pro Gly Ser Ala Arg Ser Thr Arg His Leu Glu Ile Glu
        675                 680                 685
Leu Pro Lys Glu Ala Ser Tyr Gln Glu Gly Asp His Leu Gly Val Ile
    690                 695                 700
Pro Arg Asn Tyr Glu Gly Ile Val Asn Arg Val Thr Ala Arg Phe Gly
705                 710                 715                 720
Leu Asp Ala Ser Gln Gln Ile Arg Leu Glu Ala Glu Glu Lys Leu
                725                 730                 735
Ala His Leu Pro Leu Ala Lys Thr Val Ser Val Glu Glu Leu Leu Gln
            740                 745                 750
Tyr Val Glu Leu Gln Asp Pro Val Thr Arg Thr Gln Leu Arg Ala Met
        755                 760                 765
Ala Ala Lys Thr Val Cys Pro His Lys Val Glu Leu Glu Ala Leu
    770                 775                 780
Leu Glu Lys Gln Ala Tyr Lys Glu Gln Val Leu Ala Lys Arg Leu Thr
785                 790                 795                 800
Met Leu Glu Leu Leu Glu Lys Tyr Pro Ala Cys Glu Met Lys Phe Ser
                805                 810                 815
Glu Phe Ile Ala Leu Leu Pro Ser Ile Arg Pro Arg Tyr Tyr Ser Ile
            820                 825                 830
Ser Ser Ser Pro Arg Val Asp Glu Lys Gln Ala Ser Ile Thr Val Ser
        835                 840                 845
Val Val Ser Gly Glu Ala Trp Ser Gly Tyr Gly Glu Tyr Lys Gly Ile
    850                 855                 860
Ala Ser Asn Tyr Leu Ala Glu Leu Gln Glu Gly Asp Thr Ile Thr Cys
865                 870                 875                 880
Phe Ile Ser Thr Pro Gln Ser Glu Phe Thr Leu Pro Lys Asp Pro Glu
                885                 890                 895
Thr Pro Leu Ile Met Val Gly Pro Gly Thr Gly Val Ala Pro Phe Arg
            900                 905                 910
Gly Phe Val Gln Ala Arg Lys Gln Leu Lys Glu Gln Gly Gln Ser Leu
        915                 920                 925
Gly Glu Ala His Leu Tyr Phe Gly Cys Arg Ser Pro His Glu Asp Tyr
    930                 935                 940
Leu Tyr Gln Glu Glu Leu Glu Asn Ala Gln Ser Glu Gly Ile Ile Thr
945                 950                 955                 960
Leu His Thr Ala Phe Ser Arg Met Pro Asn Gln Pro Lys Thr Tyr Val
                965                 970                 975
Gln His Val Met Glu Gln Asp Gly Lys Lys Leu Ile Glu Leu Leu Asp
            980                 985                 990
Gln Gly Ala His Phe Tyr Ile Cys Gly Asp Gly Ser Gln Met Ala Pro
        995                 1000                1005
Ala Val Glu Ala Thr Leu Met Lys Ser Tyr Ala Asp Val His Gln
    1010                1015                1020
Val Ser Glu Ala Asp Ala Arg Leu Trp Leu Gln Gln Leu Glu Glu
    1025                1030                1035
Lys Gly Arg Tyr Ala Lys Asp Val Trp Ala Gly
    1040                1045
```

```
<210> SEQ ID NO 140
<211> LENGTH: 1049
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140
```

| Met | Thr | Ile | Lys | Glu | Met | Pro | Gln | Pro | Lys | Thr | Phe | Gly | Glu | Leu | Lys |
|---|---|---|---|---|---|---|---|---|---|---|---|---|---|---|---|
| 1 | | | | 5 | | | | | 10 | | | | | 15 | |

| Asn | Leu | Pro | Leu | Leu | Asn | Thr | Asp | Lys | Pro | Val | Gln | Ala | Leu | Met | Lys |
|---|---|---|---|---|---|---|---|---|---|---|---|---|---|---|---|
| | | 20 | | | | | 25 | | | | | 30 | | | |

| Ile | Ala | Asp | Glu | Leu | Gly | Glu | Ile | Phe | Lys | Phe | Glu | Ala | Pro | Gly | Arg |
|---|---|---|---|---|---|---|---|---|---|---|---|---|---|---|---|
| | 35 | | | | | 40 | | | | | 45 | | | | |

| Val | Thr | Arg | Tyr | Leu | Ser | Ser | Gln | Arg | Leu | Ile | Lys | Glu | Ala | Cys | Asp |
|---|---|---|---|---|---|---|---|---|---|---|---|---|---|---|---|
| 50 | | | | | 55 | | | | | 60 | | | | | |

| Glu | Ser | Arg | Phe | Asp | Lys | Asn | Leu | Ser | Gln | Ala | Ala | Lys | Phe | Ala | Arg |
|---|---|---|---|---|---|---|---|---|---|---|---|---|---|---|---|
| 65 | | | | | 70 | | | | | 75 | | | | | 80 |

| Asp | Phe | Ala | Gly | Asp | Gly | Leu | Val | Thr | Ser | Trp | Thr | His | Glu | Lys | Asn |
|---|---|---|---|---|---|---|---|---|---|---|---|---|---|---|---|
| | | | | 85 | | | | | 90 | | | | | 95 | |

| Trp | Lys | Lys | Ala | His | Asn | Ile | Leu | Leu | Pro | Ser | Phe | Ser | Gln | Gln | Ala |
|---|---|---|---|---|---|---|---|---|---|---|---|---|---|---|---|
| | | | 100 | | | | | 105 | | | | | 110 | | |

| Met | Lys | Gly | Tyr | His | Ala | Met | Met | Val | Asp | Ile | Ala | Val | Gln | Leu | Val |
|---|---|---|---|---|---|---|---|---|---|---|---|---|---|---|---|
| | | 115 | | | | | 120 | | | | | 125 | | | |

| Gln | Lys | Trp | Glu | Arg | Leu | Asn | Ala | Asp | Glu | His | Ile | Glu | Val | Ser | Glu |
|---|---|---|---|---|---|---|---|---|---|---|---|---|---|---|---|
| 130 | | | | | 135 | | | | | 140 | | | | | |

| Asp | Met | Thr | Arg | Leu | Thr | Leu | Asp | Thr | Ile | Gly | Leu | Cys | Gly | Phe | Asn |
|---|---|---|---|---|---|---|---|---|---|---|---|---|---|---|---|
| 145 | | | | | 150 | | | | | 155 | | | | | 160 |

| Tyr | Arg | Phe | Asn | Ser | Phe | Tyr | Arg | Asp | Gln | Pro | His | Pro | Phe | Ile | Ile |
|---|---|---|---|---|---|---|---|---|---|---|---|---|---|---|---|
| | | | | 165 | | | | | 170 | | | | | 175 | |

| Ser | Ala | Val | Arg | Ala | Ala | Asp | Glu | Val | Met | Asn | Lys | Leu | Gln | Arg | Ala |
|---|---|---|---|---|---|---|---|---|---|---|---|---|---|---|---|
| | | | 180 | | | | | 185 | | | | | 190 | | |

| Asn | Pro | Asp | Asp | Pro | Ala | Tyr | Asp | Glu | Asn | Lys | Arg | Gln | Phe | Gln | Glu |
|---|---|---|---|---|---|---|---|---|---|---|---|---|---|---|---|
| | | 195 | | | | | 200 | | | | | 205 | | | |

| Asp | Ile | Lys | Val | Met | Asn | Asp | Leu | Val | Asp | Lys | Ile | Ile | Ala | Asp | Arg |
|---|---|---|---|---|---|---|---|---|---|---|---|---|---|---|---|
| | 210 | | | | | 215 | | | | | 220 | | | | |

| Lys | Ala | Arg | Gly | Glu | Gln | Ser | Asp | Asp | Leu | Leu | Thr | Gln | Met | Leu | Asn |
|---|---|---|---|---|---|---|---|---|---|---|---|---|---|---|---|
| 225 | | | | | 230 | | | | | 235 | | | | | 240 |

| Gly | Lys | Asp | Pro | Glu | Thr | Gly | Glu | Pro | Leu | Asp | Asp | Gly | Asn | Ile | Arg |
|---|---|---|---|---|---|---|---|---|---|---|---|---|---|---|---|
| | | | | 245 | | | | | 250 | | | | | 255 | |

| Tyr | Gln | Ile | Ile | Thr | Phe | Leu | Ile | Ala | Gly | His | Glu | Thr | Thr | Ser | Gly |
|---|---|---|---|---|---|---|---|---|---|---|---|---|---|---|---|
| | | | 260 | | | | | 265 | | | | | 270 | | |

| Leu | Leu | Ser | Phe | Ala | Leu | Tyr | Phe | Leu | Val | Lys | Asn | Pro | His | Val | Leu |
|---|---|---|---|---|---|---|---|---|---|---|---|---|---|---|---|
| | | 275 | | | | | 280 | | | | | 285 | | | |

| Gln | Lys | Val | Ala | Glu | Glu | Ala | Ala | Arg | Val | Leu | Val | Asp | Pro | Val | Pro |
|---|---|---|---|---|---|---|---|---|---|---|---|---|---|---|---|
| 290 | | | | | 295 | | | | | 300 | | | | | |

| Ser | Tyr | Lys | Gln | Val | Lys | Gln | Leu | Lys | Tyr | Val | Gly | Met | Val | Leu | Asn |
|---|---|---|---|---|---|---|---|---|---|---|---|---|---|---|---|
| 305 | | | | | 310 | | | | | 315 | | | | | 320 |

| Glu | Ala | Leu | Arg | Leu | Trp | Pro | Thr | Ala | Pro | Ala | Phe | Ser | Leu | Tyr | Ala |
|---|---|---|---|---|---|---|---|---|---|---|---|---|---|---|---|
| | | | | 325 | | | | | 330 | | | | | 335 | |

| Lys | Glu | Asp | Thr | Val | Leu | Gly | Gly | Glu | Tyr | Pro | Leu | Glu | Lys | Gly | Asp |
|---|---|---|---|---|---|---|---|---|---|---|---|---|---|---|---|
| | | | 340 | | | | | 345 | | | | | 350 | | |

| Glu | Val | Met | Val | Leu | Ile | Pro | Gln | Leu | His | Arg | Asp | Lys | Thr | Val | Trp |
|---|---|---|---|---|---|---|---|---|---|---|---|---|---|---|---|
| | | 355 | | | | | 360 | | | | | 365 | | | |

```
Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Lys Gly Phe Val Val Lys
        435                 440                 445

Ala Lys Ser Lys Lys Ile Pro Leu Gly Gly Ile Pro Ser Pro Ser Thr
450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
770                 775                 780

Leu Glu Lys Gln Ala Tyr Lys Glu Gln Val Leu Ala Lys Arg Leu Thr
```

```
                785               790                795                800
Met Leu Glu Leu Leu Glu Lys Tyr Pro Ala Cys Glu Met Lys Phe Ser
                    805                810                815

Glu Phe Ile Ala Leu Leu Pro Ser Ile Arg Pro Arg Tyr Tyr Ser Ile
                820                825                830

Ser Ser Ser Pro Arg Val Asp Glu Lys Gln Ala Ser Ile Thr Val Ser
                835                840                845

Val Val Ser Gly Glu Ala Trp Ser Gly Tyr Gly Glu Tyr Lys Gly Ile
    850                855                860

Ala Ser Asn Tyr Leu Ala Glu Leu Gln Glu Gly Asp Thr Ile Thr Cys
865                870                875                880

Phe Ile Ser Thr Pro Gln Ser Glu Phe Thr Leu Pro Lys Asp Pro Glu
                    885                890                895

Thr Pro Leu Ile Met Val Gly Pro Gly Thr Gly Val Ala Pro Phe Arg
                900                905                910

Gly Phe Val Gln Ala Arg Lys Gln Leu Lys Glu Gln Gly Gln Ser Leu
                915                920                925

Gly Glu Ala His Leu Tyr Phe Gly Cys Arg Ser Pro His Glu Asp Tyr
    930                935                940

Leu Tyr Gln Glu Glu Leu Glu Asn Ala Gln Ser Glu Gly Ile Ile Thr
945                950                955                960

Leu His Thr Ala Phe Ser Arg Met Pro Asn Gln Pro Lys Thr Tyr Val
                    965                970                975

Gln His Val Met Glu Gln Asp Gly Lys Lys Leu Ile Glu Leu Leu Asp
                980                985                990

Gln Gly Ala His Phe Tyr Ile Cys Gly Asp Gly Ser Gln Met Ala Pro
    995                1000                1005

Ala Val Glu Ala Thr Leu Met Lys Ser Tyr Ala Asp Val His Gln
    1010                1015                1020

Val Ser Glu Ala Asp Ala Arg Leu Trp Leu Gln Gln Leu Glu Glu
    1025                1030                1035

Lys Gly Arg Tyr Ala Lys Asp Val Trp Ala Gly
    1040                1045

<210> SEQ ID NO 141
<211> LENGTH: 1049
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Ala Lys Phe Ala Arg
65                  70                  75                  80

Asp Phe Ala Gly Asp Gly Leu Val Thr Ser Trp Thr His Glu Lys Asn
                85                  90                  95
```

```
Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
            115                 120                 125

Gln Lys Trp Glu Arg Leu Asn Ala Asp Glu His Ile Glu Val Ser Glu
        130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Ile
                165                 170                 175

Ser Ala Val Arg Ala Ala Asp Glu Val Met Asn Lys Leu Gln Arg Ala
                180                 185                 190

Asn Pro Asp Asp Pro Ala Tyr Asp Glu Asn Lys Arg Gln Phe Gln Glu
                195                 200                 205

Asp Ile Lys Val Met Asn Asp Leu Val Asp Lys Ile Ile Ala Asp Arg
210                 215                 220

Lys Ala Arg Gly Glu Gln Ser Asp Asp Leu Leu Thr Gln Met Leu Asn
225                 230                 235                 240

Gly Lys Asp Pro Glu Thr Gly Glu Pro Leu Asp Asp Gly Asn Ile Arg
                245                 250                 255

Tyr Gln Ile Ile Ala Phe Leu Ile Ala Gly His Glu Thr Thr Ser Gly
            260                 265                 270

Leu Leu Ser Phe Ala Leu Tyr Phe Leu Val Lys Asn Pro His Val Leu
            275                 280                 285

Gln Lys Val Ala Glu Glu Ala Ala Arg Val Leu Val Asp Pro Val Pro
        290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Glu Tyr Pro Leu Glu Lys Gly Asp
                340                 345                 350

Glu Val Met Val Leu Ile Pro Gln Leu His Arg Asp Lys Thr Val Trp
            355                 360                 365

Gly Asp Asp Val Glu Glu Phe Arg Pro Glu Arg Phe Glu Asn Pro Ser
370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
                420                 425                 430

Asp Ile Lys Glu Thr Leu Thr Leu Lys Pro Lys Gly Phe Val Val Lys
            435                 440                 445

Ala Lys Ser Lys Lys Ile Pro Leu Gly Gly Ile Pro Ser Pro Ser Thr
            450                 455                 460

Glu Gln Ser Ala Lys Lys Val Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
                500                 505                 510

Gln Val Ala Thr Leu Asp Ser His Ala Gly Asn Leu Pro Arg Glu Gly
```

```
            515                 520                 525
Ala Val Leu Ile Val Thr Ala Ser Tyr Asn Gly His Pro Pro Asp Asn
        530                 535                 540
Ala Lys Gln Phe Val Asp Trp Leu Asp Gln Ala Ser Ala Asp Glu Val
545                 550                 555                 560
Lys Gly Val Arg Tyr Ser Val Phe Gly Cys Gly Asp Lys Asn Trp Ala
                565                 570                 575
Thr Thr Tyr Gln Lys Val Pro Ala Phe Ile Asp Glu Thr Leu Ala Ala
                580                 585                 590
Lys Gly Ala Glu Asn Ile Ala Asp Arg Gly Glu Ala Asp Ala Ser Asp
                595                 600                 605
Asp Phe Glu Gly Thr Tyr Glu Glu Trp Arg Glu His Met Trp Ser Asp
        610                 615                 620
Val Ala Ala Tyr Phe Asn Leu Asp Ile Glu Asn Ser Glu Asp Asn Lys
625                 630                 635                 640
Ser Thr Leu Ser Leu Gln Phe Val Asp Ser Ala Ala Asp Met Pro Leu
                645                 650                 655
Ala Lys Met His Gly Ala Phe Ser Thr Asn Val Val Ala Ser Lys Glu
                660                 665                 670
Leu Gln Gln Pro Gly Ser Ala Arg Ser Thr Arg His Leu Glu Ile Glu
                675                 680                 685
Leu Pro Lys Glu Ala Ser Tyr Gln Gly Asp His Leu Gly Val Ile
                690                 695                 700
Pro Arg Asn Tyr Glu Gly Ile Val Asn Arg Val Thr Ala Arg Phe Gly
705                 710                 715                 720
Leu Asp Ala Ser Gln Gln Ile Arg Leu Glu Ala Glu Glu Lys Leu
                725                 730                 735
Ala His Leu Pro Leu Ala Lys Thr Ser Val Glu Glu Leu Leu Gln
                740                 745                 750
Tyr Val Glu Leu Gln Asp Pro Val Thr Arg Thr Gln Leu Arg Ala Met
                755                 760                 765
Ala Ala Lys Thr Val Cys Pro Pro His Lys Val Glu Leu Glu Ala Leu
        770                 775                 780
Leu Glu Lys Gln Ala Tyr Lys Glu Gln Val Leu Ala Lys Arg Leu Thr
785                 790                 795                 800
Met Leu Glu Leu Leu Glu Lys Tyr Pro Ala Cys Glu Met Lys Phe Ser
                805                 810                 815
Glu Phe Ile Ala Leu Leu Pro Ser Ile Arg Pro Arg Tyr Tyr Ser Ile
                820                 825                 830
Ser Ser Ser Pro Arg Val Asp Glu Lys Gln Ala Ser Ile Thr Val Ser
        835                 840                 845
Val Val Ser Gly Glu Ala Trp Ser Gly Tyr Gly Glu Tyr Lys Gly Ile
        850                 855                 860
Ala Ser Asn Tyr Leu Ala Glu Leu Gln Glu Gly Asp Thr Ile Thr Cys
865                 870                 875                 880
Phe Ile Ser Thr Pro Gln Ser Glu Phe Thr Leu Pro Lys Asp Pro Glu
                885                 890                 895
Thr Pro Leu Ile Met Val Gly Pro Gly Thr Gly Val Ala Pro Phe Arg
                900                 905                 910
Gly Phe Val Gln Ala Arg Lys Gln Leu Lys Glu Gln Gly Gln Ser Leu
                915                 920                 925
Gly Glu Ala His Leu Tyr Phe Gly Cys Arg Ser Pro His Glu Asp Tyr
                930                 935                 940
```

| | | | | | | | | | | | |
|---|---|---|---|---|---|---|---|---|---|---|---|
|Leu|Tyr|Gln|Glu|Glu|Leu|Glu|Asn|Ala|Gln|Ser|Glu|Gly|Ile|Ile|Thr|
|945| | | | |950| | | | |955| | | | |960|

| | | | | | | | | | | | |
|---|---|---|---|---|---|---|---|---|---|---|---|
|Leu|His|Thr|Ala|Phe|Ser|Arg|Met|Pro|Asn|Gln|Pro|Lys|Thr|Tyr|Val|
| | | | |965| | | | |970| | | | |975| |

Gln His Val Met Glu Gln Asp Gly Lys Lys Leu Ile Glu Leu Leu Asp
         980                  985                990

Gln Gly Ala His Phe Tyr Ile Cys Gly Asp Gly Ser Gln Met Ala Pro
       995                 1000              1005

Ala Val Glu Ala Thr Leu Met Lys Ser Tyr Ala Asp Val His Gln
   1010                1015              1020

Val Ser Glu Ala Asp Ala Arg Leu Trp Leu Gln Gln Leu Glu Glu
   1025                1030              1035

Lys Gly Arg Tyr Ala Lys Asp Val Trp Ala Gly
   1040                1045

<210> SEQ ID NO 142
<211> LENGTH: 3150
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 142

| | | |
|---|---|---|
|atgaccatca aagaaatgcc acaacctaag actttcggtg aattgaagaa tttgcctttg|60|
|ttgaacaccg ataagccagt tcaagctttg atgaagattg ctgatgaatt gggtgaaatc|120|
|ttcaagtttg aagctccagg tagagtcact agatacttgt catctcaaag attgatcaaa|180|
|gaagcctgcg acgaatccag atttgataag aatttgtctc aagctttgaa gttcgctaga|240|
|gattttgctg gtgatggttt ggttacttct tggactcacg aaaagaattg aagaaggcc|300|
|cataacattt tgttgccatc tttctcacaa caagccatga agggttatca tgctatgatg|360|
|gttgatatcg ccgttcaatt ggttcaaaag tgggaaagat gaacgccga tgaacatatc|420|
|gaagtctctg aagatatgac cagattgacc ttggatacca ttggtttgtg tggtttcaac|480|
|tacagattca actccttcta cagagatcaa ccacatccat tcatcatctc tatggttaga|540|
|gctttggatg aagtcatgaa caaattgcaa agagctaatc cagacgatcc agcttatgac|600|
|gaaaacaaga gacaattcca agaagatatc aaggtcatga cgatttggt cgataagatt|660|
|atcgctgata gaaaggctag aggtgaacaa tctgatgatt tgttgaccca atgttgaac|720|
|ggtaaggatc cagaaactgg tgaaccattg atgatggta acatcagata ccaaattatc|780|
|accttcttga ttgctggtca cgaaactaca tctggtttgt tgtcttttgc cttgtacttt|840|
|ttggttaaga acccacacgt cttgcaaaag gttgctgaag aagctgcaag agttttggtt|900|
|gatccagttc catcttacaa gcaagtcaag caattgaagt acgttggtat ggttttgaac|960|
|gaagctttga gattgtggcc aactgctcca gcttttcat tatacgctaa gaagatacc|1020|
|gtcttgggtg gtgaatatcc attggaaaaa ggtgatgaag ttatggtctt gatcccacaa|1080|
|ttgcatagag ataagactgt ttggggtgat gatgtcgaag aattcagacc agaaagattc|1140|
|gaaaacccat ctgctattcc acaacatgct tttaagccat tggtaacgg tcaaagagct|1200|
|tgcattggtc aacaattcgc tttacatgaa gctaccttgg ttttgggtat gatgttgaaa|1260|
|cacttcgact tcgaagatca caccaactac gaattggata tcaaagaaac cgctaccttg|1320|
|aagccaaagg gttttgttgt taaggctaag tccaaaaaga ttccattggg tggtattcca|1380|

```
tctccatcta ctgaacaatc cgctaagaag gttagaaaga aagctgaaaa cgctcataac    1440
acacctttgt tggtcttgta cggttctaat atgggtactg ctgaaggtac agcaagagat    1500
ttggcagata ttgctatgtc taaaggtttc gctccacaag ttgctacttt ggattctcat    1560
gctggtaatt tgccaagaga aggtgctgtt ttgatagtta ctgcttctta caatggtcac    1620
ccaccagata atgctaagca attcgttgat tggttggatc aagcttcagc tgatgaagta    1680
aaaggtgtta gatactctgt tttcggttgc ggtgacaaaa attgggctac tacttatcaa    1740
aaggttccag cctttattga cgaaactttg gctgctaaag gtgctgaaaa cattgctgac    1800
agaggtgaag ctgatgcctc cgacgacttc gaaggtactt acgaagaatg gagagaacac    1860
atgtggtctg acgttgctgc ttacttcaac ttggacatcg aaaactctga agacaacaag    1920
tccactttgt ctttgcaatt cgttgactcc gctgctgaca tgccattggc taagatgcac    1980
ggtgctttct ctaccaacgt cgttgcctcc aaggaattgc aacaaccagg ttctgctaga    2040
tctactagac acttggaaat cgaattgcca aggaagcttc ctaccaaga aggtgaccac     2100 ttgggcgtta ttccaagaaa ctacgaaggt atcgtcaaca gagttactgc tagattcggt    2160
ttggatgctt ctcaacaaat cagattagaa gctgaagaag aaaagttggc tcacttgcca    2220
ttagctaaga ctgtctccgt tgaagaattg ttgcaatacg tcgaattgca agacccagtt    2280
accagaaccc aattgagagc catggctgcc aagaccgtct gtccaccaca caaggttgaa    2340
ttggaagcct tgttggaaaa gcaagcctac aaggaacaag ttttggctaa gagattgacc    2400
atgttggaat tgttggaaaa gtacccagcc tgcgaaatga agttctctga atttatcgcc    2460
ttgttgccat ctatcagacc acgttactac tctatttctt cctctccacg tgttgacgaa    2520
aagcaagctt ctattactgt ttccgttgtc tccggtgaag cttggtccgg ttacggtgaa    2580
tacaaggtta ttgcttctaa ctacttggct gaattgcaag aaggtgacac cattacttgt    2640
ttcatctcta ctccacaatc cgaatttact ttgccaaagg acccagaaac tccattgatc    2700
atggttggtc caggtactgg tgtcgctcca ttcagaggtt tcgttcaagc tagaaaacaa    2760
ttgaaggaac aaggtcaatc tttgggtgaa gctcacttgt acttcggttg tagatctcca    2820
cacgaagact acttatacca agaagaattg gaaaacgctc aatccgaagg tattatcact    2880
ttgcacaccg ctttctccag aatgccaaac caaccaaaga cttacgtcca acacgttatg    2940
gaacaagacg gtaagaagtt gattgaattg ttggaccaag gtgctcactt ctacatttgt    3000
ggtgatggtt ctcaaatggc tccagccgtt gaagccactt tgatgaagtc ttacgctgat    3060
gttcaccaag tttccgaagc cgatgctaga ttatggttgc aacaattgga agaaaaggt     3120 cgttacgcta aggatgtctg ggccggttga                                    3150
```

<210> SEQ ID NO 143
<211> LENGTH: 3150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143

```
atgaccatca aagaaatgcc acaacctaag actttcggtg aattgaagaa tttgcctttg      60
ttgaacaccg ataagccagt tcaagctttg atgaagattg ctgatgaatt gggtgaaatc     120
ttcaagtttg aagctccagg tagagtcact agatacttgt catctcaaag attgatcaaa    180
gaagcctgcg acgaatccag atttgataag aatttgtctc aagctttgaa gttcgctaga    240
```

```
gattttgctg gtgatggttt ggttacttct tggactcacg aaaagaattg gaagaaggcc    300
cataacattt tgttgccatc tttctcacaa caagccatga agggttatca tgctatgatg    360
gttgatatcg ccgttcaatt ggttcaaaag tgggaaagat tgaacgccga tgaacatatc    420
gaagtctctg aagatatgac cagattgacc ttggatacca ttggtttgtg tggtttcaac    480
tacagattca actccttcta cagagatcaa ccacatccat tcatcatctc tatggttaga    540
gctgcagatg aagtcatgaa caaattgcaa agagctaatc cagacgatcc agcttatgac    600
gaaaacaaga gacaattcca agaagatatc aaggtcatga acgatttggt cgataagatt    660
atcgctgata gaaaggctag aggtgaacaa tctgatgatt tgttgaccca aatgttgaac    720
ggtaaggatc cagaaactgg tgaaccattg gatgatggta acatcagata ccaaattatc    780
gctttcttga ttgctggtca cgaaactaca tctggtttgt tgtcttttgc cttgtacttt    840
ttggttaaga acccacacgt cttgcaaaag gttgctgaag aagctgcaag agttttggtt    900
gatccagttc catcttacaa gcaagtcaag caattgaagt acgttggtat ggttttgaac    960
gaagctttga gattgtggcc aactgctcca gctttttcat tatacgctaa agaagatacc   1020
gtcttgggtg gtaatatcc attggaaaaa ggtgatgaag ttatggtctt gatcccacaa   1080
ttgcatagag ataagactgt ttggggtgat gatgtcgaag aattcagacc agaaagattc   1140
gaaaacccat ctgctattcc acaacatgct tttaagccat tggtaacgg tcaaagagct   1200 tgcattggtc aacaattcgc tttacatgaa gctaccttgg ttttgggtat gatgttgaaa   1260
cacttcgact tcgaagatca caccaactac gaattggata tcaagaaaac cgctaccttg   1320
aagccaaagg ttttgttgt taaggctaag tccaaaaaga ttccattggg tggtattcca   1380
tctccatcta ctgaacaatc cgctaagaag gttagaaaga agctgaaaa cgctcataac   1440 acacctttgt tggtcttgta cggttctaat atgggtactg ctgaaggtac agcaagagat   1500
ttggcagata ttgctatgtc taaaggtttc gctccacaag ttgctacttt ggattctcat   1560
gctggtaatt tgccaagaga aggtgctgtt ttgatagtta ctgcttctta caatggtcac   1620
ccaccagata atgctaagca attcgttgat tggttggatc aagcttcagc tgatgaagta   1680
aaaggtgtta gatactctgt tttcggttgc ggtgacaaaa attgggctac tacttatcaa   1740
aaggttccag cctttattga cgaaactttg gctgctaaag gtgctgaaaa cattgctgac   1800
agaggtaagc tgatgcctc cgacgacttc gaaggtactt acgaagaatg gagagaaacac   1860 atgtggtctg acgttgctgc ttacttcaac ttggacatcg aaaactctga agacaacaag   1920
tccactttgt ctttgcaatt cgttgactcc gctgctgaca tgccattggc taagatgcac   1980
ggtgctttct ctaccaacgt cgttgcctcc aaggaattgc aacaaccagg ttctgctaga   2040
tctactagac acttggaaat cgaattgcca aaggaagctt cctaccaaga aggtgaccac   2100
ttgggcgtta ttccaagaaa ctacgaaggt atcgtcaaca gagttactgc tagattcggt   2160
ttggatgctt ctcaacaaat cagattgaaa gctgaagaag aaaagttggc tcacttgcca   2220
ttagctaaga ctgtctccgt tgaagaattg ttgcaatacg tcgaattgca agacccagtt   2280
accagaaccc aattgagagc catggctgcc aagaccgtct gtccaccaca caaggttgaa   2340
ttggaagcct tgttggaaaa gcaagcctac aaggaacaag ttttggctaa agattgacc   2400 atgttggaat tgttggaaaa gtacccagcc tgcgaaatga agttctctga atttatcgcc   2460
ttgttgccat ctatcagacc acgttactac tctatttctt cctctccacg tgttgacgaa   2520
aagcaagctt ctattactgt ttccgttgtc tccggtgaag cttggtccgg ttacggtgaa   2580
tacaagggta ttgcttctaa ctacttggct gaattgcaag aaggtgacac cattacttgt   2640
```

| | |
|---|---|
| ttcatctcta ctccacaatc cgaatttact tgccaaagg acccagaaac tccattgatc | 2700 |
| atggttggtc caggtactgg tgtcgctcca ttcagaggtt tcgttcaagc tagaaaacaa | 2760 |
| ttgaaggaac aaggtcaatc tttgggtgaa gctcacttgt acttcggttg tagatctcca | 2820 |
| cacgaagact acttatacca agaagaattg gaaaacgctc aatccgaagg tattatcact | 2880 |
| ttgcacaccg ctttctccag aatgccaaac caaccaaaga cttacgtcca acacgttatg | 2940 |
| gaacaagacg gtaagaagtt gattgaattg ttggaccaag gtgctcactt ctacatttgt | 3000 |
| ggtgatggtt ctcaaatggc tccagccgtt gaagccactt tgatgaagtc ttacgctgat | 3060 |
| gttcaccaag tttccgaagc cgatgctaga ttatggttgc aacaattgga agaaaaaggt | 3120 |
| cgttacgcta aggatgtctg ggccggttga | 3150 |

<210> SEQ ID NO 144
<211> LENGTH: 3150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144

| | |
|---|---|
| atgaccatca agaaatgcc acaacctaag actttcggtg aattgaagaa tttgcctttg | 60 |
| ttgaacaccg ataagccagt tcaagctttg atgaagattg ctgatgaatt gggtgaaatc | 120 |
| ttcaagtttg aagctccagg tagagtcact agatacttgt catctcaaag attgatcaaa | 180 |
| gaagcctgcg acgaatccag atttgataag aatttgtctc aagctgctaa gttcgctaga | 240 |
| gattttgctg gtgatggttt ggttacttct tggactcacg aaaagaattg gaagaaggcc | 300 |
| cataacattt tgttgccatc tttctcacaa caagccatga agggttatca tgctatgatg | 360 |
| gttgatatcg ccgttcaatt ggttcaaaag tgggaaagat tgaacgccga tgaacatatc | 420 |
| gaagtctctg aagatatgac cagattgacc ttggatacca ttggtttgtg tggtttcaac | 480 |
| tacagattca actccttcta cagagatcaa ccacatccat tcatcatctc tatggttaga | 540 |
| gctgcagatg aagtcatgaa caaattgcaa agagctaatc cagacgatcc agcttatgac | 600 |
| gaaaacaaga gacaattcca agaagatatc aaggtcatga acgatttggt cgataagatt | 660 |
| atcgctgata gaaaggctag aggtgaacaa tctgatgatt tgttgaccca aatgttgaac | 720 |
| ggtaaggatc cagaaactgg tgaaccattg gatgatggta acatcagata ccaaattatc | 780 |
| accttcttga ttgctggtca cgaaactaca tctggttttgt tgtcttttgc cttgtacttt | 840 |
| ttggttaaga acccacacgt cttgcaaaag gttgctgaag aagctgcaag agttttggtt | 900 |
| gatccagttc catcttacaa gcaagtcaag caattgaagt acgttggtat ggttttgaac | 960 |
| gaagctttga gattgtggcc aactgctcca gcttttttcat tatacgctaa gaagatacc | 1020 |
| gtcttgggtg gtaatatcc attggaaaaa ggtgatgaag ttatggtctt gatcccacaa | 1080 |
| ttgcatagag ataagactgt ttggggtgat gatgtcgaag aattcagacc agaaagattc | 1140 |
| gaaaacccat ctgctattcc acaacatgct tttaagccat tggtaacgg tcaaagagct | 1200 |
| tgcattggtc aacaattcgc tttacatgaa gctaccttgg ttttgggtat gatgttgaaa | 1260 |
| cacttcgact tcgaagatca caccaactac gaattggata tcaagaaaac cttgaccttg | 1320 |
| aagccaaagg gttttgttgt taaggctaag tccaaaaaga ttccattggg tggtattcca | 1380 |
| tctccatctcta ctgaacaatc cgctaagaag gttagaaaga aagctgaaaa cgctcataac | 1440 |
| acacctttgt tggtcttgta cggttctaat atgggtactg ctgaaggtac agcaagagat | 1500 |

-continued

```
ttggcagata ttgctatgtc taaaggtttc gctccacaag ttgctacttt ggattctcat    1560
gctggtaatt tgccaagaga aggtgctgtt ttgatagtta ctgcttctta caatggtcac    1620
ccaccagata atgctaagca attcgttgat tggttggatc aagcttcagc tgatgaagta    1680
aaaggtgtta gatactctgt tttcggttgc ggtgacaaaa attgggctac tacttatcaa    1740
aaggttccag cctttattga cgaaactttg gctgctaaag gtgctgaaaa cattgctgac    1800
agaggtgaag ctgatgcctc cgacgacttc gaaggtactt acgaagaatg gagagaaacac   1860 atgtggtctg acgttgctgc ttacttcaac ttggacatcg aaaactctga agacaacaag    1920
tccactttgt ctttgcaatt cgttgactcc gctgctgaca tgccattggc taagatgcac    1980
ggtgctttct ctaccaacgt cgttgcctcc aaggaattgc aacaaccagg ttctgctaga    2040
tctactagac acttggaaat cgaattgcca aggaagcttc ctaccaaga aggtgaccac     2100 ttgggcgtta ttccaagaaa ctacgaaggt atcgtcaaca gagttactgc tagattcggt    2160
ttggatgctc tcaacaaat cagattagaa gctgaagaag aaaagttggc tcacttgcca    2220
ttagctaaga ctgtctccgt tgaagaattg ttgcaatacg tcgaattgca agacccagtt    2280
accagaaccc aattgagagc catggctgcc aagaccgtct gtccaccaca caaggttgaa    2340
ttggaagcct tgttggaaaa gcaagcctac aaggaacaag ttttggctaa gagattgacc    2400
atgttggaat tgtggaaaaa gtacccagcc tgcgaaatga agttctctga atttatcgcc    2460
ttgttgccat ctatcagacc acgttactac tctatttctt cctctccacg tgttgacgaa    2520
aagcaagctt ctattactgt ttccgttgtc tccggtgaag cttggtccgg ttacggtgaa    2580
tacaagggta ttgcttctaa ctacttggct gaattgcaag aaggtgacac cattacttgt    2640
ttcatctcta ctcccacaatc cgaatttact ttgccaaagg acccagaaac tccattgatc   2700
atggttggtc caggtactgg tgtcgctcca ttcagaggtt tcgttcaagc tagaaaacaa    2760
ttgaaggaac aaggtcaatc tttgggtgaa gctcacttgt acttcggttg tagatctcca   2820
cacgaagact acttatacca agaagaattg gaaaacgctc aatccgaagg tattatcact   2880
ttgcacaccg ctttctccag aatgccaaac caaccaaaga cttacgtcca acacgttatg   2940
gaacaagacg gtaagaagtt gattgaattg ttggaccaag gtgctcactt ctacatttgt   3000
ggtgatggtt ctcaaatggc tccagccgtt gaagccactt tgatgaagtc ttacgctgat   3060
gttcaccaag tttccgaagc cgatgctaga ttatggttgc aacaattgga agaaaaaggt   3120
cgttacgcta aggatgtctg ggccggttga                                    3150
```

<210> SEQ ID NO 145
<211> LENGTH: 3150
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 145

```
atgaccatca agaaatgcc acaacctaag actttcggtg aattgaagaa tttgcctttg      60
ttgaacaccg ataagccagt tcaagctttg atgaagattg ctgatgaatt gggtgaaatc    120
ttcaagtttg aagctccagg tagagtcact agatacttgt catctcaaag attgatcaaa    180
gaagcctgcg acgaatccag atttgataag aattgtctc aagctgctaa gttcgctaga    240
gattttgctg gtgatggttt ggttacttct tggactcacg aaaagaattg gaagaaggcc    300
cataacattt tgttgccatc tttctcacaa caagccatga agggttatca tgctatgatg    360
```

```
gttgatatcg ccgttcaatt ggttcaaaag tgggaaagat tgaacgccga tgaacatatc    420
gaagtctctg aagatatgac cagattgacc ttggatacca ttggtttgtg tggtttcaac    480
tacagattca actccttcta cagagatcaa ccacatccat tcatcatctc tgctgttaga    540
gctgcagatg aagtcatgaa caaattgcaa agagctaatc cagacgatcc agcttatgac    600
gaaaacaaga gacaattcca agaagatatc aaggtcatga acgatttggt cgataagatt    660
atcgctgata gaaaggctag aggtgaacaa tctgatgatt tgttgaccca aatgttgaac    720
ggtaaggatc cagaaactgg tgaaccattg gatgatggta acatcagata ccaaattatc    780
accttcttga ttgctggtca cgaaactaca tctggtttgt tgtcttttgc cttgtacttt    840
ttggttaaga acccacacgt cttgcaaaag gttgctgaag aagctgcaag agttttggtt    900
gatccagttc catcttacaa gcaagtcaag caattgaagt acgttggtat ggttttgaac    960
gaagctttga gattgtggcc aactgctcca gcttttcat tatacgctaa agaagatacc    1020
gtcttgggtg tgaatatcc attggaaaaa ggtgatgaag ttatggtctt gatcccacaa    1080
ttgcatagag ataagactgt tggggtgat gatgtcgaag aattcagacc agaaagattc    1140
gaaaacccat ctgctattcc acaacatgct tttaagccat tggtaacgg tcaaagagct    1200
tgcattggtc aacaattcgc tttacatgaa gctaccttgg ttttgggtat gatgttgaaa    1260
cacttcgact tcgaagatca caccaactac gaattggata tcaaagaaac cttgaccttg    1320
aagccaaagg ttttgttgt taaggctaag tccaaaaaga ttccattggg tggtattcca    1380
tctccatcta ctgaacaatc cgctaagaag gttagaaaga agctgaaaa cgctcataac    1440
acacctttgt tggtcttgta cggttctaat atgggtactg ctgaaggtac agcaagagat    1500
ttggcagata ttgctatgtc taaaggtttc gctccacaag ttgctacttt ggattctcat    1560
gctggtaatt tgccaagaga aggtgctgtt ttgatagtta ctgcttctta caatggtcac    1620
ccaccagata atgctaagca attcgttgat tggttggatc aagcttcagc tgatgaagta    1680
aaaggtgtta gatactctgt tttcggttgc ggtgacaaaa attgggctac tacttatcaa    1740
aaggttccag cctttattga cgaaactttg gctgctaaag gtgctgaaaa cattgctgac    1800
agaggtgaag ctgatgcctc cgacgacttc gaaggtactt acgaagaatg gagagaacac    1860
atgtggtctg acgttgctgc ttacttcaac ttggacatcg aaaactctga agacaacaag    1920
tccactttgt ctttgcaatt cgttgactcc gctgctgaca tgccattggc taagatgcac    1980
ggtgctttct ctaccaacgt cgttgcctcc aaggaattgc aacaaccagg ttctgctaga    2040
tctactagac acttggaaat cgaattgcca aggaagcttc ctaccaaga aggtgaccac    2100
ttgggcgtta ttccaagaaa ctacgaaggt atcgtcaaca gagttactgc tagattcggt    2160
ttggatgctt ctcaacaaat cagattagaa gctgaagaag aaaagttggc tcacttgcca    2220
ttagctaaga ctgtctccgt tgaagaattg ttgcaatacg tcgaattgca agacccagtt    2280
accagaaccc aattgagagc catggctgcc aagaccgtct gtccaccaca caaggttgaa    2340
ttggaagcct tgttggaaaa gcaagcctac aaggaacaag ttttggctaa gagattgacc    2400
atgttggaat tgttggaaaa gtacccagcc tgcgaaatga gttctctga atttatcgcc    2460
ttgttgccat ctatcagacc acgttactac tctatttctt cctctccacg tgttgacgaa    2520
aagcaagctt ctattactgt ttccgttgtc tccggtgaag cttggtccgg ttacggtgaa    2580
tacaagggta ttgcttctaa ctacttggct gaattgcaag aaggtgacac cattacttgt    2640
ttcatctcta ctccacaatc cgaatttact ttgccaaagg acccagaaac tccattgatc    2700
```

| | | |
|---|---|---|
| atggttggtc caggtactgg tgtcgctcca ttcagaggtt tcgttcaagc tagaaaacaa | 2760 | |
| ttgaaggaac aaggtcaatc tttgggtgaa gctcacttgt acttcggttg tagatctcca | 2820 | |
| cacgaagact acttatacca agaagaattg gaaaacgctc aatccgaagg tattatcact | 2880 | |
| ttgcacaccg ctttctccag aatgccaaac caaccaaaga cttacgtcca acacgttatg | 2940 | |
| gaacaagacg gtaagaagtt gattgaattg ttggaccaag gtgctcactt ctacatttgt | 3000 | |
| ggtgatggtt ctcaaatggc tccagccgtt gaagccactt tgatgaagtc ttacgctgat | 3060 | |
| gttcaccaag tttccgaagc cgatgctaga ttatggttgc aacaattgga agaaaaaggt | 3120 | |
| cgttacgcta aggatgtctg ggccggttga | 3150 | |

<210> SEQ ID NO 146
<211> LENGTH: 3150
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 146

| | | |
|---|---|---|
| atgaccatca aagaaatgcc acaacctaag actttcggtg aattgaagaa tttgcctttg | 60 | |
| ttgaacaccg ataagccagt tcaagctttg atgaagattg ctgatgaatt gggtgaaatc | 120 | |
| ttcaagtttg aagctccagg tagagtcact agatacttgt catctcaaag attgatcaaa | 180 | |
| gaagcctgcg acgaatccag atttgataag aatttgtctc aagctgctaa gttcgctaga | 240 | |
| gattttgctg gtgatggttt ggttacttct tggactcacg aaaagaattg gaagaaggcc | 300 | |
| cataacattt tgttgccatc tttctcacaa caagccatga gggttatca tgctatgatg | 360 | |
| gttgatatcg ccgttcaatt ggttcaaaag tgggaaagat gaacgccga tgaacatatc | 420 | |
| gaagtctctg aagatatgac cagattgacc ttggatacca ttggtttgtg tggtttcaac | 480 | |
| tacagattca actccttcta cagagatcaa ccacatccat tcatcatctc tgctgttaga | 540 | |
| gctgcagatg aagtcatgaa caaattgcaa agagctaatc agacgatcc agcttatgac | 600 | |
| gaaaacaaga gacaattcca agaagatatc aaggtcatga acgatttggt cgataagatt | 660 | |
| atcgctgata gaaaggctag aggtgaacaa tctgatgatt tgttgaccca atgttgaac | 720 | |
| ggtaaggatc cagaaactgg tgaaccattg gatgatggta acatcagata ccaaattatc | 780 | |
| gctttcttga ttgctggtca cgaaactaca tctggttttgt tgtcttttgc cttgtacttt | 840 | |
| ttggttaaga acccacacgt cttgcaaaag gttgctgaag aagctgcaag agttttggtt | 900 | |
| gatccagttc catcttacaa gcaagtcaag caattgaagt acgttggtat ggttttgaac | 960 | |
| gaagctttga gattgtggcc aactgctcca gcttttttcat tatacgctaa gaagatacc | 1020 | |
| gtcttgggtg gtgaatatcc attggaaaaa ggtgatgaag ttatggtctt gatcccacaa | 1080 | |
| ttgcatagag ataagactgt ttggggtgat gatgtcgaag aattcagacc agaaagattc | 1140 | |
| gaaaacccat ctgctattcc acaacatgct tttaagccat tggtaacgg tcaaagagct | 1200 | |
| tgcattggtc aacaattcgc tttacatgaa gctaccttgg ttttgggtat gatgttgaaa | 1260 | |
| cacttcgact tcgaagatca caccaactac gaattggata tcaaagaaac cttgaccttg | 1320 | |
| aagccaaagg gttttgttgt taaggctaag tccaaaaaga ttccattggg tggtattcca | 1380 | |
| tctccatcta ctgaacaatc cgctaagaag gttagaaaga agctgaaaa cgctcataac | 1440 | |
| acacctttgt tggtcttgta cggttctaat atgggtactg ctgaaggtac agcaagagat | 1500 | |
| ttggcagata ttgctatgtc taaaggtttc gctccacaag ttgctacttt ggattctcat | 1560 | |

-continued

```
gctggtaatt tgccaagaga aggtgctgtt ttgatagtta ctgcttctta caatggtcac    1620
ccaccagata atgctaagca attcgttgat tggttggatc aagcttcagc tgatgaagta    1680
aaaggtgtta gatactctgt tttcggttgc ggtgacaaaa attgggctac tacttatcaa    1740
aaggttccag cctttattga cgaaactttg gctgctaaag gtgctgaaaa cattgctgac    1800
agaggtgaag ctgatgcctc cgacgacttc gaaggtactt acgaagaatg gagagaacac    1860
atgtggtctg acgttgctgc ttacttcaac ttggacatcg aaaactctga agacaacaag    1920
tccactttgt ctttgcaatt cgttgactcc gctgctgaca tgccattggc taagatgcac    1980
ggtgctttct ctaccaacgt cgttgcctcc aaggaattgc aacaaccagg ttctgctaga    2040
tctactagac acttggaaat cgaattgcca aaggaagctt cctaccaaga aggtgaccac    2100
ttgggcgtta ttccaagaaa ctacgaaggt atcgtcaaca gagttactgc tagattcggt    2160
ttggatgctt ctcaacaaat cagattagaa gctgaagaag aaaagttggc tcacttgcca    2220
ttagctaaga ctgtctccgt tgaagaattg ttgcaatacg tcgaattgca agacccagtt    2280
accagaaccc aattgagagc catggctgcc aagaccgtct gtccaccaca caaggttgaa    2340
ttggaagcct tgttggaaaa gcaagcctac aaggaacaag ttttggctaa gagattgacc    2400
atgttggaat tgttggaaaa gtacccagcc tgcgaaatga agttctctga atttatcgcc    2460
ttgttgccat ctatcagacc acgttactac tctatttctt cctctccacg tgttgacgaa    2520
aagcaagctt ctattactgt ttccgttgtc tccggtgaag cttggtccgg ttacggtgaa    2580
tacaagggta ttgcttctaa ctacttggct gaattgcaag aaggtgacac cattacttgt    2640
ttcatctcta ctccacaatc cgaatttact ttgccaaagg acccagaaac tccattgatc    2700
atggttggtc aggtactggt tgtcgctcca ttcagaggtt tcgttcaagc tagaaaacaa    2760
ttgaaggaac aaggtcaatc tttgggtgaa gctcacttgt acttcggttg tagatctcca    2820
cacgaagact acttatacca agaagaattg gaaaacgctc aatccgaagg tattatcact    2880
ttgcacaccg ctttctccag aatgccaaac caaccaaaga cttacgtcca acacgttatg    2940
gaacaagacg gtaagaagtt gattgaattg ttggaccaag gtgctcactt ctacatttgt    3000
ggtgatggtt ctcaaatggc tccagccgtt gaagccactt tgatgaagtc ttacgctgat    3060
gttcaccaag tttccgaagc cgatgctaga ttatggttgc aacaattgga agaaaaaggt    3120
cgttacgcta aggatgtctg ggccggttga                                    3150
```

<210> SEQ ID NO 147
<211> LENGTH: 5372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 147

```
cctcgccgca gttaattaaa gtcagtgagc gaggaagcgc gtaactataa cggtcctaag      60
gtagcgaatc ctgatgcggt attttctcct tacgcatctg tgcggtattt cacaccgcat     120
agatcggcaa gtgcacaaac aatacttaaa taaatactac tcagtaataa cctatttctt     180 agcattttg acgaaatttg ctattttgtt agagtctttt acaccatttg tctccacacc      240
tccgcttaca tcaacaccaa taacgccatt taatctaagc gcatcaccaa cattttctgg     300
cgtcagtcca ccagctaaca taaaatgtaa gctttcgggg ctctcttgcc ttccaaccca     360 gtcagaaaatc gagttccaat ccaaaagttc acctgtccca cctgcttctg aatcaaacaa     420
```

-continued

```
gggaataaac gaatgaggtt tctgtgaagc tgcactgagt agtatgttgc agtcttttgg    480
aaatacgagt cttttaataa ctggcaaacc gaggaactct tggtattctt gccacgactc    540
atctccatgc agtggagcca atcaattctt gcggtcaact ttggacgata tcaatgccgt    600
aatcattgac cagagccaaa acatcctcct taagttgatt acgaaacacg ccaaccaagt    660
atttcggagt gcctgaacta tttttatatg cttttacaag acttgaaatt ttccttgcaa    720
taaccgggtc aattgttctc tttctattgg gcacacatat aatacccagc aagtcagcat    780
cggaatctag agcacattct gcggcctctg tgctctgcaa gccgcaaact ttcaccaatg    840
gaccagaact acctgtgaaa ttaataacag acatactcca agctgccttt gtgtgcttaa    900
tcacgtatac tcacgtgctc aatagtcacc aatgccctcc ctcttggccc tctccttttc    960 tttttcgac cgaattaatt cttaatcgga aaaaaagaa aagctccgga tcaagattgt    1020
acgtaaggtg acaagctatt tttcaataaa gaatatcttc cactactgcc atctggcgtc    1080
ataactgcaa agtacacata tattacgatg ctgttctatt aaatgcttcc tatattatat    1140
atatagtaat gtcgtgatct atggtgcact ctcagtacaa tctgctctga tgccgcatag    1200
ttaagccagc cccgacaccc gccaacaccc gctgacgcgc cctgacgggc ttgtctgctc    1260
ccggcatccg cttacagaca agctgtgacc gtctccggga gctgcatgtg tcagaggttt    1320
tcaccgtcat caccgaaacg cgcgagacga agggcctcg tgatacgcct attttatag    1380 gttaatgtca tgataataat ggtttcttag acggatcgct tgcctgtaac ttacacgcgc    1440
ctcgtatctt ttaatgatgg ataaatttgg gaatttactc tgtgtttatt tattttatg    1500 ttttgtattt ggattttaga aagtaaataa agaaggtaga agagttacgg aatgaagaaa    1560
aaaaaataaa caaggttta aaaaatttca acaaaaagcg tactttacat atatatttat    1620
tagacaagaa aagcagatta aatagatata cattcgatta acgataagta aaatgtaaaa    1680
tcacaggatt ttcgtgtgtg gtcttctaca cagacaaggt gaaacaattc ggcattaata    1740
cctgagagca ggaagagcaa gataaaaggt agtatttgtt ggcgatcccc ctagagtctt    1800
ttacatcttc ggaaaacaaa aactattttt tctttaattt cttttttac tttctatttt    1860 taatttatat atttatatta aaaaatttaa attataatta ttttttatagc acgtgatgaa    1920 aaggacccag gtggcacttt tcggggaaat gtgcgcggaa ccctatttg tttattttc    1980 taaatacatt caaatatgta tccgctcatg agacaataac cctgataaat gcttcaataa    2040
tattgaaaaa ggaagagtat gagtattcaa catttccgtg tcgcccttat tccctttttt    2100
gcggcatttt gccttcctgt ttttgctcac ccagaaacgc tggtgaaagt aaaagatgct    2160
gaagatcagt tgggacgcgt agtctagacc agccaggaca gaaatgcctc gacttcgctg    2220
ctacccaagg ttgccgggtg acgcacaccg tggaaacgga tgaaggcacg aacccagtgg    2280
acataagcct gttcggttcg taagctgtaa tgcaagtagc gtatgcgctc acgcaactgg    2340
tccagaacct tgaccgaacg cagcggtggt aacggcgcag tggcggtttt catggcttgt    2400
tatgactgtt tttttggggt acagtctatg cctcgggcat ccaagcagca agcgcgttac    2460
gccgtgggtc gatgtttgat gttatggagc agcaacgatg ttacgcagca gggcagtcgc    2520
cctaaaacaa agttaaacat tatgagggaa gcggtgatcg ccgaagtatc gactcaacta    2580
tcagaggtag ttggcgccat cgagcgccat ctcgaaccga cgttgctggc cgtacatttg    2640
tacggctccg cagtggatgg cggcctgaag ccacacagtg atattgattt gctggttacg    2700
gtgaccgtaa ggcttgatga aacaacgcgg cgagctttga tcaacgacct tttggaaact    2760
tcggcttccc ctggagagag cgagattctc cgcgctgtag aagtcaccat tgttgtgcac    2820
```

```
gacgacatca ttccgtggcg ttatccagct aagcgcgaac tgcaatttgg agaatggcag   2880
cgcaatgaca ttcttgcagg tatcttcgag ccagccacga tcgacattga tctggctatc   2940
ttgctgacaa aagcaagaga acatagcgtt gccttggtag gtccagcggc ggaggaactc   3000
tttgatccgg ttcctgaaca ggatctattt gaggcgctaa atgaaacctt aacgctatgg   3060
aactcgccgc ccgactgggc tggcgatgag cgaaatgtag tgcttacgtt gtcccgcatt   3120
tggtacagcg cagtaaccgg caaaatcgcg ccgaaggatg tcgctgccgg ctgggcaatg   3180
gagcgcctgc cggcccagta tcagcccgtc atacttgaag ctagacaggc ttatcttgga   3240
caagaagaag atcgcttggc ctcgcgcgca gatcagttgg aagaatttgt ccactacgtg   3300
aaaggcgaga tcaccaaggt agtcggcaaa taaccctcga gcattcaagg cgccttgatt   3360
atttgacgtg gtttgatggc ctccacgcac gttgtgatat gtagatgatt cagttcgagt   3420
ttatcattat caatactgcc atttcaaaga atacgtaaat aattaatagt agtgattttc   3480
ctaactttat ttagtcaaaa aattagcctt ttaattctgc tgtaacccgt acatgcccaa   3540 aataggggc gggttacaca gaatatataa catcgtaggt gtctgggtga acagtttatt   3600
cctggcatcc actaaatata atggagcccg cttttttaagc tggcatccag aaaaaaaaag   3660
aatcccagca ccaaaatatt gttttcttca ccaaccatca gttcataggt ccattctctt   3720
agcgcaacta cagagaacag gggcacaaac aggcaaaaaa cgggcacaac ctcaatggag   3780
tgatgcaacc tgcctggagt aaatgatgac acaaggcaat tgacccacgc atgtatctat   3840 ctcatttct tacaccttct attaccttct gctctctctg atttggaaaa agctgaaaaa   3900
aaaggttgaa accagttccc tgaaattatt ccctacttg actaataagt atataaagac   3960
ggtaggtatt gattgtaatt ctgtaaatct atttcttaaa cttcttaaat tctacttta   4020 tagttagtct ttttttagt tttaaaacac caagaactta gtttcgaata aacacacata   4080
aacaaacaaa acaggcccct tttcctttgt cgatatcatg taattagtta tgtcacgctt   4140
acattcacgc cctcctccca catccgctct aaccgaaaag gaaggagtta gacaacctga   4200
agtctaggtc cctatttatt tttttaata gttatgttag tattaagaac gttatttata   4260
tttcaaattt ttctttttt tctgtacaaa cgcgtgtacg catgtaacat tatactgaaa   4320
accttgcttg agaaggtttt gggacgctcg aaggctttaa tttgtaatca ttatcacttt   4380
acgggtcctt tccggtgatc cgacaggtta cggggcggcg acctcgcggg ttttcgctat   4440
ttatgaaaat tttccggttt aaggcgtttc cgttcttctt cgtcataact taatgttttt   4500
atttaaaata cctcgcgagt ggcaacactg aaaatacca tggagcggcg taaccgtcgc   4560
acaggatcta ggtgaagatc cttttgata atctcatgac caaaatccct taacgtgagt   4620
tttcgttcca ctgagcgtca gacccgtag aaaagatcaa aggatcttct tgagatcctt   4680
tttttctgcg cgtaatctgc tgcttgcaaa caaaaaaacc accgctacca gcggtggttt   4740
gtttgccgga tcaagagcta ccaactcttt tccgaaggt aactggcttc agcagagcgc   4800
agataccaaa tactgtcctt ctagtgtagc cgtagttagg ccaccacttc aagaactctg   4860
tagcaccgcc tacatacctc gctctgctaa tcctgttacc agtggctgct gccagtggcg   4920
ataagtcgtg tcttaccggg ttggactcaa gacgatagtt accggataag cgcagcggt   4980 cgggctgaac ggggggttcg tgcacacagc ccagcttgga gcgaacgacc tacaccgaac   5040
tgagatacct acagcgtgag ctatgagaaa gcgccacgct tcccgaaggg agaaaggcgg   5100
acaggtatcc ggtaagcggc agggtcggaa caggagagcg cacgagggag cttccagggg   5160
```

| | |
|---|---|
| gaaacgcctg gtatctttat agtcctgtcg ggtttcgcca cctctgactt gagcgtcgat | 5220 |
| ttttgtgatg ctcgtcaggg gggcggagcc tatggaaaaa cgccagcaac gcggcagtgg | 5280 |
| aacgtgcatt atgaattagt tacgctaggg ataacagggt aatatagaac ccgaacgacc | 5340 |
| gagcgcagcg gcggccgcgc tgataccgcc gc | 5372 |

<210> SEQ ID NO 148
<211> LENGTH: 4977
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 148

| | |
|---|---|
| aacgacctac accgaactga gatacctaca gcgtgagcta tgagaaagcg ccacgcttcc | 60 |
| cgaagggaga aggcggaca ggtatccggt aagcggcagg gtcggaacag gagagcgcac | 120 |
| gagggagctt ccagggggaa acgcctggta tctttatagt cctgtcgggt ttcgccacct | 180 |
| ctgacttgag cgtcgatttt tgtgatgctc gtcaggggg cggagcctat ggaaaaacgc | 240 |
| cagcaacgcg gcagtggaac gtgcattatg aattagttac gctagggata cagggtaat | 300 |
| atagaacccg aacgaccgag cgcagcggcg gccgcgctga taccgccgcc ctcgccgcag | 360 |
| ttaattaaag tcagtgagcg aggaagcgcg taactataac ggtcctaagg tagcgaatcc | 420 |
| tgatgcggta ttttctcctt acgcatctgt gcggtatttc acaccgcata gatcggcaag | 480 |
| tgcacaaaca atacttaaat aaatactact cagtaataac ctatttctta gcatttttga | 540 |
| cgaaatttgc tattttgtta gagtctttta caccatttgt ctccacacct ccgcttacat | 600 |
| caacaccaat aacgccattt aatctaagcg catcaccaac attttctggc gtcagtccac | 660 |
| cagctaacat aaaatgtaag ctttcggggc tctcttgcct tccaacccag tcagaaatcg | 720 |
| agttccaatc caaaagttca cctgtcccac ctgcttctga atcaaacaag ggaataaacg | 780 |
| aatgaggttt ctgtgaagct gcactgagta gtatgttgca gtcttttgga atacgagtc | 840 |
| ttttaataac tggcaaaccg aggaactctt ggtattcttg ccacgactca tctccatgca | 900 |
| gtggagccaa tcaattcttg cggtcaactt tggacgatat caatgccgta atcattgacc | 960 |
| agagccaaaa catcctcctt aagttgatta cgaaacacgc caaccaagta tttcggagtg | 1020 |
| cctgaactat ttttatatgc ttttacaaga cttgaaattt ccttgcaat aaccgggtca | 1080 |
| attgttctct ttctattggg cacacatata atacccagca agtcagcatc ggaatctaga | 1140 |
| gcacattctg cggcctctgt gctctgcaag ccgcaaactt tcaccaatgg accagaacta | 1200 |
| cctgtgaaat taataacaga catactccaa gctgcctttg tgtgcttaat cacgtatact | 1260 |
| cacgtgctca atagtcacca atgccctccc tcttggccct ctccttttct ttttcgacc | 1320 |
| gaattaattc ttaatcggca aaaaagaaa agctccggat caagattgta cgtaaggtga | 1380 |
| caagctattt ttcaataaag aatatcttcc actactgcca tctggcgtca taactgcaaa | 1440 |
| gtacacatat attacgatgc tgttctatta aatgcttcct atattatata tatagtaatg | 1500 |
| tcgtgatcta tggtgcactc tcagtacaat ctgctctgat gccgcatagt taagccagcc | 1560 |
| ccgacacccg ccaacacccg ctgacgcgcc ctgacgggct tgtctgctcc cggcatccgc | 1620 |
| ttacagacaa gctgtgaccg tctccgggag ctgcatgtgt cagaggtttt caccgtcatc | 1680 |
| accgaaacgc gcgagacgaa agggcctcgt gatacgccta ttttttatagg ttaatgtcat | 1740 |
| gataataatg gtttcttaga cggatcgctt gcctgtaact tacacgcgcc tcgtatcttt | 1800 |

```
taatgatgga ataatttggg aatttactct gtgtttattt attttttatgt tttgtatttg   1860 gattttagaa agtaaataaa gaaggtagaa gagttacgga atgaagaaaa aaaaataaac   1920
aaaggtttaa aaaatttcaa caaaaagcgt actttacata tatatttatt agacaagaaa   1980
agcagattaa atagatatac attcgattaa cgataagtaa aatgtaaaat cacaggattt   2040
tcgtgtgtgg tcttctacac agacaaggtg aaacaattcg gcattaatac ctgagagcag   2100
gaagagcaag ataaaaggta gtatttgttg gcgatccccc tagagtcttt tacatcttcg   2160
gaaaacaaaa actatttttt ctttaatttc tttttttact ttctattttt aatttatata   2220
tttatattaa aaaatttaaa ttataattat ttttatagca cgtgatgaaa aggacccagg   2280
tggcactttt cggggaaatg tgcgcggaac ccctatttgt ttatttttct aaatacattc   2340
aaatatgtat ccgctcatga gacaataacc ctgataaatg cttcaataat attgaaaaag   2400
gaagagtatg agtattcaac atttccgtgt cgcccttatt ccctttttttg cggcattttg   2460 ccttcctgtt tttgctcacc cagaaacgct ggtgaaagta aaagatgctg aagatcagtt   2520
gggacgcgta gtctagacca gccaggacag aaatgcctcg acttcgctgc tacccaaggt   2580
tgccgggtga cgcacaccgt ggaaacggat gaaggcacga acccagtgga cataagcctg   2640
ttcggttcgt aagctgtaat gcaagtagcg tatgcgctca cgcaactggt ccagaacctt   2700
gaccgaacgc agcggtggta acggcgcagt ggcggttttc atggcttgtt atgactgttt   2760
ttttggggta cagtctatgc ctcgggcatc caagcagcaa gcgcgttacg ccgtgggtcg   2820
atgtttgatg ttatggagca gcaacgatgt tacgcagcag gcagtcgccc taaaacaaa   2880 gttaaacatt atgagggaag cggtgatcgc cgaagtatcg actcaactat cagaggtagt   2940
tggcgccatc gagcgccatc tcgaaccgac gttgctggcc gtacatttgt acggctccgc   3000
agtggatggc ggcctgaagc cacacagtga tattgatttg ctggttacgg tgaccgtaag   3060
gcttgatgaa acaacgcggc gagctttgat caacgacctt ttggaaactt cggcttcccc   3120
tggagagagc gagattctcc gcgctgtaga agtcaccatt gttgtgcacg acgacatcat   3180
tccgtggcgt tatccagcta agcgcgaact gcaatttgga gaatggcagc gcaatgacat   3240
tcttgcaggt atcttcgagc cagccacgat cgacattgat ctggctatct tgctgacaaa   3300
agcaagagaa catagcgttg ccttggtagg tccagcggcg gaggaactct ttgatccggt   3360
tcctgaacag gatctatttg aggcgctaaa tgaaaccta cgctatgga actcgccgcc   3420 cgactgggct ggcgatgagc gaaatgtagt gcttacgttg tcccgcattt ggtacagcgc   3480
agtaaccggc aaaatcgcgc cgaaggatgt cgctgccggc tgggcaatgg agcgcctgcc   3540
ggcccagtat cagcccgtca tacttgaagc tagacaggct tatcttggac aagaagaaga   3600
tcgcttggcc tcgcgcgcag atcagttgga agaatttgtc cactacgtga aaggcgagat   3660
caccaaggta gtcggcaaat aaccctcgag cattcaaggc gccttgatta tttgacgtgg   3720
tttgatggcc tccacgcacg ttgtgatatg tagatgagag cgttggttgg tggatcaagc   3780
ccacgcgtag gcaatcctcg agcagatccg ccaggcgtgt atatatagcg tggatggcca   3840
ggcaacttta gtgctgacac atacaggcat atatatatgt gtgcgacaac acatgatcat   3900
atggcatgca tgtgctctgt atgtatataa aactcttgtt ttcttctttt ctctaaatat   3960
tctttcctta tacattagga cctttgcagc ataaattact atacttctat agacacacaa   4020
acacaaatac acacactaaa ttaataacag gcccctttc ctttgtcgat atcatgtaat   4080
tagttatgtc acgcttacat tcacgccctc cccccacatc cgctctaacc gaaaaggaag   4140
gagttagaca acctgaagtc taggtcccta tttattttt tatagttatg ttagtattaa   4200
```

```
gaacgttatt tatatttcaa attttttcttt tttttctgta caaacgcgtg tacgcatgta    4260
acattatact gaaaaccttg cttgagaagg ttttgggacg ctcgaaggct ttaatttgta    4320
atcattatca ctttacgggt cctttccggt gatccgacag gttacggggc ggcgacctcg    4380
cgggttttcg ctatttatga aaattttccg gtttaaggcg tttccgttct tcttcgtcat    4440
aacttaatgt ttttatttaa aatacctcgc gagtggcaac actgaaaata cccatggagc    4500
ggcgtaaccg tcgcacagga tctaggtgaa gatccttttt gataatctca tgaccaaaat    4560
cccttaacgt gagttttcgt tccactgagc gtcagacccc gtagaaaaga tcaaaggatc    4620
ttcttgagat cctttttttc tgcgcgtaat ctgctgcttg caaacaaaaa aaccaccgct    4680
accagcggtg gtttgtttgc cggatcaaga gctaccaact cttttccga aggtaactgg     4740 cttcagcaga gcgcagatac caaatactgt ccttctagtg tagccgtagt taggccacca    4800
cttcaagaac tctgtagcac cgcctacata cctcgctctg ctaatcctgt taccagtggc    4860
tgctgccagt ggcgataagt cgtgtcttac cgggttggac tcaagacgat agttaccgga    4920
taaggcgcag cggtcgggct gaacggggg ttcgtgcaca cagcccagct tggagcg       4977
```

<210> SEQ ID NO 149
<211> LENGTH: 5079
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 149

```
acgacctaca ccgaactgag atacctacag cgtgagctat gagaaagcgc cacgcttccc      60
gaagggagaa aggcggacag gtatccggta agcggcaggg tcggaacagg agagcgcacg     120
agggagcttc caggggaaa cgcctggtat ctttatagtc ctgtcgggtt tcgccacctc      180
tgacttgagc gtcgattttt gtgatgctcg tcagggggc ggagcctatg gaaaaacgcc      240
agcaacgcgg cagtggaacg tgcattatga attagttacg ctagggataa cagggtaata     300
tagaacccga cgaccgagc gcagcggcgg ccgcgctgat accgccgccc tcgccgcagt      360
taattaaagt cagtgagcga ggaagcgcgt aactataacg gtcctaaggt agcgaatcct     420
gatgcggtat tttctcctta cgcatctgtg cggtatttca caccgcatag atcggcaagt     480
gcacaaacaa tacttaaata aatactactc agtaataacc tatttcttag catttttgac     540
gaaatttgct atttttgttag agtctttac accattgtc tccacacctc cgcttacatc     600
aacaccaata acgccattta atctaagcgc atcaccaaca ttttctggcg tcagtccacc     660
agctaacata aaatgtaagc tttcgggggct ctcttgcctt ccaacccagt cagaaatcga    720
gttccaatcc aaagtttcac ctgtcccacc tgcttctgaa tcaaacaagg gaataaacga    780
atgaggtttc tgtgaagctg cactgagtag tatgttgcag tcttttggaa atacgagtct    840
tttaataact ggcaaaccga ggaactcttg gtattcttgc cacgactcat ctccatgcag    900
tggagccaat caattcttgc ggtcaacttt ggacgatatc aatgccgtaa tcattgacca    960
gagccaaaac atcctcctta agttgattac gaaacacgcc aaccaagtat tcggagtgc    1020 ctgaactatt tttatatgct tttacaagac ttgaaatttt ccttgcaata accgggtcaa    1080
ttgttctctt tctattgggc acacatataa tacccagcaa gtcagcatcg gaatctagag    1140
cacattctgc ggcctctgtg ctctgcaagc cgcaaacttt caccaatgga ccagaactac    1200
ctgtgaaatt aataacagac atactccaag ctgcctttgt gtgcttaatc acgtatactc    1260
```

```
acgtgctcaa tagtcaccaa tgccctccct cttggccctc tccttttctt ttttcgaccg    1320
aattaattct taatcggcaa aaaaagaaaa gctccggatc aagattgtac gtaaggtgac    1380
aagctatttt tcaataaaga atatcttcca ctactgccat ctggcgtcat aactgcaaag    1440
tacacatata ttacgatgct gttctattaa atgcttccta tattatatat atagtaatgt    1500
cgtgatctat ggtgcactct cagtacaatc tgctctgatg ccgcatagtt aagccagccc    1560
cgacacccgc caacacccgc tgacgcgccc tgacgggctt gtctgctccc ggcatccgct    1620
tacagacaag ctgtgaccgt ctccgggagc tgcatgtgtc agaggttttc accgtcatca    1680
ccgaaacgcg cgagacgaaa gggcctcgtg atacgcctat ttttataggt taatgtcatg    1740
ataataatgg tttcttagac ggatcgcttg cctgtaactt acacgcgcct cgtatctttt    1800
aatgatggaa taatttggga atttactctg tgtttattta tttttatgtt ttgtatttgg    1860
attttagaaa gtaaataaag aaggtagaag agttacggaa tgaagaaaaa aaaataaaca    1920
aaggtttaaa aaatttcaac aaaaagcgta ctttacatat atatttatta gacaagaaaa    1980
gcagattaaa tagatataca ttcgattaac gataagtaaa atgtaaaatc acaggatttt    2040
cgtgtgtggt cttctacaca gacaaggtga acaattcgg cattaatacc tgagagcagg    2100
aagagcaaga taaaggtag tatttgttgg cgatccccct agagtctttt acatcttcgg    2160
aaaacaaaaa ctattttttc tttaatttct tttttttactt tctatttta atttatatat    2220 ttatattaaa aaatttaaat tataattatt tttatagcac gtgatgaaaa ggacccaggt    2280
ggcacttttc ggggaaatgt gcgcggaacc cctatttgtt tatttttcta aatacattca    2340
aatatgtatc cgctcatgag acaataaccc tgataaatgc ttcaataata ttgaaaaagg    2400
aagagtatga gtattcaaca tttccgtgtc gcccttattc cctttttgc ggcatttgc     2460 cttcctgttt ttgctcaccc agaaacgctg gtgaaagtaa aagatgctga agatcagttg    2520
ggacgcgtag tctagaccag ccaggacaga aatgcctcga cttcgctgct acccaaggtt    2580
gccgggtgac gcacaccgtg aaacggatg aaggcacgaa cccagtggac ataagcctgt    2640
tcggttcgta agctgtaatg caagtagcgt atgcgctcac gcaactggtc cagaaccttg    2700
accgaacgca gcggtggtaa cggcgcagtg gcggttttca tggcttgtta tgactgtttt    2760
tttggggtac agtctatgcc tcgggcatcc aagcagcaag gcgcttacgc cgtgggtcga    2820
tgtttgatgt tatggagcag caacgatgtt acgcagcagg gcagtcgccc taaaacaaag    2880
ttaaacatta tgagggaagc ggtgatcgcc gaagtatcga ctcaactatc agaggtagtt    2940
ggcgccatcg agcgccatct cgaaccgacg ttgctggccg tacatttgta cggctccgca    3000
gtggatggcg gcctgaagcc acacagtgat attgatttgc tggttacggt gaccgtaagg    3060
cttgatgaaa caacgcggcg agctttgatc aacgaccttt tggaaacttc ggcttcccct    3120
ggagagagcg agattctccg cgctgtagaa gtcaccattg ttgtgcacga cgacatcatt    3180
ccgtggcgtt atccagctaa gcgcgaactg caatttggag aatggcagcg caatgacatt    3240
cttgcaggta tcttcgagcc agccacgatc gacattgatc tggctatctt gctgacaaaa    3300
gcaagagaac atagcgttgc cttggtaggt ccagcggcgg aggaactctt tgatccggtt    3360
cctgaacagg atctatttga ggcgctaaat gaaaccttaa cgctatggaa ctcgccgccc    3420
gactgggctg gcgatgagcg aaatgtagtg cttacgttgt cccgcatttg gtacagcgca    3480
gtaaccggca aaatcgcgcc gaaggatgtc gctgccggct gggcaatgga gcgcctgccg    3540
gcccagtatc agcccgtcat acttgaagct agacaggctt atcttggaca agaagaagat    3600
```

```
cgcttggcct cgcgcgcaga tcagttggaa gaatttgtcc actacgtgaa aggcgagatc    3660
accaaggtag tcggcaaata accctcgagc attcaaggcg ccttgattat ttgacgtggt    3720
ttgatggcct ccacgcacgt tgtgatatgt agatgactcg taggaacaat tcgggcccc     3780 tgcgtgttct tctgaggttc atcttttaca tttgcttctg ctggataatt ttcagaggca    3840
acaaggaaaa attagatggc aaaaagtcgt cttccaagga aaatccccca ccatctttcg    3900
agatcccctg taacttattg gcaactgaaa gaatgaaaag gaggaaaata caaaatatac    3960
tagaactgaa aaaaaaaaag tataaataga gacgatatat gccaatactt cacaatgttc    4020
gaatctattc ttcatttgca gctattgtaa aataataaaa catcaagaac aaacaagctc    4080
aacttgtctt ttctaagaac aaagaataaa cacaaaaaca aaagttttt ttaatttaa      4140 tcaaaaaaca ggccccttt ccttgtcga tatcatgtaa ttagttatgt cacgcttaca      4200
ttcacgccct ccccccacat ccgctctaac cgaaaaggaa ggagttagac aacctgaagt    4260
ctaggtccct atttatttt ttatagttat gttagtatta agaacgttat ttatatttca     4320
aatttttctt tttttctgt acaaacgcgt gtacgcatgt aacattatac tgaaaacctt    4380
gcttgagaag gttttgggac gctcgaaggc tttaatttgt aatcattatc actttacggg    4440
tcctttccgg tgatccgaca ggttacgggg cggcgacctc gcgggttttc gctatttatg    4500 aaaatttcc ggtttaaggc gtttccgttc ttcttcgtca taacttaatg ttttatta      4560 aaatacctcg cgagtggcaa cactgaaaat acccatggag cggcgtaacc gtcgcacagg    4620
atctaggtga agatccttt tgataatctc atgaccaaaa tcccttaacg tgagttttcg    4680
ttccactgag cgtcagaccc cgtagaaaag atcaaaggat cttcttgaga tccttttttt    4740
ctgcgcgtaa tctgctgctt gcaaacaaaa aaaccaccgc taccagcggt ggtttgtttg    4800
ccggatcaag agctaccaac tcttttccg aaggtaactg gcttcagcag agcgcagata    4860
ccaaatactg tccttctagt gtagccgtag ttaggccacc acttcaagaa ctctgtagca    4920
ccgcctacat acctcgctct gctaatcctg ttaccagtgg ctgctgccag tggcgataag    4980
tcgtgtctta ccgggttgga ctcaagacga tagttaccgg ataaggcgca gcggtcgggc    5040
tgaacggggg gttcgtgcac acagcccagc ttggagcga                           5079
```

<210> SEQ ID NO 150
<211> LENGTH: 21
<212> TYPE: PRT
<213> ORGANISM: Papaver rhoeas

<400> SEQUENCE: 150

Thr Gln Gly Leu Met Ser Tyr Lys Val Val Pro Leu Asp Ile Leu Leu
1               5                   10                  15

Thr Arg Arg Met Leu
            20

<210> SEQ ID NO 151
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Thr Pro Gly Leu Met Ser Tyr Lys Val Val Pro Leu Asp Ile Leu Leu
1               5                   10                  15

Thr His Arg Arg Ile Lys Ser Cys Val Gln Leu Ala Ser Ser Glu Arg

```
                    20                  25                  30
Asp Met Glu Ser Ser Gly Val Pro Val Ile Thr Leu Ser Ser Gly Lys
            35                  40                  45

Val Met Pro Val Leu Gly Met Gly Thr Phe Glu Lys
        50                  55                  60

<210> SEQ ID NO 152
<211> LENGTH: 27
<212> TYPE: PRT
<213> ORGANISM: Papaver rhoeas

<400> SEQUENCE: 152

Met Asp Ser Ser Gly Val Pro Val Ile Pro Leu Ser Ser Gly Lys Gly
1               5                   10                  15

Met Pro Ala Leu Ala Leu Gly Thr Phe Glu Thr
            20                  25

<210> SEQ ID NO 153
<211> LENGTH: 900
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Met Glu Leu Gln Tyr Ile Ser Tyr Phe Gln Pro Thr Ser Ser Val Val
1               5                   10                  15

Ala Leu Leu Leu Ala Leu Val Ser Ile Leu Ser Ser Val Val Val Leu
            20                  25                  30

Arg Lys Thr Phe Leu Asn Asn Tyr Ser Ser Ser Pro Ala Ser Ser Thr
        35                  40                  45

Lys Thr Ala Val Leu Ser His Gln Arg Gln Ser Cys Ala Leu Pro
    50                  55                  60

Ile Ser Gly Leu Leu His Ile Phe Met Asn Lys Asn Gly Leu Ile His
65                  70                  75                  80

Val Thr Leu Gly Asn Met Ala Asp Lys Tyr Gly Pro Ile Phe Ser Phe
                85                  90                  95

Pro Thr Gly Ser His Arg Thr Leu Val Val Ser Ser Trp Glu Met Val
            100                 105                 110

Lys Glu Cys Phe Thr Gly Asn Asn Asp Thr Ala Phe Ser Asn Arg Pro
        115                 120                 125

Ile Pro Leu Ala Phe Lys Thr Ile Phe Tyr Ala Cys Gly Gly Ile Asp
    130                 135                 140

Ser Tyr Gly Leu Ser Ser Val Pro Tyr Gly Lys Tyr Trp Arg Glu Leu
145                 150                 155                 160

Arg Lys Val Cys Val His Asn Leu Leu Ser Asn Gln Gln Leu Leu Lys
                165                 170                 175

Phe Arg His Leu Ile Ile Ser Gln Val Asp Thr Ser Phe Asn Lys Leu
            180                 185                 190

Tyr Glu Leu Cys Lys Asn Ser Glu Asp Asn Gln Gly Asn Tyr Pro Thr
        195                 200                 205

Thr Thr Thr Ala Ala Gly Met Val Arg Ile Asp Asp Trp Leu Ala Glu
    210                 215                 220

Leu Ser Phe Asn Val Ile Gly Arg Ile Val Cys Gly Phe Gln Ser Gly
225                 230                 235                 240

Pro Lys Thr Gly Ala Pro Ser Arg Val Glu Gln Phe Lys Glu Ala Ile
```

```
                    245                 250                 255
Asn Glu Ala Ser Tyr Phe Met Ser Thr Ser Pro Val Ser Asp Asn Val
                260                 265                 270
Pro Met Leu Gly Trp Ile Asp Gln Leu Thr Gly Leu Thr Arg Asn Met
            275                 280                 285
Lys His Cys Gly Lys Lys Leu Asp Leu Val Val Glu Ser Ile Ile Asn
        290                 295                 300
Asp His Arg Gln Lys Arg Arg Phe Ser Arg Thr Lys Gly Gly Asp Glu
305                 310                 315                 320
Lys Asp Asp Glu Gln Asp Asp Phe Ile Asp Ile Cys Leu Ser Ile Met
                325                 330                 335
Glu Gln Pro Gln Leu Pro Gly Asn Asn Asn Pro Ser Gln Ile Pro Ile
                340                 345                 350
Lys Ser Ile Val Leu Asp Met Ile Gly Gly Thr Asp Thr Thr Lys
            355                 360                 365
Leu Thr Thr Ile Trp Thr Leu Ser Leu Leu Asn Asn Pro His Val
        370                 375                 380
Leu Asp Lys Ala Lys Gln Glu Val Asp Ala His Phe Arg Thr Lys Arg
385                 390                 395                 400
Arg Ser Thr Asn Asp Ala Ala Ala Val Asp Phe Asp Ile
                405                 410                 415
Arg Asn Leu Val Tyr Ile Gln Ala Ile Ile Lys Glu Ser Met Arg Leu
                420                 425                 430
Tyr Pro Ala Ser Pro Val Val Glu Arg Leu Ser Gly Glu Asp Cys Val
                435                 440                 445
Val Gly Gly Phe His Val Pro Ala Gly Thr Arg Leu Trp Ala Asn Val
            450                 455                 460
Trp Lys Met Gln Arg Asp Pro Lys Val Trp Asp Pro Leu Val Phe
465                 470                 475                 480
Arg Pro Asp Arg Phe Leu Ser Asp Glu Gln Lys Met Val Asp Val Arg
                485                 490                 495
Gly Gln Asn Tyr Glu Leu Leu Pro Phe Gly Ala Gly Arg Arg Val Cys
                500                 505                 510
Pro Gly Val Ser Phe Ser Leu Asp Leu Met Gln Leu Val Leu Thr Arg
            515                 520                 525
Leu Ile Leu Glu Phe Glu Met Lys Ser Pro Ser Gly Lys Val Asp Met
        530                 535                 540
Thr Ala Thr Pro Gly Leu Met Ser Tyr Lys Val Ile Pro Leu Asp Ile
545                 550                 555                 560
Leu Leu Thr His Arg Arg Ile Lys Pro Cys Val Gln Ser Ala Ala Ser
                565                 570                 575
Glu Arg Asp Met Glu Ser Ser Gly Val Pro Val Ile Thr Leu Gly Ser
                580                 585                 590
Gly Lys Val Met Pro Val Leu Gly Met Gly Thr Phe Glu Lys Val Gly
            595                 600                 605
Lys Gly Ser Glu Arg Glu Arg Leu Ala Ile Leu Lys Ala Ile Glu Val
        610                 615                 620
Gly Tyr Arg Tyr Phe Asp Thr Ala Ala Tyr Glu Thr Glu Glu Val
625                 630                 635                 640
Leu Gly Glu Ala Ile Ala Glu Ala Leu Gln Leu Gly Leu Val Lys Ser
                645                 650                 655
Arg Asp Glu Leu Phe Ile Ser Ser Met Leu Trp Cys Thr Asp Ala His
                660                 665                 670
```

-continued

```
Ala Asp Arg Val Leu Leu Ala Leu Gln Asn Ser Leu Arg Asn Leu Lys
        675                 680                 685

Leu Glu Tyr Val Asp Leu Tyr Met Leu Pro Phe Pro Ala Ser Leu Lys
        690                 695                 700

Pro Gly Lys Ile Thr Met Asp Ile Pro Glu Glu Asp Ile Cys Arg Met
705                 710                 715                 720

Asp Tyr Arg Ser Val Trp Ala Ala Met Glu Glu Cys Gln Asn Leu Gly
                725                 730                 735

Phe Thr Lys Ser Ile Gly Val Ser Asn Phe Ser Cys Lys Lys Leu Gln
                740                 745                 750

Glu Leu Met Ala Thr Ala Asn Ile Pro Pro Ala Val Asn Gln Val Glu
        755                 760                 765

Met Ser Pro Ala Phe Gln Gln Lys Lys Leu Arg Glu Tyr Cys Asn Ala
        770                 775                 780

Asn Asn Ile Leu Val Ser Ala Ile Ser Val Leu Gly Ser Asn Gly Thr
785                 790                 795                 800

Pro Trp Gly Ser Asn Ala Val Leu Gly Ser Glu Val Leu Lys Lys Ile
                805                 810                 815

Ala Met Ala Lys Gly Lys Ser Val Ala Gln Val Ser Met Arg Trp Val
                820                 825                 830

Tyr Glu Gln Gly Ala Ser Leu Val Val Lys Ser Phe Ser Glu Glu Arg
        835                 840                 845

Leu Arg Glu Asn Leu Asn Ile Phe Asp Trp Glu Leu Thr Lys Glu Asp
    850                 855                 860

His Glu Lys Ile Gly Glu Ile Pro Gln Cys Arg Ile Leu Ser Ala Tyr
865                 870                 875                 880

Phe Leu Val Ser Pro Asn Gly Pro Phe Lys Ser Gln Glu Glu Leu Trp
                885                 890                 895

Asp Asp Glu Ala
                900
```